(12) United States Patent
Minatti et al.

(10) Patent No.: US 9,296,734 B2
(45) Date of Patent: Mar. 29, 2016

(54) PERFLUORINATED 5,6-DIHYDRO-4H-1,3-OXAZIN-2-AMINE COMPOUNDS AS BETA-SECRETASE INHIBITORS AND METHODS OF USE

(71) Applicant: AMGEN INC., Thousand Oaks, CA (US)

(72) Inventors: Ana Elena Minatti, Santa Monica, CA (US); Jonathan D. Low, Tarzana, CA (US); Jennifer R. Allen, Newbury Park, CA (US); Jian Chen, Camarillo, CA (US); Ning Chen, Thousand Oaks, CA (US); Yuan Cheng, Newbury Park, CA (US); Ted Judd, Granada Hills, CA (US); Qingyian Liu, Camarillo, CA (US); Patricia Lopez, Woodland Hills, CA (US); Wenyuan Qian, Newbury Park, CA (US); Shannon Rumfelt, Camarillo, CA (US); Robert M. Rzasa, Ventura, CA (US); Nuria A. Tamayo, Newbury Park, CA (US); Qiufen Xue, Newbury Park, CA (US); Bryant Yang, Agoura Hills, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/192,710

(22) Filed: Feb. 27, 2014

(65) Prior Publication Data
US 2014/0249104 A1    Sep. 4, 2014

Related U.S. Application Data

(60) Provisional application No. 61/928,898, filed on Jan. 17, 2014, provisional application No. 61/826,431, filed on May 22, 2013, provisional application No. 61/771,615, filed on Mar. 1, 2013.

(51) Int. Cl.
| C07D 413/14 | (2006.01) |
|---|---|
| C07D 413/12 | (2006.01) |
| C07D 471/04 | (2006.01) |
| C07D 513/04 | (2006.01) |
| C07F 7/08 | (2006.01) |
| C07D 413/04 | (2006.01) |

(Continued)

(52) U.S. Cl.
CPC ............ C07D 413/14 (2013.01); C07D 265/08 (2013.01); C07D 413/04 (2013.01); C07D 413/10 (2013.01); C07D 413/12 (2013.01); C07D 471/04 (2013.01); C07D 498/04 (2013.01); C07D 513/04 (2013.01); C07F 7/0812 (2013.01)

(58) Field of Classification Search
CPC .. C07D 413/14; C07D 413/12; C07D 471/04; C07D 513/04

USPC .......................................... 514/228.8; 544/96
See application file for complete search history.

(56) References Cited

U.S. PATENT DOCUMENTS

| 5,441,870 A | 8/1995 | Seubert et al. |
|---|---|---|
| 5,712,130 A | 1/1998 | Hajko et al. |

(Continued)

FOREIGN PATENT DOCUMENTS

| EP | 1942105 A1 | 6/2010 |
|---|---|---|
| EP | 2500344 A1 | 9/2012 |

(Continued)

OTHER PUBLICATIONS

International Search Report for analogous PCT Application No. /US2014/019100, mailed on May 8, 2014.
Hilpert, H. et al., "β-Secretase (BACE1) Inhibitors with high in Vivo Efficacy Suitable for Clinical Evaluation in Alzheimer's Disease," Journal of Medicinal Chemistry, vol. 56, pp. 3980-3995 (2013).
CAS Registry No. 145976-71-4, Oct. 14, 2013.
Yan, R. et al., "Targeting the β Secretase BACE1 for Alzheimer's Disease Therapy," Lancet Neurol. vol. 13. pp. 319-329 (2014).
Written Opinion of the International Searching Authority for International Patent Application No. PCT/US2014/019100, mailed May 8, 2014, pp. 1-7.

(Continued)

*Primary Examiner* — Kahsay Habte
(74) *Attorney, Agent, or Firm* — G. Prabhaker Reddy; Bernard P. Friedrichsen; Markus Bergauer

(57) ABSTRACT

The present invention provides a new class of compounds useful for the modulation of beta-secretase enzyme (BACE) activity. The compounds have a general Formula I:

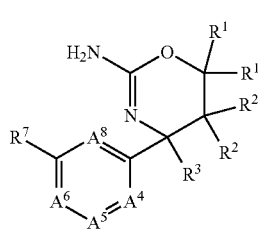

wherein variables $A^4, A^5, A^6, A^8$, each of $R^1$ and $R^2$, $R^3$ and $R^7$ of Formula I, independently, are defined herein. The invention also provides pharmaceutical compositions comprising the compounds, and corresponding uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formulas II and III, and sub-formula embodiments thereof, intermediates and processes and methods useful for the preparation of compounds of Formulas I-III.

39 Claims, No Drawings

(51) Int. Cl.
*C07D 413/10* (2006.01)
*C07D 265/08* (2006.01)
*C07D 498/04* (2006.01)

(56) References Cited

U.S. PATENT DOCUMENTS

| | | | |
|---|---|---|---|
| 5,942,400 | A | 8/1999 | Anderson et al. |
| 8,168,630 | B2 | 5/2012 | Tamura et al. |
| 8,173,642 | B2 | 5/2012 | Kobayashi et al. |
| 8,389,513 | B2 * | 3/2013 | Banner et al. ............ 514/228.8 |
| 8,637,504 | B2 | 1/2014 | Hori et al. |
| 8,653,067 | B2 | 2/2014 | Kobayashi et al. |
| 9,085,576 | B2 | 7/2015 | Minatti et al. |
| 9,133,129 | B2 | 9/2015 | Yamashita et al. |
| 2006/0111370 | A1 | 5/2006 | Zhu et al. |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0160290 | A1 | 6/2010 | Kobayashi et al. |
| 2011/0152253 | A1 | 6/2011 | Motoki et al. |
| 2011/0294149 | A1 | 12/2011 | Gurney et al. |
| 2012/0202803 | A1 | 8/2012 | Hilpert et al. |
| 2012/0238557 | A1 | 9/2012 | Masui et al. |
| 2012/0245154 | A1 | 9/2012 | Anan et al. |
| 2012/0245157 | A1 | 9/2012 | Masui et al. |
| 2012/0258962 | A1 | 10/2012 | Hilpert et al. |
| 2012/0302549 | A1 | 11/2012 | Narquizian et al. |
| 2013/0072478 | A1 | 3/2013 | Hilpert et al. |
| 2014/0051691 | A1 | 2/2014 | Masui et al. |
| 2014/0235626 | A1 | 8/2014 | Tada et al. |
| 2014/0249104 | A1 | 9/2014 | Minatti et al. |
| 2015/0252011 | A1 | 9/2015 | Minatti et al. |

FOREIGN PATENT DOCUMENTS

| | | |
|---|---|---|
| EP | 2514747 A1 | 10/2012 |
| EP | 2511268 A1 | 12/2012 |
| EP | 2703401 A1 | 3/2014 |
| JP | 2012/250933 A | 12/2012 |
| WO | 2000/017369 A2 | 3/2000 |
| WO | 2005/058311 A1 | 6/2005 |
| WO | 2006/065277 A2 | 6/2006 |
| WO | 2007/049532 A1 | 3/2007 |
| WO | 2008/103351 A2 | 8/2008 |
| WO | 2008/133273 A1 | 11/2008 |
| WO | 2009/134617 A1 | 11/2009 |
| WO | 2009/151098 A1 | 12/2009 |
| WO | 2010/013302 A1 | 2/2010 |
| WO | 2010/013794 A1 | 2/2010 |
| WO | 2010/128058 A1 | 11/2010 |
| WO | 2011/005738 A1 | 1/2011 |
| WO | 2011/009898 A1 | 1/2011 |
| WO | 2011/020806 A1 | 2/2011 |
| WO | 2011/029803 A1 | 3/2011 |
| WO | 2011/044181 A1 | 4/2011 |
| WO | 2011/058763 A1 | 5/2011 |
| WO | 2011/069934 A1 | 6/2011 |
| WO | 2011/070029 A1 | 6/2011 |
| WO | 2011/070781 A1 | 6/2011 |
| WO | 2011/071057 A1 | 6/2011 |
| WO | 2011/071109 A1 | 6/2011 |
| WO | 2011/071135 A1 | 6/2011 |
| WO | 2012/095463 A1 | 7/2012 |
| WO | 2012/095521 A1 | 7/2012 |
| WO | 2012/138734 A1 | 10/2012 |
| WO | 2012/139425 A1 | 10/2012 |
| WO | 2012/139993 A1 | 10/2012 |
| WO | 2012/147762 A1 | 11/2012 |
| WO | 2012/147763 A1 | 11/2012 |
| WO | 2012/156284 A1 | 11/2012 |
| WO | 2012/162330 A1 | 11/2012 |
| WO | 2012/162334 A1 | 11/2012 |
| WO | 2012/168164 A1 | 12/2012 |
| WO | 2012/168175 A1 | 12/2012 |
| WO | 2013/004676 A1 | 1/2013 |
| WO | 2013/027188 A1 | 2/2013 |
| WO | 2013/028670 A1 | 2/2013 |
| WO | 2013/030713 A1 | 3/2013 |
| WO | 2013/054291 A1 | 4/2013 |
| WO | 2013/061962 A1 | 5/2013 |
| WO | 2013/110622 A1 | 8/2013 |
| WO | 2013/142613 A1 | 9/2013 |
| WO | 2013/164730 A1 | 11/2013 |
| WO | 2013/182638 A1 | 12/2013 |
| WO | 2014/001228 A1 | 1/2014 |
| WO | 2014/013076 A1 | 1/2014 |
| WO | 2014/045162 A1 | 3/2014 |
| WO | 2014/062549 A1 | 4/2014 |
| WO | 2014/062553 A1 | 4/2014 |
| WO | 2014/065434 A1 | 5/2014 |
| WO | 2014/066132 A1 | 5/2014 |
| WO | 2014/093190 A1 | 6/2014 |
| WO | 2014/097038 A1 | 6/2014 |
| WO | 2014/098831 A1 | 6/2014 |
| WO | 2014/099788 A9 | 6/2014 |
| WO | 2014/099794 A1 | 6/2014 |
| WO | 2014/114532 A1 | 7/2014 |
| WO | 2014/134341 A1 | 9/2014 |
| WO | 2014/166906 A1 | 10/2014 |
| WO | 2014/173917 A1 | 10/2014 |
| WO | 2015/1586421 A1 | 10/2015 |

OTHER PUBLICATIONS

U.S. Appl. No. 14/819,256, filed Aug. 5, 2015, Amgen Inc.
U.S. Appl. No. 14/932,787, filed Nov. 4, 2015, Amgen Inc.
Alzforum Networking For A Cure, "Barcelona: Out of Left Field—Hit to The Eye Kills BACE Inhibitor," pp. 1-7 (Mar. 31, 2011); access online: www.alzforum.org/news/conference-coverage/barcelona-out-left-field-hit-eye-kills-bace-inhibitor (last accessed Dec. 16, 2015).
Best, J. D. et al., "Quantitative Measurement of Changes in Amyloid-β(40) in the Rat Brain and Cerebrospinal Fluid Following Treatment with the γ-Secretase Inhibitor LY-411575 [N2-[(2S)-2-(3,5-Difluorophenyl)-2-hydroxyethanoyl]-N1-[(7S)-5-methyl-6-oxo-6,7- dihydro-5H-dibenzo[b,d]azepin-7-yl1]L-alaninamide]," *Journal of Pharmacology and Experimental Therapeutics* 313(2):902-908 (2005).
Citron, M., "β-Secretase inhibition for the treatment of Alzheimer's disease—promise and challenge," *TRENDS in Pharmacological Sciences* 25(2):92-97 (2004).
Cole, S.L. and Vassar, R., "The Alzheimer's disease β-secretase enzyme, BACE1," *Molecular Neurodegeneration* 2(22):1-25 (2007).
De Meyer, G. et al., "Diagnosis-Independent Alzheimer Disease Biomarker Signature in Cognitively Normal Elderly People," *Arch. Neurol.* 67(8):949-956 (2010).
Dovey, H. F. et al., "Functional gamma-secretasae inhibitors reduce beta-amyloid peptide levels in brain," *Journal of Neurochemistry* 76:173-181 (2001).
Follo, C. et al., "Knock-Down of Cathepsin D Affects the Retinal Pigment Epithelium, Impairs Swim-Bladder Ontogenesis and Causes Premature Death in Zebrafish," *PLoS One* 6(7):e21908, pp. 1-13 (2011).
Games, D. et al., "Alzheimer-type neuropathology in transgenic mice overexpressing V717F β-amyloid precursor protein," *Nature* 373:523-527 (1995).
Götz, J. et al., "Transgenic animal models of Alzheimer's disease and related disorders: histopathology, behavior and therapy," *Molecular Psychiatry* 9:664-683 (2004).
Gulnik, S. V. et al. "Design of sensitive fluorogenic substrates for human cathespin D," *FEBS Letters* 413:379-384 (1997).
Harris, J. A. et al, "Transsynaptic Progression of Amyloid-β-Induced Neuronal Dysfunction within the Entorhinal-Hippocampal Network," *Neuron* 68:428-441 (2010).
Henley, D. B. et al., "Development of semagacestat (LY450139), a functional g-secretase inhibitor, for the treatment of Alzheimer's disease," *Expert Opin. Pharmacother.* 10(10):1657-1664 (2009).
Hsia, A. Y. et al., "Plaque-independent disruption of neural circuits in Alzheimer's disease mouse models," *Proc. Natl. Acad. Sci. USA* 96:3228-3233 (1999).

(56) References Cited

OTHER PUBLICATIONS

Hsiao, K. et al., "Correlative Memory Deficits, Ab Elevation, and Amyloid Plaques in Transgenic Mice," *Science* 274:99-102 (1996).
International Preliminary Report on Patentability and Written Opinion for International Patent Application No. PCT/US2014/021412, issued Sep. 8, 2015, pp. 1-7.
International Search Report for International Patent Application No. PCT/US2014/019100, mailed Aug. 5, 2014, pp. 1-6.
International Search Report for International Patent Application No. PCT/US2014/021412, mailed May 13, 2014, pp. 1-3.
Joachim, C. L. and Selkoe, D. J., "The Seminal Role of β-Amyloid in the Pathogenesis of Alzheimer Disease," *Alzheimer Disease and Associated Disorders* 6(1):7-34 (1992).
Karran, E. et al. "The amyloid cascade hypothesis for Alzheimer's disease: an appraisal for the development of therapeutics," *Nature Reviews Drug Discovery* 10:698-712 (2011).
Koike, M. et al., "Involvement of two different cell death pathways in retinal atrophy of cathepsin D-deficient mice," *Molecular and Cellular Neuroscience* 22:146-161 (2003).
Luo, Y et al., "Mice deficient in BACE1, the Alzheimer's β-secretase, have normal phenotype and abolished β-amyloid generation," *Nature Neuroscience* 4:231-232 (2001).
May, P. C. et al., "Robust Central Reduction of Amyloid-β in Humans with an Orally Available, Non-Peptidic β-Secretase Inhibitor," *Journal of Neuroscience* 31(46):16507-16516 (2011).
Office Action mailed May 22, 2015 for U.S. Appl. No. 14/691,715, filed Apr. 21, 2015, pp. 1-5.
Palop, J. J. and Mucke, L., "Amyloid-β-induced neuronal in Alzheimer's disease: from synapses toward neural networks," *Nature Neuroscience* 13(7):812-818 (2010).
Sabbagh, M. N. et al., "β-Amyloid and Treatment Opportunities for Alzheimer's Disease," *Alzheimer's Disease Review* 3:1-19 (1997).
Selkoe, D. J., "Soluble oligomers of the amyloid β-protein impair synaptic plasticity and behavior," *Behavioural Brain Research* 192:106-113 (2008).
Selkoe, D. J., "The Molecular Pathology of Alzheimer's Disease," *Neuron* 6:487-498 (1991).
Seubert, P. et al., "Isolation and quantification of soluble Alzheimer's β-peptide from biological fluids," *Nature* 359:325-327 (1992).
Shacka, J. J. and Roth, K. A., "Cathepsin D Deficiency and NCL/Batten Disease: There's More to Death than Apoptosis," *Autophagy*, 3(5):474-476 (2007).
Shankar, G. M. et al., "Amyloid-β protein dimers isolated directly from Alzheimer's brains impair synaptic plasticity and memory," *Nature Medicine* 14(8):837-842 (2008).
Siemers, E. R. et al., "Effects of a γ-secretase inhibitor in a randomized study of patients with Alzheimer's disease," *Neurology* 66:602-604 (2006).
Siemers, E. R. et al., "Safety, Tolerability, and Effects on Plasma and Cerebrospinal Fluid Amyloid-β After Inhibition of γ-Secretase," *Clin. Neuropharmacol.* 30(6):317-325 (2007).
Sinha, S. et al., "Purification and cloning of amyloid precursor protein β-secretase from human brain," *Nature* 402:537-540 (1999).
Tanzi, R. E. and Bertram, L., "Twenty Years of the Alzheimer's Disease Amyloid Hypothesis: A Genetic Perspective," *Cell* 120(4):545-555 (2005).
Vassar, R. et al, "The β-Secretase Enzyme BACE in Health and Alzheimer's Disease: Regulation, Cell Biology, Function, and Therapeutic Potential," *Journal of Neuroscience* 29(41):12787-12794 (2009).
Walsh, D. M. and Selkoe, D. J., "Deciphering the Molecular Basis of Memory Failure in Alzheimer's Disease," *Neuron* 44(1):181-193 (2004).
Yasuda, Y. et al., "Characterization of New Fluorogenic Substrates for the Rapid and Sensitive Assay of Cathepsin E and Cathepsin D," *J. Biochem.* 125(6):1137-1143 (1999).

\* cited by examiner

PERFLUORINATED 5,6-DIHYDRO-4H-1,3-OXAZIN-2-AMINE COMPOUNDS AS BETA-SECRETASE INHIBITORS AND METHODS OF USE

RELATED APPLICATIONS

This application claims the benefit of U.S. Provisional Patent Application Nos. 61/771,615, filed on Mar. 1, 2013, 61/826,431 filed on May 22, 2013, and 61/928,898, filed on Jan. 17, 2014, which specifications are hereby incorporated herein by reference in their entireties.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million aging people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. Vassar & Yan, *Lancet Neurology*, 13:319-329 (2014). The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide comprised of about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention, support and commitment from both researchers and investors alike. A small molecule gamma-secretase inhibitor, LY450139 ("Semagacestat"), an A-beta lowering agent, advanced to phase III clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology*, 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. Vassar & Yan, *Lancet Neurology*, 13:319-329 (2014). For example, each of the following PCT publications: WO07/049,532, WO12/147,763, WO12/168,164, WO12/168,175, WO12/156,284, WO11/020,806, WO 11/070,029, WO11/058,763, WO11/071,135, WO11/069,934, WO12/139,993, WO11/009,898, WO08133273, US20120238557, US20120245157, US20120258962 and EP01942105 describe inhibitors of BACE, useful for treating AD and other beta-secretase mediated disorders. For Example, US20120245157 describes "Oxazine Derivatives" as BACE inhibitors for the treatment of neurological disorders of the general formula:

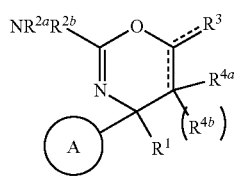

while WO2012168164 describes "Halogen-Alkyl-1,3-Oxazines as BACE1 and/or BACE2 Inhibitors" and discloses compounds of the general formula:

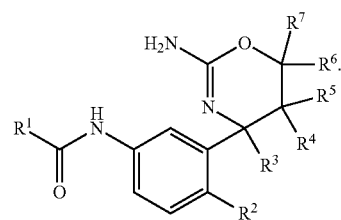

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein Cathepsin D has been implicated in undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by nitrc oxide release from microglial cells. However, in the very same mice, it was also found that no atrophic change was detected in the retina of mice deficient in cathepsin B or L. *Mol. Cell. Neurosci*, 2003, February 22(2):146-161. Further, Animal models of cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy*, 2007, September-October; 3(5):474-476. Finally, an adverse effect of the inhibition of Cat D is evident from the data presented in *PLoS One*, 2011; 6(7):e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyper-pigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human Bace-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities (Alzheimer's Research Forum News, Mar. 31, 2011 reporting on Martin Citron's presentation at the AD/PD Conference 3-2011 in Barcelona, Spain)

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

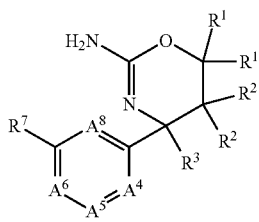

I wherein each of $A^4$, $A^5$, $A^6$, $A^8$, $R^1$, $R^2$, $R^3$ and $R^7$ of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In embodiment 1 of the invention, there are provided compounds, including stereoisomers, tautomers, hydrates, solvates and pharmaceutically acceptable salts thereof, which are generally defined by Formula I:

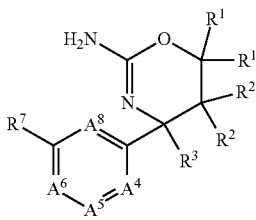

I wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$, —NH—C(=O)—$R^9$, —C(=O)NH—$R^9$, —NH—C(=S)—$R^9$, —O—$R^9$ or —S—$R^9$;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that the compound of Formula I is not a compound wherein (1) each $R^1$, independently, is H or $C_{1-6}$alkyl; (2) each $R^2$, independently, is F when both $R^1$'s are H and $R^3$ is $CH_3$; (3) each $R^2$ taken together form an unsubstituted cyclopropyl ring when both $R^1$'s are H and $R^3$ is $CH_3$; (4) one $R^2$ is H and the other $R^2$ is F, both $R^1$'s are H and $R^3$ is $CH_3$; or (5) $R^3$ is $CH_3$, $CH_2F$, $CHF_2$ or $CH_2CH_3$ when both $R^1$'s and both $R^2$'s are H, respectively.

In embodiment 1-a of the invention, there are provided compounds, including stereoisomers, tautomers, hydrates, solvates and pharmaceutically acceptable salts thereof, which are generally defined by Formula I:

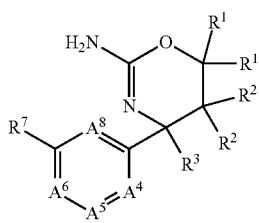

I wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —NH—C(=S)—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that the compound of Formula I is not a compound wherein (1) each $R^1$, independently, is H or $C_{1-6}$alkyl; (2) each $R^2$, independently, is F when both $R^1$'s are H and $R^3$ is $CH_3$; (3) each $R^2$ taken together form an unsubstituted cyclopropyl ring when both $R^1$'s are H and $R^3$ is $CH_3$; (4) one $R^2$ is H and the other $R^2$ is F, both $R^1$'s are H and $R^3$ is $CH_3$; (5) $R^3$ is $CH_3$, $CH_2F$, $CHF_2$ or $CH_2CH_3$ when both $R^1$'s and both $R^2$'s are H; or (6) the compound of Formula I is not

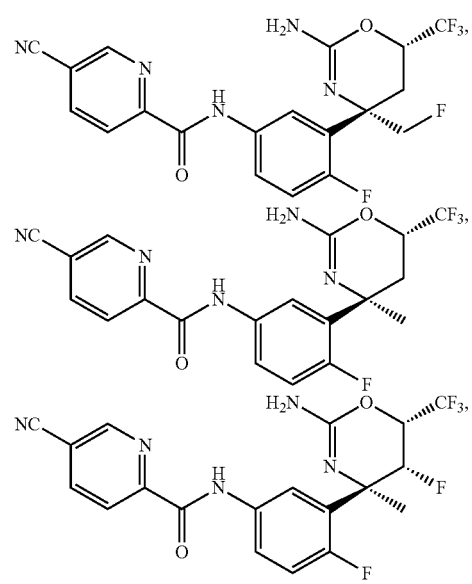

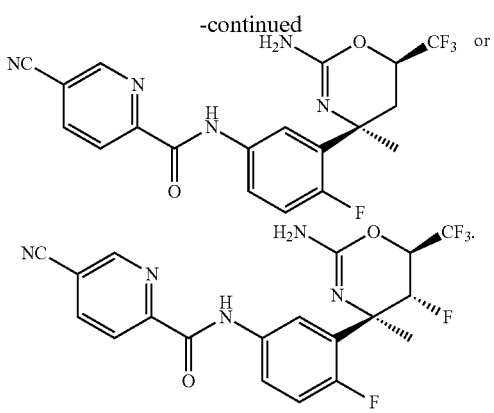

In embodiment 1-b of the invention, there are provided compounds, including stereoisomers, tautomers, hydrates, solvates and pharmaceutically acceptable salts thereof, which are generally defined by Formula I:

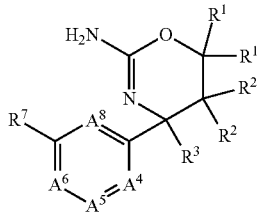

wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N; one $R^1$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_o$ $C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
the other $R^1$ is F, $C_1$ or $C_{1-6}$-haloalkyl;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
each $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_o$ $C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$, —NH—C(=O)—$R^9$, —C(=O)NH—$R^9$, —NH—C(=S)—$R^9$, —O—$R^9$, —S—$R^9$;
or $R^7$ is

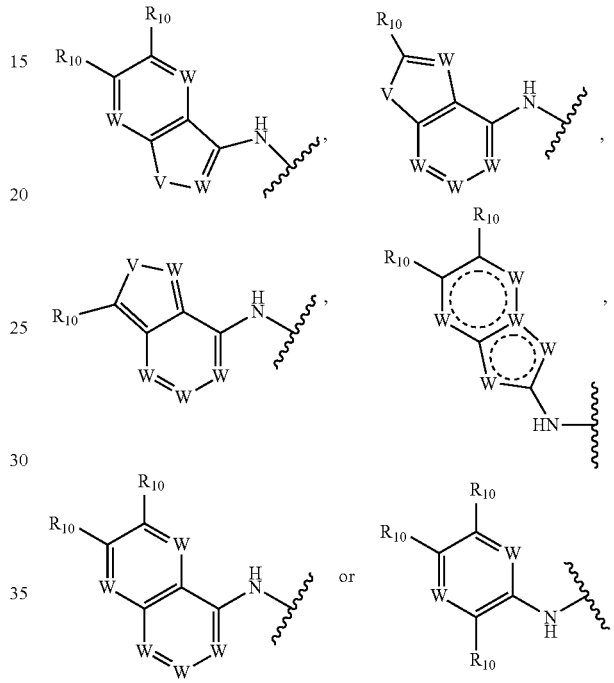

wherein V is $NR^{10}$, O or S; and
each W, independently, is CH, CF, CCl or N;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

In embodiment 1-c of the invention, there are provided compounds, including stereoisomers, tautomers, hydrates, solvates and pharmaceutically acceptable salts thereof, which are generally defined by Formula I:

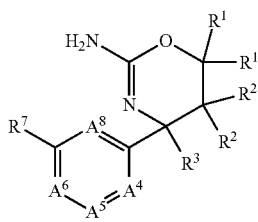

I wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
one $R^1$ is $C_{1-3}$haloalkyl and the other $R^1$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
each of $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$, —NH—C(=O)—$R^9$, —C(=O)NH—$R^9$, —NH—C(=S)—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

In embodiment 2 of the invention, there are provided compounds, including stereoisomers, tautomers, hydrates, solvates and pharmaceutically acceptable salts thereof, which are generally defined by Formula I-A:

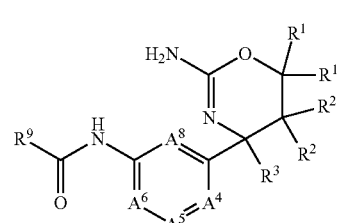

I-A wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H or F;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that the compound of Formula I-A is not a compound wherein (1) each $R^1$, independently, is H or $C_{1-6}$alkyl; (2) each $R^2$, independently, is F when both $R^1$'s are H and $R^3$ is $CH_3$; (3) each $R^2$ taken together form an unsubstituted cyclopropyl ring when both $R^1$'s are H and $R^3$ is $CH_3$; (4) one $R^2$ is H and the other $R^2$ is F, both $R^1$'s are H and $R^3$ is $CH_3$; or (5) $R^3$ is $CH_3$, $CH_2F$, $CHF_2$ or $CH_2CH_3$ when both $R^1$'s and both $R^2$'s are H, respectively.

In embodiment 2-a of the invention, there are provided compounds, including stereoisomers, tautomers, hydrates, solvates and pharmaceutically acceptable salts thereof, which are generally defined by Formula I-A (shown above) wherein one $R^1$ is $C_{1-3}$haloalkyl and the other $R^1$ is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;

and variables $A^4$, $A^5$, $A^6$, $A^8$, $R^2$, $R^3$, $R^4$, $R^5$, $R^6$, $R^7$, $R^8$, $R^9$ and $R^{10}$ are as defined in embodiment 2 of the invention;

provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

In embodiment 2-b of the invention, there are provided compounds, including stereoisomers, tautomers, hydrates, solvates and pharmaceutically acceptable salts thereof, which are generally defined by Formula I-A (shown above) wherein one $R^1$ is $CF_3$ and the other $R^1$ is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH; and each of variables $A^4$, $A^5$, $A^6$, $A^8$, $R^2$, $R^3$, $R^4$, $R^5$, $R^6$, $R^7$, $R^8$, $R^9$ and $R^{10}$ are as defined in embodiment 2 of the invention;

provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is F or $CH_3$.

In embodiment 3 of the invention, there are provided compounds, including stereoisomers, tautomers, hydrates, solvates and pharmaceutically acceptable salts thereof, which are generally defined by Formula I-B:

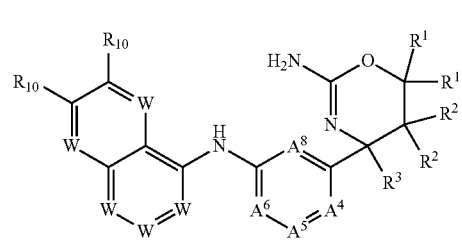

I-B wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, —CH$_2$OC$_{1-3}$-alkyl, —OC$_{1-3}$-alkyl, wherein each of the $C_{1-4}$-alkyl, $C_{2-4}$alkenyl, $C_{2-4}$alkynyl and $C_{1-4}$-alkyl portion of —CH$_2$OC$_{1-3}$-alkyl and —OC$_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl; and each W, independently, is CH, CF, CCl or N.

In embodiment 3-a of the invention, there are provided compounds, including stereoisomers, tautomers, hydrates, solvates and pharmaceutically acceptable salts thereof, which are generally defined by Formula I-B (shown above) wherein one $R^1$ is $CF_3$ and the other $R^1$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH; and each of variables $A^4$, $A^5$, $A^6$, $A^8$, $R^2$, $R^3$, $R^4$, $R^5$, $R^6$, $R^8$ and $R^{10}$ are as defined in embodiment 3 of the invention;

provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is F or $CH_3$.

In embodiment 4 of the invention, there are provided compounds, including stereoisomers, tautomers, hydrates, solvates and pharmaceutically acceptable salts thereof, which are generally defined by Formula I-C:

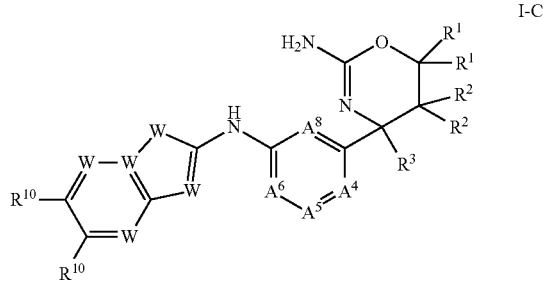

I-C wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl;

V is $NR^{10}$, O or S; and each W, independently, is CH, CF, CCl or N.

In embodiment 5 of the invention, there are provided compounds, including stereoisomers, tautomers, hydrates, solvates and pharmaceutically acceptable salts thereof, which are generally defined by Formula I-D:

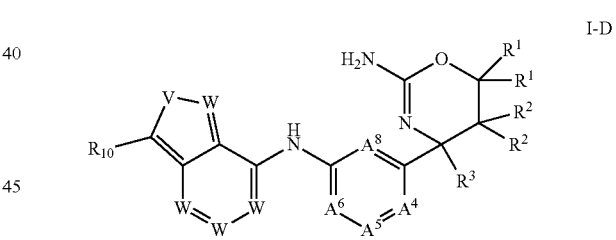

I-D wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl;

V is $NR^{10}$, O or S; and each W, independently, is CH, CF, CCl or N.

In embodiment 5-a of the invention, there are provided compounds, including stereoisomers, tautomers, hydrates, solvates and pharmaceutically acceptable salts thereof, which are generally defined by Formula I-B (shown above) wherein one $R^1$ is $CF_3$ and the other $R^1$ is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH; and each of variables $A^4$, $A^5$, $A^6$, $A^8$, $R^2$, $R^3$, $R^4$, $R^5$, $R^6$, $R^8$ and $R^{10}$ are as defined in embodiment 5 of the invention;

provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is F or $CH_3$.

In embodiment 6 of the invention, there are provided compounds, including stereoisomers, tautomers, hydrates, solvates and pharmaceutically acceptable salts thereof, which are generally defined by Formula II:

II wherein $A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

each $R^2$, independently, is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$ C$_{1-6}$-alkyl, —NHC$_{1-6}$-alkyl or —C(O)C$_{1-6}$-alkyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$ C$_{1-6}$-alkyl, —NHC$_{1-6}$-alkyl and —C(O)C$_{1-6}$-alkyl are optionally substituted with 1-4 substituents of F, oxo or OH;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;

$R^7$ is —NH—$R^9$, —NH—C(=O)—$R^9$, —C(=O)NH—$R^9$, —O—$R^9$, —S—$R^9$;

or $R^7$ is wherein V is $NR^{10}$, O or S; and each W, independently, is CH, CF, CCl or N;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, C$_{1-3}$alkylamino-, C$_{1-3}$dialkylamino, C$_{1-3}$thioalkoxyl oxazolyl, or oxetan-3yl, provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is not H.

In embodiment 6-a of the invention, there are provided compounds, including stereoisomers, tautomers, hydrates, solvates and pharmaceutically acceptable salts thereof, which are generally defined by Formula I-B (shown above) wherein each of variables A$^4$, A$^5$, A$^6$, A$^8$, R$^2$, R$^3$, R$^4$, R$^5$, R$^6$, R$^7$, R$^8$, R$^9$ and R$^{10}$ are as defined in embodiment 6 of the invention;

provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is F or CH$_3$.

In embodiment 7 of the invention, there are provided compounds, including stereoisomers, tautomers, hydrates, solvates and pharmaceutically acceptable salts thereof, which are generally defined by Formula III:

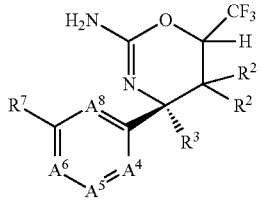

III wherein
A$^4$ is CR$^4$ or N;
A$^5$ is CR$^5$ or N;
A$^6$ is CR$^6$ or N;
A$^8$ is CR$^8$ or N, provided that no more than two of A$^4$, A$^5$, A$^6$ and A$^8$ is N;
each R$^2$, independently, is H, F, Cl, C$_{1-6}$-alkyl, C$_{2-4}$alkenyl, C$_{2-4}$alkynyl, CN, —CH$_2$OC$_{1-6}$-alkyl, —OC$_{1-6}$-alkyl, —S(O)$_o$ C$_{1-6}$-alkyl, —NHC$_{1-6}$-alkyl or —C(O)C$_{1-6}$-alkyl, wherein each of the C$_{1-6}$-alkyl, C$_{2-4}$alkenyl, C$_{2-4}$alkynyl, and C$_{1-6}$-alkyl portion of —CH$_2$OC$_{1-6}$-alkyl, —OC$_{1-6}$-alkyl, —S(O)$_o$ C$_{1-6}$-alkyl, —NHC$_{1-6}$-alkyl and —C(O)C$_{1-6}$-alkyl are optionally substituted with 1-4 substituents of F, oxo or OH;

alternatively, each R$^2$ taken together with the carbon atom to which they are attached form a C$_{3-6}$ spirocarbocyclic ring optionally including one heteroatom selected from O and N and optionally substituted with 1-4 F atoms on the carbon atoms and optionally substituted with a substituent of C$_{1-3}$alkyl, CH$_2$OC$_{1-2}$alkyl or C$_{1-3}$haloalkyl on the nitrogen atom;

R$^3$ is C$_{1-4}$alkyl, CH$_2$OC$_{1-4}$alkyl, CH$_2$OH, C$_{1-4}$haloalkyl or cyclopropyl, wherein each of the C$_{1-4}$alkyl, CH$_2$OC$_{1-4}$alkyl, C$_{1-4}$haloalkyl and cyclopropyl is optionally substituted with 1-4 F atoms;

each of R$^4$, R$^5$, R$^6$ and R$^8$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;

R$^7$ is —NH—R$^9$, —NH—C(=O)—R$^9$, —C(=O)NH—R$^9$, —NH—C(=S)—R$^9$, —O—R$^9$ or —S—R$^9$;

R$^9$ is acetyl, C$_{1-6}$-alkyl, C$_{2-4}$alkenyl, C$_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, C$_{1-3}$alkylamino-, C$_{1-3}$dialkylamino, C$_{1-3}$thioalkoxyl oxazolyl, or oxetan-3yl, provided that (1) no more than one of A$^5$ and A$^8$ is N; and (2) when A$^4$ is CR$^4$, A$^5$ is CR$^5$, A$^6$ is CR$^6$ and A$^8$ is CR$^8$, and each of R$^6$ and R$^8$, independently, is H, then R$^5$ is F, CF$_3$, CF$_2$H, CH$_2$F or CH$_3$.

In embodiment 7-a of the invention, there are provided compounds, including stereoisomers, tautomers, hydrates, solvates and pharmaceutically acceptable salts thereof, which are generally defined by Formula I-B (shown above) wherein each of variables A$^4$, A$^5$, A$^6$, A$^8$, R$^2$, R$^3$, R$^4$, R$^5$, R$^6$, R$^7$, R$^8$, R$^9$ and R$^{10}$ are as defined in embodiment 7 of the invention;

provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is F or CH$_3$.

In embodiment 8 of the invention, there are provided compounds, including stereoisomers, tautomers, hydrates, solvates and pharmaceutically acceptable salts thereof, which are generally defined by Formula III-A:

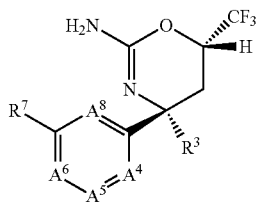

III-A wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —NH—C(=S)—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that (1) no more than one of $A^5$ and $A^8$ is N; and (2) when $A^4$ is $CR^4$, $A^5$ is $CR^5$, $A^6$ is $CR^6$ and $A^8$ is $CR^8$, and each of $R^6$ and $R^8$, independently, is H, then $R^5$ is F, $CF_3$, $CF_2H$, $CH_2F$ or $CH_3$.

In embodiment 8-a of the invention, there are provided compounds, including stereoisomers, tautomers, hydrates, solvates and pharmaceutically acceptable salts thereof, which are generally defined by Formula I-B (shown above) wherein each of variables $A^4$, $A^5$, $A^6$, $A^8$, $R^3$, $R^4$, $R^5$, $R^6$, $R^7$, $R^8$, $R^9$ and $R^{10}$ are as defined in embodiment 8 of the invention;

provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is F or $CH_3$.

In embodiment 9 of the invention, there are provided compounds, including stereoisomers, tautomers, hydrates, solvates and pharmaceutically acceptable salts thereof, which are generally defined by Formula III-B:

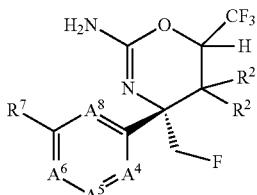

III-B wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

each $R^2$, independently, is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$ $C_{1-6}$-alkyl, —NHC$_{1-6}$-alkyl or —C(O)C$_{1-6}$-alkyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —NH—C(=S)—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that (1) no more than one of $A^5$ and $A^8$ is N; and (2) when $A^4$ is $CR^4$, $A^5$ is $CR^5$, $A^6$ is $CR^6$ and $A^8$ is $CR^8$, and each of $R^6$ and $R^8$, independently, is H, then $R^5$ is F, $CF_3$, $CF_2H$, $CH_2F$ or $CH_3$.

In embodiment 9-a of the invention, there are provided compounds, including stereoisomers, tautomers, hydrates, solvates and pharmaceutically acceptable salts thereof, which are generally defined by Formula I-B (shown above) wherein
each of variables $A^4$, $A^5$, $A^6$, $A^8$, $R^2$, $R^4$, $R^5$, $R^6$, $R^7$, $R^8$, $R^9$ and $R^{10}$ are as defined in embodiment 9 of the invention;
provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is F or $CH_3$.

Similarly, in additional embodiments 10, 11, 12 and 13, the invention provides compounds of sub-formulas III-C, III-D, III-E and III-F, respectively, as described below.

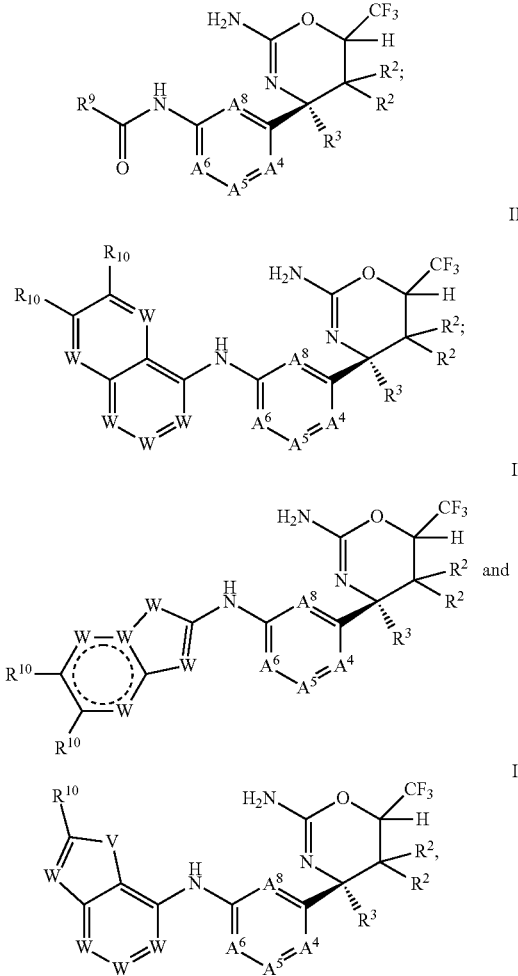

in conjunction with any of the above or below embodiments, including those described in embodiments 1-27 and embodiments A, A-1 to A-4, B, B-1 to B-10, C, C-1 to C-10, D, D-1 to D-6, E, E-1 to E-4, F, F-1 to F-4, G, G-1 to G-4, H, H-1 to H-4, I, I-1 to I-9, J, J-1 to J-8, K-1 to K-2, L, M, N-1 to N-2, O-1 to O-2 and P-1 to P-2 described herein.

Further, in embodiment 14, the invention provides compounds, including stereoisomers, tautomers, hydrates, solvates and pharmaceutically acceptable salts thereof, which are generally defined by Formula III-C-A:

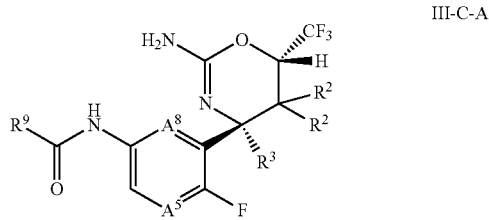

$A^5$ is CH, C—F, C—Cl, C—$CH_3$ or N;

$A^8$ is CH or N;

each $R^2$, independently, is H, F, $C_1$ or $C_{1-3}$-alkyl, wherein the $C_{1-3}$-alkyl, is optionally substituted with 1-3 substituents of F;

$R^3$ is $C_{1-4}$alkyl, $CH_2OC_{1-4}$alkyl, $CH_2OH$ or cyclopropyl, wherein each of the $C_{1-4}$alkyl, $CH_2OC_{1-4}$alkyl and cyclopropyl is optionally substituted with 1-4 F atoms;

$R^9$ is acetyl, $C_{1-6}$-alkyl, $C_{2-4}$alkenyl, $C_{2-4}$alkynyl or a ring selected form the group consisting of phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyrido[3,4-b]pyrazinyl, pyrazolo[3,4-c]pyridinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that (1) no more than one of $A^5$ and $A^8$ is N; and (2) when $A^8$ is N then $A^5$ is CH, C—F, C—Cl, C—$CH_3$ and when $A^8$ is CH then $A^5$ is C—F, C—Cl, C—$CH_3$ or N.

Note that in embodiment 14, both of $A^5$ and $A^8$ cannot be CH.

Further, in embodiment 15, the invention provides compounds, including stereoisomers, tautomers, hydrates, solvates and pharmaceutically acceptable salts thereof, which are generally defined by Formula III-C-A of embodiment 14, wherein $R^3$ is $CH_3$, $CH_2F$, $CHF_2$ or $CF_3$.

Further, in embodiment 16, the invention provides compounds, including stereoisomers, tautomers, hydrates, solvates and pharmaceutically acceptable salts thereof, which are generally defined by Formula III-C-A of any one of embodiments 14 and 15, including a proviso that (1) no more than one of $A^5$ and $A^8$ is N; and (2) when $A^8$ is CH then $A^5$ is C—F, C—$CH_3$ or N Further, in embodiment 17, the invention provides compounds, including stereoisomers, tautomers, hydrates, solvates and pharmaceutically acceptable salts thereof, which are generally defined by Formula III-C-A:

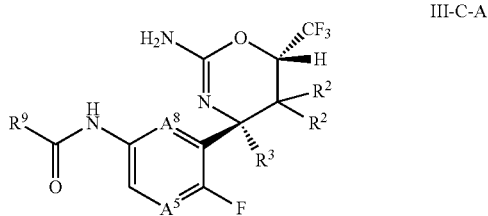

III-C-A $A^5$ is CH when $A^8$ is N; or
$A^5$ is C—F, C—$CH_3$ or N when $A^8$ is CH;
$A^8$ is CH or N;
each $R^2$, independently, is H or F;
$R^3$ is $C_{1-2}$alkyl or $C_{1-2}$alkyl substituted with 1-3 F atoms;
$R^9$ is a ring selected from the group consisting of pyridyl, pyrimidyl, pyrazinyl, pyridazinyl, pyrazolyl, wherein the ring is optionally substituted, independently, with 1-5 substituents of $R^{10}$; and
each $R^{10}$, independently, is H, halo, haloalkyl, CN, acetyl, —C(O)NHCH$_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl, $C_{1-6}$thioalkoxyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl or $C_{1-6}$thioalkoxyl is optionally substituted independently with 1-5 substituents of F, Cl, CN, $NO_2$, $NH_2$, OH, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl.

Further, in embodiment 18, the invention provides compounds, including stereoisomers, tautomers, hydrates, solvates and pharmaceutically acceptable salts thereof, which are generally defined by Formula III-C-A of embodiment 17, wherein $R^3$ is $CH_3$, $CH_2F$, $CHF_2$ or $CF_3$.

Further, in embodiment 19, the invention provides compounds, including stereoisomers, tautomers, hydrates, solvates and pharmaceutically acceptable salts thereof, which are generally defined by Formula III-C-A of embodiments 17 or 18, wherein $R^3$ is $CH_3$ or $CH_2F$.

Further, in embodiment 20, the invention provides compounds, including stereoisomers, tautomers, hydrates, solvates and pharmaceutically acceptable salts thereof, which are generally defined by Formula III-C-A of embodiments 17, 18 or 19, wherein $R^3$ is $CH_3$.

Further, in embodiment 21, the invention provides compounds, including stereoisomers, tautomers, hydrates, solvates and pharmaceutically acceptable salts thereof, which are generally defined by Formula III-C-A of embodiments 17, 18 or 19, wherein $R^3$ is $CH_2F$.

Further, in embodiment 22, the invention provides compounds, including stereoisomers, tautomers, hydrates, solvates and pharmaceutically acceptable salts thereof, which are generally defined by Formula III-C-A of embodiments 17-21, wherein each $R^2$ is H.

Further, in embodiment 22, the invention provides compounds, including stereoisomers, tautomers, hydrates, solvates and pharmaceutically acceptable salts thereof, which are generally defined by Formula III-C-A of embodiments 17-22, wherein each $R^5$ is C—F, C—$CH_3$ or N; and $A^8$ is CH.

Further, in embodiment 23, the invention provides compounds, including stereoisomers, tautomers, hydrates, solvates and pharmaceutically acceptable salts thereof, which are generally defined by Formula III-C-A of embodiments 17-22, wherein each $R^5$ is C—F or C—$CH_3$; and $A^8$ is CH.

Further, in embodiment 24, the invention provides compounds, including stereoisomers, tautomers, hydrates, solvates and pharmaceutically acceptable salts thereof, which are generally defined by Formula III-C-A of embodiments 17-23, wherein each $R^5$ is C—F; and $A^8$ is CH.

Further, in embodiment 25, the invention provides compounds, including stereoisomers, tautomers, hydrates, solvates and pharmaceutically acceptable salts thereof, which are generally defined by Formula III-C-A of embodiments 17-23, wherein each $R^5$ is C—$CH_3$; and $A^8$ is CH.

Further, in embodiment 26, the invention provides compounds, including stereoisomers, tautomers, hydrates, solvates and pharmaceutically acceptable salts thereof, which are generally defined by Formula III-C-A of embodiments 17-21, wherein each $R^5$ is C—F or C—$CH_3$; and $A^8$ is N.

Further, in embodiment 27, the invention provides compounds, including stereoisomers, tautomers, hydrates, solvates and pharmaceutically acceptable salts thereof, which are generally defined by Formula III-C-A of embodiments 17-26, wherein each $R^9$ is 2-pyridyl, 2-pyrazinyl or 3-pyrazolyl, wherein the 2-pyridyl, 2-pyrazinyl or 3-pyrazolyl are optionally substituted with 1-3 substituent of F, Cl, Br, $CH_3$, CHF2, —$OCH_3$, —$OCHF_2$, —$CH_2OCH_3$, —$CH_2OCF_3$, CN, —$OCH_2$-oxazol-2-yl, 2-propynyloxy, 2-butynyloxy and cyclopropyl-$C_2$-alkynyl.

Further, in embodiment 28, the invention provides compounds, including stereoisomers, tautomers, hydrates, solvates and pharmaceutically acceptable salts thereof, which are generally defined by Formula III-C-A-1:

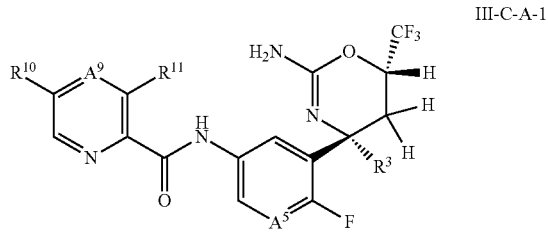

III-C-A-1

$A^5$ is C—F, C—$CH_3$ or N;
$A^9$ is CH or N;
$R^3$ is $CH_3$, $CH_2F$ or $CHF_2$; and
each of $R^{10}$ and $R^{11}$, independently, is H, halo, haloalkyl, CN, acetyl, —C(O)NHCH$_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$thioalkoxyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl or $C_{1-6}$thioalkoxyl is optionally substituted independently with 1-5 substituents of F, Cl, CN, $NO_2$, $NH_2$, OH, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl.

Further, in embodiment 29, the invention provides compounds, including stereoisomers, tautomers, hydrates, solvates and pharmaceutically acceptable salts thereof, which are generally defined by Formula III-C-A-1 of embodiment 28, wherein each of $R^{10}$ and $R^{11}$, independently, is H, F, Cl, Br, $CH_3$, CHF2, $-OCH_3$, $-OCHF_2$, $-CH_2OCH_3$, $-CH_2OCF_3$, CN, $-OCH_2$-oxazol-2-yl, 2-propynyloxy, 2-butynyloxy and cyclopropyl-$C_2$-alkynyl.

The present invention contemplates that the various different embodiments of Formulas I, II and III, and sub-Formulas I-A, I-B, I-C and III-A through III-F thereof, described herein, may comprise the following embodiments with respect to individual variables of $A^4$, $A^5$, $A^6$, $A^8$, $R^1$, $R^2$, $R^3$, $R^7$, V and W, where applicable, as described below. Hence, these embodiments with respect to individual variables $A^4$, $A^5$, $A^6$, $A^8$, $R^1$, $R^2$, $R^3$, $R^7$, V and W where applicable, may be applied "in conjunction with any of the other {above and below} embodiments" to create various embodiments of general Formulas I, II and III, and each sub-formula thereof, which are not literally or identically described herein. More specifically, the term "in conjunction with any of the above or below embodiments" includes embodiments A, A-1 to A-4, B, B-1 to B10, C, C-1 to C-10, D, D-1 to D-6, E, E-1 to E-4, F, F-1 to F-4, G, G-1 to G-4, H, H-1 to H-4, I, I-1 to I-9, J, J-1 to J-9, K-1 to K-2, L, M, N-1 to N-2, O-1 to O-2 and P-1 to P-2 described herein, as it applies to general Formulas I, II and III, and sub-formulas I-A, I-B and I-C and III-A through III-F, also described herein.

The compounds of the invention do not include those compounds wherein any one or more of the following conditions occur: (1) each $R^1$, independently, is H or $C_{1-6}$alkyl; (2) each $R^2$, independently, is F when both $R^1$'s are H and $R^3$ is $CH_3$; (3) each $R^2$ taken together form an unsubstituted cyclopropyl ring when both $R^1$'s are H and $R^3$ is $CH_3$; (4) one $R^2$ is H and the other $R^2$ is F, both $R^1$'s are H and $R^3$ is $CH_3$; or (5) $R^3$ is $CH_3$, $CH_2F$, $CHF_2$ or $CH_2CH_3$ when both $R^1$'s and both $R^2$'s are H, respectively, regardless of how the remaining A and R variables may be defined.

In addition, the compounds of the invention do not include the following compounds:

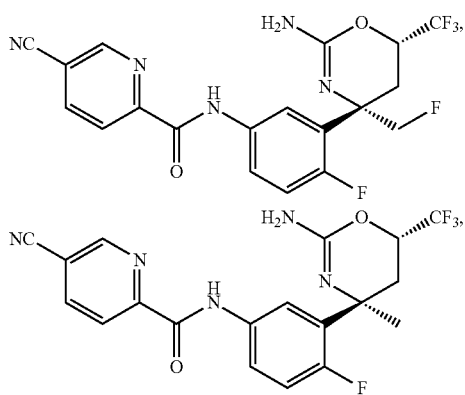

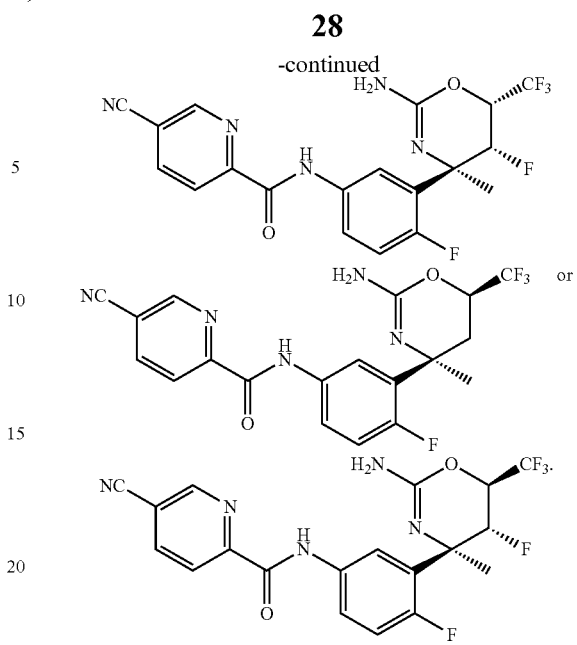

In another embodiment A, the invention includes compounds of Formula I, wherein the compound of Formula I is not a compound wherein each $R^1$, independently, is H or $C_{1-6}$alkyl, in conjunction with any of the above or below embodiments.

In another embodiment A-1, the invention includes compounds of Formula I, wherein the compound of Formula I is not a compound wherein each $R^2$, independently, is F when both $R^1$'s are H and $R^3$ is $CH_3$, in conjunction with any of the above or below embodiments.

In another embodiment A-2, the invention includes compounds of Formula I, wherein the compound of Formula I is not a compound wherein each $R^2$ taken together form an unsubstituted cyclopropyl ring when both $R^1$'s are H and $R^3$ is $CH_3$, in conjunction with any of the above or below embodiments.

In another embodiment A-3, the invention includes compounds of Formula I, wherein the compound of Formula I is not a compound wherein one $R^2$ as H and the other $R^2$ is F, both $R^1$'s are H and $R^3$ is $CH_3$, in conjunction with any of the above or below embodiments.

In another embodiment A-4, the invention includes compounds of Formula I, wherein the compound of Formula I is not a compound wherein $R^3$ is $CH_3$, $CH_2F$, $CHF_2$ or $CH_2CH_3$ when both $R^1$'s and both $R^2$'s are H, respectively, in conjunction with any of the above or below embodiments.

In another embodiment B, the invention includes compounds wherein each $R^1$, independently, is H, F, Cl, $C_{1-6}$-alkyl, $C_{2-4}$alkenyl, $C_{2-4}$alkynyl, CN, $-CH_2OC_{1-6}$-alkyl, $-OC_{1-6}$-alkyl, $-S(O)_oC_{1-6}$-alkyl, $-NHC_{1-6}$-alkyl or $-C(O)C_{1-6}$-alkyl, wherein each of the $C_{1-6}$-alkyl, $C_{2-4}$alkenyl, $C_{2-4}$alkynyl, and $C_{1-6}$-alkyl portion of $-CH_2OC_{1-6}$-alkyl, $-OC_{1-6}$-alkyl, $-S(O)_oC_{1-6}$-alkyl, $-NHC_{1-6}$-alkyl and $-C(O)C_{1-6}$-alkyl are optionally substituted with 1-4 substituents of F, oxo or OH, in conjunction with any of the above or below embodiments.

In another embodiment B-1, the invention includes compounds wherein each $R^1$, independently, is H, F, Cl, $C_{2-4}$alkenyl, $C_{2-4}$alkynyl, CN, $-CH_2OC_{1-3}$-alkyl, $-OC_{1-3}$-alkyl, wherein each of the $C_{2-4}$alkenyl, $C_{2-4}$alkynyl and $C_{1-3}$-alkyl portion of $-CH_2OC_{1-3}$-alkyl and $-OC_{1-3}$-alkyl are optionally substituted with 1-4 substituents of F, in conjunction with any of the above or below embodiments.

In another embodiment B-2, the invention includes compounds wherein each $R^1$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment B-3, the invention includes compounds wherein each $R^1$, independently, is H, F, $CH_3$, $C_2H_5$, $CF_2H$, $CH_2F$, $CH_2OCH_2F$, $CH_2OCF_2H$ or $CH_2OCF_3$ provided both $R^1$'s are not H, both $R^1$'s are not $CH_3$ or both $R^1$'s are not $C_2H_5$, in conjunction with any of the above or below embodiments.

In another embodiment B-4, the invention includes compounds wherein each $R^1$, independently, is H, F, Cl, $CF_3$, $CH_3$, $CF_2H$ or $CH_2F$, in conjunction with any of the above or below embodiments.

In another embodiment B-5, the invention includes compounds wherein each $R^1$, independently, is H, F, $CF_3$, $CH_3$, $CF_2H$ or $CH_2F$, provided both $R^1$'s are each not H or $CH_3$, in conjunction with any of the above or below embodiments.

In another embodiment B-6, the invention includes compounds wherein one $R^1$ is H and the other $R^1$ is F, Cl, $CF_3$, $CF_2H$ or $CH_2F$, in conjunction with any of the above or below embodiments.

In another embodiment B-7, the invention includes compounds wherein one $R^1$ is H and the other $R^1$ is $CF_3$, in conjunction with any of the above or below embodiments.

In another embodiment B-8, the invention includes compounds wherein each $R^1$, taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom, in conjunction with any of the above or below embodiments.

In another embodiment B-9, the invention includes compounds wherein each $R^1$, taken together with the carbon atom to which they are attached form a cyclopropyl, cyclobutyl or cyclopentyl ring optionally substituted with 1-4 F atoms on the carbon atoms, in conjunction with any of the above or below embodiments.

In another embodiment B-10, the invention includes compounds wherein each $R^1$, taken together with the carbon atom to which they are attached form a cyclopropyl or cyclopentyl ring optionally substituted with 1-4 F atoms on the carbon atoms, in conjunction with any of the above or below embodiments.

In another embodiment C, the invention includes compounds wherein each $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment C-1, the invention includes compounds wherein each $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment C-2, the invention includes compounds wherein each $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment C-3, the invention includes compounds wherein each $R^2$, independently, is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment C-4, the invention includes compounds wherein each $R^2$, independently, is H, F, Cl, $CF_3$, $CH_3$, $CF_2H$ or $CH_2F$, in conjunction with any of the above or below embodiments.

In another embodiment C-5, the invention includes compounds wherein each $R^2$, independently, is H, F, $CF_3$, $CH_3$, $CF_2H$ or $CH_2F$, in conjunction with any of the above or below embodiments.

In another embodiment C-6, the invention includes compounds wherein each $R^2$, independently, is H or F, in conjunction with any of the above or below embodiments.

In another embodiment C-7, the invention includes compounds wherein each $R^2$, independently, is H, in conjunction with any of the above or below embodiments.

In another embodiment C-8, the invention includes compounds wherein each $R^2$, taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom, in conjunction with any of the above or below embodiments.

In another embodiment C-9, the invention includes compounds wherein each $R^2$, taken together with the carbon atom to which they are attached form a cyclopropyl, cyclobutyl or cyclopentyl ring optionally substituted with 1-4 F atoms on the carbon atoms, in conjunction with any of the above or below embodiments.

In another embodiment C-10, the invention includes compounds wherein each $R^2$, taken together with the carbon atom to which they are attached form a cyclopropyl or cyclopentyl ring optionally substituted with 1-4 F atoms on the carbon atoms, in conjunction with any of the above or below embodiments.

In another embodiment D, the invention includes compounds wherein $R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms, in conjunction with any of the above or below embodiments.

In another embodiment D-1, the invention includes compounds wherein $R^3$ is $C_{1-4}$alkyl, $C_{1-4}$haloalkyl, $CH_2OH$, $CH_2OCHF_2$ or cyclopropyl, wherein each of the $C_{1-4}$alkyl, $C_{1-4}$haloalkyl and cyclopropyl is optionally substituted with 1-4 F atoms, in conjunction with any of the above or below embodiments.

In another embodiment D-2, the invention includes compounds wherein $R^3$ is $C_{1-4}$alkyl, $CH_2OH$, $CH_2OCH_2F$, $CH_2OCF_2H$, or cyclopropyl, wherein each of the $C_{1-4}$alkyl and cyclopropyl is optionally substituted with 1-2 F atoms, in conjunction with any of the above or below embodiments.

In another embodiment D-3, the invention includes compounds wherein $R^3$ is $CH_3$, $CF_3$, $C_2H_5$, $CF_2H$ or $CH_2F$, in conjunction with any of the above or below embodiments.

In another embodiment D-4, the invention includes compounds wherein $R^3$ is $CF_3$, $CH_3$, $CF_2H$ or $CH_2F$, in conjunction with any of the above or below embodiments.

In another embodiment D-5, the invention includes compounds wherein $R^3$ is $CH_3$ or $CH_2F$, in conjunction with any of the above or below embodiments.

In another embodiment D-6, the invention includes compounds wherein $R^3$ is $CH_2F$, in conjunction with any of the above or below embodiments.

In another embodiment E, the invention includes compounds wherein $A^4$ is $CR^4$ wherein $R^4$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment E-1, the invention includes compounds wherein $A^4$ is $CR^4$ wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment E-2, the invention includes compounds wherein $A^4$ is $CR^4$ wherein $R^4$ is H, F, $CF_3$, $CF_2H$, $CH_2F$ or $CH_3$, in conjunction with any of the above or below embodiments.

In another embodiment E-3, the invention includes compounds wherein $A^4$ is $CR^4$ wherein $R^4$ is H or F, in conjunction with any of the above or below embodiments.

In another embodiment E-4, the invention includes compounds wherein $A^4$ is N, in conjunction with any of the above or below embodiments.

In another embodiment F, the invention includes compounds wherein $A^5$ is $CR^5$ wherein $R^5$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment F-1, the invention includes compounds wherein $A^5$ is $CR^5$ wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment F-2, the invention includes compounds wherein $A^5$ is $CR^5$ wherein $R^5$ is H, F, $CF_3$, $CF_2H$, $CH_2F$ or $CH_3$, in conjunction with any of the above or below embodiments.

In another embodiment F-3, the invention includes compounds wherein $A^5$ is $CR^5$ wherein $R^5$ is H or F, in conjunction with any of the above or below embodiments.

In another embodiment F-4, the invention includes compounds wherein $A^5$ is N, in conjunction with any of the above or below embodiments.

In another embodiment G, the invention includes compounds wherein $A^6$ is $CR^6$ wherein $R^6$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment G-1, the invention includes compounds wherein $A^6$ is $CR^6$ wherein $R^6$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment G-2, the invention includes compounds wherein $A^6$ is $CR^6$ wherein $R^6$ is H, F, $CF_3$, $CF_2H$, $CH_2F$ or $CH_3$, in conjunction with any of the above or below embodiments.

In another embodiment G-3, the invention includes compounds wherein $A^6$ is $CR^6$ wherein $R^6$ is H or F, in conjunction with any of the above or below embodiments.

In another embodiment G-4, the invention includes compounds wherein $A^6$ is N, in conjunction with any of the above or below embodiments.

In another embodiment H, the invention includes compounds wherein $A^8$ is $CR^8$ wherein $R^8$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment H-1, the invention includes compounds wherein $A^8$ is $CR^8$ wherein $R^8$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment H-2, the invention includes compounds wherein $A^8$ is $CR^8$ wherein $R^8$ is H, F, $CF_3$, $CF_2H$, $CH_2F$ or $CH_3$, in conjunction with any of the above or below embodiments.

In another embodiment H-3, the invention includes compounds wherein $A^8$ is $CR^8$ wherein $R^8$ is H or F, in conjunction with any of the above or below embodiments.

In another embodiment H-4, the invention includes compounds wherein $A^8$ is N, in conjunction with any of the above or below embodiments.

In another embodiment I, the invention includes compounds wherein no more than two of $A^4$, $A^5$, $A^6$ and $A^8$ is N, in conjunction with any of the above or below embodiments.

In another embodiment I-1, the invention includes compounds wherein no more than one of $A^4$, $A^5$, $A^6$ and $A^8$ is N, in conjunction with any of the above or below embodiments.

In another embodiment I-2, the invention includes compounds wherein $A^4$ is $CR^4$, $A^5$ is $CR^5$ or N, $A^6$ is $CR^6$ and $A^8$ is $CR^8$, in conjunction with any of the above or below embodiments.

In another embodiment, the invention includes compounds wherein $A^4$ is $CR^4$ or N, $A^5$ is $CR^5$, $A^6$ is $CR^6$ and $A^8$ is $CR^8$, in conjunction with any of the above or below embodiments.

In another embodiment I-3, the invention includes compounds wherein $A^4$ is N, $A^5$ is $CR^5$, $A^6$ is $CR^6$ and $A^8$ is $CR^8$, in conjunction with any of the above or below embodiments.

In another embodiment I-4, the invention includes compounds wherein $A^4$ is $CR^4$, $A^5$ is N, $A^6$ is $CR^6$, and $A^8$ is $CR^8$, in conjunction with any of the above or below embodiments.

In another embodiment I-5, the invention includes compounds wherein $A^4$ is $CR^4$, $A^5$ is $CR^5$, $A^6$ is N, and $A^8$ is $CR^8$, in conjunction with any of the above or below embodiments.

In another embodiment I-6, the invention includes compounds wherein $A^4$ is $CR^5$, $A^5$ is $CR^5$, $A^6$ is $CR^6$, and $A^8$ is N, in conjunction with any of the above or below embodiments.

In another embodiment I-7, the invention includes compounds wherein $A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N; and
each $R^1$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
each $R^2$, independently, is H, Cl, $CF_3$, $OCF_3$, methyl, ethyl, CN, OH, $OCH_3$, $SCH_3$, $NHCH_3$, $C(O)CH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment I-8, the invention includes compounds wherein $A^4$ is $CR^4$;
$A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$, in conjunction with any of the above or below embodiments.

In another embodiment I-9, the invention includes compounds wherein $A^4$ is CH, CF or N, $A^5$ is CH, CF or N, $A^6$ is CH, CF or N, $A^8$ is CH, CF or N, one of $A^4$, $A^5$, $A^6$ and $A^8$ is N, in conjunction with any of the above or below embodiments.

In another embodiment J, the invention includes compounds wherein $R^7$ is —NH—$R^9$, —NH—C(=O)—$R^9$, —C(=O)NH—$R^9$, —O—$R^9$, —S—$R^9$; or $R^7$ is

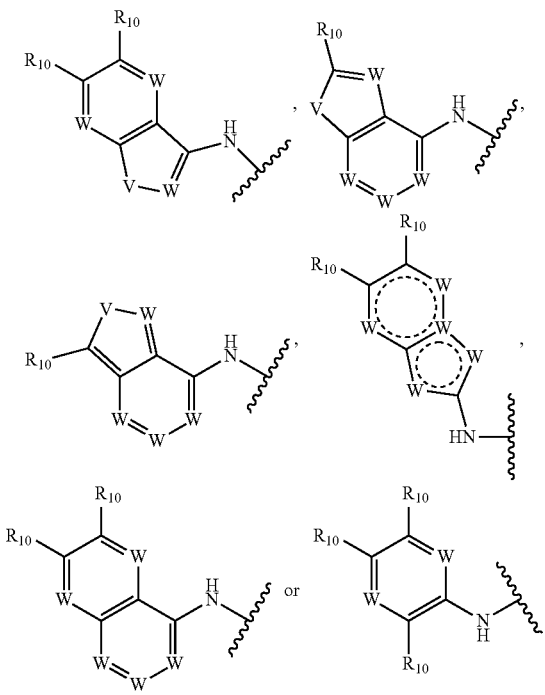

wherein V is $NR^{10}$, O or S; and
each W, independently, is CH, CF, CCl or N, in conjunction with any of the above or below embodiments.

In another embodiment J-1, the invention includes compounds wherein $R^7$ is —NH—$R^9$, —NH—C(=O)—$R^9$ or

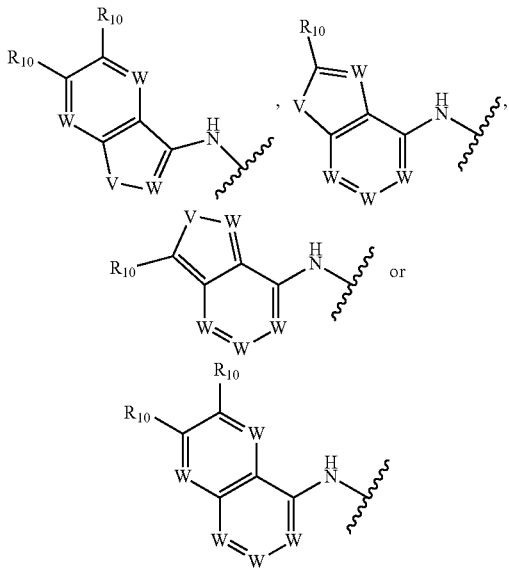

wherein V is $NR^{10}$, O or S; and each W, independently, is CH, CF, CCl or N, in conjunction with any of the above or below embodiments.

In another embodiment J-2, the invention includes compounds wherein $R^7$ is —NH—C(=O)—$R^9$ or

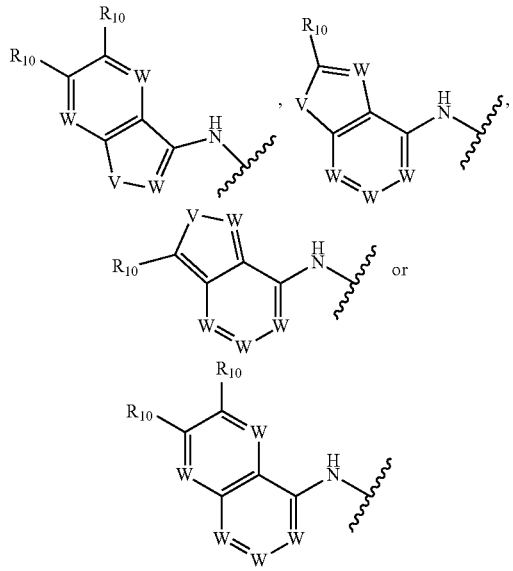

wherein V is $NR^{10}$, O or S; and
each W, independently, is CH, CF, CCl or N, in conjunction with any of the above or below embodiments.

In another embodiment J-3, the invention includes compounds wherein $R^7$ is —NH—C(=O)—$R^9$, in conjunction with any of the above or below embodiments.

In another embodiment J-4, the invention includes compounds wherein $R^7$ is —NH—$R^9$, in conjunction with any of the above or below embodiments.

In another embodiment J-5, the invention includes compounds wherein $R^7$ is

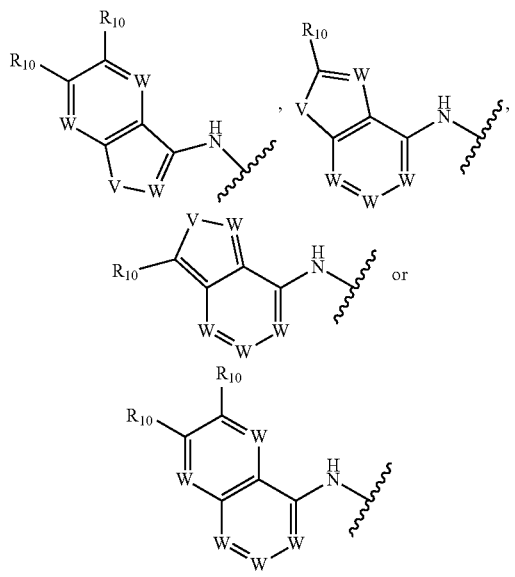

wherein V is $NR^{10}$, O or S; and
each W, independently, is CH, CF, CCl or N, in conjunction with any of the above or below embodiments.

In another embodiment J-6, the invention includes compounds wherein $R^7$ is

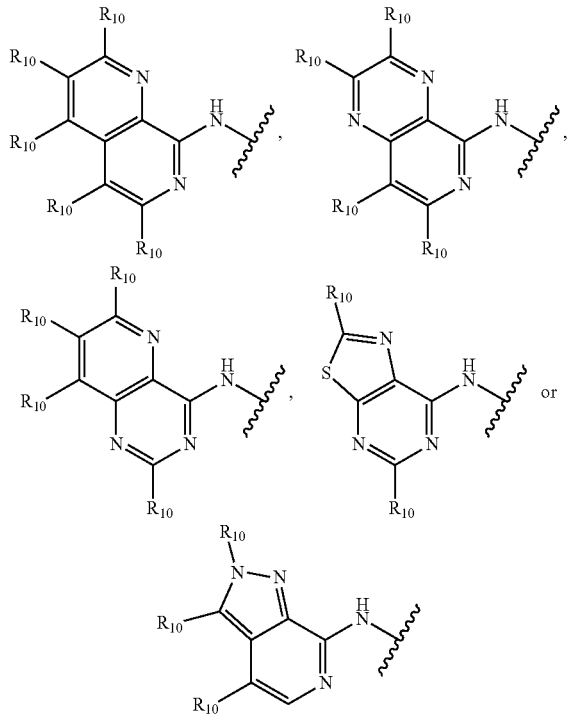

wherein each $R^{10}$, independently, is H, halo, haloalkyl, CN, $SF_5$, acetyl, —C(O)$NHCH_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, in conjunction with any of the above or below embodiments.

In another embodiment J-7, the invention includes compounds wherein $R^7$ is —NH—$R^9$, —O—$R^9$ or —S—$R^9$, in conjunction with any of the above or below embodiments.

In another embodiment J-8, the invention includes compounds wherein $R^7$ is —O—$R^9$ or —S—$R^9$, in conjunction with any of the above or below embodiments.

In another embodiment J-9, the invention includes compounds wherein $R^7$ is —NH—$R^9$, —NH—C(=O)—$R^9$, —C(=O)NH—$R^9$, —O—$R^9$ or —S—$R^9$, wherein $R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K, the invention includes compounds wherein $R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K-1, the invention includes compounds wherein $R^9$ is acetyl, $C_{1-6}$-alkyl, $C_{2-4}$alkenyl, $C_{2-4}$alkynyl or a ring selected form the group consisting of phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyrido[3,4-b]pyrazinyl, pyrazolo[3,4-c]pyridinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment L, the present invention provides compounds, and solvates, tautomers, hydrates, stereoisomers and pharmaceutically acceptable salts thereof, as defined by Formulas I, I-A, I-B, I-C or II, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^1$ and $R^2$, independently, is H, F, Cl, $CF_3$, $OCF_3$, methyl, ethyl, CN, OH, $OCH_3$, $SCH_3$, $NHCH_3$, C(O)$CH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_3$, $OCF_3$, methyl, ethyl,
CN, OH, $OCH_3$, $SCH_3$, $NHCH_3$ or C(O)$CH_3$,
provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H,
in conjunction with any of the above or below embodiments.

In another embodiment M, the present invention provides compounds, and solvates, tautomers, hydrates, stereoisomers and pharmaceutically acceptable salts thereof, as defined by Formulas I and II, wherein
$R^7$ is —NH—$R^9$, —NH—C(=O)—$R^9$ or

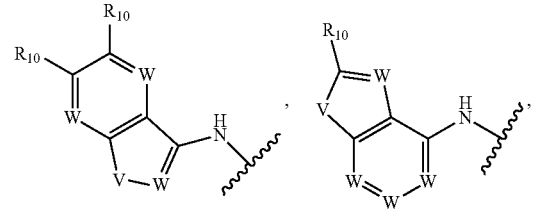

-continued wherein V is NR$^{10}$, O or S; and
each W, independently, is CH, CF, CCl or N, in conjunction with any of the above or below embodiments.

In another embodiment N-1, the invention includes compounds of Formula I-A
wherein A$^4$ is CR$^4$;
A$^5$ is CR$^5$;
A$^6$ is CR$^6$;
A$^8$ is CR$^8$; wherein each of R$^4$, R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$;
one R$^1$ is H and the other R$^1$ is CF$_3$;
alternatively, each R$^1$ taken together with the carbon atom to which they are attached form a C$_{3-6}$ spirocarbocyclic ring optionally including one heteroatom selected from O and N and optionally substituted with 1-3 F atoms;
each of R$^2$, independently, is H, F, CH$_3$, C$_2$H$_5$, CF$_2$H, CH$_2$F, CH$_2$OCH$_2$F, CH$_2$OCF$_2$H or CH$_2$OCF$_3$;
alternatively, each R$^2$ taken together with the carbon atom to which they are attached form a C$_{3-6}$ spirocarbocyclic ring optionally including one heteroatom selected from O and N and optionally substituted with 1-3 F atoms;
R$^3$ is CH$_3$, C$_2$H$_5$, CF$_2$H or CH$_2$F;
R$^9$ is acetyl, C$_{1-6}$-alkyl, C$_{2-4}$alkenyl, C$_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$; and
each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, C$_{1-3}$alkylamino-, C$_{1-3}$dialkylamino, C$_{1-3}$thioalkoxyl oxazolyl, or oxetan-3yl;
provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is not H.

In another embodiment N-2, the invention includes compounds of Formula I-A wherein A$^4$ is CR$^4$;
A$^5$ is CR$^5$;
A$^6$ is CR$^6$;
A$^8$ is CR$^8$; wherein each of R$^4$, R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$;
one R$^1$ is H and the other R$^1$ is F, Cl, CF$_3$, CF$_2$H or CH$_2$F;
alternatively, each R$^1$ taken together with the carbon atom to which they are attached form a C$_{3-6}$ spirocarbocyclic ring optionally including one heteroatom selected from O and N and optionally substituted with 1-3 F atoms;
each R$^2$, independently, is H, F, Cl, CF$_3$, CH$_3$, CF$_2$H or CH$_2$F;
alternatively, each R$^2$ taken together with the carbon atom to which they are attached form a C$_{3-6}$ spirocarbocyclic ring optionally including one heteroatom selected from O and N and optionally substituted with 1-3 F atoms;
R$^3$ is CF$_3$, CH$_3$, CF$_2$H or CH$_2$F;
R$^9$ is a ring selected from phenyl, pyridyl, pyrimidyl, pyrazinyl, pyridazinyl, pyrazolyl, isoxazolyl, thiazolyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the ring is optionally substituted, independently, with 1-5 substituents of R$^{10}$; and
each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkenyl. C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, C$_{1-3}$alkylamino-, C$_{1-3}$dialkylamino, C$_{1-3}$thioalkoxyl oxazolyl, or oxetan-3yl;
provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is not H.

In another embodiment O-1, the invention includes compounds of Formula I-B wherein A$^4$ is CR$^4$;
A$^5$ is CR$^5$;
A$^6$ is CR$^6$;
A$^8$ is CR$^8$; wherein each of R$^4$, R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$;
one R$^1$ is H and the other R$^1$ is CF$_3$;
alternatively, each R$^1$ taken together with the carbon atom to which they are attached form a C$_{3-6}$ spirocarbocyclic ring optionally including one heteroatom selected from O and N and optionally substituted with 1-3 F atoms;
each of R$^2$, independently, is H, F, CH$_3$, C$_2$H$_5$, CF$_2$H, CH$_2$F, CH$_2$OCH$_2$F, CH$_2$OCF$_2$H or CH$_2$OCF$_3$;
alternatively, each R$^2$ taken together with the carbon atom to which they are attached form a C$_{3-6}$ spirocarbocyclic ring optionally including one heteroatom selected from O and N and optionally substituted with 1-3 F atoms; and $R^3$ is $CH_3$, $C_2H_5$, $CF_2H$ or $CH_2F$, in conjunction with any of the above or below embodiments with respect to Formula I-B.

In another embodiment O-2, the invention includes compounds of Formula I-B
wherein $A^4$ $A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F, Cl, $CF_3$, $CH_3$, $CF_2H$ or $CH_2F$; and
$R^3$ is $CF_3$, $CH_3$, $CF_2H$ or $CH_2F$, in conjunction with any of the above or below embodiments with respect to Formula I-B.

In another embodiment P-1, the invention includes compounds of Formula I-C wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;
one $R^1$ is H and the other $R^1$ is $CF_3$;
alternatively, each $R^1$ taken together with the carbon atom to which they are attached form a $C_{3-6}$ spirocarbocyclic ring optionally including one heteroatom selected from O and N and optionally substituted with 1-3 F atoms;
each of $R^2$, independently, is H, F, $CH_3$, $C_2H_5$, $CF_2H$, $CH_2F$, $CH_2OCHF_2$, $CH_2OCF_2H$ or $CH_2OCF_3$; and
alternatively, each $R^2$ taken together with the carbon atom to which they are attached form a $C_{3-6}$ spirocarbocyclic ring optionally including one heteroatom selected from O and N and optionally substituted with 1-3 F atoms;
$R^3$ is $CH_3$, $C_2H_5$, $CF_2H$ or $CH_2F$, in conjunction with any of the above or below embodiments with respect to Formula I-C.

In another embodiment P-2, the invention includes compounds of Formula I-C
wherein $A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F, Cl, $CF_3$, $CH_3$, $CF_2H$ or $CH_2F$; and
$R^3$ is $CF_3$, $CH_3$, $CF_2H$ or $CH_2F$, in conjunction with any of the above or below embodiments with respect to Formula I-C.

In embodiment Q of the invention, there are provided compounds, including stereoisomers, tautomers, hydrates, solvates and pharmaceutically acceptable salts thereof, which are generally defined by Formula II:

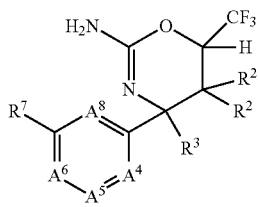

wherein $A^4$ is CH, CF or N;
$A^5$ is CH, CF or N;
$A^6$ is CH, CF or N;
$A^8$ is CH, CF or N, provided that no more than one of $A^4$, $A^5$, $A^6$ and $A^8$ is N;

each $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;

alternatively, each $R^2$ taken together with the carbon atom to which they are attached form a spirocyclopropyl, spirocyclobutyl, spirocyclopentyl or spirocyclohexyl ring, said ring optionally substituted with 1-4 F atoms;

$R^3$ is $C_{1-4}$alkyl, $C_{1-4}$haloalkyl, $CH_2OH$, $CH_2OCHF_2$ or cyclopropyl;

$R^7$ is $-NH-R^9$, $-NH-C(=O)-R^9$ or $-S-R^9$;

or $R^7$ is

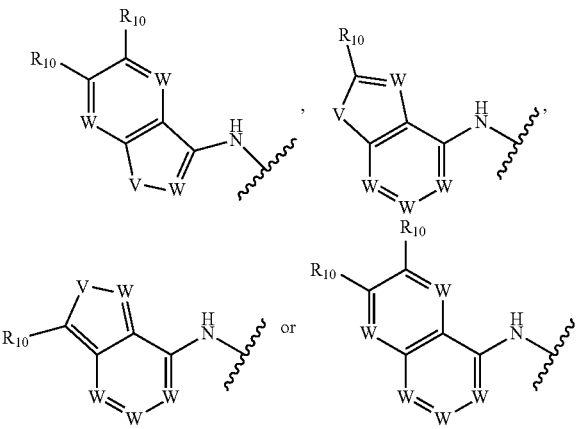

wherein V is NH, $N(CH_3)$, O or S; and
each W, independently, is CH, CF, CCl or N;

$R^9$ is a ring selected from phenyl, pyridyl, pyrimidyl, pyrazinyl, pyridazinyl, pyrazolyl, isoxazolyl, thiazolyl, furanyl, thienyl or pyrrolyl, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, $-C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

In embodiment Q-1, the invention provides compounds, including stereoisomers, tautomers, hydrates, solvates and pharmaceutically acceptable salts thereof, which are generally defined by Formula II:

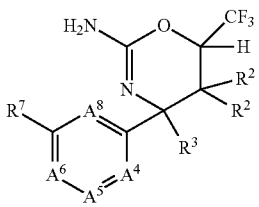

wherein $A^4$ is CH, CF or N;
$A^5$ is CH, CF or N;
$A^6$ is CH, CF or N;
$A^8$ is CH, CF or N, provided that no more than one of $A^4$, $A^5$, $A^6$ and $A^8$ is N;
each $R^2$, independently, is H, F, Cl, $CF_3$, $OCF_3$, methyl, ethyl, CN, $OCH_3$, $SCH_3$, $NHCH_3$ or $CH_2OCHF_2$;
alternatively, each $R^2$ taken together with the carbon atom to which they are attached form a spirocyclopropyl, spirocyclobutyl, spirocyclopentyl or spirocyclohexyl ring, said ring optionally substituted with 1-4 F atoms;
$R^3$ is $CH_3$, $CF_3$, $CH_2F$, $CHF_2$, $CH_2OCHF_2$ or cyclopropyl;
$R^7$ is —NH—C(=O)—$R^9$;
or $R^7$ is

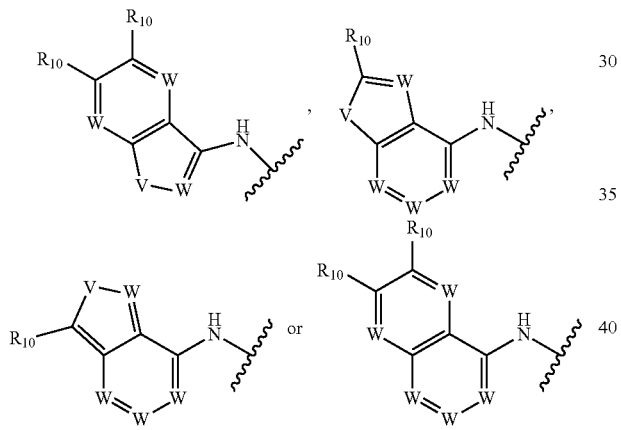

wherein V is NH, N($CH_3$), O or S; and
each W, independently, is CH, CF, CCl or N;
$R^9$ is a ring selected from phenyl, pyridyl, pyrimidyl, pyrazinyl, pyridazinyl, pyrazolyl, isoxazolyl, thiazolyl, furanyl, thienyl or pyrrolyl, wherein the ring is optionally substituted, independently, with 1-5 substituents of $R^{10}$; and
each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl,
provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

In embodiment Q-2, the invention provides compounds, including stereoisomers, tautomers, hydrates, solvates and pharmaceutically acceptable salts thereof, which are generally defined by Formula I-A-1:

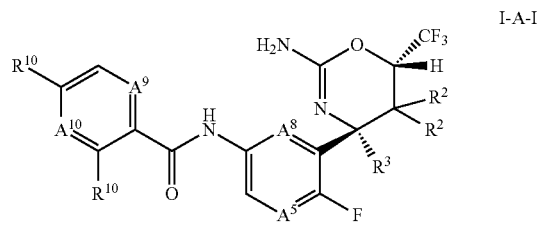

wherein $A^5$ is CH, CF, C—$CH_3$ or N;
$A^8$ is CH or N, provided that (1) no more than one of $A^5$ and $A^8$ is N and (2) when $A^8$ is CH then $A^5$ is CF, C—$CH_3$ or N;
each $R^2$, independently, is H or F;
$A^9$ is CH, CF or N;
$A^{10}$ is CH, CF or N; and
each $R^{10}$, independently, is H, F, Cl, Br, CN, acetyl, —C(O)$NHCH_3$, $C_{1-6}$alkyl, $C_{2-6}$alkenyl, $C_{2-6}$alkynyl, $C_{1-6}$alkoxyl, $C_{1-6}$thioalkoxyl cyclopropylmethoxy, 2-propynyloxy or 2-butynyloxy, wherein each of the $C_{1-6}$alkyl, $C_{2-6}$alkenyl, $C_{2-6}$alkynyl, $C_{1-6}$alkoxyl or $C_{1-6}$thioalkoxyl is optionally substituted independently with 1-5 substituents of F or cyclopropyl.

In embodiment Q-3, the invention provides compounds, including stereoisomers, tautomers, hydrates, solvates and pharmaceutically acceptable salts thereof, which are generally defined by Formula III-D-1:

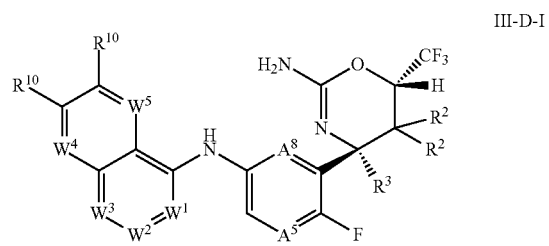

wherein $A^5$ is CH or N;
$A^8$ is CH or N, provided that no more than one of $A^5$ and $A^8$ is N;
each $R^2$, independently, is H or F;
each of $W^1$, $W^2$, $W^3$, $W^4$ and $W^5$, independently, is $CR^{10}$ or N; and
each $R^{10}$, independently, is H, F, Cl, Br, CN, acetyl, —C(O)$NHCH_3$, $C_{1-6}$alkyl, $C_{2-6}$alkenyl, $C_{2-6}$alkynyl, $C_{1-6}$alkoxyl, $C_{1-6}$thioalkoxyl cyclopropylmethoxy, 2-propynyloxy or 2-butynyloxy, wherein each of the $C_{1-6}$alkyl, $C_{2-6}$alkenyl, $C_{2-6}$alkynyl, $C_{1-6}$alkoxyl or $C_{1-6}$thioalkoxyl is optionally substituted independently with 1-5 substituents of F or cyclopropyl.

In embodiment Q-4, the invention provides compounds, including stereoisomers, tautomers, hydrates, solvates and pharmaceutically acceptable salts thereof, which are generally defined by Formula III-D-1 in embodiment Q-3 wherein each of $W^1$, $W^2$, $W^3$, $W^4$ and $W^5$, independently, is CF, CH or N.

In embodiment Q-5, the invention provides compounds, including stereoisomers, tautomers, hydrates, solvates and pharmaceutically acceptable salts thereof, which are generally defined by Formula III-D-1 in embodiment Q-3 wherein each of $W^1$, $W^3$ and $W^5$, independently, is N while each of $W^2$ and $W^4$, independently, is CF or CH.

In embodiment Q-6, the invention provides compounds, including stereoisomers, tautomers, hydrates, solvates and pharmaceutically acceptable salts thereof, which are generally defined by Formula III-D-1 in embodiment Q-3 wherein each of $W^1$ and $W^5$, independently, is N while each of $W^2$, $W^3$ and $W^4$, independently, is CF or CH.

In another embodiment, the invention provides one or more of the compounds, or a pharmaceutically acceptable salt thereof, of Formulas I, II and III, and sub-formulas thereof, as taught and described herein.

In another embodiment, the invention provides the compound of Formula I, II or III, or a stereoisomer or pharmaceutically acceptable salt thereof, selected from N-(3-((4S,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide;

Racemic mixture of N-(3-((4R,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide and N-(3-((4S,6R)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-5-chloro-2-pyridinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-3-chloro-1,7-naphthyridin-8-amine;

Racemic mixture of N-(3-((4R,6R)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine and N-(3-((4S,6S)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine;

N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methyl-2-pyridinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-6-chloro-3-methylimidazo[1,2-a]pyridine-2-carboxamide;

N-(3-((4S,6S)-2-amino-4-methyl-6-(trifluoromethyl)-5,6-dihydro-4H-1,3-oxazin-4-yl)-4-fluorophenyl)-5-methoxy-2-pyrazinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-5-(2,2,2-trifluoroethoxy)-2-pyridinecarboxamide; and 8-((3-((4S,6S)-2-amino-4-(fluoromethyl)-6-(trifluoromethyl)-5,6-dihydro-4H-1,3-oxazin-4-yl)-4-fluorophenyl)amino)-1,7-naphthyridine-3-carbonitrile.

In another embodiment, the invention provides the compound of Formula I-A, or a stereoisomer or pharmaceutically acceptable salt thereof, selected from N-(3-((4S,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-5-chloro-2-pyridinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methyl-2-pyridinecarboxamide;

N-(3-((4S,6S)-2-amino-4-methyl-6-(trifluoromethyl)-5,6-dihydro-4H-1,3-oxazin-4-yl)-4-fluorophenyl)-5-methoxy-2-pyrazinecarboxamide; and N-(3-((4S,6S)-2-amino-4-(fluoromethyl)-6-(trifluoromethyl)-5,6-dihydro-4H-1,3-oxazin-4-yl)-4-fluorophenyl)-5-(2,2,2-trifluoroethoxy)-2-pyridinecarboxamide.

In another embodiment, the invention provides the compound of Formula I-B and I-C, or a stereoisomer or pharmaceutically acceptable salt thereof, selected from N-(3-((4S,6S)-2-amino-4-(fluoromethyl)-6-(trifluoromethyl)-5,6-dihydro-4H-1,3-oxazin-4-yl)-4-fluorophenyl)-3-chloro-1,7-naphthyridin-8-amine;

N-(3-((4R,6R)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine;

N-(3-((4S,6S)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine; and 8-((3-((4S,6S)-2-amino-4-(fluoromethyl)-6-(trifluoromethyl)-5,6-dihydro-4H-1,3-oxazin-4-yl)-4-fluorophenyl)amino)-1,7-naphthyridine-3-carbonitrile.

In another embodiment, the invention provides the compound of Formula I-A, II or III, or a stereoisomer or pharmaceutically acceptable salt thereof, selected from N-(5-((4S,6S)-2-amino-4-methyl-6-(trifluoromethyl)-5,6-dihydro-4H-1,3-oxazin-4-yl)-6-fluoropyridin-3-yl)-5-chloro-3-methylpicolinamide;

N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide;

Racemic mixture of N-(3-((4S,6S)-2-amino-4-methyl-6-(trifluoromethyl)-5,6-dihydro-4H-1,3-oxazin-4-yl)-4-fluorophenyl)-5-chloro-3-methyl-2-pyridinecarboxamide and N-(3-((4R,6R)-2-amino-4-methyl-6-(trifluoromethyl)-5,6-dihydro-4H-1,3-oxazin-4-yl)-4-fluorophenyl)-5-chloro-3-methyl-2-pyridinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-3-chloro-5-cyano-2-pyridinecarboxamide;

N-(3-((4S,6S)-2-amino-4-(fluoromethyl)-6-(trifluoromethyl)-5,6-dihydro-4H-1,3-oxazin-4-yl)-4-fluorophenyl)-5-methoxy-3-methylpyrazine-2-carboxamide;

N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methoxypicolinamide;

N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide;

N-(3-((4S,6S)-2-amino-4-methyl-6-(trifluoromethyl)-5,6-dihydro-4H-1,3-oxazin-4-yl)-4-fluorophenyl)-5-chloropicolinamide;

N-(5-((4S,6S)-2-amino-4-methyl-6-(trifluoromethyl)-5,6-dihydro-4H-1,3-oxazin-4-yl)-6-fluoropyridin-3-yl)-5-cyanopicolinamide;

N-(3-((4S,6S)-2-amino-4-methyl-6-(trifluoromethyl)-5,6-dihydro-4H-1,3-oxazin-4-yl)-4-fluorophenyl)-5-cyanopicolinamide;

N-(3-((4S,6S)-2-amino-4-(fluoromethyl)-6-(trifluoromethyl)-5,6-dihydro-4H-1,3-oxazin-4-yl)-4-fluorophenyl)-3-chloro-5-methoxypicolinamide;

N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methoxypicolinamide;

N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide;

N-(3-((4S,6S)-2-amino-4-methyl-6-(trifluoromethyl)-5,6-dihydro-4H-1,3-oxazin-4-yl)-4-fluorophenyl)-5-chloropicolinamide;

N-(5-((4S,6S)-2-amino-4-methyl-6-(trifluoromethyl)-5,6-dihydro-4H-1,3-oxazin-4-yl)-6-fluoropyridin-3-yl)-5-cyanopicolinamide;

N-(3-((4S,6S)-2-amino-4-(fluoromethyl)-6-(trifluoromethyl)-5,6-dihydro-4H-1,3-oxazin-4-yl)-4-fluorophenyl)-5-methoxypicolinamide;

N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide;

N-(5-((4S,6S)-2-amino-4-methyl-6-(trifluoromethyl)-5,6-dihydro-4H-1,3-oxazin-4-yl)-6-fluoropyridin-3-yl)-5-cyano-3-methylpicolinamide;

N-(5-((4S,6S)-2-amino-4-methyl-6-(trifluoromethyl)-5,6-dihydro-4H-1,3-oxazin-4-yl)-6-fluoropyridin-3-yl)-3-chloro-5-methoxypicolinamide;

N-(5-((4S,6S)-2-amino-4-methyl-6-(trifluoromethyl)-5,6-dihydro-4H-1,3-oxazin-4-yl)-6-fluoropyridin-3-yl)-3,5-dichloropicolinamide;

N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methylpyridine-2-carbothioamide;

N-(6-((4S,6S)-2-amino-4-methyl-6-(trifluoromethyl)-5,6-dihydro-4H-1,3-oxazin-4-yl)-5-fluoropyridin-2-yl)-3,5-dichloropicolinamide;

N-(6-((4S,6S)-2-amino-4-methyl-6-(trifluoromethyl)-5,6-dihydro-4H-1,3-oxazin-4-yl)-5-fluoropyridin-2-yl)-3-chloro-5-(trifluoromethyl)picolinamide;

N-(6-((4S,6S)-2-amino-4-methyl-6-(trifluoromethyl)-5,6-dihydro-4H-1,3-oxazin-4-yl)-5-fluoropyridin-2-yl)-3-chloro-5-cyanopicolinamide;

N-(3-((4S,6S)-2-amino-4-(fluoromethyl)-6-(trifluoromethyl)-5,6-dihydro-4H-1,3-oxazin-4-yl)-4-fluorophenyl)-5-fluoropicolinamide;

N-(3-((4S,6S)-2-amino-4-(fluoromethyl)-6-(trifluoromethyl)-5,6-dihydro-4H-1,3-oxazin-4-yl)-4-fluorophenyl)-3,5-dichloropicolinamide;

N-(6-((4S,6S)-2-amino-4-methyl-6-(trifluoromethyl)-5,6-dihydro-4H-1,3-oxazin-4-yl)-5-fluoropyridin-2-yl)-5-chloropicolinamide;

N-(6-((4S,6S)-2-amino-4-methyl-6-(trifluoromethyl)-5,6-dihydro-4H-1,3-oxazin-4-yl)-5-fluoropyridin-2-yl)-5-cyano-3-methylpicolinamide; and N-(3-((4S,6S)-2-amino-4-(fluoromethyl)-6-(trifluoromethyl)-5,6-dihydro-4H-1,3-oxazin-4-yl)-4-fluorophenyl)-5-bromo-3-chloro-2-pyridinecarboxamide.

In another embodiment, the invention provides the compound of Formula I-B, I-C, II or III, or a stereoisomer or pharmaceutically acceptable salt thereof, selected from 8-((3-((4S,6S)-2-amino-4-(fluoromethyl)-6-(trifluoromethyl)-5,6-dihydro-4H-1,3-oxazin-4-yl)-4-fluorophenyl)amino)-5-fluoro-1,7-naphthyridine-3-carbonitrile;

N-(3-((4S,6S)-2-amino-4-methyl-6-(trifluoromethyl)-5,6-dihydro-4H-1,3-oxazin-4-yl)-4-fluorophenyl)-5-cyanopicolinamide;

N-(3-((4S,6S)-2-amino-4-(fluoromethyl)-6-(trifluoromethyl)-5,6-dihydro-4H-1,3-oxazin-4-yl)-4-fluorophenyl)-3-chloro-5-methoxypicolinamide;

8-((3-((4S,6S)-2-amino-4-(fluoromethyl)-6-(trifluoromethyl)-5,6-dihydro-4H-1,3-oxazin-4-yl)-4-fluorophenyl)amino)-5-fluoro-1,7-naphthyridine-3-carbonitrile;

(4S,6S)-4-(5-((3-chloro-1,7-naphthyridin-8-yl)amino)-2-fluoropyridin-3-yl)-4-methyl-6-(trifluoromethyl)-5,6-dihydro-4H-1,3-oxazin-2-amine;

(4S,6S)-4-(5-((7-chloropyrido[3,2-d]pyrimidin-4-yl)amino)-2-fluoropyridin-3-yl)-4-methyl-6-(trifluoromethyl)-5,6-dihydro-4H-1,3-oxazin-2-amine;

4-((5-((4S,6S)-2-amino-4-methyl-6-(trifluoromethyl)-5,6-dihydro-4H-1,3-oxazin-4-yl)-6-fluoropyridin-3-yl)amino)pyrido[3,2-d]pyrimidine-7-carbonitrile;

8-((5-((4S,6S)-2-amino-4-methyl-6-(trifluoromethyl)-5,6-dihydro-4H-1,3-oxazin-4-yl)-6-fluoropyridin-3-yl)amino)-1,7-naphthyridine-3-carbonitrile;

N-(3-((4S,6S)-2-amino-4-(fluoromethyl)-6-(trifluoromethyl)-5,6-dihydro-4H-1,3-oxazin-4-yl)-4-fluorophenyl)-3-methylimidazo[1,2-a]pyridine-2-carboxamide; and 8-((6-((4S,6S)-2-amino-4-methyl-6-(trifluoromethyl)-5,6-dihydro-4H-1,3-oxazin-4-yl)-5-fluoropyridin-2-yl)amino)-5-fluoro-1,7-naphthyridine-3-carbonitrile;

N-(3-((4S,6S)-2-amino-4-methyl-6-(trifluoromethyl)-5,6-dihydro-4H-1,3-oxazin-4-yl)-4,5-difluorophenyl)-5-methoxypicolinamide;

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-chloropicolinamide; and N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxypyrazine-2-carboxamide.

In another embodiment, the invention provides a compound, or a pharmaceutically acceptable salt thereof, selected from

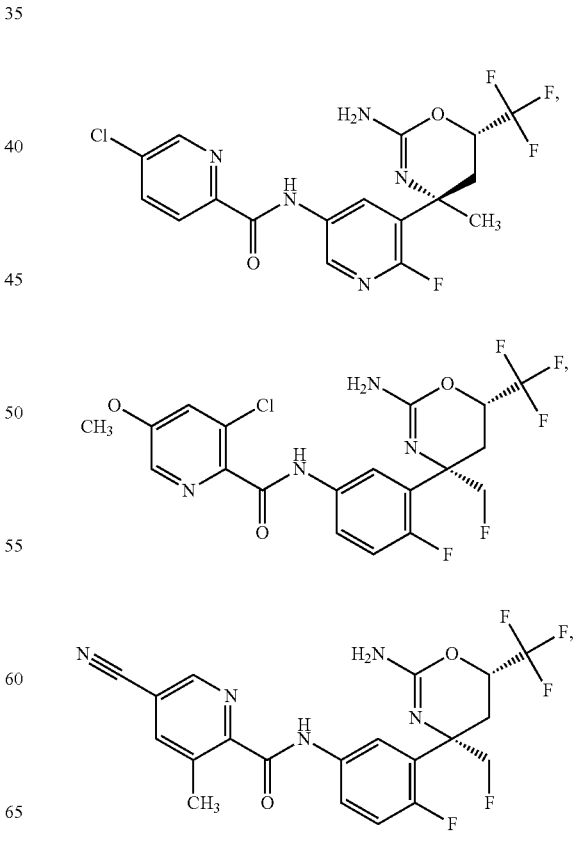

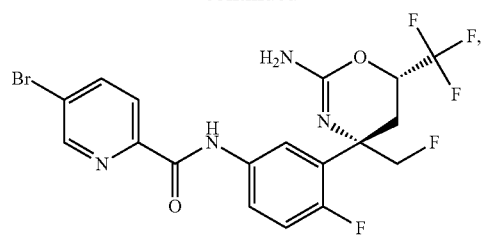
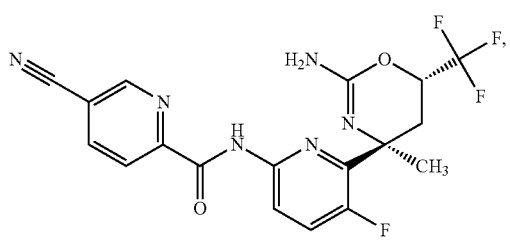
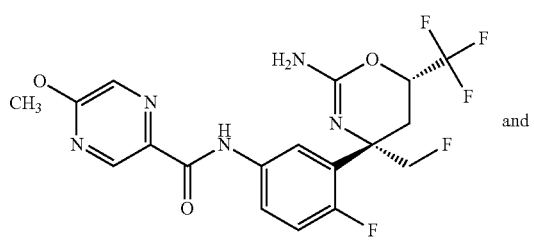 and
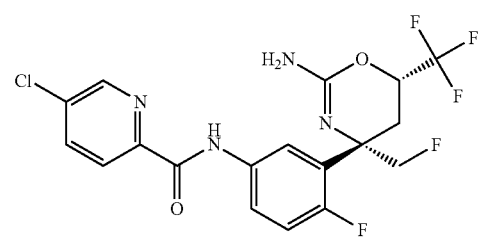
In another embodiment, the invention provides a compound, or a pharmaceutically acceptable salt thereof, selected from
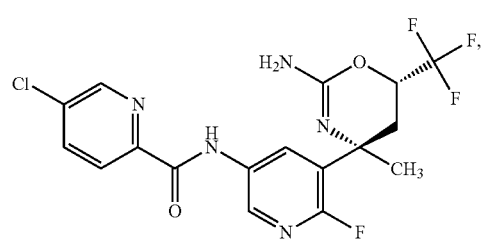
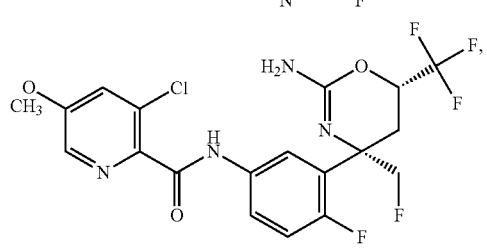
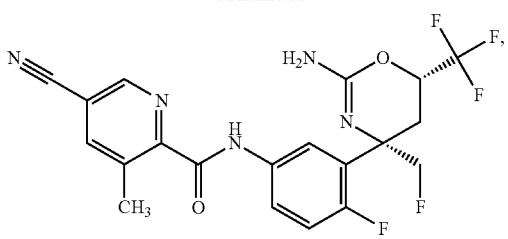
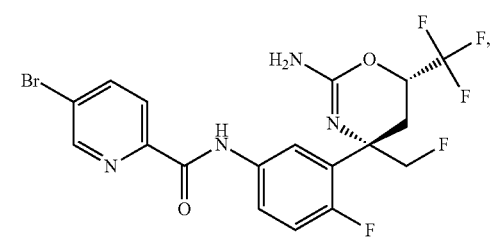
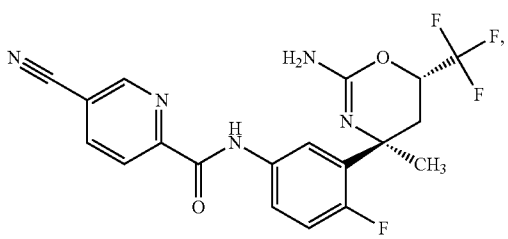
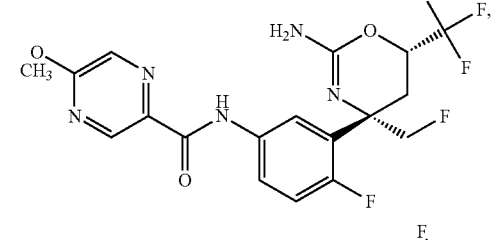
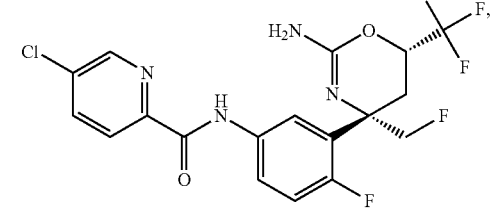
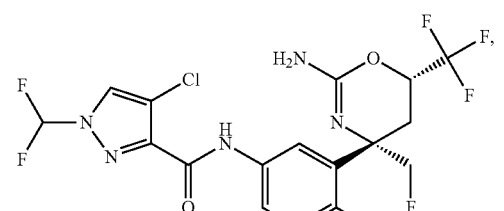
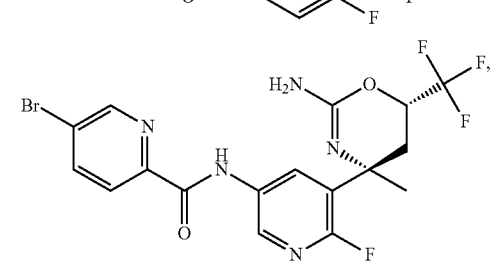

49
-continued
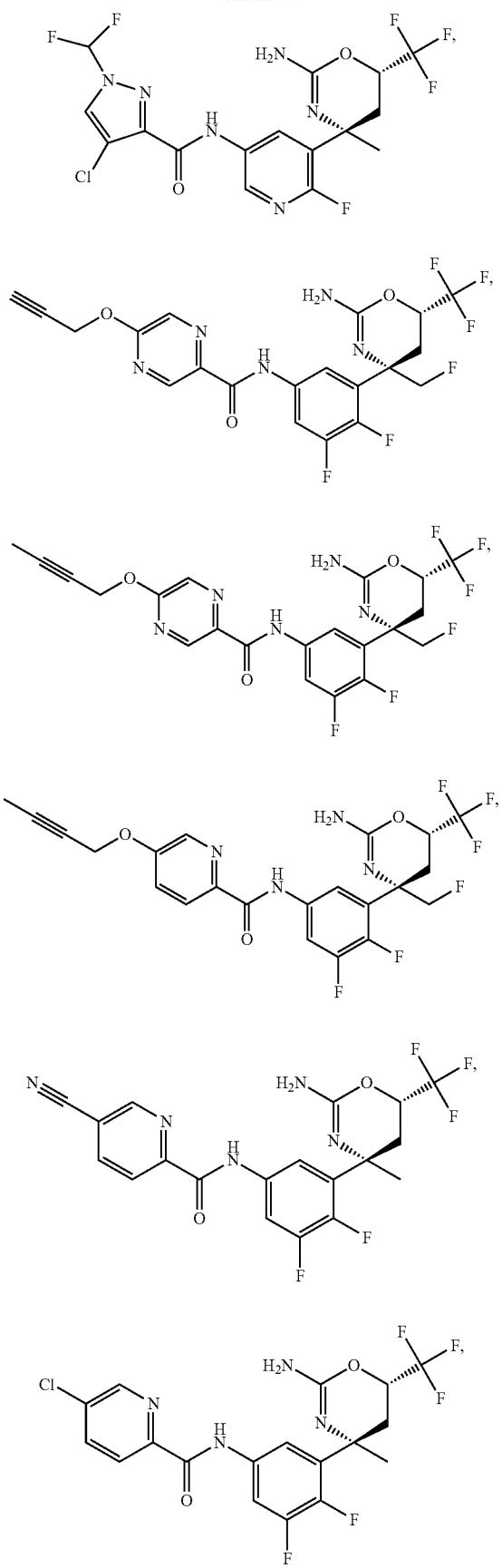
50
-continued
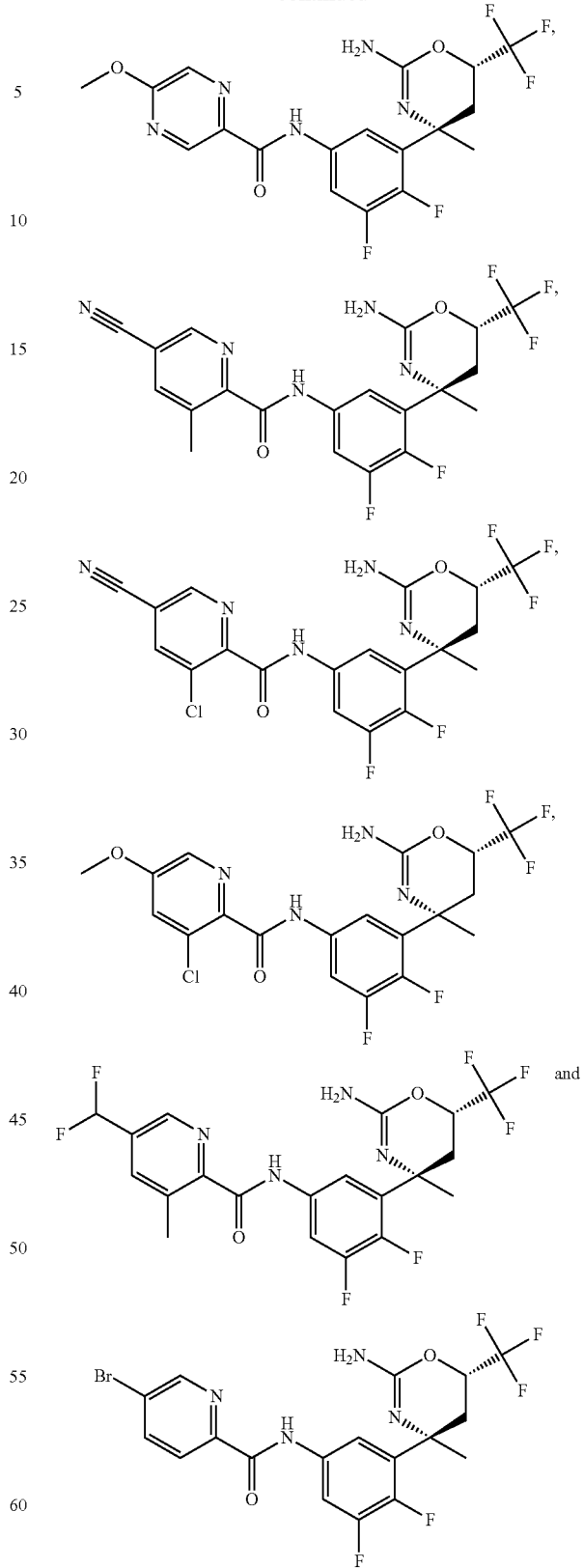
In another embodiment, the invention provides a compound, or a pharmaceutically acceptable salt thereof, selected from 51
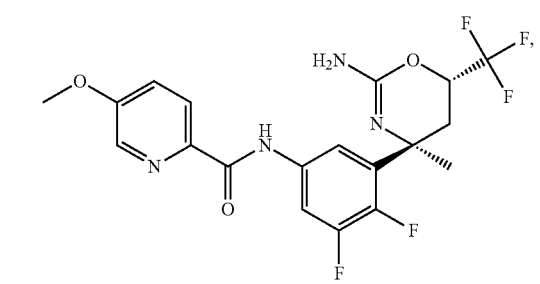
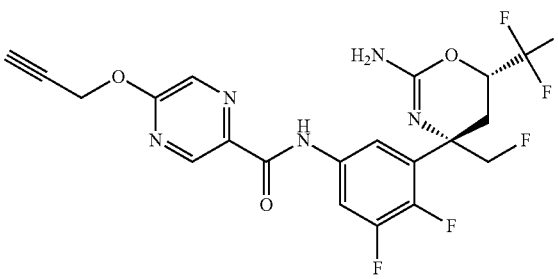
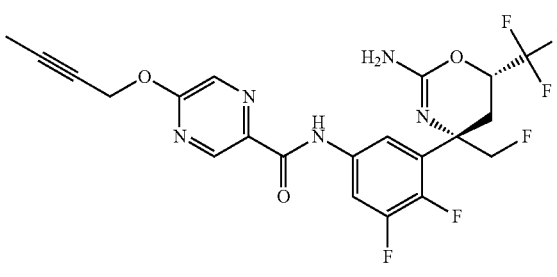
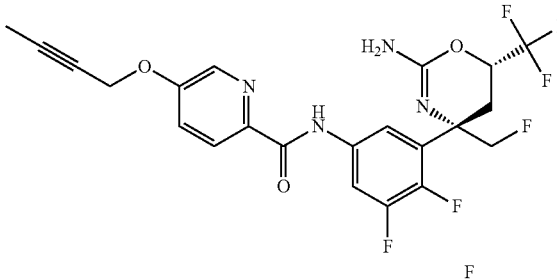
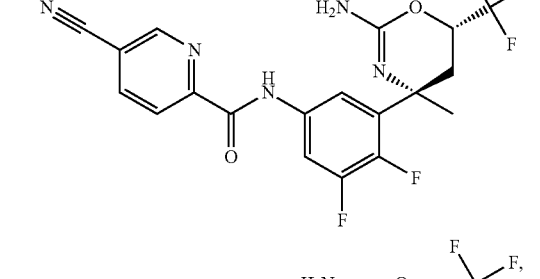
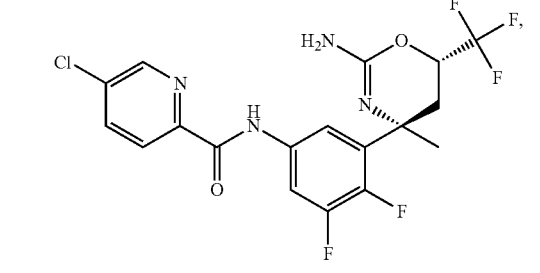
52
-continued
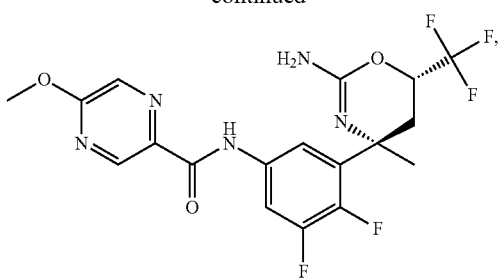
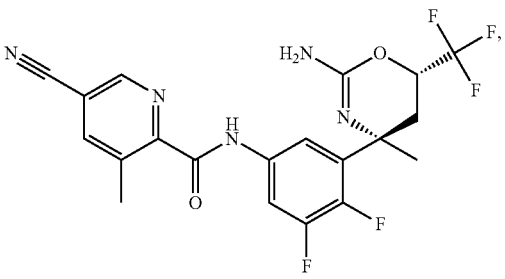
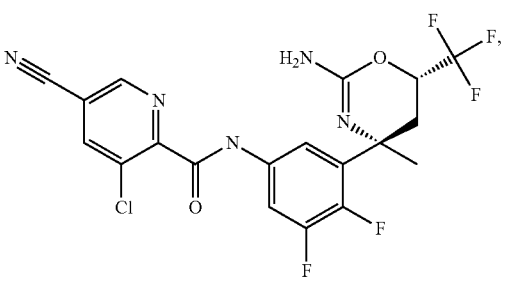
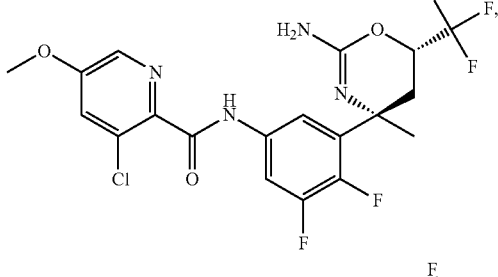
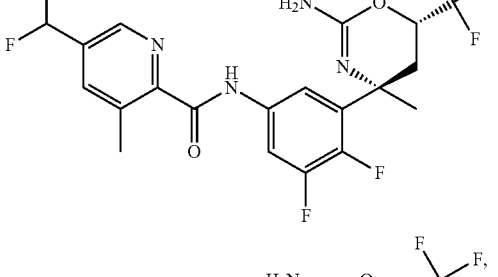
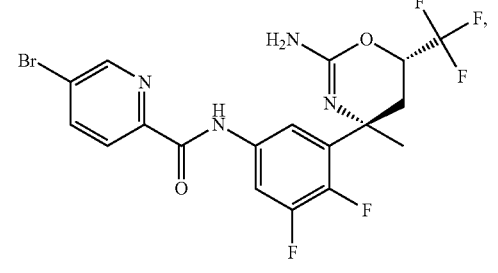

-continued

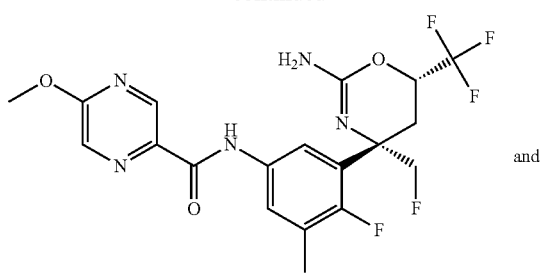

and

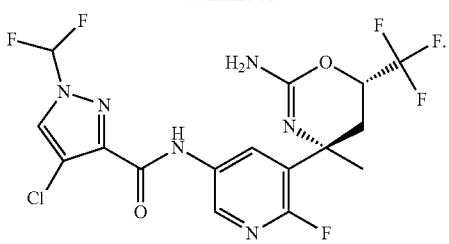

In another embodiment, the invention provides the compound,

In another embodiment, the invention provides a compound, or a pharmaceutically acceptable salt thereof, selected from

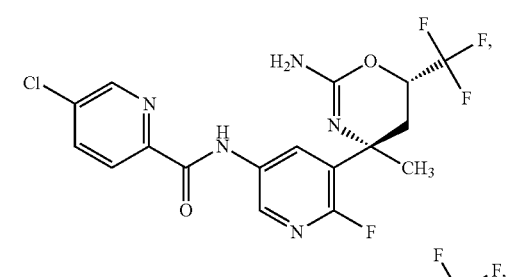

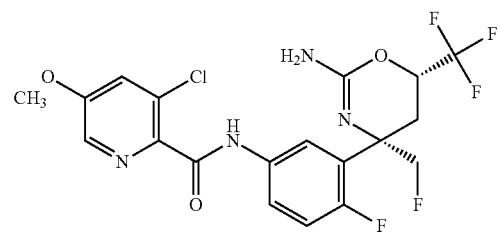

or a pharmaceutically acceptable salt thereof.

In another embodiment, the invention provides the compound,

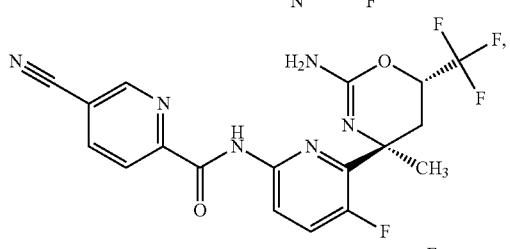

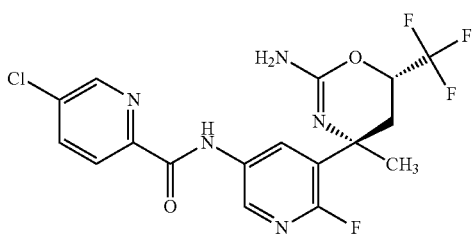 [SMILES: C[C@@]1(c2cc(NC(=O)c3ccc(Cl)cn3)cnc2F)C[C@@H](C(F)(F)F)OC(N)=N1]

or a pharmaceutically acceptable salt thereof.

In another embodiment, the invention provides the compound,

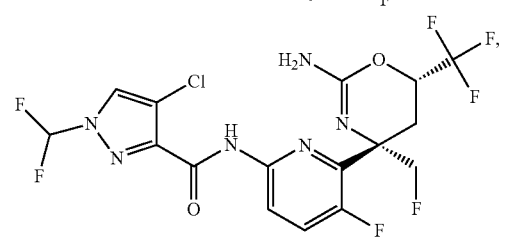

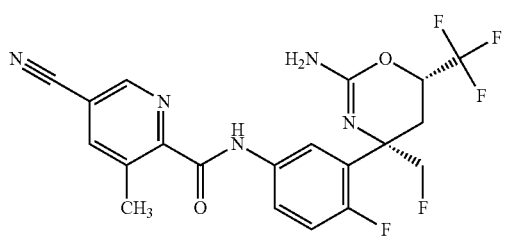 [SMILES: Cc1cc(C#N)cnc1C(=O)Nc1ccc(F)c([C@]2(CF)C[C@@H](C(F)(F)F)OC(N)=N2)c1]

and

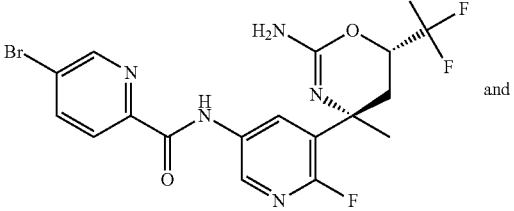

or a pharmaceutically acceptable salt thereof.

In another embodiment, the invention provides the compound,

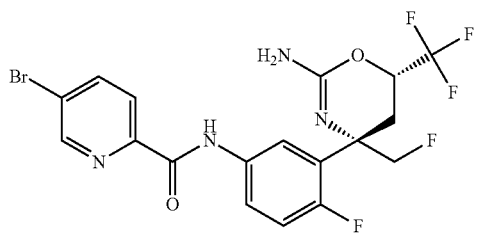 [SMILES: NC1=N[C@](CF)(c2cc(NC(=O)c3ccc(Br)cn3)ccc2F)C[C@@H](C(F)(F)F)O1]

or a pharmaceutically acceptable salt thereof.

In another embodiment, the invention provides the compound,

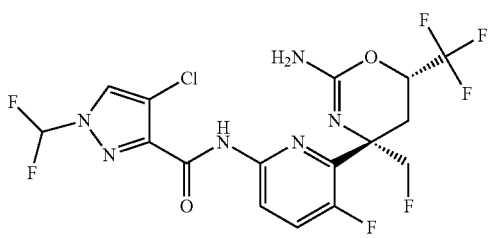

or a pharmaceutically acceptable salt thereof.

In another embodiment, the invention provides the compound,

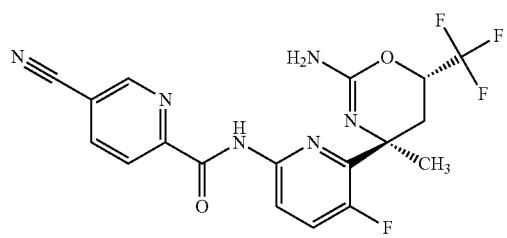 [SMILES: C[C@@]1(c2nc(NC(=O)c3ccc(C#N)cn3)ccc2F)C[C@@H](C(F)(F)F)OC(N)=N1]

or a pharmaceutically acceptable salt thereof.

In another embodiment, the invention provides the compound,

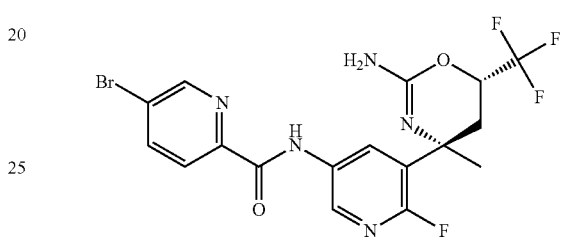

or a pharmaceutically acceptable salt thereof.

In another embodiment, the invention provides the compound,

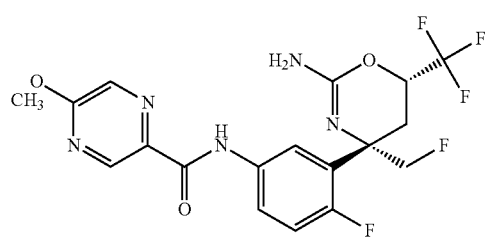

or a pharmaceutically acceptable salt thereof.

In another embodiment, the invention provides the compound,

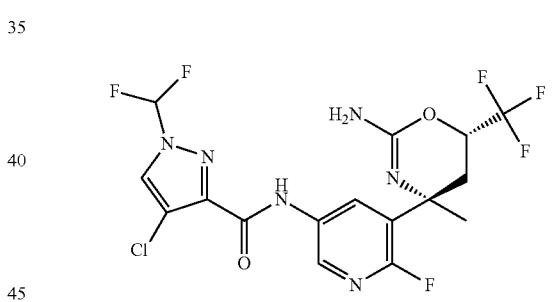

or a pharmaceutically acceptable salt thereof.

In another embodiment, the invention provides the compound,

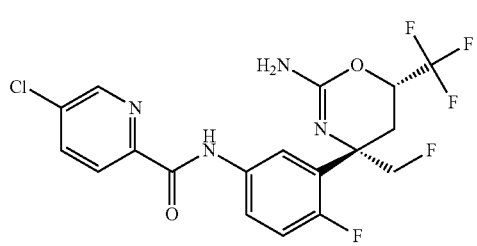

or a pharmaceutically acceptable salt thereof.

In another embodiment, the invention provides the compound,

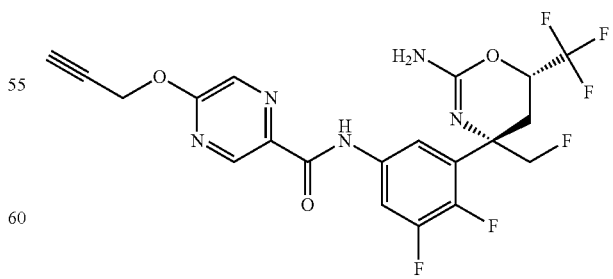

or a pharmaceutically acceptable salt thereof.

In another embodiment, the invention provides the compound,

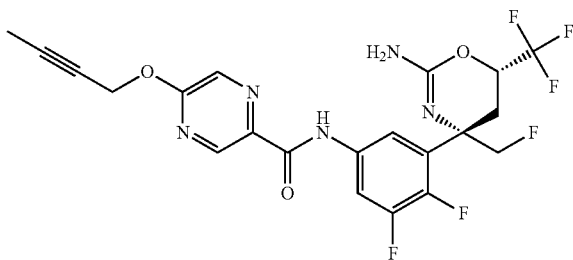 [SMILES: CC#CCOc1cnc(C(=O)Nc2cc(F)c(F)c([C@]3(CF)C[C@@H](C(F)(F)F)OC(N)=N3)c2)cn1]

or a pharmaceutically acceptable salt thereof.

In another embodiment, the invention provides the compound,

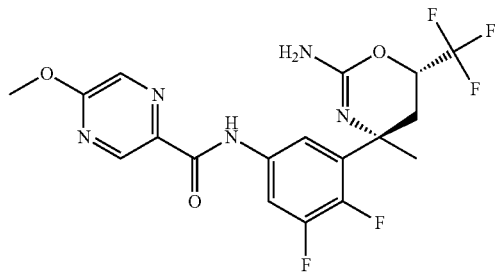 [SMILES: COc1cnc(C(=O)Nc2cc(F)c(F)c([C@]3(C)C[C@@H](C(F)(F)F)OC(N)=N3)c2)cn1]

or a pharmaceutically acceptable salt thereof.

In another embodiment, the invention provides the compound,

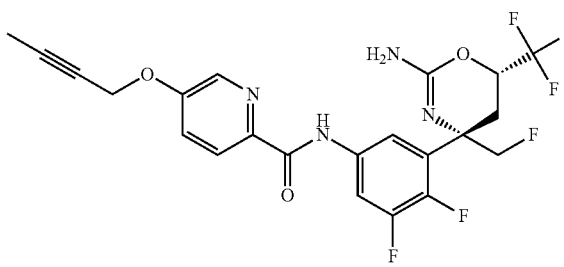

or a pharmaceutically acceptable salt thereof.

In another embodiment, the invention provides the compound,

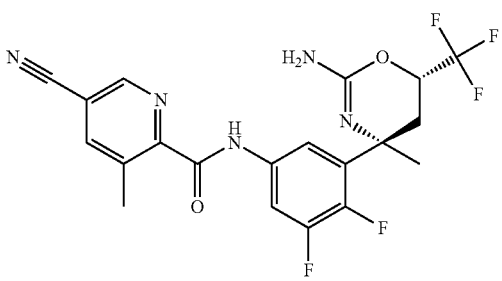 [SMILES: Cc1cc(C#N)cnc1C(=O)Nc1cc(F)c(F)c([C@]2(C)C[C@@H](C(F)(F)F)OC(N)=N2)c1]

or a pharmaceutically acceptable salt thereof.

In another embodiment, the invention provides the compound,

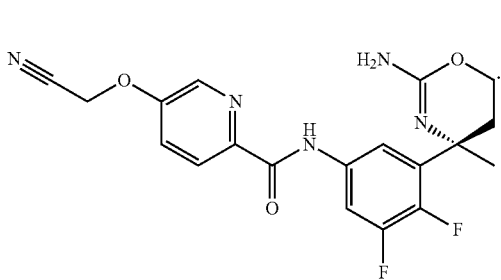

or a pharmaceutically acceptable salt thereof.

In another embodiment, the invention provides the compound,

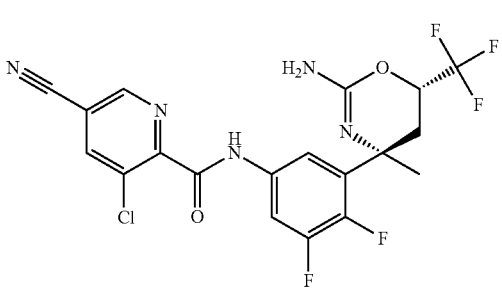

or a pharmaceutically acceptable salt thereof.

In another embodiment, the invention provides the compound,

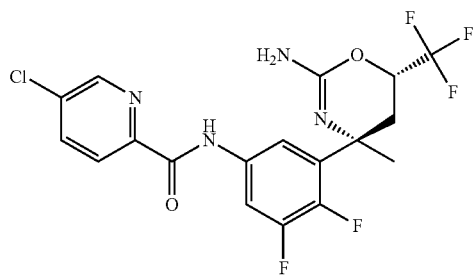

or a pharmaceutically acceptable salt thereof.

In another embodiment, the invention provides the compound,

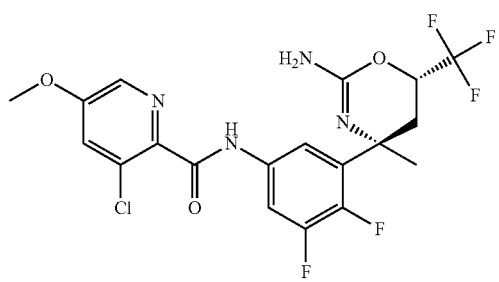 [SMILES: COc1cnc(C(=O)Nc2cc(F)c(F)c([C@]3(C)C[C@@H](C(F)(F)F)OC(N)=N3)c2)c(Cl)c1]

or a pharmaceutically acceptable salt thereof.

In another embodiment, the invention provides the compound,

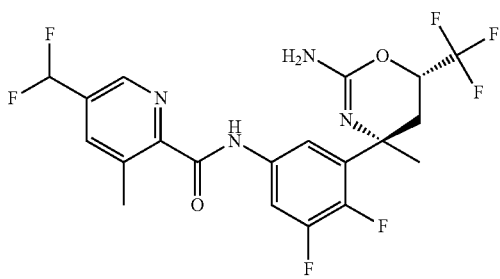 [SMILES: Cc1cc(C(F)F)cnc1C(=O)Nc1cc(F)c(F)c([C@]2(C)C[C@@H](C(F)(F)F)OC(N)=N2)c1]

or a pharmaceutically acceptable salt thereof.

In another embodiment, the invention provides the compound,

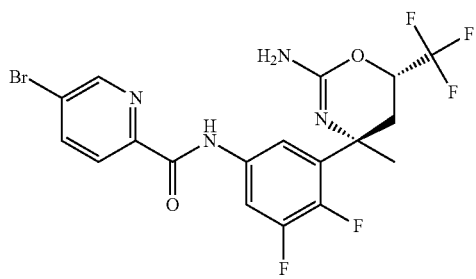

or a pharmaceutically acceptable salt thereof.

In another embodiment, the invention provides the compound,

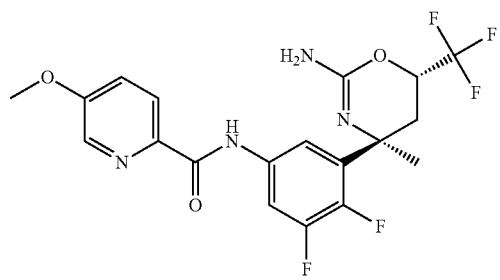 [SMILES: COc1ccc(C(=O)Nc2cc(F)c(F)c([C@]3(C)C[C@@H](C(F)(F)F)OC(N)=N3)c2)nc1]

or a pharmaceutically acceptable salt thereof.

In another embodiment, the invention provides the compound,

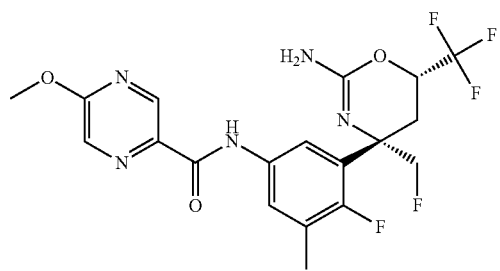 [SMILES: COc1cnc(C(=O)Nc2cc(C)c(F)c([C@]3(CF)C[C@@H](C(F)(F)F)OC(N)=N3)c2)cn1]

or a pharmaceutically acceptable salt thereof.

In another embodiment, the invention provides the compound,

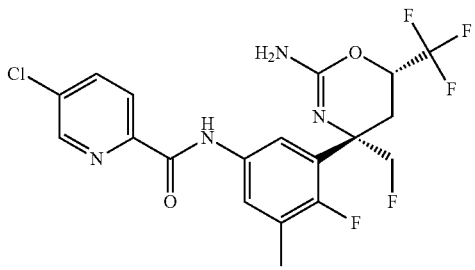 [SMILES: Cc1cc(NC(=O)c2ccc(Cl)cn2)cc([C@]2(CF)C[C@@H](C(F)(F)F)OC(N)=N2)c1F]

or a pharmaceutically acceptable salt thereof.

In the structures depicted hereinabove, an "—N" in the 1,3-oxazine head group is intended to be an —NH$_2$ (an amine groups); and lines ending without an atom are understood by persons of ordinary skill in the art to be a —CH$_3$ group.

All of the possible embodiments described herein for various of the R groups of the compounds of Formula I may be applied, as appropriate, to compounds of Formula II and any sub-formulas thereof.

In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the metes and bounds of the invention.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha\text{-}\beta}$alkyl", when used either alone or within other terms such as "haloalkyl" and "alkylamino", embraces linear or branched radicals having α to β number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha\text{-}\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha\text{-}\beta}$alkynyl", when used alone or in combination, denotes linear or branched radicals having at least one carbon-carbon triple bond in a moiety having a number of carbon atoms in the range from α and β. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" or "—OC$_{\alpha-\beta}$alkyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from α and β. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl. Similarly, the term "$C_{\alpha-\beta}$ haloalkyl" when used herein embraces linear or branched alkyl radicals having α to β number of carbon atoms (such as $C_1$-$C_6$; $C_1$-$C_4$; or $C_1$-$C_3$) and substituted with one or more halogen atoms, such as with one or more fluorine (F), chlorines (Cl), bromine (Br) or iodine (I) atoms, or a combination thereof. As described above, non-limiting, representative examples of a $C_1$haloalkyl are CH$_2$F, CHF$_2$, CF$_3$ and the like.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
Aq., aq.—aqueous
Ar—argon (gas)
BOC—tert-butoxycarbonyl
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide
$Et_2O$—diethyl ether
EtOAc—ethyl acetate
g, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
P(t-bu)$_3$—tri(tert-butyl)phosphine
Ph$_3$P—triphenylphosphine
Pd/C—palladium on carbon
Pd(PPh$_3$)$_4$—palladium(0)triphenylphosphine tetrakis
Pd(dppf)Cl$_2$—palladium(1,1-bisdiphenylphosphinoferrocene) II chloride
Pd(PhCN)$_2$Cl$_2$—palladium di-cyanophenyl dichloride
Pd(OAc)$_2$—palladium acetate
Pd$_2$(dba)$_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium fluoride
TBTU—O-benzotriazol-1-yl-N,N,N,N'-tetramethyluronium tetrafluoroborate
TEA, Et$_3$N—triethylamine
TFA—trifluoroacetic acid
THF—tetrahydrofuran
UV—ultraviolet light

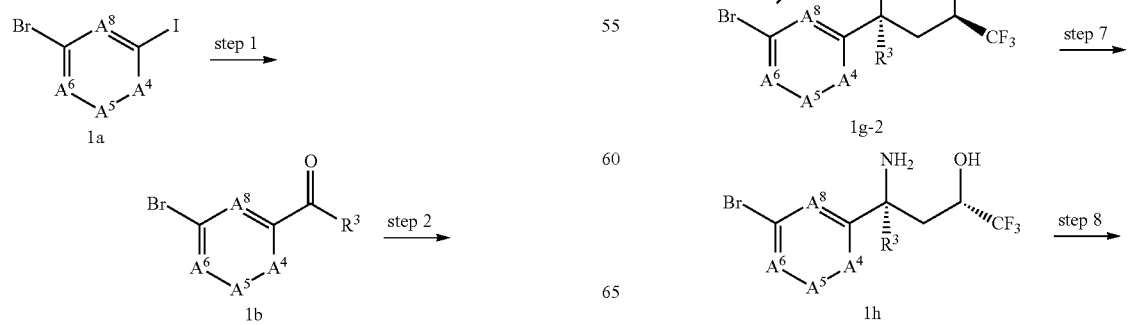

-continued

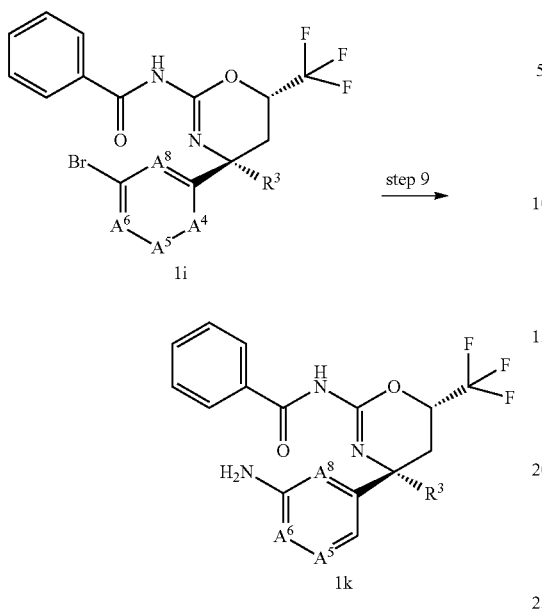

Scheme 2

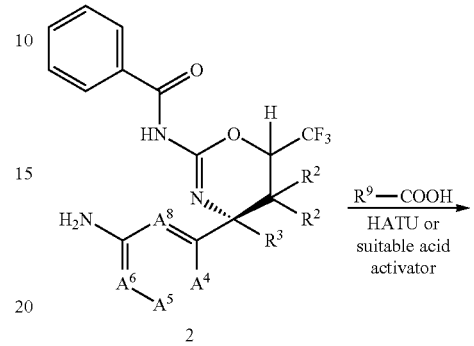

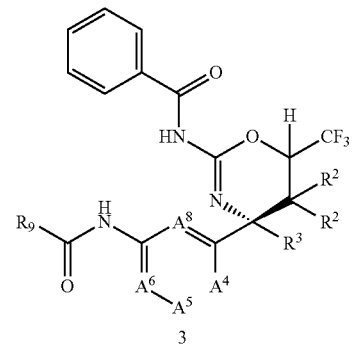

Scheme 1-A describes an exemplary method for preparing compounds 1k of Formulas I, II and III, wherein $A^4$ is $CR^4$ and $R^4$ is F, each of $A^5$, $A^6$ and $A^8$ is, independently, as defined hereunder, each $R^2$, independently, is H, and one $R^1$ is H and the other $R^1$ is $CF_3$. This procedure may be employed to prepare compounds of Formulas I, II and III wherein $R^3$ is $CH_3$, $CH_2F$, $CHF_2$ or $CF_3$. Beginning with compound 1a, one of ordinary skill in the art may acylate at the position of the iodine using an ester and a strong base, such as BuLi as described herein, under suitable conditions, to afford the corresponding acylated intermediate compound 1b. The ketone of the 1b may be converted to the corresponding sulfinamide using tetraethoxytitanium under suitable conditions, such as those described in Example 1 herein, to generate compound intermediate 1c. The corresponding methyl acetate adduct 1d may be prepared from intermediate 1c using a strong base such as LDA to afford the corresponding intermediate 1d. Note that one may also use the tert-butyl ester instead of the methyl ester 1d. Intermediate 1d may be reduced to the corresponding alcohol adduct via use of a suitable reducing agent such as a borohydride, to provide compounds 1e. Intermediate 1e can then be oxidized to the corresponding aldehyde using a suitable oxidizing agent such as dess-marin periodinane, under suitable conditions to afford aldehyde 1f. The aldehyde can be reduced using a suitable silane and quenched with TBAF to provide the corresponding $CF_3$ adduct 1g (mixture of diastereomers). The diastereomers 1g-1 and 1g-2 as drawn in scheme 1 may be separated using silica gel chromatography, such as that described in Example 1, step 6 below, or by other conventional techniques. The desired diastereomer may then be deprotected under a suitable acid, such as HCl, to free the amine 1h, and then reacted with benzoylisothiocyante under suitable conditions to afford ring closure to the corresponding benzoyl adduct 1i. The bromide of 1i can then be converted to the corresponding amine using known techniques, such as going through the corresponding azide, which in turn can be reduced to the corresponding amine compound 1k by treatment with a suitable phosphine, such as trimethylphosphine under suitable conditions.

As shown, desired $R^9$-amide-linked compounds 3 can be prepared as desired, such as by treatment with an activated acid in conjunction with an activating reagent, such as HATU or DMTMM (see Method A and B for Examples 2-7 in Table 1) to afford the desired protected amide-linked adduct. Compound 3 can be deprotected using known conditions, such as with a base, like DBU in a suitable solvent, to afford final compounds of Formula I-A.

Acid activating groups convert the OH of the acid into a strong leaving group "LG." A "leaving group" which may be a halide such as an iodide, bromide, chloride or fluoride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

Scheme 3

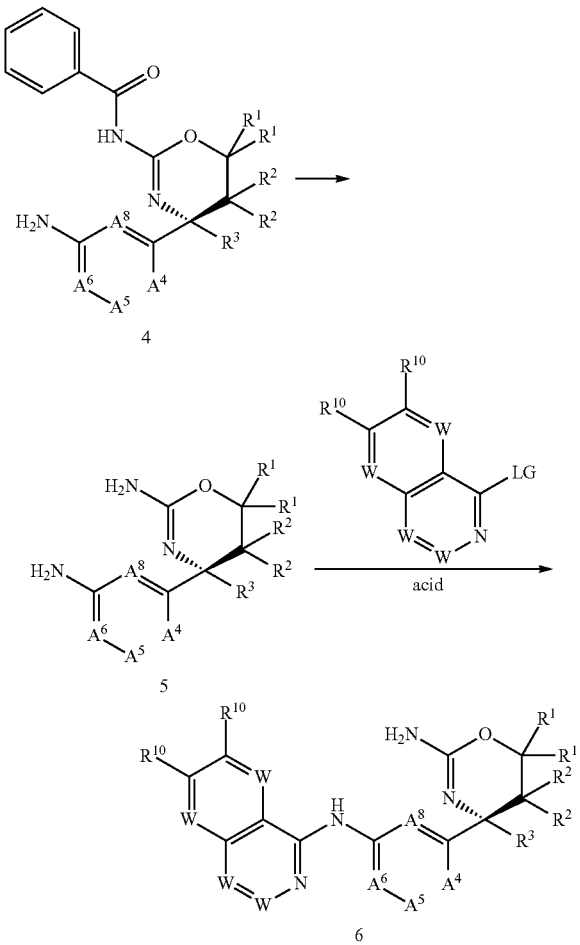

As shown, desired compounds 6 of Formula I-B can be prepared as shown in scheme 3. First, compound 4 is deprotected using conventional techniques, and the amine adduct 5 can be functionalized to the desired compound. A desired bicyclic $R^7$ group having a suitable leaving group, such as a chloride (Cl) or other aromatic leaving group, can be reacted with compound 5 in the presence of a suitable acid, such as of sulfuric acid. This allows coupling of the bicyclic heteroaromatic $R^7$ group to the amine to form 6 of Formula I-B.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

Example 1

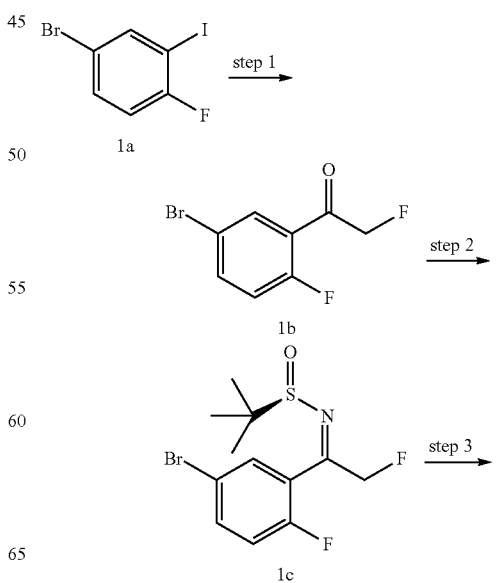

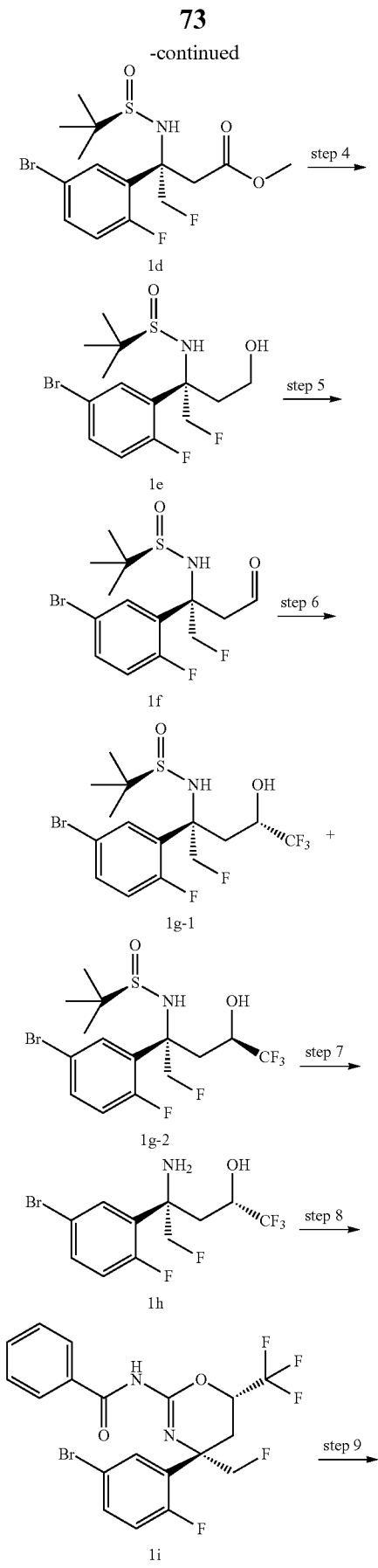

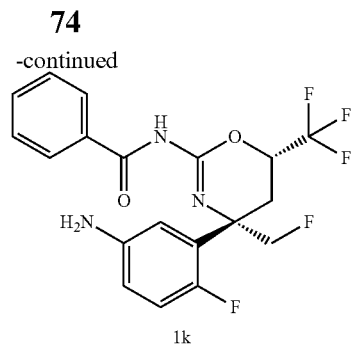

1k

Intermediate Synthesis 1: N-((4S,6S)-4-(5-amino-2-fluorophenyl)-4-(fluoromethyl)-6-(trifluoromethyl)-5,6-dihydro-4H-1,3-oxazin-2-yl)benzamide (1k)

Step 1:
1-(5-bromo-2-fluorophenyl)-2-fluoroethanone (1b)

A solution of 4-bromo-1-fluoro-2-iodobenzene (5.0 g, 116 mmol, (1), Aldrich) in THF (60 ml) under nitrogen atmosphere was cooled to −78° C. A solution of n-BuLi (2.5M in hexanes; 7.31 ml, 18.28 mmol, Aldrich) was added drop wise and the reaction was stirred at −78° C. for one hour. Ethyl monofluoroacetate (2.1 g, 19.94 mmol, Aldrich) was added drop wise and the reaction was stirred at −78° C. for one hour. The reaction was quenched with aqueous saturated ammonium chloride solution and allowed to warm to RT. The reaction was diluted with water and EtOAc. The organic layer was separated, washed with brine, dried over magnesium sulfate, and concentrated under reduced pressure. The material was purified via silica gel flash chromatography using a gradient of 0-20% EtOAc in Hexanes to afford the title compound as an off white solid. (2.45 g, 10.42 mmol, 63% yield). MS m/z=234.9 M+. Calculated for $C_8H_5BrF_2O$: 235.03

Step 2: (R)-N-(1-(5-bromo-2-fluorophenyl)-2-fluoro-ethylidene)-2-methylpropane-2-sulfinamide (1c)

To a solution of 1-(5-bromo-2-fluorophenyl)-2-fluoroethanone (14 g, 59.6 mmol, step 1) and (R)-2-methylpropane-2-sulfinamide (14.44 g, 119 mmol, AK Scientific) in THF (120 ml) was added tetraethoxytitanium (27.2 g, 119 mmol, Aldrich). The reaction was stirred at RT for 16 hours. The reaction was poured slowly into vigorously stirring water (700 ml) and the resulting suspension was stirred for 20 minutes. EtOAc (400 ml) was added and the suspension was stirred for an additional 20 minutes. The suspension was filtered through celite and the filter cake was washed with additional EtOAc. The organic layer was separated, washed with brine, dried over magnesium sulfate and concentrated under reduced pressure. The material was purified via silica gel flash chromatography using a gradient of 0-25% EtOAc in Hexanes to afford the title compound as a yellow oil (15.35 g, 45.4 mmol, 76% yield). MS m/z=338.0 M+. Calculated for $C_{12}H_{14}BrF_2NOS$: 338.211

Step 3: (S)-methyl 3-(5-bromo-2-fluorophenyl)-3-((R)-1,1-dimethylethylsulfinamido)-4-fluorobutanoate (1d)

A flame dried RBF equipped with an addition funnel was charged with DIPA (9.32 ml, 66.5 mmol, Aldrich) and THF (70 ml). The solution was cooled to 0° C. before adding a solution of n-butyllithium (2.5M in hexanes; 26.8 ml, 67 mmol, Aldrich) drop wise. The reaction was stirred at 0° C. for 15 minutes then cooled to −78° C. A solution of methyl acetate (4.9 g, 66.5 mmol, Aldrich) in THF (25 ml) was added dropwise via cannula to the LDA solution at −78° C. After 30 minutes, a solution of chlorotitanium triisopropoxide, (18.5 g, 71.0 mmol, Aldrich) in THF (70 ml) was added drop wise via cannula and the reaction was stirred at −78° C. After 1 h, a solution of (R)—N-(1-(5-bromo-2-fluorophenyl)-2-fluoroethylidene)-2-methylpropane-2-sulfinamide (15.0 g, 27.1 mmol, step 3) in THF (100 ml), was added drop wise via cannula at −78° C. and the reaction was stirred at −78° C. for 45 minutes. The reaction was quenched with aqueous, saturated ammonium chloride solution, diluted with water and EtOAc and stirred vigorously for 20 minutes. The reaction was filtered through celite and the filter cake was washed with additional EtOAc. The organic layer was separated, washed with brine, dried over MgSO₄ and concentrated under reduced pressure. The crude material was purified via silica gel flash chromatography using a solvent gradient of 10-60% acetone in hexanes to afford the title compound as a light yellow oil (12.0 g, 29.1 mmol, 65.6% yield, dr: 97:3 by LC/MS). MS m/z=411.9 M⁺. Calculated for $C_{15}H_{20}BrF_2NO_3S$: 412.290

Step 4: (R)q-N-((S)-2-(5-bromo-2-fluorophenyl)-1-fluoro-4-hydroxybutan-2-yl)-2-methylpropane-2-sulfinamide (1e)

Sodium borohydride (4.04 g, 107 mmol, Aldrich) was added in portions to a solution of (S)-methyl 3-(5-bromo-2-fluorophenyl)-3-((R)-1,1-dimethylethylsulfinamido)-4-fluorobutanoate (14.67 g, 35.6 mmol, dr: 92:8, step 3) in MeOH (29.7 ml)/THF (148 ml). The reaction was stirred at RT for 10 minutes. The reaction was slowly quenched with water, further diluted with water and EtOAc. The organic layer was separated, washed with brine, dried over magnesium sulfate and concentrated under reduced pressure. The crude material was subjected to chromatography using supercritical $CO_2$ (additives 12% methanol with 20 mM $NH_3$) on a IC column (21×250 mm, 5 μm) eluting at a flow rate 75 ml/min (100 bar pressure, 40° C. column temperature) to afford the title compound as a white foam (10.51 g, 27.3 mmol, 77% yield, ee>99%, de>99%, retention time: 1.4 min). MS m/z=383.9 M⁺. Calculated for $C_{14}H_{20}BrF_2NO_2S$: 384.280

An alternative synthesis of intermediate 1e follows steps and procedures analogous to those described in Method E (Example 15) steps 1 and 2 below.

Step 5: (R)-N-((S)-2-(5-bromo-2-fluorophenyl)-1-fluoro-4-oxobutan-2-yl)-2-methylpropane-2-sulfinamide (1f)

To a solution of (R)-N-((S)-2-(5-bromo-2-fluorophenyl)-1-fluoro-4-hydroxybutan-2-yl)-2-methylpropane-2-sulfinamide (4.84 g, 12.59 mmol, step 4) in DCM (100 ml) was added Dess-martin periodinane (5.88 g, 13.85 mmol, Aldrich) at RT. The reaction was stirred for 2.5 hours. The reaction was quenched with water, followed by the addition of aqueous, saturated sodium bicarbonate solution, and DCM. The organic layer was washed with sequentially with saturated sodium bicarbonate solution three times and brine before drying over magnesium sulfate and concentrating under reduced pressure. The crude residue was purified via silica gel flash chromatography using a gradient of 10-60% acetone in hexanes to afford the title compound as a clear oil (4.04 g, 10.58 mmol, 84% yield). MS m/z=382.0 M⁺. Calculated for $C_{14}H_{18}BrF_2NO_2S$: 382.264

Alternative Synthesis of Intermediate 1e:
N,NDdiisopropylethylamine (13.58 mL, 78 mmol, Aldrich) was added dropwise to a solution of (R)-N-((S)-2-(5-bromo-2-fluorophenyl)-1-fluoro-4-hydroxybutan-2-yl)-2-methylpropane-2-sulfinamide (1e, 10 g, 26.0 mmol) in dichloromethane (88 mL) and DMSO (44.0 mL)-10° C. Pyridine sulfur trioxide (Aldrich, 6.21 g, 39.0 mmol) was added portionwise while maintaining the internal temperature below 0° C. The reaction temperature was raised to 0° C. after 5 min and the reaction mixture was stirred for 2.5 hours at 0° C. The reaction mixture was poured into water and extracted with EtOAc. The combined organic extracts were washed with saturated aqueous ammonium chloride, water, saturated aqueous sodium chloride, and dried over sodium sulfate. The solution was filtered and concentrated under reduced pressure to give 1e.

Step 6: (R)-N-((2S,4S)-2-(5-bromo-2-fluorophenyl)-1,5,5,5-tetrafluoro-4-hydroxypentan-2-yl)-2-methylpropane-2-sulfinamide (1g)

Trifluoromethyl)trimethylsilane (36.8 g, 256 mmol, Aldrich) was added to a solution of (R)-N-((S)-2-(5-bromo-2-fluorophenyl)-1-fluoro-4-oxobutan-2-yl)-2-methylpropane-2-sulfinamide (9.8 g, 25.6 mmol, step 5) in THF (300 ml) at −78° C. The solution was stirred at −78° C. for 15 minutes before adding tetrabutylammonium fluoride, 1.0M in THF (38.5 ml, 38.5 mmol, Aldrich) drop wise. The reaction mixture was stirred at −78° C. for two hours. The reaction was quenched by the slow addition of HCl (1.0M aqueous solution; 35 ml) and warmed to RT. The reaction was diluted with water and EtOAc. The organic layer was washed with brine, dried over magnesium sulfate and concentrated under reduced pressure. The crude material was purified via silica gel flash chromatography using a gradient of 0-40% EtOAc in DCM to afford the desired title compound, (R)—N-((2S,4S)-2-(5-bromo-2-fluorophenyl)-1,5,5,5-tetrafluoro-4-hydroxypentan-2-yl)-2-methylpropane-2-sulfinamide (1g-1) (white solid; 1.6 g, 3.54 mmol, 13.8% yield) as well as the diastereomer (R)—N-((2S,4R)-2-(5-bromo-2-fluorophenyl)-1,5,5,5-tetrafluoro-4-hydroxypentan-2-yl)-2-methylpropane-2-sulfinamide (1g-2) (white solid; 2.4 g, 5.31 mmol, 20.7% yield). MS m/z=451.9 M⁺ (for both diastereosiomers). Calculated for $C_{15}H_{19}BrF_5NO_2S$: 452.278

Step 7: (2S,4S)-4-amino-4-(5-bromo-2-fluorophenyl)-1,1,1,5-tetrafluoropentan-2-ol (1h)

To a solution of (R)—N-((2S,4S)-2-(5-bromo-2-fluorophenyl)-1,5,5,5-tetrafluoro-4-hydroxypentan-2-yl)-2-methylpropane-2-sulfinamide (1.6 g, 3.54 mmol, step 6) in DCM (20 mL)/MeOH (10 mL) was added HCl (4.0M in dioxane; 1.075 ml, 35.4 mmol, Aldrich) at RT. The reaction was stirred for one hour. The reaction was concentrated under reduced pressure and the crude residue was taken up in EtOAc. The solution was washed sequentially with water, saturated aqueous sodium bicarbonate solution, and brine. The organic layer was dried over magnesium sulfate and concentrated under reduced pressure to afford the title compound as yellow oil, used without further purification. MS m/z=347.9 M⁺. Calculated for $C_{11}H_{11}BrF_5NO$: 348.11

Step 8: N-((4S,6S)-4-(5-bromo-2-fluorophenyl)-4-(fluoromethyl)-6-(trifluoromethyl)-5,6-dihydro-4H-1,3-oxazin-2-yl)benzamide (1i)

To a solution of (2S,4S)-4-amino-4-(5-bromo-2-fluorophenyl)-1,1,1,5-tetrafluoropentan-2-ol (1.23 g, 3.54 mmol, step 7) [theoretical yield from step 7] in THF (20 mL) was added benzoyl isothiocyanate (0.524 ml, 3.89 mmol, Aldrich). The reaction was stirred at RT for 30 minutes. The reaction was concentrated under reduced pressure and the crude residue was taken up in acetonitrile (20 mL). Dicyclohexylcarbodiimide (0.766 g, 3.71 mmol) was added followed by TEA (0.098 ml, 0.708 mmol). The reaction was heated to 50° C. and stirred for 16 hours. The reaction was cooled to ambient temperature and diluted with water and EtOAc. The organic layer was washed with brine, dried over magnesium sulfate and concentrated under reduced pressure. The crude material was purified via silica gel flash chromatography using a gradient of 0-45% EtOAc in Hexanes to afford the title compound as a white solid (1.14 g, 2.40 mmol, 67.7% step 7 &8 yield). MS m/z=476.9 M+. Calculated for $C_{19}H_{14}BrF5N_2O_2$: 477.223

Step 9: N-((4S,6S)-4-(5-amino-2-fluorophenyl)-4-(fluoromethyl)-6-(trifluoromethyl)-5,6-dihydro-4H-1,3-oxazin-2-yl)benzamide (1k)

A sealable vial was charged with (+)-sodium L-ascorbate (0.048 g, 0.241 mmol, Arcos Organics), sodium azide (0.470 g, 7.20 mmol, Aldrich), copper(I) iodide (0.138 g, 0.723 mmol, Aldrich), and N-((4S,6S)-4-(5-bromo-2-fluorophenyl)-4-(fluoromethyl)-6-(trifluoromethyl)-5,6-dihydro-4H-1,3-oxazin-2-yl)benzamide (1.15 g, 2.41 mmol, step 8). The sealed vial was evacuated and backfilled with nitrogen gas. EtOH (5.62 ml) was added followed by water (2.41 ml) and trans-N,N'-dimethylcyclohexane-1,2-diamine (0.069 g, 0.482 mmol). The reaction was stirred in a pre-heated 80° C. oil bath for 16 hours. The reaction mixture was cooled to RT and partitioned between water and EtOAc. The organic layer was washed with brine, dried over magnesium sulfate and concentrated under reduced pressure. The crude residue was taken up in MeOH (20 mL) and sodium borohydride (0.091 g, 2.41 mmol, Aldrich) was added. The reaction was stirred at room temperature for 30 minutes. The reaction was quenched with water and further diluted with water and EtOAc. The organic layer was washed three times with a solution of aqueous saturated ammonium hydroxide and aqueous saturated ammonium chloride solution (1:9), and brine. The organic phase was dried over magnesium sulfate and concentrated under reduced pressure to afford the crude title compound as a grey oil, which was used without further purification assuming theoretical yield. MS m/z=413.9 [M+H]+. Calculated for $C_{19}H_{16}F_5N_3O_2$: 413.341.

Example 2 (Method A)

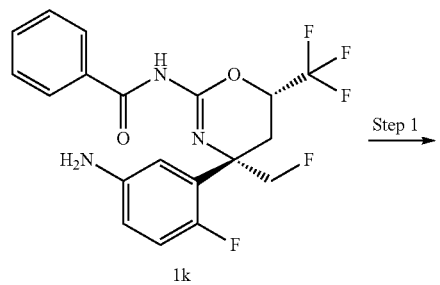

1k

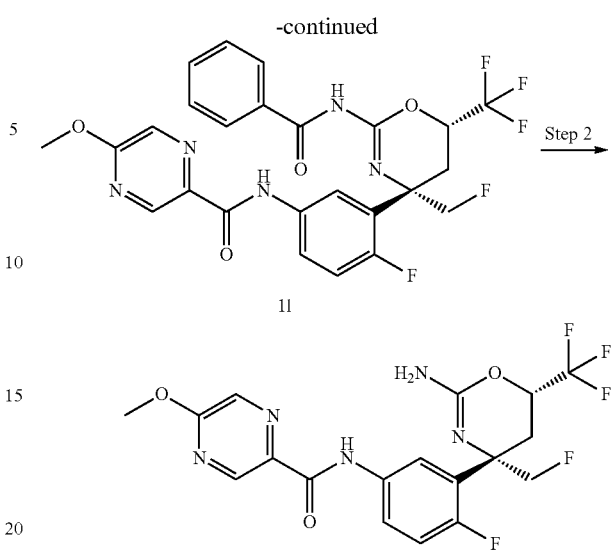

Step 1: N-(3-((4S,6S)-2-benzamido-4-(fluoromethyl)-6-(trifluoromethyl)-5,6-dihydro-4H-1,3-oxazin-4-yl)-4-fluorophenyl)-5-methoxypyrazine-2-carboxamide (11)

To a solution of crude N-((4S,6S)-4-(5-amino-2-fluorophenyl)-4-(fluoromethyl)-6-(trifluoromethyl)-5,6-dihydro-4H-1,3-oxazin-2-yl)benzamide (1k, 0.25 g, 0.605 mmol, step 9) in DMF (3 ml) was added 5-methoxypyrazine-2-carboxylic acid (0.117 g, 0.756 mmol, Ark Pharm), 1-[Bis(dimethylamino)methylene]-1H-1,2,3-triazolo[4,5-b]pyridinium 3-oxid hexafluorophosphate (0.345 g, 0.907 mmol, Oakwood Products) and di-isopropylethylamine (0.156 g, 1.210 mmol, Aldrich). The reaction was stirred at ambient temperature for 10 minutes. The reaction was diluted with water and EtOAc. The organic layer was separated and washed sequentially with aqueous saturated sodium bicarbonate solution, 1 M aqueous LiCl solution, and brine. The organic layer was dried over magnesium sulfate and concentrated under reduced pressure. The crude material was purified via silica gel flash chromatography using a gradient of 0-45% EtOAc in hexanes to afford the title compound as a white solid (0.110 g, 0.2 mmol, 33% overall yield for this step and steps 9 in Example 1). MS m/z=550.0 [M+H]+. Calculated for $C_{25}H_{20}F_5N_5O_4$: 549.449

Step 2: N-(3-((4S,6S)-2-amino-4-(fluoromethyl)-6-(trifluoromethyl)-5,6-dihydro-4H-1,3-oxazin-4-yl)-4-fluorophenyl)-5-methoxypyrazine-2-carboxamide (Example 2)

A microwave vial was charged with N-(3-((4S,6S)-2-benzamido-4-(fluoromethyl)-6-(trifluoromethyl)-5,6-dihydro-4H-1,3-oxazin-4-yl)-4-fluorophenyl)-5-methoxypyrazine-2-carboxamide (0.11 g, 0.200 mmol, step 1). MeOH (2 ml) was added followed by 1,8-diazabicyclo[5.4.0]undec-7-ene (0.122 g, 0.801 mmol, Aldrich). The vial was sealed and heated to 75° C. in a microwave (Biotage Initiator) for 1.5 hours. The reaction was cooled to RT and concentrated under reduced pressure. The crude material was purified via silica gel flash chromatography using a gradient of 5-70% EtOAc in hexanes to afford the title compound as a white solid (0.0741 g, 0.166 mmol, 83% yield). MS m/z=446.0 [M+H]+. Calculated for $C_{18}H_{16}F_5N_5O_3$: 445.343

¹H NMR (300 MHz, CHLOROFORM-d) δ ppm 2.25 (t, J=13.15 Hz, 1 H) 2.74 (dd, J=13.74, 2.78 Hz, 1 H) 4.08 (s, 3 H) 4.14-4.27 (m, 1 H) 4.41-4.62 (m, 1 H) 4.63-4.84 (m, 1 H) 7.14 (dd, J=11.55, 8.92 Hz, 1 H) 7.56 (dd, J=6.87, 2.78 Hz, 1 H) 8.03-8.10 (m, 1 H) 8.17 (d, J=1.32 Hz, 1 H) 9.02 (d, J=1.17 Hz, 1 H) 9.54 (s, 1 H)

Example 3

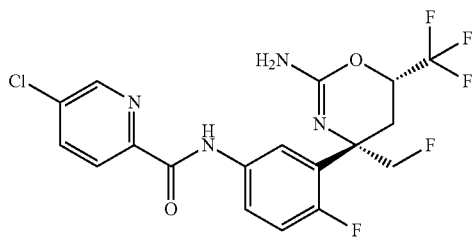 [SMILES: NC1=N[C@](CF)(c2cc(NC(=O)c3ccc(Cl)cn3)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide The title compound was synthesized by procedures and steps analogous to those described in Method A, Example 2 above, but using 5-chloropicolinic acid (Ark Pharm) in step 1. MS m/z=448.9 [M+H]⁺. Calculated for $C_{18}H_{14}ClF_5N_4O_2$: 448.774

¹H NMR (300 MHz, CHLOROFORM-d) δ ppm 2.27 (t, J=13.23 Hz, 1 H) 2.76 (dd, J=13.74, 2.63 Hz, 1 H) 4.16-4.29 (m, 1 H) 4.43-4.63 (m, 1 H) 4.64-4.85 (m, 1 H) 7.15 (dd, J=11.47, 8.84 Hz, 1 H) 7.59 (dd, J=6.94, 2.85 Hz, 1 H) 7.90 (dd, J=8.33, 2.34 Hz, 1H) 8.05-8.11 (m, 1 H) 8.25 (d, J=8.33 Hz, 1 H) 8.58 (d, J=1.75 Hz, 1 H) 9.88 (s, 1 H).

Example 4

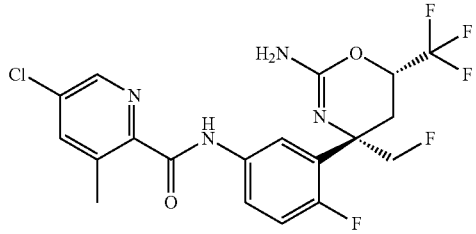 [SMILES: Cc1cc(Cl)cnc1C(=O)Nc1ccc(F)c([C@]2(CF)C[C@@H](C(F)(F)F)OC(N)=N2)c1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methylpicolinamide The title compound was synthesized by procedures and steps analogous to those described in Method A in Example 2 above, but using 5-chloro-3-methylpicolinic acid (Intermediate 6) in step 1. MS m/z=463.0 [M+H]⁺. Calculated for $C_{19}H_{16}ClF_5N_4O_2$: 462.801

¹H NMR (400 MHz, CHLOROFORM-d) δ ppm 2.22 (t, J=13.20 Hz, 1 H) 2.73 (dd, J=13.60, 2.64 Hz, 1 H) 2.79 (s, 3 H) 4.14-4.22 (m, 1 H) 4.41-4.58 (m, 1 H) 4.63-4.79 (m, 1 H) 7.11 (dd, J=11.54, 9.00 Hz, 1 H) 7.47 (dd, J=6.94, 2.84 Hz, 1 H) 7.65 (d, J=1.76 Hz, 1 H) 8.08 (ddd, J=8.85, 4.16, 2.84 Hz, 1 H) 8.39 (d, J=1.76 Hz, 1 H) 10.04 (s, 1 H).

Example 5

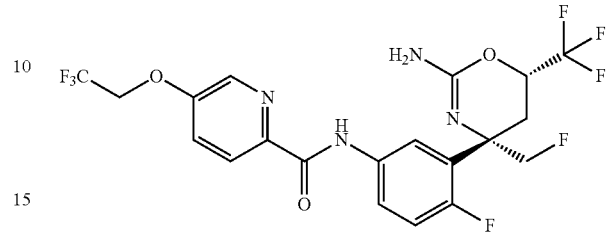

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(2,2,2-trifluoroethoxy)picolinamide The title compound was synthesized by procedures and steps analogous to those described in Method A, Example 2 above, but using 5-(2,2,2-trifluoroethoxy)picolinic acid (intermediate 5) in step 1. MS m/z=512.9 [M+H]⁺. Calculated for $C_{20}H_{16}F_8N_4O_3$: 512.353

¹H NMR (400 MHz, CHLOROFORM-d) δ ppm 2.23 (t, J=13.11 Hz, 1 H) 2.73 (dd, J=13.69, 2.54 Hz, 1 H) 4.14-4.24 (m, 1 H) 4.43-4.60 (m, 3 H) 4.65-4.81 (m, 1 H) 7.13 (dd, J=11.54, 8.80 Hz, 1 H) 7.41 (dd, J=8.71, 2.84 Hz, 1 H) 7.59 (dd, J=7.04, 2.74 Hz, 1 H) 8.05 (ddd, J=8.85, 4.16, 2.84 Hz, 1 H) 8.28 (d, J=8.61 Hz, 1 H) 8.35 (d, J=2.54 Hz, 1 H) 9.85 (s, 1 H)

Example 6

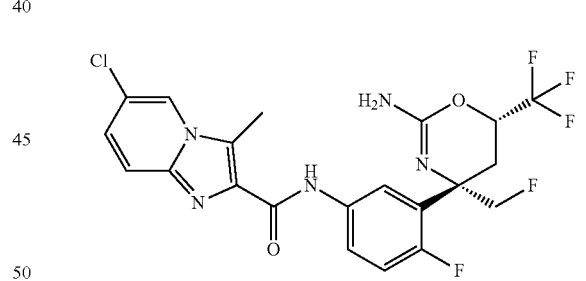

Synthesis of N-(3-((4S,6S)-2-amino-4-(fluoromethyl)-6-(trifluoromethyl)-5,6-dihydro-4H-1,3-oxazin-4-yl)-4-fluorophenyl)-6-chloro-3-methylimidazo[1,2-a]pyridine-2-carboxamide The title compound was synthesized by procedures and steps analogous to those described in Method A, Example 2 above, but using 6-chloro-3-methylimidazo[1,2-a]pyridine-2-carboxylic acid (described in WO 2012/078994) in step 10. MS m/z=501.9 [M+H]⁺. Calculated for $C_{21}H_{17}ClF_5N_5O_2$: 501.837

¹H NMR (300 MHz, CHLOROFORM-d) δ ppm 2.22 (t, J=13.23 Hz, 1H) 2.72 (dd, J=13.59, 2.63 Hz, 1 H) 2.86 (s, 3 H) 4.10-4.26 (m, 1 H) 4.38-4.60 (m, 1 H) 4.63-4.84 (m, 1 H) 7.11

(dd, J=11.47, 8.99 Hz, 1 H) 7.24 (m, J=2.00 Hz, 1 H) 7.49-7.56 (m, 2 H) 7.98-8.02 (m, 1 H) 8.07-8.14 (m, 1 H) 9.35 (s, 1H)

Example 7

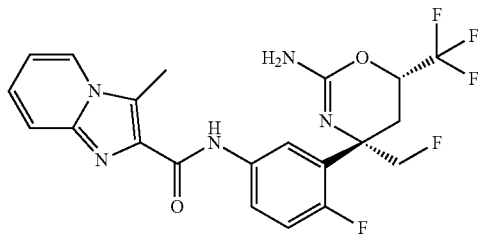 [SMILES: Cc1c(C(=O)Nc2ccc(F)c([C@]3(CF)C[C@@H](C(F)(F)F)OC(N)=N3)c2)nc2ccccn12]

N-(3-((4S,6S)-2-amino-4-(fluoromethyl)-6-(trifluoromethyl)-5,6-dihydro-4H-1,3-oxazin-4-yl)-4-fluorophenyl)-3-methylimidazo[1,2-a]pyridine-2-carboxamide A sealable vial was charged with N-(3-((4S,6S)-2-amino-4-(fluoromethyl)-6-(trifluoromethyl)-5,6-dihydro-4H-1,3-oxazin-4-yl)-4-fluorophenyl)-6-chloro-3-methylimidazo[1,2-a]pyridine-2-carboxamide (0.0513 g, 0.102 mmol, Example 6), bis[di-tert-butyl(4-dimethylaminophenyl)phosphine]dichloropalladium(II) (7.24 mg, 10.22 μmol) and sodium formate (21 mg, 0.307 mmol, Alfa Aesar). The sealed vial was evacuated and backfilled with nitrogen. DMF (1.3 ml) was added and the reaction was stirred in a preheated 110° C. oil bath for 1 hour. The reaction was cooled to RT and partitioned between water and EtOAc. The organic layer was separated, washed with brine, dried over magnesium sulfate and concentrated under reduced pressure. The crude residue was purified by silica gel flash chromatography using a gradient of 10-100% EtOAc in hexanes to afford the title compound as a white solid. (0.0385 g, 0.082 mmol, 81% yield). MS m/z=467.9 [M+H]$^+$. Calculated for $C_{21}H_{18}F_5N_5O_2$: 467.39

$^1$H NMR (300 MHz, CHLOROFORM-d) δ ppm 2.25 (t, J=13.15 Hz, 1H) 2.73 (dd, J=13.74, 2.63 Hz, 1 H) 2.88 (s, 3 H) 4.17-4.28 (m, 1 H) 4.40-4.61 (m, 1 H) 4.64-4.86 (m, 1 H) 6.94 (td, J=6.87, 1.02 Hz, 1 H) 7.12 (dd, J=11.55, 8.92 Hz, 1 H) 7.28-7.34 (m, 1 H) 7.51-7.62 (m, 2 H) 7.96 (d, J=7.02 Hz, 1H) 8.13 (ddd, J=8.84, 4.24, 2.85 Hz, 1 H) 9.44 (s, 1 H)

Example 8 (Method B)

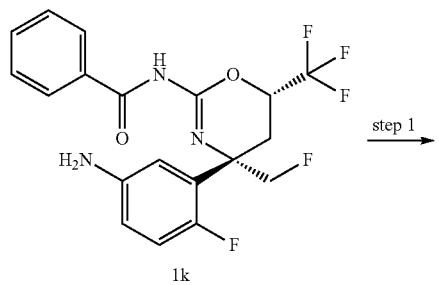

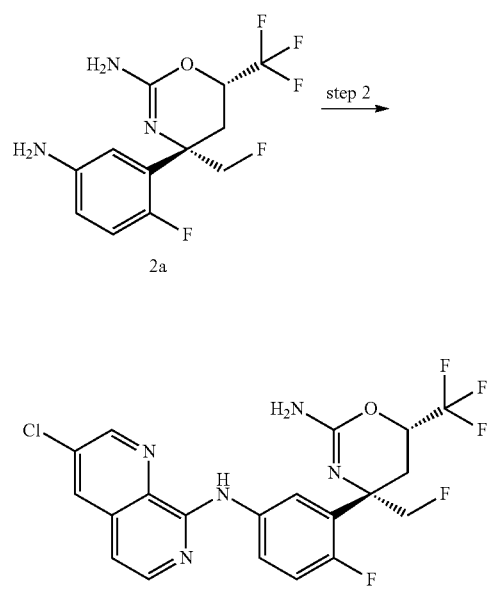

Step 1: (4S,6S)-4-(5-amino-2-fluorophenyl)-4-(fluoromethyl)-6-(trifluoromethyl)-5,6-dihydro-4H-1,3-oxazin-2-amine (2a)

A microwave vial was charged with a solution of crude N-((4S,6S)-4-(5-amino-2-fluorophenyl)-4-(fluoromethyl)-6-(trifluoromethyl)-5,6-dihydro-4H-1,3-oxazin-2-yl)benzamide (1k, 0.561 g, 1.357 mmol, Example 1 step 9) in MeOH (9 mL). 1,8-diazabicyclo[5.4.0]undec-7-ene (1.653 g, 10.86 mmol, Aldrich) was added and the vial was sealed. The reaction was heated to 80° C. in a microwave (Biotage Initiator) for a total of 135 minutes. The reaction was concentrated under reduced pressure. The crude material was taken up in EtOAc and washed with water (3x). The organic layer was extracted with 1N HCl (two times). The acidic aqueous layer was washed with EtOAc (twice). The acidic aqueous layer was basified with 5N NaOH to pH=12 and back extracted with EtOAc (twice). The organic layer was washed with brine, dried over magnesium sulfate and concentrated under reduced pressure to afford the crude title compound as a grey oil (0.345 g, 1.116 mmol, 82% crude yield) which was used in the next step without further purification. MS m/z=310.0 [M+H]$^+$. Calculated for $C_{12}H_{12}F_5N_3O$: 309.235

The crude material was also purified via reversed-phase preparative HPLC using a Phenomenex Gemini column, 10 micron, C18, 110 Å, 100×50 mm, 0.1% TFA in CH$_3$CN/H$_2$O, gradient 10% to 50% over 11 minutes to afford pure title compound as a white solid. MS m/z=310.0 [M+H]$^+$. Calculated for $C_{12}H_{12}F_5N_3O$: 309.235

$^1$H NMR (300 MHz, CHLOROFORM-d) δ ppm 2.20 (t, J=13.15 Hz, 1 H) 2.69 (dd, J=13.59, 2.78 Hz, 1 H) 3.50 (br. s, 2 H) 4.15-4.27 (m, 1 H) 4.37-4.57 (m, 1 H) 4.60-4.82 (m, 1 H) 6.60 (dt, J=8.51, 3.42 Hz, 1 H) 6.77 (dd, J=6.65, 3.00 Hz, 1 H) 6.88 (dd, J=11.69, 8.62 Hz, 1 H)

Step 2: (4S,6S)-4-(5-((3-chloro-1,7-naphthyridin-8-yl)amino)-2-fluorophenyl)-4-(fluoromethyl)-6-(trifluoromethyl)-5,6-dihydro-4H-1,3-oxazin-2-amine (Example 8)

A sealable vial was charged with crude (4S,6S)-4-(5-amino-2-fluorophenyl)-4-(fluoromethyl)-6-(trifluoromethyl)-5,6-dihydro-4H-1,3-oxazin-2-amine (345 mg, 1.116 mmol, step 1) and 3,8-dichloro-1,7-naphthyridine (Intermediate 2; 233 mg, 1.171 mmol). iPrOH (8 mL) was added and the suspension was briefly sonicated. Sulfuric acid (0.059 mL, 1.116 mmol, Aldrich) was added and the vial was sealed. The reaction was heated to 55° C. in an oil bath for one hour then cooled to RT and stirred for additional 16 hours. The reaction was diluted with water and EtOAc. The aqueous layer separated was basified to pH=12 by the addition of 1N NaOH. The aqueous layer was extracted with EtOAc (3×). The combined organic layers were washed with brine, dried over magnesium sulfate and concentrated under reduced pressure. The crude material was purified via silica gel chromatography using a gradient of 0-50% EtOAc:Hexanes to afford the title compound as a white solid. (130.8 mg, 0.277 mmol, 24.85% yield). MS m/z=472.0 [M+H]$^+$. Calculated for $C_{20}H_{15}ClF_5N_5O$: 471.811

$^1$H NMR (300 MHz, CHLOROFORM-d) δ ppm 2.23 (t, J=13.08 Hz, 1 H) 2.73 (dd, J=13.59, 2.78 Hz, 1 H) 4.24 (ddd, J=12.53, 5.66, 2.56 Hz, 1 H) 4.43-4.65 (m, 1H) 4.66-4.88 (m, 1 H) 6.92 (d, J=5.85 Hz, 1 H) 7.13 (dd, J=11.55, 8.92 Hz, 1 H) 7.77 (dd, J=6.94, 2.85 Hz, 1 H) 7.99 (d, J=2.34 Hz, 1 H) 8.12 (d, J=5.70 Hz, 1 H) 8.23 (ddd, J=8.84, 4.17, 2.92 Hz, 1 H) 8.67 (d, J=2.34 Hz, 1 H) 8.94 (s, 1 H).

Example 9

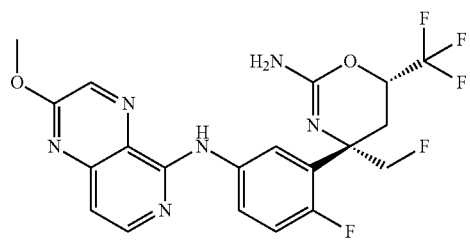 [SMILES: COc1cnc2c(Nc3ccc(F)c([C@]4(CF)C[C@@H](C(F)(F)F)OC(N)=N4)c3)nccc2n1]

Synthesis of (4S,6S)-4-(2-fluoro-5-((2-methoxypyrido[3,4-b]pyrazin-5-yl)amino)phenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 5-chloro-2-methoxypyrido[3,4-b]pyrazine (intermediate 3) in step 2. MS m/z=469.0 [M+H]$^+$. Calculated for $C_{20}H-F_5N_6O_2$: 468.380

$^1$H NMR (300 MHz, CHLOROFORM-d) δ ppm 2.24 (t, J=13.08 Hz, 1H) 2.73 (dd, J=13.59, 2.63 Hz, 1 H) 4.13 (s, 3 H) 4.19-4.32 (m, 1 H) 4.43-4.65 (m, 1 H) 4.66-4.87 (m, 1 H) 7.06 (d, J=5.99 Hz, 1 H) 7.12 (dd, J=11.55, 8.92 Hz, 1 H) 7.70 (dd, J=6.94, 2.85 Hz, 1 H) 8.18-8.26 (m, 2 H) 8.30 (s, 1 H) 8.62 (s, 1 H)

Example 10

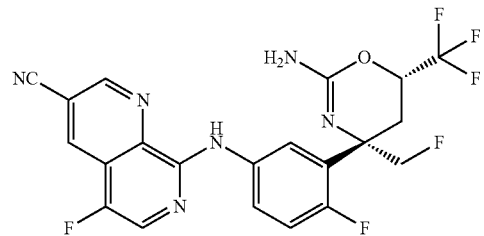 [SMILES: N#Cc1cnc2c(Nc3ccc(F)c([C@]4(CF)C[C@@H](C(F)(F)F)OC(N)=N4)c3)ncc(F)c2c1]

Synthesis of 8-((3-((4S,6S)-2-amino-4-(fluoromethyl)-6-(trifluoromethyl)-5,6-dihydro-4H-1,3-oxazin-4-yl)-4-fluorophenyl)amino)-5-fluoro-1,7-naphthyridine-3-carbonitrile The title compound was synthesized by procedures and steps analogous to those described in Method B, Example 8 above, but using 8-chloro-5-fluoro-1,7-naphthyridine-3-carbonitrile (intermediate 17) in step 2. MS m/z=480.9 [M+H]$^+$. Calculated for $C_{21}H_{14}F_6N_6O$: 480.11

$^1$H NMR (300 MHz, CHLOROFORM-d) δ ppm 2.19 (t, J=13.08 Hz, 1H) 2.70 (dd, J=13.67, 2.70 Hz, 1 H) 4.15-4.25 (m, 1 H) 4.37 (s, 1 H) 4.40-4.61 (m, 1 H) 4.61-4.84 (m, 1 H) 7.12 (dd, J=11.55, 8.77 Hz, 1 H) 7.74 (dd, J=6.87, 2.78 Hz, 1 H) 8.12 (d, J=1.17 Hz, 1 H) 8.13-8.19 (m, 1 H) 8.66 (d, J=1.90 Hz, 1 H) 8.83 (s, 1 H) 9.00 (d, J=1.90 Hz, 1 H).

Example 11

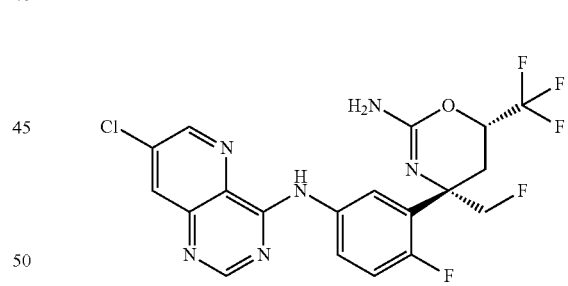

Synthesis of (4S,6S)-4-(5-((7-chloropyrido[3,2-d]pyrimidin-4-yl)amino)-2-fluorophenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 4,7-dichloropyrido[3,2-d]pyrimidine (intermediate 9) in step 2. MS m/z=472.9 [M]$^+$. Calculated for $C_{19}H_{14}ClF_5N_6O$: 472.8

$^1$H NMR (300 MHz, DMSO-$d_6$) δ ppm 2.00 (t, J=12.90 Hz, 2H) 4.30-4.81 (m, 3 H) 6.14 (br. s., 2 H) 7.25 (dd, J=11.77, 8.84 Hz, 1 H) 8.01 (dt, J=8.62, 3.58 Hz, 1 H) 8.16 (dd, J=7.38, 2.70 Hz, 1 H) 8.41 (d, J=2.19 Hz, 1H) 8.66 (s, 1 H) 8.94 (d, J=2.34 Hz, 1 H) 10.52 (s, 1 H)

Example 12

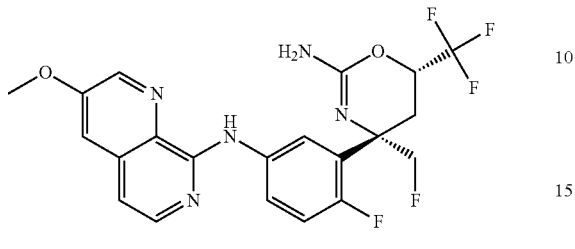

Synthesis of (4S,6S)-4-(2-fluoro-5-((3-methoxy-1,7-naphthyridin-8-yl)amino)phenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 8-chloro-3-methoxy-1,7-naphthyridine (intermediate 3l) in step 2. MS m/z=468 [M+H]$^+$. Calculated for $C_{21}H_{18}F_5N_5O_2$: 467.4

$^1$H NMR (400 MHz, CDCl$_3$) δ ppm 8.92 (s, 1 H), 8.49 (s, 1 H), 8.26 (m, 1 H), 8.06 (d, J=5.9 Hz, 1H), 7.72 (d, J=6.8 Hz, 1 H), 7.23 (s, 1 H), 7.11 (t, J=10.3 Hz, 1 H), 6.95 (d, J=5.7 Hz, 1 H), 4.85 (dd, J=9.2, 47.8, 1 H), 4.60 (dd, J=9.0, 47.4 Hz, 1 H), 4.46 (s broad, 1 H), 3.97 (s, 3 H), 2.74 (d, J=13.9 Hz, 1 H), 2.28 (t, J=13.1 Hz, 1 H).

Example 13

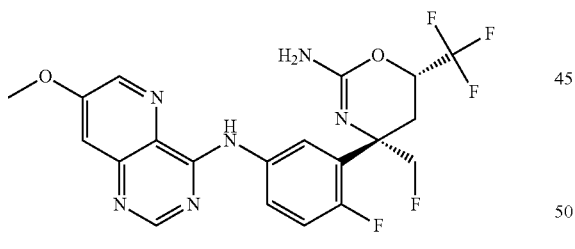

Synthesis of (4S,6S)-4-(2-fluoro-5-((7-methoxypyrido[3,2-d]pyrimidin-4-yl)amino)phenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 4-chloro-7-methoxypyrido[3,2-d]pyrimidine (intermediate 10) in step 2. MS m/z=469.1 [M+H]$^+$. Calculated for $C_{20}H_{17}F_5N_6O_2$: 468.4

$^1$H NMR (400 MHz, CDCl$_3$) δ ppm 8.96 (s, 1 H), 8.69 (s, 1 H), 8.49, (s, 1 H), 8.21 (m, 1H), 7.76 (d, J=6.6 Hz, 1 H), 7.41 (s, 1 H), 7.16 (t, J=10.0 Hz, 1 H), 4.81 (dd, J=8.8, 47.5, 1 H), 4.60 (dd, J=8.8, 47.1 Hz, 1 H), 4.46 (s broad, 1 H), 3.99 (s, 3 H), 2.73 (d, J=13.6 Hz, 1 H), 2.25 (t, J=13.7 Hz, 1 H).

Example 14

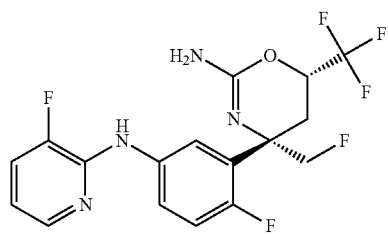 [SMILES: NC1=N[C@](CF)(c2cc(Nc3ncccc3F)ccc2F)C[C@@H](C(F)(F)F)O1]

Synthesis of (4S,6S)-4-(2-fluoro-5-((3-fluoropyridin-2-yl)-amino)phenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 2-chloro-3-fluoropyridine in step 2. MS m/z=405 [M+H]$^+$. Calculated for $C_{17}H_{14}F_6N_4O$: 404.3.

$^1$H NMR (400 MHz, CHLOROFORM-d) δ=7.97 (d, J=4.9 Hz, 1H), 7.94-7.86 (m, 1H), 7.46 (dd, J=2.9, 6.8 Hz, 1H), 7.31-7.23 (m, 1H), 7.06 (dd, J=8.8, 11.5 Hz, 1H), 6.72 (ddd, J=3.5, 4.8, 8.1 Hz, 1H), 6.62 (d, J=2.3 Hz, 1H), 4.81-4.36 (m, 2H), 4.27-4.12 (m, 1H), 2.67 (dd, J=2.7, 13.5 Hz, 1H), 2.17 (t, J=13.1 Hz, 1H).

Example 15

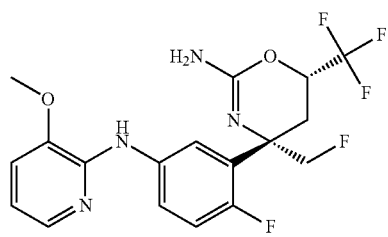 [SMILES: COc1cccnc1Nc1ccc(F)c([C@]2(CF)C[C@@H](C(F)(F)F)OC(N)=N2)c1]

Synthesis of (4S,6S)-4-(2-fluoro-5-((3-methoxypyridin-2-yl)-amino)phenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 2-bromo-3-methoxypyridine in step 2. MS m/z=417 [M+H]$^+$. Calculated for $C_{18}H_{17}F_5N_4O_2$: 416.3.

$^1$H NMR (400 MHz, CHLOROFORM-d) δ=8.02 (ddd, J=2.9, 4.1, 8.8 Hz, 1H), 7.79 (dd, J=1.4, 5.1 Hz, 1H), 7.42 (dd, J=2.8, 6.9 Hz, 1H), 7.10-6.94 (m, 3H), 6.71 (dd, J=5.1, 7.8

Hz, 1H), 4.81-4.27 (m, 4H), 4.25-4.15 (m, 1H), 3.90 (s, 3H), 2.67 (dd, J=2.7, 13.5 Hz, 1H), 2.17 (t, J=13.0 Hz, 1H).

Example 16

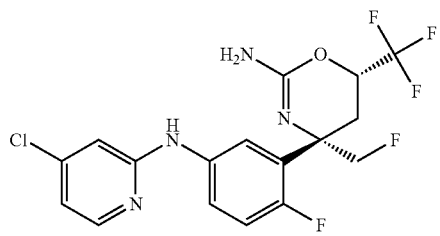 [SMILES: NC1=N[C@](CF)(c2cc(Nc3cc(Cl)ccn3)ccc2F)C[C@@H](C(F)(F)F)O1]

Synthesis of (4S,6S)-4-(5-((4-chloropyridin-2-yl) amino)-2-fluorophenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 2-bromo-4-chloropyridine in step 2. MS m/z=421 [M+H]⁺. Calculated for $C_{17}H_{14}ClF_5N_4O$: 420.8.

¹H NMR (400 MHz, CHLOROFORM-d) δ=8.79 (br. s., 1H), 8.23-8.10 (m, 1H), 7.41-7.23 (m, 2H), 7.03 (t, J=10.1 Hz, 1H), 6.58 (d, J=5.1 Hz, 1H), 6.56 (s, 1H), 5.75 (br. s., 2H), 4.61 (br. s., 1H), 4.49 (br. s., 1H), 4.19-4.05 (m, 1H), 2.67 (d, J=13.3 Hz, 1H), 2.10-1.98 (m, 1H).

Example 17

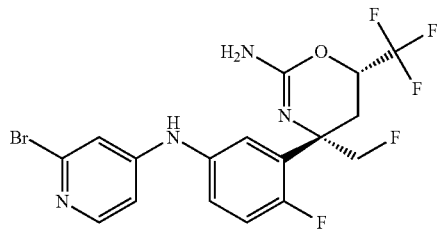

Synthesis of (4S,6S)-4-(5-((2-bromopyridin-4-yl) amino)-2-fluorophenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 2-bromo-4-chloropyridine in step 2. MS m/z=465, 467 [M+H]⁺. Calculated for $C_{17}H_{14}BrF_5N_4O$: 465.2.

¹H NMR (400 MHz, CHLOROFORM-d) δ=8.02 (d, J=5.5 Hz, 1H), 7.29 (d, J=6.5 Hz, 1H), 7.17 (br. s., 1H), 7.14-7.06 (m, 1H), 6.94 (s, 1H), 6.70 (d, J=5.5 Hz, 1H), 6.31 (br. s., 1H), 4.78-4.06 (m, 5H), 2.68 (d, J=13.5 Hz, 1H), 2.13 (t, J=13.1 Hz, 1H).

Example 18

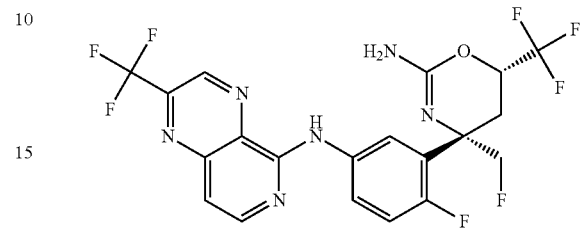

Synthesis of (4S,6S)-4-(2-fluoro-5-((2-(trifluoromethyl)pyrido[3,4-b]pyrazin-5-yl)amino)phenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 5-chloro-2-(trifluoromethyl)pyrido[3,4-b]pyrazine (ACES). MS m/z=506.9 [M+H]⁺. Calculated for $C_{20}H_{14}F_8N_6O$: 506.11

¹H NMR (300 MHz, DMSO-d₆) δ ppm 2.00 (t, J=12.72 Hz, 1 H) 4.30-4.74 (m, 3 H) 6.13 (s, 2 H) 7.22 (dd, J=11.77, 8.84 Hz, 1 H) 7.38 (d, J=5.99 Hz, 1 H) 8.00-8.11 (m, 1 H) 8.21 (dd, J=7.45, 2.78 Hz, 1 H) 8.40 (d, J=5.85 Hz, 1 H) 9.37 (s, 1 H) 10.14 (s, 1 H).

Example 19

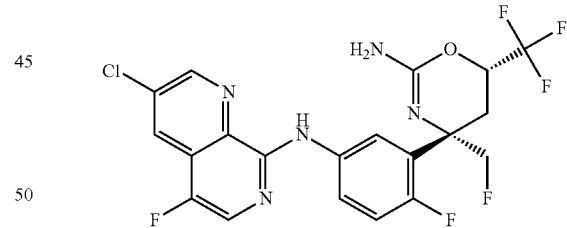

Synthesis of (4S,6S)-4-(5-((3-chloro-5-fluoro-1,7-naphthyridin-8-yl)amino)-2-fluorophenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 3,8-dichloro-5-fluoro-1,7-naphthyridine (Intermediate 7). MS m/z=489.8 [M+H]⁺. Calculated for $C_{20}H_{14}ClF_6N_5O$: 489.08

¹H NMR (300 MHz, DMSO-d₆) δ ppm 1.99 (dt, J=13.30, 1.00 Hz, 1 H) 4.27-4.75 (m, 3 H) 6.12 (s, 2 H) 7.18 (dd, J=11.84, 8.92 Hz, 1 H) 7.96-8.08 (m, 1 H) 8.11-8.21 (m, 2 H) 8.59 (d, J=2.19 Hz, 1 H) 9.02 (d, J=2.19 Hz, 1 H) 9.67 (s, 1 H).

Example 20

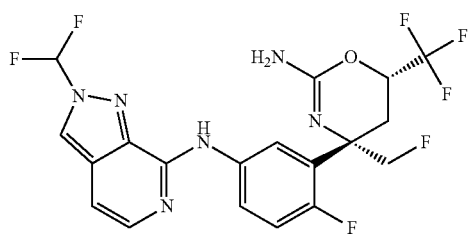 [SMILES: NC1=N[C@](CF)(c2cc(Nc3nccc4cn(C(F)F)nc34)ccc2F)C[C@@H](C(F)(F)F)O1]

Synthesis of (4S,6S)-4-(5-((2-(difluoromethyl)-2H-pyrazolo[3,4-c]pyridin-7-yl)amino)-2-fluorophenyl)-4-(fluoromethyl)-6-(trifluoromethyl)-5,6-dihydro-4H-1,3-oxazin-2-amine 2,2,2-trifluoroacetate The title compound was synthesized by procedures and steps analogous to those described in Method B, Example 8 above, but using 7-chloro-2-(difluoromethyl)-2H-pyrazolo[3,4-c]pyridine (intermediate 30). MS m/z=476.9 [M+H]$^+$. Calculated for $C_{19}H_{15}F_7N_6O$: 476.3

$^1$H NMR (400 MHz, CHLOROFORM-d) δ ppm 1.27 (s, 2 H) 2.62 (t, J=13.60 Hz, 1 H) 3.06 (d, J=14.08 Hz, 1 H) 4.76 (dd, J=18.88, 10.07 Hz, 1 H) 4.90 (d, J=9.98 Hz, 1 H) 5.08 (br. s., 1 H) 5.90 (br. s., 1 H) 7.28-7.36 (m, 2 H) 7.50-7.92 (m, 3 H) 7.88 (t, J=59.30 Hz, 1 H) 7.71-7.71 (m, 1 H) 8.27 (s, 1 H)

Example 21

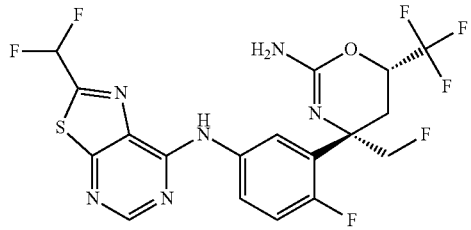 [SMILES: NC1=N[C@](CF)(c2cc(Nc3ncnc4sc(C(F)F)nc34)ccc2F)C[C@@H](C(F)(F)F)O1]

Synthesis of (4S,6S)-4-(5-((2-(difluoromethyl)thiazolo[5,4-d]pyrimidin-7-yl)amino)-2-fluorophenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using 7-chloro-2-(difluoromethyl)thiazolo[5,4-d]pyrimidine (intermediate 1) in step 2. MS m/z=494.9 [M+H]$^+$. Calculated for $C_{18}H_{13}F_7N_6OS$: 494.4

$^1$H NMR (300 MHz, DMSO-d$_6$) δ ppm 10.57 (s, 1 H), 8.59 (s, 1 H), 8.06 (dd, J=7.38, 2.70 Hz, 1 H), 7.81-7.95 (m, 1 H), 7.49 (t, J=53.93 Hz, 1 H), 7.23 (dd, J=11.84, 8.92 Hz, 1 H), 6.11 (s, 2 H), 4.22-4.77 (m, 3 H), 2.47 (d, J=2.63 Hz, 1 H), 1.99 (t, J=12.93 Hz, 1 H)

Example 22 (Method C)

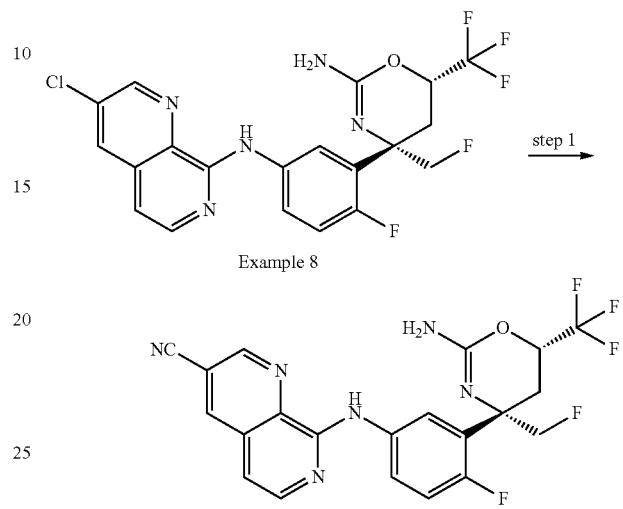

Example 8

Step 1: 8-((3-((4S,6S)-2-amino-4-(fluoromethyl)-6-(trifluoromethyl)-5,6-dihydro-4H-1,3-oxazin-4-yl)-4-fluorophenyl)amino)-1,7-naphthyridine-3-carbonitrile (Example 12)

A microwave vial was charged with (4S,6S)-4-(5-((3-chloro-1,7-naphthyridin-8-yl)amino)-2-fluorophenyl)-4-(fluoromethyl)-6-(trifluoromethyl)-5,6-dihydro-4H-1,3-oxazin-2-amine (0.123 g, 0.261 mmol, (Example 8), 2-Dicyclohexylphosphino-2',6'-dimethoxybiphenyl (0.021 g, 0.052 mmol, Strem), zinc cyanide (0.046 g, 0.392 mmol, Aldrich), and Pd$_2$(dba)$_3$ (0.019 g, 0.021 mmol, Strem). The sealed vial was evacuated and backfilled with nitrogen gas. A solution of DMF/water (1.30 ml; 100:1) was added and the reaction was stirred in a pre-heated 120° C. oil bath for 1 hour. The reaction was cooled to RT and additional Pd$_2$(dba)$_3$ (0.019 g, 0.021 mmol, Strem), zinc cyanide (0.046 g, 0.392 mmol, Aldrich), and 2-Dicyclohexylphosphino-2',6'-dimethoxybiphenyl (0.021 g, 0.052 mmol, Strem) were added. The vial was re-sealed and flushed with nitrogen gas. The reaction was stirred in a pre-heated 120° C. oil bath for 1 hour. The reaction was cooled to RT and additional Pd$_2$(dba)$_3$ (0.019 g, 0.021 mmol, Strem), zinc cyanide (0.046 g, 0.392 mmol, Aldrich), and 2-dicyclohexylphosphino-2',6'-dimethoxybiphenyl (0.021 g, 0.052 mmol, Strem) were added. The vial was re-sealed, flushed with nitrogen gas and heated to 120° C. in the microwave (Biotage Initiator) for 15 minutes. The reaction was cooled to RT and stirred for 16 hours. The reaction was diluted with water and EtOAc. The organic layer was washed with brine, dried over magnesium sulfate and concentrated under reduced pressure. The crude residue was purified via silica gel flash chromatography using a gradient of 0-50% EtOAc:Hexanes to afford the title compound as a white solid (51.44 mg, 0.111 mmol, 42.6% yield). MS m/z=463.0 [M+H]$^+$. Calculated for $C_{21}H_{15}F_5N_6O$: 462.375

$^1$H NMR (300 MHz, CHLOROFORM-d) δ ppm 2.35 (t, J=13.37 Hz, 1 H) 2.82 (dd, J=13.67, 2.56 Hz, 1 H) 4.35 (br. s., 1 H) 4.51-4.92 (m, 2 H) 7.06 (d, J=5.85 Hz, 1 H) 7.18 (dd, J=11.55, 8.92 Hz, 1 H) 7.88 (dd, J=7.02, 2.92 Hz, 1 H) 8.18-8.25 (m, 1 H) 8.27 (d, J=5.70 Hz, 1 H) 8.41 (d, J=2.05 Hz, 1 H) 8.96 (d, J=2.05 Hz, 1 H) 9.05 (s, 1 H)

Example 23

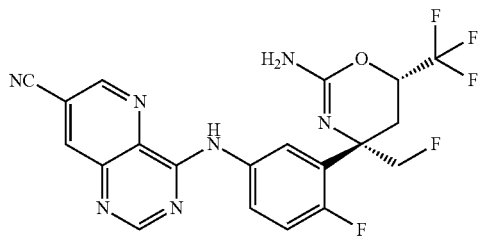 [SMILES: N#Cc1cnc2c(Nc3ccc(F)c([C@]4(CF)C[C@@H](C(F)(F)F)OC(N)=N4)c3)ncnc2c1]

Synthesis of 4-((3-((4S,6S)-2-amino-4-(fluoromethyl)-6-(trifluoromethyl)-5,6-dihydro-4H-1,3-oxazin-4-yl)-4-fluorophenyl)amino)pyrido[3,2-d]pyrimidine-7-carbonitrile The title compound was synthesized by procedures and steps analogous to those described in Method C, Example 11 above, but using (4S,6S)-4-(5-((7-chloropyrido[3,2-d]pyrimidin-4-yl)amino)-2-fluorophenyl)-4-(fluoromethyl)-6-(trifluoromethyl)-5,6-dihydro-4H-1,3-oxazin-2-amine (Example 11). MS m/z=464 [M+H]$^+$. Calculated for $C_{20}H_{14}F_5N_7O$: 463.4

$^1$H NMR (300 MHz, DMSO-d$_6$) δ ppm 2.00 (t, J=12.90 Hz, 1 H) 2.50 (m, under DMSO solvent peak, 1 H) 4.25-4.83 (m, 3 H) 6.13 (br. s., 2 H) 7.26 (dd, J=11.84, 8.92 Hz, 1 H) 8.00 (dt, J=8.37, 3.64 Hz, 1 H) 8.17 (dd, J=7.31, 2.63 Hz, 1 H) 8.72 (s, 1 H) 8.88 (d, J=1.90 Hz, 1 H) 9.25 (d, J=1.90 Hz, 1 H) 10.66 (s, 1 H)

Example 24

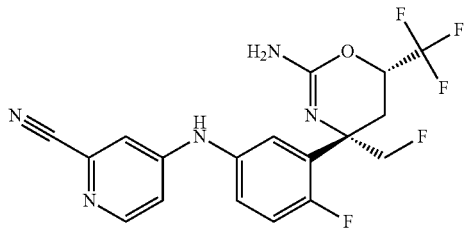 [SMILES: N#Cc1cc(Nc2ccc(F)c([C@]3(CF)C[C@@H](C(F)(F)F)OC(N)=N3)c2)ccn1]

Synthesis of 4-((3-((4S,6S)-2-amino-4-(fluoromethyl)-6-(trifluoromethyl)-5,6-dihydro-4H-1,3-oxazin-4-yl)-4-fluorophenyl)amino)picolinonitrile The title compound was synthesized by procedures and steps analogous to those described in Method C, Example 12, but using (4S,6S)-4-(5-((2-bromopyridin-4-yl)amino)-2-fluorophenyl)-4-(fluoromethyl)-6-(trifluoromethyl)-5,6-dihydro-4H-1,3-oxazin-2-amine (Example 17). MS m/z=412 [M+H]$^+$. Calculated for $C_{18}H_{14}F_5N_5O$: 411.3.

$^1$H NMR (400 MHz, CHLOROFORM-d) δ=8.30 (d, J=5.7 Hz, 1H), 7.32 (d, J=6.7 Hz, 1H), 7.28-7.09 (m, 2H), 7.05 (br. s., 1H), 6.99-6.92 (m, 1H), 4.98 (br. s., 2H), 4.74-4.43 (m, 2H), 4.14 (d, J=6.1 Hz, 1H), 2.67 (d, J=13.5 Hz, 1H), 2.11 (t, J=13.1 Hz, 1H).

Example 25 (Method D)

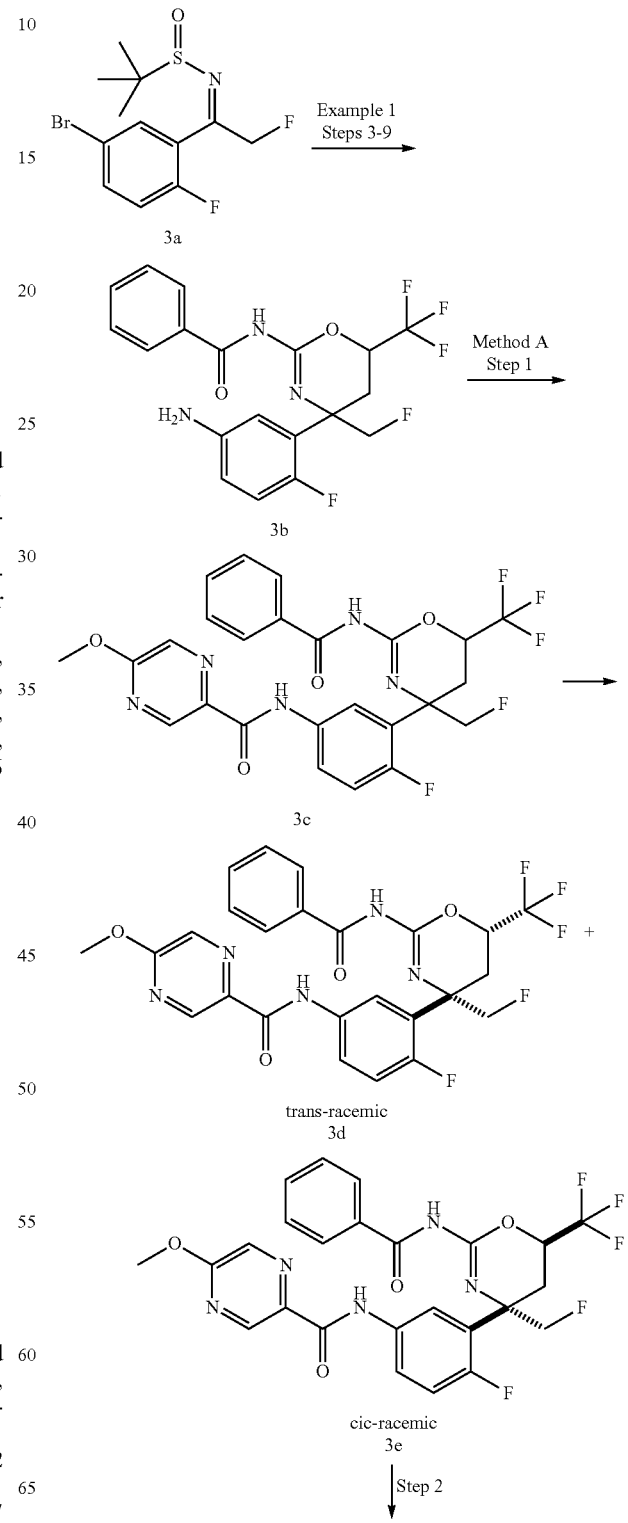

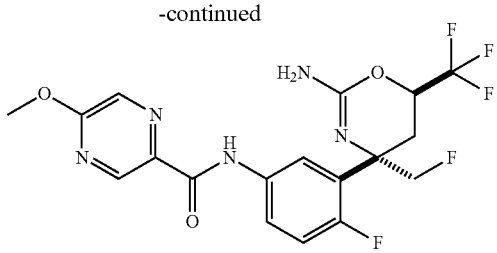

pound as a white solid (24.8 mg, 0.056 mmol, 24.09% yield). MS m/z=446.0 [M+H]⁺. Calculated for $C_{18}H_{16}F_5N_5O_3$: 445.343

¹H NMR (300 MHz, CHLOROFORM-d) δ ppm 1.94 (t, J=14.03 Hz, 1 H) 2.96-3.06 (m, 1 H) 4.08 (s, 2 H) 4.22-4.44 (m, 1 H) 4.83-5.06 (m, 2 H) 7.09 (dd, J=11.40, 8.77 Hz, 1 H) 7.96 (dd, J=6.58, 2.78 Hz, 1 H) 8.00-8.09 (m, 1 H) 8.17 (d, J=1.17 Hz, 1 H) 9.03 (d, J=1.17 Hz, 1 H) 9.56 (s, 1 H).

Example 26 (Method E)

Synthesis of N-(3-((4S,6S)-2-amino-4-methyl-6-(trifluoromethyl)-5,6-dihydro-4H-1,3-oxazin-4-yl)-4-fluorophenyl)-5-chloropicolinamide

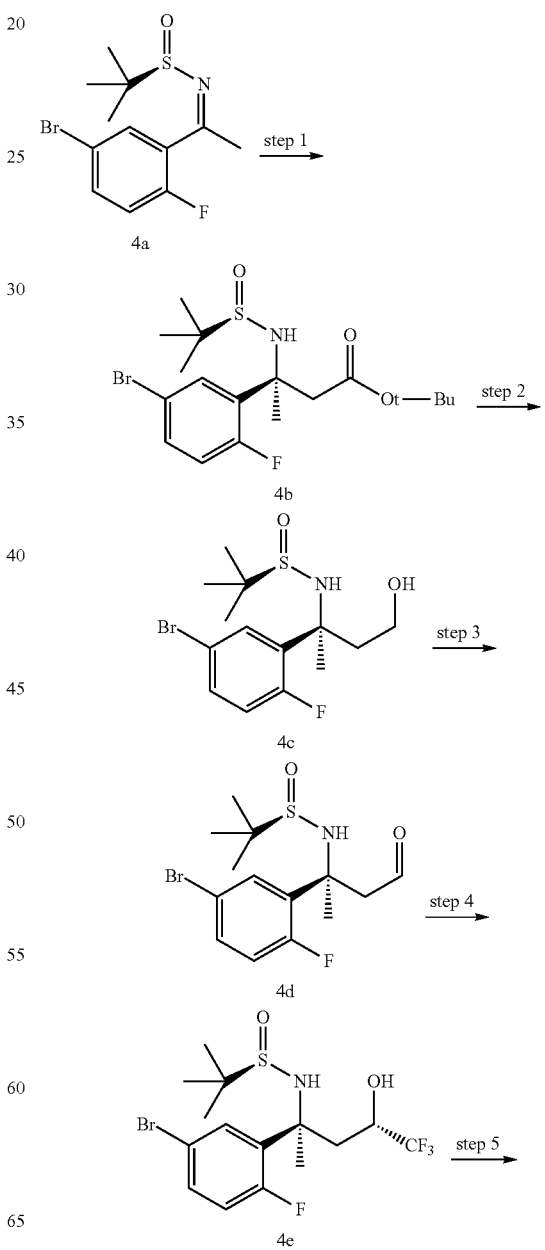

Synthesis of N-(4-(5-amino-2-fluorophenyl)-4-(fluoromethyl)-6-(trifluoromethyl)-5,6-dihydro-4H-1,3-oxazin-2-yl)-benzamide (3b)

The title compound was synthesized using steps and procedures analogous to those described in Example 1 (Intermediate Synthesis steps 3-9) above but using racemic N-(1-(5-bromo-2-fluorophenyl)-2-fluoroethylidene)-2-methylpropane-2-sulfinamide (3a). MS m/z=413.9 [M+H]⁺. Calculated for $C_{19}H_{16}F_5N_3O_2$: 413.341

Synthesis of N-(3-(2-benzamido-4-(fluoromethyl)-6-(trifluoromethyl)-5,6-dihydro-4H-1,3-oxazin-4-yl)-4-fluorophenyl)-5-methoxypyrazine-2-carboxamide (3c)

The title compound was synthesized using a procedure analogous to Example 2 Method A, step 1 above but using racemic N-(4-(5-amino-2-fluorophenyl)-4-(fluoromethyl)-6-(trifluoromethyl)-5,6-dihydro-4H-1,3-oxazin-2-yl)benzamide (3b).

Separation of racemic diastereomers N-(3-((4S,6S)-2-benzamido-4-(fluoromethyl)-6-(trifluoromethyl)-5,6-dihydro-4H-1,3-oxazin-4-yl)-4-fluorophenyl)-5-methoxypyrazine-2-carboxamide (3d) and N-(3-((4S,6R)-2-benzamido-4-(fluoromethyl)-6-(trifluoromethyl)-5,6-dihydro-4H-1,3-oxazin-4-yl)-4-fluorophenyl)-5-methoxypyrazine-2-carboxamide (3e)

The two diastereomers were separated via silica gel flash chromatography using a gradient of 10-70% EtOAc in Hexanes to afford racemic (3d) and (3e) MS m/z=550.0 [M+H]⁺ for both sets of racemic diastereomers: Calculated for $C_{25}H_{20}F_5N_5O_4$: 549.449

Step 2: N-(3-((4S,6R)-2-amino-4-(fluoromethyl)-6-(trifluoromethyl)-5,6-dihydro-4H-1,3-oxazin-4-yl)-4-fluorophenyl)-5-methoxypyrazine-2-carboxamide (racemic Example 14)

A sealable vial was charged with racemic-cis N-(3-((4S,6R)-2-benzamido-4-(fluoromethyl)-6-(trifluoromethyl)-5,6-dihydro-4H-1,3-oxazin-4-yl)-4-fluorophenyl)-5-methoxypyrazine-2-carboxamide (0.127 g, 0.231 mmol, (3e) step 1) and ammonia, 2.0M in MeOH (3.47 ml, 6.93 mmol, Aldrich). The vial was sealed and heated to 80° C. for 16 hours. The reaction was cooled to room temperature and concentrated under reduced pressure. The material was taken up in EtOAc and washed with water (3×) and brine. The organic layer was dried over magnesium sulfate and concentrated under reduced pressure. The crude material was purified via silica gel flash chromatography using a gradient of 0-10% 2M ammonia in MeOH in DCM to afford the racemic title com-

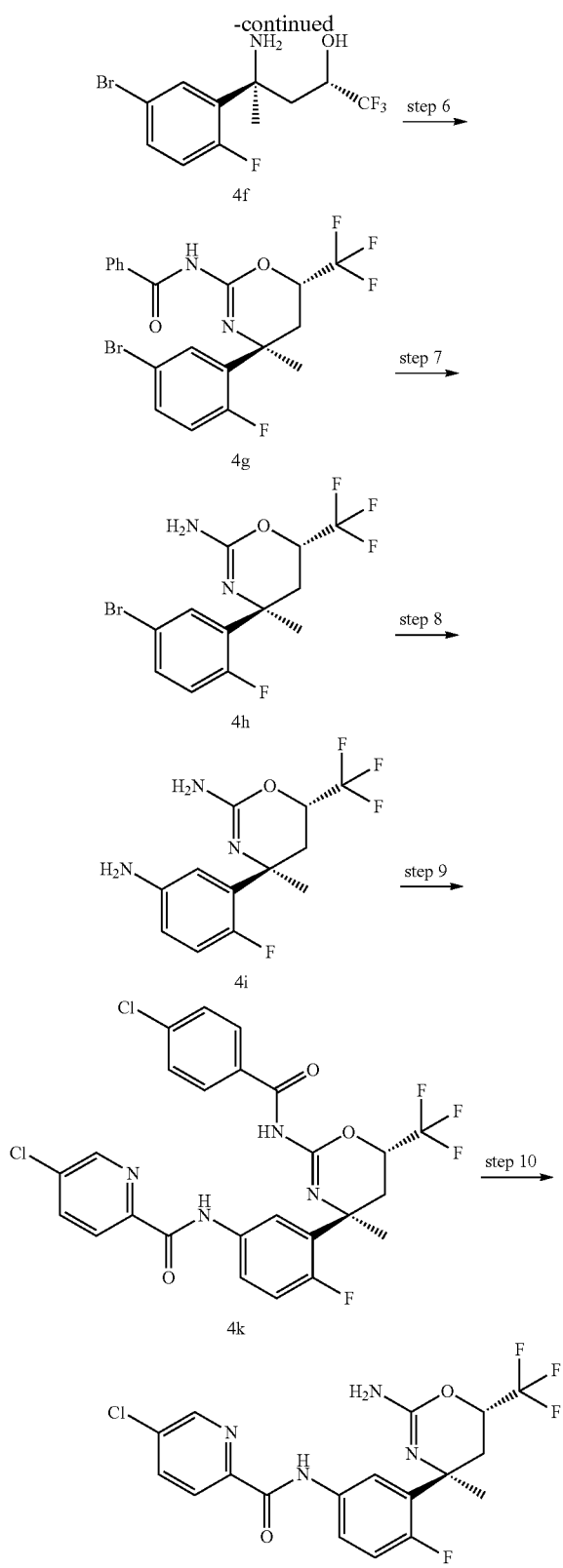

sized according to procedure in WO2009134617, 8.649 g, 27.0 mmol) in THF (100 mL) was cooled to −78° C. under Argon. A 0.5 M solution of (2-(tert-butoxy)-2-oxoethyl)zinc (II) chloride (Riecke Metals; 140 mL, 70.0 mmol) in diethyl ether was added dropwise over 45 min. The resulting solution was allowed to slowly warm up to ambient temperature over ~5 h (warming rate: ~10° C. per 30 min) and then stirred overnight.

The solution was cooled to −20° C. and quenched with saturated aqueous $NH_4Cl$ (~7 M; 12 mL, ~84 mmol) added dropwise. The mixture was allowed to warm to ambient temperature and then concentrated. The resulting semi-solid was extracted into $CH_2Cl_2$ from saturated aqueous $NaHCO_3$. The organic extracts were dried over $MgSO_4$ and concentrated to give (S)-tert-butyl 3-(5-bromo-2-fluorophenyl)-3-((R)-1,1-dimethylethylsulfinamido)butanoate (11.946 g, 27.4 mmol) as an orange gum, which was taken on crude to the next step. MS m/z=436 $M^+$, Calculated for $C_{18}H_{27}BrFNO_3S$: 436.4

Step 2: (R)-N-((S)-2-(5-bromo-2-fluorophenyl)-4-hydroxybutan-2-yl)-2-methylpropane-2-sulfinamide (4c)

A solution of (S)-tert-butyl 3-(5-bromo-2-fluorophenyl)-3-((R)-1,1-dimethylethylsulfinamido)butanoate (4b, 11.946 g, 27.4 mmol) in THF (100 mL) was placed in a water bath at 20° C. and stirred for 5 min. Lithium borohydride (Aldrich, 1.193 g, 54.8 mmol) was added and the resulting solution was stirred for 10 min. Anhydrous methanol (2.2 mL, 54.3 mmol) was added dropwise over 10 min. The reaction was stirred at ambient temperature. The reaction mixture was heated to 65° C. and maintained at that temperature for 20 h. The mixture was cooled to room temperature and quenched with methanol (10 mL). The mixture was diluted with saturated aqueous $NaHCO_3$ (250 mL) and then EtOAc (300 mL) and stirred for 15 min. The aqueous layer was separated and extracted with EtOAc (2×100 mL). The combined organic extracts were dried over $MgSO_4$ and concentrated to give an orange oil (9.92 g). Purification by silica gel chromatography (Gradient: 50%→100% EtOAc/hexane) gave (R)-N-((S)-2-(5-bromo-2-fluorophenyl)-4-hydroxybutan-2-yl)-2-methylpropane-2-sulfinamide (2.632 g, 7.19 mmol) as a single diastereomer. MS m/z=365.9 $M^+$ Calculated for $C_{14}H_{21}BrFNO_2S$: 366.3

Step 3: (R)-N-((S)-2-(5-bromo-2-fluorophenyl)-4-oxobutan-2-yl)-2-methylpropane-2-sulfinamide (4d)

A 100 mL flask containing (R)-N-((S)-2-(5-Bromo-2-fluorophenyl)-4-hydroxybutan-2-yl)-2-methylpropane-2-sulfinamide (4c, 2.472 g, 6.75 mmol) under nitrogen was placed in a water bath and treated with Dess-Martin periodinane (Aldrich; 0.3 M in $CH_2Cl_2$; 25 mL, 7.50 mmol). The mixture was stirred at ambient temperature for 3 h, after which the reaction was quenched with saturated aqueous sodium thiosulfate solution (7.5 mL) and stirred for 15 min. The product was extracted into $CH_2Cl_2$ from saturated aqueous $NaHCO_3$, dried over $Na_2SO_4$, concentrated, and purified by chromatography on silica gel [Gradient: 20%→100% EtOAc/hexane] to give (R)-N-((S)-2-(5-bromo-2-fluorophenyl)-4-oxobutan-2-yl)-2-methylpropane-2-sulfinamide (2.03 g, 5.57 mmol) as a colorless gum. MS m/z=365.9 $[M+H]^+$. Calculated for $C_{14}H_{19}BrFNO_2S$: 364.3

Step 4: (R)-N-((2S,4S)-2-(5-bromo-2-fluorophenyl)-5,5,5-trifluoro-4-hydroxypentan-2-yl)-2-methylpropane-2-sulfinamide (4e)

A solution of (R)-N-((S)-2-(5-bromo-2-fluorophenyl)-4-oxobutan-2-yl)-2-methylpropane-2-sulfinamide (4d, 2.03 g, Step 1: (S)-tert-butyl 3-(5-bromo-2-fluorophenyl)-3-((R)-1,1-dimethylethylsulfinamido)-butanoate (4b)

A solution of (R,E)-N-(1-(5-bromo-2-fluorophenyl)ethylidene)-2-methylpropane-2-sulfinamide (4a was synthe- 5.57 mmol) in THF (70 mL) was cooled to −78° C. under Nitrogen. Trimethyl(trifluoromethyl)silane (Aldrich; 8.24 mL, 55.7 mmol) was added dropwise over 10 min, and the mixture was then stirred for 15 min. A solution of TBAF (Aldrich; 1.0 M in THF) (5.57 mL, 5.57 mmol) in THF (20 mL) was added dropwise over 3 h. Stirring was continued for a further 3 h at −78° C. The reaction was quenched at −78° C. by the dropwise addition of saturated aqueous ammonium chloride solution (25 mL) and then allowed to slowly warm up to ambient temperature overnight.

The mixture was concentrated and then extracted into EtOAc from saturated aqueous NaHCO$_3$. The organic extract was dried over MgSO$_4$, concentrated, and purified by flash chromatography on silica gel [Gradient: 0%→100% EtOAc/CH$_2$Cl$_2$] to give (R)-N-((2S,4S)-2-(5-bromo-2-fluorophenyl)-5,5,5-trifluoro-4-hydroxypentan-2-yl)-2-methylpropane-2-sulfinamide (821 mg, 1.890 mmol) as a white crystalline solid. MS m/z=433.9 M$^+$. Calculated for C$_{15}$H$_{20}$BrF$_4$NO$_2$S: 434.3

Step 5: (2S,4S)-4-amino-4-(5-bromo-2-fluorophenyl)-1,1,1-trifluoropentan-2-ol hydrochloride (4f)

A solution of (R)-N-((2S,4S)-2-(5-bromo-2-fluorophenyl)-5,5,5-trifluoro-4-hydroxypentan-2-yl)-2-methylpropane-2-sulfinamide (4e, 821 mg, 1.89 mmol) in CH$_2$Cl$_2$ (20 mL) and MeOH (10 mL) was treated with HCl (Aldrich; 4.0 M in 1,4-dioxane) (4.7 mL, 18.80 mmol). The solution was allowed to stir for 30 min at room temperature. The solution was concentrated to give a pale yellow gum. The gum was dissolved in a small volume of diethyl ether (~5 mL) and diluted with hexane (~50 mL) resulting in a fine white precipitate. The mixture was concentrated to remove most of the solvent and then rediluted with hexane (~20 mL). The white solid was filtered off, washed with hexane and identified as (2S,4S)-4-amino-4-(5-bromo-2-fluorophenyl)-1,1,1-trifluoropentan-2-ol hydrochloride (732 mg, 1.997 mmol). MS m/z=329.9 M$^+$. Calculated for C$_{11}$H$_{12}$BrF$_4$NO: 330

Step 6: N-((4S,6S)-4-(5-bromo-2-fluorophenyl)-4-methyl-6-(trifluoromethyl)-5,6-dihydro-4H-1,3-oxazin-2-yl)benzamide (4g)

A solution of (2S,4S)-4-amino-4-(5-bromo-2-fluorophenyl)-1,1,1-trifluoropentan-2-ol hydrochloride (4f, 693 mg, 1.890 mmol) in THF (10 mL) was treated with diisopropylethylamine (Aldrich; 823 µL, 4.73 mmol) and stirred for 5 min. Benzoyl isothiocyanate (Aldrich; 280 µL, 2.083 mmol) was added dropwise and the reaction mixture was stirred for 3 h. The reaction mixture was treated with 1-[3-(dimethylamino)propyl]-3-ethylcarbodiimide methiodide (Aldrich; 674 mg, 2.270 mmol) and heated to 70° C. for 2 h and subsequently to 50° C. for 16 h. The reaction mixture was concentrated and extracted into EtOAc from saturated brine. The combined organic extracts were dried over MgSO$_4$, concentrated, and purified by flash chromatography on silica gel (Gradient: 0%→25% EtOAc/hexane to give N-((4S,6S)-4-(5-bromo-2-fluorophenyl)-4-methyl-6-(trifluoromethyl)-5,6-dihydro-4H-1,3-oxazin-2-yl)benzamide (789 mg, 1.718 mmol) as a white solid. MS m/z=460.9 [M+H]$^+$. Calculated for C$_{19}$H$_{15}$BrF$_4$N$_2$O$_2$: 459.2

Step 7: (4S,6S)-4-(5-bromo-2-fluorophenyl)-4-methyl-6-(trifluoromethyl)-5,6-dihydro-4H-1,3-oxazin-2-amine (4h)

A solution of N-((4S,6S)-4-(5-bromo-2-fluorophenyl)-4-methyl-6-(trifluoromethyl)-5,6-dihydro-4H-1,3-oxazin-2-yl)benzamide (4 g, 789 mg, 1.718 mmol) in anhydrous MeOH (20 mL) was treated with 1,8-diazabicyclo-[5.4.0]undec-7-ene (Aldrich; 311 µL, 2.063 mmol) and heated to 65° C. for 16 h. The reaction mixture was concentrated and extracted into EtOAc from saturated aqueous NH$_4$Cl. The organic extract was dried over MgSO$_4$, concentrated, and purified by flash chromatography on silica gel (Gradient: 0%→50% EtOAc/hexane) to give (4S,6S)-4-(5-bromo-2-fluorophenyl)-4-methyl-6-(trifluoromethyl)-5,6-dihydro-4H-1,3-oxazin-2-amine (585 mg, 1.647 mmol) as a white foam. MS m/z=355 M$^+$. Calculated for C$_{12}$H$_{11}$BrF$_4$N$_2$O: 355.1

Step 8: (4S,6S)-4-(5-amino-2-fluorophenyl)-4-methyl-6-(trifluoromethyl)-5,6-dihydro-4H-1,3-oxazin-2-amine (4i)

A sealable vial was charged with (4S,6S)-4-(5-bromo-2-fluorophenyl)-4-methyl-6-(trifluoromethyl)-5,6-dihydro-4H-1,3-oxazin-2-amine (4h, 585 mg, 1.647 mmol), sodium L-ascorbate (Acros; 32.6 mg, 0.165 mmol), sodium azide (Aldrich; 321 mg, 4.94 mmol), and copper(I) iodide (Aldrich; 94 mg, 0.494 mmol). The vial was evacuated and backfilled with Argon. EtOH (5.0 mL) and water (2.1 mL) were added, the reaction mixture purged with Argon, and then treated with N,N'-dimethyl-trans-1,2-cyclohexanediamine (Aldrich; 52.0 µL, 0.330 mmol). The reaction mixture was heated to 80° C. for 5 h and then stirred at ambient temperature for 16 h. A mixture of saturated aqueous NH$_4$Cl and concentrated ammoniumhydroxide (5 mL; 9:1) was added, followed by EtOAc (10 mL). After 30 min, the reaction mixture was poured into a mixture of saturated aqueous NH$_4$Cl/concentrated ammoniumhydroxide (50 mL; 9:1) and extracted with EtOAc (3×50 mL). The combined organic extracts were dried over Na$_2$SO$_4$ and concentrated to give a brown foam, which was dissolved in THF/water (8 mL; 3:1) and treated with trimethylphosphine (Aldrich; 1.0 M in THF) (2.0 mL, 2.000 mmol). The reaction mixture was stirred for 2 days and then concentrated under reduced pressure. The crude product was purified by flash chromatography on silica gel (Gradient: 0%→10% MeOH/CH$_2$Cl$_2$) to give (4S,6S)-4-(5-amino-2-fluorophenyl)-4-methyl-6-(trifluoromethyl)-5,6-dihydro-4H-1,3-oxazin-2-amine (419 mg, 1.439 mmol) as a white foam. MS m/z=292.1 [M+H]$^+$. Calculated for C$_{12}$H$_{13}$F$_4$N$_3$O: 291.2

Step 9: 5-chloro-N-((4S,6S)-4-(5-(5-chloropicolinamidophenyl)-4-methyl-6-(trifluoromethyl)-5,6-dihydro-4H-1,3-oxazin-2-yl)picolinamide (4k)

A stock solution of (5-chloropyridin-2-yl)(1H-imidazol-1-yl)methanone was prepared by adding N,N'-carbonyldiimidazole (Aldrich; 278 mg, 1.72 mmol) to a solution of 5-chloropicolinic acid (ShaoYuan; 280 mg, 1.78 mmol) in THF (5.0 mL) and heating the reaction mixture to 60° C. for 2 h. (4S,6S)-4-(5-amino-2-fluorophenyl)-4-methyl-6-(trifluoromethyl)-5,6-dihydro-4H-1,3-oxazin-2-amine (4i, 50 mg, 0.172 mmol) was added to a flask containing 0.55 mL (1.1 equiv.) of the (5-chloropyridin-2-yl)(1H-imidazol-1-yl) methanone stock solution. The reaction mixture was allowed to stir for 30 min at ambient temperature, after which a second aliquot of (5-chloropyridin-2-yl)(1H-imidazol-1-yl)methanone solution (0.55 mL, 1.1 equiv.) was added. After 16 hs, saturated aqueous NaHCO$_3$ (50 mL) was added to the reaction mixture and the product was extracted with EtOAc (3×50 mL). The combined organic extracts were dried over MgSO$_4$, concentrated, and purified by flash chromatography on silica gel (Gradient: 0%→50% EtOAc/hexane) to give 5-chloro-N-((4S,6S)-4-(5-(5-chloropicolinamido)-2-fluorophenyl)-4-methyl-6-(trifluoromethyl)-5,6-dihydro-4H-1,3-oxazin-2-yl)picolinamide (85.3 mg, 0.150 mmol) as a colorless glass. MS m/z=570 M$^+$. Calculated for C$_{24}$H$_{17}$Cl$_2$F$_4$N$_5$O$_3$: 570.3

Step 10: N-(3-((4S,6S)-2-amino-4-methyl-6-(trifluoromethyl)-5,6-dihydro-4H-1,3-oxazin-4-yl)-4-fluorophenyl)-5-chloropicolinamide A solution of 5-chloro-N-((4S,6S)-4-(5-(5-chloropicolinamido)-2-fluorophenyl)-4-methyl-6-(trifluoromethyl)-5,6-dihydro-4H-1,3-oxazin-2-yl)picolinamide (4k 85.3 mg, 0.150 mmol) in 2 M NH$_3$/MeOH (Aldrich; 4.0 mL) was heated to 50° C. for 16 h. The solution was concentrated and purified by flash chromatography on silica gel (Gradient: 20%→100% EtOAc/hexane) to give the title compound (48.2 mg, 0.112 mmol) as a white solid. MS m/z=431.0, [M+H]$^+$. Calculated for C$_{18}$H$_{15}$ClF$_4$N$_4$O$_2$: 430.8

$^1$H NMR (400 MHz, CDCl$_3$): δ 9.82 (s, 1 H), 8.55-8.49 (m, 1 H), 8.21 (dd, J=8.3, 0.5 Hz, 1 H), 8.00-7.92 (m, 1 H), 7.86 (dd, J=8.4, 2.3 Hz, 1 H), 7.50 (dd, J=7.1, 2.8 Hz, 1 H), 7.08 (dd, J=11.5, 8.8 Hz, 1 H), 4.5-3.5 (br s, 2 H), 4.09-3.99 (m, 1 H), 2.81 (dd, J=13.7, 2.7 Hz, 1 H), 1.89 (dd, J=13.5, 12.7 Hz, 1 H), 1.65 (d, J=0.8 Hz, 3 H); $^{19}$F NMR (377 MHz, CDCl$_3$): δ −79.30 (s, 3 F), −116.37 (s, 1 F).

Example 26-a

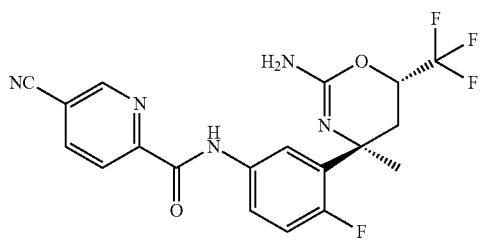 [SMILES: C[C@@]1(c2cc(NC(=O)c3ccc(C#N)cn3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-5-cyanopicolinamide The title compound was synthesized by procedures and steps analogous to those described in Method E, Example 26 above, but using 5-cyanopicolinic acid (Aldrich)) in step 9. MS m/z=422.1 [M+H]$^+$. Calculated for C$_{19}$H$_{15}$F$_4$NO$_2$: 421.35

$^1$H NMR (400 MHz, CDCl$_3$): δ 9.88 (br s, 1 H), 8.97-8.86 (m, 1 H), 8.42 (dd, J=8.1, 0.9 Hz, 1 H), 8.21 (dd, J=8.2, 2.0 Hz, 1 H), 8.03 (dt, J=8.9, 3.4 Hz, 1 H), 7.55-7.43 (m, 1 H) 7.15 (dd, J=11.5, 8.8 Hz, 1 H), 4.22-4.10 (m, 1 H) 2.91 (d, J=14.1 Hz, 1 H), 2.00 (t, J=13.3 Hz, 1 H), 1.75 (s, 3 H); $^{19}$F NMR (377 MHz, CDCl$_3$): δ −79.00 (br s, 3 F), −115.82 (s, 1 F).

Example 27

Synthesis of N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide

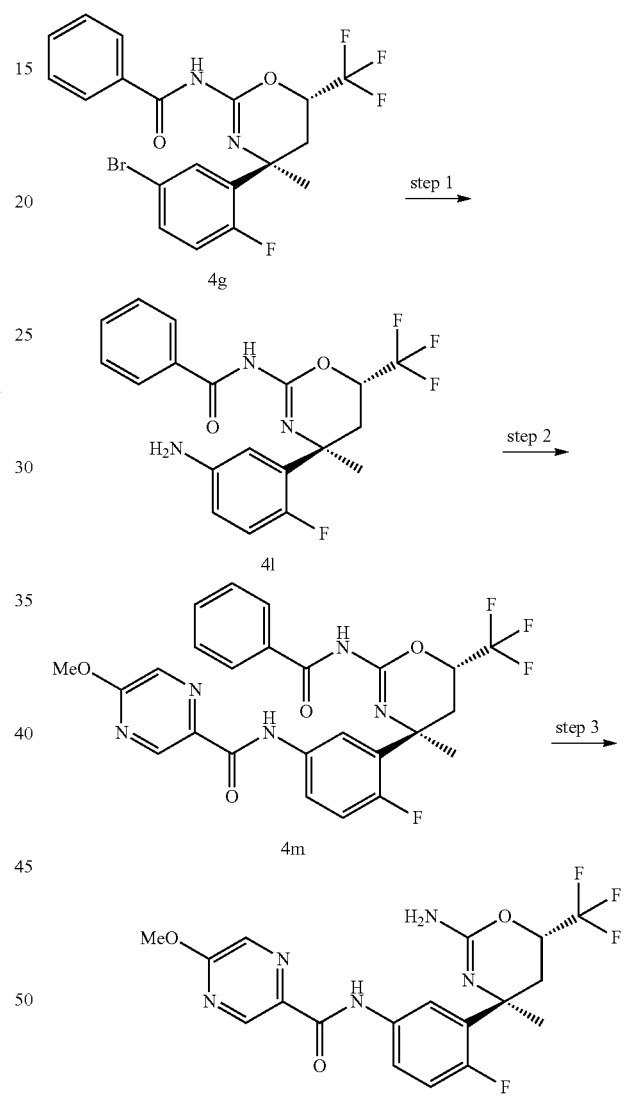

Step 1: N-((4S,6S)-4-(5-amino-2-fluorophenyl)-4-methyl-6-(trifluoromethyl)-5,6-dihydro-4H-1,3-oxazin-2-yl)benzamide (4l)

The title compound was synthesized following steps and procedures analogous to those described in Example 1 (step 9) above, but starting from N-((4S,6S)-4-(5-bromo-2-fluorophenyl)-4-methyl-6-(trifluoromethyl)-5,6-dihydro-4H-1,3-oxazin-2-yl)benzamide (4g). MS m/z=395.9 [M+H]$^+$; Calculated for C$_{19}$H$_{17}$F$_4$N$_3$O$_2$: 395.35

Step 2: N-(3-((4S,6S)-2-benzamido-4-methyl-6-(trifluoromethyl)-5,6-dihydro-4H-1,3-oxazin-4-yl)-4-fluorophenyl)-5-methoxypyrazine-2-carboxamide (4m)

The title compound was synthesized following steps and procedures analogous to those described in Method A (step 1) above, but using N-((4S,6S)-4-(5-amino-2-fluorophenyl)-4-methyl-6-(trifluoromethyl)-5,6-dihydro-4H-1,3-oxazin-2-yl)benzamide (4l). MS m/z=: 532.0 [M+H]$^+$; Calculated for $C_{25}H_{21}F_4N_5O_4$: 531.46

Step 3: N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide The title compound was synthesized using steps and procedures analogous to those described in Example 2 (Method A, step 2) above, but using -((4S,6S)-4-((5-amino-2-fluorophenyl)-4-methyl-6-(trifluoromethyl)-5,6-dihydro-4H-1,3-oxazin-2-yl)benzamide (4m). MS m/z=428 [M+H]$^+$. Calculated for $C_{18}H_{17}F_4N_5O_3$: 427.353

$^1$H NMR (300 MHz, DMSO-$d_6$) δ ppm 1.52 (s, 3 H) 4.02 (s, 3 H) 4.14 (d, J=4.09 Hz, 1 H) 5.89 (s, 2 H) 7.17 (dd, J=11.91, 8.55 Hz, 1 H) 7.75-7.84 (m, 2 H) 8.41 (d, J=1.32 Hz, 1 H) 8.88 (d, J=1.32 Hz, 1 H) 10.51 (s, 1 H)

Example 28

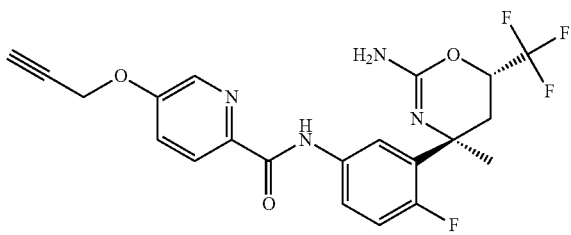 [SMILES: C#CCOc1ccc(C(=O)Nc2ccc(F)c([C@]3(C)C[C@@H](C(F)(F)F)OC(N)=N3)c2)nc1]

Synthesis of N-(3-((4S,6S)-2-amino-4-methyl-6-(trifluoromethyl)-5,6-dihydro-4H-1,3-oxazin-4-yl)-4-fluorophenyl)-5-(prop-2-yn-1-yloxy)picolinamide The title compound was synthesized using steps and procedures analogous to those described in Example 27 above, but using 5-(prop-2-yn-1-yloxy)picolinic acid (intermediate 26). MS m/z=451 [M+H]$^+$. Calculated for $C_{21}H_{18}F_4N_4O_3$: 450.4.

$^1$H NMR (400 MHz, CHLOROFORM-d) δ ppm 1.91 (s, 3 H) 2.24 (t, J=13.11 Hz, 1 H) 2.58 (s, 1 H) 3.00 (d, J=13.69 Hz, 1 H) 4.35 (d, J=5.48 Hz, 1 H) 4.79 (s, 2 H) 7.19 (t, J=10.17 Hz, 1 H) 7.31 (d, J=6.65 Hz, 1 H) 7.39-7.49 (m, 3 H) 7.51-7.58 (m, 1 H) 8.21 (d, J=8.02 Hz, 2 H) 8.26-8.36 (m, 3 H) 9.87 (br. s., 1 H) 11.72-11.94 (m, 1 H).

Example 29

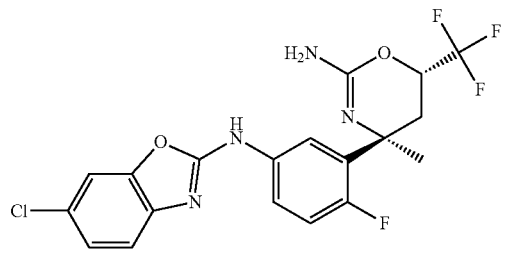 [SMILES: C[C@@]1(c2cc(Nc3nc4ccc(Cl)cc4o3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-6-chlorobenzo[d]oxazol-2-amine Step 1: N-((4S,6S)-4-(5-((6-chlorobenzo[d]oxazol-2-yl)amino)-2-fluorophenyl)-4-methyl-6-(trifluoromethyl)-5,6-dihydro-4H-1,3-oxazin-2-yl)benzamide A mixture of N-((4S,6S)-4-(5-amino-2-fluorophenyl)-4-methyl-6-(trifluoromethyl)-5,6-dihydro-4H-1,3-oxazin-2-yl)benzamide (0.200 g, 0.506 mmol, prepared as described in Example 1 Step 9 but using N-((4S,6S)-4-(5-bromo-2-fluorophenyl)-4-methyl-6-(trifluoromethyl)-5,6-dihydro-4H-1,3-oxazin-2-yl)benzamide 4g), 2,6-dichlorobenzoxazole (0.133 g, 0.708 mmol), potassium carbonate (4l, 0.126 g, 0.911 mmol) and NMP (2 mL) was stirred at 120° C. for 4.5 h, the mixture was diluted with water and EtOAc. The organic layer was washed with water and brine, dried over $Na_2SO_4$ and concentrated in vacuo. The crude was purified by silica gel chromatography: 40 g, 0-30% DCM-hexane in 15 min. The product was obtained as a white solid (0.200 g). MS m/z=547 [M+H]$^+$. Calculated for $C_{26}H_{19}ClF_4N_4O_3$: 546.9.

Step 2: N-(3-((4S,6S)-2-amino-4-methyl-6-(trifluoromethyl)-5,6-dihydro-4H-1,3-oxazin-4-yl)-4-fluorophenyl)-6-chlorobenzo[d]oxazol-2-amine A mixture of N-((4S,6S)-4-(5-((6-chlorobenzo[d]oxazol-2-yl)amino)-2-fluorophenyl)-4-methyl-6-(trifluoromethyl)-5,6-dihydro-4H-1,3-oxazin-2-yl)benzamide (0.200 g, 0.366 mmol), DBU (0.072 mL, 0.475 mmol) and MeOH (3 mL) was stirred at 65° C. After 4 h, the mixture was diluted with saturated $NH_4Cl$ and EtOAc. The organic layer was washed with water and brine, dried over $Na_2SO_4$ and concentrated in vacuo. The crude was purified by silica gel chromatography: 0-100% in 15 min, then 100% EtOAc-hexane. The product was obtained as a white solid (67.4 mg, 91% pure). The crude was further purified by reverse phase HPLC: 10-100% in 16 min, MeCN in water with 0.1% TFA. The combined fractions were neutralized with solid $Na_2CO_3$, and extracted with DCM three times. The organic phase was dried over $Na_2SO_4$ and concentrated in vacuo. The product was obtained as a white solid (12.7 mg, 8% yield). MS m/z=443 [M+H]$^+$. Calculated for $C_{19}H_{15}ClF_4N_4O_2$: 442.8.

$^1$H NMR (400 MHz, CHLOROFORM-d) δ=7.94 (d, J=8.0 Hz, 1 H), 7.39 (d, J=6.5 Hz, 1 H), 7.36-7.24 (m, 2 H), 7.19 (d,

J=8.4 Hz, 1 H), 7.10 (t, J=10.1 Hz, 1 H), 4.09 (d, J=6.1 Hz, 1 H), 2.84 (d, J=13.7 Hz, 1 H), 1.96 (t, J=13.1 Hz, 1 H), 1.71 (s, 3 H).

Example 30

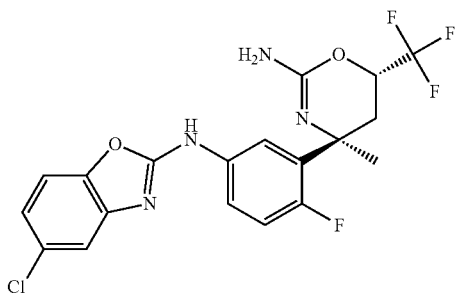 [SMILES: C[C@@]1(c2cc(Nc3nc4cc(Cl)ccc4o3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-5-chlorobenzo[d]oxazol-2-amine The title compound was synthesized using steps and procedures analogous to those described in Example 29 above, but using 2,5-dichlorobenzo[d]oxazole. MS m/z=443 [M+H]$^+$. Calculated for $C_{19}H_{15}ClF_4N_4O_2$: 442.8.

$^1$H NMR (400 MHz, CHLOROFORM-d) δ=7.92-7.85 (m, 1H), 7.43-7.38 (m, 2 H), 7.20 (d, J=8.6 Hz, 1 H), 7.14-7.03 (m, 2 H), 4.14-4.02 (m, 1 H), 2.84 (dd, J=2.7, 13.7 Hz, 1 H), 1.95 (t, J=13.1 Hz, 1 H), 1.68 (s, 3 H).

Example 31

Synthesis of N-(3-((4SR,6SR)-2-amino-4-methyl-6-(trifluoromethyl)-5,6-dihydro-4H-1,3-oxazin-4-yl)-4-fluorophenyl)-5-chloro-3-methyl-2-pyridinecarboxamide

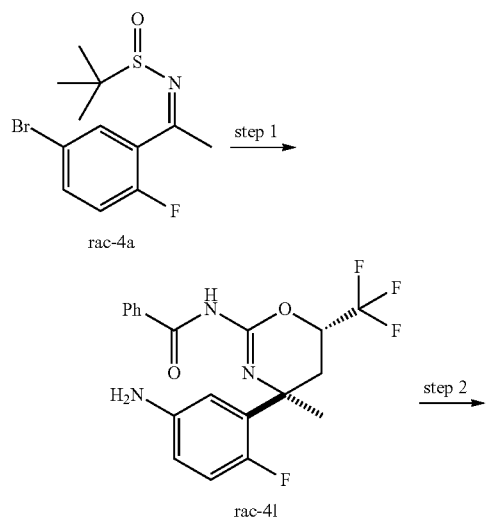

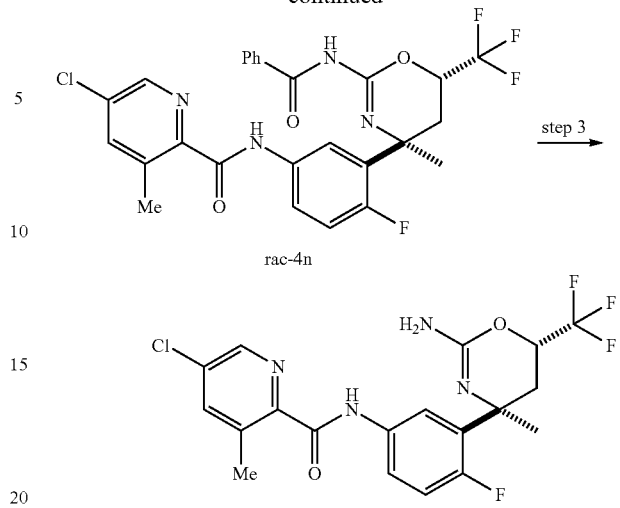

Step 1: N-((4SR,6SR)-4-(5-bromo-2-fluorophenyl)-4-methyl-6-(trifluoromethyl)-5,6-dihydro-4H-1,3-oxazin-2-yl)benzamide (rac-4l)

The title compound was synthesized using steps and procedures analogous to those described in Method E (steps 1-6) followed by step 1 (Example 27), but starting with racemic (Z)-N-(1-(5-bromo-2-fluorophenyl)ethylidene)-2-methyl-propane-2-sulfinamide (rac-4-a, synthesized following the procedure described in WO2009/11880). MS m/z=460.9 [M+H]$^+$. Calculated for $C_{19}H_{15}BrF_4N_2O_2$: 459.2

Step 2: N-(3-((4S,6S)-2-benzamido-4-methyl-6-(trifluoromethyl)-5,6-dihydro-4H-1,3-oxazin-4-yl)-4-fluorophenyl)-5-chloro-3-methylpicolinamide (rac-4-n)

A round-bottomed flask was charged with N-((4S,6S)-4-(5-amino-2-fluorophenyl)-4-methyl-6-(trifluoromethyl)-5,6-dihydro-4H-1,3-oxazin-2-yl)benzamide (rac-4l, 0.233 g, 0.589 mmol), DCM (8 mL), N,N-diisopropylethylamine (0.133 mL, 0.766 mmol), 5-chloro-3-methylpicolinic acid (intermediate 6) 0.131 g, 0.766 mmol) and finally with 1-propanephosphonic acid cyclic anhydride (50% solution in ethyl acetate; 0.347 mL, 0.589 mmol). The reaction mixture was stirred at room temperature for 15 min. The Reaction mixture was poured into aqueous saturated NaHCO$_3$ (50 mL) and then extracted with EtOAc (2×50 mL). The combined extracts were washed with brine, dried over Na$_2$SO$_4$ and loaded onto silica gel. Purification by silica gel chromatography (gradient 0 to 30% EtOAc/hexane) gave the title compound (50 mg). MS m/z=549.1 [M+H]$^+$. Calculated for $C_{26}H_{21}ClF_4N_4O_3$: 548.9

Step 3: N-(3-((4SR,6SR)-2-amino-4-methyl-6-(trifluoromethyl)-5,6-dihydro-4H-1,3-oxazin-4-yl)-4-fluorophenyl)-5-chloro-3-methyl-2-pyridinecarboxamide A sealable vial was charged with N-(3-((4S,6S)-2-benzamido-4-methyl-6-(trifluoromethyl)-5,6-dihydro-4H-1,3-oxazin-4-yl)-4-fluorophenyl)-5-chloro-3-methylpicolinamide (rac 4n, 0.050 g, 0.091 mmol) and ammonia (2.0M solution in methanol; 3.0 ml, 6.00 mmol). The reaction mixture was heated to 80° C. for 17 hs. The reaction mixture was concentrated an the residue was diluted with a minimal amount of CH₂Cl₂. Purification by silica gel chromatography (gradient 0.0 to 5.0% 2 M ammonia in MeOH/CH₂Cl₂) afforded the title compound (0.0104 g, 0.023 mmol, 51.3% yield) as a white solid. MS m/z=445.0 [M+H]⁺. Calculated for $C_{19}H_{17}ClF_4N_4O_2$: 444.098.

¹H NMR (400 MHz, DMSO-d₆) δ ppm 10.60 (s, 1 H), 8.57 (d, J=2.0 Hz, 1 H), 8.02 (dd, J=2.3, 0.6 Hz, 1 H), 7.78-7.85 (m, 1 H), 7.67 (dd, J=7.6, 2.7 Hz, 1 H), 7.16 (dd, J=11.9, 8.8 Hz, 1 H), 5.92 (s, 2 H), 4.11-4.21 (m, 1 H), 2.53-2.60 (m, 5 H), 1.51 (s, 3 H).

Example 32 (Method F)

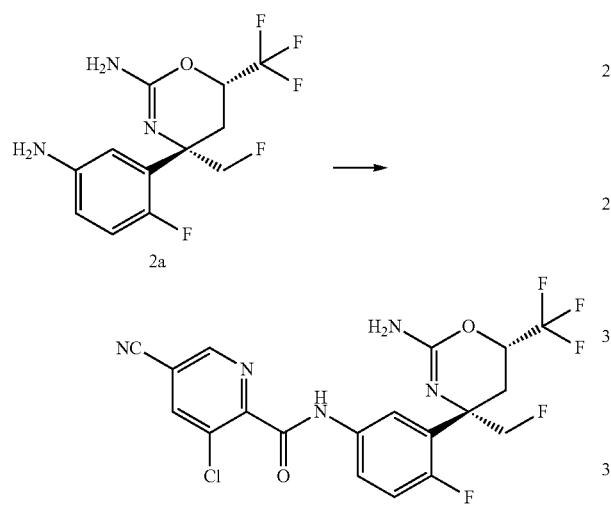

Synthesis of N-(3-((4S,6S)-2-amino-4-(fluoromethyl)-6-(trifluoromethyl)-5,6-dihydro-4H-1,3-oxazin-4-yl)-4-fluorophenyl)-3-chloro-5-cyano-2-pyridinecarboxamide To solution of (4S,6S)-4-(5-amino-2-fluorophenyl)-4-(fluoromethyl)-6-(trifluoromethyl)-5,6-dihydro-4H-1,3-oxazin-2-amine (2b, 0.093 g, 0.301 mmol) and 3-chloro-5-cyano-2-pyridinecarboxylic acid (Bionet Research, 0.056 g, 0.307 mmol) in THF (1 mL) and MeOH (0.25 mL) at 0° C. was added 4-(4,6-dimethoxy-1,3,5-triazin-2-yl)-4-methylmorpholin-4-ium chloride (Aldrich, 0.084 g, 0.304 mmol). The reaction mixture was warmed to room temperature, stirred for 17 h and concentrated. Purification by flash column chromatography on silica gel (24 g, 10% to 60% EtOAc (10% 2M NH3 in MeOH) in hexanes) afforded the title compound (0.069 g, 0.146 mmol, 48.4% yield) as a pale yellow solid. MS m/z=474.0 (M+H); Calculated mass for $C_{19}H_{13}ClF_5N_5O_2$: 473.1

¹H NMR (400 MHz, CDCl₃): δ 9.71 (s br, 1H), 8.77 (d, J=1.8 Hz, 1H), 8.17 (d, J=1.8 Hz, 1H), 8.08 (ddd, J=8.8, 4.1, 3.0 Hz, 1H), 7.49 (dd, J=6.8, 2.7 Hz, 1H), 7.17 (dd, J=11.3, 8.8 Hz, 1H), 4.67 (dd, J=47.5, 8.8, 1.3 Hz, 1H), 4.48 (dd, J=46.9, 8.6 Hz, 1H), 4.44 (s br, 2H), 4.18-4.10 (m, 1H), 2.71 (dd, J=13.7, 2.7 Hz, 1H), 2.17 (t, J=13.1 Hz, 1H).

Example 33

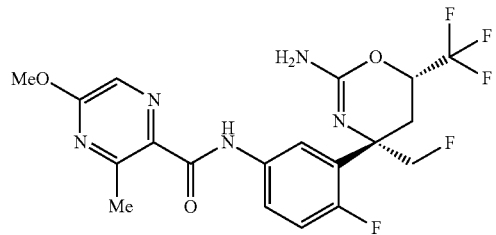 [SMILES: COc1cnc(C(=O)Nc2ccc(F)c([C@]3(CF)C[C@@H](C(F)(F)F)OC(N)=N3)c2)c(C)n1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-methoxy-3-methylpyrazine-2-carboxamide The title compound was synthesized by procedures and steps analogous to those described in Method F (Example 32) above, but using 5-methoxy-3-methylpyrazine-2-carboxylic acid (intermediate 13). MS m/z=460.1 [M+H]⁺. Calculated mass for $C_{19}H_{18}F_5N_5O_3$: 459.1

¹H NMR (300 MHz, DMSO-d₆) δ ppm 1.79-2.19 (m, 1 H) 2.50 (m, under DMSO solvent peak, 1 H) 3.99 (s, 3 H) 2.75 (s, 3 H) 4.19-4.72 (m, 3 H) 6.11 (s, 2 H) 7.20 (dd, J=11.91, 8.84 Hz, 1 H) 7.68-7.92 (m, 2 H) 8.24 (s, 1 H) 10.51 (s, 1 H)

Example 34

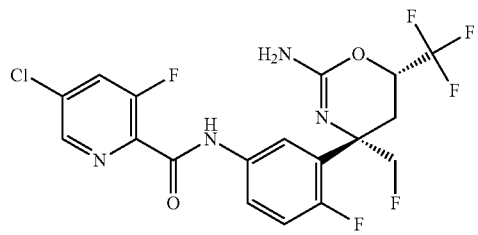 [SMILES: NC1=N[C@](CF)(c2cc(NC(=O)c3ncc(Cl)cc3F)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-chloro-3-fluoropicolinamide The title compound was synthesized by procedures and steps analogous to those described in Method F, Example 32 above, but using 5-chloro-3-fluoropyridine-2-carboxylic acid (Frontier Scientific). MS m/z=466.8 [M+H]⁺. Calculated for $C_{18}H_{13}ClF_6N_4O_2$:466.06

¹H NMR (300 MHz, CHLOROFORM-d) δ ppm 2.24 (t, J=13.15 Hz, 1 H) 2.74 (dd, J=13.67, 2.70 Hz, 1 H) 4.15-4.26 (m, 1 H) 4.40-4.84 (m, 2 H) 7.14 (dd, J=11.55, 8.92 Hz, 1 H) 7.52 (dd, J=6.87, 2.78 Hz, 1 H) 7.67 (dd, J=9.94, 1.90 Hz, 1 H) 8.09 (dt, J=7.27, 4.26 Hz, 1 H) 8.43 (d, J=1.32 Hz, 1 H) 9.69 (s, 1 H).

Example 35

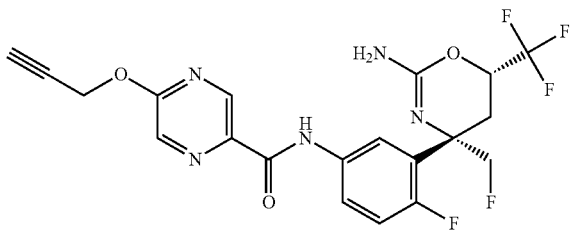 [SMILES: C#CCOc1cnc(C(=O)Nc2ccc(F)c([C@]3(CF)C[C@@H](C(F)(F)F)OC(N)=N3)c2)cn1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(prop-2-yn-1-yloxy)pyrazine-2-carboxamide The title compound was synthesized by procedures and steps analogous to those described in Method F, Example 32 above, but using 5-(prop-2-yn-1-yloxy)pyrazine-2-carboxylic acid (J. Med. Chem. 2013, 56, 3980). MS m/z=469.9 [M+H]$^+$. Calculated for $C_{20}H_{16}F_5N_5O_3$: 469.12

$^1$H NMR (300 MHz, CHLOROFORM-d) δ ppm 2.33 (m, J=11.40, 1.00, 1.00 Hz, 1 H) 2.56 (br. s., 1 H) 2.80 (d, J=14.47 Hz, 1 H) 4.43-4.90 (m, 2 H) 5.11 (s, 3 H) 7.16 (t, J=10.16 Hz, 1 H) 7.51-7.60 (m, 1 H) 8.04-8.17 (m, 1 H) 8.25 (s, 1 H) 9.05 (s, 1 H) 9.57 (br. s., 1 H).

Example 36

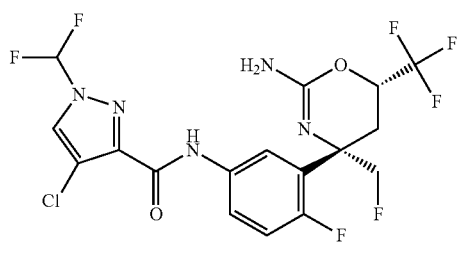 [SMILES: NC1=N[C@](CF)(c2cc(NC(=O)c3nn(C(F)F)cc3Cl)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-4-chloro-1-(difluoromethyl)-1H-pyrazole-3-carboxamide The title compound was synthesized by procedures and steps analogous to those described in Method F, Example 32 above, but using 4-chloro-1-(difluoromethyl)-1H-pyrazole-3-carboxylic acid (WO2011069934). MS m/z=487.8 [M+H]$^+$. Calculated for $C_{17}H_{13}ClF_7N_5O_2$: 487.06

$^1$H NMR (300 MHz, CHLOROFORM-d) δ ppm 2.21 (t, J=13.15 Hz, 1 H) 2.72 (dd, J=13.59, 2.63 Hz, 1 H) 4.14-4.24 (m, 1 H) 4.35-4.81 (m, 2 H) 6.93-7.13 (m, 1 H) 7.15 (s, 1 H) 7.42 (dd, J=6.87, 2.78 Hz, 1 H) 7.92 (s, 1 H) 7.97-8.13 (m, 1 H) 8.58 (s, 1 H).

Example 37

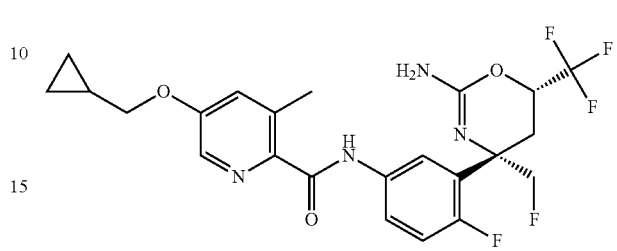

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(cyclopropylmethoxy)-3-methylpicolinamide The title compound was synthesized by procedures and steps analogous to those described in Method F, Example 32 above, but using 5-(cyclopropylmethoxy)-3-methylpicolinic acid (Aurigene Discovery). MS m/z=498.9 [M+H]$^+$. Calculated for $C_{23}H_{23}F_5N_4O_3$: 498.17

$^1$H NMR (300 MHz, CHLOROFORM-d) δ ppm 0.35-0.44 (m, 1 H) 0.64-0.75 (m, 1 H) 1.21-1.36 (m, 1 H) 2.22 (t, J=13.08 Hz, 1 H) 2.72 (dd, J=13.74, 2.63 Hz, 1 H) 2.77 (s, 3 H) 3.92 (d, J=7.02 Hz, 2 H) 4.13-4.27 (m, 1 H) 4.36-4.87 (m, 2 H) 7.06 (d, J=2.05 Hz, 1 H) 7.07-7.15 (m, 1 H) 7.42 (dd, J=6.87, 2.78 Hz, 1 H) 8.06-8.17 (m, 2 H) 10.10 (s, 1 H).

Example 38

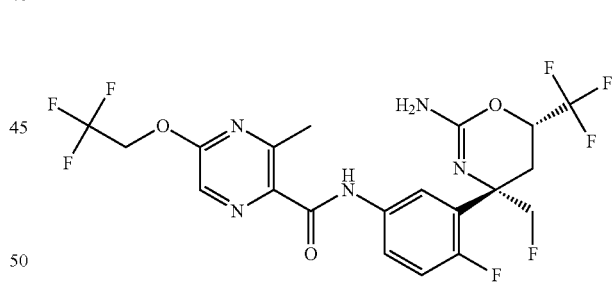

Synthesis of N-(3-((4S,6S)-2-amino-4-(fluoromethyl)-6-(trifluoromethyl)-5,6-dihydro-4H-1,3-oxazin-4-yl)-4-fluorophenyl)-3-methyl-5-(2,2,2-trifluoroethoxy)pyrazine-2-carboxamide The title compound was synthesized by procedures and steps analogous to those described in Method F, Example 32 above, but using 3-methyl-5-(2,2,2-trifluoroethoxy)pyrazine-2-carboxylic acid (Intermediate 24). MS m/z=527.8 [M+H]$^+$. Calculated for $C_{20}H_{17}F_8N_5O_3$: 527.12

$^1$H NMR (300 MHz, CHLOROFORM-d) δ ppm 2.23 (t, J=13.08 Hz, 1 H) 2.73 (dd, J=13.67, 2.56 Hz, 1 H) 2.95 (s, 3 H) 3.65-3.89 (m, 1 H) 4.11-4.26 (m, 1 H) 4.36-4.69 (m, 2 H)

4.74-4.93 (m, 3 H) 7.12 (dd, J=11.62, 8.84 Hz, 1 H) 7.45 (dd, J=6.87, 2.63 Hz, 1 H) 8.08 (dt, J=7.31, 4.31 Hz, 1 H) 8.16 (s, 1 H) 9.78 (s, 1 H).

Example 39

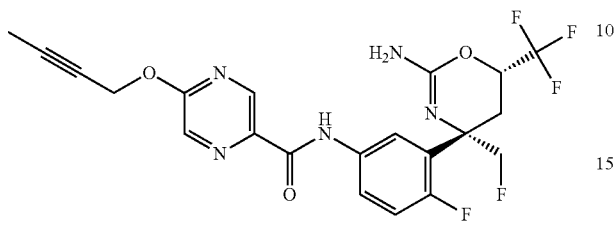

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(but-2-yn-1-yloxy) pyrazine-2-carboxamide The title compound was synthesized by procedures and steps analogous to those described in Method F, Example 32 above, but using 5-(but-2-yn-1-yloxy)pyrazine-2-carboxylic acid (J. Med. Chem. 2013, 56, 3980). MS m/z=483.9 [M+H]$^+$. Calculated for $C_{21}H_{18}F_5N_5O_3$: 483.13

$^1$H NMR (300 MHz, CHLOROFORM-d) δ ppm 1.89 (t, J=2.34 Hz, 3 H) 2.25 (t, J=13.23 Hz, 1 H) 2.74 (dd, J=13.59, 2.63 Hz, 1 H) 4.14-4.27 (m, 1 H) 4.38-4.84 (m, 2 H) 5.05 (q, J=2.34 Hz, 2 H) 7.13 (dd, J=11.55, 8.92 Hz, 1 H) 7.54 (dd, J=6.87, 2.78 Hz, 1 H) 8.06 (dt, J=7.34, 4.29 Hz, 1 H) 8.20 (d, J=1.32 Hz, 1 H) 9.02 (d, J=1.32 Hz, 1 H) 9.54 (s, 1 H).

Example 40

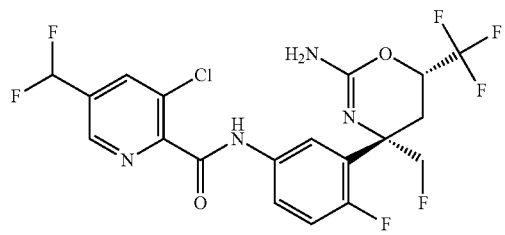 [SMILES: NC1=N[C@](CF)(c2cc(NC(=O)c3ncc(C(F)F)cc3Cl)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-3-chloro-5-(difluoromethyl)picolinamide The title compound was synthesized by procedures and steps analogous to those described in Method F, Example 32 above, but using 3-chloro-5-(difluoromethyl)picolinic acid (WO2012095521). MS m/z=498.8 [M+H]$^+$. Calculated for $C_{19}H_{14}ClF_7N_4O_2$: 498.07

$^1$H NMR (300 MHz, CHLOROFORM-d) δ ppm 2.29 (t, J=13.30 Hz, 1 H) 2.78 (dd, J=13.74, 2.34 Hz, 1 H) 4.16-4.32 (m, 1 H) 4.40-4.88 (m, 2 H) 6.78 (m, J=55.83, 1.00, 1.00 Hz, 1 H) 7.16 (dd, J=11.47, 8.84 Hz, 1 H) 7.47 (dd, J=6.80, 2.70 Hz, 1 H) 8.03 (s, 1 H) 8.18 (dd, J=7.31, 4.38 Hz, 1 H) 8.68 (s, 1 H) 9.90 (s, 1 H).

Example 41

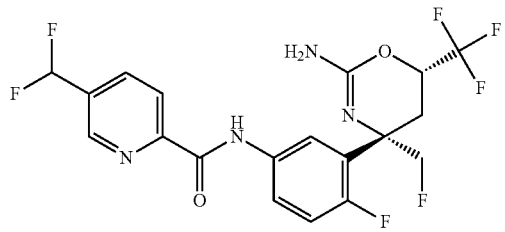 [SMILES: NC1=N[C@](CF)(c2cc(NC(=O)c3ccc(C(F)F)cn3)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(difluoromethyl)picolinamide The title compound was synthesized by procedures and steps analogous to those described in Method F, Example 32 above, but using 5-(difluoromethyl)picolinic acid. MS m/z=464.9 [M+H]$^+$. Calculated for $C_{19}H_{15}F_7N_4O_2$: 464.11

$^1$H NMR (300 MHz, CHLOROFORM-d) δ ppm 2.29 (t, J=13.30 Hz, 1 H) 2.77 (dd, J=13.74, 2.63 Hz, 1 H) 4.18-4.32 (m, 1 H) 4.41-4.87 (m, 2 H) 6.90 (m, J=55.98, 1.00, 1.00 Hz, 1 H) 7.16 (dd, J=11.40, 8.92 Hz, 1 H) 7.61 (dd, J=6.87, 2.48 Hz, 1 H) 8.01-8.15 (m, 2 H) 8.39 (d, J=8.04 Hz, 1 H) 8.78 (s, 1 H) 10.02 (s, 1 H).

Example 42

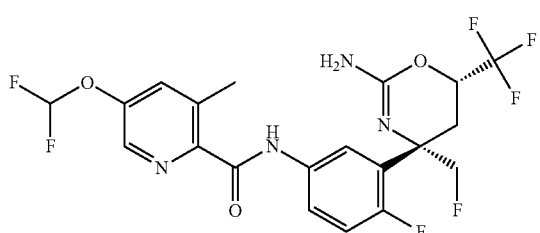

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(difluoromethoxy)-3-methylpicolinamide The title compound was synthesized by procedures and steps analogous to those described in Method F, Example 32 above, but using 5-(difluoromethoxy)-3-methylpicolinic acid (WO2012095463). MS m/z=494.9 [M+H]$^+$. Calculated for $C_{20}H_{17}F_7N_4O_3$: 494.12

$^1$H NMR (300 MHz, CHLOROFORM-d) δ ppm 2.29 (t, J=13.30 Hz, 1 H) 2.72-2.86 (m, 4 H) 4.15-4.32 (m, 1 H) 4.40-4.87 (m, 2 H) 6.66 (t, J=71.30 Hz, 1 H) 7.13 (dd, J=11.55, 8.92 Hz, 1 H) 7.41 (d, J=1.90 Hz, 1 H) 7.45 (dd, J=6.94, 2.70 Hz, 1 H) 8.12 (dt, J=7.31, 4.31 Hz, 1 H) 8.32 (d, J=2.34 Hz, 1 H) 9.87-10.18 (m, 1 H).

Example 44

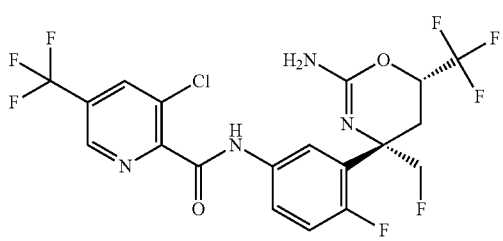 [SMILES: NC1=N[C@](CF)(c2cc(NC(=O)c3ncc(C(F)(F)F)cc3Cl)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-3-chloro-5-(trifluoromethyl)picolinamide The title compound was synthesized by procedures and steps analogous to those described in Method F, Example 32 above, but using 3-chloro-5-(trifluoromethyl)-2-pyridine carboxylic acid (Bionet Research). MS m/z=516.8 [M+H]+. Calculated for $C_{19}H_{13}ClF_8N_4O_2$: 516.06

$^1$H NMR (300 MHz, CHLOROFORM-d) δ ppm 2.23 (t, J=13.23 Hz, 1 H) 2.75 (dd, J=13.67, 2.56 Hz, 1 H) 4.14-4.28 (m, 1 H) 4.38-4.83 (m, 2 H) 7.15 (dd, J=11.55, 8.92 Hz, 1 H) 7.48 (dd, J=6.87, 2.78 Hz, 1 H) 8.08-8.20 (m, 2 H) 8.79 (d, J=1.02 Hz, 1 H) 9.82 (s, 1 H).

Example 45

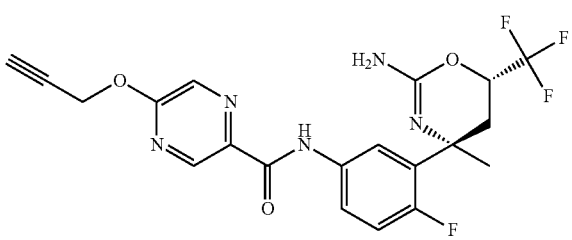 [SMILES: C#CCOc1cnc(C(=O)Nc2ccc(F)c([C@]3(C)C[C@@H](C(F)(F)F)OC(N)=N3)c2)cn1]

Synthesis of N-(3-((4S,6S)-2-amino-4-methyl-6-(trifluoromethyl)-5,6-dihydro-4H-1,3-oxazin-4-yl)-4-fluorophenyl)-5-(prop-2-yn-1-yloxy)pyrazine-2-carboxamide The title compound was synthesized by procedures and steps analogous to those described in Method F (Example 32) above, but using (4S,6S)-4-(5-amino-2-fluorophenyl)-4-methyl-6-(trifluoromethyl)-5,6-dihydro-4H-1,3-oxazin-2-amine (intermediate 4i) and 5-(prop-2-yn-1-yloxy)pyrazine-2-carboxylic acid (J. Med. Chem. 2013, 56, 3980). The desired product was purified by reversed-phase preparative HPLC using a Phenomenex Gemini column, 10 micron, C18, 110 Å, 100×50 mm, 0.1% TFA in $CH_3CN/H_2O$, gradient 10% to 80% over 20 min. The product containing fractions were combined and neutralized with 1N NaOH solution. The free-based product was extracted with DCM. The organic phase was dried over $Na_2SO_4$ and the solvent was removed under reduced pressure to afford the title compound. MS m/z=452.1 [M+H]+. Calculated for $C_{20}H_{17}ClF_4N_5O_3$: 451.1

$^1$H NMR (400 MHz, CHLOROFORM-d) δ 9.48 (s, 1H), 9.03 (d, J=1.37 Hz, 1H), 8.22 (d, J=1.37 Hz, 1H), 7.89-8.00 (m, 1H), 7.44 (dd, J=2.74, 7.04 Hz, 1H), 7.08 (dd, J=8.80, 11.54 Hz, 1H), 5.09 (d, J=2.35 Hz, 2H), 4.28 (br. s., 2H), 3.99-4.09 (m, 1H), 2.80 (dd, J=2.74, 13.69 Hz, 1H), 2.55 (t, J=2.45 Hz, 1H), 1.84-1.93 (m, 1H), 1.64 (d, J=0.98 Hz, 3H)

Example 46

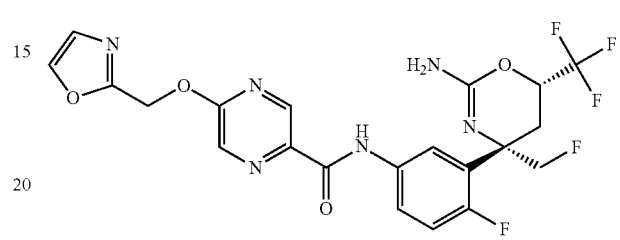

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(oxazol-2-ylmethoxy)pyrazine-2-carboxamide The title compound was synthesized by procedures and steps analogous to those described in Method F, Example 32 above, but using 5-(oxazol-2-ylmethoxy)pyrazine-2-carboxylic acid (intermediate 23) in step 2. MS m/z=512.9 [M+H]+. Calculated for $C_{21}H_{17}F_5N_6O_4$: 512.123

$^1$H NMR (400 MHz, CHLOROFORM-d) δ ppm 2.26 (t, J=13.20 Hz, 1 H) 2.75 (dd, J=13.69, 2.54 Hz, 1 H) 4.15-4.28 (m, 1 H) 4.42-4.84 (m, 2 H) 5.60 (s, 2 H) 7.15 (dd, J=11.54, 9.00 Hz, 1 H) 7.19 (d, J=0.59 Hz, 1 H) 7.56 (dd, J=6.85, 2.74 Hz, 1 H) 7.72 (d, J=0.78 Hz, 1 H) 8.01-8.13 (m, 1 H) 8.28 (d, J=1.17 Hz, 1 H) 9.03 (d, J=1.17 Hz, 1 H) 9.54 (s, 1 H)

Example 47

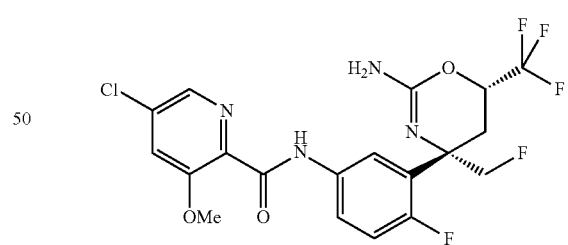

Synthesis of N-(3-((4S,6S)-2-amino-4-(trifluoromethyl)-6-(trifluoromethyl)-5,6-dihydro-4H-1,3-oxazin-4-yl)-4-fluorophenyl)-5-chloro-3-methoxypicolinamide The title compound was synthesized by procedures and steps analogous to those described in Method F (Example 32) above, but using 5-chloro-3-methoxypicolinic acid (intermediate 14). MS m/z=478.9 [M+H]+. Calculated for $C_{19}H_{16}ClF_5N_4O_3$: 478.1

$^1$H NMR (300 MHz, DMSO-d$_6$) δ ppm 1.97 (t, J=12.93 Hz, 1H) 2.50 (m, under DMSO solvent peak, 1 H) 3.89 (s, 3 H) 4.20-4.79 (m, 3 H) 6.11 (s, 2 H) 7.20 (dd, J=11.91, 8.84 Hz, 1 H) 7.71 (dd, J=7.23, 2.70 Hz, 1 H) 7.77-7.96 (m, 2 H) 8.26 (d, J=1.75 Hz, 1 H) 10.56 (s, 1 H)

Example 48

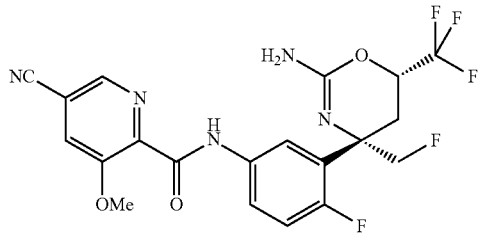 [SMILES: COc1cc(C#N)cnc1C(=O)Nc1ccc(F)c([C@]2(CF)C[C@@H](C(F)(F)F)OC(N)=N2)c1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-cyano-3-methoxypicolinamide The title compound was synthesized by procedures and steps analogous to those described in Method F (Example 32) above, but using N-(3-((4S,6S)-2-amino-4-(fluoromethyl)-6-(trifluoromethyl)-5,6-dihydro-4H-1,3-oxazin-4-yl)-4-fluorophenyl)-5-methoxy-3-methylpyrazine-2-carboxamide (Example 21). MS m/z=470 [M+H]$^+$. Calculated for C$_{20}$H$_{16}$F$_5$N$_5$O$_3$: 469.1

$^1$H NMR (300 MHz, DMSO-d$_6$) δ ppm 2.00 (t, J=12.90 Hz, 1 H) 2.50 (m, under DMSO solvent peak, 1 H) 3.91 (s, 3 H) 4.25-4.76 (m, 3 H) 6.11 (s, 2 H) 7.21 (dd, J=11.84, 8.92 Hz, 1 H) 7.68 (dd, J=7.23, 2.56 Hz, 1 H) 7.78-7.98 (m, 1 H) 8.21 (d, J=1.02 Hz, 1 H) 8.66 (d, J=1.17 Hz, 1 H) 10.73 (s, 1 H)

Example 49

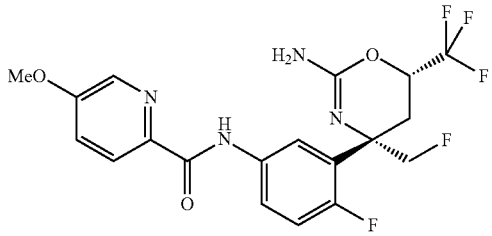 [SMILES: COc1ccc(C(=O)Nc2ccc(F)c([C@]3(CF)C[C@@H](C(F)(F)F)OC(N)=N3)c2)nc1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-methoxypicolinamide The title compound was synthesized by procedures and steps analogous to those described in Method F (Example 32) above, but using 5-methoxypicolinic acid (ArkPharm) MS m/z=445 [M+H]$^+$. Calculated for C$_{19}$H$_{17}$F$_5$N$_4$O$_3$: 444.1

$^1$H NMR (400 MHz, DMSO-d$_6$) δ ppm 1.89-2.10 (m, 1H) 2.50 (m, under DMSO solvent peak, 1 H) 3.94 (s, 3 H) 4.28-4.73 (m, 3 H) 6.11 (s, 2 H) 7.20 (dd, J=11.93, 8.61 Hz, 1 H) 7.61 (dd, J=8.80, 2.93 Hz, 1 H) 7.79-7.95 (m, 2 H) 8.04-8.21 (m, 1 H) 8.33-8.47 (m, 1 H) 10.52 (s, 1 H)

Example 50

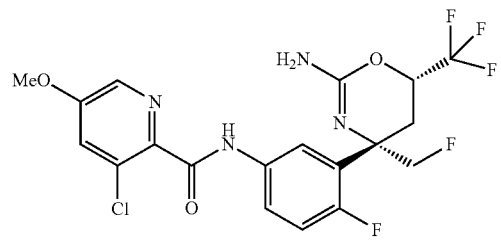 [SMILES: COc1cnc(C(=O)Nc2ccc(F)c([C@]3(CF)C[C@@H](C(F)(F)F)OC(N)=N3)c2)c(Cl)c1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-3-chloro-5-methoxypicolinamide The title compound was synthesized by procedures and steps analogous to those described in Method F (Example 32) above, but using 3-chloro-5-methoxypicolinic acid (AfferChem). MS m/z=478.9 [M+H]$^+$. Calculated for C$_{19}$H$_{16}$ClF$_5$N$_4$O$_3$: 478.08

$^1$H NMR (300 MHz, CHLOROFORM-d) δ ppm 2.19 (t, J=13.08 Hz, 1 H) 2.69 (dd, J=13.59, 2.78 Hz, 1 H) 3.95 (s, 3 H) 4.12-4.20 (m, 1 H) 4.32 (s, 2 H) 4.34-4.56 (m, 1 H) 4.58-4.80 (m, 1 H) 7.10 (dd, J=11.55, 8.92 Hz, 1 H) 7.32 (d, J=2.48 Hz, 1 H) 7.39 (dd, J=6.87, 2.78 Hz, 1 H) 8.16 (dt, J=8.66, 3.49 Hz, 1 H) 8.20 (d, J=2.63 Hz, 1 H) 9.84 (s, 1 H).

Example 51

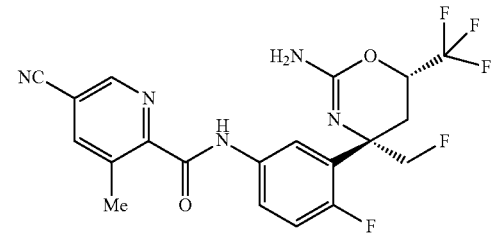 [SMILES: Cc1cc(C#N)cnc1C(=O)Nc1ccc(F)c([C@]2(CF)C[C@@H](C(F)(F)F)OC(N)=N2)c1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-cyano-3-methylpicolinamide The title compound was synthesized by procedures and steps analogous to those described in Method F (Example 32) above, but using 5-cyano-3-methylpicolinic acid (prepared according to WO2012095521 A1). MS m/z=453.8 [M+H]$^+$. Calculated for C$_{20}$H$_{16}$F$_5$N$_5$O$_2$: 453.1

$^1$H NMR (300 MHz, CHLOROFORM-d) δ ppm 2.12 (t, J=13.1 Hz, 1 H) 2.68 (dd, J=13.5, 2.4 Hz, 1 H) 2.80 (s, 3 H) 4.09-4.19 (m, 1 H) 4.45 (dd, J=47.2, 8.6 Hz, 1H) 4.61 (dd, J=47.3, 8.6 Hz, 1H) 7.08 (dd, J=11.4, 8.8 Hz, 1 H) 7.56 (dd, J=6.9, 2.5 Hz, 1 H) 7.92 (s, 1 H) 7.97-8.01 (m, 1 H) 8.62 (s, 1 H) 10.01 (s, 1 H).

Example 52

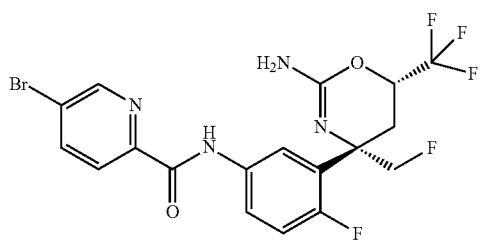 [SMILES: NC1=N[C@](CF)(c2cc(NC(=O)c3ccc(Br)cn3)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-bromopicolinamide The title compound was synthesized by procedures and steps analogous to those described in Method F (Example 32) above, but using 5-bromopyridine-2-carboxylic acid (Alfa Aesar). MS m/z=492.9 [M+H]$^+$. Calculated for $C_{18}H_{14}BrF_5N_4O_2$: 492

$^1$H NMR (300 MHz, CHLOROFORM-d) δ ppm 2.22 (t, J=13.08 Hz, 1 H) 2.72 (dd, J=13.67, 2.70 Hz, 1 H) 4.18 (ddd, J=12.53, 5.74, 2.63 Hz, 1 H) 4.38-4.84 (m, 2 H) 7.14 (dd, J=11.55, 8.92 Hz, 1 H) 7.59 (dd, J=6.87, 2.78 Hz, 1 H) 8.00-8.11 (m, 2 H) 8.18 (dd, J=8.33, 0.58 Hz, 1 H) 8.68 (dd, J=2.19, 0.58 Hz, 1 H) 9.86 (s, 1 H)

Example 53

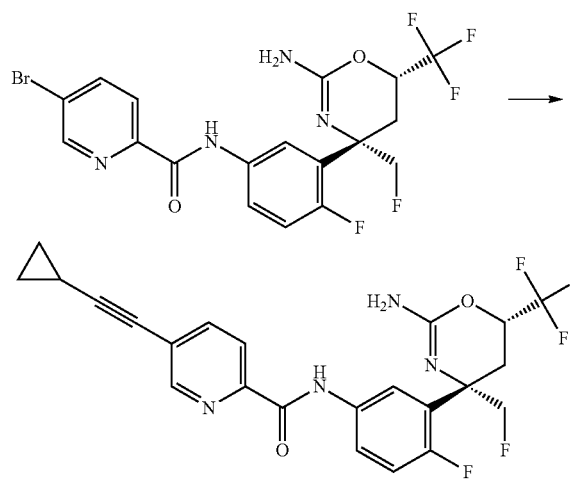

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-(cyclopropylethynyl)picolinamid N-(3-((4S,6S)-2-amino-4-(fluoromethyl)-6-(trifluoromethyl)-5,6-dihydro-4H-1,3-oxazin-4-yl)-4-fluorophenyl)-5-bromopicolinamide (Example 52) was transferred to a microwave vial followed by the addition of diethylamine (0.580 ml, 5.55 mmol), tetrakis(triphenylphosphine)palladium (0.053 g, 0.046 mmol), copper(I) iodide (0.021 g, 0.111 mmol), cyclopropylacetylene, 70 wt. % solution in toluene (0.179 ml, 1.480 mmol) and DMF (1.5 mL). The vial was sealed, purged with N$_2$ and heated in microwaved at 90° C. for 45 min. The reaction went to completion, diluted in water (10 mL) and extracted with EtOAc. The combined organics were dried over Na$_2$SO$_4$, filtered, concentrated and chromatographed on silica gel using 0-3% MeOH/DCM and 0-50% EtOAc/hexanes to afford a light yellow solid as N-(3-((4S,6S)-2-amino-4-(fluoromethyl)-6-(trifluoromethyl)-5,6-dihydro-4H-1,3-oxazin-4-yl)-4-fluorophenyl)-5-(cyclopropylethynyl)picolinamide. MS m/z=479 [M+H]$^+$. Calculated for $C_{23}H_{19}F_5N_4O_2$: 478.14

$^1$H NMR (300 MHz, CHLOROFORM-d) δ ppm 0.81-1.03 (m, 4 H) 1.44-1.60 (m, 1 H) 2.24 (t, J=13.15 Hz, 1 H) 2.73 (d, J=11.40 Hz, 1 H) 4.13-4.27 (m, 1 H) 4.37-4.86 (m, 2 H) 7.12 (dd, J=11.47, 8.99 Hz, 1 H) 7.58 (d, J=4.24 Hz, 1 H) 7.83 (dd, J=8.11, 1.68 Hz, 1 H) 8.02-8.12 (m, 1 H) 8.17 (d, J=8.04 Hz, 1 H) 8.56 (s, 1 H) 9.94 (s, 1 H).

Example 54

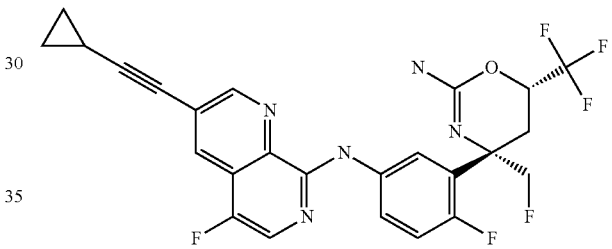

The title compound was synthesized by procedures and steps analogous to those described in Example 53 but using (4S,6S)-4-(5-((3-chloro-5-fluoro-1,7-naphthyridin-8-yl)amino)-2-fluorophenyl)-4-(fluoromethyl)-6-(trifluoromethyl)-5,6-dihydro-4H-1,3-oxazin-2-amine (Example 19). MS m/z=519.9 [M+H]$^+$. Calculated for $C_{25}H_{19}F_6N_5O$: 519.15

$^1$H NMR (300 MHz, DMSO-d$_6$) δ ppm 0.82-0.93 (m, 2 H) 0.95-1.05 (m, 2 H) 1.60-1.75 (m, 1 H) 4.28-4.73 (m, 3 H) 6.12 (s, 2 H) 7.17 (dd, J=11.91, 8.84 Hz, 1 H) 7.99-8.07 (m, 1 H) 8.10 (d, J=1.32 Hz, 1 H) 8.14 (dd, J=7.38, 2.85 Hz, 1 H) 8.37 (d, J=1.90 Hz, 1 H) 8.93 (d, J=1.90 Hz, 1 H) 9.62 (s, 1 H).

Example 55

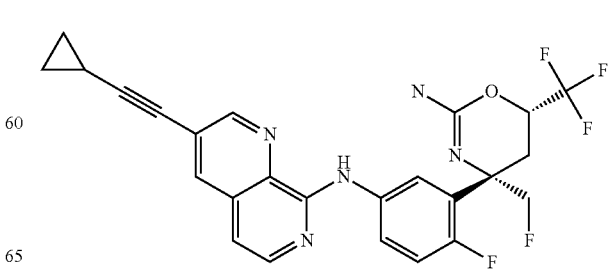

Synthesis of (4S,6S)-4-(5-((3-(cyclopropylethynyl)-1,7-naphthyridin-8-yl)amino)-2-fluorophenyl)-4-(fluoromethyl)-6-(trifluoromethyl)-5,6-dihydro-4H-1,3-oxazin-2-amine The title compound was synthesized by procedures and steps analogous to those described in Example 53 above, but using (4S,6S)-4-(5-((3-chloro-1,7-naphthyridin-8-yl)amino)-2-fluorophenyl)-4-(fluoromethyl)-6-(trifluoromethyl)-5,6-dihydro-4H-1,3-oxazin-2-amine (Example 8). MS m/z=501.9 [M+H]$^+$. Calculated for $C_{25}H_{20}F_5N_5O$: 501.16

$^1$H NMR (300 MHz, DMSO-d$_6$) δ ppm 0.80-0.90 (m, 2 H) 0.93-1.03 (m, 2 H) 1.59-1.75 (m, 1 H) 4.31-4.74 (m, 3 H) 6.12 (s, 2 H) 7.05-7.24 (m, 2 H) 8.01-8.16 (m, 3 H) 8.32 (d, J=2.05 Hz, 1 H) 8.83 (d, J=2.05 Hz, 1 H) 9.62 (s, 1 H).

Example 56

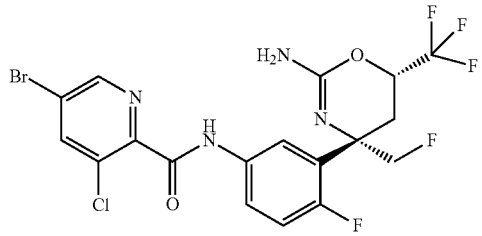

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-bromo-3-chloro-2-pyridinecarboxamide The title compound was synthesized by procedures and steps analogous to those described in Method F (Example 32) above, but using 5-bromo-3-chloropyridine-2-carboxylic acid (Matrix). MS m/z=526.8 [M+H]$^+$. Calculated for $C_{18}H_{13}BrClF_5N_4O_2$: 527.67.

$^1$H NMR (400 MHz, DMSO-d$_6$) δ ppm 1.97 (t, J=13.01 Hz, 1 H) 4.30-4.65 (m, 3 H) 6.12 (s, 2 H) 7.23 (dd, J=11.93, 8.80 Hz, 1 H) 7.69 (dd, J=7.24, 2.74 Hz, 1 H) 7.83-7.92 (m, 1 H) 8.54 (d, J=1.96 Hz, 1 H) 8.78 (d, J=1.96 Hz, 1 H) 10.83 (s, 1 H)

Example 57

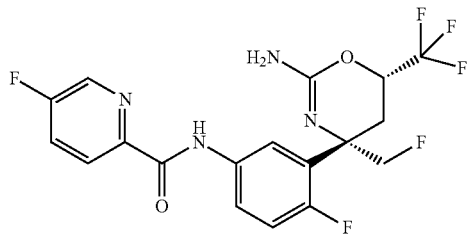 [SMILES: NC1=N[C@](CF)(c2cc(NC(=O)c3ccc(F)cn3)ccc2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-fluoropicolinamide The title compound was synthesized by procedures and steps analogous to those described in Method F (Example 32) above, but using 5-fluoropicolinic acid (Matrix). MS m/z=433 [M+H]$^+$. Calculated for $C_{15}H_{14}F_6N_4O_2$: 432.

$^1$H NMR (300 MHz, CHLOROFORM-d) δ ppm 9.82 (br, 1H), 8.45 (d, 1H, J=2.7), 8.32 (dd, 1H, J=8.7, 4.6), 8.03 (m, 1H), 7.59 (m, 2H), 7.12 (dd, 1H, J=11.5, 8.8), 4.69 (dd, 1H, J=47.5, 8.6), 4.47 (dd, 1H, J=47.5, 8.6), 4.15 (m, 1H), 2.69 (dd, 1H, J=13.5, 2.7), 2.20 (t, 1H, J=13.3).

Example 58

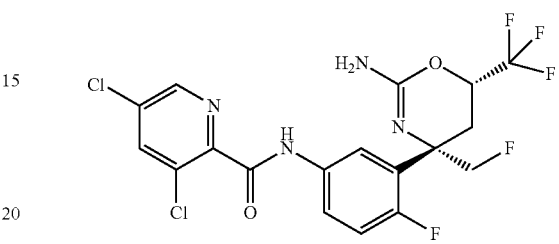

Synthesis of N-(3-((4S,6S)-2-amino-4-(fluoromethyl)-6-(trifluoromethyl)-5,6-dihydro-4H-1,3-oxazin-4-yl)-4-fluorophenyl)-3,5-dichloropicolinamide The title compound was synthesized by procedures and steps analogous to those described in Method F (Example 32) above, but using 3,5-dichloropicolinic acid (Matrix). MS m/z=483 [M+H]$^+$. Calculated for $C_{18}H_{13}Cl_2F_5N_4O_2$: 482.

H NMR (300 MHz, CHLOROFORM-d) δ ppm 9.74 (br, 1H), 8.47 (d, 1H, J=2.2), 8.10 (m, 1H), 7.91 (d, 1H, J=2.2), 7.45 (dd, 1H, J=6.8, 2.7), 7.11 (dd, 1H, J=11.5, 9.0), 4.68 (dd, 1H, J=47.5, 9.1), 4.46 (dd, 1H, J=47.0, 9.1), 4.13 (m, 1H), 2.70 (dd, 1H, J=13.3, 2.6), 2.17 (t, 1H, J=13.3).

Example 59

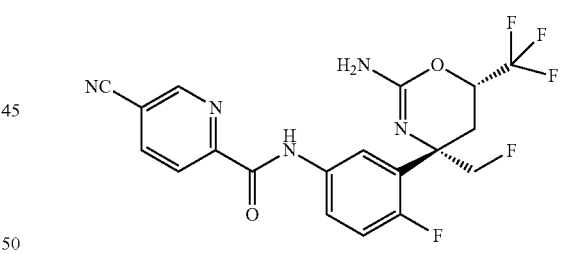

N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide To a solution of (4S,6S)-4-(5-amino-2-fluorophenyl)-4-(fluoromethyl)-6-(trifluoromethyl)-5,6-dihydro-4H-1,3-oxazin-2-amine (2a, 0.125 g, 0.404 mmol) in DCM (3 mL) was added N,N-diisopropylethylamine (0.074 mL, 0.424 mmol, Aldrich), 5-cyanopicolinic acid (0.060 g, 0.404 mmol, Aldrich) and 1-propanephosphonic acid cyclic anhydride (50% solution in ethyl acetate; 0.238 mL, 0.404 mmol, Alfa Aesar). The reaction was stirred at ambient temperature for 15 minutes. The reaction was diluted with water and DCM. The organic layer was separated and washed sequentially with aqueous saturated sodium bicarbonate solution and brine.

The organic layer was dried over MgSO$_4$ and concentrated under reduced pressure. The crude material was purified by silica gel flash chromatography (gradient of 10-70% EtOAc in hexanes) to afford the title compound as a white solid. (0.0745 g, 0.170 mmol, 42.0% yield). MS m/z=440.0 [M+H]$^+$. Calculated for C$_{19}$H$_{14}$F$_5$N$_5$O$_2$: 439.34

$^1$H NMR (300 MHz, CHLOROFORM-d) δ ppm 2.26 (t, J=13.23 Hz, 1 H) 2.76 (dd, J=13.74, 2.63 Hz, 1 H) 4.17-4.28 (m, 1 H) 4.43-4.84 (m, 2 H) 7.17 (dd, J=11.55, 8.92 Hz, 1 H) 7.62 (dd, J=6.94, 2.70 Hz, 1 H) 8.04-8.12 (m, 1 H) 8.22 (dd, J=8.18, 2.05 Hz, 1 H) 8.43 (dd, J=8.11, 0.80 Hz, 1 H) 8.91 (dd, J=1.97, 0.80 Hz, 1 H) 9.90 (s, 1 H)

Example 60 (Method G)

Synthesis of N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide

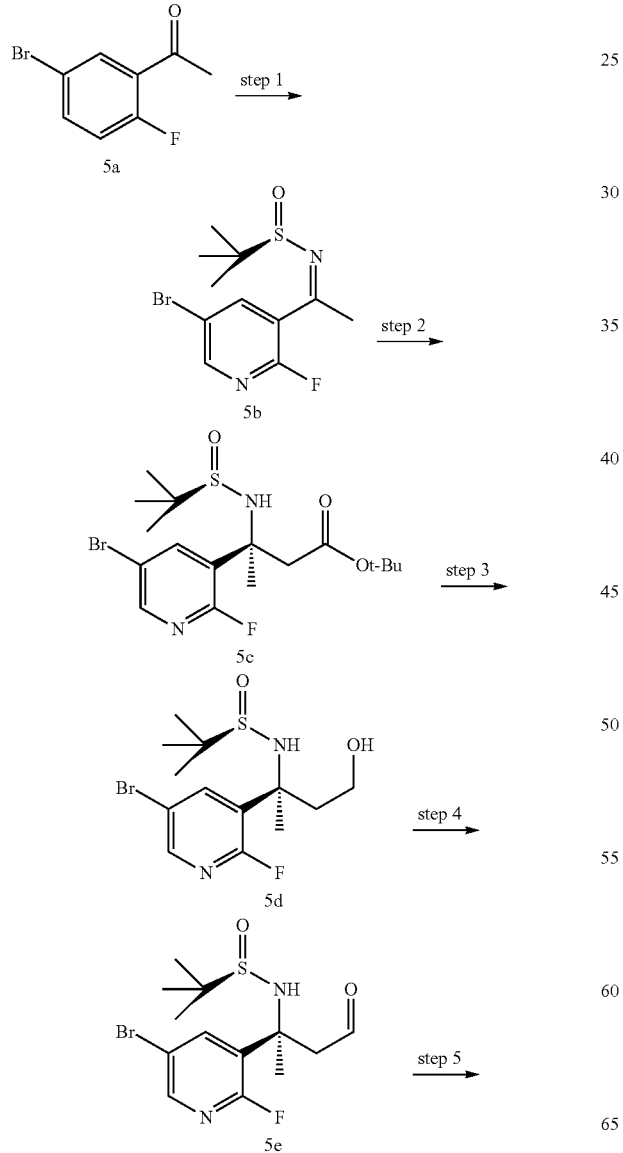

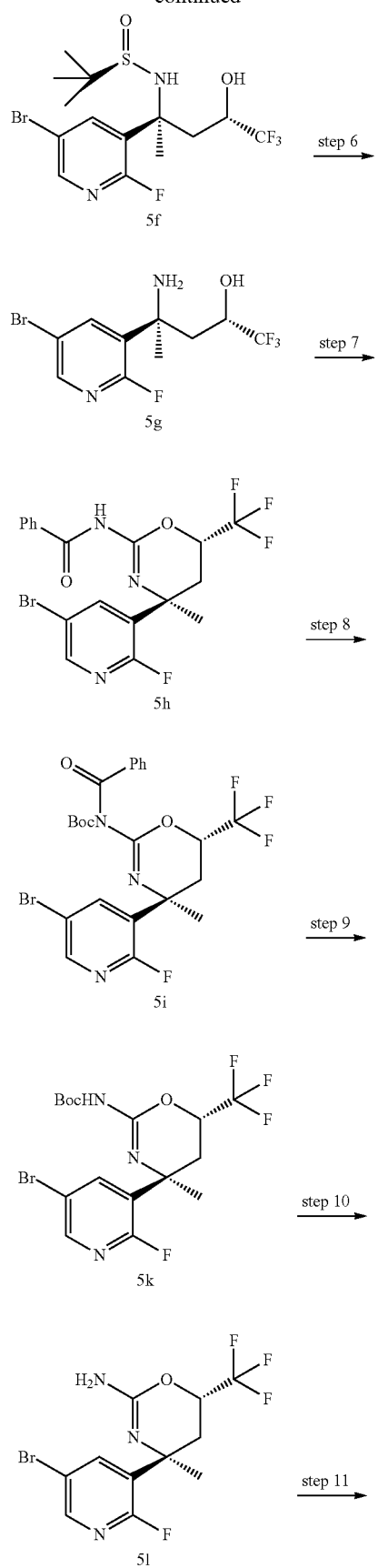

-continued

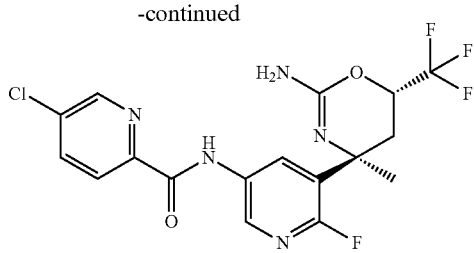

Step 1: (R,Z)—N-(1-(5-bromo-2-fluoropyridin-3-yl)ethylidene)-2-methylpropane-2-sulfinamide (5b)

A mixture of 1-(5-bromo-2-fluoropyridin-3-yl)ethanone (5a, synthesized according to procedures described in WO2009016460; 11 g, 50.5 mmol), (R)-2-methylpropane-2-sulfinamide (Ak Scientific, 12.23 g, 101 mmol) and titanium (IV) ethoxide (Aldrich, 26.1 ml, 126 mmol) in THF (100 mL) was heated to reflux for 2 h. The mixture was cooled to room temperature, and brine (200 mL) was added. The suspension was vigorously stirred for 10 min. The suspension was filtered through a pad of silica gel and the organic phase was separated. The aqueous phase was extracted with EtOAc. The combined organic layers were washed with brine, dried over $Na_2SO_4$ and concentrated under reduced pressure. The residue was purified by silica gel chromatography (gradient 0-20% EtOAc/hexanes) to afford the title compound as a bright yellow oil (16 g, 49.8 mmol, 99% yield). MS m/z=320.8 [M+H]$^+$; Calculated for $C_{11}H_{14}BrFN_2OS$: 320.0

Step 2: (5)-tert-butyl 3-(5-bromo-2-fluoropyridin-3-yl)-3-((R)-1,1-dimethylethylsulfinamido)butanoate (5c)

The title compound was synthesized following steps and procedures analogous to those described in Method E (step 1) above, but starting from (R,Z)—N-(1-(5-bromo-2-fluoropyridin-3-yl)ethylidene)-2-methylpropane-2-sulfinamide (5b). MS m/z=460.9 [M+Na]$^+$; Calculated for $C_{17}H_{26}BrFN_2O_3S$: 436.1

Step 3: (R)-N-(2-(5-bromo-2-fluoropyridin-3-yl)-4-hydroxybutan-2-yl)-2-methylpropane-2-sulfinamide (5d)

The title compound was synthesized using steps and procedures analogous to those described in Method E (step 2) above, but using (5c)
MS m/z=367 [M]$^+$; Calculated: 367.27

Step 4: (R)-N-(2-(5-bromo-2-fluoropyridin-3-yl)-4-oxobutan-2-yl)-2-methylpropane-2-sulfinamide (5e)

The title compound was synthesized using steps and procedures analogous to those described in Method E (step 3) above, but using (5d)
MS m/z=367 [M+H]$^+$; Calculated: 365.26

Step 5: (R)-N-((2S,4S)-2-(5-bromo-2-fluoropyridin-3-yl)-5,5,5-trifluoro-4-hydroxypentan-2-yl)-2-methylpropane-2-sulfinamide (5f)

The title compound was synthesized using steps and procedures analogous to those described in Method E (step 4) above, but using (5e).
MS m/z=434.9 [M]$^+$; Calculated: 435.27

Step 6: (2S,4S)-4-amino-4-(5-bromo-2-fluoropyridin-3-yl)-1,1,1-trifluoropentan-2-ol (5g)

The title compound was synthesized using steps and procedures analogous to those described in Method E (step 5) above, but using (5f).
MS m/z=331 [M]$^+$; Calculated: 331.1

Steps 7: N-((4S,6S)-4-(5-bromo-2-fluoropyridin-3-yl)-4-methyl-6-(trifluoromethyl)-5,6-dihydro-4H-1,3-oxazin-2-yl)benzamide (5h)

The title compound was synthesized using steps and procedures analogous to those described in Method E (step 6) above, but using (5g).
MS m/z=460/462 [M]$^+$/[M+2]$^+$. Calculated for $C_{18}H_{14}BrF_4N_3O_2$: 460.22

Step 8: tert-Butyl benzoyl((4S,6S)-4-(5-bromo-2-fluoropyridin-3-yl)-4-methyl-6-(trifluoromethyl)-5,6-dihydro-4H-1,3-oxazin-2-yl)carbamate (5i)

To a solution of N-((4S,6S)-4-(5-bromo-2-fluoropyridin-3-yl)-4-methyl-6-(trifluoromethyl)-5,6-dihydro-4H-1,3-oxazin-2-yl)benzamide (5h, 0.665 g, 1.445 mmol) in DCM (24 mL) was added di-t-butyldicarbonate (Aldrich, 0.347 g, 1.589 mmol) followed by 4-dimethylaminopyridine (Aldrich, 0.018 g, 0.144 mmol). The reaction mixture was stirred for 15 min at room temperature. The solvent was removed under reduced pressure to give the title compound, which was used in the next step without further purification. MS m/z=582, 584 [M+Na]$^+$/[M+2+Na]$^+$). Calculated for $C_{23}H_{22}BrF_4N_3O_4$: 560.3

Step 9: tert-Butyl ((4S,6S)-4-(5-bromo-2-fluoropyridin-3-yl)-4-methyl-6-(trifluoromethyl)-5,6-dihydro-4H-1,3-oxazin-2-yl)carbamate (5k)

The crude product (5i) from step 7 was dissolved in MeOH (15 mL). Potassium carbonate (Aldrich, 0.200 g, 1.445 mmol) was added and the reaction was stirred at room temperature for 40 min. Hydrogen chloride (4M in 1,4-dioxane; 1.1 mL, 4.40 mmol) was added to the reaction mixture and the solvent was removed under the reduced pressure. The residue was diluted with EtOAc and water. The organic layer was washed with brine, and dried over sodium sulfate. The filtrate was concentrated and the residue used in the next step without further purification. MS m/z=400, 402 [M−tBu]$^+$/[M+2−tBu]$^+$; Calculated for $C_{16}H_{18}BrF_4N_0O_3$: 456.2

Step 10: (4S,6S)-4-(5-bromo-2-fluoropyridin-3-yl)-4-methyl-6-(trifluoromethyl)-5,6-dihydro-4H-1,3-oxazin-2-amine (5l)

The crude product (5k) from step 8 was dissolved in MeOH (5 mL). To this solution was added hydrogen chloride (4M in 1,4-dioxane; 8.0 mL, 32.0 mmol) and the reaction mixture was stirred at room temperature for 14 hours and was heated subsequently to 55° C. for 3.5 hours. The reaction mixture was concentrated, the residue was dissolved in water and the pH was adjusted to neutral with saturated sodium bicarbonate. The solution was extracted with DCM. The combined organic extracts were washed with brine and dried over sodium sulfate. The filtrate was concentrated and purified by silica gel column (gradient 0-5% MeOH/DCM) to afford the title compound (0.335 g, 0.941 mmol, 65.1% yield) as white solid. MS m/z=356, 358 [M]⁺/[M+2]⁺. Calculated for C₁₁H₁₀BrFF₄N₃O: 356.2

Step 11: N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide A sealable vial was charged with (4S,6S)-4-(5-bromo-2-fluoropyridin-3-yl)-4-methyl-6-(trifluoromethyl)-5,6-dihydro-4H-1,3-oxazin-2-amine (5l, 0.093 g, 0.261 mmol), 5-chloropicolinamide (intermediate 18, 0.082 g, 0.522 mmol), copper(I) iodide (10 mg, 0.052 mmol) and potassium carbonate (0.108 mg, 0.783 mmol). The vial was purged with Nitrogen, followed by the addition of 1,4-dioxane (2.0 mL) and (1R,2R)-N,N'-dimethyl-cyclohexane-1,2-diamine (0.033 mL, 0.209 mmol). The vial was sealed and heated to 125° C. for 17 h. The reaction mixture was allowed to cool to room temperature and partitioned between EtOAc and water. The aqueous layer was backextracted with EtOAc. The combined organic layers were washed with brine and dried over sodium sulfate. The filtrate was concentrated and the residue was purified by reversed-phase preparative HPLC using a Phenomenex Gemini column, 10 micron, C18, 110 Å, 100× 50 mm, 0.1% TFA in CH₃CN/H₂O, gradient 10% to 80% over 20 min. The product containing fractions were combined and neutralized with aqueous saturated sodium bicarbonate solution. The free-based product was extracted with DCM. The organic phase was dried over MgSO₄ and the solvent was removed under reduced pressure to afford the title compound (0.060 g, 0.139 mmol, 53.2% yield) as white solid (free base). MS m/z=432.0 [M+H]⁺. Calculated for C₁₇H₁₄ClF₄N₅O₂: 431.8

¹H NMR (300 MHz, CHLOROFORM-d) δ=9.88 (br. s., 1 H), 8.72-8.47 (m, 2 H), 8.32-8.10 (m, 2 H), 7.90 (d, J=7.5 Hz, 1 H), 4.04 (br. s., 1 H), 2.84 (d, J=13.0 Hz, 1 H), 1.95 (t, J=13.2 Hz, 1 H), 1.67 (s, 3 H)

Example 61

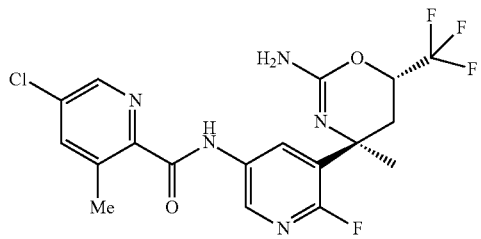 [SMILES: Cc1cc(Cl)cnc1C(=O)Nc1cnc(F)c([C@]2(C)C[C@@H](C(F)(F)F)OC(N)=N2)c1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-chloro-3-methylpicolinamide The title compound was synthesized by procedures and steps analogous to those described in Method G (Example 60) above, but using 5-chloro-3-methylpicolinamide (intermediate 20) in step 10. MS m/z=466 [M]⁺; Calculated for C₁₈H₁₆ClF₄N₅O₂: 466

¹H NMR (400 MHz, CHLOROFORM-d) δ=10.07 (br. s., 1 H), 8.69 (s, 1 H), 8.39 (s, 1H), 8.06 (d, J=7.8 Hz, 1 H), 7.66 (s, 1 H), 4.02 (d, J=5.5 Hz, 1 H), 2.97-2.81 (m, 1 H), 2.78 (s, 3 H), 1.93 (t, J=13.3 Hz, 1 H), 1.66 (br. s., 3 H).

Example 62

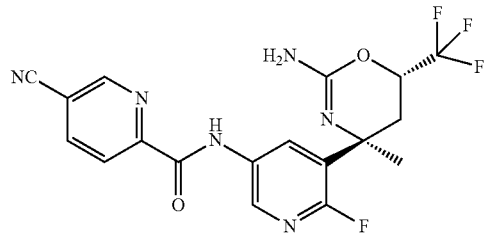 [SMILES: C[C@@]1(c2cc(NC(=O)c3ccc(C#N)cn3)cnc2F)C[C@@H](C(F)(F)F)OC(N)=N1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-cyanopicolinamide The title compound was synthesized by procedures and steps analogous to those described in Method G (Example 60) above, but using 5-cyanopicolinamide (intermediate 19) in step 10. MS m/z=423.0 [M+H]⁺. Calculated for C₁₈H₁₄F₄N₆O₂: 422.3

¹H NMR (400 MHz, CHLOROFORM-d) δ=9.92 (br. s., 1 H), 8.91 (s, 1 H), 8.67 (br. s., 1 H), 8.43 (d, J=8.2 Hz, 1 H), 8.22 (ddd, J=2.1, 8.5, 13.5 Hz, 2 H), 4.03 (d, J=5.3 Hz, 1H), 2.85 (d, J=13.9 Hz, 1 H), 1.96 (t, J=13.3 Hz, 1 H), 1.68 (s, 3 H).

Example 63

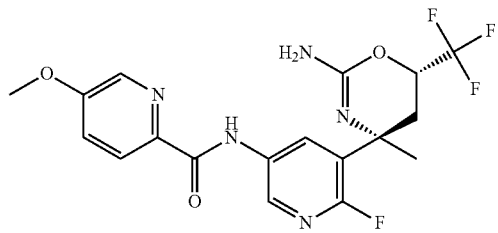 [SMILES: COc1ccc(C(=O)Nc2cnc(F)c([C@]3(C)C[C@@H](C(F)(F)F)OC(N)=N3)c2)nc1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-methoxypicolinamide The title compound was synthesized by procedures and steps analogous to those described in Method G (Example 60) above, but using 5-methoxypicolinamide in step 10. MS m/z=428.1 [M+H]⁺. Calculated for C₁₈H₁₇F₄N₅O₃: 427.4

¹H NMR (400 MHz, CHLOROFORM-d) δ=9.91 (s, 1 H), 8.65 (t, J=2.2 Hz, 1 H), 8.26 (d, J=2.7 Hz, 0 H), 8.22 (d, J=8.6 Hz, 1 H), 8.19 (dd, J=2.6, 8.9 Hz, 1 H), 7.34 (dd, J=2.8, 8.7

Hz, 1 H), 4.11-4.00 (m, 1 H), 2.84 (dd, J=2.6, 14.0 Hz, 1 H), 1.95 (dd, J=12.9, 13.7 Hz, 1 H), 1.68 (s, 3 H)

Example 64

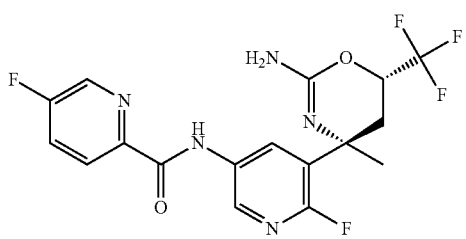 [SMILES: C[C@@]1(c2cc(NC(=O)c3ccc(F)cn3)cnc2F)C[C@@H](C(F)(F)F)OC(N)=N1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-fluoropicolinamide The title compound was synthesized by procedures and steps analogous to those described in Method G (Example 60) above, but using 5-fluoropicolinamide in step 10. MS m/z=416.1 [M+H]$^+$. Calculated for $C_{17}H_{14}F_5N_5O_2$: 415.3

$^1$H NMR (400 MHz, CHLOROFORM-d) δ=9.85 (s, 1 H), 8.67-8.62 (m, 1 H), 8.46 (d, J=2.7 Hz, 1 H), 8.33 (dd, J=4.5, 8.8 Hz, 1 H), 8.17 (dd, J=2.7, 8.8 Hz, 1 H), 7.62 (dt, J=2.7, 8.3 Hz, 1 H), 4.06-3.96 (m, 1 H), 2.82 (dd, J=2.7, 13.9 Hz, 1 H), 1.93 (dd, J=12.7, 13.7 Hz, 1 H), 1.65 (d, J=1.0 Hz, 3 H)

Example 65

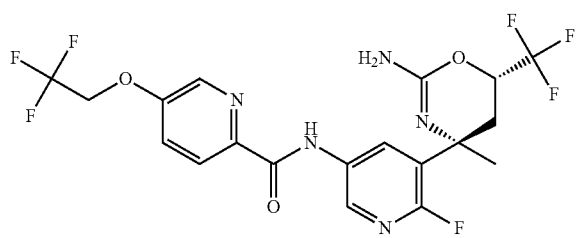 [SMILES: C[C@@]1(c2cc(NC(=O)c3ccc(OCC(F)(F)F)cn3)cnc2F)C[C@@H](C(F)(F)F)OC(N)=N1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-(2,2,2-trifluoroethoxy)picolinamide The title compound was synthesized by procedures and steps analogous to those described in Method G (Example 60) above, but using 5-((2,2,2-trifluoroethoxy)picolinamide (intermediate 5) in step 10. MS m/z=496.1 [M+H]$^+$. Calculated for $C_{19}H_{16}F_7N_5O_3$: 495.4

$^1$H NMR (400 MHz, CHLOROFORM-d) δ=9.85 (s, 1 H), 8.66-8.62 (m, 1 H), 8.35 (d, J=2.7 Hz, 1 H), 8.28 (d, J=8.6 Hz, 1 H), 8.17 (dd, J=2.7, 8.8 Hz, 1 H), 7.42 (dd, J=2.9, 8.6 Hz, 1 H), 4.50 (q, J=7.8 Hz, 2 H), 4.07-3.96 (m, 1 H), 2.82 (dd, J=2.7, 13.9 Hz, 1 H), 1.92 (dd, J=12.8, 13.8 Hz, 1 H), 1.65 (d, J=0.8 Hz, 3 H)

Example 66 (Method H)

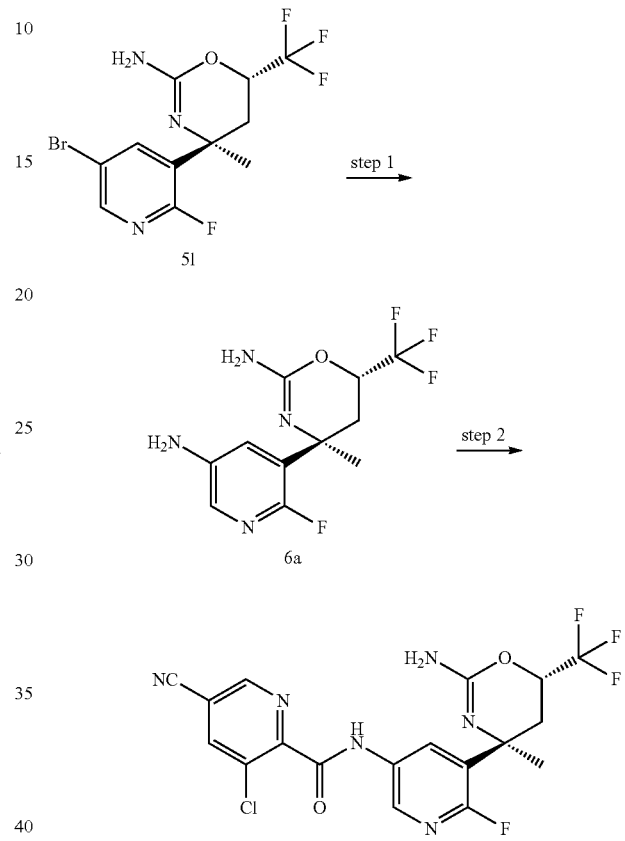

Step 1: N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide (6a)

A sealable vial was charged with (4S,6S)-4-(5-bromo-2-fluoropyridin-3-yl)-4-methyl-6-(trifluoromethyl)-5,6-dihydro-4H-1,3-oxazin-2-amine (5l; 0.126 g, 0.354 mmol), 2,2,2-trifluoroacetamide (Fluka, 0.080 g, 0.708 mmol), copper(I) iodide (Aldrich, 3.00 μl, 0.088 mmol) and potassium carbonate (Aldrich, 0.147 g, 1.061 mmol). The vial was purged with Nitrogen for 5 min and 1,4-dioxane (2.5 mL) and (1R,2R)-N,N'-dimethyl-cyclohexane-1,2-diamine (Aldrich, 0.028 mL, 0.177 mmol) were added. The vial was sealed and heated to 120° C. for 17 hours. MeOH (1 ml) and water (1 ml) were added to the cooled reaction mixture and heating was continued at 80° C. for 1 hour. The mixture was diluted with aqueous saturated ammonium chloride and extracted with DCM (2×). The combined organic extracts were washed with brine and dried over sodium sulfate. The filtrate was concentrated under reduced pressure and the residue was purified by silica gel column (gradient 0-6% 2M ammonia in MeOH/DCM) to afford the title compound as tan solid. MS m/z=293.1 [M+H]$^+$. Calculated for $C_{11}H_{12}F_4N_4O$: 292.2

Step 2: N-(5-((4S,6S)-2-amino-4-methyl-6-(trifluoromethyl)-5,6-dihydro-4H-1,3-oxazin-4-yl)-6-fluoropyridin-3-yl)-3-chloro-5-cyanopicolinamide A flask was charged with (4S,6S)-4-(5-amino-2-fluoropyridin-3-yl)-4-methyl-6-(trifluoromethyl)-5,6-dihydro-4H-1,3-oxazin-2-amine (6a, 0.075 g, 0.257 mmol) and 3-chloro-5-cyanopicolinic acid (Bionet Research, 0.047 g, 0.257 mmol). The solids were dissolved in a mixture of THF (2 mL)/MeOH (1 mL) and 4-(4,6-dimethoxy-1,3,5-triazin-2-yl)-4-methylmorpholinium chloride (Aldrich, 0.129 g, 0.436 mmol) was added. The reaction was stirred at RT for 25 min. Additional 0.5 equiv. chloro-5-cyanopicolinic acid and 1 equiv. 4-(4,6-dimethoxy-1,3,5-triazin-2-yl)-4-methylmorpholinium chloride were added. After 1 hour, the reaction was quenched with aqueous saturated sodium bicarbonate solution and extracted with EtOAc. The organic layer was washed with brine and dried over sodium sulfate. The filtrate was concentrated and purified by reversed-phase preparative HPLC using a Phenomenex Gemini column, 10 micron, C18, 110 Å, 100×50 mm, 0.1% TFA in CH$_3$CN/H$_2$O, gradient 10% to 80% over 20 min. The product containing fractions were combined and neutralized with aqueous sodium bicarbonate solution. The free-based product was extracted with DCM. The organic phase was dried over MgSO$_4$ and the solvent was removed under reduced pressure to afford the title compound (0.026 g, 0.057 mmol, 22.18% yield) as white solid. MS m/z=457 [M+H]$^+$. Calculated for C$_{18}$H$_{13}$ClF$_4$N$_6$O$_2$: 456.8

$^1$H NMR (400 MHz, CHLOROFORM-d) δ=9.78 (br. s., 1 H), 8.79 (s, 1 H), 8.74-8.67 (m, 1 H), 8.20 (s, 1 H), 8.06 (d, J=8.0 Hz, 1 H), 4.09-3.94 (m, J=9.6 Hz, 1 H), 2.84 (d, J=13.5 Hz, 1 H), 1.94 (t, J=13.3 Hz, 1 H), 1.65 (s, 3 H).

Example 67

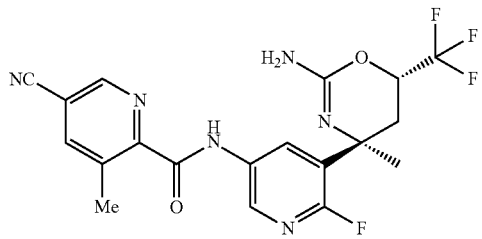 [SMILES: Cc1cc(C#N)cnc1C(=O)Nc1cnc(F)c([C@]2(C)C[C@@H](C(F)(F)F)OC(N)=N2)c1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-cyano-3-methylpicolinamide The title compound was synthesized using steps and procedures analogous to those described in Method H (Example 66) above, but using 5-cyano-3-methylpicolinic acid (intermediate 16) in step 2. MS m/z=437.1 [M+H]$^+$. Calculated for C$_{19}$H$_{16}$F$_4$N$_6$O$_2$: 436.4

$^1$H NMR (400 MHz, CHLOROFORM-d) δ=10.05 (br. s., 1 H), 8.67 (s, 1 H), 8.64 (br. s., 1 H), 8.00 (d, J=6.7 Hz, 1 H), 7.91 (s, 1 H), 4.05-3.92 (m, J=5.5 Hz, 1 H), 2.86-2.80 (m, 1 H), 2.80 (s, 3 H), 1.90 (t, J=13.3 Hz, 1 H), 1.62 (s, 3 H)

Example 68

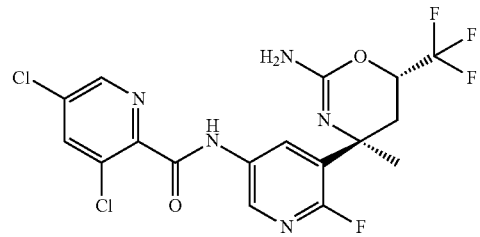 [SMILES: C[C@@]1(c2cc(NC(=O)c3ncc(Cl)cc3Cl)cnc2F)C[C@@H](C(F)(F)F)OC(N)=N1]

Synthesis of N-(5-((4S,6S)-2-amino-4-methyl-6-(trifluoromethyl)-5,6-dihydro-4H-1,3-oxazin-4-yl)-6-fluoropyridin-3-yl)-3,5-dichloropicolinamide The title compound was synthesized using steps and procedures analogous to those described in Method H (Example 66) above, but using 3,5-dichloropyridine-2-carboxylic acid (Matrix Scientific) in step 2. MS m/z=466 [M]$^+$. Calculated for C$_{17}$H$_{13}$Cl$_2$F$_4$N$_5$O$_2$: 466.2

$^1$H NMR (400 MHz, CHLOROFORM-d) δ=9.87 (br. s., 1 H), 8.80-8.71 (m, 1 H), 8.53 (d, J=2.2 Hz, 1 H), 8.08 (dd, J=2.3, 8.8 Hz, 1 H), 7.96 (d, J=2.0 Hz, 1 H), 4.14-4.03 (m, 1 H), 2.89 (dd, J=2.4, 14.0 Hz, 1 H), 1.98 (t, J=13.3 Hz, 1 H), 1.70 (s, 3 H)

Example 69

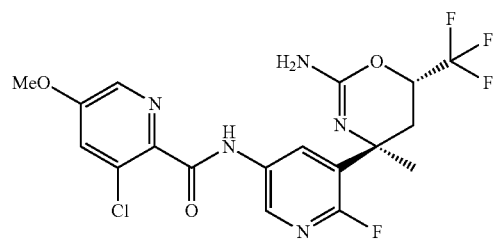 [SMILES: COc1cnc(C(=O)Nc2cnc(F)c([C@]3(C)C[C@@H](C(F)(F)F)OC(N)=N3)c2)c(Cl)c1]

Synthesis of N-(5-((4S,6S)-2-amino-4-methyl-6-(trifluoromethyl)-5,6-dihydro-4H-1,3-oxazin-4-yl)-6-fluoropyridin-3-yl)-3-chloro-5-methoxypicolinamide The title compound was synthesized using steps and procedures analogous to those described in Method H (Example 66) above, but using 3-chloro-5-methoxypicolinic acid (AfferChem) in step 2. MS m/z=462 [M+H]$^+$. Calculated for C$_{18}$H$_{16}$ClF$_4$N$_5$O$_3$: 461.8

$^1$H NMR (400 MHz, CHLOROFORM-d) δ 9.91 (s, 1H), 8.70 (t, J=2.15 Hz, 1H), 8.16 (d, J=2.54 Hz, 1H), 8.08 (dd, J=2.54, 8.80 Hz, 1H), 7.31 (d, J=2.54 Hz, 1H), 3.97-4.07 (m,

1H), 3.95 (s, 3H), 2.82 (dd, J=2.74, 13.89 Hz, 1H), 1.92 (dd, J=13.60, 12.80 Hz, 1H), 1.64 (s, 3H)

Example 70

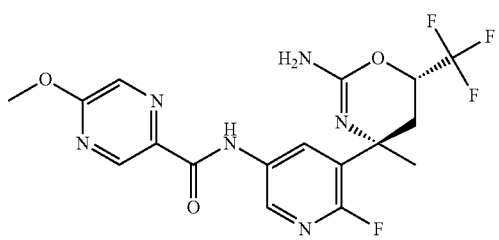 [SMILES: COc1cnc(C(=O)Nc2cnc(F)c([C@]3(C)C[C@@H](C(F)(F)F)OC(N)=N3)c2)cn1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-methoxypyrazine-2-carboxamide The title compound was synthesized using steps and procedures analogous to those described in Method H (Example 66) above, but using 5-methoxypyrazine-2-carboxylic acid (Ark Pharm, Inc.) in step 2. MS m/z=429.0 [M+H]$^+$. Calculated for $C_{17}H_{16}F_4N_6O_3$: 428.3

$^1$H NMR (400 MHz, CHLOROFORM-d) δ=9.54 (s, 1H), 9.01 (s, 1 H), 8.63 (s, 1 H), 8.19-8.15 (m, 1 H), 8.15 (s, 1 H), 4.08 (s, 3 H), 4.06-3.95 (m, 1 H), 2.82 (dd, J=2.5, 13.9 Hz, 1 H), 1.93 (t, J=13.2 Hz, 1 H), 1.65 (s, 3 H).

Example 71

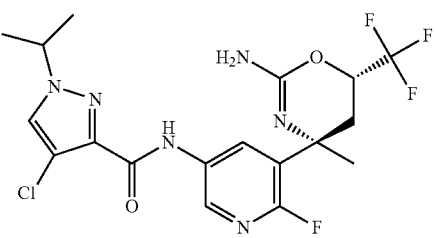 [SMILES: CC(C)n1cc(Cl)c(C(=O)Nc2cnc(F)c([C@]3(C)C[C@@H](C(F)(F)F)OC(N)=N3)c2)n1]

Synthesis of N-(5-((4S,6S)-2-amino-4-methyl-6-(trifluoromethyl)-5,6-dihydro-4H-1,3-oxazin-4-yl)-6-fluoropyridin-3-yl)-4-chloro-1-isopropyl-1H-pyrazole-3-carboxamide The title compound was synthesized using steps and procedures analogous to those described in Method H (Example 66) above, but using 4-chloro-1-isopropyl-1H-pyrazole-3-carboxylic acid (intermediate 28) in step 2. MS m/z=463.1 [M+H]$^+$. Calculated for $C_{18}H_{19}ClF_4N_6O_2$: 462.8

$^1$H NMR (400 MHz, CHLOROFORM-d) δ ppm 1.54 (s, 3 H) 1.55 (s, 3 H) 1.70 (s, 3 H) 1.99 (t, J=13.30 Hz, 1 H) 2.88 (dd, J=14.08, 2.15 Hz, 1 H) 4.10 (m, J=10.17, 5.09 Hz, 1 H) 4.50 (dt, J=13.35, 6.72 Hz, 1 H) 7.51 (s, 1 H) 8.03 (d, J=8.02 Hz, 1 H) 8.66 (s, 1 H) 8.73 (br. s., 1 H).

Example 72

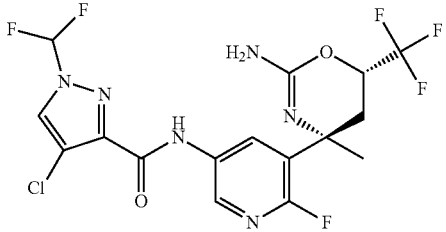 [SMILES: C[C@@]1(c2cc(NC(=O)c3nn(C(F)F)cc3Cl)cnc2F)C[C@@H](C(F)(F)F)OC(N)=N1]

Synthesis of N-(5-((4S,6S)-2-amino-4-methyl-6-(trifluoromethyl)-5,6-dihydro-4H-1,3-oxazin-4-yl)-6-fluoropyridin-3-yl)-4-chloro-1-(difluoromethyl)-1H-pyrazole-3-carboxamide The title compound was synthesized using steps and procedures analogous to those described in Method H (Example 66) above, but using 4-chloro-1-(difluoromethyl)-1H-pyrazole-3-carboxylic acid (WO2011069934) in step 2. MS m/z=471.0 [M+H]$^+$. Calculated for $C_{16}H_{13}ClF_6N_6O_2$: 470.8

$^1$H NMR (400 MHz, CHLOROFORM-d) δ ppm 1.63 (s, 3 H) 1.91 (t, J=13.30 Hz, 1 H) 2.81 (dd, J=13.99, 2.25 Hz, 1 H) 3.99 (m, J=9.88, 5.38 Hz, 1 H) 4.41 (br. s., 2 H) 7.14 (s, 1 H) 7.93 (s, 1 H) 8.04 (dd, J=8.80, 2.54 Hz, 1 H) 8.54-8.67 (m, 2 H).

Example 73

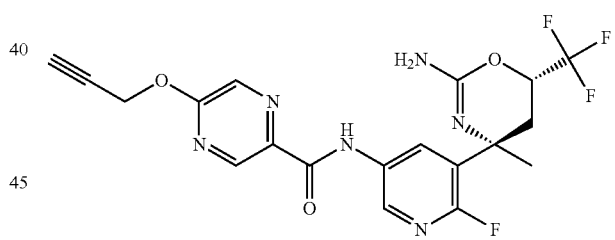

Synthesis of N-(5-((4S,6S)-2-amino-4-methyl-6-(trifluoromethyl)-5,6-dihydro-4H-1,3-oxazin-4-yl)-6-fluoropyridin-3-yl)-5-(prop-2-yn-1-yloxy)pyrazine-2-carboxamide The title compound was synthesized using steps and procedures analogous to those described in Method H (Example 66) above, but using 5-(prop-2-yn-1-yloxy)pyrazine-2-carboxylic acid (J. Med. Chem. 2013, 56, 3980) in step 2. After HPLC purification as described in Method H, the product was further purified again by prep-TLC using 5% MeOH in DCM as the eluent. Desired band was cut-out, eluted with 5% MeOH in DCM and concentrated to give a white solid after drying (33.0 mg, 31.4% yield). MS m/z=453.0 [M+H]$^+$. Calculated for $C_{19}H_{16}F_4N_6O_3$: 452.1

$^1$H NMR (400 MHz, CHLOROFORM-d) δ 9.56 (br. s., 1H), 9.00 (s, 1H), 8.61 (br. s., 1H), 8.22 (d, J=2.35 Hz, 1H), 8.19 (s, 1H), 5.09 (d, J=2.15 Hz, 2H), 4.01 (dd, J=5.48, 9.98

Hz, 1H), 2.81 (dd, J=2.25, 13.79 Hz, 1H), 2.56 (s, 1H), 1.92 (t, J=13.30 Hz, 1H), 1.64 (s, 3H)

Example 74 (Method I)

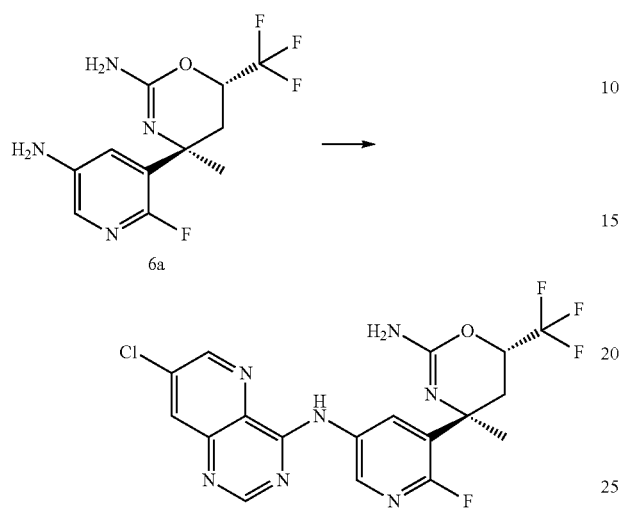

6a

Synthesis of (4S,6S)-4-(5-((7-chloropyrido[3,2-d]pyrimidin-4-yl)amino)-2-fluoropyridin-3-yl)-4-methyl-6-(trifluoromethyl)-5,6-dihydro-4H-1,3-oxazin-2-amine The title compound was synthesized using steps and procedures analogous to those described in Method B (step 2) above, but using (4S,6S)-4-(5-amino-2-fluoropyridin-3-yl)-4-methyl-6-(trifluoromethyl)-5,6-dihydro-4H-1,3-oxazin-2-amine (6a) and 4,7-dichloropyrido[3,2-d]pyrimidine (intermediate 9). MS m/z=456.0 [M+H]$^+$. Calculated for C$_{18}$H$_{14}$ClF$_4$N$_7$O: 455.8

$^1$H NMR (400 MHz, CHLOROFORM-d) δ=9.01 (s, 1 H), 8.82-8.79 (m, 1 H), 8.78 (s, 1 H), 8.74 (d, J=2.2 Hz, 1 H), 8.40 (dd, J=2.7, 8.8 Hz, 3 H), 8.19 (d, J=2.2 Hz, 1 H), 4.10-4.00 (m, 1 H), 2.84 (dd, J=2.8, 14.0 Hz, 1 H), 1.94 (dd, J=12.8, 13.8 Hz, 1 H), 1.67 (s, 3 H)

Example 75

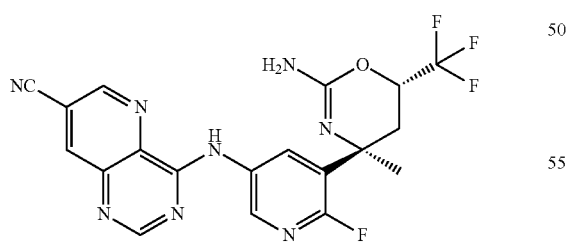

Synthesis of 4-((5-((4S,6S)-2-amino-4-methyl-6-(trifluoromethyl)-5,6-dihydro-4H-1,3-oxazin-4-yl)-6-fluoropyridin-3-yl)amino)pyrido[3,2-d]pyrimidine-7-carbonitrile The title compound was synthesized by procedures and steps analogous to those described in Method C (Example 22) above, but using (4S,6S)-4-(5-((7-chloropyrido[3,2-d]pyrimidin-4-yl)amino)-2-fluoropyridin-3-yl)-4-methyl-6-(trifluoromethyl)-5,6-dihydro-4H-1,3-oxazin-2-amine (Example 74). MS m/z=447.0 [M+H]$^+$. Calculated for C$_{19}$H$_{14}$F$_4$N$_8$O: 446.4

$^1$H NMR (400 MHz, CHLOROFORM-d) δ=9.16 (br. s., 1 H), 9.02 (s, 1 H), 8.90 (d, J=11.3 Hz, 2 H), 8.58 (s, 1 H), 8.45 (d, J=6.7 Hz, 1 H), 4.19-4.03 (m, 1 H), 2.91 (d, J=13.1 Hz, 1 H), 2.02 (t, J=13.2 Hz, 1 H), 1.74 (s, 3 H)

Example 76

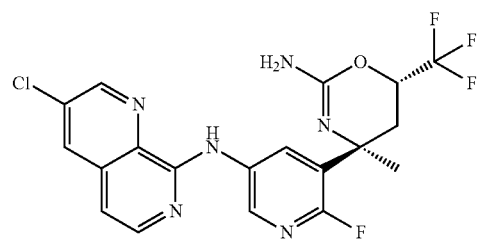 [SMILES: C[C@@]1(c2cc(Nc3nccc4cc(Cl)cnc34)cnc2F)C[C@@H](C(F)(F)F)OC(N)=N1]

Synthesis of (4S,6S)-4-(5-((3-chloro-1,7-naphthyridin-8-yl)amino)-2-fluoropyridin-3-yl)-4-methyl-6-(trifluoromethyl)-5,6-dihydro-4H-1,3-oxazin-2-amine The title compound was synthesized by procedures and steps analogous to those described in Method I above, but using 3,8-dichloro-1,7-naphthyridine (intermediate 2). MS m/z=455.0 (M+H). Calculated for C$_{19}$H$_{15}$ClF$_4$N$_6$O: 454.8

$^1$H NMR (400 MHz, CHLOROFORM-d) δ=8.88 (s, 1 H), 8.85-8.80 (m, 1 H), 8.67 (d, J=2.3 Hz, 1 H), 8.37 (dd, J=2.7, 9.0 Hz, 1 H), 8.12 (d, J=5.9 Hz, 1 H), 8.00 (d, J=2.3 Hz, 1 H), 6.95 (d, J=5.9 Hz, 1 H), 4.63-4.36 (m, 2 H), 4.15-4.00 (m, 1 H), 2.83 (dd, J=2.7, 13.9 Hz, 1 H), 1.92 (dd, J=12.7, 13.7 Hz, 1 H), 1.67 (s, 3 H)

Example 77

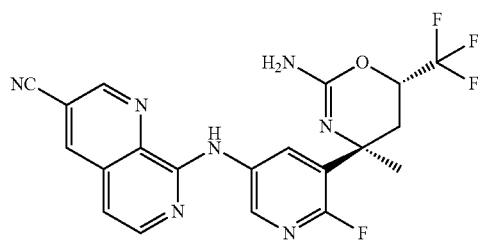 [SMILES: C[C@@]1(c2cc(Nc3nccc4cc(C#N)cnc34)cnc2F)C[C@@H](C(F)(F)F)OC(N)=N1]

Synthesis of 8-((5-((4S,6S)-2-amino-4-methyl-6-(trifluoromethyl)-5,6-dihydro-4H-1,3-oxazin-4-yl)-6-fluoropyridin-3-yl)amino)-1,7-naphthyridine-3-carbonitrile The title compound was synthesized by procedures and steps analogous to those described in Method C (Example 12)

above, but using (4S,6S)-4-(5-(((3-chloro-1,7-naphthyridin-8-yl)amino)-2-fluoropyridin-3-yl)-4-methyl-6-(trifluoromethyl)-5,6-dihydro-4H-1,3-oxazin-2-amine (Example 76). MS m/z=446.1 (M+H). Calculated for $C_{20}H_{15}F_4N_7O$: 445.4

¹H NMR (400 MHz, CHLOROFORM-d) δ=8.98 (d, J=7.2 Hz, 2 H), 8.87 (br. s., 1 H), 8.49-8.37 (m, 2 H), 8.28 (d, J=5.9 Hz, 1 H), 7.11 (d, J=5.7 Hz, 1 H), 4.21-4.01 (m, J=4.9 Hz, 1 H), 2.88 (dd, J=2.0, 13.7 Hz, 1 H), 1.98 (t, J=13.3 Hz, 1 H), 1.73 (s, 3 H)

Example 78

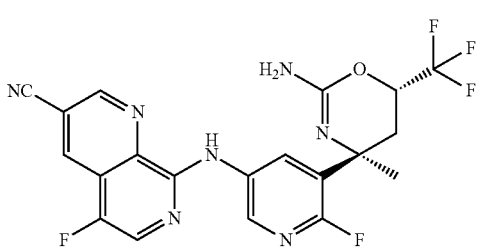 [SMILES: C[C@@]1(c2cc(Nc3ncc(F)c4cc(C#N)cnc34)cnc2F)C[C@@H](C(F)(F)F)OC(N)=N1]

Synthesis of 8-((5-((4S,6S)-2-amino-4-methyl-6-(trifluoromethyl)-5,6-dihydro-4H-1,3-oxazin-4-yl)-6-fluoropyridin-3-yl)amino)-5-fluoro-1,7-naphthyridine-3-carbonitrile To a solution of (4S,6S)-4-(5-amino-2-fluoropyridin-3-yl)-4-methyl-6-(trifluoromethyl)-5,6-dihydro-4H-1,3-oxazin-2-amine (6a, 0.076 g, 0.260 mmol) and 8-chloro-5-fluoro-1,7-naphthyridine-3-carbonitrile (intermediate 17, 0.065 g, 0.312 mmol) in 2-propanol (2.6 ml) was added 4-methylbenzene sulfonic acid (monohydrate, Fluka, 0.099 g, 0.520 mmol). The reaction mixture was heated to 100° C. for 1.5 hours. The reaction mixture was cooled to room temperature and concentrated under reduced pressure. The residue was partitioned between DCM and aqueous saturated sodium bicarbonate. The aqueous layer was backextracted with DCM. The combined organic extracts were washed with brine and dried over sodium sulfate. The filtrate was concentrated and the residue was purified by reversed-phase preparative HPLC using a Phenomenex Gemini column, 10 micron, C18, 110 Å, 100×50 mm, 0.1% TFA in $CH_3CN/H_2O$, gradient 10% to 100% over 20 min. The product containing fractions were combined and neutralized with aqueous sodium bicarbonate solution. The free-based product was extracted with DCM. The organic phase was dried over $MgSO_4$ and the solvent was removed under reduced pressure to afford the title compound (0.054 g, 0.117 mmol, 44.8% yield) as yellow solid. MS m/z=464.0 [M+H]⁺. Calculated for $C_{20}H_{14}F_5N_7O$: 463.4

¹H NMR (300 MHz, CHLOROFORM-d) δ=9.03 (d, J=1.9 Hz, 1 H), 8.84 (br. s, 1 H), 8.80 (t, J=2.3 Hz, 1 H), 8.70 (d, J=1.9 Hz, 1 H), 8.44-8.37 (m, 1 H), 8.18 (s, 1 H), 4.18-4.03 (m, 1 H), 2.94-2.83 (m, 1 H), 1.98 (t, J=1.0 Hz, 1 H), 1.72 (s, 3 H)

Example 79 (Method K)

Synthesis of N-(6-(((4S,6S)-2-amino-4-methyl-6-(trifluoromethyl)-5,6-dihydro-4H-1,3-oxazin-4-yl)-5-fluoropyridin-2-yl)-5-cyanopicolinamide

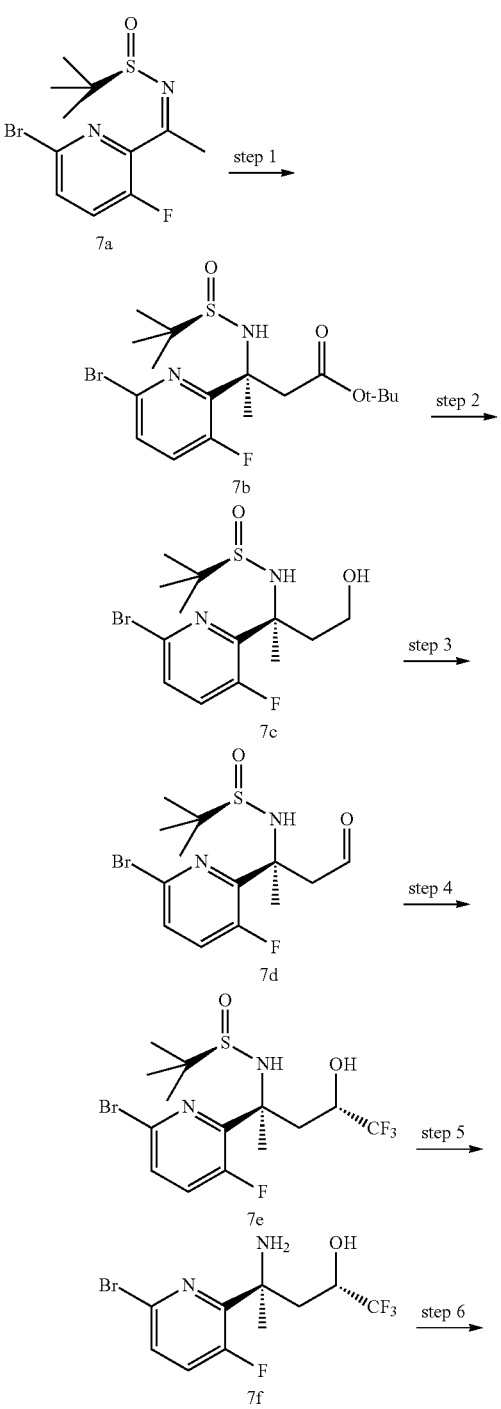

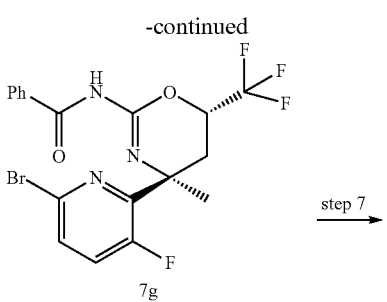

7g

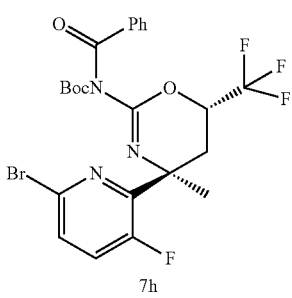

7h

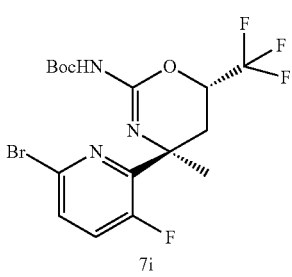

7i

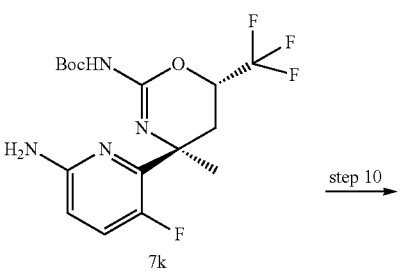

7k

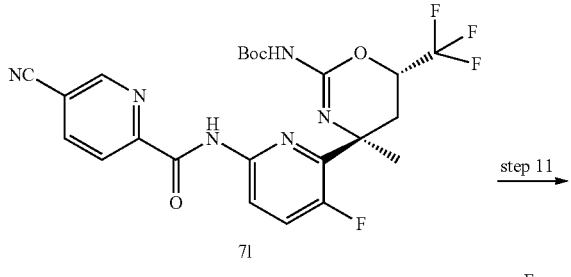

7l

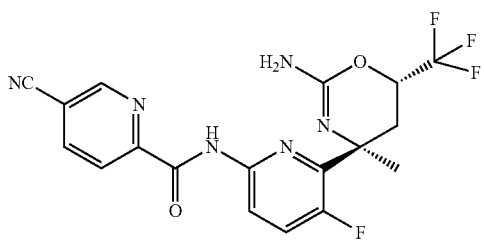

Step 1: (S)-tert-butyl 3-(6-bromo-3-fluoropyridin-2-yl)-3-((R)-1,1-dimethylethylsulfinamido)butanoate (7b)

The title compound was synthesized using steps and procedures analogous to those described in Method E (step 1) above, but using (R,Z)—N-(1-(6-bromo-3-fluoropyridin-2-yl)ethylidene)-2-methylpropane-2-sulfinamide (7a, synthesized following procedure described in WO2012139425).
MS m/z=437 [M]⁺. Calculated: 437.37

Step 2: (R)-N-((S)-2-(6-bromo-3-fluoropyridin-2-yl)-4-hydroxybutan-2-yl)-2-methylpropane-2-sulfinamide (7c)

The title compound was synthesized using steps and procedures analogous to those described in Method E (step 2) above, but using (7b).
MS m/z=367 [M+H]⁺. Calculated: 367.3

Step 3: (R)-N-((S)-2-(6-bromo-3-fluoropyridin-2-yl)-4-oxobutan-2-yl)-2-methylpropane-2-sulfinamide (7d)

The title compound was synthesized using steps and procedures analogous to those described in Method E (step 3) above, but using (7c).
MS m/z=366.9 [M+H]⁺. Calculated: 365.3

Step 4: (R)-N-((2S,4S)-2-(6-bromo-3-fluoropyridin-2-yl)-5,5,5-trifluoro-4-hydroxypentan-2-yl)-2-methylpropane-2-sulfinamide (7e)

The title compound was synthesized using steps and procedures analogous to those described in Method E (step 4) above, but using (7d).
MS m/z=434.9 [M]⁺. Calculated: 435.3

Step 5: (2S,4S)-4-amino-4-(6-bromo-3-fluoropyridin-2-yl)-1,1,1-trifluoropentan-2-ol (7f)

The title compound was synthesized using steps and procedures analogous to those described in Method E (step 5) above, but using (7e).
MS m/z=332.9 [M+H]⁺. Calculated: 331.1

Step 6: N-((4S,6S)-4-(6-bromo-3-fluoropyridin-2-yl)-4-methyl-6-(trifluoromethyl)-5,6-dihydro-4H-1,3-oxazin-2-yl)benzamide (7g)

The title compound was synthesized using steps and procedures analogous to those described in Method E (step 6) above, but using (7f).
MS m/z=460 [M]⁺. Calculated: 460.2

Step 7: tert-butyl benzoyl((4S,6S)-4-(6-bromo-3-fluoropyridin-2-yl)-4-methyl-6-(trifluoromethyl)-5,6-dihydro-4H-1,3-oxazin-2-yl)carbamate (7h)

The title compound was synthesized using steps and procedures analogous to those described in Method G (step 7) above, but using (7g).
MS m/z=560 [M]⁺. Calculated: 560.3

Step 8: tert-butyl ((4S,6S)-4-(6-bromo-3-fluoropyridin-2-yl)-4-methyl-6-(trifluoromethyl)-5,6-dihydro-4H-1,3-oxazin-2-yl)carbamate (7i)

The title compound was synthesized using steps and procedures analogous to those described in Method G (step 8) above, but using (7h).
MS m/z=456 [M]$^+$. Calculated: 456.2

Step 9: tert-Butyl ((4S,6S)-4-(6-amino-3-fluoropyridin-2-yl)-4-methyl-6-(trifluoromethyl)-5,6-dihydro-4H-1,3-oxazin-2-yl)carbamate (7k)

A sealable vial was charged with (+)-sodium L-ascorbate (0.026 g, 0.13 mmol, Aldrich), sodium azide (0.102 g, 1.56 mmol, Aldrich), copper(I) iodide (0.026 g, 0.13 mmol, Acros), and tert-butyl ((4S,6S)-4-(6-bromo-3-fluoropyridin-2-yl)-4-methyl-6-(trifluoromethyl)-5,6-dihydro-4H-1,3-oxazin-2-yl)carbamate (7i, 0.238 g, 0.52 mmol). The sealed vial was evacuated and backfilled with Nitrogen. EtOH (2.5 mL) was added followed by water (1 mL) and trans-N,N'-dimethylcyclohexane-1,2-diamine (0.021 mL, 0.130 mmol, Aldrich). The reaction mixture was heated to 70° C. for 3 hs. The cooled reaction mixture was partitioned between NH$_4$Cl/NH$_4$OH (9:1) (10 mL) and EtOAc (10 mL). The organic layer was separated, dried over sodium sulfate, and concentrated under reduced pressure. The crude material was purified via silica gel flash chromatography (gradient 10-50% EtOAc in hexanes) to afford the title compound as a white solid (0.119 g, 0.3 mmol, 58% yield). MS m/z=393.2 [M+H]$^+$. Calculated for C$_{16}$H$_{20}$F$_4$N$_4$O$_3$: 392.3

Step 10: tert-Butyl ((4S,6S)-4-(6-(5-cyanopicolinamido)-3-fluoropyridin-2-yl)-4-methyl-6-(trifluoromethyl)-5,6-dihydro-4H-1,3-oxazin-2-yl)carbamate (7l)

To a solution of tert-butyl ((4S,6S)-4-(6-amino-3-fluoropyridin-2-yl)-4-methyl-6-(trifluoromethyl)-5,6-dihydro-4H-1,3-oxazin-2-yl)carbamate (7k, 0.101 mg, 0.13 mmol) in EtOAc (4 mL) was added 5-cyano-2-pyridinecarboxylic acid (0.042 mg, 0.28 mmol, Aldrich), di-isopropylethylamine (0.09 mL, 0.51 mmol), and 1-propanephosphonic acid cyclic anhydride (0.18 mL, 0.28 mmol, 50 wt. % solution in ethyl acetate, Alfa-Aesar). The reaction mixture was stirred at room temperature for 2 hs. The reaction was diluted with saturated aqueous sodium bicarbonate and extracted with EtOAc (10 mL). The organic layer was washed sequentially with water and brine and dried over sodium sulfate. The solution was concentrated under reduced pressure and the crude material was purified via silica gel flash chromatography (gradient 0-30% EtOAc in hexanes) to afford the title compound as a white solid (0.097 g, 0.19 mmol, 72% yield). MS m/z=523.2 [M+H]$^+$. Calculated for C$_{23}$H$_{22}$F$_4$N$_6$O$_4$: 522.4

Step 11: N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide To a solution of tert-butyl ((4S,6S)-4-(6-(5-cyanopicolinamido)-3-fluoropyridin-2-yl)-4-methyl-6-(trifluoromethyl)-5,6-dihydro-4H-1,3-oxazin-2-yl)carbamate (7l, 0.096 g, 0.18 mmol) in DCM (3 mL) was added TFA (1 mL). The reaction mixture was stirred at room temperature for 1 h and the solvent was removed under reduced pressure. The residue was treated with 1 N NaOH (5 mL) and extracted with DCM (3×5 mL). The combined organic extracts were dried over sodium sulfate and concentrated under reduced pressure. The crude material was triturated with ether and the solid was filtered off to give the title compound as a white solid (0.065 g, 84% yield, 0.15 mmol) after drying under vacuum. MS m/z=423.0 [M+H]$^+$. Calculated for C$_{18}$H$_{14}$F$_4$N$_6$O$_2$: 422

$^1$H NMR (400 MHz, CHLOROFORM-d) δ 1.65 (s, 3H), 1.79 (t, J=12.90 Hz, 1H), 3.00 (d, J=13.50, 1H), 4.11 (br s, 2H), 4.50 (br s, 1H), 7.51 (t, J=9.68 Hz, 1H), 8.22 (d, J=8.22 Hz, 1H), 8.32 (d, J=8.61 Hz, 1H), 8.44 (d, J=8.02 Hz, 1H), 8.95 (s, 1H), 10.23 (br, 1H).

Example 80

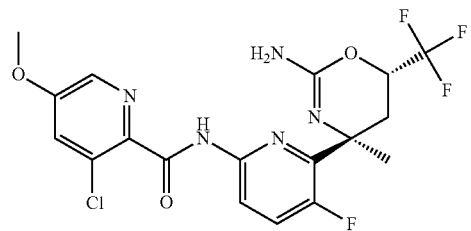 [SMILES: COc1cnc(C(=O)Nc2ccc(F)c([C@]3(C)C[C@@H](C(F)(F)F)OC(N)=N3)n2)c(Cl)c1]

Synthesis of N-(6-((4S,6S)-2-amino-4-methyl-6-(trifluoromethyl)-5,6-dihydro-4H-1,3-oxazin-4-yl)-5-fluoropyridin-2-yl)-3-chloro-5-methoxypicolinamide The title compound was synthesized by procedures and steps analogous to those described in Method K, Example 79 above, but using 3-chloro-5-methoxypicolinic acid (intermediate 27) in step 10. MS m/z=461.9 [M+H]$^+$. Calculated for C$_{15}$H$_{16}$ClF$_4$N$_5$O$_3$: 461.1.

$^1$H NMR (400 MHz, DMSO-d$_6$) δ ppm 1.42-1.67 (m, 4 H), 2.86 (d, J=9.78 Hz, 1 H), 3.94 (s, 3 H), 5.01 (br. s., 1 H), 5.75 (br. s, 2 H), 7.71 (dd, J=10.86, 8.90 Hz, 1 H), 7.75 (d, J=2.54 Hz, 1 H), 8.04 (d, J=7.63 Hz, 1 H), 8.39 (d, J=2.35 Hz, 1 H), 10.62 (s, 1 H).

Example 81 (Method L)

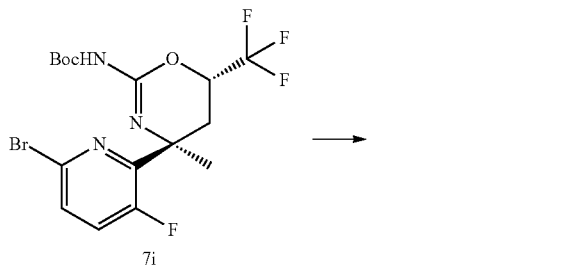

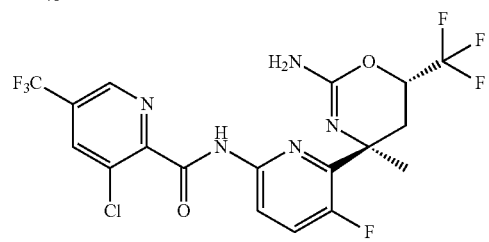

Synthesis of N-(6-((4S,6S)-2-amino-4-methyl-6-(trifluoromethyl)-5,6-dihydro-4H-1,3-oxazin-4-yl)-5-fluoropyridin-2-yl)-3-chloro-5-(trifluoromethyl)-picolinamide A sealable vial was charged with Pd$_2$(dba)$_3$ (Strem, 9.03 mg, 9.86 μmol), (9,9-dimethyl-9H-xanthene-4,5-diyl)bis(diphenylphosphine) (Strem, 22.83 mg, 0.039 mmol) and dioxane (0.5 mL). The reaction mixture was stirred under Nitrogen atmosphere for 10 min. A solution of tert-butyl ((4S,6S)-4-(6-bromo-3-fluoropyridin-2-yl)-4-methyl-6-(trifluoromethyl)-5,6-dihydro-4H-1,3-oxazin-2-yl)carbamate (7i, 60 mg, 0.132 mmol) in 1,4-dioxane (1.3 mL), 3-chloro-5-(trifluoromethyl)picolinamide (intermediate 22, 42.8 mg, 0.191 mmol), and cesium carbonate (Aldrich, 107 mg, 0.329 mmol) were added. The vial was sealed flushed with nitrogen for 10 min and the reaction was heated to 90° C. for 3 h. The reaction mixture was cooled to RT and filtered through a pad of celite. The filter cake was washed with EtOAc. The filtrate was concentrated under reduced pressure and the residue was purified by reverse-phase preparative HPLC using a Phenomenex Gemini column, 10 micron, C18, 110 Å, 150×30 mm, 0.1% TFA in CH$_3$CN/H$_2$O, gradient 10% to 70% over 25 min. The product containing fractions were combined and neutralized with aqueous sodium bicarbonate solution. The free-based product was extracted with DCM. The organic phase was dried over MgSO$_4$ and the solvent was removed under reduced pressure to afford the title compound (9 mg, 0.018 mmol, 13.69% yield) as white solid. MS m/z=500 [M]$^+$. Calculated for C$_{18}$H$_{13}$ClF$_7$N$_5$O$_2$: 499.7

$^1$H NMR (400 MHz, CHLOROFORM-d) ppm 1.93 (s, 3 H) 2.19 (t, J=13.30 Hz, 1 H) 3.13 (dd, J=13.89, 2.74 Hz, 1 H) 4.54 (br. s., 1 H) 5.45 (br. s., 2 H) 7.61 (t, J=9.49 Hz, 1 H) 8.16 (s, 1 H) 8.48 (dd, J=8.70, 3.03 Hz, 1 H) 8.87 (s, 1 H) 10.21 (s, 1 H).

Example 82

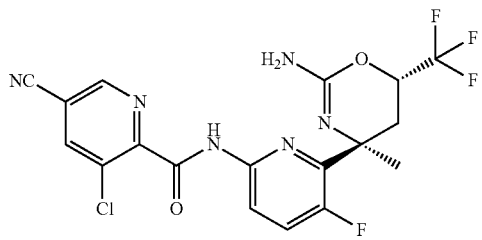 [SMILES: C[C@@]1(c2nc(NC(=O)c3ncc(C#N)cc3Cl)ccc2F)C[C@@H](C(F)(F)F)OC(N)=N1]

Synthesis of N-(6-((4S,6S)-2-amino-4-methyl-6-(trifluoromethyl)-5,6-dihydro-4H-1,3-oxazin-4-yl)-5-fluoropyridin-2-yl)-3-chloro-5-cyanopicolinamide The title compound was synthesized using steps and procedures analogous to those described in Method L (Example 81) above, but using 3-chloro-5-cyanopicolinamide (intermediate 2l). MS m/z=457 [M]$^+$. Calculated for C$_{17}$H$_{13}$Cl$_2$F$_4$N$_5$O$_2$: 457

$^1$H NMR (400 MHz, CHLOROFORM-d) ppm 1.65 (s, 3 H) 1.77 (m, 1 H) 2.98 (dd, J=13.30, 3.13 Hz, 1 H) 4.41-4.54 (m, 1 H) 7.46-7.55 (m, 1 H) 8.19 (d, J=1.76 Hz, 1 H) 8.31 (dd, J=8.80, 2.93 Hz, 1 H) 8.83 (d, J=1.56 Hz, 1 H) 10.05 (br. s., 1 H).

Example 83

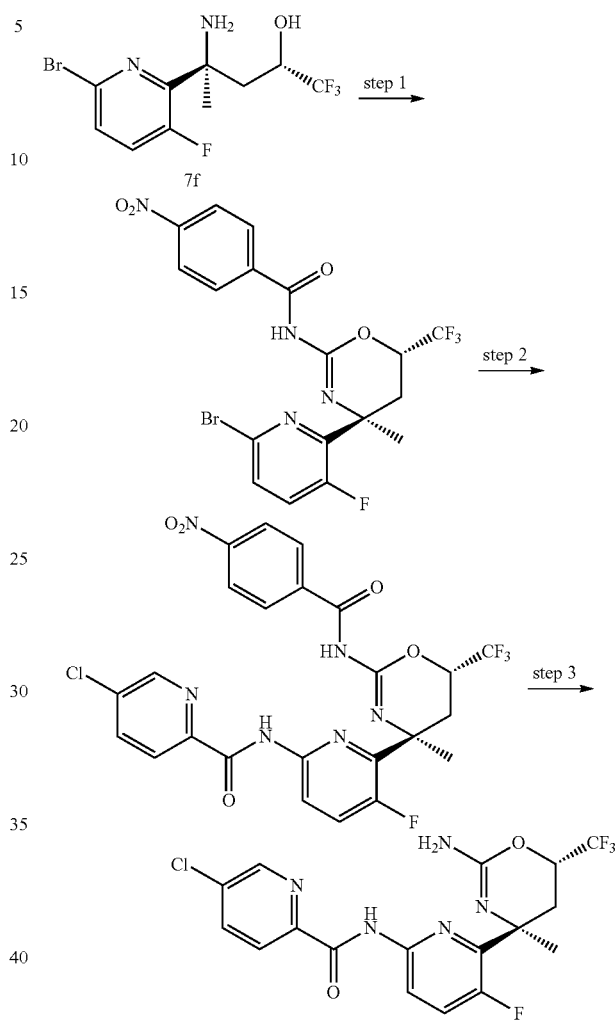

Step 1: N-((4S,6R)-4-(6-bromo-3-fluoropyridin-2-yl)-4-methyl-6-(trifluoromethyl)-5,6-dihydro-4H-1,3-oxazin-2-yl)-4-nitrobenzamide To a solution of (2R,4S)-4-amino-4-(6-bromo-3-fluoropyridin-2-yl)-1,1,1-trifluoropentan-2-ol (7f, 0.183 g, 0.553 mmol) in MeCN (3 mL) was added 4-nitrobenzoyl isothiocyanate (Matrix, 0.150 g, 0.719 mmol). The mixture was stirred at room temperature for 30 min. Additional 4-nitrobenzoyl isothiocyanate (30 mg) was added and the reaction was allowed to stir for additional 20 min. N1-((Ethylimino)methylene)-N3,N3-dimethylpropane-1,3-diamine hydrochloride (Aldrich, 0.170 g, 0.884 mmol) and N-ethyl-N-isopropylpropan-2-amine (0.241 mL, 1.382 mmol) was added and the reaction mixture was heated to 70° C. for 1 h. The reaction mixture was partitioned between water and EtOAc. The organic layer was separated washed with brine, and dried over sodium sulfate. The filtrate was concentrated under reduced pressure and the crude material was purified by silica gel chromatography (0-60% EtOAc/hexanes) to obtain the title compound as an off-white solid. MS m/z=505/507 [M]$^+$/[M+2]$^+$. Calculated: 505.2

Step 2: 5-chloro-N-(5-fluoro-6-((4S,6S)-4-methyl-2-(4-nitrobenzamido)-6-(trifluoromethyl)-5,6-dihydro-4H-1,3-oxazin-4-yl)pyridin-2-yl)picolinamide A mixture of A sealable vial was charged with N-((4S,6S)-4-(6-bromo-3-fluoropyridin-2-yl)-4-methyl-6-(trifluoromethyl)-5,6-dihydro-4H-1,3-oxazin-2-yl)-4-nitrobenzamide (8a, 0.297 g, 0.588 mmol), 5-chloropicolinamide (intermediate 18, 0.101 g, 0.647 mmol), cesium carbonate (0.479 g, 1.470 mmol, Aldrich), Pd$_2$(dba)$_3$ (0.040 g, 0.044 mmol, Strem), (9,9-dimethyl-9H-xanthene-4,5-diyl)bis(diphenylphosphine) (0.102 g, 0.176 mmol, Aldrich), and 1,4-dioxane (4 mL). The reaction was purged with Argon and heated to 110° C. overnight. The reaction mixture was filtered through celite and the filter cake was washed with EtOAc. The filtrate was washed with water and brine, dried over sodium sulfate and concentrated under reduced pressure. The crude material was purified via silica gel flash chromatography (gradient 0-35% EtOAc in hexanes) to afford the title compound as a light yellow solid. MS m/z=581 [M+H]$^+$. Calculated for $C_{24}H_{17}ClF_4N_6O_5$: 580.

Step 3: N-(6-((4S,6S)-2-amino-4-methyl-6-(trifluoromethyl)-5,6-dihydro-4H-1,3-oxazin-4-yl)-5-fluoropyridin-2-yl)-5-chloropicolinamide To a suspension of 5-chloro-N-(5-fluoro-6-((4S,6S)-4-methyl-2-(4-nitrobenzamido)-6-(trifluoromethyl)-5,6-dihydro-4H-1,3-oxazin-4-yl)pyridin-2-yl)picolinamide (8b, 76 mg, 0.131 mmol) in MeOH (1.3 mL) was added 1,8-diazabicyclo[5.4.0]undec-7-ene (Aldrich, 254 µl, 1.701 mmol). The reaction mixture was stirred at 70° C. for 1 h. The reaction was diluted with MeOH and purified by reverse-phase preparative HPLC using a Phenomenex Gemini column, 10 micron, C18, 110 Å, 150×30 mm, 0.1% TFA in CH$_3$CN/H$_2$O, gradient 10% to 70% over 16 min. The product containing fractions were combined and neutralized with aqueous saturated sodium bicarbonate solution. The free-based product was extracted with DCM. The organic phase was dried over MgSO$_4$ and the solvent was removed under reduced pressure to afford the title compound as a white solid (39 mg, 12% yield over two steps). MS m/z=432 [M+H]$^+$. Calculated for $C_{17}H_{14}ClF_4N_5O_2$: 431.

$^1$H NMR (400 MHz, CHLOROFORM-d) ppm 1.67 (s, 3H) 1.79 (m, 1 H) 3.02 (dd, J=13.40, 3.23 Hz, 1 H) 4.52 (ddd, J=12.13, 5.97, 3.03 Hz, 1 H) 7.49 (dd, J=10.37, 9.00 Hz, 1 H) 7.90 (dd, J=8.41, 2.35 Hz, 1 H) 8.25 (d, J=8.22 Hz, 1 H) 8.33 (dd, J=8.90, 3.03 Hz, 1 H) 8.62 (d, J=2.35 Hz, 1 H) 10.23 (s, 1 H).

Example 84

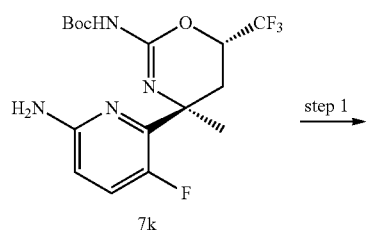

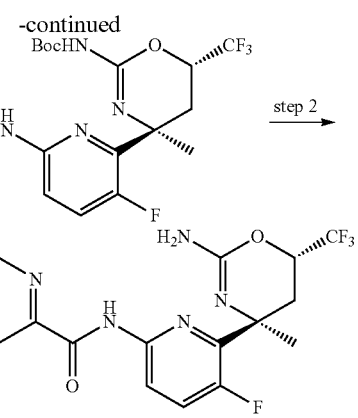

Step 1: tert-butyl ((4S,6S)-4-(6-(5-cyano-3-methylpicolinamido)-3-fluoropyridin-2-yl)-4-methyl-6-(trifluoromethyl)-5,6-dihydro-4H-1,3-oxazin-2-yl)carbamate To a solution of 5-cyano-3-methylpicolinic acid (intermediate 16, 0.050 g, 0.308 mmol) in DCM (2.5 mL) was added oxalyl chloride (0.040 mL, 0.463 mmol) and a drop of DMF. The reaction mixture was stirred for 30 min at room temperature. The reaction mixture was concentrated under reduced pressure and the residue was dissolved in DCM (1 mL). A flask was charged with a solution of tert-butyl ((4S,6S)-4-(6-amino-3-fluoropyridin-2-yl)-4-methyl-6-(trifluoromethyl)-5,6-dihydro-4H-1,3-oxazin-2-yl)carbamate (7k, 0.080 g, 0.204 mmol) and N,N-diisopropylethylamine (0.142 mL, 0.816 mmol, Aldrich) in DCM (2 mL). The solution of 5-cyano-3-methylpicolinoyl chloride was added and the reaction mixture was stirred at room temperature for 30 min, diluted with aqueous saturated NaHCO$_3$ solution and extracted with EtOAc. The organic extract was washed with brine and dried over Na$_2$SO$_4$. The solution was concentrated under reduced pressure. The crude material was purified by silica gel chromatography (gradient of 5-50% EtOAc in hexane) to afford the title compound as a white solid (52 mg, 48% yield). MS m/z=537 [M+H]$^+$. Calculated for $C_{24}H_{24}F_4N_6O_4$: 536.

Step 2: N-(6-((4S,6S)-2-amino-4-methyl-6-(trifluoromethyl)-5,6-dihydro-4H-1,3-oxazin-4-yl)-5-fluoropyridin-2-yl)-5-cyano-3-methylpicolinamide A solution of tert-butyl ((4S,6S)-4-(6-(5-cyano-3-methylpicolinamido)-3-fluoropyridin-2-yl)-4-methyl-6-(trifluoromethyl)-5,6-dihydro-4H-1,3-oxazin-2-yl)carbamate (9a, 0.052 g, 0.097 mmol) in DCM (1.5 mL) was treated with trifluoroacetic acid (0.747 mL, 9.69 mmol) and stirred at room temperature for 30 min. The reaction mixture was diluted with aqueous saturated Na$_2$CO$_3$ and extracted with DCM. The organic extract was washed with brine and dried over Na$_2$SO$_4$. The solution was concentrated under reduced pressure and the title compound was obtained as a white solid (40 mg, 95% yield). MS m/z=437 [M+H]$^+$. Calculated for $C_{19}H_{16}F_4N_6O_2$: 436.

$^1$H NMR (400 MHz, CHLOROFORM-d) ppm 1.65 (s, 3 H) 1.77 (m, 1 H) 2.86 (s, 3 H) 3.00 (dd, J=13.40, 3.03 Hz, 1 H) 4.44-4.56 (m, 1 H) 7.48 (dd, J=10.27, 8.90 Hz, 1 H) 7.96 (d, J=0.98 Hz, 1 H) 8.28 (dd, J=8.80, 2.93 Hz, 1 H) 8.77 (d, J=1.37 Hz, 1 H) 10.36 (br. s., 1 H).

Example 85

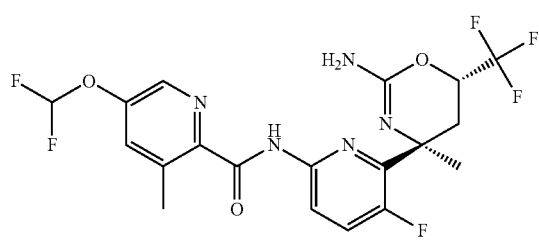 [SMILES: Cc1cc(OC(F)F)cnc1C(=O)Nc1ccc(F)c([C@]2(C)C[C@@H](C(F)(F)F)OC(N)=N2)n1]

Synthesis of N-(6-((4S,6S)-2-amino-4-methyl-6-(trifluoromethyl)-5,6-dihydro-4H-1,3-oxazin-4-yl)-5-fluoropyridin-2-yl)-5-(difluoromethoxy)-3-methylpicolinamide The title compound was synthesized by procedures and steps analogous to those described in Example 84, but using 5-(difluoromethoxy)-3-methylpicolinic acid (WO2012095463) in step 1. MS m/z=478 [M+H]$^+$. Calculated for $C_{19}H_{17}F_6N_5O_3$: 477.360.

$^1$H NMR (400 MHz, CHLOROFORM-d)=10.38 (s, 1 H), 8.36 (d, J=2.2 Hz, 1 H), 8.29 (dd, J=2.9, 8.8 Hz, 1 H), 7.50-7.39 (m, 2 H), 6.84-6.40 (m, 1 H), 4.60-4.46 (m, 1 H), 4.10 (br. s., 2 H), 3.01 (dd, J=2.9, 13.3 Hz, 1 H), 2.82 (s, 3 H), 1.82-1.71 (m, 1 H), 1.65 (s, 3 H).

Example 86

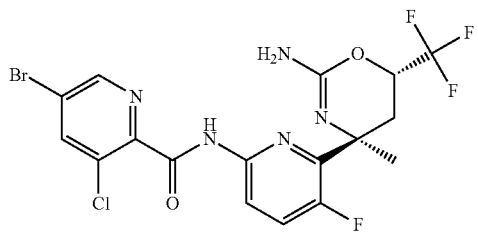 [SMILES: C[C@@]1(c2nc(NC(=O)c3ncc(Br)cc3Cl)ccc2F)C[C@@H](C(F)(F)F)OC(N)=N1]

Synthesis of N-(6-((4S,6S)-2-amino-4-methyl-6-(trifluoromethyl)-5,6-dihydro-4H-1,3-oxazin-4-yl)-5-fluoropyridin-2-yl)-5-bromo-3-chloropicolinamide The title compound was synthesized by procedures and steps analogous to those described in Example 84, but using 5-bromo-3-chloropyridine-2-carboxylic acid in step 1. MS m/z=510, 512 [M+H]$^+$. Calculated for $C_{17}H_{13}BrClF_4N_5O_2$: 510.668.

$^1$H NMR (400 MHz, CHLOROFORM-d)=10.13 (br. s., 1 H), 8.64 (d, J=2.0 Hz, 1 H), 8.39 (dd, J=3.0, 8.9 Hz, 1 H), 8.08 (d, J=2.0 Hz, 1 H), 7.58-7.48 (m, 1 H), 4.60-4.44 (m, 1 H), 3.06 (dd, J=3.1, 13.7 Hz, 1 H), 2.02-1.90 (m, 1 H), 1.78 (s, 3 H).

Example 87

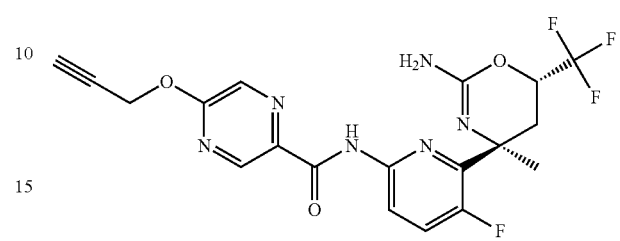

Synthesis of N-(6-((4S,6S)-2-amino-4-methyl-6-(trifluoromethyl)-5,6-dihydro-4H-1,3-oxazin-4-yl)-5-fluoropyridin-2-yl)-5-(prop-2-yn-1-yloxy)pyrazine-2-carboxamide The title compound was synthesized by procedures and steps analogous to those described in Example 84, but using 5-(prop-2-yn-1-yloxy)pyrazine-2-carboxylic acid (J. Med. Chem. 2013, 56, 3980) in step 1. MS m/z=453 [M+H]$^+$. Calculated for $C_{19}H_{16}F_4N_6O_3$: 452.362.

$^1$H NMR (400 MHz, CHLOROFORM-d)=9.90 (s, 1 H), 9.05 (d, J=1.2 Hz, 1 H), 8.31 (dd, J=3.0, 8.9 Hz, 1 H), 8.26 (d, J=1.2 Hz, 1 H), 7.48 (dd, J=9.0, 10.4 Hz, 1 H), 5.10 (d, J=2.5 Hz, 2 H), 4.50 (ddd, J=3.1, 6.0, 12.2 Hz, 1 H), 2.99 (dd, J=3.1, 13.3 Hz, 1 H), 2.55 (t, J=2.3 Hz, 1 H), 1.77 (t, J=12.8 Hz, 1 H), 1.65 (s, 3 H).

Example 88

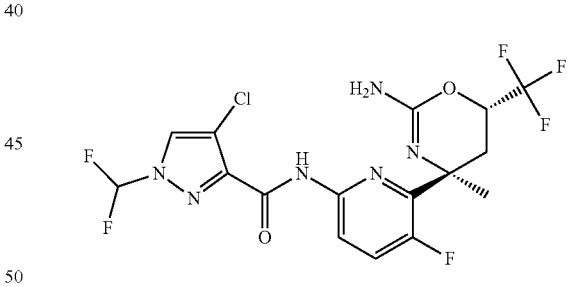

Synthesis of N-(6-((4S,6S)-2-amino-4-methyl-6-(trifluoromethyl)-5,6-dihydro-4H-1,3-oxazin-4-yl)-5-fluoropyridin-2-yl)-4-chloro-1-(difluoromethyl)-1H-pyrazole-3-carboxamide The title compound was synthesized by procedures and steps analogous to those described in Example 84, but using 4-chloro-1-(difluoromethyl)-1H-pyrazole-3-carboxylic acid (WO2011069934) in step 1. MS m/z=471 [M+H]$^+$. Calculated for $C_{16}H_{13}ClF_6N_6O_2$: 470.8.

$^1$H NMR (400 MHz, CHLOROFORM-d) ppm 1.64 (s, 3 H) 1.77 (t, J=13.01 Hz, 1 H) 2.97 (dd, J=13.50, 3.13 Hz, 1 H) 4.45 (ddd, J=12.18, 6.02, 2.93 Hz, 1 H) 7.00-7.36 (m, 1 H) 7.48 (dd, J=10.37, 9.00 Hz, 1 H) 7.94 (s, 1 H) 8.27 (dd, J=8.80, 2.93 Hz, 1 H) 9.05 (br. s., 1 H).

Example 89

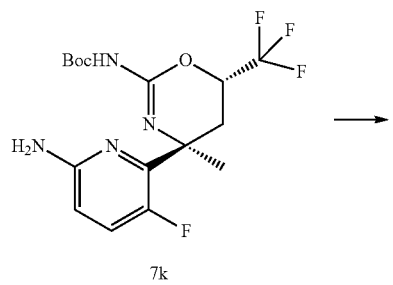

7k

Synthesis of 8-((6-((4S,6S)-2-amino-4-methyl-6-(trifluoromethyl)-5,6-dihydro-4H-1,3-oxazin-4-yl)-5-fluoropyridin-2-yl)amino)-5-fluoro-1,7-naphthyridine-3-carbonitrile The title compound was synthesized by procedures and steps analogous to those described for Example 78 above, but using tert-butyl ((4S,6S)-4-(6-amino-3-fluoropyridin-2-yl)-4-methyl-6-(trifluoromethyl)-5,6-dihydro-4H-1,3-oxazin-2-yl)carbamate (7k). MS m/z=464 [M+H]⁺. Calculated for $C_{19}H_{16}F_4N_6O_2$: 463

¹H NMR (400 MHz, CHLOROFORM-d) ppm 1.72 (s, 3H) 1.80-1.89 (m, 1 H) 3.07 (dd, J=13.50, 3.13 Hz, 1 H) 4.53-4.66 (m, 1 H) 7.50 (dd, J=10.27, 9.10 Hz, 1 H) 8.19 (s, 1 H) 8.61 (dd, J=9.00, 2.93 Hz, 1 H) 8.69 (d, J=1.96 Hz, 1 H) 9.08 (d, J=1.76 Hz, 1 H) 9.40 (s, 1 H).

Example 90

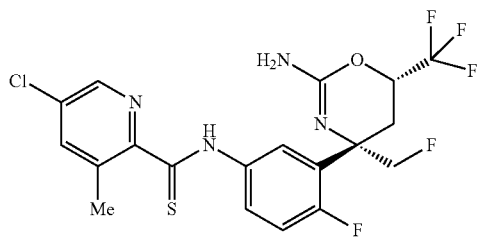

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methylpyridine-2-carbothioamide A sealable vial was charged with N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methylpicolinamide (Example 4, 0.068 g, 0.147 mmol) and toluene (1 mL). 2,4-Bis(4-methoxyphenyl)-2,4-dithioxo-1,3,2,4-dithiadiphosphetane (0.059 g, 0.147 mmol) was added and the reaction mixture was heated to 120° C. overnight. Upon cooling to room temperature, the reaction mixture was taken up in EtOAc (75 mL). The organic layer was washed with aqueous saturated NaHCO₃ and with brine, dried over MgSO₄ and concentrated under reduced pressure. The residue was purified through silica gel (gradient 30%-50% EtOAc-hexane) affording the title compound as a yellow solid (8.4 mg, 0.018 mmol, 12%). MS m/z=479 [M+H]⁺. Calculated for $C_{19}H_{16}ClF_5N_4OS$: 478.

¹H NMR (300 MHz, CHLOROFORM-d) δ ppm 10.91 (br, 1H), 8.33 (s, 1H), 8.12 (m, 1H), 7.84 (d, 1H, J=4.7), 7.65 (m, 1H), 7.15 (dd, 1H, J=11.3, 8.8), 4.68 (dd, 1H, J=47.1, 8.6), 4.51 (dd, 1H, J=47.0, 8.6), 4.20 (m, 1H), 2.75 (s, 3H), 2.67 (dd, 1H, J=13.6, 2.2), 2.18 (m, 1H).

Example 91

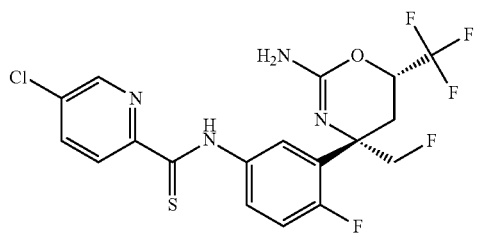

Synthesis of N-(3-((4S,6S)-2-amino-4-(fluoromethyl)-6-(trifluoromethyl)-5,6-dihydro-4H-1,3-oxazin-4-yl)-4-fluorophenyl)-5-chloropyridine-2-carbothioamide The title compound was synthesized by procedures and steps analogous to those described in Example 90, but using N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide (see Example 3).

MS m/z=465 [M+H]⁺. Calculated for $C_{18}H_{14}ClF_5N_4OS$: 464.84

¹H NMR (300 MHz, CHLOROFORM-d) ppm 2.18 (t, J=13.1 Hz, 1 H), 2.69 (dd, J=13.6, 2.6 Hz, 1 H), 4.20 (m, 1 H), 4.51 (dd, J=46.9, 8.9 Hz, 1 H), 4.70 (dd, J=47.3, 8.6 Hz, 1 H), 7.18 (dd, J=11.3, 8.8 Hz, 1 H), 7.85 (dd, J=8.6, 2.4 Hz, 1 H), 7.96 (dd, J=6.8, 2.7 Hz, 1 H), 8.25 (m, 1 H), 8.50 (d, J=2.2 Hz, 1 H), 8.73 (d, J=8.4, 1 H), 11.77 (br, 1 H).

Example 92 (Method M)

Synthesis of (4S,6S)-4-(2-fluoro-5-(pyrazin-2-yloxy)phenyl)-4-(fluoromethyl)-6-(trifluoromethyl)-5,6-dihydro-4H-1,3-oxazin-2-amine

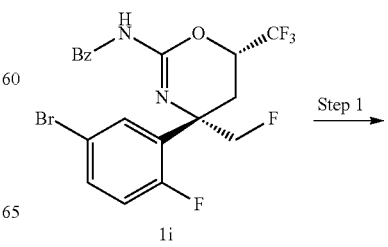

1i

Step 1 →

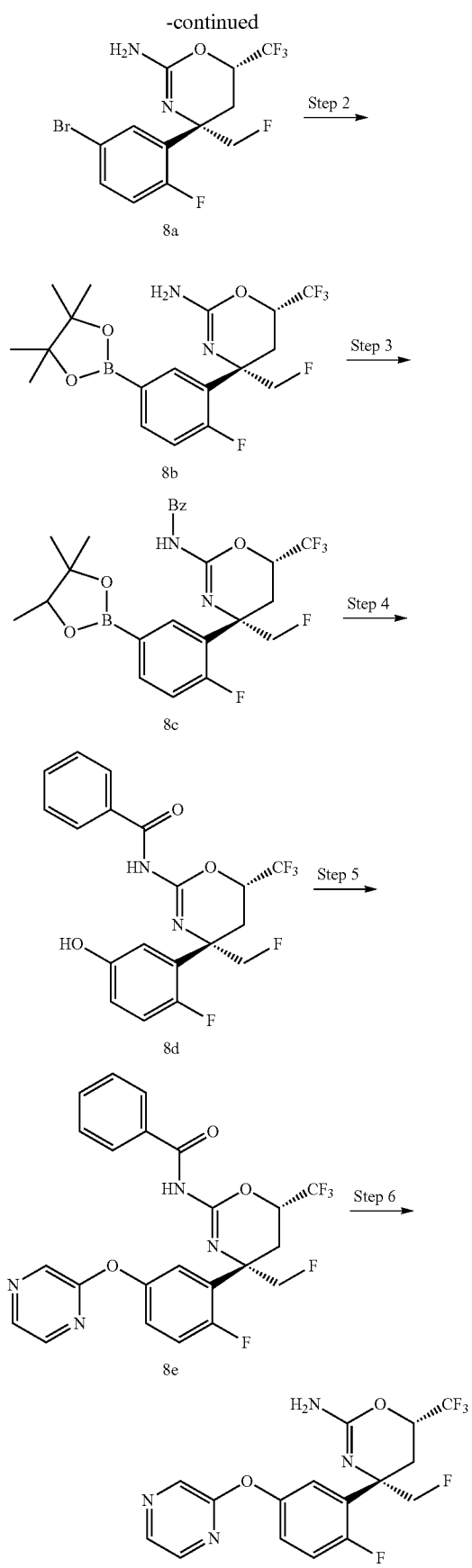

Step 1: (4S,6S)-4-(5-bromo-2-fluorophenyl)-4-(fluoromethyl)-6-(trifluoromethyl)-5,6-dihydro-4H-1,3-oxazin-2-amine (8a)

To a solution of N-((4S,6S)-4-(5-bromo-2-fluorophenyl)-4-(fluoromethyl)-6-(trifluoromethyl)-5,6-dihydro-4H-1,3-oxazin-2-yl)benzamide (1i, 8.58 g, 17.98 mmol) in MeOH (50 mL) was added 1,8-diazabicyclo-[5.4.0]undec-7-ene (3.22 ml, 21.57 mmol) and the resulting mixture was heated at 65° C. for 5 h. The reaction went to completion. The mixture was concentrated, diluted with EtOAc, washed with water, saturated NH$_4$Cl solution, dried over Na$_2$SO$_4$, filtered, concentrated and chromatographed on silica gel using a gradient of 0-20% EtOAc/hexanes to afford a white solid as (4S,6S)-4-(5-bromo-2-fluorophenyl)-4-(fluoromethyl)-6-(trifluoromethyl)-5,6-dihydro-4H-1,3-oxazin-2-amine (5.43 g, 14.55 mmol, 81% yield). MS m/z=374.9 [M+H]$^+$. Calculated for C$_{12}$H$_{10}$BrF$_5$N$_2$O: 373.1

Step 2: (4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-amine (8b)

A mixture of (4S,6S)-4-(5-bromo-2-fluorophenyl)-4-(fluoromethyl)-6-(trifluoromethyl)-5,6-dihydro-4H-1,3-oxazin-2-amine (3.7 g, 9.92 mmol), bis(pinacolato)diboron (3.02 g, 11.90 mmol), potassium acetate (2.92 g, 29.7 mmol), and (1,1'-bis(diphenylphosphino)ferrocene)dichloropalladium(II) dichloromethane adduct (0.726 g, 0.992 mmol) was evacuated under vacuum and then flushed with nitrogen. DMSO (39.7 mL) was added and the reaction mixture was stirred in at 85° C. for 3 h. After cooling to room temperature, the reaction mixture was partitioned between EtOAc and water. The aqueous layer was back extracted with EtOAc (2×) and the combined organics was washed with brine, dried (MgSO$_4$) and concentrated. The crude material was purified by chromatography through a Redi-Sep pre-packed silica gel column (120 g), eluting with a gradient of 0-50% EtOAc in hexane, to provide (4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-amine (4.16 g, 9.9 mmol, 99% yield) as brown oil. MS m/z=421 [M]$^+$. Calculated for C$_{18}$H$_{22}$BF$_5$N$_2$O$_3$: 420.18.

Step 3: N-((4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-yl)benzamide (8c)

To a flask was added (4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-amine (4.16 g, 9.90 mmol) and triethylamine (1.653 mL, 11.88 mmol) in DMF (33.0 mL) to stir at 0° C. Benzoic anhydride (2.509 g, 11.09 mmol) was added and the reaction mixture was stirred at room temperature for 3.5 h. Then the reaction mixture was partitioned between EtOAc, water and brine. The aqueous layer was back extracted with EtOAc (2×) and the combined organics was washed with brine, dried (Na$_2$SO$_4$) and concentrated. The crude material was purified by chromatography through a Redi-Sep pre-packed silica gel column (120 g), eluting with a gradient of 0-30% EtOAc in hexane, to provide N-((4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-yl)benzamide (4.16 g, 7.93 mmol, 80% yield) as off-white solid. MS m/z=525 [M]⁺. Calculated for $C_{25}H_{26}BF_5N_2O_4$: 524.29.

Step 4: N-((4S,6S)-4-(2-fluoro-5-hydroxyphenyl)-4-(fluoromethyl)-6-(trifluoromethyl)-5,6-dihydro-4H-1,3-oxazin-2-yl)benzamide (8d)

To a solution of N-((4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-yl)benzamide (4.16 g, 7.93 mmol) in THF (22.67 mL) at 0° C. was added hydrogen peroxide 30% in water (2.431 mL, 23.80 mmol). The reaction mixture was stirred at 0° C. to room temperature for 16 h. The reaction mixture was acidified to pH 5-7 by addition of saturated NaHCO₃, and extracted with EtOAc (2×). The combined organics were washed with water and brine, dried and concentrated. The crude material was purified by chromatography through a Redi-Sep pre-packed silica gel column (40 g), eluting with a gradient of 0-30% EtOAc in hexane, to provide N-((4S,6S)-4-(2-fluoro-5-hydroxyphenyl)-4-(fluoromethyl)-6-(trifluoromethyl)-5,6-dihydro-4H-1,3-oxazin-2-yl)benzamide (1.84 g, 4.44 mmol, 56.0% yield) as white foam. MS m/z=415 [M]⁺. Calculated for $C_{19}H_{15}F_5N_2O_3$: 414.33.

Step 5: N-((4S,6S)-4-(2-fluoro-5-(pyrazin-2-yloxy) phenyl)-4-(fluoromethyl)-6-(trifluoromethyl)-5,6-dihydro-4H-1,3-oxazin-2-yl)benzamide (8e)

To a microwave vial were added N-((4S,6S)-4-(2-fluoro-5-hydroxyphenyl)-4-(fluoromethyl)-6-(trifluoromethyl)-5,6-dihydro-4H-1,3-oxazin-2-yl)benzamide (95 mg, 0.229 mmol), 2-fluoro-pyrazine (24.74 mg, 0.252 mmol), cesium carbonate (90 mg, 0.275 mmol) in DMSO (459 μL). The vial was heated in microwave instrument at 100° C. for 30 min. After cooling to room temperature, water was added to the reaction mixture and precipitate was observed. After stirring for 10 min, the precipitate was collected by filtration, washed with water and hexane, dried in vacuum oven at 60° C. for 1 h to provide N-((4S,6S)-4-(2-fluoro-5-(pyrazin-2-yloxy)phenyl)-4-(fluoromethyl)-6-(trifluoromethyl)-5,6-dihydro-4H-1,3-oxazin-2-yl)benzamide (85 mg, 0.173 mmol, 75% yield) as off-white solid. MS m/z=493 [M]⁺. Calculated for $C_{23}H_{17}F_5N_4O_3$: 492.4.

Step 6: (4S,6S)-4-(2-fluoro-5-(pyrazin-2-yloxy)phenyl)-4-(fluoromethyl)-6-(trifluoromethyl)-5,6-dihydro-4H-1,3-oxazin-2-amine To a solution of N-((4S,6S)-4-(2-fluoro-5-(pyrazin-2-yloxy)phenyl)-4-(fluoromethyl)-6-(trifluoromethyl)-5,6-dihydro-4H-1,3-oxazin-2-yl)benzamide (85 mg, 0.173 mmol) in MeOH (690 μL) was added 1,8-diazabicyclo-[5.4.0]undec-7-ene (77 μL, 0.518 mmol) dropwise. The reaction mixture was stirred at 60° C. for 1 h, then at 80° C. for another hour. After cooling to room temperature, the crude material was purified by reverse-phase preparative HPLC using a Phenomenex Gemini column, 10 micron, C18, 110 Å, 150×30 mm, 0.1% TFA in CH₃CN/H₂O, gradient 10% to 70% over 30 min. The fractions were combined and concentrated. It was partitioned between DCM and saturated NaHCO₃. The aqueous layer was back extracted with DCM and the combined organic was dried (Na₂SO₄) and concentrated to provide (4S,6S)-4-(2-fluoro-5-(pyrazin-2-yloxy)phenyl)-4-(fluoromethyl)-6-(trifluoromethyl)-5,6-dihydro-4H-1,3-oxazin-2-amine (38 mg, 0.098 mmol, 56.7% yield) as white solid. MS m/z=389 [M]⁺. Calculated for $C_{16}H_{13}F_5N_4O_2$: 388.29.

¹H NMR (300 MHz, CHLOROFORM-d) δ ppm 2.18 (t, J=13.15 Hz, 1 H) 2.69 (dd, J=13.67, 2.70 Hz, 1 H) 4.16 (ddd, J=12.57, 5.85, 2.63 Hz, 1 H) 4.38-4.60 (m, 1 H) 4.59-4.81 (m, 1 H) 7.08-7.20 (m, 2 H) 7.28-7.34 (m, 1 H) 8.07 (dd, J=2.70, 1.39 Hz, 1 H) 8.28 (d, J=2.78 Hz, 1 H) 8.44 (d, J=1.32 Hz, 1 H).

Example 93

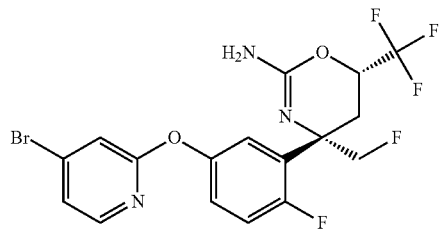

and side product

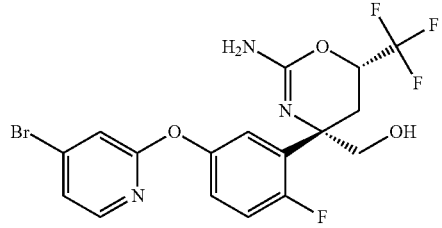 [SMILES: NC1=N[C@](CO)(c2cc(Oc3cc(Br)ccn3)ccc2F)C[C@@H](C(F)(F)F)O1]

Synthesis of (4S,6S)-4-(5-((4-bromopyridin-2-yl)oxy)-2-fluorophenyl)-4-(fluoromethyl)-6-(trifluoromethyl)-5,6-dihydro-4H-1,3-oxazin-2-amine and ((4S,6S)-2-amino-4-(5-((4-bromopyridin-2-yl)oxy)-2-fluorophenyl)-6-(trifluoromethyl)-5,6-dihydro-4H-1,3-oxazin-4-yl)-methanol The title compounds were synthesized using steps and procedures analogous to those described in Method M (Example 92) above, but using 4-bromo-2-fluoropyridine (Aldrich) in step 5. The product and the side product was separated by reverse-phase preparative HPLC using a Phenomenex Gemini column, 10 micron, C18, 110 Å, 150×30 mm, 0.1% TFA in CH₃CN/H₂O, gradient 10% to 70% over 15 min. to afford the product: (4S,6S)-4-(5-((4-bromopyridin-2-yl)oxy)-2-fluorophenyl)-4-(fluoromethyl)-6-(trifluoromethyl)-5,6-dihydro-4H-1,3-oxazin-2-amine MS m/z=466, 468 [M]⁺. Calculated for $C_{17}H_{13}BrF_5N_3O_2$: 466.2.

¹H NMR (400 MHz, CHLOROFORM-d) ppm 2.17 (t, J=13.11 Hz, 1 H) 2.68 (dd, J=13.50, 2.74 Hz, 1 H) 4.10-4.22 (m, 1 H) 4.41 (d, J=9.59 Hz, 0.5 H) 4.49-4.57 (m, 0.5 H) 4.64 (dd, J=8.71, 1.66 Hz, 0.5 H) 4.76 (dd, J=8.61, 1.56 Hz, 0.5 H) 7.10 (d, J=1.57 Hz, 1 H) 7.11-7.13 (m, 2 H) 7.16 (dd, J=5.48, 1.56 Hz, 1 H) 7.23-7.29 (m, 1 H) 7.97 (d, J=5.28 Hz, 1 H).

And Side Product: ((4S,6S)-2-amino-4-(5-((4-bromopyridin-2-yl)oxy)-2-fluorophenyl)-6-(trifluoromethyl)-5,6-dihydro-4H-1,3-oxazin-4-yl)methanol MS m/z=464, 466 [M]⁺. Calculated for $C_{17}H_{14}BrF_4N_3O_3$: 464.21.

¹H NMR (400 MHz, CHLOROFORM-d) δ ppm 2.00-2.14 (m, 1 H) 2.39 (d, J=13.50 Hz, 1 H) 3.78 (dd, J=11.93, 6.06 Hz, 1 H) 4.42-4.61 (m, 2 H) 7.02-7.20 (m, 4 H) 7.39-7.51 (m, 1 H) 7.98 (d, J=5.48 Hz, 1 H).

Example 94

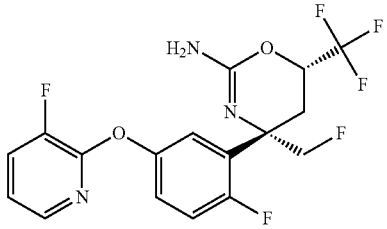

Synthesis of (4S,6S)-4-(5-((4-bromopyridin-2-yl)oxy)-2-fluorophenyl)-4-(fluoromethyl)-6-(trifluoromethyl)-5,6-dihydro-4H-1,3-oxazin-2-amine The title compound was synthesized using steps and procedures analogous to those described in Method M (Example 92) above, but using 2,3-difluoropyridine Alfa Aesar) in step 5. MS m/z=406 [M]⁺. Calculated for $C_{17}H_{13}F_6N_3O_2$: 405.297.

¹H NMR (300 MHz, CHLOROFORM-d) ppm 2.19 (t, J=13.15 Hz, 1 H) 2.69 (dd, J=13.59, 2.78 Hz, 1 H) 4.07-4.26 (m, 1 H) 4.36-4.59 (m, 1 H) 4.61-4.83 (m, 1 H) 7.01 (ddd, J=7.97, 4.82, 3.29 Hz, 1 H) 7.08-7.21 (m, 2 H) 7.32 (dd, J=6.65, 2.41 Hz, 1 H) 7.48 (ddd, J=9.79, 8.04, 1.46 Hz, 1 H) 7.89 (dd, J=4.90, 1.53 Hz, 1 H).

Example 95

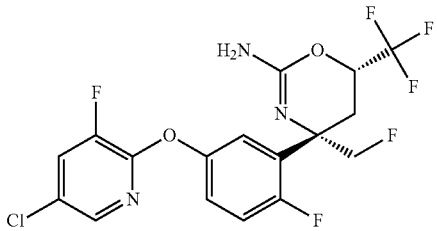 [SMILES: NC1=N[C@](CF)(c2cc(Oc3ncc(Cl)cc3F)ccc2F)C[C@@H](C(F)(F)F)O1]

(4S,6S)-4-(5-((5-chloro-3-fluoropyridin-2-yl)oxy)-2-fluorophenyl)-4-(fluoromethyl)-6-(trifluoromethyl)-5,6-dihydro-4H-1,3-oxazin-2-amine The title compound was synthesized using steps and procedures analogous to those described in Method M (Example 92) above, but 5-chloro-2,3-difluoropyridine (Combi-Blocks) in step 5. MS m/z=440 [M]⁺. Calculated for $C_{17}H_{12}ClF_6N_3O_2$: 439.74.

¹H NMR (300 MHz, CHLOROFORM-d) ppm 2.20 (d, J=13.15 Hz, 1 H) 2.68 (dd, J=13.59, 2.63 Hz, 1 H) 4.15 (ddd, J=12.64, 5.70, 2.70 Hz, 1 H) 4.36-4.57 (m, 1 H) 4.59-4.81 (m, 1 H) 7.08-7.19 (m, 2 H) 7.26-7.35 (m, 1 H) 7.52 (dd, J=9.06, 2.19 Hz, 1 H) 7.86 (d, J=2.19 Hz, 1 H).

Example 96

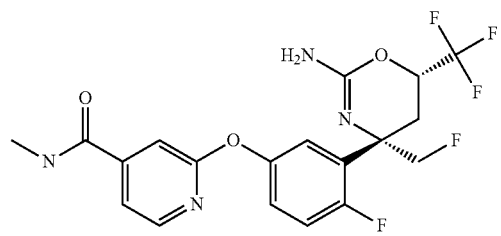 [SMILES: CNC(=O)c1ccnc(Oc2ccc(F)c([C@]3(CF)C[C@@H](C(F)(F)F)OC(N)=N3)c2)c1]

2-(3-((4S,6S)-2-amino-4-(fluoromethyl)-6-(trifluoromethyl)-5,6-dihydro-4H-1,3-oxazin-4-yl)-4-fluorophenoxy)-N-methylisonicotinamide The title compound was synthesized using steps and procedures analogous to those described in Method M (Example 92) above, but 2-bromo-n-methylisonicotinamide (Combi-Blocks) in step 5. MS m/z=445 [M]⁺. Calculated for $C_{19}H_{17}F_5N_4O_3$: 444.36.

¹H NMR (400 MHz, CHLOROFORM-d) ppm 2.18 (t, J=13.40 Hz, 1 H) 2.68 (d, J=13.50 Hz, 1 H) 3.04 (d, J=4.69 Hz, 3 H) 4.39-4.57 (m, 1 H) 4.61-4.79 (m, 1 H) 7.12 (d, J=7.63 Hz, 2 H) 7.22 (s, 1 H) 8.24 (d, J=5.48 Hz, 1 H).

Example 97

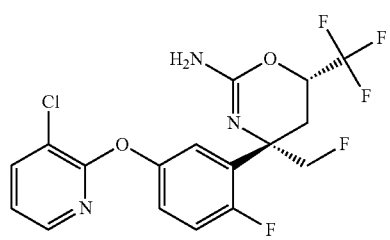 [SMILES: NC1=N[C@](CF)(c2cc(Oc3ncccc3Cl)ccc2F)C[C@@H](C(F)(F)F)O1]

(4S,6S)-4-(5-((3-chloropyridin-2-yl)oxy)-2-fluorophenyl)-4-(fluoromethyl)-6-(trifluoromethyl)-5,6-dihydro-4H-1,3-oxazin-2-amine The title compound was synthesized using steps and procedures analogous to those described in Method M (Example 92) above, but using 3-chloro-2-fluoropyridine (Matrix) in step 5. MS m/z=422 [M]⁺. Calculated for $C_{17}H_{13}ClF_5N_3O_2$: 421.75.

¹H NMR (300 MHz, CHLOROFORM-d) ppm 2.19 (t, J=13.15 Hz, 1 H) 2.69 (d, J=13.74 Hz, 1 H) 4.18 (d, J=8.92 Hz, 3 H) 4.34-4.58 (m, 1 H) 4.61-4.86 (m, 1 H) 6.98 (dd, J=7.38, 4.90 Hz, 1 H) 7.12 (d, J=8.62 Hz, 2 H) 7.30 (d, J=7.31 Hz, 2 H) 7.76 (d, J=7.60 Hz, 1 H) 8.00 (d, J=4.82 Hz, 1 H).

Example 98

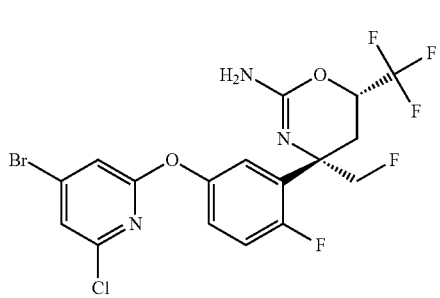 [SMILES: NC1=N[C@](CF)(c2cc(Oc3cc(Br)cc(Cl)n3)ccc2F)C[C@@H](C(F)(F)F)O1]

(4S,6S)-4-(5-((4-Bromo-6-chloropyridin-2-yl)oxy)-2-fluorophenyl)-4-(fluoromethyl))-6-(trifluoromethyl)-5,6-dihydro-4H-1,3-oxazin-2-amine The title compound was synthesized using steps and procedures analogous to those described in Method M (Example 92) above, but using 4-bromo-2,6-dichloropyridine (Combi-Blocks) in step 5. MS m/z=500, 502 [M]$^+$. Calculated for $C_{17}H_{12}BrClF_5N_3O_2$: 500.65.

$^1$H NMR (300 MHz, CHLOROFORM-d) δ ppm 2.63 (t, J=13.88 Hz, 1 H) 2.84-2.93 (m, 1 H) 4.54 (m, 1 H) 4.68-4.85 (m, 1 H) 4.85-5.03 (m, 1 H), 7.13 (s, 1 H) 7.21 (m, 4 H).

Example 99

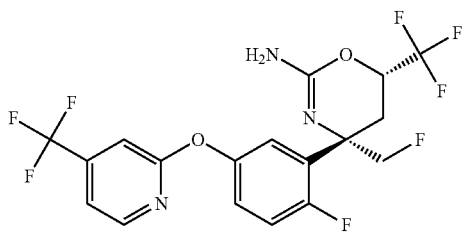 [SMILES: NC1=N[C@](CF)(c2cc(Oc3cc(C(F)(F)F)ccn3)ccc2F)C[C@@H](C(F)(F)F)O1]

(4S,6S)-4-(2-Fluoro-5-((4-(trifluoromethyl)pyridin-2-yl)oxy)phenyl)-4-(fluoromethyl)-6-(trifluoromethyl)-5,6-dihydro-4H-1,3-oxazin-2-amine The title compound was synthesized using steps and procedures analogous to those described in Method M (Example 92) above, but using 2-fluoro-4-(trifluoromethyl) Pyridine (Aldrich) in step 5. MS m/z=455.9 [M]$^+$. Calculated for $C_{18}H_{13}F_8N_3O_2$: 455.30.

$^1$H NMR (300 MHz, CHLOROFORM-d) ppm 2.18 (t, J=13.08 Hz, 1 H) 2.69 (dd, J=13.67, 2.41 Hz, 1 H) 4.17 (dd, J=10.23, 5.55 Hz, 1 H) 4.37-4.58 (m, 1 H) 4.59-4.81 (m, 1 H) 7.11-7.18 (m, 3 H) 7.21 (d, J=5.41 Hz, 1 H) 7.29 (br. s., 1 H) 8.29 (d, J=5.26 Hz, 1 H).

Example 100

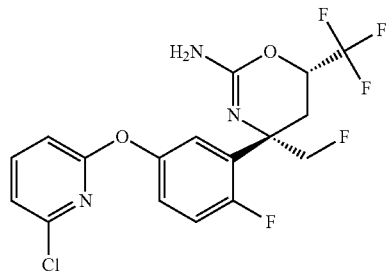 [SMILES: NC1=N[C@](CF)(c2cc(Oc3cccc(Cl)n3)ccc2F)C[C@@H](C(F)(F)F)O1]

Synthesis of (4S,6S)-4-(5-((6-chloropyridin-2-yl)oxy)-2-fluorophenyl)-4-(fluoromethyl)-6-(trifluoromethyl)-5,6-dihydro-4H-1,3-oxazin-2-amine The title compound was synthesized by procedures and steps analogous to those described in Example 92, Method M, but using 2-chloro-6-fluoropyridine in step 5. MS m/z=422 [M+H]$^+$. Calculated for $C_{17}H_{13}ClF_5N_3O_2$: 421.7.

$^1$H NMR (400 MHz, CHLOROFORM-d) δ=7.64 (t, J=7.9 Hz, 1H), 7.33-7.23 (m, 1H), 7.16-7.01 (m, 3H), 6.79 (d, J=8.0 Hz, 1H), 4.81-4.40 (m, 2H), 4.33-4.15 (m, 3H), 2.66 (dd, J=2.7, 13.5 Hz, 1H), 2.16 (t, J=13.1 Hz, 1H).

Example 101

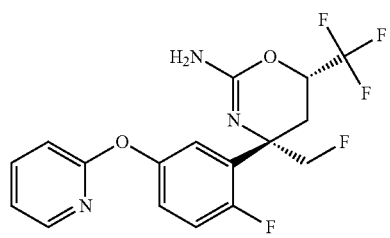 [SMILES: NC1=N[C@](CF)(c2cc(Oc3ccccn3)ccc2F)C[C@@H](C(F)(F)F)O1]

Synthesis of (4S,6S)-4-(2-fluoro-5-(pyridin-2-yloxy)phenyl)-4-(fluoromethyl)-6-(trifluoromethyl)-5,6-dihydro-4H-1,3-oxazin-2-amine The title compound was synthesized by procedures and steps analogous to those described in Example 92, Method M, but using 2-bromopyridine in step 5. MS m/z=388 [M+H]$^+$. Calculated for $C_{17}H_{14}F_5N_3O_2$: 387.3.

$^1$H NMR (400 MHz, CHLOROFORM-d) δ=8.16 (dd, J=1.4, 4.9 Hz, 1H), 7.74-7.65 (m, 1H), 7.30-7.23 (m, 1H), 7.16-7.05 (m, 2H), 7.00 (dd, J=5.1, 6.5 Hz, 1H), 6.92 (d, J=8.2 Hz, 1H), 4.79-4.14 (m, 5H), 2.67 (dd, J=2.5, 13.7 Hz, 1H), 2.17 (t, J=13.1 Hz, 1H).

Example 102

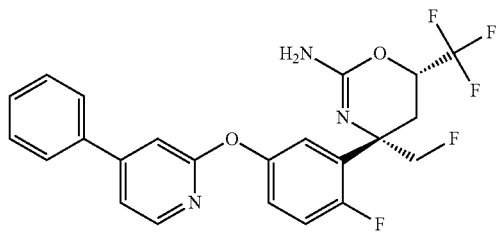 [SMILES: NC1=N[C@](CF)(c2cc(Oc3cc(-c4ccccc4)ccn3)ccc2F)C[C@@H](C(F)(F)F)O1]

Synthesis of (4S,6S)-4-(2-fluoro-5-((4-phenylpyridin-2-yl)oxy)phenyl)-4-(fluoromethyl)-6-(trifluoromethyl)-5,6-dihydro-4H-1,3-oxazin-2-amine A vial was charged with (4S,6S)-4-(5-((4-bromopyridin-2-yl)oxy)-2-fluorophenyl)-4-(fluoromethyl)-6-(trifluoromethyl)-5,6-dihydro-4H-1,3-oxazin-2-amine (11.85 mg, 0.025 mmol, Example 17), phenylboronic acid (4.65 mg, 0.038 mmol) and trans-dichlorobis(triphenylphosphine)palladium (II) (27.8 mg, 0.04 mmol). The vial was placed under nitrogen atmosphere using two evacuation/backfill cycles. 1,4-dioxane (254 μl) and sodium carbonate (8.08 mg, 0.076 mmol) in water (85 μl) were added. The reaction mixture was sealed under nitrogen and heated at 80° C. for 1.5 h. The reaction mixture was partitioned between EtOAc and brine. The aqueous layer was back extracted with EtOAc (2×) and the combined EtOAc layers were dried ($Na_2SO_4$) and concentrated. The crude material was purified by chromatography through a Redi-Sep pre-packed silica gel column (12 g), eluting with a gradient of 0% to 40% EtOAc in hexane, to provide (4S,6S)-4-(2-fluoro-5-((4-phenylpyridin-2-yl)oxy)phenyl)-4-(fluoromethyl)-6-(trifluoromethyl)-5,6-dihydro-4H-1,3-oxazin-2-amine (7.6 mg, 0.016 mmol, 64.5% yield) as white solid. MS m/z=464 $[M]^+$. Calculated for $C_{23}H_{18}F_5N_3O_2$: 463.4.

$^1$H NMR (300 MHz, CHLOROFORM-d) ppm 2.19 (t, J=13.23 Hz, 1 H) 2.69 (dd, J=13.30, 2.48 Hz, 1 H) 4.06-4.16 (m, 1 H) 4.37-4.59 (m, 1 H) 4.60-4.86 (m, 1 H) 7.07-7.18 (m, 3 H) 7.29-7.36 (m, 1 H) 7.48 (d, J=7.16 Hz, 3 H) 7.63 (d, J=6.87 Hz, 2 H) 8.20 (d, J=5.26 Hz, 1 H).

Example 103

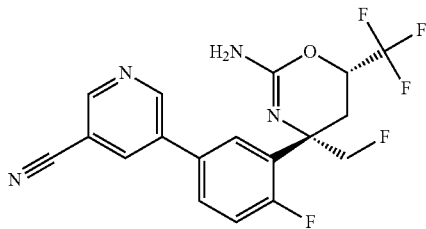 [SMILES: N#Cc1cncc(-c2ccc(F)c([C@]3(CF)C[C@@H](C(F)(F)F)OC(N)=N3)c2)c1]

Synthesis of 5-(3-((4S,6S)-2-amino-4-(fluoromethyl)-6-(trifluoromethyl)-5,6-dihydro-4H-1,3-oxazin-4-yl)-4-fluorophenyl)nicotinonitrile In a microwave vial a mixture of (4S,6S)-4-(5-bromo-2-fluorophenyl)-4-(fluoromethyl)-6-(trifluoromethyl)-5,6-dihydro-4H-1,3-oxazin-2-amine (8a, 110 mg, 0.295 mmol), 5-cyano-3-pyridinyl boronic acid (43.6 mg, 0.295 mmol), and cesium carbonate (384 mg, 1.179 mmol) in THF (2.0 mL) and water (983 μL) was purged with argon for 5 min. Dichloro[1,1'-bis(diphenylphosphino)ferrocene]palladium (II) dichloromethane adduct (12.04 mg, 0.015 mmol) was added and the tube was sealed and the mixture was heated at 80° C. overnight. Additional 3-cyanopyridine-5-boronic acid pinacol ester (67.8 mg, 0.295 mmol) and dichloro[1,1'-bis(diphenylphosphino)ferrocene]palladium (II) dichloromethane adduct (12.04 mg, 0.015 mmol) were added. The reaction mixture was stirred at 80° C. for another 6 h. After cooling to room temperature, the reaction mixture was partitioned between EtOAc and water and brine. The aqueous layer was back extracted with EtOAc (2×) and the combined organics was washed with brine, dried ($Na_2SO_4$) and concentrated. The crude material was purified by chromatography through a Redi-Sep pre-packed silica gel column (12 g), eluting with a gradient of 0% to 0% EtOAc in hexane, to provide 5-(3-((4S,6S)-2-amino-4-(fluoromethyl)-6-(trifluoromethyl)-5,6-dihydro-4H-1,3-oxazin-4-yl)-4-fluorophenyl)nicotinonitrile (77 mg, 0.194 mmol, 65.9% yield) as off-white solid. MS m/z=397 $[M]^+$. Calculated for $C_{18}H_{13}F_5N_4O$: 396.31.

$^1$H NMR (300 MHz, CHLOROFORM-d) ppm 2.10-2.26 (m, 1 H) 2.74 (dd, J=13.67, 2.70 Hz, 1 H) 4.05-4.21 (m, 1 H) 4.44 (dd, J=8.62, 1.02 Hz, 1 H) 4.55-4.66 (m, 1 H) 4.75 (dd, J=8.62, 1.61 Hz, 1 H) 7.19-7.34 (m, 1 H) 7.54 (ddd, J=8.48, 4.46, 2.56 Hz, 1 H) 7.72 (dd, J=7.45, 2.48 Hz, 1 H) 8.10 (t, J=2.12 Hz, 1 H) 8.86 (d, J=1.90 Hz, 1 H) 9.00 (d, J=2.34 Hz, 1 H).

Example 104

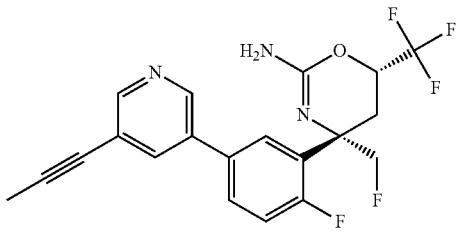 [SMILES: CC#Cc1cncc(-c2ccc(F)c([C@]3(CF)C[C@@H](C(F)(F)F)OC(N)=N3)c2)c1]

Synthesis of (4S,6S)-4-(2-fluoro-5-(5-(prop-1-yn-1-yl)pyridin-3-yl)phenyl)-4-(fluoromethyl)-6-(trifluoromethyl)-5,6-dihydro-4H-1,3-oxazin-2-amine A mixture of potassium phosphate (0.168 g, 0.792 mmol), (4S,6S)-4-(5-bromo-2-fluorophenyl)-4-(fluoromethyl)-6-(trifluoromethyl)-5,6-dihydro-4H-1,3-oxazin-2-amine (8a, 0.0985 g, 0.264 mmol), (5-(prop-1-yn-1-yl)pyridin-3-yl)boronic acid (0.106 g, 0.660 mmol) and 1,1-bis[(di-t-butyl-p-methylaminophenyl]palladium(ii) chloride (9.35 mg, 0.013 mmol) in dioxane/water (2.0/0.5 mL) was irradiated at 110° C. for 30 min. The reaction mixture was diluted with water and extracted with DCM three times. The combined organic layers were washed with brine, dried over sodium sulfate, filtered and concentrated in vacuo. The crude material was purified by silica gel chromatography: 12 g, 0-100% EtOAc/DCM. The product was obtained as a white solid (0.060 g, 55% yield). MS m/z=410 $[M+H]^+$. Calculated for $C_{20}H_{16}F_5N_3O$: 409.4.

$^1$H NMR (400 MHz, CHLOROFORM-d)=8.66 (br. s., 1 H), 8.58 (s, 1 H), 7.82 (s, 1 H), 7.69 (d, J=7.4 Hz, 1 H), 7.52 (br. s., 1 H), 7.24-7.14 (m, 1 H), 4.82-4.41 (m, 2 H), 4.23-4.08 (m, 1 H), 2.74 (d, J=13.7 Hz, 1 H), 2.21 (t, J=13.2 Hz, 1 H), 2.10 (s, 3 H), 1.70 (br. s., 2 H).

Example 105

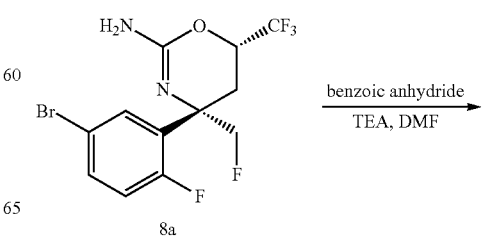

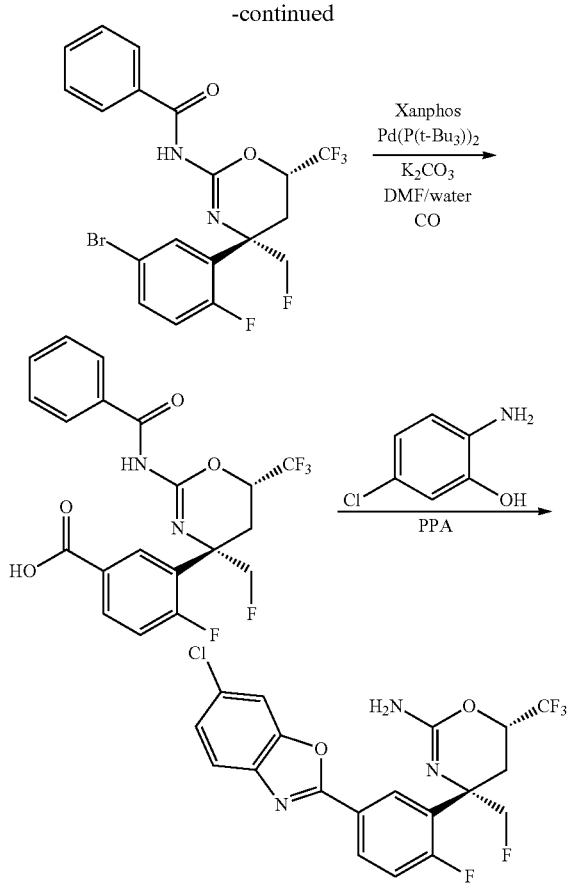

Synthesis of (4S,6S)-4-(5-(6-chlorobenzo[d]oxazol-2-yl)-2-fluorophenyl)-4-(fluoromethyl)-6-(trifluoromethyl)-5,6-dihydro-4H-1,3-oxazin-2-amine Step 1: N-((4S,6S)-4-(5-bromo-2-fluorophenyl)-4-(fluoromethyl)-6-(trifluoromethyl)-5,6-dihydro-4H-1,3-oxazin-2-yl)benzamide To a mixture of (4S,6S)-4-(5-bromo-2-fluorophenyl)-4-(fluoromethyl)-6-(trifluoromethyl)-5,6-dihydro-4H-1,3-oxazin-2-amine (8a, 4.15 g, 11.12 mmol) in DMF (40 mL) under $N_2$ was added triethylamine (2.32 mL, 16.68 mmol) and benzoic anhydride (2.82 g, 12.46 mmol). The mixture was stirred at rt for 3.5 h, then was diluted with saturated $Na_2CO_3$ and extracted with EtOAc twice. The organic solution was washed with water, brine, dried over $Na_2SO_4$ and concentrated in vacuo. The crude was purified by silica gel chromatography: 0-50% EtOAc-hexane in 25 min. The product was obtained as a white solid (5.37 g, 100% yield). MS m/z=477, 479 [M+H]$^+$. Calculated for $C_{19}H_{14}BrF_5N_2O_2$: 477.2.

Step 2: 3-((4S,6S)-2-benzamido-4-(fluoromethyl)-6-(trifluoromethyl)-5,6-dihydro-4H-1,3-oxazin-4-yl)-4-fluorobenzoic acid To a mixture of N-((4S,6S)-4-(5-bromo-2-fluorophenyl)-4-(fluoromethyl)-6-(trifluoromethyl)-5,6-dihydro-4H-1,3-oxazin-2-yl)benzamide (2.19 g, 4.59 mmol), bis(tri-t-butylphosphine)palladium(0) (0.23 g, 0.46 mmol), xantphos (0.53 g, 0.92 mmol), potassium carbonate (1.90 g, 13.76 mmol) in DMF (15 mL) and water (0.83 ml, 45.9 mmol) was bubbled CO gas for 10 min. The mixture was heated at 90° C. for 4 h, then was allowed to cool to rt. 1N HCl was added until pH~4. Water was then added and a precipitate was formed. The solid was filtered, washed with water, and dried. The filtrate was concentrated in vacuo. The crude product was purified by silica gel chromatographed, eluting with a gradient of 1% to 8% MeOH in 0.5% AcOH/DCM, to provide the acid as a white solid (0.44 g, 21.45% yield). MS m/z=443 [M+H]$^+$. Calculated for $C_{20}H_{15}F_5N_2O_4$: 442.3.

Step 3: (4S,6S)-4-(5-(6-chlorobenzo[d]oxazol-2-yl)-2-fluorophenyl)-4-(fluoromethyl)-6-(trifluoromethyl)-5,6-dihydro-4H-1,3-oxazin-2-amine To a 3 mL microwave vial was added 3-((4S,6S)-2-benzamido-4-(fluoromethyl)-6-(trifluoromethyl)-5,6-dihydro-4H-1,3-oxazin-4-yl)-4-fluorobenzoic acid (76.5 mg, 0.17 mmol). 2-amino-5-chlorophenol (74.0 mg, 0.52 mmol) and polyphosphoric acid (0.50 mL). The mixture was purged with Ar for 1 min, then the tube was sealed and heated to 160° C. for 1 h. The mixture was then diluted with $Na_2CO_3$ in water and extracted with DCM three times. The organic layer was dried over $Na_2SO_4$, and concentrated in vacuo. The crude was purified by reverse phase HPLC: 10-100% in 26 min, MeCN in water with 0.1% TFA. The combined fractions were neutralized with solid $Na_2CO_3$, and extracted with DCM three times. The organic phase was dried over $Na_2SO_4$ and concentrated in vacuo. The product was obtained as an off-white solid (2.6 mg, 3.6% yield). MS m/z=446 [M+H]$^+$. Calculated for $C_{19}H_{13}ClF_5N_3O_2$: 445.8.

$^1$H NMR (400 MHz, CHLOROFORM-d) δ=8.38-8.16 (m, 2 H), 7.71-7.65 (m, 1 H), 7.61 (d, J=1.8 Hz, 1 H), 7.38-7.27 (m, 2 H), 4.90-4.54 (m, 2 H), 4.29 (br. s., 1 H), 2.88-2.81 (m, 1 H), 2.50-2.30 (m, 1 H).

Example 106 (Method N)

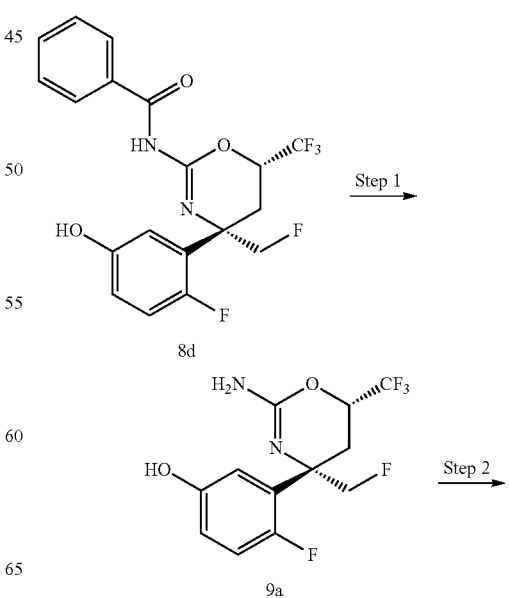

-continued

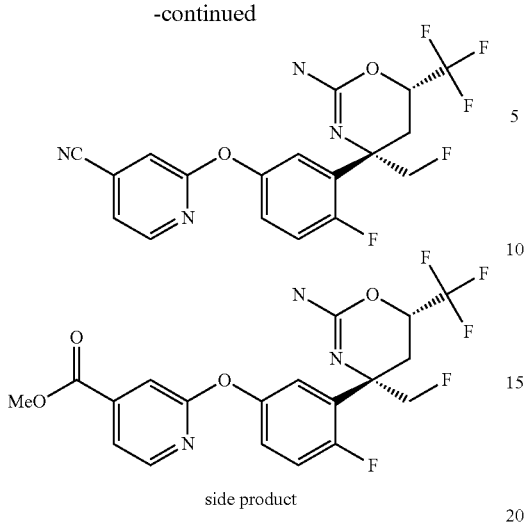

side product

Synthesis of 2-(3-((4S,6S)-2-amino-4-(fluoromethyl)-6-(trifluoromethyl)-5,6-dihydro-4H-1,3-oxazin-4-yl)-4-fluorophenoxy)isonicotinonitrile and methyl 2-(3-((4S,6S)-2-amino-4-(fluoromethyl)-6-(trifluoromethyl)-5,6-dihydro-4H-1,3-oxazin-4-yl)-4-fluorophenoxy)isonicotinate

Step 1: 3-((4S,6S)-2-amino-4-(fluoromethyl)-6-(trifluoromethyl)-5,6-dihydro-4H-1,3-oxazin-4-yl)-4-fluorophenol (9a)

In a microwave vial was dissolved N-((4S,6S)-4-(2-fluoro-5-hydroxyphenyl)-4-(fluoromethyl)-6-(trifluoromethyl)-5,6-dihydro-4H-1,3-oxazin-2-yl)benzamide (8d, 116 mg, 0.280 mmol) in MeOH (1120 μl) and added 1,8-diazabicyclo-[5.4.0]undec-7-ene (84 μl 0.560 mmol). The reaction mixture was stirred at 75° C. overnight. Cooled to room temperature. Concentrated down and used directly in the following step.
MS m/z=311 [M]$^+$. Calculated for $C_{12}H_{11}F_5N_2O_2$: 310.22.

Step 2. 2-(3-((4S,6S)-2-amino-4-(fluoromethyl)-6-(trifluoromethyl)-5,6-dihydro-4H-1,3-oxazin-4-yl)-4-fluorophenoxy)isonicotinonitrile The crude product from step 1,4-cyano-2-fluoropyridine (37.7 mg, 0.308 mmol), cesium carbonate (110 mg, 0.337 mmol) and DMSO (561 μl) were stirred in a microwave at 100° C. for 25 min. After cooling to RT, the reaction mixture was partitioned between EtOAc and water. The aqueous layer was back extracted with EtOAc (2×) and the combined organics was dried ($Na_2SO_4$) and concentrated. The crude material was purified by chromatography through a Redi-Sep prepacked silica gel column (12 g), eluting with a gradient of 0% to 50% EtOAc in hexane twice to give 2-(3-((4S,6S)-2-amino-4-(fluoromethyl)-6-(trifluoromethyl)-5,6-dihydro-4H-1,3-oxazin-4-yl)-4-fluorophenoxy)isonicotinonitrile (36 mg, 0.087 mmol, 31.1% yield) as white solid. MS m/z=413 [M]$^+$. Calculated for $C_{18}H_{13}F_5N_4O_2$: 412.31.
$^1$H NMR (400 MHz, CHLOROFORM-d) ppm 2.23 (t, J=13.30 Hz, 1 H) 2.73 (d, J=13.89 Hz, 1 H) 4.19 (m, 1 H) 4.41-4.81 (m, 2 H) 7.06-7.24 (m, 4 H) 7.29 (d, J=6.46 Hz, 1 H) 8.28 (d, J=4.50 Hz, 1 H).
2-(3-((4S,6S)-2-amino-4-(fluoromethyl)-6-(trifluoromethyl)-5,6-dihydro-4H-1,3-oxazin-4-yl)-4-fluorophenoxy) isonicotinate was also isolated. MS m/z=446 [M]$^+$. Calculated for $C_{16}H_{16}F_5N_3O_4$: 445.34.
$^1$H NMR (300 MHz, CHLOROFORM-d) δ ppm 2.18 (t, J=13.08 Hz, 1 H) 2.69 (d, J=13.15 Hz, 1 H) 3.96 (s, 3 H) 4.11-4.21 (m, 1 H) 4.36-4.59 (m, 1 H) 4.59-4.84 (m, 1 H) 4.60-4.60 (m, 1 H) 7.12 (d, J=8.62 Hz, 2 H) 7.42-7.60 (m, 2 H) 8.27 (d, J=5.26 Hz, 1 H).

Example 107

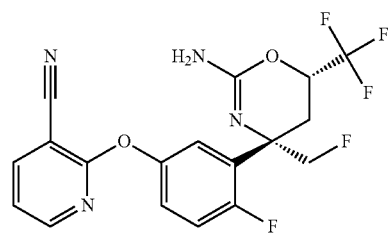 [SMILES: N#Cc1cccnc1Oc1ccc(F)c([C@]2(CF)C[C@@H](C(F)(F)F)OC(N)=N2)c1]

2-(3-((4S,6S)-2-amino-4-(fluoromethyl)-6-(trifluoromethyl)-5,6-dihydro-4H-1,3-oxazin-4-yl)-4-fluorophenoxy)nicotinonitrile The title compound was synthesized using steps and procedures analogous to those described in Method N (Example 106) above, but using 3-cyano-2-fluoropyridine (Alfa Aesar). MS m/z=413 [M]$^+$. Calculated for $C_{15}H_{13}F_5N_4O_2$: 412.31.
$^1$H NMR (300 MHz, CHLOROFORM-d) ppm 2.19 (t, J=13.15 Hz, 1 H) 2.69 (d, J=13.59 Hz, 1 H) 4.13 (t, J=6.94 Hz, 1 H) 4.40 (d, J=8.92 Hz, 1 H) 4.51-4.69 (m, 1 H) 4.78 (d, J=8.33 Hz, 3 H) 7.05-7.22 (m, 3 H) 7.33 (d, J=5.12 Hz, 1 H) 8.02 (d, J=7.31 Hz, 1 H) 8.29 (d, J=3.36 Hz, 1 H).

Example 108

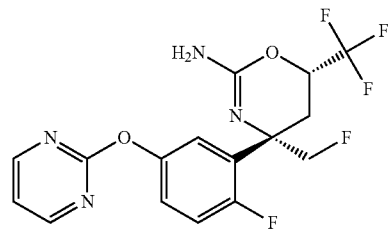 [SMILES: NC1=N[C@](CF)(c2cc(Oc3ncccn3)ccc2F)C[C@@H](C(F)(F)F)O1]

Synthesis of (4S,6S)-4-(2-fluoro-5-(pyrimidin-2-yloxy)phenyl)-4-(fluoromethyl)-6-(trifluoromethyl)-5,6-dihydro-4H-1,3-oxazin-2-amine The title compound was synthesized using steps and procedures analogous to those described in Method N (Example 106) above, but using 2-chloropyrimidine (Aldrich). MS m/z=389 [M]$^+$. Calculated for $C_{16}H_{13}F_5N_4O_2$: 388.29.
$^1$H NMR (400 MHz, CHLOROFORM-d) ppm 2.18 (t, J=13.11 Hz, 1 H) 2.68 (d, J=13.69 Hz, 1 H) 4.14 (dd, J=15.06, 7.63 Hz, 1 H) 4.37-4.59 (m, 1 H) 4.62-4.83 (m, 1 H) 7.00-7.23 (m, 3 H) 7.34 (d, J=6.46 Hz, 1 H) 8.55 (d, J=4.50 Hz, 2 H).

Example 109

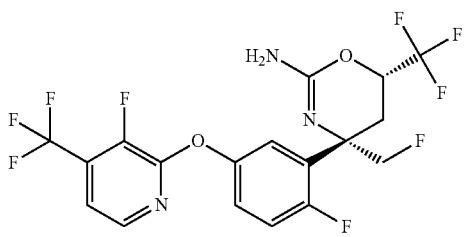 [SMILES: NC1=N[C@](CF)(c2cc(Oc3nccc(C(F)(F)F)c3F)ccc2F)C[C@@H](C(F)(F)F)O1]

Synthesis of (4S,6S)-4-(2-fluoro-5-((3-fluoro-4-(trifluoromethyl)pyridin-2-yl)oxy)phenyl)-4-(fluoromethyl)-6-(trifluoromethyl)-5,6-dihydro-4H-1,3-oxazin-2-amine The title compound was synthesized using steps and procedures analogous to those described in Method N (Example 106) above, but using 2,3-difluoro-4-(trifluoromethyl)pyridine (Matrix). MS m/z=474 [M]$^+$. Calculated for $C_{18}H_{12}F_9N_3O_2$: 473.29.

$^1$H NMR (300 MHz, CHLOROFORM-d) ppm 2.18 (t, J=13.30 Hz, 1 H) 2.69 (d, J=13.45 Hz, 1 H) 4.07 (s, 1 H) 4.37-4.82 (m, 2 H) 7.18 (d, J=7.31 Hz, 4 H) 7.33 (d, J=5.41 Hz, 2 H) 7.99 (d, J=4.68 Hz, 1 H).

Example 110

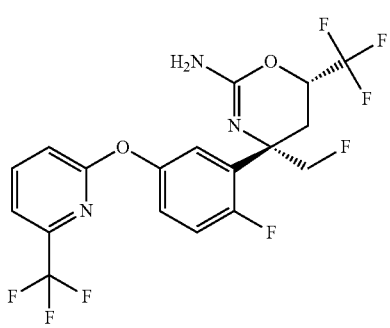 [SMILES: NC1=N[C@](CF)(c2cc(Oc3cccc(C(F)(F)F)n3)ccc2F)C[C@@H](C(F)(F)F)O1]

Synthesis of (4S,6S)-4-(2-fluoro-5-((6-(trifluoromethyl)pyridin-2-yl)oxy)phenyl)-4-(fluoromethyl)-6-(trifluoromethyl)-5,6-dihydro-4H-1,3-oxazin-2-amine The title compound was synthesized using steps and procedures analogous to those described in Method N (Example 106) above, but using 2-fluoro-6-(trifluoromethyl)pyridine. MS m/z=456 [M]$^+$. Calculated for $C_{18}H_{13}F_8N_3O_2$: 455.30.

$^1$H NMR (300 MHz, CHLOROFORM-d) ppm 2.16 (t, J=13.08 Hz, 1 H) 2.65 (dd, J=13.59, 2.34 Hz, 1 H) 4.10-4.23 (m, 1 H) 4.39-4.61 (m, 1 H) 4.61-4.83 (m, 1 H) 7.06-7.16 (m, 3 H) 7.30-7.35 (m, 1 H) 7.38 (d, J=7.45 Hz, 1 H) 7.85 (t, J=7.89 Hz, 1 H).

Example 111 (Method O)

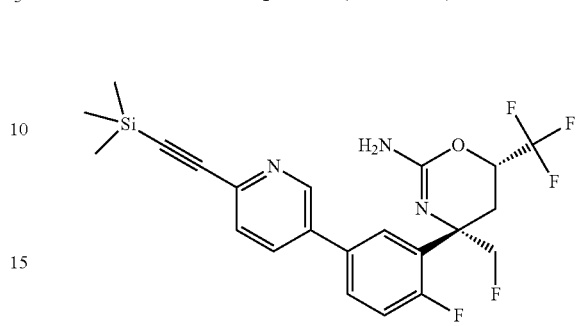

Synthesis of (4S,6S)-4-(2-fluoro-5-(6-((trimethylsilyl)ethynyl)pyridin-3-yl)phenyl)-4-(fluoromethyl)-6-(trifluoromethyl)-5,6-dihydro-4H-1,3-oxazin-2-amine A mixture of potassium phosphate (0.676 g, 3.19 mmol), (4S,6S)-4-(2-fluoro-5-(4,4,5,5-tetramethyl-1,3,2-dioxaborolan-2-yl)phenyl)-4-(fluoromethyl)-6-(trifluoromethyl)-5,6-dihydro-4H-1,3-oxazin-2-amine (8b, 1.428 g, 3.40 mmol), 5-bromo-2-((trimethylsilyl)ethynyl)pyridine (0.270 g, 1.062 mmol) and 1,1-bis[(di-t-butyl-p-methylaminophenyl]palladium(II) chloride (0.038 g, 0.053 mmol) in dioxane/water (5.0/1.2 mL) was heated in microwave reactor at 110° C. for 35 min. The reaction mixture was diluted with water and extracted with DCM three times. The combined organic layers were washed with brine, dried on sodium sulfate, filtered and concentrated. The crude material was purified by silica gel chromatography: 0-100% EtOAc/hexane in 15 min. The product was obtained as an off-white solid. Trituration with hexane afforded the pure product as a white solid (0.22 g, 44% yield). MS m/z=468 [M+H]$^+$. Calculated for $C_{22}H_{22}F_5N_3OSi$: 467.5.

$^1$H NMR (400 MHz, CHLOROFORM-d)=8.77 (s, 1 H), 7.80 (d, J=8.0 Hz, 1 H), 7.70 (d, J=7.4 Hz, 1 H), 7.58-7.48 (m, 2 H), 7.19 (t, J=10.2 Hz, 1 H), 4.83-4.42 (m, 2 H), 4.33 (br. s., 2 H), 4.13 (d, J=5.7 Hz, 1 H), 2.72 (d, J=13.7 Hz, 1 H), 2.18 (t, J=13.2 Hz, 1 H), 0.29 (s, 9 H).

Example 112

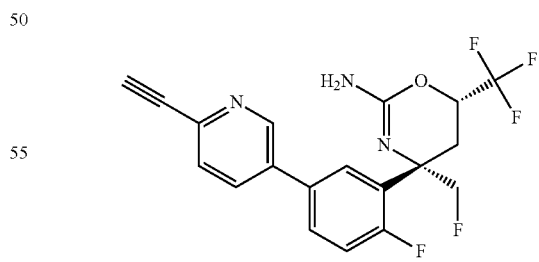

(4S,6S)-4-(5-(6-ethynylpyridin-3-yl)-2-fluorophenyl)-4-(fluoromethyl)-6-(trifluoromethyl)-5,6-dihydro-4H-1,3-oxazin-2-amine A mixture of (4S,6S)-4-(2-fluoro-5-(6-((trimethylsilyl)ethynyl)pyridin-3-yl)phenyl)-4-(fluoromethyl)-6-(trifluoromethyl)-5,6-dihydro-4H-1,3-oxazin-2-amine (0.2034 g, 0.435 mmol, Example 111), potassium carbonate (0.301 g, 2.175 mmol), and MeOH (3 mL) was stirred at room temperature for 1.25 h. The reaction mixture was concentrated in vacuo, diluted with water and extracted with DCM three times. The combined organic layers were washed with brine, dried over sodium sulfate, filtered and concentrated. The crude material was purified by silica gel chromatography: 0-100% EtOAc/hexane in 12 min. The product was obtained as a white solid (0.16 g, 93% yield). MS m/z=396 [M+H]+. Calculated for $C_{19}H_{14}F_5N_3O$: 395.3.

$^1$H NMR (400 MHz, CHLOROFORM-d)=8.79 (s, 1 H), 7.82 (d, J=8.0 Hz, 1 H), 7.71 (d, J=7.4 Hz, 1 H), 7.55 (d, J=7.8 Hz, 2 H), 7.20 (t, J=10.2 Hz, 1 H), 4.79-4.42 (m, 2 H), 4.36 (br. s., 2 H), 4.13 (d, J=6.1 Hz, 1 H), 3.22 (s, 1 H), 2.72 (d, J=13.7 Hz, 1 H), 2.18 (t, J=13.1 Hz, 1 H).

Example 113

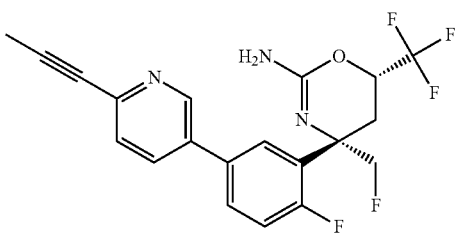 [SMILES: CC#Cc1ccc(-c2ccc(F)c([C@]3(CF)C[C@@H](C(F)(F)F)OC(N)=N3)c2)cn1]

Synthesis of (4S,6S)-4-(2-fluoro-5-(6-(prop-1-yn-1-yl)pyridin-3-yl)phenyl)-4-(fluoromethyl)-6-(trifluoromethyl)-5,6-dihydro-4H-1,3-oxazin-2-amine The title compound was synthesized by procedures and steps analogous to those described in Example 111, Method O, but using 5-bromo-2-(prop-1-yn-1-yl)pyridine. MS m/z=410 [M+H]+. Calculated for $C_{20}H_{16}F_5N_3O$: 409.4.

$^1$H NMR (400 MHz, CHLOROFORM-d)=8.73 (s, 1 H), 7.77 (d, J=8.0 Hz, 1 H), 7.69 (d, J=7.4 Hz, 1 H), 7.52 (br. s., 1 H), 7.42 (d, J=8.2 Hz, 1 H), 7.19 (t, J=10.0 Hz, 1 H), 4.79-4.42 (m, 2 H), 4.36 (br. s., 2 H), 4.13 (d, J=5.9 Hz, 1 H), 2.72 (d, J=13.3 Hz, 1 H), 2.18 (t, J=13.2 Hz, 1 H), 2.11 (s, 3 H).

Example 114

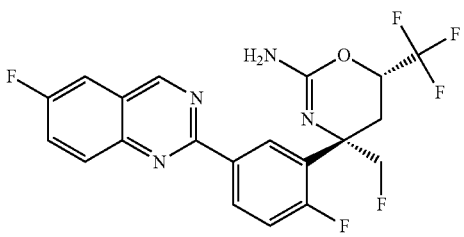

Synthesis of (4S,6S)-4-(2-fluoro-5-(6-fluoroquinazolin-2-yl)phenyl)-4-(fluoromethyl)-6-(trifluoromethyl)-5,6-dihydro-4H-1,3-oxazin-2-amine The title compound was synthesized by procedures and steps analogous to those described in Example 111, Method O, but using 2-chloro-6-fluoroquinazoline. MS m/z=441 [M+H]+. Calculated for $C_{20}H_{14}F_6N_4O$: 440.3.

$^1$H NMR (400 MHz, CHLOROFORM-d)=9.40 (s, 1 H), 8.75 (dd, J=2.3, 8.0 Hz, 1 H), 8.57 (ddd, J=2.2, 4.9, 8.5 Hz, 1 H), 8.07 (dd, J=5.0, 9.3 Hz, 1 H), 7.67 (dt, J=2.7, 8.8 Hz, 1 H), 7.53 (dd, J=2.8, 7.7 Hz, 1 H), 7.25-7.19 (m, 1 H), 4.85-4.45 (m, 4 H), 4.25-4.14 (m, 1 H), 2.76 (dd, J=2.6, 13.6 Hz, 1 H), 2.25 (t, J=13.1 Hz, 1 H).

Example 115

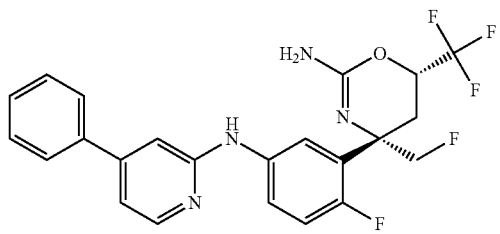 [SMILES: NC1=N[C@](CF)(c2cc(Nc3cc(-c4ccccc4)ccn3)ccc2F)C[C@@H](C(F)(F)F)O1]

Synthesis of (4S,6S)-4-(2-fluoro-5-((4-phenylpyridin-2-yl)amino)phenyl)-4-(fluoromethyl)-6-(trifluoromethyl)-5,6-dihydro-4H-1,3-oxazin-2-amine The title compound was synthesized by procedures and steps analogous to those described in Method O, Example 111, but using phenylboronic acid and (4S,6S)-4-(5-((4-chloropyridin-2-yl)amino)-2-fluorophenyl)-4-(fluoromethyl)-6-(trifluoromethyl)-5,6-dihydro-4H-1,3-oxazin-2-amine (Example 16) as coupling partners. MS m/z=463 [M+H]+. Calculated for $C_{23}H_{19}F_5N_4O$: 462.4.

$^1$H NMR (400 MHz, CHLOROFORM-d) δ=8.24 (d, J=4.1 Hz, 1H), 7.63-7.34 (m, 7H), 7.13-6.87 (m, 4H), 4.78-4.29 (m, 4H), 4.25-4.14 (m, 1H), 2.68 (dd, J=2.7, 13.5 Hz, 1H), 2.15 (t, J=13.1 Hz, 1H).

Example 116

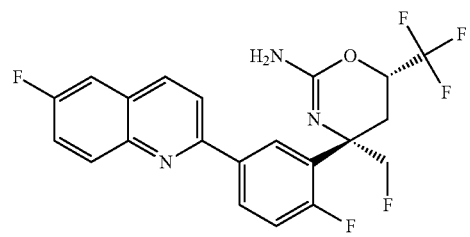 [SMILES: NC1=N[C@](CF)(c2cc(-c3ccc4cc(F)ccc4n3)ccc2F)C[C@@H](C(F)(F)F)O1]

(4S,6S)-4-(2-fluoro-5-(6-fluoroquinolin-2-yl)phenyl)-4-(fluoromethyl)-6-(trifluoromethyl)-5,6-dihydro-4H-1,3-oxazin-2-amine The title compound was synthesized by procedures and steps analogous to those described in Example 111, Method O, but using 6-fluoroquinolin-2-yl trifluoromethanesulfonate. MS m/z=440 [M+H]+. Calculated for $C_{21}H_{15}F_6N_3O$: 439.4.

$^1$H NMR (400 MHz, CHLOROFORM-d)=8.26-8.09 (m, 4 H), 7.84 (d, J=8.6 Hz, 1 H), 7.53-7.39 (m, 2 H), 7.26-7.20 (m,

1 H), 4.86-4.40 (m, 4 H), 4.23-4.12 (m, 1 H), 2.75 (dd, J=2.7, 13.7 Hz, 1 H), 2.22 (t, J=13.2 Hz, 1 H).

Example 117

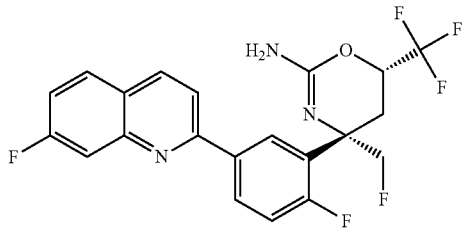 [SMILES: NC1=N[C@](CF)(c2cc(-c3ccc4ccc(F)cc4n3)ccc2F)C[C@@H](C(F)(F)F)O1]

Synthesis of (4S,6S)-4-(2-fluoro-5-(7-fluoroquinolin-2-yl)phenyl)-4-(fluoromethyl)-6-(trifluoromethyl)-5,6-dihydro-4H-1,3-oxazin-2-amine The title compound was synthesized by procedures and steps analogous to those described in Example 111, Method O, but using 2-chloro-7-fluoroquinoline. MS m/z=440 [M+H]$^+$. Calculated for $C_{21}H_{15}F_6N_3O$: 439.4.

$^1$H NMR (400 MHz, CHLOROFORM-d)=8.30-8.09 (m, 4 H), 7.85 (d, J=8.8 Hz, 1 H), 7.55-7.40 (m, 2 H), 7.25-7.20 (m, 1 H), 4.85-4.35 (m, 4 H), 4.17 (d, J=6.1 Hz, 1 H), 2.75 (d, J=13.5 Hz, 1 H), 2.22 (t, J=13.3 Hz, 1 H).

Example 118

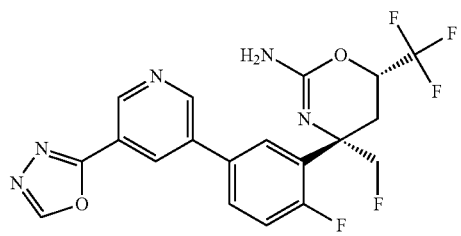 [SMILES: NC1=N[C@](CF)(c2cc(-c3cncc(-c4nnco4)c3)ccc2F)C[C@@H](C(F)(F)F)O1]

Synthesis of (4S,6S)-4-(5-(5-(1,3,4-oxadiazol-2-yl)pyridin-3-yl)-2-fluorophenyl)-4-(fluoromethyl)-6-(trifluoromethyl)-5,6-dihydro-4H-1,3-oxazin-2-amine The title compound was synthesized by procedures and steps analogous to those described in Example 111, Method O, but using 2-(5-bromopyridin-3-yl)-1,3,4-oxadiazole. MS m/z=440 [M+H]$^+$. Calculated for $C_{19}H_{14}F_5N_5O_2$: 439.3.

$^1$H NMR (400 MHz, CHLOROFORM-d)=9.25 (s, 1 H), 8.97 (s, 1 H), 8.55 (br. s., 2 H), 7.80 (d, J=7.4 Hz, 1 H), 7.60 (br. s., 1 H), 7.25-7.20 (m, 1 H), 4.78-4.39 (m, 4 H), 4.22-4.08 (m, 1 H), 2.75 (d, J=13.9 Hz, 1 H), 2.19 (t, J=13.0 Hz, 1 H).

Example 119 (Method P)

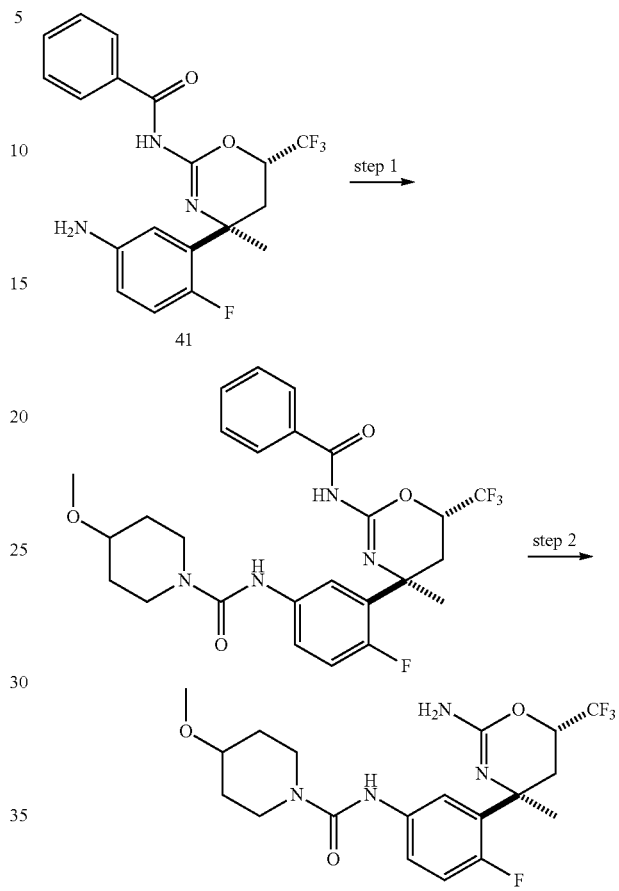

Synthesis of N-(3-((4S,6S)-2-amino-4-methyl-6-(trifluoromethyl)-5,6-dihydro-4H-1,3-oxazin-4-yl)-4-fluorophenyl)-4-methoxypiperidine-1-carboxamide Step 1: Synthesis of N-(3-((4S,6S)-2-benzamido-4-methyl-6-(trifluoromethyl)-5,6-dihydro-4H-1,3-oxazin-4-yl)-4-fluorophenyl)-4-methoxypiperidine-1-carboxamide To a cooled (0° C.) solution of N-((4S,6S)-4-(5-amino-2-fluorophenyl)-4-methyl-6-(trifluoromethyl)-5,6-dihydro-4H-1,3-oxazin-2-yl)benzamide (4l, 0.200 g, 0.506 mmol) in dichloromethane (4 mL) was added 4-nitrophenyl chloroformate (0.111 g, 0.551 mmol) as a solid. After 10 min the reaction was allowed to warm to room temperature. After 3 h 4-methoxy-piperidine (0.100 mL, 1.036 mmol) was added dropwise via syringe and the reaction was stirred overnight. The reaction was evaporated onto silica gel and purified by flash chromatography (Isco, 25 g) eluting with (25% EtOH/EtOAc):hexanes (0:1→2:3) to give N-(3-((4S,6S)-2-benzamido-4-methyl-6-(trifluoromethyl)-5,6-dihydro-4H-1,3-oxazin-4-yl)-4-fluorophenyl)-4-methoxypiperidine-1-carboxamide (166 mg. 61% yield) of a clear, colorless tar. MS m/z=537 [M+H]$^+$. Calculated for $C_{26}H_{28}F_4N_4O_4$: 536

Step 2: Synthesis of N-(3-((4S,6S)-2-amino-4-methyl-6-(trifluoromethyl)-5,6-dihydro-4H-1,3-oxazin-4-yl)-4-fluorophenyl)-4-methoxypiperidine-1-carboxamide To a solution of N-(3-((4S,6S)-2-benzamido-4-methyl-6-(trifluoromethyl)-5,6-dihydro-4H-1,3-oxazin-4-yl)-4-fluorophenyl)-4-methoxypiperidine-1-carboxamide (0.166 g, 0.309 mmol) in MeOH (3 mL) at room temperature was added 1,8-diazabicyclo-[5.4.0]undec-7-ene (0.100 mL, 0.669 mmol). The reaction was heated at 60° C. for 4 h. Then the reaction was cooled to room temperature, diluted with MeOH, purified by reverse-phase HPLC (Gilson; Gemini-NX 10m C18 110A AXIA, 100×50 mm column) eluting with 0.1% TFA-H$_2$O:0.1% TFA CH$_3$CN (9:1→1:9). The fractions containing the desired product were combined and concentrated in vacuo. The material was dissolved in MeOH and eluted with MeOH, through an Silicycle carbonate cartridge to give the titled compound as a white crystalline solid (68 mg, 51%). MS m/z=433 [M+H]$^+$. Calculated for C$_{19}$H$_{24}$F$_4$N$_4$O$_3$: 432

$^1$H NMR (400 MHz, DMSO-d$_6$) ppm 8.58 (s, 1 H), 7.36-7.42 (m, 1 H), 7.34 (dd, J=7.63, 2.74 Hz, 1 H), 7.02 (dd, J=11.93, 8.80 Hz, 1 H), 5.84 (s, 2 H), 4.07 (td, J=6.06, 3.91 Hz, 1 H), 3.69-3.82 (m, 2 H), 3.33-3.41 (m, 1 H), 3.26 (s, 3 H), 3.09 (ddd, J=13.20, 9.68, 3.13 Hz, 2 H), 2.56 (dd, J=13.30, 2.35 Hz, 1 H), 1.80-1.92 (m, 2 H), 1.76 (t, J=13.01 Hz, 1 H), 1.48 (s, 3 H), 1.29-1.42 (m, 2 H)

Example 120

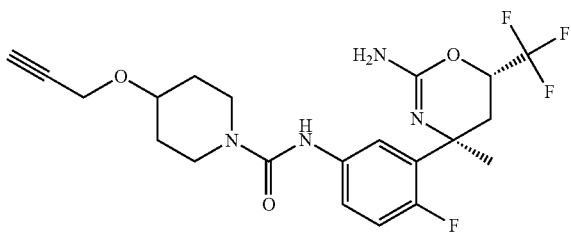 [SMILES: C#CCOC1CCN(C(=O)Nc2ccc(F)c([C@]3(C)C[C@@H](C(F)(F)F)OC(N)=N3)c2)CC1]

Synthesis of N-(3-((4S,6S)-2-amino-4-methyl-6-(trifluoromethyl)-5,6-dihydro-4H-1,3-oxazin-4-yl)-4-fluorophenyl)-4-(prop-2-yn-1-yloxy)piperidine-1-carboxamide Step 1: Synthesis of tert-butyl 4-(prop-2-yn-1-yloxy)piperidine-1-carboxylate To a RT solution of 1-boc-4-hydroxypiperidine (1.20 g, 5.96 mmol) in THF (20 mL) was added sodium hydride dispersion in mineral oil (0.440 g, 11.00 mmol, 57%), in portions, as a solid. After 30 min propargyl bromide, 80% solution in toluene (1.80 mL, 16.16 mmol) was added dropwise via syringe and the reaction was allowed to stir for 2 h. The reaction was cooled to 0° C., quenched with water and extracted with EtOAc (3×). The combined organic layers were washed with brine, evaporated onto silica gel and purified by flash chromatography (Isco (80 gram)) eluting with (EtOAc):hexanes (0:1→1:1) to give the titled compound as a colorless oil (861 mg, 60%). MS m/z=183.9 [M−tBu]$^+$. Calculated for C$_9$H$_{12}$NO$_3$: 182

Step 2: Synthesis of 4-(prop-2-yn-1-yloxy)piperidine hydrochloride

To a RT solution of tert-butyl 4-(prop-2-yn-1-yloxy)piperidine-1-carboxylate (0.826 g, 3.45 mmol) in 1,4-dioxane (10 mL) was added 4.0M HCl solution in 1,4-dioxane (1.80 mL, 7.20 mmol). After 2 h an additional amount of 4.0M HCl solution in 1,4-dioxane (1.80 mL, 7.20 mmol) was added and the reaction was stirred for 1 h. The solvent was removed in vacuo to yield the titled compound as a white crystalline solid (632 mg, quant).

Step 3: Synthesis of N-(3-((4S,6S)-2-benzamido-4-methyl-6-(trifluoromethyl)-5,6-dihydro-4H-1,3-oxazin-4-yl)-4-fluorophenyl)-4-(prop-2-yn-1-yloxy)piperidine-1-carboxamide The title compound was synthesized using steps and procedures analogous to those described in Method P, Example 119 (step 1) above, but using 4-(prop-2-yn-1-yloxy)piperidine hydrochloride. MS m/z=561 [M+H]$^+$. Calculated for C$_{28}$H$_{28}$F$_4$N$_4$O$_4$: 560

Step 4: Synthesis of N-(3-((4S,6S)-2-amino-4-methyl-6-(trifluoromethyl)-5,6-dihydro-4H-1,3-oxazin-4-yl)-4-fluorophenyl)-4-(prop-2-yn-1-yloxy)piperidine-1-carboxamide The title compound was synthesized using steps and procedures analogous to those described in Method P, Example 119 (step 2) above, but using N-(3-((4S,6S)-2-benzamido-4-methyl-6-(trifluoromethyl)-5,6-dihydro-4H-1,3-oxazin-4-yl)-4-fluorophenyl)-4-(prop-2-yn-1-yloxy)piperidine-1-carboxamide. MS m/z=457 [M+H]$^+$. Calculated for C$_{21}$H$_{24}$F$_4$N$_4$O$_3$: 456

$^1$H NMR (300 MHz, DMSO-d$_6$) ppm 8.59 (s, 1 H), 7.25-7.46 (m, 2 H), 7.02 (dd, J=12.06, 8.70 Hz, 1 H), 5.84 (s, 2 H), 4.19 (d, J=2.34 Hz, 2 H), 4.06 (m, J=12.31, 6.10, 2.19 Hz, 1 H), 3.71-3.86 (m, 2 H), 3.67 (tt, J=8.26, 3.95 Hz, 1 H), 3.39 (t, J=2.41 Hz, 1 H), 3.10 (ddd, J=13.19, 9.68, 3.00 Hz, 2 H), 2.52-2.63 (m, 1 H), 1.68-1.93 (m, 3 H), 1.47 (s, 3 H), 1.28-1.45 (m, 2 H)

Example 121

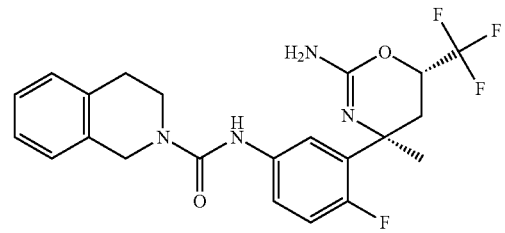 [SMILES: C[C@@]1(c2cc(NC(=O)N3CCc4ccccc4C3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-3,4-dihydroisoquinoline-2(1H)-carboxamide Step 1: Synthesis of N-(3-((4S,6S)-2-benzamido-4-methyl-6-(trifluoromethyl)-5,6-dihydro-4H-1,3-oxazin-4-yl)-4-fluorophenyl)-3,4-dihydroisoquinoline-2(1H)-carboxamide The title compound was synthesized using steps and procedures analogous to those described in Method P, Example 119 (step 1) above, but using 1,2,3,4-tetrahydroisoquinoline (Aldrich). MS m/z=555 [M+H]⁺. Calculated for $C_{29}H_{26}F_4N_4O_3$: 554

Step 2: Synthesis of N-(3-((4S,6S)-2-amino-4-methyl-6-(trifluoromethyl)-5,6-dihydro-4H-1,3-oxazin-4-yl)-4-fluorophenyl)-3,4-dihydroisoquinoline-2(1H)-carboxamide The title compound was synthesized using steps and procedures analogous to those described in Method P, Example 119 (step 2) above, but using N-(3-((4S,6S)-2-benzamido-4-methyl-6-(trifluoromethyl)-5,6-dihydro-4H-1,3-oxazin-4-yl)-4-fluorophenyl)-3,4-dihydroisoquinoline-2(1H)-carboxamide. MS m/z=451 [M+H]⁺. Calculated for $C_{22}H_{22}F_4N_4O_2$: 450

¹H NMR (300 MHz, DMSO-d₆) ppm 8.68 (s, 1 H), 7.31-7.54 (m, 2 H), 7.18 (s, 4 H), 7.04 (dd, J=12.06, 8.55 Hz, 1 H), 5.85 (br. s., 2 H), 4.62 (s, 2 H), 3.98-4.19 (m, 1 H), 3.69 (t, J=5.92 Hz, 2 H), 2.84 (t, J=5.85 Hz, 2 H), 2.57 (dd, J=13.30, 2.48 Hz, 1 H), 1.77 (t, J=12.86 Hz, 1 H), 1.49 (s, 3 H)

Example 122

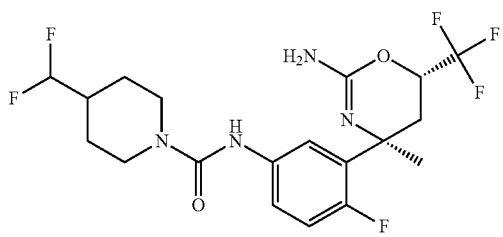 [SMILES: C[C@@]1(c2cc(NC(=O)N3CCC(C(F)F)CC3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-4-(difluoromethyl)piperidine-1-carboxamide Step 1: Synthesis of benzyl 4-(difluoromethyl)piperidine-1-carboxylate To a cooled (0° C.) solution of XtalFluor-E (4.50 g, 19.65 mmol) in dichloromethane (50 mL) was added a solution of 4-formyl-N-CBZ-piperidine (2.30 g, 9.30 mmol, Oakwood) in dichloromethane (7 mL) followed by triethylamine trihydrofluoride (3.00 mL, 18.40 mmol). The reaction was allowed to warm to room temperature overnight. Then the reaction mixture was cooled to 0° C. and quenched slowly with saturated NaHCO₃ solution. The layers were separated and the aqueous layer was extracted with dichloromethane (3×). The combined organic layers were evaporated onto silica gel and purified by flash chromatography (Isco 40 g) eluting with (EtOAc):hexanes (0:1→1:1) to give benzyl 4-(difluoromethyl)piperidine-1-carboxylate as a light-yellow oil (1.16 g, 46% yield).

Step 2: Synthesis of 4-(difluoromethyl)piperidine

A 250 flask charged with benzyl 4-(difluoromethyl)piperidine-1-carboxylate (1.16 g, 4.31 mmol), palladium, 10 wt. % (dry basis) on activated carbon, wet, degussa type e101 ne/w (0.563 g, 0.265 mmol) and EtOH (25 mL) was evacuated/backfilled with hydrogen (1 atm, 3×). After stirring overnight at room temperature, more palladium, 10 wt. % (dry basis) on activated carbon, wet, degussa type e101 ne/w (1.09 g) was added and the reaction was evacuated/backfilled with hydrogen (1 atm, 3×). After stirring overnight the reaction was filtered through a pad of Celite and the pad was washed with EtOH. Concentration of the filtrate in vacuo gave 4-(difluoromethyl)piperidine as a light-yellow oil (90 mg, 15% yield).

Step 3: Synthesis of N-(3-((4S,6S)-2-benzamido-4-methyl-6-(trifluoromethyl)-5,6-dihydro-4H-1,3-oxazin-4-yl)-4-fluorophenyl)-4-(difluoromethyl)piperidine-1-carboxamide The title compound was synthesized using steps and procedures analogous to those described in Method P, Example 119 (step 1) above, but using 4-(difluoromethyl)piperidine. MS m/z=557 [M+H]⁺. Calculated for $C_{26}H_{26}F_6N_4O_3$: 556

Step 4: Synthesis of N-(3-((4S,6S)-2-amino-4-methyl-6-(trifluoromethyl)-5,6-dihydro-4H-1,3-oxazin-4-yl)-4-fluorophenyl)-4-(difluoromethyl)piperidine-1-carboxamide The title compound was synthesized using steps and procedures analogous to those described in Method P, Example 119 (step 2) above, but using N-(3-((4S,6S)-2-amino-4-methyl-6-(trifluoromethyl)-5,6-dihydro-4H-1,3-oxazin-4-yl)-4-fluorophenyl)-4-(difluoromethyl)piperidine-1-carboxamide. MS m/z=453 [M+H]⁺. Calculated for $C_{19}H_{22}F_6N_4O_2$: 452

¹H NMR (400 MHz, DMSO-d₆) δ ppm 8.13-9.05 (m, 1 H), 7.36-7.44 (m, 1 H), 7.34 (dd, J=7.63, 2.74 Hz, 1 H), 7.02 (dd, J=11.93, 8.80 Hz, 1 H), 5.92 (td, J=56.73, 4.11 Hz, 1 H), 5.85 (br. s., 2 H), 4.16 (d, J=13.30 Hz, 2 H), 4.01-4.12 (m, 1 H), 2.77 (td, J=12.86, 2.25 Hz, 2 H), 2.53-2.62 (m, 1 H), 1.93-2.15 (m, 1 H), 1.76 (t, J=12.91 Hz, 1 H), 1.69 (m, J=10.56 Hz, 2 H), 1.48 (s, 3 H), 1.19-1.36 (m, 2 H)

Example 123

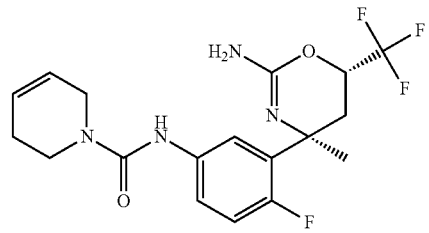 [SMILES: C[C@@]1(c2cc(NC(=O)N3CC=CCC3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-5,6-dihydropyridine-1(2H)-carboxamide Step 1: Synthesis of N-(3-((4S,6S)-2-benzamido-4-methyl-6-(trifluoromethyl)-5,6-dihydro-4H-1,3-oxazin-4-yl)-4-fluorophenyl)-4-(difluoromethyl)piperidine-1-carboxamide The title compound was synthesized using steps and procedures analogous to those described in Method P, Example 119 (step 1) above, but using 1,2,3,6-tetrahydropyridine (Aldrich). MS m/z=505 [M+H]$^+$. Calculated for $C_{25}H_{24}F_4N_4O_3$: 504

Step 2: Synthesis of N-(3-((4S,6S)-2-amino-4-methyl-6-(trifluoromethyl)-5,6-dihydro-4H-1,3-oxazin-4-yl)-4-fluorophenyl)-5,6-dihydropyridine-1(2H)-carboxamide The title compound was synthesized using steps and procedures analogous to those described in Method P, Example 119 (step 2) above, but using N-(3-((4S,6S)-2-benzamido-4-methyl-6-(trifluoromethyl)-5,6-dihydro-4H-1,3-oxazin-4-yl)-4-fluorophenyl)-4-(difluoromethyl)piperidine-1-carboxamide. MS m/z=401 [M+H]$^+$. Calculated for $C_{18}H_{20}F_4N_4O_2$: 400

$^1$H NMR (400 MHz, DMSO-d$_6$) δ ppm 8.54 (s, 1 H), 7.27-7.48 (m, 2 H), 7.03 (t, J=10.27 Hz, 1 H), 5.64-6.07 (m, 4 H), 4.08 (m, J=5.87 Hz, 1 H), 3.92 (br. s., 2 H), 3.50 (t, J=5.18 Hz, 2 H), 2.56 (d, J=13.30 Hz, 1 H), 2.12 (br. s., 2 H), 1.76 (t, J=12.91 Hz, 1H), 1.48 (s, 3 H)

Example 124

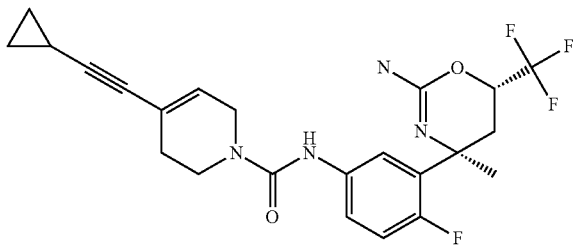 [SMILES: C[C@@]1(c2cc(NC(=O)N3CC=C(C#CC4CC4)CC3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-4-(cyclopropylethynyl)-5,6-dihydropyridine-1(2H)-carboxamide Step 1: Synthesis of tert-butyl 4-(((trifluoromethyl)sulfonyl)oxy)-5,6-dihydropyridine-1(2H)-carboxylate To a cooled (−78° C.) solution of 1-Boc-4-piperidone (1.98 g, 9.94 mmol, Lancaster) in THF (25 mL) was added lithium diisopropylamide, 2.0M solution in THF/heptane/ethylbenzene (8 mL, 16.00 mmol) dropwise via syringe. After 30 min a solution of N-phenyl-bis(trifluoromethanesulfonimide) (4.02 g, 11.25 mmol) in THF (10 mL) was added via syringe and the reaction was allowed to warm to room temperature overnight. The reaction was partitioned between EtOAc/water and the aqueous layer was extracted with EtOAc (3×). The combined organic layers were evaporated onto silica gel and purified by flash chromatography (Isco (80 gram)) eluting with (EtOAc):hexanes (0:1→1:4) to give tert-butyl 4-(((trifluoromethyl)sulfonyl)oxy)-5,6-dihydropyridine-1(2H)-carboxylate as a light-yellow oil (2.14 g, 65% yield).

Step 2: Synthesis of tert-butyl 4-(cyclopropylethynyl)-5,6-dihydropyridine-1(2H)-carboxylate A RT mixture of tert-butyl 4-(((trifluoromethyl)sulfonyl)oxy)-5,6-dihydropyridine-1(2H)-carboxylate (0.750 g, 2.264 mmol), trans-dichlorobis(triphenylphosphine)palladium (II) (0.081 g, 0.115 mmol) and copper (I) iodide (0.023 g, 0.121 mmol) in toluene (10 mL) was bubbled with argon for 15 min. cyclopropylacetylene (0.600 ml, 7.08 mmol, Aldrich) and triethylamine (0.350 ml, 2.52 mmol) were added resulting in a brown mixture after 5 min. The reaction mixture was partitioned between CH$_2$Cl$_2$/water and the aqueous layer was extracted with CH$_2$Cl$_2$ (3×). The combined organic layers were washed with brine and dried over MgSO$_4$. The solution was filtered and the filtrate was evaporated onto silica gel and purified by flash chromatography (Isco (80 gram)) eluting with (EtOAc):hexanes (0:1→1:9) to give tert-butyl 4-(cyclopropylethynyl)-5,6-dihydropyridine-1(2H)-carboxylate as a yellow tar (344 mg, 61%). MS m/z=192 [M+H-tBu]$^+$. Calculated for $C_{11}H_{13}NO_2$: 191

Step 3: Synthesis of 4-(cyclopropylethynyl)-1,2,3,6-tetrahydropyridine

To a rt solution of tert-butyl 4-(cyclopropylethynyl)-5,6-dihydropyridine-1(2H)-carboxylate (0.344 g, 1.391 mmol) in 1,4-dioxane (4.0 mL) was added hydrogen chloride, 4.0 m solution in 1,4-dioxane (4.0 mL, 16.00 mmol) dropwise via syringe resulting in a dark brown solution. After 2 h the solvent was removed in vacuo and the residue was dissolved in DCM and washed with satd. NaHCO$_3$. The organic solution was dried over MgSO$_4$, filtered and concentrated to dryness to give 4-(cyclopropylethynyl)-1,2,3,6-tetrahydropyridine as a brown tar (186 mg, 91%).

Step 4: Synthesis of N-(3-((4S,6S)-2-benzamido-4-methyl-6-(trifluoromethyl)-5,6-dihydro-4H-1,3-oxazin-4-yl)-4-fluorophenyl)-4-(cyclopropylethynyl)-5,6-dihydropyridine-1(2H)-carboxamide The title compound was synthesized using steps and procedures analogous to those described in Method P, Example 119 (step 1) above, but using 4-(cyclopropylethynyl)-1,2,3,6-tetrahydropyridine. MS m/z=569 [M+H]$^+$. Calculated for $C_{25}H_{24}F_4N_4O_3$: 568

Step 5: Synthesis of N-(3-((4S,6S)-2-amino-4-methyl-6-(trifluoromethyl)-5,6-dihydro-4H-1,3-oxazin-4-yl)-4-fluorophenyl)-4-(cyclopropylethynyl)-5,6-dihydropyridine-1(2H)-carboxamide The title compound was synthesized using steps and procedures analogous to those described in Method P, Example 119 (step 2) above, but using N-(3-((4S,6S)-2-benzamido-4-methyl-6-(trifluoromethyl)-5,6-dihydro-4H-1,3-oxazin-4-yl)-4-fluorophenyl)-4-(cyclopropylethynyl)-5,6-dihydropyridine-1(2H)-carboxamide. MS m/z=465 [M+H]$^+$. Calculated for $C_{23}H_{24}F_4N_4O_2$: 464

$^1$H NMR (400 MHz, DMSO-d$_6$) δ ppm 8.59 (s, 1 H), 7.30-7.45 (m, 2 H), 7.03 (dd, J=11.93, 8.80 Hz, 1 H), 5.95 (m, J=1.37, 1.37 Hz, 1 H), 5.84 (s, 2 H), 4.07 (m, J=10.07, 6.16 Hz, 1 H), 3.97 (d, J=2.93 Hz, 2 H), 3.49 (t, J=5.67 Hz, 2 H), 2.56 (dd, J=13.30, 2.54 Hz, 1 H), 2.15 (m, J=1.76 Hz, 2 H), 1.76 (t, J=12.91 Hz, 1 H), 1.48 (s, 3 H), 1.37-1.46 (m, 1 H), 0.77-0.87 (m, 2 H), 0.57-0.66 (m, 2 H)

Example 125 (Method Q)

Synthesis of 6-((3-((4S,6S)-2-amino-4-(fluoromethyl)-6-(trifluoromethyl)-5,6-dihydro-4H-1,3-oxazin-4-yl)-4-fluorophenyl)ethynyl)nicotinonitrile

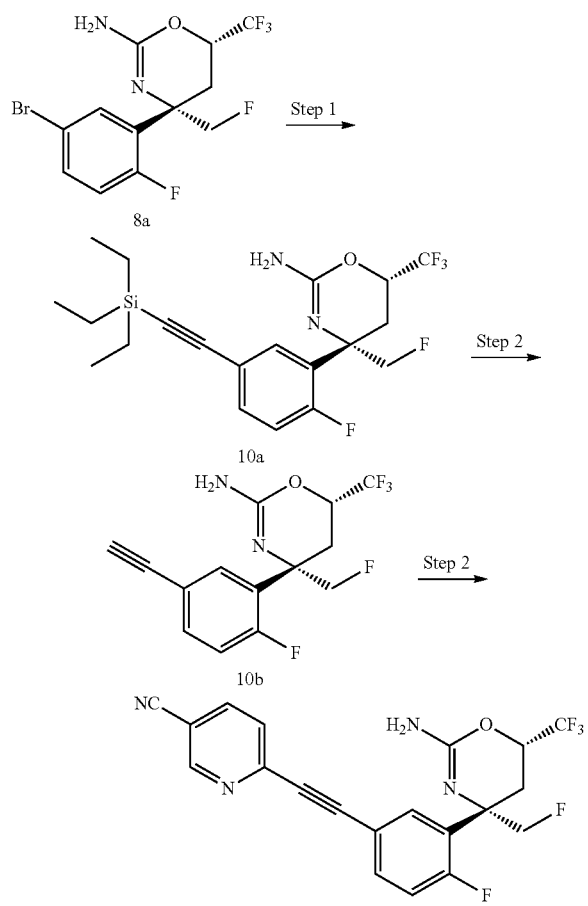

Step 1: Synthesis of (4S,6S)-4-(2-fluoro-5-((triethylsilyl)ethynyl)phenyl)-4-(fluoromethyl)-6-(trifluoromethyl)-5,6-dihydro-4H-1,3-oxazin-2-amine (10a)

A 25 mL microwave vial was charged with (4S,6S)-4-(5-bromo-2-fluorophenyl)-4-(fluoromethyl)-6-(trifluoromethyl)-5,6-dihydro-4H-1,3-oxazin-2-amine (1.465 g, 3.93 mmol), triethylamine (2.74 mL, 19.63 mmol), 10 mL of THF, triethyl(ethynyl)silane (2.176 mL, 11.78 mmol), Pd(0) tetrakis(triphenylphosphine) (0.343 g, 0.297 mmol), and copper (I) iodide (0.112 g, 0.589 mmol). The resulting mixture was then heated at 110° C. for 30 min in a Biotage microwave synthesizer (waited for 25 min to get on the instrument). The solids were filtered off and the solvent was removed under vacuum and the residue was redissolved in 60 mL of EtOAc, washed with 50 mL of saturated NH$_4$Cl solution twice, dried (Na$_2$SO$_4$) and concentrated to give an oil that was purified by Shoko silica gel instrument (pre-packed GRACE column 120 g, with EtOAc in hexane as eluent, 0-10% 17 min; 10% 8 min; 10-30% 5 min; 30% 10 min) to give the titled compound as a light yellow oil, 1.285 g, 76% yield. MS m/z=433.0 [M+H]$^+$. Calculated for C$_{20}$H$_{25}$F$_5$N$_2$OSi: 432.2.

Step 2: Synthesis of (4S,6S)-4-(5-ethynyl-2-fluorophenyl)-4-(fluoromethyl)-6-(trifluoromethyl)-5,6-dihydro-4H-1,3-oxazin-2-amine (10b)

A solution of (4S,6S)-4-(2-fluoro-5-((triethylsilyl)ethynyl)phenyl)-4-(fluoromethyl)-6-(trifluoromethyl)-5,6-dihydro-4H-1,3-oxazin-2-amine (1.285 g, 2.97 mmol from above) in 20 mL of THF was treated with tetrabutylammonium fluoride (1.0 M in THF) (3.27 mL, 3.27 mmol) at rt for 45 min. The solvent was removed under vacuum and the residue was dissolved in 2 mL of DCM and purified using the Shoko instrument with 40 g pre-packed silica gel column and EtOAc in hexanes as eluent (0-50% 20 min, 50% 10 min). Desired fractions were combined and concentrated to dryness to give the titled compound as a slightly colored oil: 0.905 g, 96% yield. MS m/z=319.0 [M+H]$^+$. Calculated for C$_{14}$H$_{11}$F$_5$N$_2$O: 318.1.

Step 3: Synthesis of 6-((3-((4S,6S)-2-amino-4-(fluoromethyl)-6-(trifluoromethyl)-5,6-dihydro-4H-1,3-oxazin-4-yl)-4-fluorophenyl)ethynyl)nicotinonitrile A mixture of (4S,6S)-4-(5-ethynyl-2-fluorophenyl)-4-(fluoromethyl)-6-(trifluoromethyl)-5,6-dihydro-4H-1,3-oxazin-2-amine (70 mg, 0.220 mmol), 6-bromonicotinonitrile (60.4 mg, 0.330 mmol), triethylamine (92 μl, 0.660 mmol), tetrakis (25.4 mg, 0.022 mmol), and copper(I) iodide (8.38 mg, 0.044 mmol) in 2 mL of THF in a microwave vial was heated at 80° C. for 20 min. The reaction mixture was filtered and purified by reverse-phase preparative HPLC using a Phenomenex Gemini column, 10 micron, C18, 110 Å, 150×30 mm, 0.1% TFA in CH$_3$CN/H$_2$O, gradient 10% to 70% over 16 min. The desired fractions were combined, neutralized with 1N NaOH, extracted with 3×25 mL of DCM, dried over Na$_2$SO$_4$ and concentrated to afford the title compound as a white solid: 49 mg, 53% yield. MS m/z=421.0 [M+H]$^+$. Calculated for C$_{20}$H$_{13}$F$_5$N$_4$O: 420.1.

$^1$H NMR (400 MHz, CHLOROFORM-d) δ 8.87 (d, J=1.37 Hz, 1H), 7.96 (dd, J=2.15, 8.22 Hz, 1H), 7.78 (dd, J=1.96, 7.63 Hz, 1H), 7.60-7.64 (m, 1H), 7.59 (td, J=1.91, 4.40 Hz, 1H), 7.12 (dd, J=8.41, 11.74 Hz, 1H), 4.50-4.62 (m, 1H), 4.41 (d, J=8.80 Hz, 1H), 4.38 (b, 1H), 4.05-4.15 (m, 1H), 2.66 (dd, J=2.54, 13.69 Hz, 1H), 2.17 (t, J=13.20 Hz, 1H)

Example 126

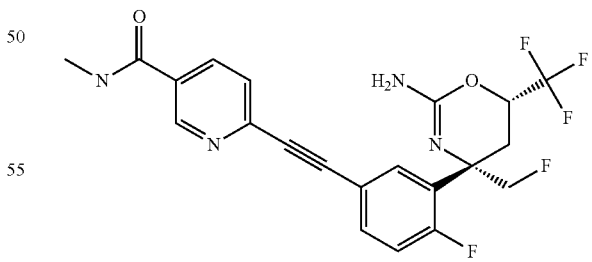

Synthesis of 6-((3-((4S,6S)-2-amino-4-(fluoromethyl)-6-(trifluoromethyl)-5,6-dihydro-4H-1,3-oxazin-4-yl)-4-fluorophenyl)ethynyl)-N-methylnicotinamide The title compound was synthesized by procedures and steps analogous to those described in Method Q for Example 125 above, but using 6-chloro-N-methylnicotinamide. Light yellow solid. MS m/z=452.9 [M+H]+. Calculated for $C_{21}H_{17}F_5N_4O_2$: 452.1

$^1$H NMR (400 MHz, CHLOROFORM-d) δ 8.93 (d, J=1.57 Hz, 1H), 8.11 (dd, J=2.25, 8.12 Hz, 1H), 7.77 (dd, J=2.15, 7.63 Hz, 1H), 7.55-7.61 (m, 2H), 7.10 (dd, J=8.41, 11.74 Hz, 1H), 6.30 (d, J=4.11 Hz, 1H), 4.58-4.75 (m, 1H), 4.39-4.57 (m, 3H), 4.02-4.15 (m, 1H), 3.06 (d, J=4.69 Hz, 3H), 2.65 (dd, J=2.54, 13.69 Hz, 1H), 2.16 (t, J=13.11 Hz, 1H)

Example 127

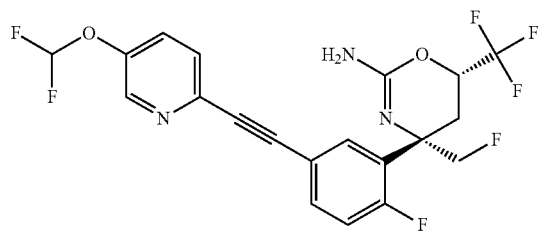 [SMILES: NC1=N[C@](CF)(c2cc(C#Cc3ccc(OC(F)F)cn3)ccc2F)C[C@@H](C(F)(F)F)O1]

Synthesis of (4S,6S)-4-(5-((5-(difluoromethoxy) pyridin-2-yl)ethynyl)-2-fluorophenyl)-4-(fluoromethyl)-6-(trifluoromethyl)-5,6-dihydro-4H-1,3-oxazin-2-amine Step 1: Synthesis of 2-bromo-5-(difluoromethoxy)pyridine A mixture of 6-bromopyridin-3-ol (1.20 g, 6.90 mmol), sodium 2-chloro-2,2-difluoroacetate (1.577 g, 10.35 mmol), and potassium carbonate (1.239 g, 8.97 mmol) in 10 mL of anhydrous DMF was heated at 85° C. for 1.5 days. The reaction mixture was diluted with 50 mL of EtOAc, washed with 50 mL of H2O, followed by washing with 50 mL of NaOH (1N) solution, the EtOAc layer was dried (Na$_2$SO$_4$) and concentrated to give a light brown oil that was purified by Shoko silica gel chromatography instrument eluting with 0-10% EtOAc in hexanes (0-10% over 25 min; GRACE column: 80 g pre-packed). Desired fraction were combined and concentrated to give the titled compound as a colorless oil: 0.85 g, 55% yield. MS m/z=223.9, 225.9 [M+H]+. Calculated for $C_6H_4BrF_2NO$: 222.9, 224.9.

Step 2: Synthesis of (4S,6S)-4-(5-((5-(difluoromethoxy)pyridin-2-yl)ethynyl)-2-fluorophenyl)-4-(fluoromethyl)-6-(trifluoromethyl)-5,6-dihydro-4H-1,3-oxazin-2-amine The title compound was synthesized by procedures and steps analogous to those described in Method Q for Example 125 above, but using 2-bromo-5-(difluoromethoxy)pyridine. The product obtained as in Method Q was further purified two times by prep-TLC using 8% MeOH in DCM as the eluent to afford the title compound as an off-white solid. MS m/z=461.9 [M+H]+. Calculated for $C_{20}H_{14}F_7N_3O_2$: 461.1

$^1$H NMR (400 MHz, CHLOROFORM-d) δ 8.48 (d, J=2.54 Hz, 1H), 7.74 (dd, J=2.25, 7.73 Hz, 1H), 7.52-7.59 (m, 2H), 7.46-7.51 (m, 1H), 7.09 (dd, J=8.51, 11.84 Hz, 1H), 6.39-6.78 (m, 1H), 4.57-4.76 (m, 1H), 4.39-4.54 (m, 1H), 4.05-4.14 (m, 1H), 2.65 (dd, J=2.74, 13.69 Hz, 1H), 2.17 (t, J=13.11 Hz, 1H)

Example 128

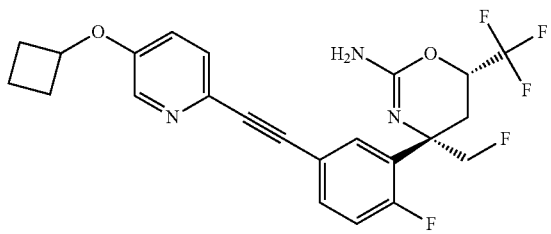 [SMILES: NC1=N[C@](CF)(c2cc(C#Cc3ccc(OC4CCC4)cn3)ccc2F)C[C@@H](C(F)(F)F)O1]

Synthesis of (4S,6S)-4-(5-((5-cyclobutoxypyridin-2-yl)ethynyl)-2-fluorophenyl)-4-(fluoromethyl)-6-(trifluoromethyl)-5,6-dihydro-4H-1,3-oxazin-2-amine Step 1: Synthesis of 2-bromo-5-cyclobutoxypyridine The mixture of 2-bromo-5-hydroxypyridine (1 g, 5.75 mmol), bromocyclobutane (0.783 mL, 8.33 mmol) and potassium carbonate (1.589 g, 11.49 mmol) in DMF (11.5 mL) was stirred at 60° C. for 5 h, then at 80° C. for 14 h. The reaction mixture was diluted with EtOAc and washed with water, saturated NaHCO$_3$, and brine. The organic layer was dried (Na$_2$SO$_4$) and concentrated. The crude product was purified by ISCO (40 g), eluting with a gradient of EtOAc/hexane 0-10% to provide to give 2-bromo-5-cyclobutoxypyridine (0.916 g, 4.02 mmol, 69.9% yield) as white solid. MS: M+ 228, 230. $C_9H_{10}BrNO$, MW=228.09

Step 2: Synthesis of (4S,6S)-4-(5-((5-cyclobutoxypyridin-2-yl)ethynyl)-2-fluorophenyl)-4-(fluoromethyl)-6-(trifluoromethyl)-5,6-dihydro-4H-1,3-oxazin-2-amine The title compound was synthesized by procedures and steps analogous to those described in Method Q for Example 125 above, but using 2-bromo-5-cyclobutoxypyridine. Light yellow solid. MS m/z=466.0 [M+H]+. Calculated for $C_{23}H_{20}F_5N_3O_2$: 465.2

$^1$H NMR (400 MHz, CHLOROFORM-d) δ 8.21 (d, J=2.74 Hz, 1H), 7.71 (dd, J=2.15, 7.63 Hz, 1H), 7.53 (ddd, J=2.15, 4.69, 8.41 Hz, 1H), 7.43 (d, J=8.61 Hz, 1H), 7.02-7.10 (m, 2H), 4.59-4.77 (m, 2H), 4.33-4.57 (m, 2H), 4.04-4.15 (m, 1H), 2.64 (dd, J=2.64, 13.60 Hz, 1H), 2.42-2.55 (m, 2H), 2.12-2.27 (m, 3H), 1.84-1.98 (m, 1H), 1.68-1.79 (m, 1H)

Example 129

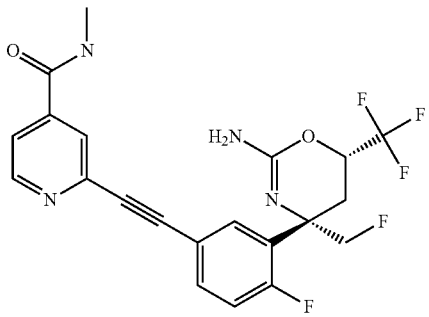 [SMILES: CNC(=O)c1ccnc(C#Cc2ccc(F)c([C@]3(CF)C[C@@H](C(F)(F)F)OC(N)=N3)c2)c1]

Synthesis of 2-((3-((4S,6S)-2-amino-4-(fluoromethyl)-6-(trifluoromethyl)-5,6-dihydro-4H-1,3-oxazin-4-yl)-4-fluorophenyl)ethynyl)-N-methylisonicotinamide The title compound was synthesized by procedures and steps analogous to those described in Method Q for Example 125 above, but using 2-bromo-N-methylisonicotinamide. White solid. MS m/z=452.9 [M+H]+. Calculated for $C_{21}H_{17}F_5N_4O_2$: 452.1

$^1$H NMR (400 MHz, CHLOROFORM-d) δ 8.70 (d, J=5.09 Hz, 1H), 7.83 (s, 1H), 7.76 (d, J=7.63 Hz, 1H), 7.55 (d, J=4.69 Hz, 2H), 7.10 (dd, J=8.51, 11.64 Hz, 1H), 6.42 (br. s., 1H), 4.59-4.77 (m, 1H), 4.32-4.57 (m, 1H), 4.11 (dd, J=5.48, 10.56 Hz, 1H), 3.05 (d, J=4.69 Hz, 3H), 2.65 (dd, J=1.96, 13.50 Hz, 1H), 2.17 (t, J=13.20 Hz, 1H)

Example 130

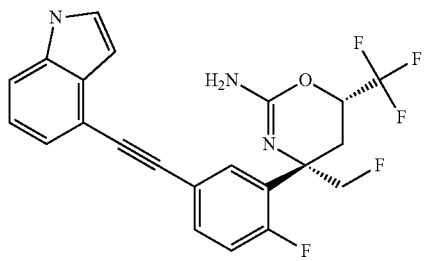 [SMILES: NC1=N[C@](CF)(c2cc(C#Cc3cccc4[nH]ccc34)ccc2F)C[C@@H](C(F)(F)F)O1]

Synthesis of (4S,6S)-4-(5-((1H-indol-4-yl)ethynyl)-2-fluorophenyl)-4-(fluoromethyl)-6-(trifluoromethyl)-5,6-dihydro-4H-1,3-oxazin-2-amine The title compound was synthesized by procedures and steps analogous to those described in Method Q for Example 125 above, but using 4-bromo-1H-indole (Aldrich). The product from HPLC purification was further purified by prepTLC using 55% EtOAc in hexanes as the eluent. The desired band was cut-out and the desired product was eluted with EtOAc to afford the title compound as a yellow solid. MS m/z=434.0 [M+H]+. Calculated for $C_{22}H_{16}F_5N_3O$: 433.1

$^1$H NMR (400 MHz, CHLOROFORM-d) δ 8.30 (br. s., 1H), 7.72 (dd, J=2.15, 7.82 Hz, 1H), 7.56 (ddd, J=2.15, 4.74, 8.36 Hz, 1H), 7.41 (d, J=8.22 Hz, 1H), 7.34 (d, J=6.85 Hz, 1H), 7.29 (t, J=2.74 Hz, 1H), 7.15-7.21 (m, 1H), 7.08 (dd, J=8.41, 11.93 Hz, 1H), 6.76-6.81 (m, 1H), 4.61-4.79 (m, 1H), 4.41-4.57 (m, 1H), 4.35 (br. s., 2H), 4.07-4.21 (m, 1H), 2.68 (dd, J=2.64, 13.60 Hz, 1H), 2.13-2.24 (m, 1H), 2.18 (t, J=13.11 Hz, 1H)

Example 131

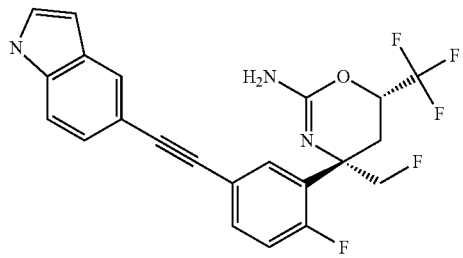 [SMILES: NC1=N[C@](CF)(c2cc(C#Cc3ccc4[nH]ccc4c3)ccc2F)C[C@@H](C(F)(F)F)O1]

Synthesis of (4S,6S)-4-(5-((1H-indol-5-yl)ethynyl)-2-fluorophenyl)-4-(fluoromethyl)-6-(trifluoromethyl)-5,6-dihydro-4H-1,3-oxazin-2-amine The title compound was synthesized by procedures and steps analogous to those described in Method Q for Example 125 above, but using 5-bromo-1H-indole (Aldrich). The product from HPLC purification was further purified by prepTLC using 55% EtOAc in hexanes as the eluent. The desired band was cut-out and the desired product was eluted with EtOAc to afford the title compound as a light yellow solid. MS m/z=434.0 [M+H]+. Calculated for $C_{22}H_{16}F_5N_3O$: 433.1

$^1$H NMR (400 MHz, CHLOROFORM-d) δ 8.28 (br. s., 1H), 7.85 (s, 1H), 7.67 (dd, J=2.25, 7.73 Hz, 1H), 7.50 (ddd, J=2.15, 4.74, 8.36 Hz, 1H), 7.33-7.40 (m, 2H), 7.25 (d, J=3.13 Hz, 1H), 7.05 (dd, J=8.41, 11.93 Hz, 1H), 6.54-6.59 (m, 1H), 4.61-4.79 (m, 1H), 4.39-4.54 (m, 1H), 4.36 (d, J=8.61 Hz, 1H), 4.08-4.18 (m, 1H), 2.66 (dd, J=2.64, 13.60 Hz, 1H), 2.18 (t, J=13.11 Hz, 1H)

Example 132

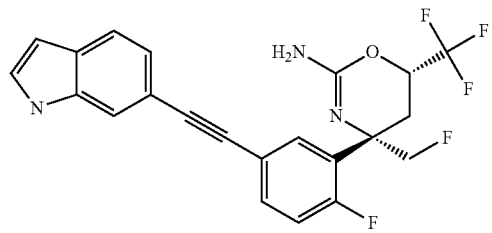 [SMILES: NC1=N[C@](CF)(c2cc(C#Cc3ccc4cc[nH]c4c3)ccc2F)C[C@@H](C(F)(F)F)O1]

Synthesis of (4S,6S)-4-(5-((1H-indol-6-yl)ethynyl)-2-fluorophenyl)-4-(fluoromethyl)-6-(trifluoromethyl)-5,6-dihydro-4H-1,3-oxazin-2-amine The title compound was synthesized by procedures and steps analogous to those described in Method Q for Example 125 above, but using 6-bromo-1H-indole (Aldrich). The product from HPLC purification was further purified by prepTLC using 55% EtOAc in hexanes as the eluent. The desired band was cut-out and the desired product was eluted with EtOAc to afford the title compound as a light yellow solid. MS m/z=434.0 [M+H]+. Calculated for $C_{22}H_{16}F_5N_3O$: 433.1

$^1$H NMR (400 MHz, CHLOROFORM-d) δ 8.23 (br. s., 1H), 7.67 (d, J=7.04 Hz, 1H), 7.56-7.64 (m, 2H), 7.50 (br. s.,

1H), 7.28 (d, J=5.67 Hz, 2H), 7.01-7.12 (m, 1H), 6.57 (br. s., 1H), 4.60-4.80 (m, 1H), 4.25-4.58 (m, 3H), 4.13 (br. s., 1H), 2.67 (d, J=12.72 Hz, 1H), 2.12-2.24 (m, 1H)

Example 133

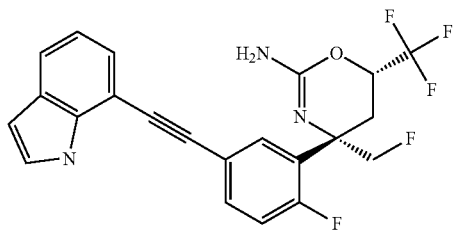 [SMILES: NC1=N[C@](CF)(c2cc(C#Cc3cccc4cc[nH]c34)ccc2F)C[C@@H](C(F)(F)F)O1]

Synthesis of (4S,6S)-4-(5-((1H-indol-7-yl)ethynyl)-2-fluorophenyl)-4-(fluoromethyl)-6-(trifluoromethyl)-5,6-dihydro-4H-1,3-oxazin-2-amine The title compound was synthesized by procedures and steps analogous to those described in Method Q for Example 125 above, but using 7-bromo-1H-indole (Alfa-Aesar). The product from HPLC purification was further purified by prepTLC using 55%

EtOAc in hexanes as the eluent. The desired band was cut-out and the desired product was eluted with EtOAc to afford the title compound as an off-white solid. MS m/z=434.0 [M+H]$^+$. Calculated for $C_{22}H_{16}F_5N_3O$: 433.1

$^1$H NMR (400 MHz, CHLOROFORM-d) δ 8.56 (br. s., 1H), 7.72 (dd, J=2.15, 7.82 Hz, 1H), 7.66 (d, J=8.02 Hz, 1H), 7.54 (ddd, J=2.35, 4.69, 8.41 Hz, 1H), 7.38 (d, J=6.85 Hz, 1H), 7.27 (d, J=2.93 Hz, 1H), 7.05-7.15 (m, 2H), 6.60 (dd, J=2.15, 3.13 Hz, 1H), 4.59-4.77 (m, 1H), 4.42-4.58 (m, 1H), 4.09-4.19 (m, 1H), 2.69 (dd, J=2.64, 13.60 Hz, 1H), 2.17 (t, J=13.20 Hz, 1H)

Example 134 (Method R)

Synthesis of N-(6-((4S,6S)-2-amino-4-(fluoromethyl)-6-(trifluoromethyl)-5,6-dihydro-4H-1,3-oxazin-4-yl)-5-fluoropyridin-2-yl)-5-cyanopicolinamide

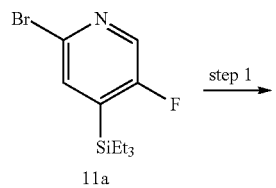
11a

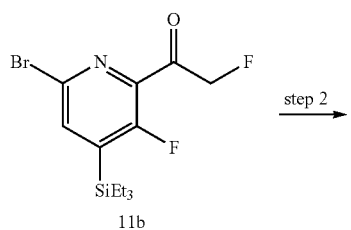
11b

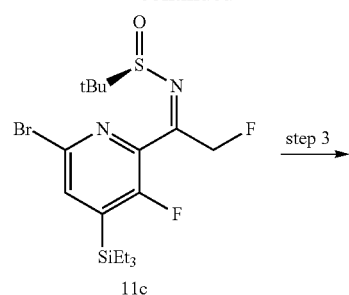
11c

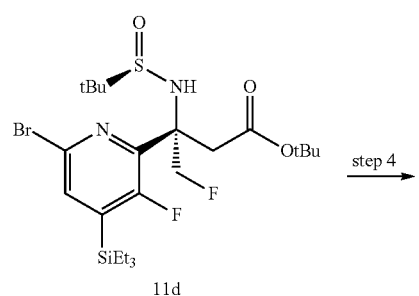
11d

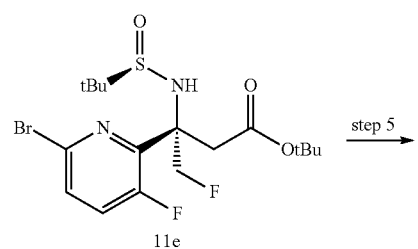
11e

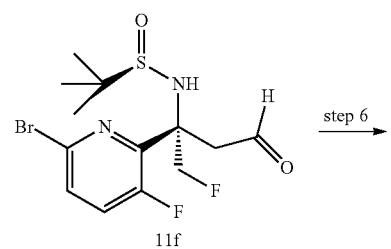
11f

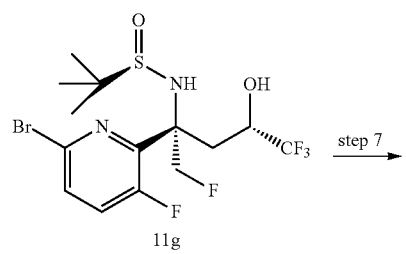
11g

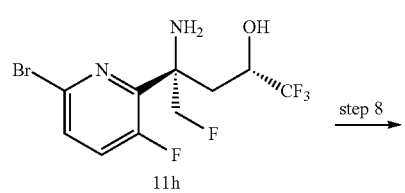
11h

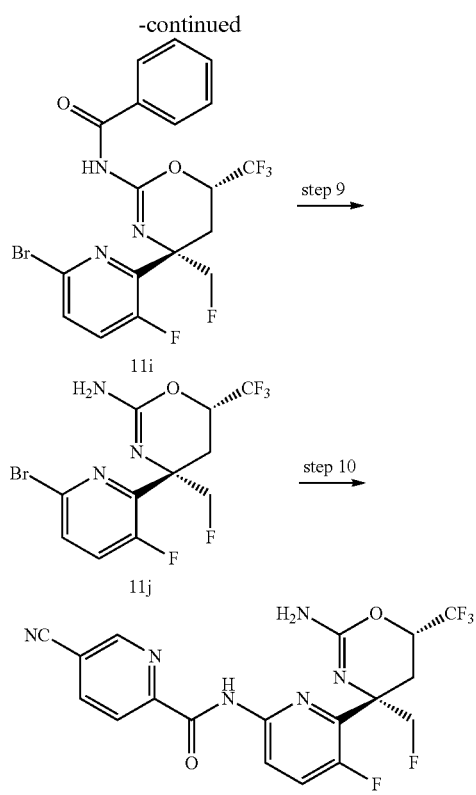

Step 1: 1-(6-bromo-3-fluoro-4-(triethylsilyl)pyridin-2-yl)-2-fluoroethanone (11b)

To a 3-neck 500-mL round bottomed flask was added THF (180 mL). The solvent was cooled to −78° C. and lithium diisopropylamide, (Aldrich; 40.3 mL, 81 mmol, 2.0 M solution in tetrahydrofuran/heptane/ethylbenzene) was added over 2 min. To the solution was added 2-bromo-5-fluoro-4-(triethylsilyl)pyridine (11a, synthesized according to procedure in WO 2012/095469 A1; 18.0 g, 62.0 mmol) in 5 mL THF over 5 min. The temperature was not allowed to go above −70° C. during the addition. After 50 min, ethyl fluoroacetate (Aldrich; 7.79 mL, 81 mmol) was added over 3 min. The temperature was not allowed to go above −60° C. during the addition. The solution was stirred at −78° C. for 10 min and then the cold bath was removed and the solution was allowed to warm to −40° C. At that point the solution was poured into a solution of 1 N HCl/10% NH4Cl (1:1, 200 mL). The solution was extracted with EtOAc (3×200 mL) and the combined extracts were washed with brine (100 mL), dried (Na$_2$SO$_4$) and concentrated onto silica. Purification by silica gel chromatography (Gradient: 0.0 to 20% EtOAc/hexane) afforded 1-(6-bromo-3-fluoro-4-(triethylsilyl)pyridin-2-yl)-2-fluoroethanone (20.35 g, 58.1 mmol, 94% yield) as a yellow oil. MS m/z=350.0 [M+H]$^+$. Calculated for C$_{13}$H$_{18}$BrF$_2$NOSi: 349.0.

Step 2: (R,E)-N-(1-(6-bromo-3-fluoro-4-(triethylsilyl)pyridin-2-yl)-2-fluoroethylidene)-2-methylpropane-2-sulfinamide (11c)

To a 1000 mL, 3-neck, round-bottomed flask equipped with an internal temperature probe was added 1-(6-bromo-3-fluoro-4-(triethylsilyl)pyridin-2-yl)-2-fluoroethanone (35 g, 100 mmol), THF (350 mL), (R)-2-methylpropane-2-sulfinamide (AK Scientific; 25.4 g, 210 mmol) and titanium (iv) ethoxide (Aldrich; 51.7 mL, 250 mmol). The solution was heated and stirred at 30° C. for 15 h and then at 40° C. for 2 h. The solution was allowed to cool to rt and then brine (200 mL) was added followed by EtOAc (200 mL). A white precipitate formed. The solution was filtered through Celite (600 mL medium fritted funnel) and the filtercake was washed with EtOAc. The filtrate was washed with brine, dried (Na$_2$SO$_4$) and concentrated to afford the crude product as a yellow semi-solid. The material was dissolved in 20% EtOAc/hexane (300 mL) and washed with water (2×100 mL) and brine (100 mL) and then dried and concentrated to afford (R,E)-N-(1-(6-bromo-3-fluoro-4-(triethylsilyl)pyridin-2-yl)-2-fluoroethylidene)-2-methylpropane-2-sulfinamide (37.8 g, 83 mmol, 84% yield) as a yellow oil which was carried on directly. MS m/z=453.0 [M+H]$^+$. Calculated for C$_{17}$H$_{27}$BrF$_2$N$_2$OSSi: 452.1.

Step 3: (S)-tert-butyl 3-(6-bromo-3-fluoro-4-(triethylsilyl)pyridin-2-yl)-3-((R)-1,1-dimethylethylsulfinamido)-4-fluorobutanoate (11d)

To a 1000 mL 3-neck round-bottomed flask equipped with an addition funnel and internal temperature probe was added (R,E)-N-(1-(6-bromo-3-fluoro-4-(triethylsilyl)pyridin-2-yl)-2-fluoroethylidene)-2-methylpropane-2-sulfinamide (43.3 g, 95 mmol) and THF (400 mL). The mixture was cooled to 0° C. and 2-tert-butoxy-2-oxoethylzinc chloride (Rieke Metals; 458 mL, 229 mmol, 0.5 M in diethyl ether) was added dropwise over 1 h keeping the internal temperature under 3° C. After the addition the ice bath was allowed to melt and warm to rt overnight. The reaction mixture was diluted with sat NaHCO$_3$ (200 mL) and water (200 mL) and extracted with EtOAc (3×200 mL). The combined extracts were washed with brine, dried (Na$_2$SO$_4$) and concentrated onto silica. Purification by silica gel chromatography (Gradient: 0.0 to 25% EtOAc/hexane, 1500 g RediSep column) afforded:
Peak 1: Minor peak assigned as (R)-tert-butyl 3-(6-bromo-3-fluoro-4-(triethylsilyl)pyridin-2-yl)-3-((R)-1,1-dimethylethylsulfinamido)-4-fluorobutanoate.
Peak 2: Major peak assigned as (S)-tert-butyl 3-(6-bromo-3-fluoro-4-(triethylsilyl)pyridin-2-yl)-3-((R)-1,1-dimethylethylsulfinamido)-4-fluorobutanoate (18.3 g, 32.1 mmol, 33.6% yield). Isolated as a yellow oil. MS m/z=569.0 [M+H]$^+$. Calculated for C$_{23}$H$_{39}$BrF$_2$N$_2$O$_3$SSi: 568.2.

Step 4: (S)-tert-butyl 3-(6-bromo-3-fluoropyridin-2-yl)-3-((R)-1,1-dimethylethylsulfinamido)-4-fluorobutanoate (11e)

To a polypropylene vial with cap was added (S)-tert-butyl 3-(6-bromo-3-fluoro-4-(triethylsilyl)pyridin-2-yl)-3-((R)-1,1-dimethylethylsulfinamido)-4-fluorobutanoate (9.8 g, 17.2 mmol), THF (50 mL) and DMF (50.0 mL). To the solution was added potassium fluoride (Aldrich; 2.75 g, 47.3 mmol) and acetic acid (2.71 mL, 47.3 mmol). The solution was stirred at rt for 17 h. The mixture was poured into sat NaHCO$_3$ (200 mL) and then diluted with water (200 mL). The solution was extracted with EtOAc (3×100 mL) and the combined extracts were washed with water (3×100 mL) and brine (100 mL) and then dried (Na$_2$SO$_4$) and concentrated onto silica. Purification by silica gel chromatography (Gradient: 0.0 to 40% EtOAc/hexane, 120 g Silicycle column) afforded (S)-tert-butyl 3-(6-bromo-3-fluoropyridin-2-yl)-3-((R)-1,1-dimethylethylsulfinamido)-4-fluorobutanoate (6.93 g, 15.22 mmol, 88% yield) as a yellow oil. MS m/z=455.0 [M+H]$^+$. Calculated for $C_{17}H_{25}BrF_2N_2O_3S$: 454.1.

Step 5: (R)-N-((S)-2-(6-bromo-3-fluoropyridin-2-yl)-1-fluoro-4-oxobutan-2-yl)-2-methylpropane-2-sulfinamide (11f)

To a 500 mL 3-neck round-bottomed flask equipped with internal temperature monitoring and a magnetic stir bar was added (5)-tert-butyl 3-(6-bromo-3-fluoropyridin-2-yl)-3-((R)-1,1-dimethylethylsulfinamido)-4-fluorobutanoate (8.90 g, 19.55 mmol) and DCM (200 mL). The solution was cooled to −78° C. and DIBAL-H (Aldrich; 48.9 mL, 48.9 mmol, 1.0 M in hexane) was added over 30 min with the solution running down the side of the flask to precool it. The solution did not go above −74° C. during the addition. After 75 min at −78° C., an additional 5 mL of the DIBALH solution was added. After 10 min the solution was quenched with MeOH (4 mL) dropwise with the MeOH running down the inside of the flask. The solution was allowed to warm to rt and 4 mL of sat NaHCO$_3$ was added. This was stirred for 10 min and then solid Na$_2$SO$_4$ was added (~20 g). This was stirred for 10 min and then filtered through Celite and the filtercake was washed with DCM. The filtrate was concentrated onto silica. Purification by silica gel chromatography (Gradient: 0.0 to 60% EtOAc/hexane) afforded (R)-N-((S)-2-(6-bromo-3-fluoropyridin-2-yl)-1-fluoro-4-oxobutan-2-yl)-2-methylpropane-2-sulfinamide (5.08 g, 13.25 mmol, 67.8% yield) as a pale yellow oil. MS m/z=383.0 [M+H]$^+$. Calculated for $C_{13}H_{17}BrF_2N_2O_2S$: 382.0.

Step 6: (R)-N-((2S,4S)-2-(6-bromo-3-fluoropyridin-2-yl)-1,5,5,5-tetrafluoro-4-hydroxypentan-2-yl)-2-methylpropane-2-sulfinamide (11g)

To a 250 mL round-bottomed flask was added (R)-N-((S)-2-(6-bromo-3-fluoropyridin-2-yl)-1-fluoro-4-oxobutan-2-yl)-2-methylpropane-2-sulfinamide (5.9 g, 15.39 mmol) and THF (130 mL). The mixture was cooled to −78° C. and (trifluoromethyl)trimethylsilane (Apollo Scientific Ltd.; 24.46 mL, 154 mmol) was added. After stirring for 10 min, tetrabutylammonium fluoride (Aldrich; 27.7 mL, 27.7 mmol, 1.0 M in THF) was added over 10 min. The solution was stirred at −78° C. for 2 h. To the solution was added 1 N HCl (10 mL) and the solution was allowed to warm to rt. The solution was carefully diluted with water (50 mL) and extracted with EtOAc (2×100 mL). The combined extracts were washed with water (100 mL) and brine (50 mL) and then dried (Na$_2$SO$_4$) and concentrated onto silica. Purification by silica gel chromatography (Gradient: 0.0 to 60% EtOAc/hexane, 120 g Silicycle HP) afforded:
Peak 1: (R)-N-((2S,4S)-2-(6-bromo-3-fluoropyridin-2-yl)-1,5,5,5-tetrafluoro-4-hydroxypentan-2-yl)-2-methylpropane-2-sulfinamide (1.53 g, 3.38 mmol, 21.93% yield). MS m/z=453.0 [M+H]$^+$. Calculated for $C_{14}H_{18}BrF_5N_2O_2S$: 452.0.
Peak 2: (R)-N-((2S,4R)-2-(6-bromo-3-fluoropyridin-2-yl)-1,5,5,5-tetrafluoro-4-hydroxypentan-2-yl)-2-methylpropane-2-sulfinamide (2.10 g, 4.63 mmol, 30.1% yield).

Step 7: (2S,4S)-4-amino-4-(6-bromo-3-fluoropyridin-2-yl)-1,1,1,5-tetrafluoropentan-2-ol (11h)

To a 150 mL round-bottomed flask was added (R)-N-((2S,4S)-2-(6-bromo-3-fluoropyridin-2-yl)-1,5,5,5-tetrafluoro-4-hydroxypentan-2-yl)-2-methylpropane-2-sulfinamide (2.01 g, 4.43 mmol), 1,4-dioxane (30 mL) and finally HCl in 1,4-dioxane (Aldrich; 4.43 mL, 17.7 mmol, 4 M). The solution was stirred at rt for 45 min and then poured into sat NaHCO$_3$ (100 mL) and extracted with EtOAc (2×100 mL). The combined extracts were dried (Na$_2$SO$_4$) and concentrated to afford (2S,4S)-4-amino-4-(6-bromo-3-fluoropyridin-2-yl)-1,1,1,5-tetrafluoropentan-2-ol which was carried on directly. MS m/z=351.0 [M+H]$^+$. Calculated for $C_{10}H_{10}BrF_5N_2O$: 350.0.

Step 8: N-((4S,6S)-4-(6-bromo-3-fluoropyridin-2-yl)-4-(fluoromethyl)-6-(trifluoromethyl)-5,6-dihydro-4H-1,3-oxazin-2-yl)benzamide (11i)

To a 150 mL round-bottomed flask was added (2S,4S)-4-amino-4-(6-bromo-3-fluoropyridin-2-yl)-1,1,1,5-tetrafluoropentan-2-ol (1.54 g, 4.41 mmol), MeCN (30 mL) and benzoyl isothiocyanate (Aldrich; 0.712 mL, 5.29 mmol). The reaction mixture was stirred at rt for 45 min and then 1-(3-dimethylaminopropyl)-3-ethylcarbodiimide HCl (Oakwook Products, Inc.; 1.015 g, 5.29 mmol) and N,N-diisopropylethylamine (Aldrich; 1.54 mL, 8.82 mmol) were added. The solution was stirred at rt for 2 h and then treated with sat NaHCO$_3$ and extracted with EtOAc (2×100 mL). The combined extracts were washed with water (1×100 mL) and brine and then dried (Na$_2$SO$_4$) and concentrated onto silica. Purification by silica gel chromatography (Gradient: 0.0 to 20% EtOAc/hexane) afforded N-((4S,6S)-4-(6-bromo-3-fluoropyridin-2-yl)-4-(fluoromethyl)-6-(trifluoromethyl)-5,6-dihydro-4H-1,3-oxazin-2-yl)benzamide (1.74 g, 3.64 mmol, 82% yield) as an off-white foam. MS m/z=480.0 [M+H]$^+$. Calculated for $C_{18}H_{13}BrF_5N_3O_2$: 479.0.

Step 9: (4S,6S)-4-(6-bromo-3-fluoropyridin-2-yl)-4-(fluoromethyl)-6-(trifluoromethyl)-5,6-dihydro-4H-1,3-oxazin-2-amine (11j)

To a 20 mL resealable vial was added N-((4S,6S)-4-(6-bromo-3-fluoropyridin-2-yl)-4-(fluoromethyl)-6-(trifluoromethyl)-5,6-dihydro-4H-1,3-oxazin-2-yl)benzamide (0.500 g, 1.046 mmol), MeOH (10 mL) and finally 1,8-diazabicyclo-[5.4.0]undec-7-ene (Aldrich; 0.312 mL, 2.091 mmol). The vial was sealed and stirred at 75° C. for 2 h. The reaction mixture was poured into sat NaHCO$_3$ and extracted with EtOAc. The combined extracts were washed with water and then dried (Na$_2$SO$_4$) and concentrated onto silica. Purification by silica gel chromatography (Gradient: 0.0 to 9.0% MeOH/CH$_2$Cl$_2$) afforded (4S,6S)-4-(6-bromo-3-fluoropyridin-2-yl)-4-(fluoromethyl)-6-(trifluoromethyl)-5,6-dihydro-4H-1,3-oxazin-2-amine. The material still contained some impurities. MS m/z=375.8 [M+H]$^+$. Calculated for $C_{11}H_9BrF_5N_3O$: 375.0.

Step 10: N-(6-((4S,6S)-2-amino-4-(fluoromethyl)-6-(trifluoromethyl)-5,6-dihydro-4H-1,3-oxazin-4-yl)-5-fluoropyridin-2-yl)-5-cyanopicolinamide To a resealable vial was added (4S,6S)-4-(6-bromo-3-fluoropyridin-2-yl)-4-(fluoromethyl)-6-(trifluoromethyl)-5,6-dihydro-4H-1,3-oxazin-2-amine (0.200 g, 0.535 mmol), 5-cyanopicolinamide (0.118 g, 0.802 mmol), 1,4-dioxane (4 mL), and cesium carbonate (Strem Chemicals; 0.435 g, 1.337 mmol). The reaction vessel was carefully evacuated and backfilled with N₂. This was repeated twice. To the solution was added tris(dibenzylideneacetone)dipalladium (0) (Aldrich; 0.049 g, 0.053 mmol) and 4,5-bis(diphenylphosphino)-9,9-dimethylxanthene (Aldrich; 0.062 g, 0.107 mmol). The reaction vessel was carefully evacuated and backfilled with N₂. This was repeated twice. The solution was stirred and heated at 100° C. for 3 h. The reaction mixture was allowed to cool to rt and poured into sat NaHCO₃ (50 mL) and extracted with EtOAc (2×100 mL). The combined extracts were washed with water (100 mL) and brine (50 mL) and then dried (Na₂SO₄) and concentrated onto silica. Purification by silica gel chromatography (Gradient; 0.0 to 10% MeOH/CH₂Cl₂, Silicycle HP column, 40 g) followed by further purification by reverse phase preparative-HPLC afforded N-(6-((4S,6S)-2-amino-4-(fluoromethyl)-6-(trifluoromethyl)-5,6-dihydro-4H-1,3-oxazin-4-yl)-5-fluoropyridin-2-yl)-5-cyanopicolinamide (0.0675 g, 0.153 mmol, 28.7% yield) as a white solid. MS m/z=440.9 [M+H]⁺. Calculated for C₁₈H₁₃F₅N₆O₂: 440.1.

¹H NMR (400 MHz, DMSO-d₆) δ ppm 1.76 (t, J=12.23 Hz, 1 H), 2.98 (d, J=11.74 Hz, 1 H), 4.49 (dd, J=47.20, 8.50 Hz, 1 H), 4.78 (dd, J=47.55, 8.45 Hz, 1 H), 5.19 (br. s., 1 H), 5.98 (s, 2 H), 7.82 (t, J=9.78 Hz, 1 H), 8.11 (d, J=8.61 Hz, 1 H), 8.33 (d, J=8.02 Hz, 1 H), 8.62 (d, J=8.41 Hz, 1 H), 9.25 (s, 1 H), 10.73 (s, 1 H)

Example 135

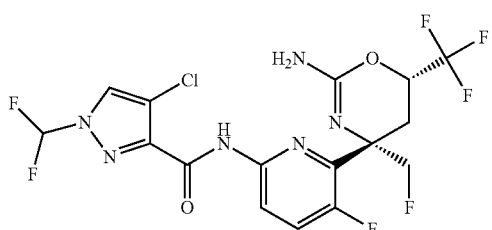

Synthesis of N-(6-((4S,6S)-2-amino-4-(fluoromethyl)-6-(trifluoromethyl)-5,6-dihydro-4H-1,3-oxazin-4-yl)-5-fluoropyridin-2-yl)-4-chloro-1-(difluoromethyl)-1H-pyrazole-3-carboxamide The title compound was synthesized by procedures and steps analogous to those described in Method R, Example 134 above, except N-((4S,6S)-4-(6-bromo-3-fluoropyridin-2-yl)-4-(fluoromethyl)-6-(trifluoromethyl)-5,6-dihydro-4H-1,3-oxazin-2-yl)benzamide (11i) underwent the conditions described in step 10 with 4-chloro-1-(difluoromethyl)-1H-pyrazole-3-carboxamide (intermediate 32) followed by the conditions described in step 9. MS m/z=488.9 [M+H]⁺. Calculated for C₁₆H₁₂ClF₇N₆O₂: 488.1.

¹H NMR (400 MHz, CHLOROFORM-d) δ ppm 1.92 (t, J=12.72 Hz, 1 H), 3.10 (dd, J=13.20, 2.84 Hz, 1 H), 4.21 (br. s., 2 H), 4.50 (dd, J=47.50, 8.70 Hz, 1 H), 4.58-4.68 (m, 1 H), 4.82 (dd, J=47.00, 8.70 Hz, 1 H), 7.19 (t, J=59.85 Hz, 1 H), 7.48-7.57 (m, 1 H), 7.96 (s, 1 H), 8.34 (dd, J=8.90, 3.03 Hz, 1 H), 9.06 (s, 1 H).

Example 136

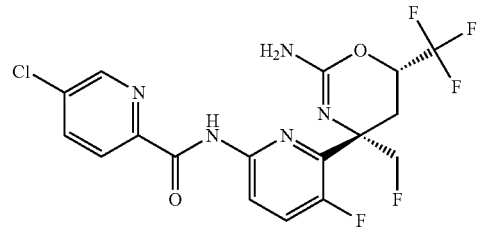 [SMILES: NC1=N[C@](CF)(c2nc(NC(=O)c3ccc(Cl)cn3)ccc2F)C[C@@H](C(F)(F)F)O1]

Synthesis of N-(6-((4S,6S)-2-amino-4-(fluoromethyl)-6-(trifluoromethyl)-5,6-dihydro-4H-1,3-oxazin-4-yl)-5-fluoropyridin-2-yl)-5-chloropicolinamide The title compound was synthesized by procedures and steps analogous to those described in Method R (Example 134) above, but using 5-chloropicolinamide (intermediate 18) in step 10. MS m/z=449.9 [M+H]⁺; Calculated for C₁₇H₁₃ClF₅N₅O₂: 449.07

¹H NMR (400 MHz, CHLOROFORM-d) ppm 3.13 (dd, J=3.03, 13.20 Hz, 1H), 3.37-3.44 (m, 1H), 4.21 (br. s., 2H), 4.51 (dd, J=8.80, 46.36 Hz, 1H), 4.67 (dqd, J=3.03, 5.83, 11.94 Hz, 1H), 4.82 (dd, J=8.80, 46.17 Hz, 1H), 7.52 (dd, J=9.00, 10.37 Hz, 1H), 7.90 (dd, J=2.35, 8.41 Hz, 1H), 8.25 (dd, J=0.39, 8.41 Hz, 1H), 8.38 (dd, J=3.03, 8.90 Hz, 1 H), 8.63 (d, J=1.96 Hz, 1 H), 10.24 (br. s., 1 H).

Example 137

Synthesis of N-(6-((4R,6S)-2-amino-4-(difluoromethyl)-6-(trifluoromethyl)-5,6-dihydro-4H-1,3-oxazin-4-yl)-5-fluoropyridin-2-yl)-5-chloropicolinamide

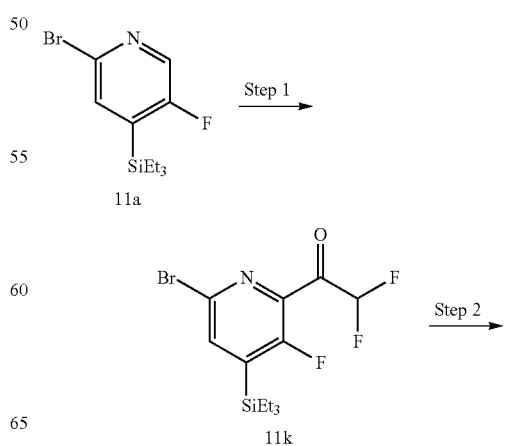

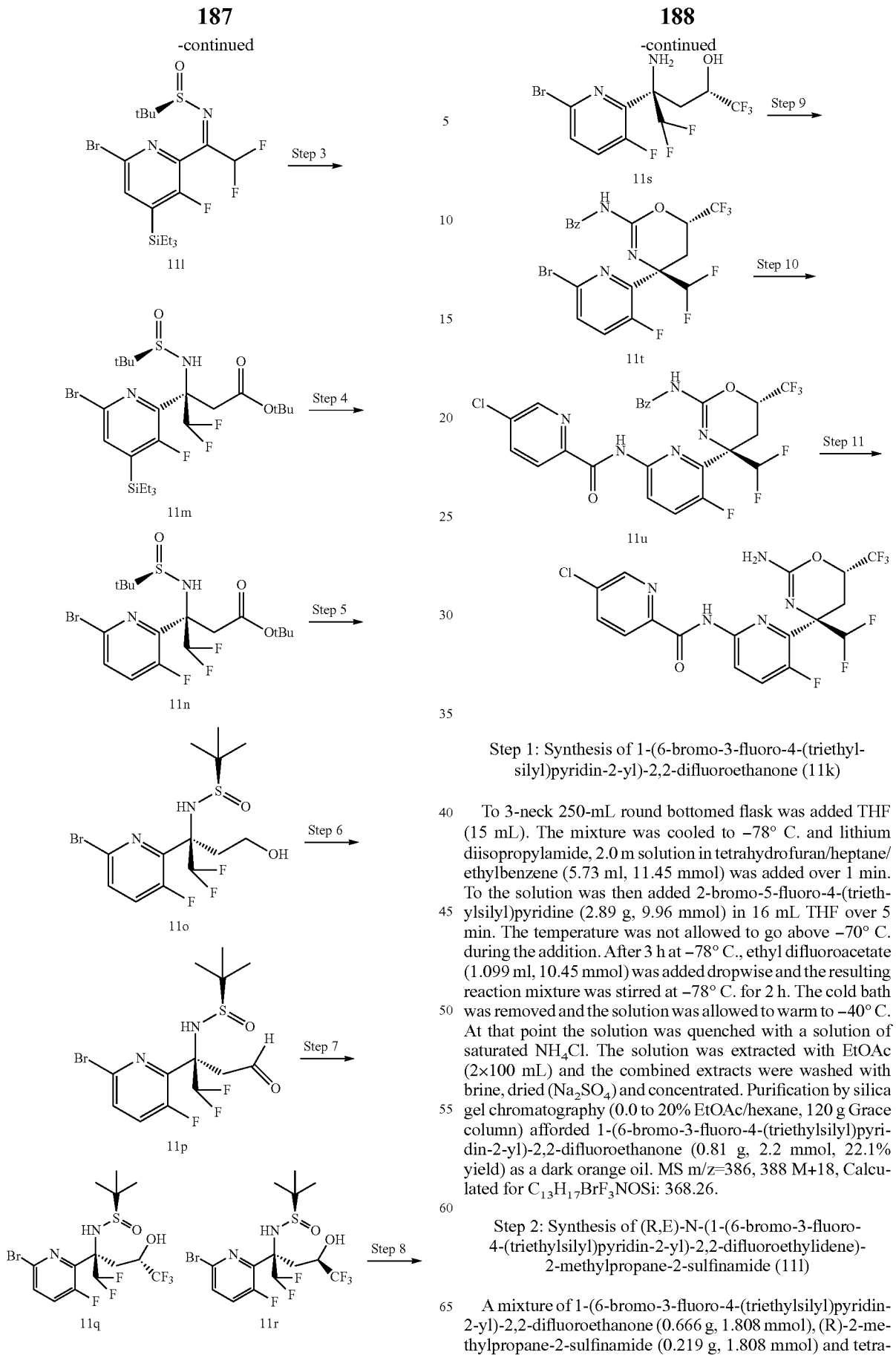

Step 1: Synthesis of 1-(6-bromo-3-fluoro-4-(triethylsilyl)pyridin-2-yl)-2,2-difluoroethanone (11k)

To 3-neck 250-mL round bottomed flask was added THF (15 mL). The mixture was cooled to −78° C. and lithium diisopropylamide, 2.0 m solution in tetrahydrofuran/heptane/ethylbenzene (5.73 ml, 11.45 mmol) was added over 1 min. To the solution was then added 2-bromo-5-fluoro-4-(triethylsilyl)pyridine (2.89 g, 9.96 mmol) in 16 mL THF over 5 min. The temperature was not allowed to go above −70° C. during the addition. After 3 h at −78° C., ethyl difluoroacetate (1.099 ml, 10.45 mmol) was added dropwise and the resulting reaction mixture was stirred at −78° C. for 2 h. The cold bath was removed and the solution was allowed to warm to −40° C. At that point the solution was quenched with a solution of saturated $NH_4Cl$. The solution was extracted with EtOAc (2×100 mL) and the combined extracts were washed with brine, dried ($Na_2SO_4$) and concentrated. Purification by silica gel chromatography (0.0 to 20% EtOAc/hexane, 120 g Grace column) afforded 1-(6-bromo-3-fluoro-4-(triethylsilyl)pyridin-2-yl)-2,2-difluoroethanone (0.81 g, 2.2 mmol, 22.1% yield) as a dark orange oil. MS m/z=386, 388 M+18, Calculated for $C_{13}H_{17}BrF_3NOSi$: 368.26.

Step 2: Synthesis of (R,E)-N-(1-(6-bromo-3-fluoro-4-(triethylsilyl)pyridin-2-yl)-2,2-difluoroethylidene)-2-methylpropane-2-sulfinamide (11l)

A mixture of 1-(6-bromo-3-fluoro-4-(triethylsilyl)pyridin-2-yl)-2,2-difluoroethanone (0.666 g, 1.808 mmol), (R)-2-methylpropane-2-sulfinamide (0.219 g, 1.808 mmol) and tetraethoxytitanium (0.758 ml, 3.62 mmol) in THF (4.52 ml) in a sealed microwave vial was stirred at 80° C. for 3 h. After cooling to RT, the reaction mixture was poured into an ice-cold saturated NaCl solution, stirred for 10 min, and the precipitate was filtered through a pad of celite and washed with EtOAc. The aqueous layer was back extracted with EtOAc (2×) and the combined EtOAc layers were dried ($MgSO_4$) and concentrated. The crude material was purified by chromatography through a Redi-Sep pre-packed silica gel column (40 g), eluting with a gradient of 0% to 30% EtOAc in hexane, to provide (R,E)-N-(1-(6-bromo-3-fluoro-4-(triethylsilyl)pyridin-2-yl)-2,2-difluoroethylidene)-2-methylpropane-2-sulfinamide (0.481 g, 1.020 mmol, 56.4% yield) as dark-brown oil.

Step 3: (R)-tert-butyl 3-(6-bromo-3-fluoro-4-(triethylsilyl)pyridin-2-yl)-3-((R)-1,1-dimethylethylsulfinamido)-4,4-difluorobutanoate (11m)

To a 25 mL round-bottomed flask was added (R,E)-N-(1-(6-bromo-3-fluoro-4-(triethylsilyl)pyridin-2-yl)-2,2-difluoroethylidene)-2-methylpropane-2-sulfinamide (0.48 g, 1.018 mmol) and THF (4 mL). The mixture was cooled to 0° C. and 2-tert-butoxy-2-oxoethylzinc chloride 0.5 m in diethyl ether (5.09 mL, 2.55 mmol) was added dropwise over 10 min. After the addition the reaction mixture was stirred at 0° C. to rt for 4 h. The reaction mixture was diluted with sat $NaHCO_3$ (50 mL) and extracted with EtOAc (3×50 mL). The combined extracts were washed with brine, dried ($Na_2SO_4$) and concentrated. The crude material was purified by chromatography through a Redi-Sep pre-packed silica gel column (40 g), eluting with a gradient of 0% to 20% EtOAc in hexane, to provide a 4:1 mixture of (R)-tert-butyl 3-(6-bromo-3-fluoro-4-(triethylsilyl)pyridin-2-yl)-3-((R)-1,1-dimethylethylsulfinamido)-4,4-difluorobutanoate and (S)-tert-butyl 3-(6-bromo-3-fluoro-4-(triethylsilyl)pyridin-2-yl)-3-((R)-1,1-dimethylethylsulfinamido)-4,4-difluorobutanoate (0.428 g, 0.728 mmol, 71.5% yield) as light-yellow oil. MS m/z=587, 589 M+, Calculated for $C_{23}H_{38}BrF_3N_2O_3SSi$: 587.61. Used directly in the following step.

Step 4: (R)-tert-butyl 3-(6-bromo-3-fluoropyridin-2-yl)-3-((R)-1,1-dimethylethylsulfinamido)-4,4-difluorobutanoate (11n)

To a polypropylene flask and cap was added a mixture of (R)-tert-butyl 3-(6-bromo-3-fluoro-4-(triethylsilyl)pyridin-2-yl)-3-((R)-1,1-dimethylethylsulfinamido)-4,4-difluorobutanoate and (S)-tert-butyl 3-(6-bromo-3-fluoro-4-(triethylsilyl)pyridin-2-yl)-3-((R)-1,1-dimethylethylsulfinamido)-4,4-difluorobutanoate (0.411 g, 0.699 mmol), THF (3 mL) and DMF (3.0 mL). To the solution was added potassium fluoride (0.112 g, 1.923 mmol) and acetic acid (0.110 mL, 1.923 mmol). The reaction mixture was stirred at rt for 18 h. The solution was poured into sat $NaHCO_3$ (25 mL) and diluted with water (25 mL). The solution was extracted with EtOAc (2×50 mL). The combined extracts were washed with water and brine and then dried ($Na_2SO_4$) and concentrated to give a 3:1 mixture of (R)-tert-butyl 3-(6-bromo-3-fluoropyridin-2-yl)-3-((R)-1,1-dimethylethylsulfinamido)-4,4-difluorobutanoate and (S)-tert-butyl 3-(6-bromo-3-fluoropyridin-2-yl)-3-((R)-1,1-dimethylethylsulfinamido)-4,4-difluorobutanoate (0.324 g, 0.684 mmol, 98% yield) as a colorless oil. This material was used directly in the following step. MS m/z=473, 475 M+, Calculated for $C_{17}H_{24}BrF_3N_2O_3S$: 473.35.

Step 5: (R)-N-((R)-2-(6-bromo-3-fluoropyridin-2-yl)-1,1-difluoro-4-hydroxybutan-2-yl)-2-methylpropane-2-sulfinamide (11o)

To a 100-mL round-bottomed flask were added a mixture of (R)-tert-butyl 3-(6-bromo-3-fluoropyridin-2-yl)-3-((R)-1,1-dimethylethylsulfinamido)-4,4-difluorobutanoate and (S)-tert-butyl 3-(6-bromo-3-fluoropyridin-2-yl)-3-((R)-1,1-dimethylethylsulfinamido)-4,4-difluorobutanoate (0.33 g, 0.697 mmol) and DCM (6.97 ml). The solution was cooled to −10° C. and lithium aluminum hydride, 1.0m solution in THF (1.394 ml, 1.394 mmol) was added dropwise over 10 min. The reaction mixture was stirred −10° C. for 4 h. Sodium sulfate decahydrate (1.8 g, 5.6 mmol) was added and the mixture was stirred for 10 min. The solid was filtered and washed with EtOAc. The filtrate was concentrated in vacuo. Purification by silica gel chromatography (0-70% EtOAc/hexane) afforded a 3:1 mixture of (R)-N-((R)-2-(6-bromo-3-fluoropyridin-2-yl)-1,1-difluoro-4-hydroxybutan-2-yl)-2-methylpropane-2-sulfinamide and (R)-N-((S)-2-(6-bromo-3-fluoropyridin-2-yl)-1,1-difluoro-4-hydroxybutan-2-yl)-2-methylpropane-2-sulfinamide (0.176 g, 0.436 mmol, 62.6% yield) as a colorless oil. MS m/z=403, 405 M+ Calculated for $C_{13}H_{18}BrF_3N_2O_2S$: 403.26. Used directly in the following step.

Step 6: (R)-N-((R)-2-(6-bromo-3-fluoropyridin-2-yl)-1,1-difluoro-4-oxobutan-2-yl)-2-methylpropane-2-sulfinamide (11p)

To a solution of the mixture of (R)-N-((R)-2-(6-bromo-3-fluoropyridin-2-yl)-1,1-difluoro-4-hydroxybutan-2-yl)-2-methylpropane-2-sulfinamide and (R)-N-((S)-2-(6-bromo-3-fluoropyridin-2-yl)-1,1-difluoro-4-hydroxybutan-2-yl)-2-methylpropane-2-sulfinamide (0.17 g, 0.422 mmol) in DCM (2.1 ml) was added Dess-Martin periodinane (0.215 g, 0.506 mmol). The reaction mixture was stirred at RT. After 1 h, the mixture was diluted with water and extracted with DCM three times. The organic layer was washed with brine, dried over $Na_2SO_4$, and concentrated in vacuo. The crude was purified by silica gel chromatography: 40 g Grace column, 0-50% EtOAc-hexane in 20 min to give a 3:1 mixture of (R)-N-((R)-2-(6-bromo-3-fluoropyridin-2-yl)-1,1-difluoro-4-oxobutan-2-yl)-2-methylpropane-2-sulfinamide and (R)-N-((S)-2-(6-bromo-3-fluoropyridin-2-yl)-1,1-difluoro-4-oxobutan-2-yl)-2-methylpropane-2-sulfinamide (0.12 g, 0.299 mmol, 70.9% yield) was obtained as a colorless oil. MS m/z=401, 403 M+, Calculated for $C_{13}H_{16}BrF_3N_2O_2S$: 401.24. Used directly in the following step.

Step 7: (R)-N-((2S,4R)-2-(6-bromo-3-fluoropyridin-2-yl)-1,1,5,5,5-pentafluoro-4-hydroxypentan-2-yl)-2-methylpropane-2-sulfinamide (11q)

To a solution of (R)-N-((R)-2-(6-bromo-3-fluoropyridin-2-yl)-1,1-difluoro-4-oxobutan-2-yl)-2-methylpropane-2-sulfinamide (0.12 g, 0.299 mmol) in THF (3 ml) at −78° C. was added (trifluoromethyl)trimethylsilane (0.475 ml, 2.99 mmol) dropwise. After 25 min, tetrabutylammonium fluoride, 1.0m in tetrahydrofuran (0.299 ml, 0.299 mmol) was added. The reaction mixture was stirred at −78° C. for 6 h (warmed up to −20° C.). Aqueous 1N HCl (0.8 mL) was added at −78° C. and the reaction was warmed up to rt, diluted with water, extracted with EtOAc (2×), washed with water, dried over $Na_2SO_4$, filtered and concentrated. The crude material was purified by chromatography through a Redi-Sep® pre-packed silica gel column (40 g), eluting with a gradient of 0% to 30% EtOAc in hexane in 20 min to give (R)-N-((2S,4R)-2-(6-bromo-3-fluoropyridin-2-yl)-1,1,5,5,5-pentafluoro-4-hydroxypentan-2-yl)-2-methylpropane-2-sulfinamide (30 mg, 0.064 mmol, 21.29% yield) as white solid. MS m/z=471, 473 M$^+$, Calculated for $C_{14}H_{17}BrF_6N_2O_2S$: 471.26.

Step 8: (2S,4R)-4-amino-4-(6-bromo-3-fluoropyridin-2-yl)-1,1,1,5,5,5-pentafluoropentan-2-ol (11s)

To a suspension of (R)-N-((2S,4R)-2-(6-bromo-3-fluoropyridin-2-yl)-1,1,5,5,5-pentafluoro-4-hydroxypentan-2-yl)-2-methylpropane-2-sulfinamide (28 mg, 0.059 mmol) in 1,4-dioxane (396 µl) was added hydrochloric acid, 4 M solution in dioxane (59.4 µl, 0.238 mmol) dropwise. The reaction mixture was stirred at RT for 1 h. The mixture was diluted with saturated $Na_2CO_3$ and extracted with EtOAc. The organic layer was washed with brine, and dried over sodium sulfate and concentrated in vacuo. The crude product was obtained as yellow oil. MS m/z=367, 369 M$^+$, Calculated for $C_{10}H_9BrF_6N_2O$: 367.09.

Step 9: N-((4R,6S)-4-(6-bromo-3-fluoropyridin-2-yl)-4-(difluoromethyl)-6-(trifluoromethyl)-5,6-dihydro-4H-1,3-oxazin-2-yl)benzamide (11t)

To a 50-mL round-bottomed flask was added (2S,4R)-4-amino-4-(6-bromo-3-fluoropyridin-2-yl)-1,1,1,5,5,5-pentafluoropentan-2-ol (22 mg, 0.060 mmol) and benzoyl isothiocyanate (8.87 µl, 0.066 mmol) in THF (599 µl). The reaction mixture was stirred at RT for 16 h. To the reaction mixture was added triethylamine (10.00 µl, 0.072 mmol), and 1-(3-dimethylaminopropyl)-3-ethylcarbodiimide hydrochloride (12.64 mg, 0.066 mmol). The mixture was heated at 75° C. for 1.5 h. The reaction mixture was allowed to cool to RT and was diluted with water and extracted with EtOAc. The organic extract was washed with satd NaCl (10 mL) and dried over $MgSO_4$. The solution was filtered and concentrated in vacuo. The crude material was purified by chromatography through a Redi-Sep pre-packed silica gel column (40 g), eluting with a gradient of 0% to 30% EtOAc in hexane, to provide N-((4R,6S)-4-(6-bromo-3-fluoropyridin-2-yl)-4-(difluoromethyl)-6-(trifluoromethyl)-5,6-dihydro-4H-1,3-oxazin-2-yl)benzamide (22 mg, 0.044 mmol, 74.0% yield) as off-white solid. MS m/z=496, 498 M$^+$, Calculated for $C_{18}H_{12}BrF_6N_3O_2$: 496.20.

Step 10: N-(6-((4R,6S)-2-benzamido-4-(difluoromethyl)-6-(trifluoromethyl)-5,6-dihydro-4H-1,3-oxazin-4-yl)-5-fluoropyridin-2-yl)-5-chloropicolinamide (11u)

A round-bottomed flask was charged with $Pd_2(dba)_3$ (2.91 mg, 3.17 µmol), (9,9-dimethyl-9H-xanthene-4,5-diyl)bis(diphenylphosphine) (7.35 mg, 0.013 mmol), N-((4R,6S)-4-(6-bromo-3-fluoropyridin-2-yl)-4-(difluoromethyl)-6-(trifluoromethyl)-5,6-dihydro-4H-1,3-oxazin-2-yl)benzamide (21 mg, 0.042 mmol), 5-chloropicolinamide (9.61 mg, 0.061 mmol), and cesium carbonate (34.5 mg, 0.106 mmol). The flask was evacuated under vacuum and then flushed with nitrogen. Dioxane (0.5 mL) was then added and the reaction was stirred in a 90° C. oil bath for 10 h. The reaction mixture was cooled to RT, filtered through celite and washed with EtOAc. The filtrate was concentrated and the residue was purified by chromatography through a Redi-Sep pre-packed silica gel column (12 g), eluting with a gradient of 0% to 30% EtOAc in hexane, to provide N-(6-((4R,6S)-2-benzamido-4-(difluoromethyl)-6-(trifluoromethyl)-5,6-dihydro-4H-1,3-oxazin-4-yl)-5-fluoropyridin-2-yl)-5-chloropicolinamide (17 mg, 0.030 mmol, 70.2% yield) as white solid. MS m/z=572, 574 M$^+$, Calculated for $C_{24}H_{16}ClF_6N_5O_3$: 571.86.

Step 11: N-(6-((4R,6S)-2-amino-4-(difluoromethyl)-6-(trifluoromethyl)-5,6-dihydro-4H-1,3-oxazin-4-yl)-5-fluoropyridin-2-yl)-5-chloropicolinamide To a solution of N-(6-((4R,6S)-2-benzamido-4-(difluoromethyl)-6-(trifluoromethyl)-5,6-dihydro-4H-1,3-oxazin-4-yl)-5-fluoropyridin-2-yl)-5-chloropicolinamide (16 mg, 0.028 mmol) in MeOH (74.60 in a flask was added 1,8-diazabicyclo-[5.4.0]undec-7-ene (336 µl, 2.249 mmol). The vial was sealed and was heated at 80° C. for 4 h. The reaction was diluted with MeOH and purified by reverse-phase preparative HPLC using a Phenomenex Gemini column, 10 micron, C18, 110 Å, 150×30 mm, 0.1% TFA in $CH_3CN/H_2O$, gradient 10% to 70% over 16 min, then neutralized with solid $NaHCO_3$ and extracted with DCM to provide N-(6-((4R,6S)-2-amino-4-(difluoromethyl)-6-(trifluoromethyl)-5,6-dihydro-4H-1,3-oxazin-4-yl)-5-fluoropyridin-2-yl)-5-chloropicolinamide (1.8 mg, 3.85 µmol, 13.75% yield) as a off-white solid. MS m/z=467, 469 M$^+$; Calculated for $C_{17}H_{12}ClF_6N_5O_2$: 467.75.

$^1$H NMR (300 MHz, CHLOROFORM-d) δ ppm 2.43-2.63 (m, 1 H) 3.15 (m, 1 H) 5.10 (m, 1 H) 6.13-6.62 (m, 1 H) 7.50-7.69 (m, 1 H) 7.88 (dd, J=8.40, 2.12 Hz, 1 H) 8.22 (d, J=8.33 Hz, 1 H) 8.53-8.59 (m, 1 H) 8.64 (d, J=2.05 Hz, 1 H) 10.54 (br. s., 1 H).

Example 138 (Method S)

Synthesis of (4S,6S)-4-(5-amino-2-fluoropyridin-3-yl)-4-(fluoromethyl)-6-(trifluoromethyl)-5,6-dihydro-4H-1,3-oxazin-2-amine

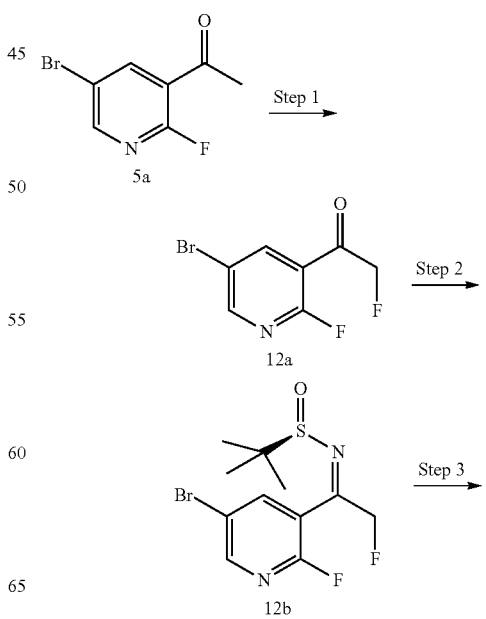

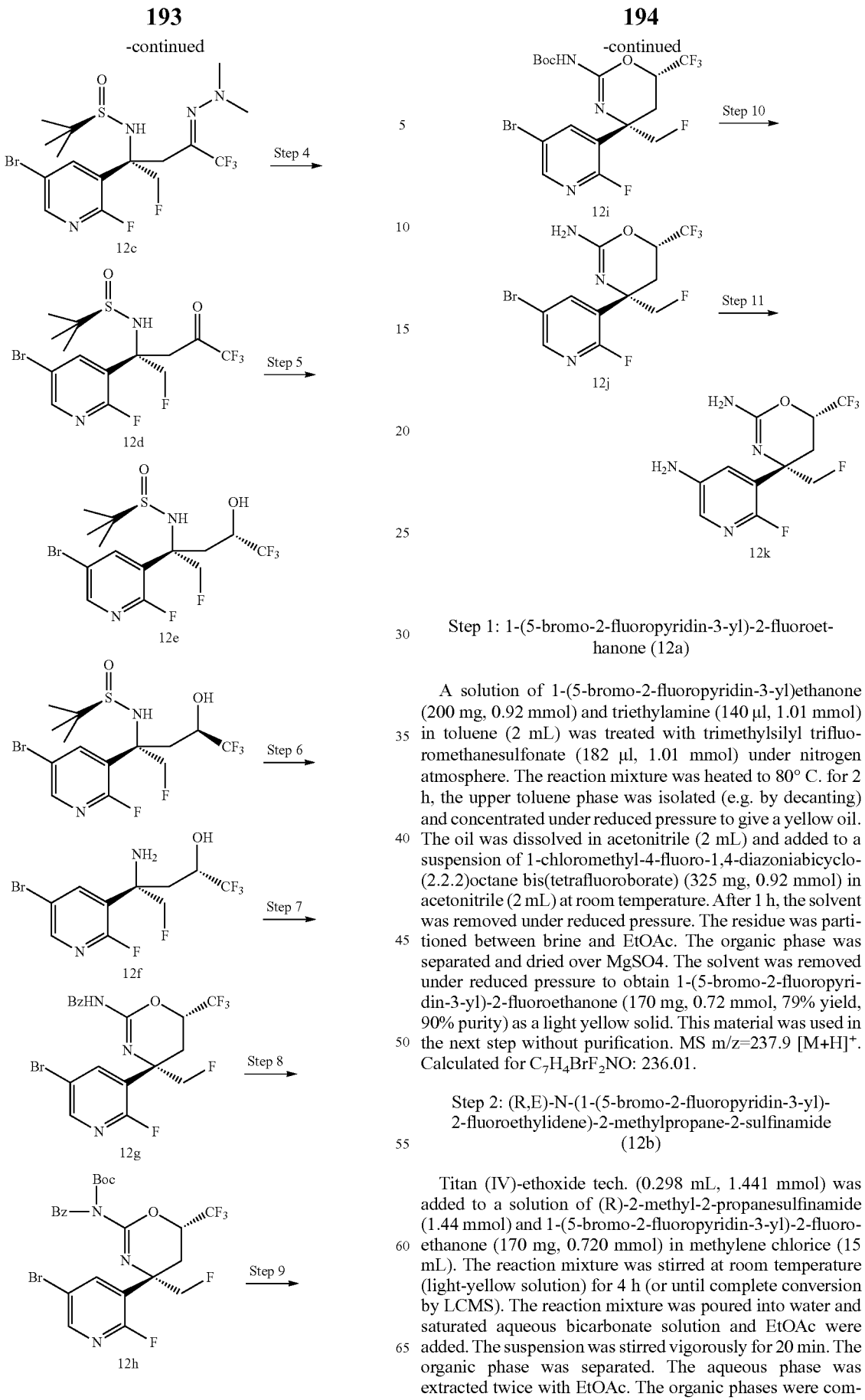

Step 1: 1-(5-bromo-2-fluoropyridin-3-yl)-2-fluoroethanone (12a)

A solution of 1-(5-bromo-2-fluoropyridin-3-yl)ethanone (200 mg, 0.92 mmol) and triethylamine (140 μl, 1.01 mmol) in toluene (2 mL) was treated with trimethylsilyl trifluoromethanesulfonate (182 μl, 1.01 mmol) under nitrogen atmosphere. The reaction mixture was heated to 80° C. for 2 h, the upper toluene phase was isolated (e.g. by decanting) and concentrated under reduced pressure to give a yellow oil. The oil was dissolved in acetonitrile (2 mL) and added to a suspension of 1-chloromethyl-4-fluoro-1,4-diazoniabicyclo-(2.2.2)octane bis(tetrafluoroborate) (325 mg, 0.92 mmol) in acetonitrile (2 mL) at room temperature. After 1 h, the solvent was removed under reduced pressure. The residue was partitioned between brine and EtOAc. The organic phase was separated and dried over MgSO4. The solvent was removed under reduced pressure to obtain 1-(5-bromo-2-fluoropyridin-3-yl)-2-fluoroethanone (170 mg, 0.72 mmol, 79% yield, 90% purity) as a light yellow solid. This material was used in the next step without purification. MS m/z=237.9 [M+H]$^+$. Calculated for $C_7H_4BrF_2NO$: 236.01.

Step 2: (R,E)-N-(1-(5-bromo-2-fluoropyridin-3-yl)-2-fluoroethylidene)-2-methylpropane-2-sulfinamide (12b)

Titan (IV)-ethoxide tech. (0.298 mL, 1.441 mmol) was added to a solution of (R)-2-methyl-2-propanesulfinamide (1.44 mmol) and 1-(5-bromo-2-fluoropyridin-3-yl)-2-fluoroethanone (170 mg, 0.720 mmol) in methylene chlorice (15 mL). The reaction mixture was stirred at room temperature (light-yellow solution) for 4 h (or until complete conversion by LCMS). The reaction mixture was poured into water and saturated aqueous bicarbonate solution and EtOAc were added. The suspension was stirred vigorously for 20 min. The organic phase was separated. The aqueous phase was extracted twice with EtOAc. The organic phases were combined and filtered through a pad of celite. The filtrate was washed with brine and dried over MgSO$_4$. The solvent was removed under reduced pressure. The residue (239 mg of a yellow oil) was purified by column chromatography (silica gel, 10-70% hexanes/EtOAc) to yield (R,E)-N-(1-(5-bromo-2-fluoropyridin-3-yl)-2-fluoroethylidene)-2-methylpropane-2-sulfinamide as a yellow oil (106 mg; 43%). MS m/z=338.9 [M+H]$^+$. Calculated for C$_{11}$H$_{13}$BrFN$_2$OS: 339.2.

Step 3: (R)-N-((S,Z)-2-(5-bromo-2-fluoropyridin-3-yl)-4-(2,2-dimethylhydrazono)-1,5,5,5-tetrafluoropentan-2-yl)-2-methylpropane-2-sulfinamide (12c)

Lithium diisopropylamide, 2.0M solution in tetrahydrofuran/heptane/ethylbenzene (1.474 ml, 2.95 mmol) was added dropwise via syringe to a solution of (E)-1,1-dimethyl-2-(1,1,1-trifluoropropan-2-ylidene)hydrazine (0.454 g, 2.95 mmol) in THF 4.0 mL at −78° C. After stirring at −78° C. for 1 h, the solution was added dropwise via cannula to a solution of (R,E)-N-(1-(5-bromo-2-fluoropyridin-3-yl)-2-fluoroethylidene)-2-methylpropane-2-sulfinamide (0.500 g, 1.474 mmol) in toluene 4 mL cooled to −78° C. The reaction was stirred 3 h at −78° C. before being quenched with saturated aqueous ammonium chloride at −78° C. The mixture was warmed up to room temperature and diluted with water and EtOAc. The layers were separated and the aqueous layer was extracted with EtOAc three times. The combined organic layers were washed with brine, dried on sodium sulfate, filtered and concentrated. The crude material was purified by column chromatography using a gradient of 10-50% EtOAC/Hexane to give 0.50 g of (R)-N-((S,Z)-2-(5-bromo-2-fluoropyridin-3-yl)-4-(2,2-dimethylhydrazono)-1,5,5,5-tetrafluoropentan-2-yl)-2-methylpropane-2-sulfinamide (0.50 g, 1.014 mmol, 68.8% yield). MS m/z=494.9 [M+H]$^+$. Calculated for C$_{16}$H$_{22}$BrF$_5$N$_4$OS: 493.3.

Step 4: (R)-N-((S)-2-(5-bromo-2-fluoropyridin-3-yl)-1,5,5,5-tetrafluoro-4-oxopentan-2-yl)-2-methylpropane-2-sulfinamide (12d)

(R)-N-((S,Z)-2-(5-bromo-2-fluoropyridin-3-yl)-4-(2,2-dimethylhydrazono)-1,5,5,5-tetrafluoropentan-2-yl)-2-methylpropane-2-sulfinamide (0.510 g, 1.034 mmol) was dissolved in THF 5 mL. Hydrochloric acid 1N solution (1.034 ml, 1.034 mmol) was added dropwise. The reaction mixture was stirred at room temperature overnight and worked up with saturated aqueous NaHCO$_3$ and extracted with EtOAc three times. The combined organic layers were washed with brine, dried on sodium sulfate, filtered and concentrated. The crude material was purified by column chromatography using a gradient of 15-50% EtOAc/hexane to give (R)-N-((S)-2-(5-bromo-2-fluoropyridin-3-yl)-1,5,5,5-tetrafluoro-4-oxopentan-2-yl)-2-methylpropane-2-sulfinamide (0.356 g, 0.789 mmol, 76% yield). MS m/z=490.9 [M+CH$_3$CN]$^+$. Calculated for C$_{14}$H$_{16}$BrF$_5$N$_2$O$_2$S: 451.250.

Step 5: (R)-N-((2S,4S)-2-(5-bromo-2-fluoropyridin-3-yl)-1,5,5,5-tetrafluoro-4-hydroxypentan-2-yl)-2-methylpropane-2-sulfinamide and (R)-N-((2S,4R)-2-(5-bromo-2-fluoropyridin-3-yl)-1,5,5,5-tetrafluoro-4-hydroxypentan-2-yl)-2-methylpropane-2-sulfinamide (12e)

(R)-N-((S)-2-(5-bromo-2-fluoropyridin-3-yl)-1,5,5,5-tetrafluoro-4-oxopentan-2-yl)-2-methylpropane-2-sulfinamide (6.32 g, 14.01 mmol) was dissolved in anhydrous methanol 75 mL and the solution was cooled in an ice bath. Sodium tetrahydroborate (0.795 g, 21.01 mmol) was added portionwise as solid. After stirring in the ice bath for 10 min, the reaction was worked up with saturated sodium bicarbonate and extracted with EtOAc three times. The combined organic layers were washed with brine and dried over sodium sulfate, filtered and concentrated. The crude material was purified by column chromatography using a gradient of 15-50% EtOAc/hexane to give (R)-N-((2S,4S)-2-(5-bromo-2-fluoropyridin-3-yl)-1,5,5,5-tetrafluoro-4-hydroxypentan-2-yl)-2-methylpropane-2-sulfinamide (12e, 3.68 g, 58% yield). MS m/z=454.9 [M+H]$^+$. Calculated for C$_{14}$H$_{18}$BrF$_5$N$_2$O$_2$S: 453.3; and (R)-N-((2S,4R)-2-(5-bromo-2-fluoropyridin-3-yl)-1,5,5,5-tetrafluoro-4-hydroxypentan-2-yl)-2-methylpropane-2-sulfinamide (1.5 g, 24% yield). MS m/z=454.9 [M+H]$^+$. Calculated for C$_{14}$H$_{18}$BrF$_5$N$_2$O$_2$S: 453.3.

Step 6: (2S,4S)-4-amino-4-(5-bromo-2-fluoropyridin-3-yl)-1,1,1,5-tetrafluoropentan-2-ol (12f)

(R)-N-((2S,4S)-2-(5-bromo-2-fluoropyridin-3-yl)-1,5,5,5-tetrafluoro-4-hydroxypentan-2-yl)-2-methylpropane-2-sulfinamide (3.68 g, 8.12 mmol) was dissolved in 36 mL methylene chloride and 18 mL MeOH. The solution was stirred at room temperature. Hydrogen chloride, 4M in 1,4-dioxane (20.30 ml, 81 mmol) was added and the reaction mixture was stirred for 1.5 h. The reaction was concentrated, then EtOAc and water was added, followed by addition of saturated sodium bicarbonate solution for neutralization. The layers were separated and the aqueous layer was extracted with EtOAc three times. The combined organic layers were washed with brine, dried over sodium sulfate, filtered and concentrated to give crude material of (2S,4S)-4-amino-4-(5-bromo-2-fluoropyridin-3-yl)-1,1,1,5-tetrafluoropentan-2-ol that was used without further purification.

Step 7: N-((4S,6S)-4-(5-bromo-2-fluoropyridin-3-yl)-4-(fluoromethyl)-6-(trifluoromethyl)-5,6-dihydro-4H-1,3-oxazin-2-yl)benzamide (12g)

(2S,4S)-4-amino-4-(5-bromo-2-fluoropyridin-3-yl)-1,1,1,5-tetrafluoropentan-2-ol (2.83 g, 8.11 mmol) in MeCN (70 mL) was added benzoyl isothiocyanate (1.20 ml, 8.92 mmol) and the mixture was stirred at room temperature for 1 h. N,N'-dicyclohexylcarbodiimide (1.840 g, 8.92 mmol) and diisopropylethylamine (2.82 ml, 16.21 mmol) were added. The mixture was stirred at 50° C. for 7 h. The reaction was worked up with water and EtOAc. The separated organic layer was washed with brine, dried over sodium sulfate, filtered and concentrated. The crude material was purified by column chromatography using a gradient of 0-25% EtOAc/hexane to give N-((4S,6S)-4-(5-bromo-2-fluoropyridin-3-yl)-4-(fluoromethyl)-6-(trifluoromethyl)-5,6-dihydro-4H-1,3-oxazin-2-yl)benzamide (2.27 g, 4.75 mmol, 58.6% yield). MS m/z=479.8 [M+H]$^+$. Calculated for C$_{18}$H$_{13}$BrF$_5$N$_3$O$_2$: 478.2.

Step 8: Tert-butyl benzoyl((4S,6S)-4-(5-bromo-2-fluoropyridin-3-yl)-4-(fluoromethyl)-6-(trifluoromethyl)-5,6-dihydro-4H-1,3-oxazin-2-yl)carbamate (12h)

N-((4S,6S)-4-(5-bromo-2-fluoropyridin-3-yl)-4-(fluoromethyl)-6-(trifluoromethyl)-5,6-dihydro-4H-1,3-oxazin-2-yl)benzamide (2.0 g, 4.18 mmol) was dissolved in methylene chloride 50 mL and di-tert-buryl dicarbonate (1.00 g, 4.60 mmol) was added followed by addition of 4-(dimethylamino) pyridine (0.051 g, 0.418 mmol). The mixture was stirred at room temperature for 15 min and reaction was complete. The reaction mixture was concentrated and the crude material was used without purification.

Step 9: Tert-butyl ((4S,6S)-4-(5-bromo-2-fluoropyridin-3-yl)-4-(fluoromethyl)-6-(trifluoromethyl)-5,6-dihydro-4H-1,3-oxazin-2-yl)carbamate (12i)

The crude material from Step 8 was dissovled in methanol and potassium carbonate (0.252 ml, 4.18 mmol) was added. The mixture was stirred at room temperature for 1 h. The reaction mixture was concentrated, water was added to the residue and the mixture was extracted with EtOAc three times. The combined organic layers were washed with brine, dried on sodium sulfate, filtered and concentrated. The crude material was used without purification.

Step 10: (4S,6S)-4-(5-bromo-2-fluoropyridin-3-yl)-4-(fluoromethyl)-6-(trifluoromethyl)-5,6-dihydro-4H-1,3-oxazin-2-amine (12j)

The crude material from Step 9 was treated with trifluoroacetic acid (25 ml, 337 mmol) and stirred at room temperature for 15 min. The reaction mixture was concentrated and worked up with saturated sodium bicarbonate and extracted with methylene chloride three times. The combined organic layers were washed with brine, dried on sodium sulfate, filtered and concentrated. The crude material was purified by column chromatography using a gradient of 5-50% EtOAc/hexane to give (4S,6S)-4-((5-bromo-2-fluoropyridin-3-yl)-4-(fluoromethyl)-6-(trifluoromethyl)-5,6-dihydro-4H-1,3-oxazin-2-amine (1.30 g, 3.47 mmol, 83% yield). MS m/z=398.0 [M+Na]$^+$. Calculated for $C_{11}H_9BrF_5N_3O$: 374.1.

Step 11: (4S,6S)-4-(5-amino-2-fluoropyridin-3-yl)-4-(fluoromethyl)-6-(trifluoromethyl)-5,6-dihydro-4H-1,3-oxazin-2-amine (12k)

In a microwave tube was added (4S,6S)-4-(5-bromo-2-fluoropyridin-3-yl)-4-(fluoromethyl)-6-(trifluoromethyl)-5,6-dihydro-4H-1,3-oxazin-2-amine (0.90 g, 2.406 mmol), potassium carbonate (1.330 g, 9.62 mmol) and copper(I) iodide (0.092 g, 0.481 mmol), 2,2,2-trifluoroacetamide (0.544 g, 4.81 mmol) and molecular sieves. The vial was purged with nitrogen followed by addition of dioxane 15 mL and trans-N,N'-dimethyl-1,2-cyclohexanediamine (0.152 ml, 0.962 mmol). The vial was sealed and heated at 120° C. for 2.5 h. To this mixture were added MeOH/water (8/4 mL) and the resulting mixture was heated at 80° C. for 3 h. The mixture was extracted with methylene chloride. The combined organic layers were dried over sodium sulfate, filtered and concentrated. The crude material was purified by column chromatography on silica gel using a gradient of 0-5% 2M $NH_3$ in MeOH/methylene chloride to afford (4S,6S)-4-(5-amino-2-fluoropyridin-3-yl)-4-(fluoromethyl)-6-(trifluoromethyl)-5,6-dihydro-4H-1,3-oxazin-2-amine (0.60 g, 1.934 mmol, 80% yield). MS m/z=311.0 [M+H]$^+$. Calculated for $C_{11}H_{11}F_5N_4O$: 310.2.

$^1$H NMR (300 MHz, $CD_3OD$) δ ppm 1.98-2.14 (m, 1 H) 2.56 (dd, J=13.52, 2.85 Hz, 1 H) 4.22-4.73 (m, 3 H) 7.29 (dd, J=8.70, 2.85 Hz, 1 H) 7.48 (t, J=2.48 Hz, 1 H)

Example 139

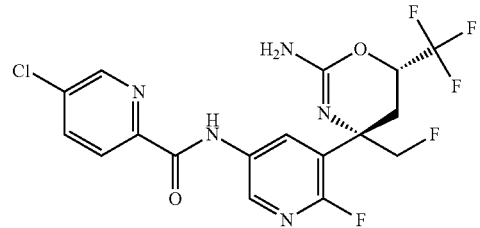 [SMILES: NC1=N[C@](CF)(c2cc(NC(=O)c3ccc(Cl)cn3)cnc2F)C[C@@H](C(F)(F)F)O1]

Synthesis of N-(5-((4S,6S)-2-amino-4-(fluoromethyl)-6-(trifluoromethyl)-5,6-dihydro-4H-1,3-oxazin-4-yl)-6-fluoropyridin-3-yl)-5-chloropicolinamide The title compound was synthesized using procedures analogous to those described in Method H Step 2 (Example 66) above, but using 5-chloropicolinic acid and (4S,6S)-4-(5-amino-2-fluoropyridin-3-yl)-4-(fluoromethyl)-6-(trifluoromethyl)-5,6-dihydro-4H-1,3-oxazin-2-amine (12k, as described in Example 138, method S). MS m/z=449.9 [M+H]$^+$. Calculated for $C_{17}H_{13}ClF_5N_5O_2$: 449.8

$^1$H NMR (400 MHz, $CD_3OD$) δ ppm 2.13 (t, J=13.01 Hz, 1 H) 2.64 (d, J=13.69 Hz, 1 H) 4.32-4.71 (m, 3 H) 8.07 (d, J=7.04 Hz, 1 H) 8.21 (d, J=8.02 Hz, 1 H) 8.41 (d, J=7.24 Hz, 1 H) 8.70 (d, J=12.13 Hz, 2 H)

Example 140

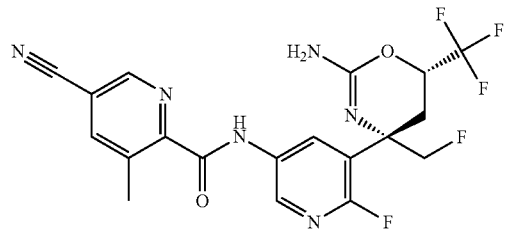 [SMILES: Cc1cc(C#N)cnc1C(=O)Nc1cnc(F)c([C@]2(CF)C[C@@H](C(F)(F)F)OC(N)=N2)c1]

Synthesis of N-(5-((4S,6S)-2-amino-4-(fluoromethyl)-6-(trifluoromethyl)-5,6-dihydro-4H-1,3-oxazin-4-yl)-6-fluoropyridin-3-yl)-5-cyano-3-methylpicolinamide The title compound was synthesized using procedures analogous to those described in Method H Step 2 (Example 66) above, but using 5-cyano-3-methylpicolinic acid and (4S,6S)-4-(5-amino-2-fluoropyridin-3-yl)-4-(fluoromethyl)-6-(trifluoromethyl)-5,6-dihydro-4H-1,3-oxazin-2-amine (12k, as described in Example 138, method S). MS m/z=455.1 [M+H]$^+$. Calculated for $C_{19}H_{15}F_5N_6O_2$: 454.4

¹H NMR (300 MHz, CD₃OD) δ ppm 2.12 (t, J=13.15 Hz, 1 H) 2.52-2.68 (m, 1 H) 2.72 (s, 3 H) 4.33-4.77 (m, 3 H) 8.20 (s, 1 H) 8.36 (d, J=8.04 Hz, 1 H) 8.67 (m, 1 H) 8.85 (s, 1 H)

Example 141

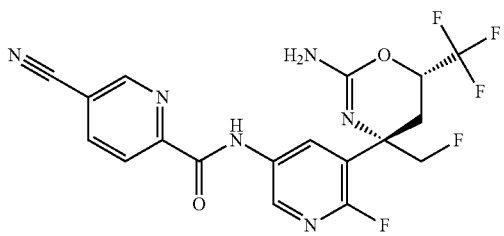 [SMILES: N#Cc1ccc(C(=O)Nc2cnc(F)c([C@]3(CF)C[C@@H](C(F)(F)F)OC(N)=N3)c2)nc1]

Synthesis of N-(5-((4S,6S)-2-amino-4-(fluoromethyl)-6-(trifluoromethyl)-5,6-dihydro-4H-1,3-oxazin-4-yl)-6-fluoropyridin-3-yl)-5-cyanopicolinamide The title compound was synthesized using procedures analogous to those described in Method H Step 2 (Example 66) above, but using 5-cyano-picolinic acid and (4S,6S)-4-(5-amino-2-fluoropyridin-3-yl)-4-(fluoromethyl)-6-(trifluoromethyl)-5,6-dihydro-4H-1,3-oxazin-2-amine (12k, as described in Example 138, method S). MS m/z=441.0 [M+H]⁺. Calculated for C₁₈H₁₃F₅N₆O₂: 440.3

¹H NMR (300 MHz, DMSO-d₆) δ ppm 1.96 (s, 1 H) 4.57 (m, 3 H) 6.19 (s, 2 H) 8.30 (d, J=8.18 Hz, 1 H) 8.50-8.63 (m, 2 H) 8.65-8.74 (m, 1 H) 9.22 (s, 1 H) 11.15-11.41 (m, 1 H)

Example 142

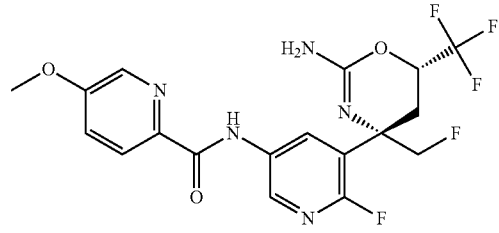 [SMILES: COc1ccc(C(=O)Nc2cnc(F)c([C@]3(CF)C[C@@H](C(F)(F)F)OC(N)=N3)c2)nc1]

Synthesis of N-(5-((4S,6S)-2-amino-4-(fluoromethyl)-6-(trifluoromethyl)-5,6-dihydro-4H-1,3-oxazin-4-yl)-6-fluoropyridin-3-yl)-5-methoxypicolinamide The title compound was synthesized using procedures analogous to those described in Method H Step 2 (Example 66) above, but using 5-methoxy-picolinic acid and (4S,6S)-4-(5-amino-2-fluoropyridin-3-yl)-4-(fluoromethyl)-6-(trifluoromethyl)-5,6-dihydro-4H-1,3-oxazin-2-amine (as described in Example 138, method S). MS m/z=446.0 [M+H]⁺. Calculated for C₁₈H₁₆F₅N₅O₃: 445.3

¹H NMR (300 MHz, CD₃OD) δ ppm 2.12 (t, J=13.37 Hz, 1 H) 2.64 (d, J=14.62 Hz, 1 H) 3.97 (s, 3 H) 4.38-4.71 (m, 3 H) 7.54 (d, J=6.58 Hz, 1 H) 8.18 (d, J=8.48 Hz, 1 H) 8.37 (m, 2 H) 8.66 (m, 1 H)

Example 143 (Method T)

Synthesis of N-(3-((4S,6S)-2-amino-4-(fluoromethyl)-6-(trifluoromethyl)-5,6-dihydro-4H-1,3-oxazin-4-yl)phenyl)-5-chloropicolinamide

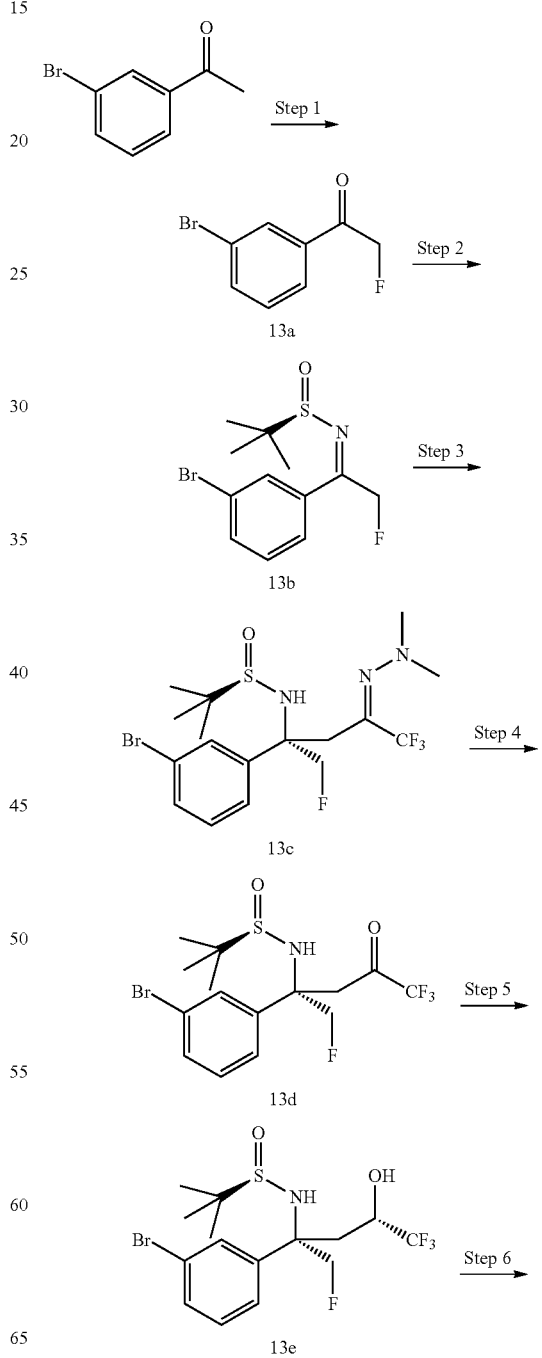

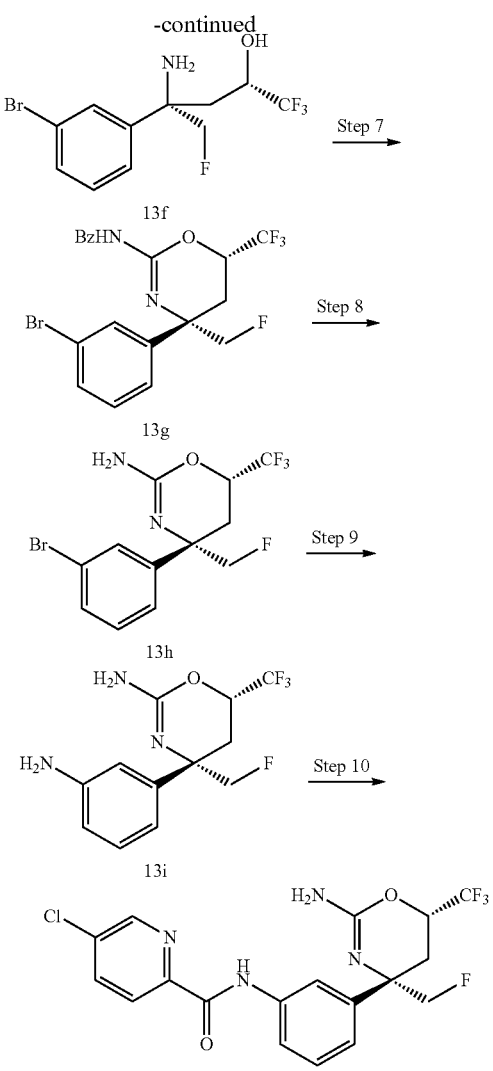

Step 1: 1-(3-bromophenyl)-2-fluoroethanone (13a)

3"-Bromoacetophenone (3.00 ml, 15.07 mmol, Aldrich), triethylamine (2.52 ml, 18.09 mmol) and toluene 30 mL were added to a 250 mL flask. Then trimethylsilyl trifluoromethanesulfonate (3.27 ml, 18.09 mmol) was added into the reaction mixture. The flask was placed into a pre-heated (83° C.) bath and allowed to stir under inert atmosphere for 4 h. The flask was removed from the heat bath and the mixture was allowed to cool to room temperature. The layers were allowed to separate and the top layer was decanted into a round-bottomed flask and the mixture was concentrated in vacuo. The residue was diluted with MeCN 23 mL, then added slowly via syringe into a stirred mixture of selectfluor (6.41 g, 18.09 mmol) in MeCN (23 mL). The reaction mixture was stirred at room temperature. The mixture was concentrated and the residue was diluted with EtOAc and water. The organic layer was separated and the aqueous layer was extracted with EtOAc three times. The combined organic layers were washed with brine, dried on sodium sulfate, filtered and concentrated. The crude material was purified by column chromatography using a gradient of EtOAc/hexane 5-20% to give 1-(3-bromophenyl)-2-fluoroethanone (2.23 g, 10.27 mmol, 68.2% yield). MS m/z=218.9 [M+H]$^+$. Calculated for $C_8H_6BrFO$: 217.0

Step 2: (R,E)-N-(1-(3-bromophenyl)-2-fluoroethylidene)-2-methylpropane-2-sulfinamide (13b)

To a round-bottomed flask charged with 1-(3-bromophenyl)-2-fluoroethanone (11.42 g, 52.6 mmol) in THF (100 ml), was added (R)-2-methylpropane-2-sulfinamide (12.75 g, 105 mmol). Then tetraisopropoxytitanium (31.2 ml, 105 mmol) was added into the reaction mixture. The reaction mixture was stirred at ambient temperature under inert atmosphere overnight. The material was poured slowly into a vigourously stirring solution of ice water. The resulting suspension was stirred vigourously for 20 min. Then methylene chloride was added into the mixture and the overall mixture was allowed to stir an additional 30 min. The mixture was filtered through a pad of celite and the filter cake was washed with methylene chloride. The organic layer was separated and the remaining aqueous layer was extracted with methylene chloride three times. The combined organic extracts were washed with brine, dried over magnesium sulfate, filtered and concentrated in-vacuo. The crude material was absorbed onto a plug of silica gel and purified by chromatography through a Redi-Sep pre-packed silica gel column, eluting with a gradient of 0-15% EtOAc/hexane to give (R,E)-N-(1-(3-bromophenyl)-2-fluoroethylidene)-2-methylpropane-2-sulfinamide (9.69 g, 57.5% yield).

Step 3: ((R)-N-((S,Z)-2-(3-bromophenyl)-4-(2,2-dimethylhydrazono)-1,5,5,5-tetrafluoropentan-2-yl)-2-methylpropane-2-sulfinamide (13c)

Lithium diisopropylamide, 2.0M heptane/tetrahydrofuran/ethylbenzene (3.12 ml, 6.25 mmol) was added dropwise via syringe to a solution of (E)-1,1-dimethyl-2-(1,1,1-trifluoropropan-2-ylidene)hydrazine (1.058 g, 6.25 mmol) in THF 8 mL at −78° C. After stirring at −78° C. for 1 h, a solution of (R)-2-methylpropane-2-sulfinamide (1.0 g, 3.12 mmol) in toluene 8 mL cooled to −78° C. was added. The reaction was stirred 3 h at −78° C. before being quenched with saturated aqueous ammonium chloride at −78° C. and diluted with water and EtOAc. The layers were separated and the aqueous layer was extracted with EtOAc three times. The combined organic layers were washed with brine, dried over sodium sulfate, filtered and concentrated. The crude material was purified by column chromatography using a gradient of 10-50% EtOAc/hexane to give ((R)-N-((S,Z)-2-(3-bromophenyl)-4-(2,2-dimethylhydrazono)-1,5,5,5-tetrafluoropentan-2-yl)-2-methylpropane-2-sulfinamide (1.11 g, 2.34 mmol, 74.9% yield). MS m/z=474.0 [M+H]$^+$. Calculated for $C_{17}H_{24}BrF_4N_3OS$: 474.36

Step 4: (R)-N-((S)-2-(3-bromophenyl)-1,5,5,5-tetrafluoro-4-oxopentan-2-yl)-2-methylpropane-2-sulfinamide (13d)

(R)-N-((Z)-2-(3-bromophenyl)-4-(2,2-dimethylhydrazono)-1,5,5,5-tetrafluoropentan-2-yl)-2-methylpropane-2-sulfinamide (1.47 g, 3.10 mmol) was dissolved in THF 16 mL and 2N hydrochloric acid (1.549 ml, 3.10 mmol) was added dropwise. The reaction mixture was stirred at room temperature for 12 h. The reaction mixture was worked up with saturated sodium bicarbonate solution and extracted with EtOAc three times. The combined organic layers were washed with brine, dried over sodium sulfate, filtered and concentrated. The crude material was purified by column chromatography using a gradient of 15-50% EtOAc/hexane to give (R)-N-(2-(3-bromophenyl)-1,5,5,5-tetrafluoro-4- oxopentan-2-yl)-2-methylpropane-2-sulfinamide (1.13 g, 84% yield). MS m/z=433.9 [M+H]+. Calculated for C$_{15}$H$_{18}$BrF$_4$NO$_2$S: 432.3

Step 5: (R)-N-((2S,4S)-2-(3-bromophenyl)-1,5,5,5-tetrafluoro-4-hydroxypentan-2-yl)-2-methylpropane-2-sulfinamide (13e)

Ru[p-cymeme](1S,2S)-N-(p-toluenesulfonyl)-1,2-diphenylethylenediamine (0.119 g, 0.198 mmol) was added in one portion to a solution of (R)-N-((S)-2-(3-bromophenyl)-1,5,5,5-tetrafluoro-4-oxopentan-2-yl)-2-methylpropane-2-sulfinamide (2.14 g, 4.95 mmol) in IPA (50 ml) (which had been degassed by bubbling nitrogen through the solution for 30 minutes prior to use) in a dry box at room temperature. After stirring overnight, the reaction was worked up with saturated sodium bicarbonate solution and extracted with EtOAc three times. The combined organic layers were washed with brine, dried over sodium sulfate, filtered and concentrated. The crude material was purified by column chromatography using 20-100% EtOAc/hexane to give (R)-N-((2S,4S)-2-(3-bromophenyl)-1,5,5,5-tetrafluoro-4-hydroxypentan-2-yl)-2-methylpropane-2-sulfinamide (1.83 g, 85% yield). MS m/z=435.8 [M+H]+. Calculated for C$_{15}$H$_{20}$BrF$_4$NO$_2$S: 434.3

Step 6: (2S,4S)-4-amino-4-(3-bromophenyl)-1,1,1,5-tetrafluoropentan-2-ol (13f)

(R)-N-((2S,4S)-2-(3-bromophenyl)-1,5,5,5-tetrafluoro-4-hydroxypentan-2-yl)-2-methylpropane-2-sulfinamide (1.83 g, 4.21 mmol) was dissolved in dichloromethane 37 mL and hydrogen chloride, 4.0M solution in 1,4-dioxane (5.27 ml, 21.07 mmol) was added dropwise. The reaction was stirred at room temperature for 10 min. The reaction was worked up by addition of 1N NaOH and extraction with dichloromethane three times. The combined organic layers were dried over sodium sulfate, filtered and concentrated to afford (2S,4S)-4-amino-4-(3-bromophenyl)-1,1,1,5-tetrafluoropentan-2-ol that was used without further purification.

Step 7: N-((4S,6S)-4-(3-bromophenyl)-4-(fluoromethyl)-6-(trifluoromethyl)-5,6-dihydro-4H-1,3-oxazin-2-yl)benzamide (13g)

To (2S,4S)-4-amino-4-(3-bromophenyl)-1,1,1,5-tetrafluoropentan-2-ol prepared from Step 6, was added THF 12 mL followed by benzoyl isothiocyanate (0.624 ml, 4.64 mmol) and the reaction mixture was stirred for 1 h to afford N-(((2S,4S)-2-((3-bromophenyl)-1,5,5,5-tetrafluoro-4-hydroxypentan-2-yl)carbamothioyl)benzamide. Then N-(3-dimethylaminopropyl)-N'-ethylcarbodiimide hydrochloride (0.889 g, 4.64 mmol) and triethylamine (0.703 ml, 5.06 mmol) were added and the reaction mixture was heated at 70° C. for 1.5 h. The reaction mixture was diluted with EtOAc, washed with water and dried over sodium sulfate, filtered and concentrated. The crude material was purified by column chromatography using 0-20% EtOAc/hexane to give N-((4S,6S)-4-(3-bromophenyl)-4-(fluoromethyl)-6-(trifluoromethyl)-5,6-dihydro-4H-1,3-oxazin-2-yl)benzamide (1.15 g, 2.504 mmol, 59.4% yield). MS m/z=460.9 [M+H]+. Calculated for C$_{19}$H$_{15}$BrF$_4$N$_2$O$_2$: 459.2

Step 8: (4S,6S)-4-(3-bromophenyl)-4-(fluoromethyl)-6-(trifluoromethyl)-5,6-dihydro-4H-1,3-oxazin-2-amine (13h)

To a solution of N-((4S,6S)-4-(3-bromophenyl)-4-(fluoromethyl)-6-(trifluoromethyl)-5,6-dihydro-4H-1,3-oxazin-2-yl)benzamide (1.15 g, 2.504 mmol) in MeOH 8 mL was added 2,3,4,6,7,8,9,10-octahydropyrimido[1,2-a]azepine (0.449 ml, 3.01 mmol) and the resulting mixture was heated at 65° C. for 9 h. The mixture was concentrated, and then diluted with EtOAc. The resulting solution was washed with water, saturated NH$_4$Cl solution, dried over sodium sulfate, filtered, concentrated. The crude material was purified by column chromatographed on silica gel using 0-40% EtOAc/Hexane to give (4S,6S)-4-(3-bromophenyl)-4-(fluoromethyl)-6-(trifluoromethyl)-5,6-dihydro-4H-1,3-oxazin-2-amine (0.480 g, 1.352 mmol, 54.0% yield). MS m/z=356.9 [M+H]+. Calculated for C$_{12}$H$_{11}$BrF$_4$NO$_2$: 355.1

Step 9: (4S,6S)-4-(3-aminophenyl)-4-(fluoromethyl)-6-(trifluoromethyl)-5,6-dihydro-4H-1,3-oxazin-2-amine (13i)

A mixture of (4S,6S)-4-(3-bromophenyl)-4-(fluoromethyl)-6-(trifluoromethyl)-5,6-dihydro-4H-1,3-oxazin-2-amine (0.480 g, 1.352 mmol), sodium azide (0.142 ml, 4.05 mmol), copper(I) iodide (9.16 µl, 11, 0.270 mmol) and L(+)-ascorbic acid sodium salt (0.027 g, 0.135 mmol) was purged with N$_2$ followed by the addition of (1R,2R)-(−)-N,N"-dimethylcyclohexane-1,2-diamine (0.064 ml, 0.405 mmol) and degassed EtOH/water (3/1.5 mL). The resulting mixture was heated at 90° C. for 30 min, then cooled to room temperature, and poured into a mixture of 9:1 saturated NH$_4$Cl solution/NH$_4$OH. The resulting mixture was extracted with EtOAc three times. The combined organic layers were dried over Na$_2$SO$_4$, filtered and concentrated. This product was dissolved in a mixture of THF/water (3/1.5 mL) followed by the addition of trimethylphosphine, 1.0M solution in tetrahydrofuran (1.622 ml, 1.622 mmol) and stirred at room temperature for 30 min. The mixture was worked up with water and extracted with dichloromethane three times. The combined organic layers were dried on sodium sulfate, filtered and concentrated. The crude material was purified by column chromatography using 5-10% MeOH/dichloromethane to give (4S,6S)-4-(3-aminophenyl)-4-(fluoromethyl)-6-(trifluoromethyl)-5,6-dihydro-4H-1,3-oxazin-2-amine (0.322 g, 82% yield). MS m/z=292.0 [M+H]+. Calculated for C$_{12}$H$_{13}$F$_4$N$_3$O: 291.2

Step 10: N-(3-((4S,6S)-2-amino-4-(fluoromethyl)-6-(trifluoromethyl)-5,6-dihydro-4H-1,3-oxazin-4-yl)-phenyl)-5-chloropicolinamide A mixture of (4S,6S)-4-(3-aminophenyl)-4-(fluoromethyl)-6-(trifluoromethyl)-5,6-dihydro-4H-1,3-oxazin-2-amine (0.080 g, 0.275 mmol) and 5-chloro-2-pyridinecarboxylic acid (0.048 g, 0.302 mmol) in THF/MeOH (3/1.2 mL) was stirred at room temperature and 4-(4,6-dimethoxy-1,3,5-triazin-2-yl)-4-methylmorpholinium chloride (0.089 g, 0.302 mmol) was added. The reaction mixture was stirred for 30 min. The reaction was quenched with saturated NaHCO$_3$ solution and extracted with dichloromethane. The combined organic layers were dried over Na$_2$SO$_4$, filtered, concentrated. The crude material was purified by column chromatographed on silica gel using 10-50% EtOAc/hexane to afford a white solid as N-(3-((4S,6S)-2-amino-4-(fluoromethyl)-6-(trifluoromethyl)-5,6-dihydro-4H-1,3-oxazin-4-yl)phenyl)-5-chloropicolinamide (0.075 g, 0.174 mmol, 63.4% yield). MS m/z=430.9 [M+H]+. Calculated for C$_{18}$H$_{15}$ClF$_4$N$_4$O$_2$: 430.8

$^1$H NMR (300 MHz, DMSO-d$_6$) δ ppm 1.91-2.05 (m, 1 H) 4.18-4.71 (m, 3 H) 6.02 (br. s., 2 H) 7.26 (d, J=7.60 Hz, 1 H)

7.38 (t, J=8.18 Hz, 1 H) 7.90 (br. s., 2 H) 8.12-8.25 (m, 2 H) 8.75-8.83 (m, 1 H) 10.61 (s, 1 H)

Example 144

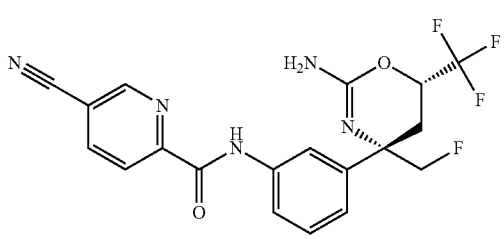 [SMILES: N#Cc1ccc(C(=O)Nc2cccc([C@]3(CF)C[C@@H](C(F)(F)F)OC(N)=N3)c2)nc1]

Synthesis of N-(3-((4S,6S)-2-amino-4-(fluoromethyl)-6-(trifluoromethyl)-5,6-dihydro-4H-1,3-oxazin-4-yl)phenyl)-5-cyanopicolinamide The title compound was synthesized using procedures analogous to those described in Method T (Example 143) above, but using 5-cyno-picolinic acid. MS m/z=422.0 [M+H]$^+$. Calculated for $C_{19}H_{15}F_4N_5O_2$: 421.3

$^1$H NMR (300 MHz, DMSO-d$_6$) δ ppm 1.98 (t, J=12.64 Hz, 1 H) 4.18-4.74 (m, 3 H) 6.00 (s, 2 H) 7.28 (d, J=7.75 Hz, 1 H) 7.39 (t, J=7.82 Hz, 1 H) 7.86-7.97 (m, 2 H) 8.30 (d, J=8.18 Hz, 1 H) 8.59 (dd, J=8.18, 1.75 Hz, 1 H) 9.21 (s, 1 H) 10.77 (s, 1 H).

Example 145

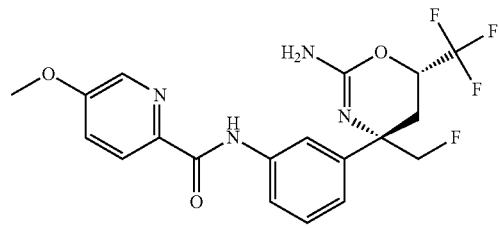 [SMILES: COc1ccc(C(=O)Nc2cccc([C@]3(CF)C[C@@H](C(F)(F)F)OC(N)=N3)c2)nc1]

Synthesis of N-(3-((4S,6S)-2-amino-4-(fluoromethyl)-6-(trifluoromethyl)-5,6-dihydro-4H-1,3-oxazin-4-yl)phenyl)-5-methoxypicolinamide The title compound was synthesized using procedures analogous to those described in Method T (Example 143) above, but using 5-methoxy-picolinic acid. MS m/z=427.0 [M+H]$^+$. Calculated for $C_{19}H_{18}F_4N_4O_3$: 426.4

$^1$H NMR (400 MHz, CHLOROFORM-d) ppm $^1$H NMR (300 MHz, DMSO-d$_6$) δ ppm 1.97 (t, J=12.72 Hz, 1 H) 3.94 (s, 3 H) 4.13-4.76 (m, 3 H) 6.00 (s, 2 H) 7.23 (d, J=7.89 Hz, 1 H) 7.36 (t, J=7.75 Hz, 1 H) 7.62 (d, J=8.62 Hz, 1 H) 7.84-7.93 (m, 2 H) 8.14 (d, J=8.62 Hz, 1 H) 8.39 (br. s., 1 H) 10.41 (s, 1 H)

Example 146

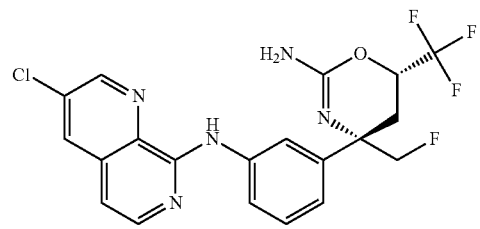 [SMILES: NC1=N[C@](CF)(c2cccc(Nc3nccc4cc(Cl)cnc34)c2)C[C@@H](C(F)(F)F)O1]

Synthesis of (4S,6S)-4-(3-((3-chloro-1,7-naphthyridin-8-yl)amino)phenyl)-4-(fluoromethyl)-6-(trifluoromethyl)-5,6-dihydro-4H-1,3-oxazin-2-amine The title compound was synthesized using procedures analogous to those described in Method B Step 2 (Example 8) above, but using (4S,6S)-4-(3-aminophenyl)-4-(fluoromethyl)-6-(trifluoromethyl)-5,6-dihydro-4H-1,3-oxazin-2-amine (13i, Method T, Example 143, Step 9). MS m/z=454.1 [M+H]$^+$. Calculated for $C_{20}H_{16}ClF_4N_5O$: 453.8

$^1$H NMR (300 MHz, DMSO-d$_6$) δ ppm 1.95-2.09 (m, 1 H) 4.20-4.69 (m, 3 H) 6.44-6.51 (m, 1 H) 7.12-7.20 (m, 2 H) 7.37 (t, J=7.66 Hz, 1 H) 7.98 (s, 1 H) 8.10-8.23 (m, 2 H) 8.52 (d, J=2.34 Hz, 1 H) 8.91 (d, J=2.34 Hz, 1 H) 9.61 (s, 1 H)

Example 147 (Method U)

Synthesis of N-(5-((4S,6S)-2-amino-4-methyl-6-(trifluoromethyl)-5,6-dihydro-4H-1,3-oxazin-4-yl)-6-methoxypyridin-3-yl)-5-chloropicolinamide

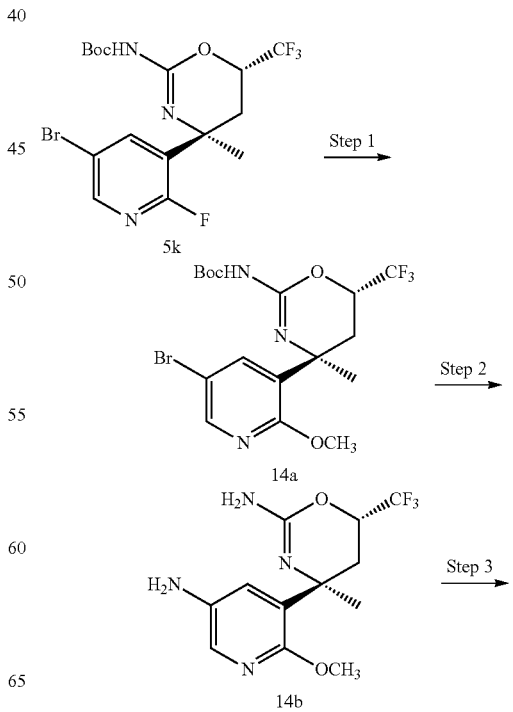

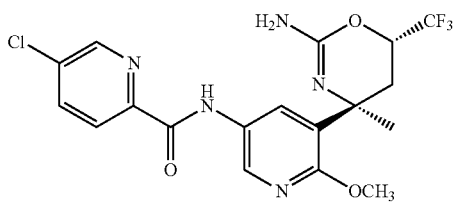

Step 1: tert-Butyl ((4S,6S)-4-(5-bromo-2-methoxy-pyridin-3-yl)-4-methyl-6-(trifluoromethyl)-5,6-dihydro-4H-1,3-oxazin-2-yl)carbamate (14a)

tert-Butyl ((4S,6S)-4-(5-bromo-2-fluoropyridin-3-yl)-4-methyl-6-(trifluoromethyl)-5,6-dihydro-4H-1,3-oxazin-2-yl)carbamate (5k, 0.500 g, 1.096 mmol, as described in Example 31, Method G, Step 9) was treated with sodium methanolate 25% MeOH (3 mL). The reaction was heated at 50° C. for 40 min. The reaction was quenched with water and methanol was removed by reduced pressure. The resulting mixture was extracted with EtOAc three times. The combined organic layers were dried on sodium sulfate, filtered and concentrated. The crude material was purified by column chromatography using a gradient of 0-30% EtOAc/hexane to give tert-Butyl ((4S,6S)-4-(5-bromo-2-methoxypyridin-3-yl)-4-methyl-6-(trifluoromethyl)-5,6-dihydro-4H-1,3-oxazin-2-yl)carbamate (0.49 g, 97% yield). MS m/z=469.9 [M+H]$^+$. Calculated for $C_{17}H_{21}BrF_3N_3O_4$: 468.3

Step 2: (4S,6S)-4-(5-amino-2-methoxypyridin-3-yl)-4-methyl-6-(trifluoromethyl)-5,6-dihydro-4H-1,3-oxazin-2-amine (14b)

tert-Butyl ((4S,6S)-4-(5-bromo-2-methoxypyridin-3-yl)-4-methyl-6-(trifluoromethyl)-5,6-dihydro-4H-1,3-oxazin-2-yl)carbamate (0.56 g, 1.196 mmol) was treated with trifluoroacetic acid, 99% (10 ml, 135 mmol) and the mixture was stirred at room temperature for 15 min. The solvent was removed and the residue was worked up with saturated sodium bicarbonate solution and extracted with dichloromethane three times. The combined organic layers were dried on sodium sulfate, filtered and concentrated. The crude material was purified by column chromatography using a gradient of 10-60% EtOAc/hexane to give (4S,6S)-4-(5-bromo-2-methoxypyridin-3-yl)-4-methyl-6-(trifluoromethyl)-5,6-dihydro-4H-1,3-oxazin-2-amine (0.366 g, 0.994 mmol, 83% yield).

Step 3: N-(5-((4S,6S)-2-amino-4-methyl-6-(trifluoromethyl)-5,6-dihydro-4H-1,3-oxazin-4-yl)-6-methoxypyridin-3-yl)-5-chloropicolinamide A microwave vial was charged with (4S,6S)-4-(5-bromo-2-methoxypyridin-3-yl)-4-methyl-6-(trifluoromethyl)-5,6-dihydro-4H-1,3-oxazin-2-amine (0.100 g, 0.272 mmol), 5-chloropicolinamide (0.064 g, 0.407 mmol), copper(I) iodide (10.35 mg, 0.054 mmol) and potassium carbonate powder (0.113 g, 0.815 mmol). The vial was purged with nitrogen followed by the addition of 1,4-dioxane 1 mL and (1R,2R)-(−)-N,N"-dimethylcyclohexane-1,2-diamine (0.043 ml, 0.272 mmol). The vial was sealed and heated at 120° C. overnight. The reaction mixture was partitioned between EtOAc and water. The aqueous layer was extracted with EtOAc three times. The organic layers were combined, washed with brine and dried over sodium sulfate, filtered and concentrated. The crude material was purified by column chromatography using a gradient of 15-85% EtOAc/hexane to give N-(5-((4S,6S)-2-amino-4-methyl-6-(trifluoromethyl)-5,6-dihydro-4H-1,3-oxazin-4-yl)-6-methoxypyridin-3-yl)-5-chloropicolinamide (0.029 g, 0.065 mmol, 24.06% yield). MS m/z=443.9 [M+H]$^+$. Calculated for $C_{18}H_{17}ClF_3N_5O_3$: 443.8

$^1$H NMR (300 MHz, DMSO-d$_6$) δ ppm 1.51 (s, 3 H) 1.66 (t, J=13.01 Hz, 1 H) 2.91 (dd, J=13.15, 2.48 Hz, 1 H) 3.92 (s, 3 H) 4.11 (d, J=4.68 Hz, 1 H) 5.88 (br. s., 2 H) 8.10-8.22 (m, 3 H) 8.54 (d, J=2.48 Hz, 1 H) 8.78 (dd, J=2.19, 0.73 Hz, 1 H) 10.74 (s, 1 H)

Example 148 (Method V)

Synthesis of N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-chloropicolinamide

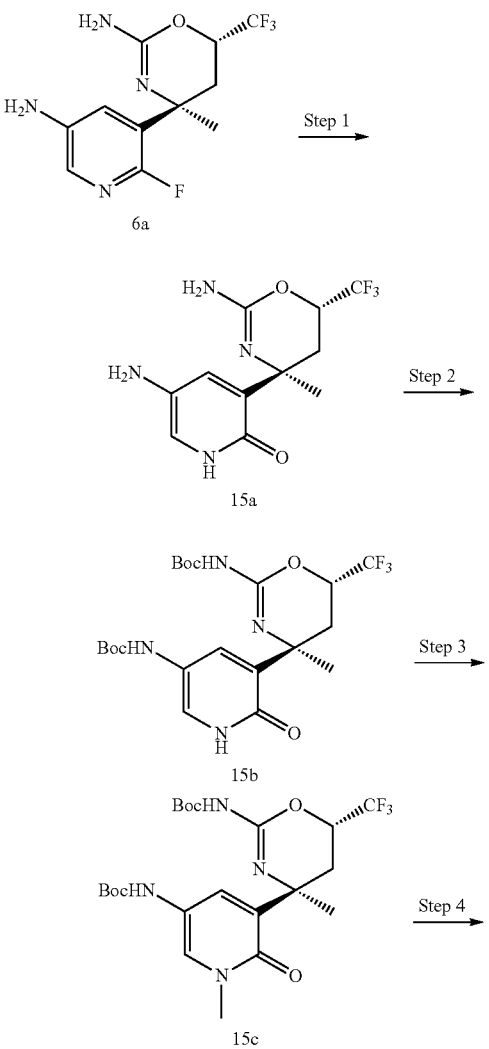

-continued

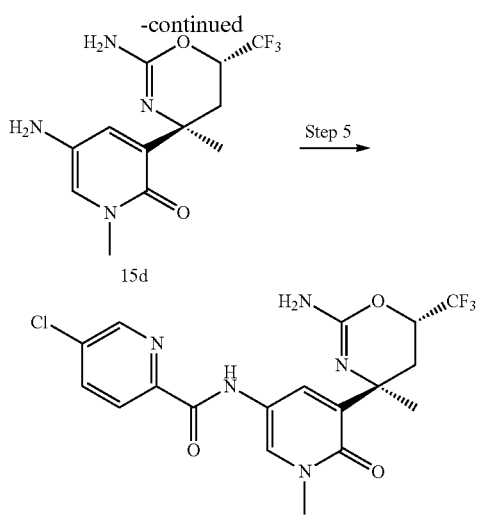

Step 1: 5-amino-3-((4S,6S)-2-amino-4-methyl-6-(trifluoromethyl)-5,6-dihydro-4H-1,3-oxazin-4-yl)pyridin-2(1H)-one (15a)

(4S,6S)-4-(5-amino-2-fluoropyridin-3-yl)-4-methyl-6-(trifluoromethyl)-5,6-dihydro-4H-1,3-oxazin-2-amine (14b, 0.650 g, 2.224 mmol, as described in Example 146, method U, Step 2), hydrogen chloride, 4.0 N solution in 1,4-dioxane (1.0 mL, 28.8 mmol) and water 0.5 mL were combined in a microwave tube. The vials was sealed and heated at 100° C. for 3 h. The mixture was concentrated to dryness and carried to the next step without purification. MS m/z=291.0 [M+H]$^+$. Calculated for $C_{11}H_{13}F_3N_4O_2$: 290.2

Step 2: tert-butyl (5-((4S,6S)-2-tert-butylcarbamate-4-methyl-6-(trifluoromethyl)-5,6-dihydro-4H-1,3-oxazin-4-yl)-6-oxo-1,6-dihydropyridin-3-yl)carbamate (15b)

To a solution of 5-amino-3-((4S,6S)-2-amino-4-methyl-6-(trifluoromethyl)-5,6-dihydro-4H-1,3-oxazin-4-yl)pyridin-2(1H)-one (0.76 g, 2.62 mmol) in dioxane 26 mL was added sodium bicarbonate saturated (26 ml, 622 mmol) followed by di-tert-butyl dicarbonate (0.552 mL, 2.401 mmol). The mixture was stirred at room temperature for 16 h. The mixture was diluted with water and extracted with EtOAc three times. The combined organic layers were washed with brine, dried on sodium sulfate, filtered and concentrated. The crude material was purified by column chromatography using a gradient of 30-90% EtOAc/hexane to give tert-butyl (5-((4S,6S)-2-tert-butylcarbamate-4-methyl-6-(trifluoromethyl)-5,6-dihydro-4H-1,3-oxazin-4-yl)-6-oxo-1,6-dihydropyridin-3-yl)carbamate (1.21 g, 94% yield). MS m/z=491.0 [M+H]$^+$. Calculated for $C_{21}H_{29}F_3N_4O_6$: 490.5

Step 3: tert-butyl (5-((4S,6S)-2-tert-butylcarbamate-4-methyl-6-(trifluoromethyl)-5,6-dihydro-4H-1,3-oxazin-4-yl)-1-methyl-6-oxo-1,6-dihydropyridin-3-yl)carbamate (15c)

To a solution of tert-butyl (5-((4S,6S)-2-tert-butylcarbamate-4-methyl-6-(trifluoromethyl)-5,6-dihydro-4H-1,3-oxazin-4-yl)-6-oxo-1,6-dihydropyridin-3-yl)carbamate (0.600 g, 1.223 mmol) in MeCN 15 mL was added potassium carbonate (0.338 g, 2.447 mmol) followed by methyl iodide (0.532 ml, 8.56 mmol). The reaction was stirred at room temperature for overnight. The reaction mixture was concentrated to dryness, worked up with water and extracted with EtOAc three times. The organic layers were combined and washed with brine, dried over sodium sulfate, filtered and concentrated. The crude material was purified by column chromatography using a gradient of 10-60% diethyl ether/dichloromethane to give tert-butyl (5-((4S,6S)-2-tert-butyl-carbamate-4-methyl-6-(trifluoromethyl)-5,6-dihydro-4H-1,3-oxazin-4-yl)-1-methyl-6-oxo-1,6-dihydropyridin-3-yl)carbamate (0.454 g, 73.6% yield). MS m/z=505.0 [M+H]$^+$. Calculated for $C_{22}H_{31}F_3N_4O_6$: 504.5

Step 4: 5-amino-3-((4S,6S)-2-amino-4-methyl-6-(trifluoromethyl)-5,6-dihydro-4H-1,3-oxazin-4-yl)-1-methylpyridin-2(1H)-one (15d)

To a solution of tert-butyl (5-((4S,6S)-2-tert-butylcarbamate-4-methyl-6-(trifluoromethyl)-5,6-dihydro-4H-1,3-oxazin-4-yl)-1-methyl-6-oxo-1,6-dihydropyridin-3-yl)carbamate (0.454 g, 0.900 mmol) in MeOH (2 mL) was added hydrogen chloride, 4.0N solution in 1,4-dioxane (2.0 mL, 8.00 mmol). The mixture was stirred at room temperature overnight. The solvent was removed to dryness. The residue was treated with neat TFA 20 mL and stirred at room temperature for 30 min. The reaction was completed. The solvent was removed to dryness and worked up with saturated sodium bicarbonate solution and extracted with CHCl$_3$/iPrOH (3:1) six times. The organic layers were combined, dried on sodium sulfate, filtered and concentrated. This material was used without purification. MS m/z=305.0 [M+H]$^+$. Calculated for $C_{12}H_{15}F_3N_4O_2$: 304.3

Step 5: N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-chloropicolinamide This step was performed using procedures analogous to those described in Method H Step 2 (Example 66) above, but using 5-chloro-picolinic acid and 5-amino-3-((4S,6S)-2-amino-4-methyl-6-(trifluoromethyl)-5,6-dihydro-4H-1,3-oxazin-4-yl)-1-methylpyridin-2(1H)-one. MS m/z=444.0 [M+H]$^+$. Calculated for $C_{18}H_{17}ClF_3N_5O_3$: 443.8

$^1$H NMR (300 MHz, DMSO-d$_6$) δ ppm 1.53 (s, 3 H) 1.99 (s, 1 H) 3.18-3.26 (m, 1 H) 3.48 (s, 3 H) 4.11-4.36 (m, 1 H) 5.62-6.13 (br, s, 2 H) 7.71 (d, J=2.92 Hz, 1 H) 8.08-8.20 (m, 2 H) 8.28 (d, J=2.92 Hz, 1 H) 8.76 (d, J=2.50 Hz, 1 H) 10.55 (s, 1 H)

Example 149

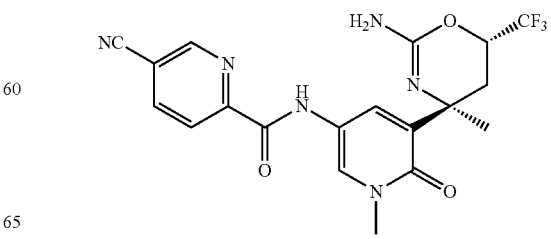

Synthesis of N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-cyanopicolinamide The title compound was synthesized using procedures analogous to those described in Method V (Example 148) above, but using 5-cyano-picolinic acid. MS m/z=434.9 [M+H]+. Calculated for $C_{19}H_{17}F_3N_6O_3$: 434.4

$^1$H NMR (400 MHz, DMSO-$d_6$) δ ppm 1.51 (s, 3 H) 1.57 (br. s., 1 H) 3.22 (d, J=12.91 Hz, 1 H) 3.48 (s, 3 H) 4.13-4.33 (m, 1 H) 5.80 (br. s, 2 H) 7.74 (br. s., 1 H) 8.23 (d, J=7.82 Hz, 1 H) 8.31 (s., 1 H) 8.56 (d, J=8.02 Hz, 1 H) 9.18 (s, 1 H) 10.73 (s, 1 H)

Example 150

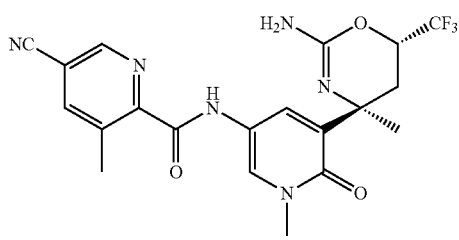 [SMILES: Cc1cc(C#N)cnc1C(=O)Nc1cc([C@]2(C)C[C@@H](C(F)(F)F)OC(N)=N2)c(=O)n(C)c1]

Synthesis of N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-cyano-3-methylpicolinamide The title compound was synthesized using procedures analogous to those described in Method V (Example 148) above, but using 5-cyano-2-methyl-picolinic acid. MS m/z=449.0 [M+H]+. Calculated for $C_{20}H_{19}F_3N_6O_3$: 448.4

$^1$H NMR (400 MHz, DMSO-$d_6$) δ ppm 1.25 (br. s., 2 H) 1.42-1.60 (m, 4 H) 2.54 (s, 3 H) 3.18-3.27 (m, 1 H) 3.49 (s, 3 H) 4.17-4.38 (m, 1 H) 5.84 (br. s, 2 H) 7.59 (br. s., 1 H) 8.34 (s, 1 H) 8.37 (s, 1 H) 8.96 (s, 1 H) 10.57 (br. s., 1 H)

Example 151 (Method X)

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-cyanopicolinamide

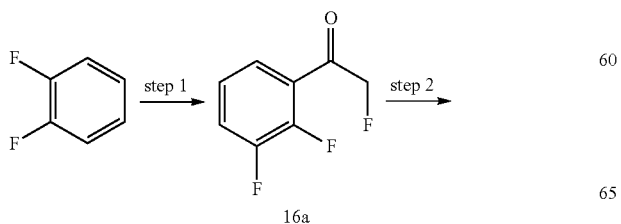

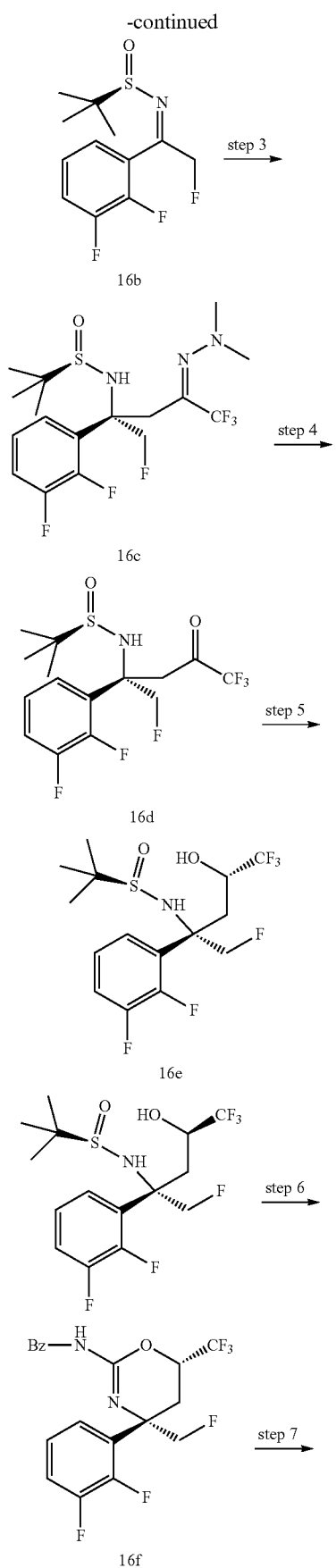

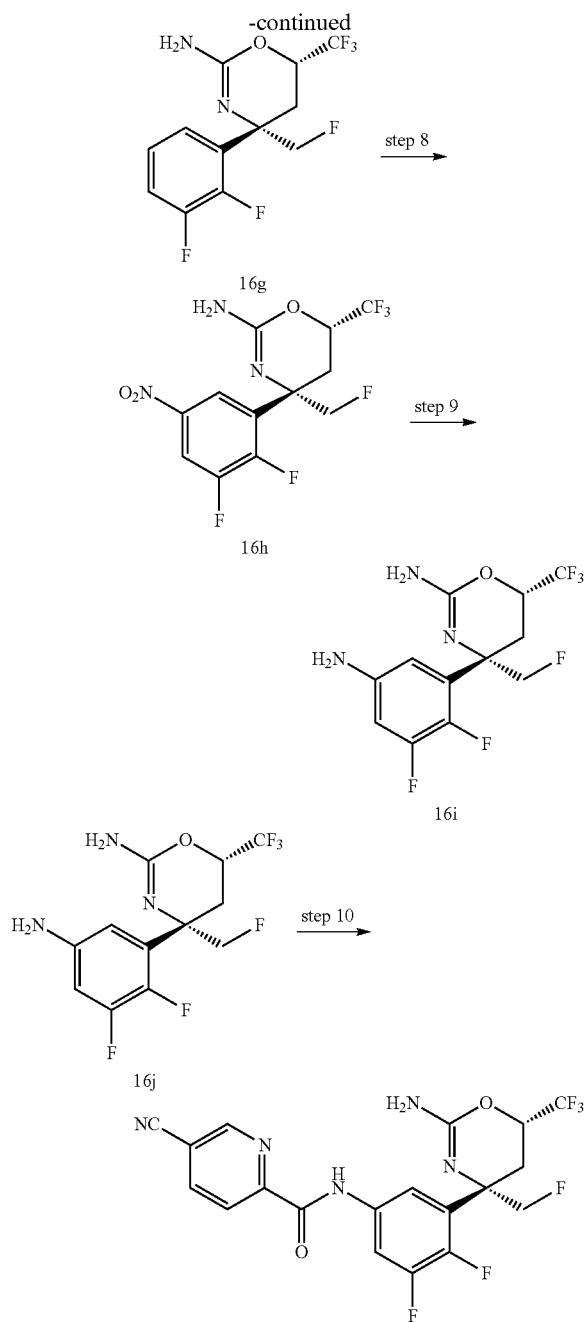

Step 1: 1-(2,3-difluorophenyl)-2-fluoroethanone (16a)

To a cooled (−78° C.) solution of 1,2-difluorobenzene (8.81 mL, 89 mmol) in THF (175 mL) was added dropwise butyllithium solution, 1.6M in hexane (61.5 mL, 98 mmol). After stirred for 2 h, ethyl fluoroacetate (8.64 mL, 89 mmol) ethyl fluoroacetate was added dropwise. The reaction was stirred for 1 h, the reaction was quenched with saturated NH$_4$Cl and then warmed to room temperature. The resulted mixture was extracted with EtOAc. The organic extracts were washed with brine, dried over Na$_2$SO$_4$ and filtered. The filtrate was concentrated and purified by silica gel column (0-30% EtOAc/hexane) to afford 6.3 g of desired product as colorless oil.

Step 2: (R,E)-N-(1-(2,3-difluorophenyl)-2-fluoroethylidene)-2-methylpropane-2-sulfinamide (16b)

To a solution of 1-(2,3-difluorophenyl)-2-fluoroethanone (18.9 g, 109 mmol) in THF (400 mL) was added (R)-(+)-2-methyl-2-propanesulfinamide (26.3 g, 217 mmol) followed by tetraisopropoxytitanium (93 g, 326 mmol). The reaction was heated to reflux for 2 h. The mixture was allowed to cool to room temperature and then treated with brine (400 ml). The resulted suspension was stirred for 15 min and filtered through a pad of celite. The filter cake was washed with EtOAc. The filtrate was extracted with EtOAc (2×). The organic extracts were washed with brine, dried over Na$_2$SO$_4$ and filtered. The filtrate was concentrated and purified by silica gel column (0-20% EtOAc/hexane) to afford (R,E)-N-(1-(2,3-difluorophenyl)-2-fluoroethylidene)-2-methylpropane-2-sulfinamide (12.3 g, 44.4 mmol, 40.9% yield) as yellow oil, MS m/z=278.0 [M+H]$^+$. calculated for C$_{12}$H$_{14}$F$_3$NOS: 277.3

Step 3: (R)-N-((Z)-2-(2,3-difluorophenyl)-4-(2,2-dimethylhydrazono)-1,5,5,5-tetrafluoropentan-2-yl)-2-methylpropane-2-sulfinamide (16c)

To a cooled (−78° C.) solution of (E)-1,1-dimethyl-2-(1,1,1-trifluoropropan-2-ylidene)hydrazine (12.78 g, 83 mmol) in THF (80 mL) was added N-1,N-1,N-2,N2-tetramethylethane-1,2-diamine (9.64 g, 83 mmol) followed by lithium diisopropylamide, 2.0M solution in heptane/tetrahydrofuran/ethylbenzene (41.5 mL, 83 mmol) via syringe, and stirred for 60 min. In a second flask, a solution of (R,E)-N-(1-(2,3-difluorophenyl)-2-fluoroethylidene)-2-methylpropane-2-sulfinamide (11.5 g, 41.5 mmol) in toluene (50 mL) was treated with trimethylaluminum solution, 2.0M in toluene (20.74 mL, 41.5 mmol) at −78° C. After stirred for 10 min, this solution was cannulated to the solution containing hydrazone at −78° C. The reaction mixture was stirred at this temperature for 3 h. Saturated NH$_4$Cl solution was added to quench the reaction. The resulted suspension was allowed to warm to room temperature and then filtered through a pad of celite. The filtrate was extracted with EtOAc (3×). The organic extracts were combined, washed with brine, dried over sodium sulfate and filtered. The filtrate was concentrated and purified by silica gel column (0-50% EtOAc/hexane) to afford (R)-N-((Z)-2-(2,3-difluorophenyl)-4-(2,2-dimethylhydrazono)-1,5,5,5-tetrafluoropentan-2-yl)-2-methylpropane-2-sulfinamide (9.0 g, 20.5 mmol) as yellow oil. The ratio of the two diastereoisomers was about 9:1 based on LCMS. MS m/z=432.2 [M+H]$^+$. Calculated for C17H23F6N3OS: 431.4

Step 4: (R)-N-(2-(2,3-difluorophenyl)-1,5,5,5-tetrafluoro-4-oxopentan-2-yl)-2-methylpropane-2-sulfinamide (16d)

A solution of (R)-N-((Z)-2-(2,3-difluorophenyl)-4-(2,2-dimethylhydrazono)-1,5,5,5-tetrafluoropentan-2-yl)-2-methylpropane-2-sulfinamide (9.0 g, 20.86 mmol) in THF (10 mL) was treated with hydrogen chloride, 2M aq. solution (10.43 mL, 20.86 mmol). The mixture was stirred at ambient temperature for 26 h. LCMS detected formation of desired product and trace of starting material. The reaction was quenched with saturated NaHCO$_3$ solution and then extracted with EtOAc (2×). The organic extracts were washed with brine, dried over Na$_2$SO$_4$ and filtered. The filtrate was concentrated and purified by silica gel column (0-50% EtOAc/hexane) to afford 5.0 g of (R)-N-(2-(2,3-difluorophenyl)-1,5, 5,5-tetrafluoro-4-oxopentan-2-yl)-2-methylpropane-2-sulfinamide as light yellow solid (91% purity). MS m/z=408.0 [M+H+H2O]$^+$. Calculated for C15H17F6NO2S: 389.4

Step 5: (R)-N-((2S,4S)-2-(2,3-difluorophenyl)-1,5,5,5-tetrafluoro-4-hydroxypentan-2-yl)-2-methylpropane-2-sulfinamide (16e)

To a cooled (−15° C.) solution of (R)-N-((S)-2-(2,3-difluorophenyl)-1,5,5,5-tetrafluoro-4-oxopentan-2-yl)-2-methylpropane-2-sulfinamide (5.0 g, 12.84 mmol) in MeOH (20 mL) was added sodium borohydrate (0.729 g, 19.26 mmol). The resulting mixture was stirred at this temperature for 10 min. LCMS indicated reaction went to completion. The mixture was quenched with saturated NaHCO$_3$, diluted with water and extracted with EtOAc (2×). The combined organics were washed with brine, dried over Na$_2$SO$_4$ and filtered. The filtrate was concentrated and the resulted residue was recrystallized in dichloromethane to afford (R)-N-((2S,4S)-2-(2,3-difluorophenyl)-1,5,5,5-tetrafluoro-4-hydroxypentan-2-yl)-2-methylpropane-2-sulfinamide (2.49 g, 6.36 mmol, 49.5% yield) as white solid. The filtrate was the undesired diastereomers and no further purification was carried out. MS m/z=392.1 [M+H]$^+$. Calculated for C15H19F6NO2S: 391.4

Step 6: N-((4S,6S)-4-(2,3-difluorophenyl)-4-(fluoromethyl)-6-(trifluoromethyl)-5,6-dihydro-4H-1,3-oxazin-2-yl)benzamide (16f)

(R)-N-((2S,4S)-2-(2,3-difluorophenyl)-1,5,5,5-tetrafluoro-4-hydroxypentan-2-yl)-2-methylpropane-2-sulfinamide (2.48 g, 6.34 mmol) was dissolved in dichloromethane (12.0 mL) and MeOH (4.0 mL). To this solution was added hydrogen chloride, 4M in 1,4-dioxane (12.0 mL, 48.0 mmol). After stirred for 10 min, the mixture was concentrated, diluted with dichloromethane and washed with 1N NaOH followed by brine. The organic layer was dried over Na$_2$SO$_4$ and then filtered. The filtrate was concentrated and dried to afford (2S,4S)-4-amino-4-(2,3-difluorophenyl)-1,1,1,5-tetrafluoropentan-2-ol as colorless oil. This crude product was dissolved in THF (60 ml) and then treated with benzoyl isothiocyanate (0.938 mL, 6.97 mmol). After stirred for 1.5 h, triethylamine (1.058 mL, 7.60 mmol) and 1-(3-dimethylaminopropyl)-3-ethylcarbodiimide hcl (1.336 g, 6.97 mmol) were added, and the resulted reaction mixture was brought to 70° C. for 2 h. Reaction mixture was partitioned between EtOAc and water. The separated organic layer was washed with brine, dried over Na$_2$SO$_4$ and filtered. The filtrate was concentrated and purified by silica gel column (0-20% EtOAc/hexane) to afford N-((4S,6S)-4-(2,3-difluorophenyl)-4-(fluoromethyl)-6-(trifluoromethyl)-5,6-dihydro-4H-1,3-oxazin-2-yl)benzamide (2.22 g, 5.33 mmol, 84% yield) as white solid. MS m/z=417.1 [M+H]$^+$. Calculated for C19H14F6N2O2: 416.3

Step 7: (4S,6S)-4-(2,3-difluorophenyl)-4-(fluoromethyl)-6-(trifluoromethyl)-5,6-dihydro-4H-1,3-oxazin-2-amine (16g)

To a solution of N-((4S,6S)-4-(2,3-difluorophenyl)-4-(fluoromethyl)-6-(trifluoromethyl)-5,6-dihydro-4H-1,3-oxazin-2-yl)benzamide (2.2 g, 5.28 mmol) in MeOH (25 mL) was added 1,8-diazabicyclo-[5.4.0]undec-7-ene (0.947 mL, 6.34 mmol) The mixture was heated in a 60° C. oil bath for 22 h. The mixture was concentrated under reduced pressure and the residue was partitioned between EtOAc and water. The separated organic layer was washed with brine, dried over Na$_2$SO$_4$ and filtered. The filtrate was concentrated and purified by silica gel column (0-40% EtOAc/hexane) to afford (4S,6S)-4-(2,3-difluorophenyl)-4-(fluoromethyl)-6-(trifluoromethyl)-5,6-dihydro-4H-1,3-oxazin-2-amine (1.62 g, 5.19 mmol, 98% yield) as light yellow solid. MS m/z=313.1 [M+H]$^+$. Calculated for C12H10F6N20: 312.2

Step 8: (4S,6S)-4-(2,3-difluoro-5-nitrophenyl)-4-(fluoromethyl)-6-(trifluoromethyl)-5,6-dihydro-4H-1,3-oxazin-2-amine (16h)

To a cooled (ice bath) solution of (4S,6S)-4-(2,3-difluorophenyl)-4-(fluoromethyl)-6-(trifluoromethyl)-5,6-dihydro-4H-1,3-oxazin-2-amine (1.62 g, 5.19 mmol) in sulfuric acid (24 mL, 450 mmol) was added sodium nitrate (0.573 g, 6.75 mmol) in one portion. After stirred for 15 min, The ice bath was removed and the mixture was stirred for 3 h at room temperature. Reaction was cooled with ice bath, quenched with ice water and basified by addition of potassium carbonate (50 g) in small portion. The resulted suspension was extracted with EtOAc (2×). The organic extracts were washed with brine, dried over Na$_2$SO$_4$ and filtered. The filtrate was concentrated and dried in vacuum to afford crude (4S,6S)-4-(2,3-difluoro-5-nitrophenyl)-4-(fluoromethyl)-6-(trifluoromethyl)-5,6-dihydro-4H-1,3-oxazin-2-amine as yellow oil. It was carried to next step without purification. Assume theoretical yield. MS m/z=358.1 [M+H]$^+$. Calculated for C12H9F6N3O3: 357.2

Step 9: (4S,6S)-4-(5-amino-2,3-difluorophenyl)-4-(fluoromethyl)-6-(trifluoromethyl)-5,6-dihydro-4H-1,3-oxazin-2-amine (16i)

A mixture of (4S,6S)-4-(2,3-difluoro-5-nitrophenyl)-4-(fluoromethyl)-6-(trifluoromethyl)-5,6-dihydro-4H-1,3-oxazin-2-amine (1.85 g, 5.18 mmol) and palladium 10 wt. % (dry basis) on activated carbon, wet (1.000 mL, 0.940 mmol) in EtOH (20 mL) was hydrogenated under a hydrogen balloon for 4 days until full conversion to the desired product. The reaction mixture was filtered through celite and the filter cake was rinsed with EtOAc followed by MeOH/DCM (10%). The filtrate was concentrated to dryness. The residue was triturated with DCM and the resulted suspension was filtered through filter paper. The filter cake was washed with DCM and dried in air to afford (4S,6S)-4-(5-amino-2,3-difluorophenyl)-4-(fluoromethyl)-6-(trifluoromethyl)-5,6-dihydro-4H-1,3-oxazin-2-amine (1.2 g, 3.67 mmol, 70.8% yield) as off-white solid. MS m/z=328.1 [M+H]$^+$. Calculated for $C_{12}H_{11}F_6N_3O$: 327.2

Step 10: N-(3-((4S,6S)-2-amino-4-(fluoromethyl)-6-(trifluoromethyl)-5,6-dihydro-4H-1,3-oxazin-4-yl)-4,5-difluorophenyl)-5-cyanopicolinamide (16j)

To a cooled (ice bath) solution of 5-cyanopicolinic acid (0.043 g, 0.293 mmol) in MeOH (10.0 mL) was added 4-(4,6-dimethoxy-1,3,5-triazin-2-yl)-4-methylmorpholinium chloride (0.094 g, 0.318 mmol). After stirred for 30 min, (4S,6S)-4-(5-amino-2,3-difluorophenyl)-4-(fluoromethyl)-6-(trifluoromethyl)-5,6-dihydro-4H-1,3-oxazin-2-amine (0.080 g, 0.244 mmol) in MeOH (10.0 mL) was added dropwise. The reaction was then stirred at room temperature for 17 h. LCMS showed about 30% remaining starting material. The reaction was quenched with saturated sodium bicarbonate solution. MeOH was removed by rotary evaporation. The aqueous residue was extracted with EtOAc (2×). The organic extracts were combined, concentrated and purified by Shimadzu HPLC to afford N-(3-((4S,6S)-2-amino-4-(fluoromethyl)-6-(trifluoromethyl)-5,6-dihydro-4H-1,3-oxazin-4-yl)-4,5-difluorophenyl)-5-cyanopicolinamide (0.041 g, 0.090 mmol, 36.7% yield) as white solid. MS m/z=458.1 [M+H]$^+$. Calculated for C19H13F6N5O2: 457.3

$^1$H NMR (400 MHz, CHLOROFORM-d) δ ppm 2.21 (t, J=12.91 Hz, 1 H) 2.71 (d, J=13.50 Hz, 1 H) 4.11-4.23 (m, 1 H) 4.41-4.76 (m, 2 H) 7.29 (br. s., 1 H) 8.14 (br. s., 1 H) 8.22 (d, J=7.43 Hz, 1 H) 8.41 (d, J=8.02 Hz, 1 H) 8.89 (br. s., 1 H) 9.91 (br. s., 1 H)

Example 152

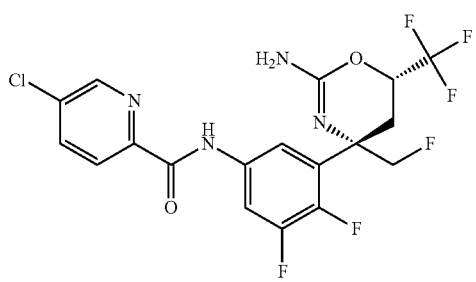 [SMILES: NC1=N[C@](CF)(c2cc(NC(=O)c3ccc(Cl)cn3)cc(F)c2F)C[C@@H](C(F)(F)F)O1]

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-chloropicolinamide The titled compound was synthesized by procedure and steps analogous to those described in Method X, Example 151 above, but using 5-chloro-2-pyridinecarboxylic acid (Oakwood Products, Inc.) in step 10. MS m/z=467.0 [M+H]$^+$. Calculated for C18H13ClF6N4O2: 466.8

$^1$H NMR (400 MHz, CHLOROFORM-d) δ ppm 2.22 (t, J=13.30 Hz, 1 H) 2.65-2.75 (m, 1 H) 4.18 (m, J=5.09 Hz, 1 H) 4.44-4.76 (m, 2 H) 4.77-5.14 (m, 1 H) 7.89 (dd, J=8.41, 2.15 Hz, 1 H) 8.09-8.18 (m, 1 H) 8.22 (d, J=8.41 Hz, 1 H) 8.55 (d, J=1.76 Hz, 1 H) 9.88 (br. s., 1 H)

Example 153

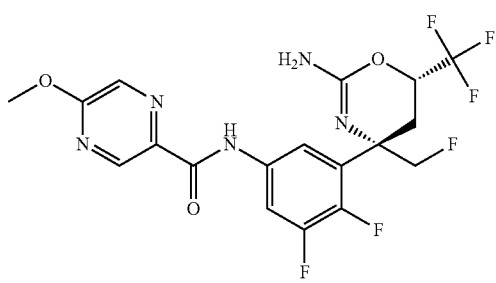 [SMILES: COc1cnc(C(=O)Nc2cc(F)c(F)c([C@]3(CF)C[C@@H](C(F)(F)F)OC(N)=N3)c2)cn1]

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-methoxypyrazine-2-carboxamide The titled compound was synthesized by procedure and steps analogous to those described in Method X, Example 151 above, but using 5-methoxypyrazine-2-carboxylic acid (Ark Pharm, Inc.) in step 10. MS m/z=464.1 [M+H]$^+$. Calculated for C18H15F6N5O3: 463.3

$^1$H NMR (400 MHz, CHLOROFORM-d) δ ppm 2.22 (t, J=13.20 Hz, 1 H) 2.70 (d, J=13.30 Hz, 1 H) 4.07 (s, 3 H) 4.14-4.28 (m, 1 H) 4.37-4.99 (m, 4 H) 7.23 (br. s., 1 H) 8.15 (br. s., 2 H) 9.00 (s, 1 H) 9.55 (br. s., 1 H)

Example 154

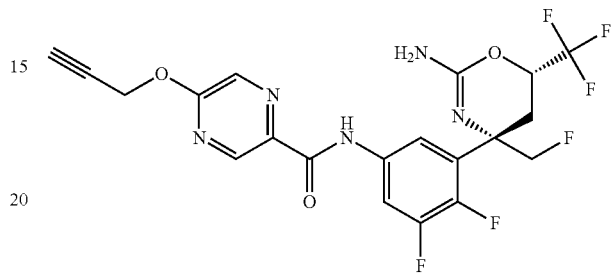

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-(prop-2-yn-1-yloxy)pyrazine-2-carboxamide The titled compound was synthesized by procedure and steps analogous to those described in Method X, Example 151 above, but using 5-(prop-2-yn-1-yloxy)pyrazine-2-carboxylic acid (J. Med. Chem. 2013, 56, 3980) in step 10. MS m/z=488.1 [M+H]$^+$. Calculated for C20H15F6N5O3: 487.4

$^1$H NMR (400 MHz, CHLOROFORM-d) δ ppm 2.21 (t, J=13.30 Hz, 1 H) 2.55 (br. s., 1 H) 2.70 (d, J=14.08 Hz, 1 H) 4.19 (br. s., 1 H) 4.40-4.78 (m, 2 H) 5.09 (br. s., 2 H) 7.22 (br. s., 1 H) 8.13 (br. s., 1 H) 8.21 (br. s., 1 H) 9.02 (br. s., 1 H) 9.55 (br. s., 1 H)

Example 155

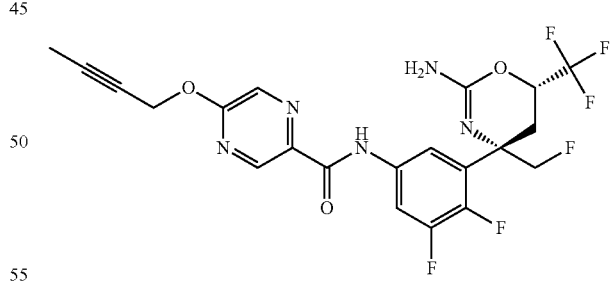

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-(but-2-yn-1-yloxy)pyrazine-2-carboxamide The titled compound was synthesized by procedure and steps analogous to those described in Method X, Example 151 above, but using 5-(but-2-yn-1-yloxy)pyrazine-2-carboxylic acid (J. Med. Chem. 2013, 56, 3980) in step 10. MS m/z=502.1 [M+H]$^+$. Calculated for C21H17F6N5O3: 501.4

¹H NMR (400 MHz, CHLOROFORM-d) δ ppm 1.89 (br. s., 3 H) 2.22 (t, J=13.11 Hz, 1 H) 2.70 (d, J=12.52 Hz, 1 H) 4.11-4.28 (m, 1 H) 4.42-4.78 (m, 2 H) 5.05 (br. s., 2 H) 7.19-7.25 (m, 1 H) 8.08-8.16 (m, 1 H) 8.18 (br. s., 1 H) 9.00 (br. s., 1 H) 9.55 (br. s., 1 H)

Example 156

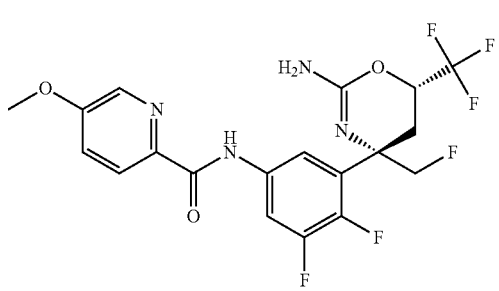

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-methoxypicolinamide The titled compound was synthesized by procedure and steps analogous to those described in Method X, Example 151 above, but using 5-methoxy-2-pyridinecarboxylic acid (Ark Pharm, Inc.) in step 10. MS m/z=463.0 [M+H]⁺. Calculated for C19H16F6N4O3: 462.3

¹H NMR (400 MHz, CHLOROFORM-d) c 2.20-2.32 (m, 1 H) 2.71 (d, J=13.69 Hz, 1 H) 3.94 (s, 3 H) 4.22 (m, J=5.48 Hz, 1 H) 4.46-4.79 (m, 2 H) 7.27-7.30 (m, 1 H) 7.33 (d, J=7.04 Hz, 1 H) 8.09-8.17 (m, 1 H) 8.19 (d, J=8.61 Hz, 1 H) 8.24 (br. s., 1 H) 9.92 (br. s., 1 H)

Example 157

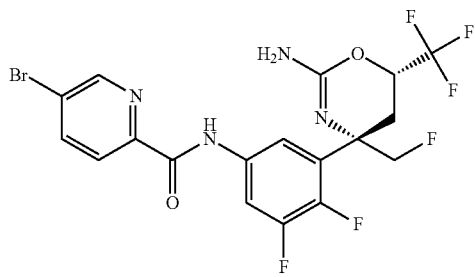

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-bromopicolinamide The titled compound was synthesized by procedure and steps analogous to those described in Method X, Example 151 above, but using 5-bromopyridine-2-carboxylic acid (Matrix Innovation Inc.) in step 10. MS m/z=510.8 [M+H]⁺. Calculated for C18H13BrF6N4O2: 511.2

¹H NMR (400 MHz, CHLOROFORM-d) δ ppm 2.25 (t, J=13.11 Hz, 1 H) 2.69-2.76 (m, 1 H) 4.15-4.26 (m, 1 H) 4.46-4.78 (m, 2 H) 7.28 (br. s., 1 H) 8.05 (dd, J=8.41, 1.96 Hz, 1 H) 8.15 (m, J=8.22 Hz, 2 H) 8.66 (d, J=1.56 Hz, 1 H) 9.92 (br. s., 1 H)

Example 158

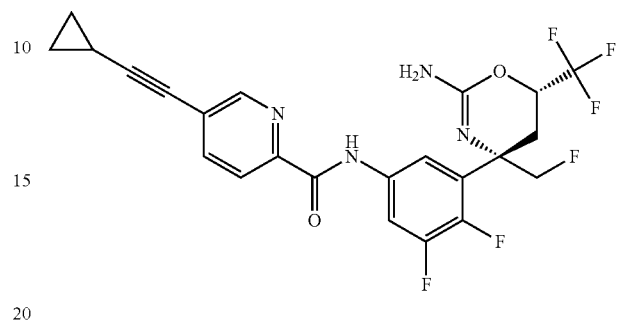

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-(cyclopropylethynyl)picolinamide To a microwave vial were charged with N-(3-((4S,6S)-2-amino-4-(fluoromethyl)-6-(trifluoromethyl)-5,6-dihydro-4H-1,3-oxazin-4-yl)-4,5-difluorophenyl)-5-bromopicolinamide (0.144 g, 0.282 mmol, Example 157), cyclopropylacetylene, 70 wt. % solution in toluene (0.061 mL, 0.507 mmol), copper(I) iodide (8.05 mg, 0.042 mmol), tetrakis(triphenylphosphine)palladium (0.016 g, 0.014 mmol), diethylamine (0.175 mL, 1.690 mmol) and DMF (2.0 mL). The vial was purged with N2 for 5 min, and then microwaved at 90° C. for 50 min. LCMS indicated full conversion to the desired product with MS+=497 (M+1). The reaction mixture was partitioned between EtOAc and water. The separated organic layer was concentrated and the resulted residue was purified by Shimadzu HPLC to afford N-(3-((4S,6S)-2-amino-4-(fluoromethyl)-6-(trifluoromethyl)-5,6-dihydro-4H-1,3-oxazin-4-yl)-4,5-difluorophenyl)-5-(cyclopropylethynyl)picolinamide (0.093 g, 0.187 mmol, 66.5% yield) as light yellow solid. MS m/z=497.1 [M+H]⁺. Calculated for C23H18F6N4O2: 496.4

¹H NMR (400 MHz, CHLOROFORM-d) δ ppm 9.96 (br. s., 1 H), 8.53 (br. s., 1 H), 8.15 (d, J=7.8 Hz, 2 H), 7.83 (d, J=8.0 Hz, 1 H), 4.79-4.38 (m, 2 H), 4.16 (br. s., 1 H), 2.69 (d, J=13.9 Hz, 1 H), 2.20 (t, J=13.0 Hz, 1 H), 1.51 (br. s., 1 H), 1.04-0.81 (m, 5 H)

Example 159

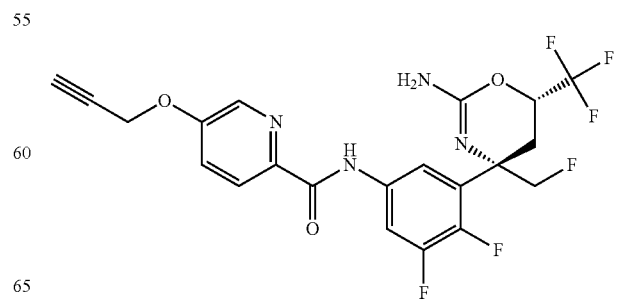

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-(prop-2-yn-1-yloxy)picolinamide The titled compound was synthesized by procedure and steps analogous to those described in Method X, Example 151 above, but using 5-(prop-2-yn-1-yloxy)picolinic acid (intermediate 26) in step 10. MS m/z=487.1 [M+H]⁺. Calculated for C21H16F6N4O3: 486.4

¹H NMR (400 MHz, CHLOROFORM-d) δ ppm 2.23 (t, J=13.11 Hz, 1 H) 2.62 (br. s., 1 H) 2.70 (d, J=13.30 Hz, 1 H) 4.14-4.26 (m, 1 H) 4.46-4.78 (m, 2 H) 4.82 (br. s., 2 H) 7.29 (br. s., 1 H) 7.44 (d, J=7.04 Hz, 1 H) 8.06-8.16 (m, 1 H) 8.20 (d, J=8.41 Hz, 1 H) 8.28 (br. s., 1 H) 9.89 (br. s., 1 H)

Example 160

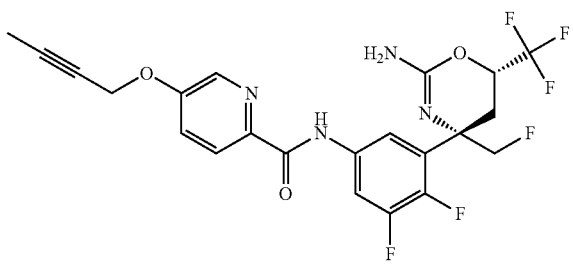 [SMILES: CC#CCOc1cnc(C(=O)Nc2cc(F)c(F)c([C@]3(CF)C[C@@H](C(F)(F)F)OC(N)=N3)c2)cn1]

Synthesis of N-(3-((4S,6S)-2-amino-4-(fluoromethyl)-6-(trifluoromethyl)-5,6-dihydro-4H-1,3-oxazin-4-yl)-4,5-difluorophenyl)-5-(but-2-yn-1-yloxy)picolinamide The titled compound was synthesized by procedure and steps analogous to those described in Method X, Example 151 above, but using 5-(but-2-yn-1-yloxy)picolinic acid (intermediate 25) in step 10. MS m/z=501.1 [M+H]⁺. Calculated for C22H18F6N4O3: 500.4

¹H NMR (400 MHz, CHLOROFORM-d) δ ppm 1.87 (br. s., 3 H) 2.30 (t, J=13.40 Hz, 1 H) 2.74 (d, J=13.30 Hz, 1 H) 4.25 (m, J=5.67 Hz, 1 H) 4.45-4.71 (m, 2 H) 4.78 (br. s., 2 H) 7.44 (d, J=7.24 Hz, 1 H) 8.21 (d, J=8.61 Hz, 2 H) 8.31 (br. s., 1 H) 9.96 (br. s., 1 H)

Example 161

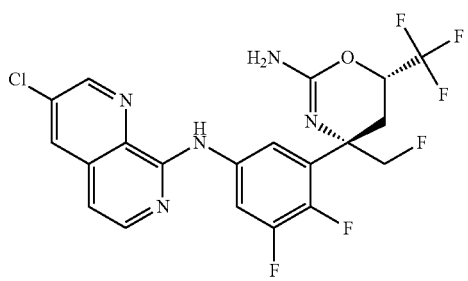 [SMILES: NC1=N[C@](CF)(c2cc(Nc3nccc4cc(Cl)cnc34)cc(F)c2F)C[C@@H](C(F)(F)F)O1]

Synthesis of (4S,6S)-4-(5-((3-chloro-1,7-naphthyridin-8-yl)amino)-2,3-difluorophenyl)-4-(fluoromethyl)-6-(trifluoromethyl)-5,6-dihydro-4H-1,3-oxazin-2-amine The title compound was synthesized by procedures and steps analogous to those described in Method B, Example 8 above, but using (4S,6S)-4-(5-amino-2,3-difluorophenyl)-4-(fluoromethyl)-6-(trifluoromethyl)-5,6-dihydro-4H-1,3-oxazin-2-amine (16j) and 3,8-dichloro-1,7-naphthyridine (intermediate 2) in step 2. MS m/z=490.1 [M+H]⁺. Calculated for C20H14ClF6N5O: 489.8

¹H NMR (400 MHz, CHLOROFORM-d) δ ppm 2.19 (t, J=13.11 Hz, 1 H) 2.68 (d, J=12.52 Hz, 1 H) 4.21 (m, J=4.89 Hz, 1 H) 4.49-4.78 (m, 2 H) 6.92 (d, J=5.48 Hz, 1 H) 7.36 (br. s., 1 H) 7.96 (s, 1 H) 8.11 (d, J=5.67 Hz, 1 H) 8.41-8.50 (m, 1 H) 8.60 (s, 1 H) 8.94 (br. s., 1 H)

Example 162

Synthesis of 8-((3-((4S,6S)-2-amino-4-(fluoromethyl)-6-(trifluoromethyl)-5,6-dihydro-4H-1,3-oxazin-4-yl)-4,5-difluorophenyl)amino)-1,7-naphthyridine-3-carbonitrile The title compound was synthesized by procedures and steps analogous to those described in Method C, but using (4S,6S)-4-(5-((3-chloro-1,7-naphthyridin-8-yl)amino)-2,3-difluorophenyl)-4-(fluoromethyl)-6-(trifluoromethyl)-5,6-dihydro-4H-1,3-oxazin-2-amine (Example 161). MS m/z=481.1 [M+H]⁺. Calculated for C21H14F6N6O: 480.4

¹H NMR (400 MHz, CHLOROFORM-d) ppm 9.03 (s, 1 H), 8.91 (d, J=1.4 Hz, 1 H), 8.45 (ddd, J=2.5, 7.0, 12.2 Hz, 1 H), 8.39 (d, J=1.4 Hz, 1 H), 8.24 (d, J=5.7 Hz, 1 H), 7.42-7.34 (m, 1 H), 7.06 (d, J=5.9 Hz, 1 H), 4.81-4.46 (m, 2 H), 4.28-4.16 (m, 1 H), 2.70 (dd, J=2.2, 13.7 Hz, 1 H), 2.22 (t, J=13.1 Hz, 1 H)

Example 163 (Method Y)
Synthesis of N-(3-((4S,6S)-2-amino-4-methyl-6-(trifluoromethyl)-5,6-dihydro-4H-1,3-oxazin-4-yl)-4,5-difluorophenyl)-5-cyanopicolinamide
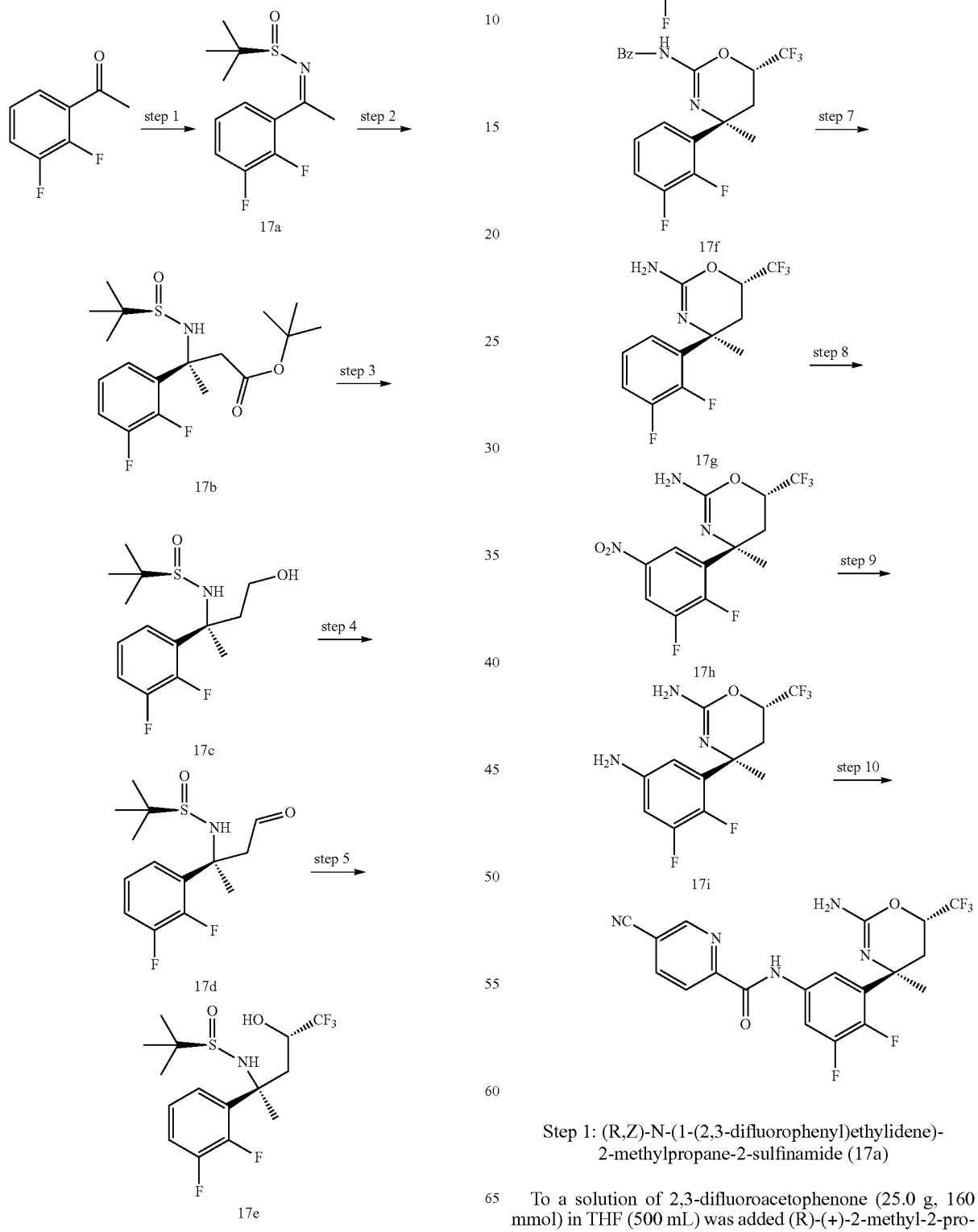
Step 1: (R,Z)-N-(1-(2,3-difluorophenyl)ethylidene)-2-methylpropane-2-sulfinamide (17a)
To a solution of 2,3-difluoroacetophenone (25.0 g, 160 mmol) in THF (500 mL) was added (R)-(+)-2-methyl-2-propanesulfinamide (38.8 g, 320 mmol) followed by tetraisopropoxytitanium (142 mL, 480 mmol). The reaction was heated to reflux for 3 days. The mixture was allowed to cool to room temperature and then treated with brine (550 ml). The resulted suspension was stirred for 15 min and filtered through celite. The filter cake was washed with EtOAc. The filtrate was extracted with EtOAc (2×). The organic extracts were washed with brine, dried over $Na_2SO_4$ and filtered. The filtrate was concentrated and purified by silica gel column (10-35% EtOAc/hexane) to afford (R,Z)-N-(1-(2,3-difluorophenyl)ethylidene)-2-methylpropane-2-sulfinamide (35.6 g, 137 mmol, 86% yield) as yellow oil. MS m/z=260.1 [M+H]$^+$ calculated for C12H15F2NOS: 259.3

Step 2: (5)-tert-butyl 3-(2,3-difluorophenyl)-3-((R)-1,1-dimethylethylsulfinamido)butanoate (17b)

To a cooled (ice bath) solution of (R,Z)-N-(1-(2,3-difluorophenyl)ethylidene)-2-methylpropane-2-sulfinamide (30.0 g, 116 mmol) in THF (600 mL) was added dropwise 2-tert-butoxy-2-oxoethylzinc chloride 0.5 m in diethyl ether (600 mL, 300 mmol). The reaction was stirred for 2 h after the addition was completed. Ice bath was removed and stirred for additional 2 h. The reaction was quenched with saturated $NH_4Cl$ solution, and then diluted with water and EtOAc. The separated organic layer was washed with brine, dried over $Na_2SO_4$ and filtered. The filtrate was concentrated and purified by silica gel chromatograph (0-50% EtOAc/hexane) to afford 18 g of (S)-tert-butyl difluorophenyl)-3-((R)-1,1-dimethylethylsulfinamido) butanoate as yellow oil. MS m/z=398.1 [M+H+Na]$^+$ calculated for C18H27F2NO3S: 375.5

Step 3: (R)-N-(2-(2,3-difluorophenyl)-4-hydroxybutan-2-yl)-2-methylpropane-2-sulfinamide (17c)

To a solution of tert-butyl 3-(2,3-difluorophenyl)-3-((R)-1,1-dimethylethylsulfinamido)butanoate (17.9 g, 47.7 mmol) in THF (250 mL) at ambient temperature was added lithium borohydride, 2m solution in THF (47.7 mL, 95 mmol) followed by MeOH (12 mL, slightly exothermic reaction. added slowly via syringe). After stirred for 2 h, the reaction was carefully quenched by the addition of saturated ammonium chloride, followed by water and EtOAc. The separated organic phase was washed with brine, dried over $Na_2SO_4$ and filtered. The filtrate was concentrated and dried in vacuum to afford (R)-N-(2-(2,3-difluorophenyl)-4-hydroxybutan-2-yl)-2-methylpropane-2-sulfinamide as light yellow foam. It was carried to next step without purification. MS m/z=306.1 [M+H]$^+$. Calculated for C14H21F2NO2S: 305.4

Step 4: (R)-N-((S)-2-(2,3-difluorophenyl)-4-oxobutan-2-yl)-2-methylpropane-2-sulfinamide (17d)

To a solution of (R)-N-((S)-2-(2,3-difluorophenyl)-4-hydroxybutan-2-yl)-2-methylpropane-2-sulfinamide (14.56 g, 47.7 mmol) in DCM (250 ml) at room temperature was added Dess-Martin periodinane (22.24 g, 52.4 mmol) in one portion. The reaction was stirred at room temperature overnight. The reaction was quenched with water (150 ml) and saturated $NaHCO_3$ solution (150 ml). The resulted solution was diluted with DCM and the layers were separated. The organic layer was washed with saturated $NaHCO_3$ (3×), water and brine. The solution was then dried over $Na_2SO_4$ and filtered. The filtrate was concentrated and purified by silica gel column (20-65% EtOAc/hexane) to afford (R)-N-((S)-2-(2,3-difluorophenyl)-4-oxobutan-2-yl)-2-methylpropane-2-sulfinamide (13.5 g, 44.5 mmol, 93% yield) as light yellow oil. MS m/z=304.1 [M+H]$^+$. Calculated for C14H19F2NO2S: 303.4

Step 5: (R)-N-((4S)-2-(2,3-difluorophenyl)-5,5,5-trifluoro-4-hydroxypentan-2-yl)-2-methylpropane-2-sulfinamide (17e)

To a cooled (−78° C.) solution of (R)-N-(2-(2,3-difluorophenyl)-4-oxobutan-2-yl)-2-methylpropane-2-sulfinamide (13.5 g, 44.5 mmol) in THF (300 mL) was added (trifluoromethyl)trimethylsilane (70.7 mL, 445 mmol) via syringe in 5 min (internal temperature was up to −55° C.). After stirring for 20 min, tetrabutylammonium fluoride, 1.0M solution in THF (66.8 mL, 66.8 mmol) was added dropwise via additional funnel (internal temperature −78 to −50° C. during addition). Addition was completed in 20 min. The reaction was stirred at the same temperature for 1 h. LCMS showed the diastereomer ratio was about 2:3 with the major one as the desired product. The reaction was quenched with 1N HCl (45 ml), and then the cool bath was removed. The reaction mixture was allowed to warm to ambient temperature during which water (100 ml) was added. The solution was extracted with EtOAc (2×). The organic extracts were washed with brine, dried over $Na_2SO_4$ and filtered. The filtrate was concentrated and the residue was triturated with minimum DCM. The resulted suspension was filtered. The filter cake was rinsed a few times with DCM and dried in air to afford 6.3 g of desired product as an white solid. The filtrate was concentrated and purified by silica gel column (0-70% EtOA/hexane) to afford additional 911 mg of desired product. MS m/z=374.1 [M+H]$^+$. Calculated for $C_{15}H_{20}F_5NO_2S$: 373.4

Step 6: N-((4S,6S)-4-(2,3-difluorophenyl)-4-methyl-6-(trifluoromethyl)-5,6-dihydro-4H-1,3-oxazin-2-yl)benzamide (17f)

(R)-N-((2S,4S)-2-(2,3-difluorophenyl)-5,5,5-trifluoro-4-hydroxypentan-2-yl)-2-methylpropane-2-sulfinamide (7.18 g, 19.23 mmol) was dissolved in DCM (50 mL) and MeOH (25 mL) to form a clear solution. To this solution was added hydrogen chloride, 4M in 1,4-dioxane (48.1 ml, 192 mmol) via syringe. After stirred for 40 min, the mixture was concentrated, basified with 1N NaOH and diluted with DCM (400 ml) and water (50 ml). The separated organic layer was washed with brine (2×), dried over $Na_2SO_4$ and then filtered. The filtrate was concentrated and dried in vacuum to afford (2S,4S)-4-amino-4-(2,3-difluorophenyl)-1,1,1-trifluoropentan-2-ol as white solid with MS+=270 (M+1). This crude product was dissolved in THF (100 ml) and then treated with benzoyl isothiocyanate (2.85 ml, 21.15 mmol). After stirred for 40 min, triethylamine (3.21 ml, 23.08 mmol) and N1-((ethylimino)methylene)-N3,N-3-dimethylpropane-1,3-diamine hydrochloride (4.05 g, 21.15 mmol) were added. The resulted suspension was brought up to 70° C. for 40 min. Then the reaction mixture was partitioned between EtOAc and water. The separated organic layer was washed with brine, dried over $Na_2SO_4$ and filtered. The filtrate was concentrated and purified by silica gel column (0-20% EtOAc/hexane) to afford N-((4S,6S)-4-(2,3-difluorophenyl)-4-methyl-6-(trifluoromethyl)-5,6-dihydro-4H-1,3-oxazin-2-yl)benzamide (7.0 g, 17.57 mmol, 91% yield) as white solid. MS m/z=399.0 [M+H]$^+$. Calculated for $C_{19}H_{15}F_5N_2O_2$: 398.3

Step 7: (4S,6S)-4-(2,3-difluorophenyl)-4-methyl-6-(trifluoromethyl)-5,6-dihydro-4H-1,3-oxazin-2-amine (17g)

To a solution of N-((4S,6S)-4-(2,3-difluorophenyl)-4-methyl-6-(trifluoromethyl)-5,6-dihydro-4H-1,3-oxazin-2-yl) benzamide (7.0 g, 17.57 mmol) in MeOH (100 mL) was added 1,8-diazabicyclo-[5.4.0]undec-7-ene (3.15 mL, 21.09 mmol). The mixture was brought up to 60° C. for 15 h until the conversion was completed. The mixture was concentrated under reduced pressure and the residue was partitioned between EtOAc and water. The separated organic layer was washed with brine, dried over $Na_2SO_4$ and filtered. The filtrate was concentrated and purified by silica gel column (0-60% EtOAc/hexane) to afford (4S,6S)-4-(2,3-difluorophenyl)-4-methyl-6-(trifluoromethyl)-5,6-dihydro-4H-1,3-oxazin-2-amine (4.94 g, 16.79 mmol, 96% yield) as white crystalline solid. MS m/z=295.1 $[M+H]^+$. Calculated for $C_{12}H_{11}F_5N_2O$: 294.2

Step 8: (4S,6S)-4-(2,3-difluoro-5-nitrophenyl)-4-methyl-6-(trifluoromethyl)-5,6-dihydro-4H-1,3-oxazin-2-amine (17h)

To a cooled (ice bath) solution of (4S,6S)-4-(2,3-difluorophenyl)-4-methyl-6-(trifluoromethyl)-5,6-dihydro-4H-1,3-oxazin-2-amine (4.94 g, 16.79 mmol) in sulfuric acid (20 ml, 375 mmol) was added sodium nitrate (1.855 g, 21.83 mmol) in one portion. After stirring for 15 min, ice bath was removed, and the mixture was stirred at room temperature for 1 h. The reaction mixture was poured into ice water containing potassium carbonate (18g). The resulting suspension was extracted with EtOAc (2×). The organic extracts were washed with brine, dried over $Na_2SO_4$ and filtered. The filtrate was concentrated and purified by silica gel column (10-60% EtOAc/hexane) to afford (4S,6S)-4-(2,3-difluoro-5-nitrophenyl)-4-methyl-6-(trifluoromethyl)-5,6-dihydro-4H-1,3-oxazin-2-amine (5.6 g, 16.51 mmol, 98% yield) as light yellow solid in 91% pure. MS m/z=340.1 $[M+H]^+$. Calculated for $C_{12}H_{10}F_5N_3O_3$: 339.2

Step 9: (4S,6S)-4-(5-amino-2,3-difluorophenyl)-4-methyl-6-(trifluoromethyl)-5,6-dihydro-4H-1,3-oxazin-2-amine (17i)

To a cooled (water bath) solution of ((4S,6S)-4-(2,3-difluoro-5-nitrophenyl)-4-methyl-6-(trifluoromethyl)-5,6-dihydro-4H-1,3-oxazin-2-amine (5.5 g, 16.21 mmol) in AcOH (65 mL) was added trifluoroacetic acid (8.43 mL, 113 mmol) followed by zinc powder, <150 micron (0.747 mL, 81 mmol) in one portion (exothermic). After stirring for 10 min, the water bath was removed. The reaction mixture was stirred at ambient temperature for 2 h. Additional TFA (2 mL) and zinc powder (0.5 g) were added and stirred for additional 2 h. LCMS showed no increased formation of the desired product (still 70%). The mixture was filtered through celite and the filtrate was concentrated. The residue was basified with saturated $NaHCO_3$ and extracted with EtOAc (2×). The organic extracts were washed with brine, dried over $Na_2SO_4$ and filtered. The filtrate was concentrated and then triturated with minimum DCM. The resulted suspension was filtered, and the filter cake was rinsed with DCM and dried in air to afford 3.1 g of desired aniline as white solid (TFA salt); The mother liquid was purified by silica gel column (50-100% EtOAc/hexane) to afford additional 0.88 g of aniline (free base). MS m/z=310.1 $[M+H]^+$. Calculated for $C_{12}H_{12}F_5N_3O$: 309.2

Step 10: N-(3-((4S,6S)-2-amino-4-methyl-6-(trifluoromethyl)-5,6-dihydro-4H-1,3-oxazin-4-yl)-4,5-difluorophenyl)-5-cyanopicolinamide To a cooled (ice bath) solution of (4S,6S)-4-(5-amino-2,3-difluorophenyl)-4-methyl-6-(trifluoromethyl)-5,6-dihydro-4H-1,3-oxazin-2-amine (0.095 g, 0.307 mmol) and 5-cyano-2-pyridinecarboxylic acid (0.055 g, 0.369 mmol) in THF (2.5 mL) and MeOH (1.5 mL) was added 4-(4,6-dimethoxy-1,3,5-triazin-2-yl)-4-methylmorpholinium chloride (0.118 g, 0.399 mmol). After stirring for 30 min, the ice bath was removed. The reaction was stirred at ambient temperature for 15 h. The reaction was quenched with saturated sodium bicarbonate solution. MeOH was removed by rotary evaporation. The aqueous residue was extracted with EtOAc (2×). The organic extracts were combined, concentrated and purified by Shimadzu HPLC to afford N-(3-((4S,6S)-2-amino-4-methyl-6-(trifluoromethyl)-5,6-dihydro-4H-1,3-oxazin-4-yl)-4,5-difluorophenyl)-5-cyanopicolinamide (0.053 g, 0.121 mmol, 39.3% yield) as white solid. MS m/z=440.1 $[M+H]^+$. Calculated for $C_{19}H_{14}F_5N_5O_2$: 439.3

$^1$H NMR (400 MHz, CHLOROFORM-d) δ ppm 1.67 (s, 3 H) 1.93 (t, J=13.20 Hz, 1 H) 2.80 (d, J=12.91 Hz, 1 H) 3.99-4.12 (m, 1 H) 7.16 (br. s., 1 H) 8.04-8.12 (m, 1 H) 8.21 (d, J=8.02 Hz, 1 H) 8.41 (d, J=8.02 Hz, 1 H) 8.89 (s, 1 H) 9.86 (br. s., 1 H)

Example 164

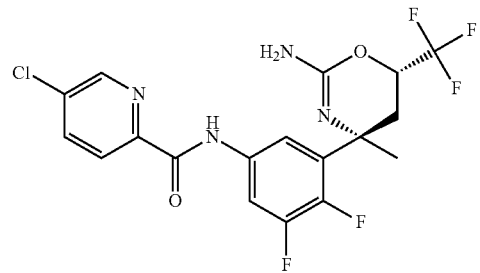 [SMILES: C[C@@]1(c2cc(NC(=O)c3ccc(Cl)cn3)cc(F)c2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4,5-difluorophenyl)-5-chloropicolinamide The titled compound was synthesized by procedure and steps analogous to those described in Method Y, Example 163 above, but using 5-chloro-2-pyridinecarboxylic acid (Oakwood Products, Inc.) in step 10. MS m/z=449.0 $[M+H]^+$. Calculated for $C18H14ClF5N4O2$: 448.8

$^1$H NMR (400 MHz, CHLOROFORM-d) δ ppm 1.68 (s, 3 H) 1.94 (t, J=13.20 Hz, 1 H) 2.81 (dd, J=13.79, 2.45 Hz, 1 H) 4.01-4.14 (m, 1 H) 7.11-7.18 (m, 1 H) 7.89 (dd, J=8.41, 2.15 Hz, 1 H) 8.08 (ddd, J=11.49, 6.90, 2.54 Hz, 1 H) 8.23 (d, J=8.41 Hz, 1 H) 8.56 (d, J=1.96 Hz, 1 H) 9.85 (br. s., 1 H)

Example 165

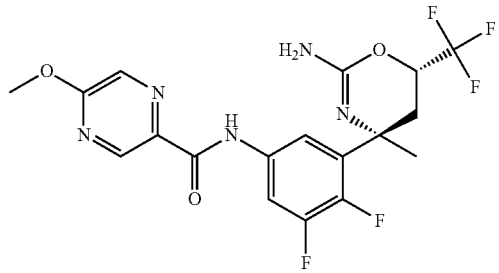 [SMILES: COc1cnc(C(=O)Nc2cc(F)c(F)c([C@]3(C)C[C@@H](C(F)(F)F)OC(N)=N3)c2)cn1]

Synthesis of N-(3-((4S,6S)-2-amino-4-methyl-6-(trifluoromethyl)-5,6-dihydro-4H-1,3-oxazin-4-yl)-4,5-difluorophenyl)-5-methoxypyrazine-2-carboxamide The titled compound was synthesized by procedure and steps analogous to those described in Method Y, Example 163 above, but using 5-methoxypyrazine-2-carboxylic acid (Ark Pharm, Inc.) in step 10. MS m/z=446.1 [M+H]$^+$. Calculated for $C_{18}H_{16}F_5N_5O_3$: 445.3

$^1$H NMR (400 MHz, CHLOROFORM-d) δ ppm 1.66 (s, 3 H) 1.92 (t, J=13.20 Hz, 1 H) 2.79 (dd, J=13.69, 2.54 Hz, 1 H) 4.01-4.06 (m, 1 H) 4.07 (s, 3 H) 7.08-7.15 (m, 1 H) 8.06 (ddd, J=11.64, 6.94, 2.54 Hz, 1 H) 8.14 (d, J=0.98 Hz, 1 H) 9.00 (d, J=1.17 Hz, 1 H) 9.51 (br. s., 1 H)

Example 166

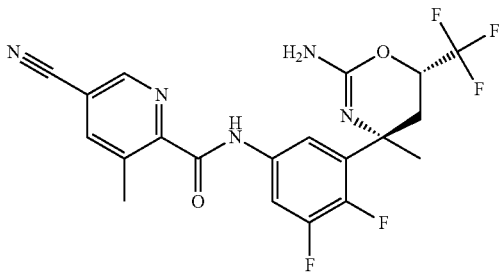 [SMILES: Cc1cc(C#N)cnc1C(=O)Nc1cc(F)c(F)c([C@]2(C)C[C@@H](C(F)(F)F)OC(N)=N2)c1]

Synthesis of N-(3-((4S,6S)-2-amino-4-methyl-6-(trifluoromethyl)-5,6-dihydro-4H-1,3-oxazin-4-yl)-4,5-difluorophenyl)-5-methoxypyrazine-2-carboxamide The titled compound was synthesized by procedure and steps analogous to those described in Method Y, Example 163 above, but using 5-methoxypyrazine-2-carboxylic acid (Ark Pharm, Inc.) in step 10. MS m/z=446.1 [M+H]$^+$. Calculated for C18H16F5N5O3: 445.3

$^1$H NMR (400 MHz, CHLOROFORM-d) δ ppm 1.66 (s, 3 H) 1.92 (t, J=13.20 Hz, 1 H) 2.79 (dd, J=13.69, 2.54 Hz, 1 H) 4.01-4.06 (m, 1 H) 4.07 (s, 3 H) 7.08-7.15 (m, 1 H) 8.06 (ddd, J=11.64, 6.94, 2.54 Hz, 1 H) 8.14 (d, J=0.98 Hz, 1 H) 9.00 (d, J=1.17 Hz, 1 H) 9.51 (br. s., 1 H)

Example 167

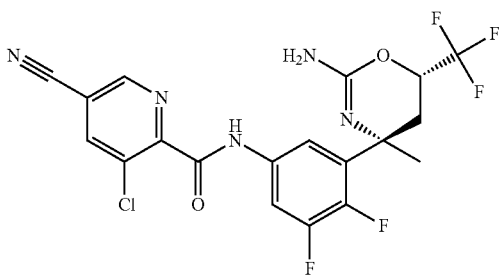 [SMILES: C[C@@]1(c2cc(NC(=O)c3ncc(C#N)cc3Cl)cc(F)c2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4,5-difluorophenyl)-3-chloro-5-cyanopicolinamide The titled compound was synthesized by procedure and steps analogous to those described in Method Y, Example 163 above, but using 3-chloro-5-cyanopicolinic acid in step 10. MS m/z=473.9 [M+H]$^+$. Calculated for C19H13ClF5N5O2: 473.8

$^1$H NMR (400 MHz, CHLOROFORM-d) δ ppm 1.66 (br. s., 3 H) 1.90-1.96 (m, 1 H) 2.81 (d, J=13.50 Hz, 1 H) 4.01-4.10 (m, 1 H) 7.05 (br. s., 1 H) 8.10-8.21 (m, 2 H) 8.78 (br. s., 1 H) 9.75 (br. s., 1 H)

Example 168

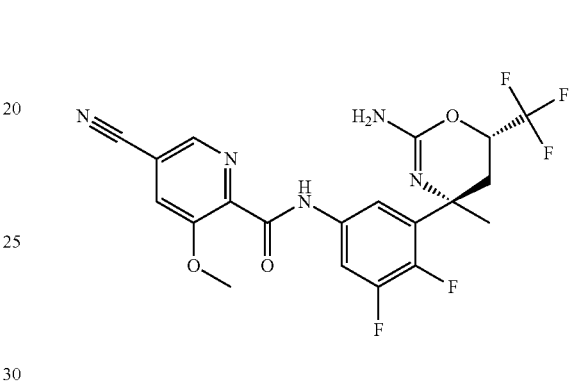

Synthesis of N-(3-((4S,6S)-2-amino-4-methyl-6-(trifluoromethyl)-5,6-dihydro-4H-1,3-oxazin-4-yl)-4,5-difluorophenyl)-5-cyano-3-methoxypicolinamide The titled compound was synthesized by procedure and steps analogous to those described in Method Y, Example 163 above, but using 5-cyano-3-methoxypicolinic acid (intermediate 15) in step 10. MS m/z=449.0 [M+H]$^+$. Calculated for $C_{20}H_{16}F_5N_5O_3$: 469.4

$^1$H NMR (400 MHz, CHLOROFORM-d) δ ppm 1.65 (br. s., 3 H) 1.87-1.97 (m, 1 H) 2.79 (d, J=13.30 Hz, 1 H) 4.05 (br. s., 4 H) 7.04 (br. s., 1 H) 7.66 (br. s., 1 H) 8.13 (br. s., 1 H) 8.47 (br. s., 1 H) 9.70 (br. s., 1 H)

Example 169

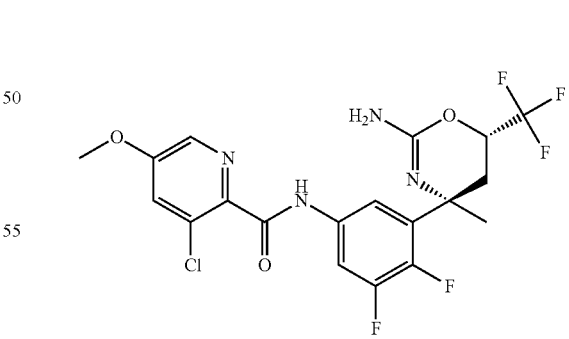

Synthesis of N-(3-((4S,6S)-2-amino-4-methyl-6-(trifluoromethyl)-5,6-dihydro-4H-1,3-oxazin-4-yl)-4,5-difluorophenyl)-3-chloro-5-methoxypicolinamide The titled compound was synthesized by procedure and steps analogous to those described in Method Y, Example 163 above, but using 3-chloro-5-methoxypicolinic acid (intermediate 27) in step 10. MS m/z=478.9 [M+H]⁺. Calculated for C19H16ClF5N4O3: 478.8

¹H NMR (400 MHz, CHLOROFORM-d) δ ppm 1.65 (s, 3 H) 1.91 (t, J=13.11 Hz, 1 H) 2.79 (d, J=12.91 Hz, 1 H) 3.95 (s, 3 H) 4.05 (br. s., 1 H) 6.99 (br. s., 1 H) 7.32 (br. s., 1 H) 8.18 (br. s., 2 H) 9.86 (br. s., 1 H)

Example 170

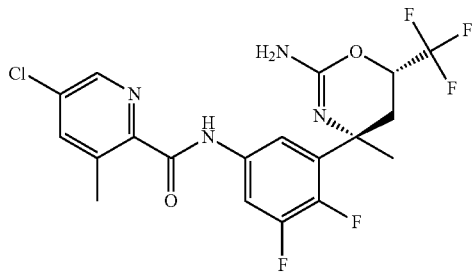 [SMILES: Cc1cc(Cl)cnc1C(=O)Nc1cc(F)c(F)c([C@]2(C)C[C@@H](C(F)(F)F)OC(N)=N2)c1]

Synthesis of N-(3-((4S,6S)-2-amino-4-methyl-6-(trifluoromethyl)-5,6-dihydro-4H-1,3-oxazin-4-yl)-4,5-difluorophenyl)-5-chloro-3-methylpicolinamide The titled compound was synthesized by procedure and steps analogous to those described in Method Y, Example 163 above, but using 5-chloro-3-methyl-pyridine-2-carboxylic acid (Frontier Scientific, Inc) in step 10. MS m/z=463.0 [M+H]⁺. Calculated for C19H16ClF5N4O2: 462.8

¹H NMR (400 MHz, CHLOROFORM-d) δ ppm 1.68 (br. s., 3 H) 1.94 (t, J=12.52 Hz, 1 H) 2.78 (br. s., 4 H) 3.99-4.15 (m, 1 H) 7.03 (br. s., 1 H) 7.66 (br. s., 1 H) 8.11 (br. s., 1 H) 8.39 (br. s., 1 H) 10.06 (br. s., 1 H)

Example 171

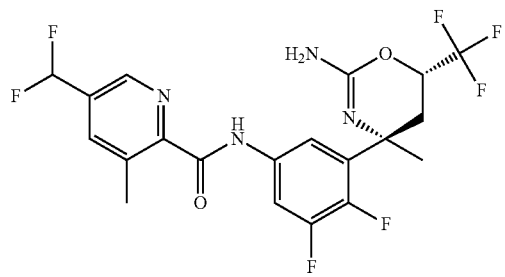 [SMILES: Cc1cc(C(F)F)cnc1C(=O)Nc1cc(F)c(F)c([C@]2(C)C[C@@H](C(F)(F)F)OC(N)=N2)c1]

Synthesis of N-(3-((4S,6S)-2-amino-4-methyl-6-(trifluoromethyl)-5,6-dihydro-4H-1,3-oxazin-4-yl)-4,5-difluorophenyl)-5-(difluoromethyl)-3-methylpicolinamide The titled compound was synthesized by procedure and steps analogous to those described in Method Y, Example 163 above, but using 5-(difluoromethyl)-3-methylpicolinic acid (WO2012095521) in step 10. MS m/z=479.0 [M+H]⁺. Calculated for C20H17F7N4O2: 478.4

¹H NMR (400 MHz, CHLOROFORM-d) δ ppm 1.67 (s, 3 H) 1.89-1.97 (m, 1 H) 2.78-2.83 (m, 1 H) 2.85 (s, 3 H) 4.02-4.13 (m, 1 H) 6.60-6.92 (m, 1 H) 7.05 (br. s., 1 H) 7.79 (s, 1 H) 8.09-8.17 (m, 1 H) 8.59 (s, 1 H) 10.19 (br. s., 1 H)

Example 172

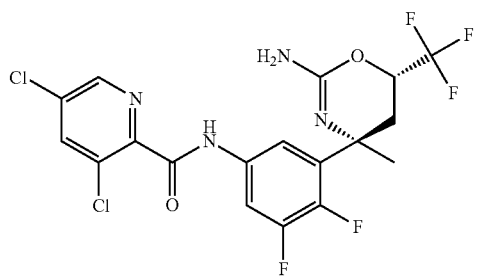 [SMILES: C[C@@]1(c2cc(NC(=O)c3ncc(Cl)cc3Cl)cc(F)c2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4,5-difluorophenyl)-3,5-dichloropicolinamide The titled compound was synthesized by procedure and steps analogous to those described in Method Y, Example 163 above, but using 3,5-dichloropyridine-2-carboxylic acid (Matrix Scientific) in step 10. MS m/z=482.9 [M+H]⁺. Calculated for C18H13Cl2F5N4O2: 483.2

¹H NMR (400 MHz, CHLOROFORM-d) δ ppm 1.69 (s, 3 H) 1.93-1.99 (m, 1 H) 2.84 (d, J=11.93 Hz, 1 H) 4.10 (m, J=5.48 Hz, 1 H) 7.01 (br. s., 1 H) 7.92 (s, 1 H) 8.11-8.22 (m, 1 H) 8.49 (s, 1 H) 9.80 (br. s., 1 H)

Example 173

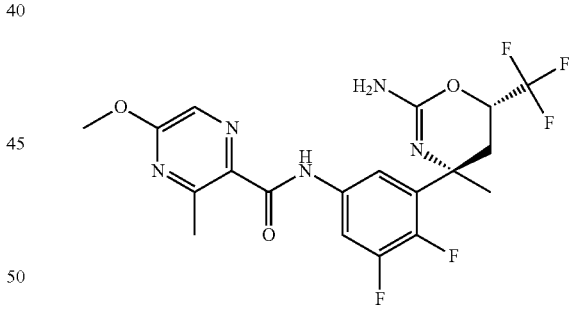

Synthesis of N-(3-((4S,6S)-2-amino-4-methyl-6-(trifluoromethyl)-5,6-dihydro-4H-1,3-oxazin-4-yl)-4,5-difluorophenyl)-5-methoxy-3-methylpyrazine-2-carboxamide The titled compound was synthesized by procedure and steps analogous to those described in Method Y, Example 163 above, but using 5-methoxy-3-methylpyrazine-2-carboxylic acid (intermediate 27) in step 10. MS m/z=460.1 [M+H]⁺. Calculated for C19H18F5N5O3: 459.4

¹H NMR (400 MHz, CHLOROFORM-d) δ ppm 1.66 (s, 3 H) 1.91 (t, J=13.11 Hz, 1 H) 2.80 (dd, J=13.89, 2.54 Hz, 1 H)

2.93 (s, 3 H) 4.05 (s, 3 H) 4.05-4.11 (m, 1 H) 6.95-7.04 (m, 1 H) 7.98 (s, 1 H) 8.12 (ddd, J=11.88, 6.99, 2.64 Hz, 1 H) 9.81 (s, 1 H)

Example 174

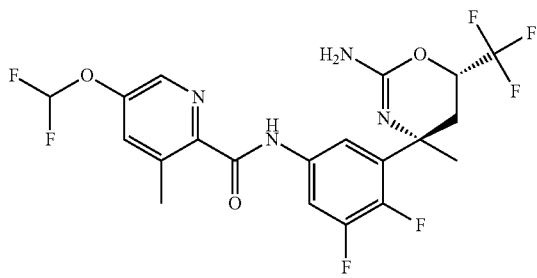 [SMILES: Cc1cc(OC(F)F)cnc1C(=O)Nc1cc(F)c(F)c([C@]2(C)C[C@@H](C(F)(F)F)OC(N)=N2)c1]

Synthesis of N-(3-((4S,6S)-2-amino-4-methyl-6-(trifluoromethyl)-5,6-dihydro-4H-1,3-oxazin-4-yl)-4,5-difluorophenyl)-5-(difluoromethoxy)-3-methylpicolinamide The titled compound was synthesized by procedure and steps analogous to those described in Method Y, Example 163 above, but using 5-(difluoromethoxy)-3-methylpicolinic acid (WO2012095463) in step 10. MS m/z=495.0 [M+H]⁺. Calculated for C20H17F7N4O3: 494.4

¹H NMR (400 MHz, CHLOROFORM-d) δ ppm 1.66 (s, 3 H) 1.91 (t, J=13.11 Hz, 1 H) 2.75-2.80 (m, 1 H) 2.81 (s, 3 H) 4.01-4.11 (m, 1 H) 6.38-6.84 (m, 1 H) 6.98-7.04 (m, 1 H) 7.41 (d, J=1.96 Hz, 1 H) 8.12 (ddd, J=11.93, 6.85, 2.74 Hz, 1 H) 8.30 (d, J=2.15 Hz, 1 H) 10.05 (s, 1 H)

Example 175

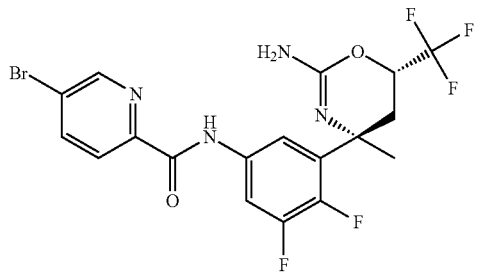

Synthesis of N-(3-((4S,6S)-2-amino-4-methyl-6-(trifluoromethyl)-5,6-dihydro-4H-1,3-oxazin-4-yl)-4,5-difluorophenyl)-5-bromopicolinamide The titled compound was synthesized by procedure and steps analogous to those described in Method Y, Example 163 above, but using 5-bromopyridine-2-carboxylic acid (Matrix Innovation Inc) in step 10. MS m/z=492.9 [M+H]⁺. Calculated for C18H14BrF5N4O2: 493.2

¹H NMR (400 MHz, CHLOROFORM-d) δ ppm 1.69 (s, 3 H) 1.96 (t, J=13.11 Hz, 1 H) 2.83 (dd, J=13.89, 2.54 Hz, 1 H) 4.10 (dd, J=10.27, 5.18 Hz, 1 H) 7.14 (br. s., 1 H) 8.00-8.12 (m, 2 H) 8.16 (d, J=8.22 Hz, 1 H) 8.67 (d, J=1.76 Hz, 1 H) 9.86 (br. s., 1 H)

Examples 176

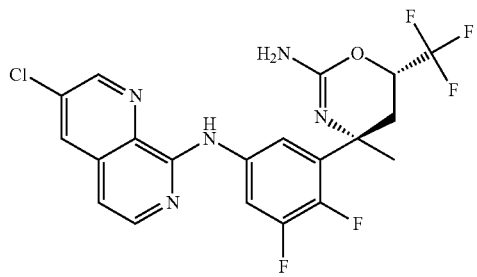 [SMILES: C[C@@]1(c2cc(Nc3nccc4cc(Cl)cnc34)cc(F)c2F)C[C@@H](C(F)(F)F)OC(N)=N1]

Synthesis of (4S,6S)-4-(5-((3-chloro-1,7-naphthyridin-8-yl)amino)-2,3-difluorophenyl)-4-methyl-6-(trifluoromethyl)-5,6-dihydro-4H-1,3-oxazin-2-amine The titled compound was synthesized by procedure and steps analogous to those described in Method B, Step 2, Example 8 above, but using (4S,6S)-4-(5-amino-2,3-difluorophenyl)-4-methyl-6-(trifluoromethyl)-5,6-dihydro-4H-1,3-oxazin-2-amine (17i, Example 163, Method Y step 9) in step 2 and 3,8-dichloro-1,7-naphthyridine (intermediate 2). MS m/z=472.1 [M+H]⁺. Calculated for C20H15ClF5N5O: 471.8

¹H NMR (400 MHz, CHLOROFORM-d) δ ppm 1.68 (s, 3 H) 1.91 (t, J=13.11 Hz, 1 H) 2.79 (dd, J=13.69, 2.54 Hz, 1 H) 4.10 (ddd, J=12.28, 5.92, 2.54 Hz, 1 H) 6.94 (d, J=5.87 Hz, 1 H) 7.18-7.23 (m, 1 H) 7.99 (d, J=2.15 Hz, 1 H) 8.13 (d, J=5.87 Hz, 1 H) 8.41 (ddd, J=12.37, 6.90, 2.84 Hz, 1 H) 8.66 (d, J=2.35 Hz, 1 H) 8.95 (s, 1 H)

Example 177

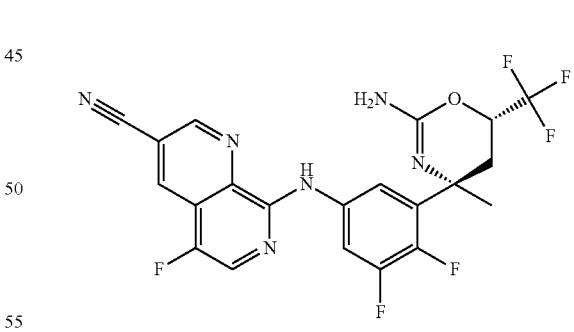

Synthesis of 8-((3-((4S,6S)-2-amino-4-methyl-6-(trifluoromethyl)-5,6-dihydro-4H-1,3-oxazin-4-yl)-4,5-difluorophenyl)amino)-5-fluoro-1,7-naphthyridine-3-carbonitrile The titled compound was synthesized by procedure and steps analogous to those described in Method B, Step 2, Example 8 above, but using (4S,6S)-4-(5-amino-2,3-difluorophenyl)-4-methyl-6-(trifluoromethyl)-5,6-dihydro-4H-1,3-oxazin-2-amine (17i, Example 163, Method Y step 9) and 8-chloro-5-fluoro-1,7-naphthyridine-3-carbonitrile (intermediate 17) in step 2. MS m/z=481.1 [M+H]⁺. Calculated for C21H14F6N6O: 480.4

¹H NMR (400 MHz, CHLOROFORM-d) δ ppm 1.79 (br. s., 3 H) 1.99-2.10 (m, 1 H) 2.91 (d, J=14.67 Hz, 1 H) 4.16-4.30 (m, 1 H) 7.32 (br. s., 1 H) 8.17 (br. s., 1 H) 8.30 (br. s., 1 H) 8.67 (br. s., 1 H) 8.92 (br. s., 1 H) 9.02 (br. s., 1 H)

Example 178

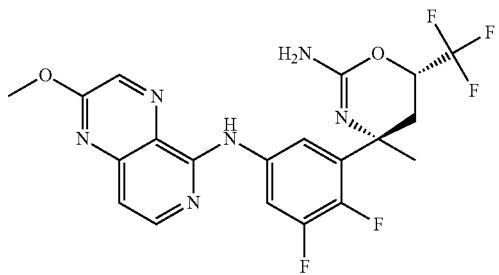 [SMILES: COc1cnc2c(Nc3cc(F)c(F)c([C@]4(C)C[C@@H](C(F)(F)F)OC(N)=N4)c3)nccc2n1]

Synthesis of (4S,6S)-4-(2,3-difluoro-5-((2-methoxy-pyrido[3,4-b]pyrazin-5-yl)amino)phenyl)-4-methyl-6-(trifluoromethyl)-5,6-dihydro-4H-1,3-oxazin-2-amine The titled compound was synthesized by procedure and steps analogous to those described in Method B, Example 8 above, but using (4S,6S)-4-(5-amino-2,3-difluorophenyl)-4-methyl-6-(trifluoromethyl)-5,6-dihydro-4H-1,3-oxazin-2-amine (17i, Example 163, Method Y, step 9) and 5-chloro-2-methoxypyrido[3,4-b]pyrazine (intermediate 3) in step 2. MS m/z=469.1 [M+H]⁺. Calculated for C20H17F5N6O2: 468.4

¹H NMR (400 MHz, CHLOROFORM-d) δ ppm 1.70 (s, 3 H) 1.94 (t, J=13.20 Hz, 1 H) 2.81 (d, J=13.11 Hz, 1 H) 4.11 (s, 3 H) 4.13-4.20 (m, 1 H) 7.05 (d, J=5.67 Hz, 1 H) 7.17 (br. s., 1 H) 8.19-8.26 (m, 2 H) 8.33-8.42 (m, 1 H) 8.60 (br. s., 1 H)

Example 179

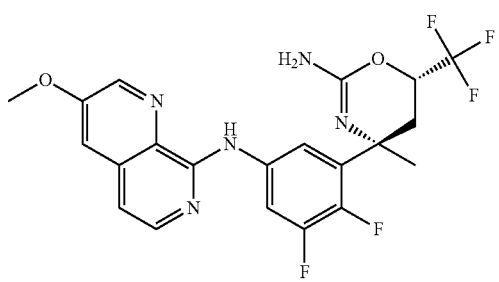 [SMILES: COc1cnc2c(Nc3cc(F)c(F)c([C@]4(C)C[C@@H](C(F)(F)F)OC(N)=N4)c3)nccc2c1]

Synthesis of (4S,6S)-4-((2,3-difluoro-5-((3-methoxy-1,7-naphthyridin-8-yl)amino)phenyl)-4-methyl-6-(trifluoromethyl)-5,6-dihydro-4H-1,3-oxazin-2-amine The titled compound was synthesized by procedure and steps analogous to those described in Method B, Example 8 above, but using (4S,6S)-4-(5-amino-2,3-difluorophenyl)-4-methyl-6-(trifluoromethyl)-5,6-dihydro-4H-1,3-oxazin-2-amine (17i, example 163, Method Y, step 9) and 8-chloro-3-methoxy-1,7-naphthyridine (intermediate 31) in step 2. MS m/z=468.2 [M+H]⁺. Calculated for C21H18F5N5O2: 467.4

¹H NMR (400 MHz, CHLOROFORM-d) δ ppm 1.72 (s, 3 H) 1.95 (t, J=13.20 Hz, 1 H) 2.83 (dd, J=13.89, 2.54 Hz, 1 H) 3.97 (s, 3 H) 4.16 (m, J=9.98, 5.48 Hz, 1 H) 6.96 (d, J=5.87 Hz, 1 H) 7.21 (br. s., 1 H) 7.23 (d, J=2.74 Hz, 1 H) 8.07 (d, J=5.87 Hz, 1 H) 8.43 (ddd, J=12.57, 6.99, 2.74 Hz, 1 H) 8.49 (d, J=2.74 Hz, 1 H) 8.95 (s, 1 H)

Example 180

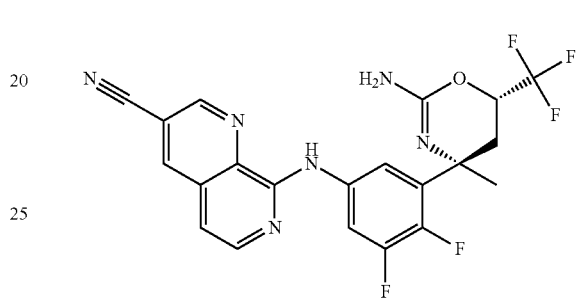

Synthesis of 8-((3-((4S,6S)-2-amino-4-methyl-6-(trifluoromethyl)-5,6-dihydro-4H-1,3-oxazin-4-yl)-4,5-difluorophenyl)amino)-1,7-naphthyridine-3-carbonitrile The titled compound was synthesized by procedure and steps analogous to those described in Method C, Example 22 above, but using (4S,6S)-4-(5-((3-chloro-1,7-naphthyridin-8-yl)amino)-2,3-difluorophenyl)-4-methyl-6-(trifluoromethyl)-5,6-dihydro-4H-1,3-oxazin-2-amine (Example 176). MS m/z=463.1 [M+H]⁺. Calculated for C21H15F5N6O: 462.4

¹H NMR (400 MHz, CHLOROFORM-d) δ ppm 1.73 (s, 3 H) 1.95-2.01 (m, 1 H) 2.85 (d, J=13.50 Hz, 1 H) 4.10-4.21 (m, 1 H) 7.07 (d, J=5.67 Hz, 1 H) 7.27-7.32 (m, 1 H) 8.26 (d, J=5.87 Hz, 1 H) 8.35-8.44 (m, 2 H) 8.94 (s, 1 H) 9.05 (br. s., 1 H)

Example 181 (Method W)

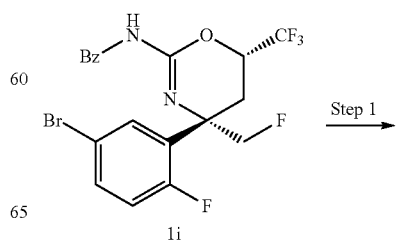

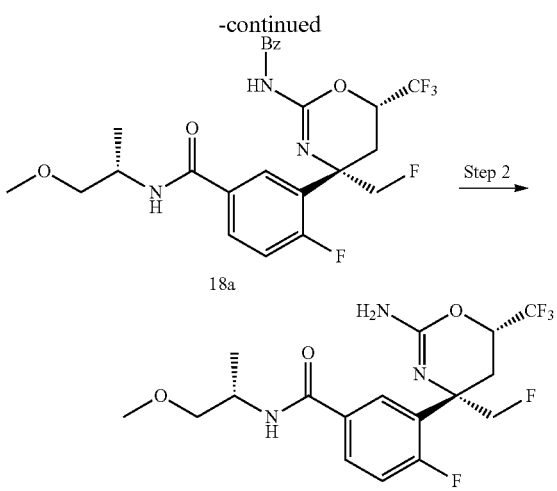

Synthesis of 3-((4S,6S)-2-amino-4-(fluoromethyl)-6-(trifluoromethyl)-5,6-dihydro-4H-1,3-oxazin-4-yl)-4-fluoro-N-((S)-1-methoxypropan-2-yl)benzamide Step 1: 3-((4S,6S)-2-benzamido-4-(fluoromethyl)-6-(trifluoromethyl)-5,6-dihydro-4H-1,3-oxazin-4-yl)-4-fluoro-N-((S)-1-methoxypropan-2-yl)benzamide (18a)

To a flask was added N-((4S,6S)-4-(5-bromo-2-fluorophenyl)-4-(fluoromethyl)-6-(trifluoromethyl)-5,6-dihydro-4H-1,3-oxazin-2-yl)benzamide (0.248 g, 0.519 mmol), palladium acetate (5.25 mg, 0.023 mmol), xantphos (0.017 g, 0.029 mmol), and sodium carbonate (0.033 ml, 0.779 mmol) in toluene (1.039 mL). (s)-(+)-1-Methoxy-2-propylamine (0.082 ml, 0.779 mmol) was added. CO gas was bubbled through the reaction mixture for 10 min. The temperature was then brought to 80° C. for 3 h. Then the reaction was allowed to cool to room temperature. The reaction mixture was diluted with water and extracted with EtOAc. The organic extract was washed with water, saturated NaHCO$_3$ solution, brine, dried over MgSO$_4$, filtered and concentrated in vacuo. The crude product was adsorbed onto a plug of silica gel and chromatographed through a Biotage SNAP Ultra silica gel column (50 g), eluting with a gradient of 5-80% EtOAc in hexane, to provide 3-((4S,6S)-2-benzamido-4-(fluoromethyl)-6-(trifluoromethyl)-5,6-dihydro-4H-1,3-oxazin-4-yl)-4-fluoro-N-((S)-1-methoxypropan-2-yl)benzamide (0.0591 g, 0.115 mmol, 22.16% yield). MS m/z=514.0 [M+H]$^+$. Calculated for C$_{24}$H$_{24}$F$_5$N$_3$O$_4$: 513.17

$^1$H NMR (400 MHz, CHLOROFORM-d) ppm 1.26 (d, J=6.85 Hz, 4 H) 2.46 (t, J=13.30 Hz, 1 H) 2.88 (dd, J=13.99, 2.05 Hz, 1 H) 3.31 (s, 3 H) 3.35-3.43 (m, 1 H) 3.43-3.51 (m, 1 H) 4.24-4.46 (m, 2 H) 4.63-4.92 (m, 2 H) 7.19-7.32 (m, 2 H) 7.40-7.49 (m, 2 H) 7.49-7.60 (m, 1 H) 7.92 (br. s., 1 H) 8.23 (d, J=6.06 Hz, 2 H)

Step 2: 3-((4S,6S)-2-amino-4-(fluoromethyl)-6-(trifluoromethyl)-5,6-dihydro-4H-1,3-oxazin-4-yl)-4-fluoro-N-((S)-1-methoxypropan-2-yl)benzamide To a solution of 3-((4S,6S)-2-benzamido-4-(fluoromethyl)-6-(trifluoromethyl)-5,6-dihydro-4H-1,3-oxazin-4-yl)-4-fluoro-N-((S)-1-methoxypropan-2-yl)benzamide (0.0591 g, 0.115 mmol) in MeOH (1.15 mL) was added 1,8-diazabicyclo-[5.4.0]undec-7-ene (0.021 ml, 0.138 mmol) and allowed to stir at 65° C. for 15 h. The reaction mixture was concentrated in vacuo. The crude product was adsorbed onto a plug of silica gel and chromatographed through a Biotage SNAP Ultra silica gel column (25 g), eluting with a gradient of 20-100% EtOAc in hexane, to provide 3-((4S,6S)-2-amino-4-(fluoromethyl)-6-(trifluoromethyl)-5,6-dihydro-4H-1,3-oxazin-4-yl)-4-fluoro-N-((S)-1-methoxypropan-2-yl)benzamide (0.0246 g, 0.060 mmol, 52.2% yield). MS m/z=410.0 [M+H]$^+$. Calculated for C$_{17}$H$_{20}$F$_5$N$_3$O$_3$: 409.14

$^1$H NMR (400 MHz, CHLOROFORM-d) ppm 1.31 (d, J=6.65 Hz, 3 H) 2.20 (t, J=13.01 Hz, 1 H) 2.72 (d, J=13.50 Hz, 1 H) 3.40 (s, 3 H) 3.46 (d, J=4.11 Hz, 2 H) 4.12 (d, J=5.67 Hz, 1 H) 4.35 (br. s., 1 H) 4.41-4.76 (m, 2 H) 6.40 (d, J=6.26 Hz, 1 H) 7.15 (t, J=10.17 Hz, 1 H) 7.82 (br. s., 1 H) 7.92 (d, J=7.63 Hz, 1 H)

Example 182

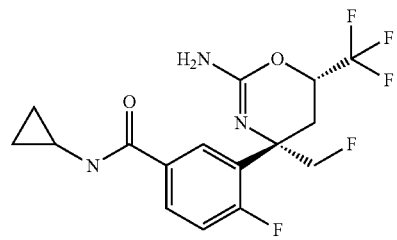 [SMILES: NC1=N[C@](CF)(c2cc(C(=O)NC3CC3)ccc2F)C[C@@H](C(F)(F)F)O1]

Synthesis of 3-((4S,6S)-2-amino-4-(fluoromethyl)-6-(trifluoromethyl)-5,6-dihydro-4H-1,3-oxazin-4-yl)-N-cyclopropyl-4-fluorobenzamide The title compound was synthesized by procedures and steps analogous to those described in Method W, Example 181 above, but using cyclopropylamine in step 1. MS m/z=377.9 [M+H]$^+$. Calculated for C$_{16}$H$_{16}$F$_5$N$_3$O$_2$: 377.116

$^1$H NMR (300 MHz, CHLOROFORM-d) ppm 0.60 (br. s., 2 H) 0.72-1.01 (m, 2 H) 2.00-2.28 (m, 1 H) 2.68 (d, J=13.59 Hz, 1 H) 2.87 (d, J=3.07 Hz, 1 H) 3.93-4.18 (m, 1 H) 4.30-4.81 (m, 2 H) 6.35 (br. s., 1 H) 7.01-7.22 (m, 1 H) 7.63-7.96 (m, 2 H)

Example 183

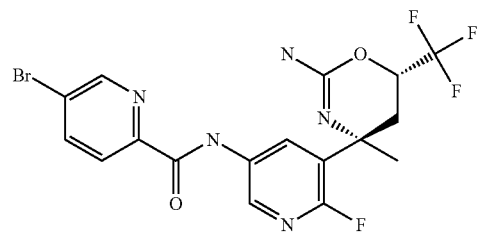 [SMILES: C[C@@]1(c2cc(NC(=O)c3ccc(Br)cn3)cnc2F)C[C@@H](C(F)(F)F)OC(N)=N1]

Synthesis of N-(5-((4S,6S)-2-amino-4-methyl-6-(trifluoromethyl)-5,6-dihydro-4H-1,3-oxazin-4-yl)-6-fluoropyridin-3-yl)-5-bromopicolinamide The title compound was synthesized using steps and procedures analogous to those described in Method H (Example 66) above, but using 5-bromopyridine-2-carboxylic acid (Sigma-Aldrich Chemical Company, Inc.) in step 2. MS m/z=476.0 [M+H]⁺. Calculated for C17H14BrF4N5O2: 476.2

¹H NMR (400 MHz, CHLOROFORM-d) δ ppm 1.66 (s, 3 H) 1.89-1.99 (m, 1 H) 2.83 (dd, J=13.89, 2.54 Hz, 1 H) 3.97-4.07 (m, 1 H) 8.06 (dd, J=8.41, 2.15 Hz, 1 H) 8.15-8.21 (m, 2 H) 8.65 (t, J=2.15 Hz, 1 H) 8.68 (d, J=1.96 Hz, 1 H) 9.88 (s, 1 H)

Example 184

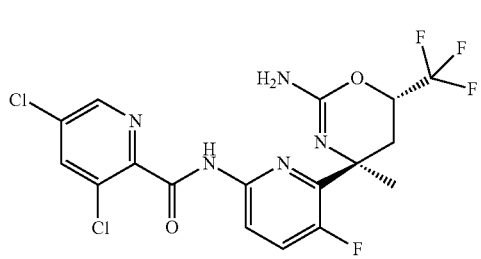 [SMILES: C[C@@]1(c2nc(NC(=O)c3ncc(Cl)cc3Cl)ccc2F)C[C@@H](C(F)(F)F)OC(N)=N1]

Synthesis of N-(6-((4S,6S)-2-amino-4-methyl-6-(trifluoromethyl)-5,6-dihydro-4H-1,3-oxazin-4-yl)-5-fluoropyridin-2-yl)-3,5-dichloropicolinamide The title compound was synthesized using steps and procedures analogous to those described in Method K (Example 79) above, but using 3,5-dichloropicolinic acid (Matrix) in step 10. MS m/z=466 [M]⁺. Calculated for C17H13Cl2F4N5O2: 466.2

¹H NMR (300 MHz, CHLOROFORM-d) ppm 1.67 (s, 3 H) 1.80 (t, J=12.72 Hz, 1 H) 3.00 (dd, J=13.45, 3.07 Hz, 1 H) 4.49 (ddd, J=9.10, 6.03, 3.00 Hz, 1 H) 7.49 (dd, J=10.45, 8.99 Hz, 1 H) 7.92 (d, J=2.05 Hz, 1 H) 8.33 (dd, J=8.84, 3.00 Hz, 1 H) 8.53 (d, J=2.05 Hz, 1 H) 10.10 (s, 3 H).

Example 185

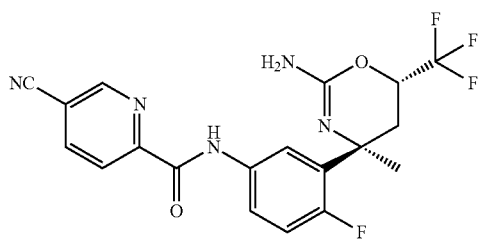 [SMILES: C[C@@]1(c2cc(NC(=O)c3ccc(C#N)cn3)ccc2F)C[C@@H](C(F)(F)F)OC(N)=N1]

Synthesis of N-(3-((4S,6S)-2-amino-4-methyl-6-(trifluoromethyl)-5,6-dihydro-4H-1,3-oxazin-4-yl)-4-fluorophenyl)-5-cyanopicolinamide The title compound was synthesized by procedures and steps analogous to those described in Method E, Example 26 above, but using 5-cyanopicolinic acid (Aldrich)) in step 9. MS m/z=422.1 [M+H]⁺. Calculated for C19H15F4NO2: 421.35

¹H NMR (400 MHz, CDCl₃): δ 9.88 (br s, 1 H), 8.97-8.86 (m, 1 H), 8.42 (dd, J=8.1, 0.9 Hz, 1 H), 8.21 (dd, J=8.2, 2.0 Hz, 1 H), 8.03 (dt, J=8.9, 3.4 Hz, 1 H), 7.55-7.43 (m, 1 H) 7.15 (dd, J=11.5, 8.8 Hz, 1 H), 4.22-4.10 (m, 1 H) 2.91 (d, J=14.1 Hz, 1 H), 2.00 (t, J=13.3 Hz, 1 H), 1.75 (s, 3 H); ¹⁹F NMR (377 MHz, CDCl₃): δ −79.00 (br s, 3F), −115.82 (s, 1F).

Example 186 (Method Z)

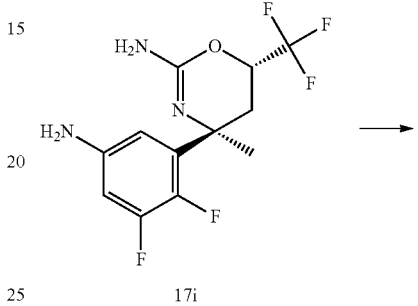

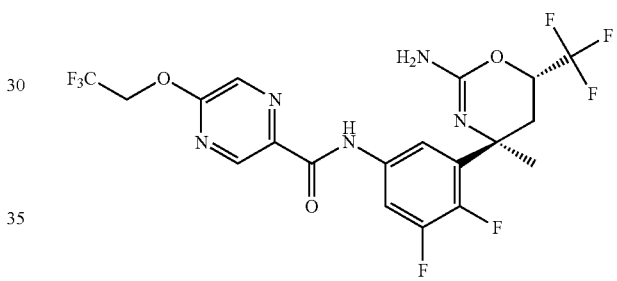

Synthesis of N-(3-((4S,6S)-2-amino-4-methyl-6-(trifluoromethyl)-5,6-dihydro-4H-1,3-oxazin-4-yl)-4,5-difluorophenyl)-5-(2,2,2-trifluoroethoxy)pyrazine-2-carboxamide To a cooled (ice bath) solution of (4S,6S)-4-(5-amino-2,3-difluorophenyl)-4-methyl-6-(trifluoromethyl)-5,6-dihydro-4H-1,3-oxazin-2-amine (0.060 g, 0.194 mmol) and 5-(2,2,2-trifluoroethoxy)pyrazine-2-carboxylic acid (0.056 g, 0.252 mmol) in DMF (1.0 mL) was added 1-propanephosphonic acid cyclic anhydride, 50 wt. % solution in ethyl acetate (0.247 mL, 0.388 mmol) via syringe. The reaction was stirred for 2 hrs (ice bath was slowly warmed to ambient temperature). LCMS detected trace of starting aniline left. Reaction was quenched with saturated NaHCO3 followed by the addition of water.

After stirred for 30 min, the resulted suspension was filtered. the filter cake was purified by Shimadzu HPLC to afford N-(3-((4S,6S)-2-amino-4-methyl-6-(trifluoromethyl)-5,6-dihydro-4H-1,3-oxazin-4-yl)-4,5-difluorophenyl)-5-(2,2,2-trifluoroethoxy)pyrazine-2-carboxamide (0.057 g, 0.111 mmol, 57.2% yield) as yellow solid. MS m/z=514.2 [M+H]⁺. Calculated for C19H15F8N5O3: 513.34

¹H NMR (300 MHz, CHLOROFORM-d) δ=9.52 (br. s., 1 H), 9.02 (br. s., 1 H), 8.31 (br. s., 1 H), 8.07 (br. s., 1 H), 7.11

(br. s., 1 H), 4.87 (d, J=8.2 Hz, 2 H), 4.16-4.01 (m, 1 H), 2.82 (d, J=14.3 Hz, 1H), 2.06-1.86 (m, 1 H), 1.68 (br. s., 3 H)

Example 187

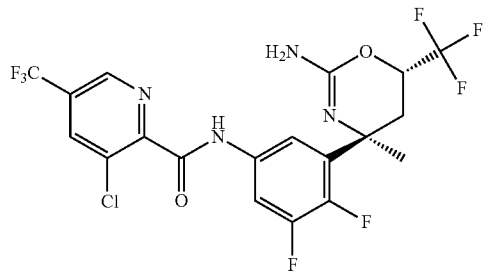 [SMILES: C[C@@]1(c2cc(NC(=O)c3ncc(C(F)(F)F)cc3Cl)cc(F)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-4,5-difluorophenyl)-3-chloro-5-(trifluoromethyl)picolinamide The title compound was synthesized by procedures and steps analogous to those described in Method Z, Example 186 above, but using 3-chloro-5-(trifluoromethyl)-2-pyridine carboxylic acid (Bionet Research). MS m/z=517.1 [M+H]$^+$. Calculated for C19H13ClF8N4O2: 516.77

$^1$H NMR (300 MHz, CHLOROFORM-d) δ=9.82 (br. s., 1H), 8.77 (s, 1H), 8.22-8.08 (m, 2H), 7.10-7.00 (m, 1H), 4.37 (br. s., 2H), 4.04 (dd, J=5.3, 9.7 Hz, 1H), 2.86-2.70 (m, 1H), 1.91 (t, J=13.2 Hz, 1H), 1.64 (s, 3H)

Example 188

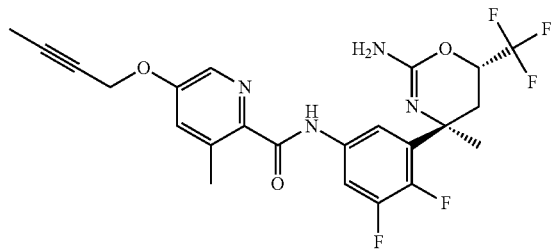 [SMILES: CC#CCOc1cnc(C(=O)Nc2cc(F)c(F)c([C@]3(C)C[C@@H](C(F)(F)F)OC(N)=N3)c2)c(C)c1]

N-(3-((4S,6S)-2-amino-4-methyl-6-(trifluoromethyl)-5,6-dihydro-4H-1,3-oxazin-4-yl)-4,5-difluorophenyl)-5-(but-2-yn-1-yloxy)-3-methylpicolinamide The title compound was synthesized by procedures and steps analogous to those described in Method Z, Example 186 above, but using 5-(but-2-yn-1-yloxy)-3-methylpicolinic acid (intermediate 32). MS m/z=497.1 [M+H]$^+$. Calculated for C23H21F5N4O3: 496.43

$^1$H NMR (300 MHz, CHLOROFORM-d) δ=10.09 (br. s., 1H), 8.22-8.07 (m, 2H), 7.16 (br. s., 1H), 6.99 (br. s., 1H), 4.76 (br. s., 2H), 4.14-3.96 (d, J=5.7 Hz, 1H), 2.87-2.70 (m, 4H), 1.96-1.85 (m, 4H), 1.65 (s, 3H)

Example 189

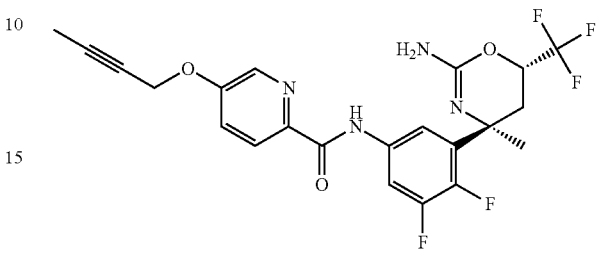

N-(3-((4S,6S)-2-amino-4-methyl-6-(trifluoromethyl)-5,6-dihydro-4H-1,3-oxazin-4-yl)-4,5-difluorophenyl)-5-(but-2-yn-1-yloxy)picolinamide The title compound was synthesized by procedures and steps analogous to those described in Method Z, Example 186 above, but using 5-(but-2-yn-1-yloxy)picolinic acid (intermediate 25). MS m/z=483.1 [M+H]$^+$. Calculated for C22H19F5N4O3: 482.40

$^1$H NMR (300 MHz, CHLOROFORM-d) δ=9.87 (br. s., 1H), 8.30 (d, J=2.3 Hz, 1H), 8.22 (d, J=8.6 Hz, 1H), 8.17-8.06 (m, 1H), 7.44 (dd, J=2.6, 8.7 Hz, 1H), 7.14-7.07 (m, 1H), 4.78 (d, J=1.9 Hz, 2H), 4.16-4.02 (m, 1H), 2.86-2.75 (m, 1H), 2.00-1.89 (m, 1H), 1.88 (br. s., 3H), 1.68 (s, 3H)

Example 190

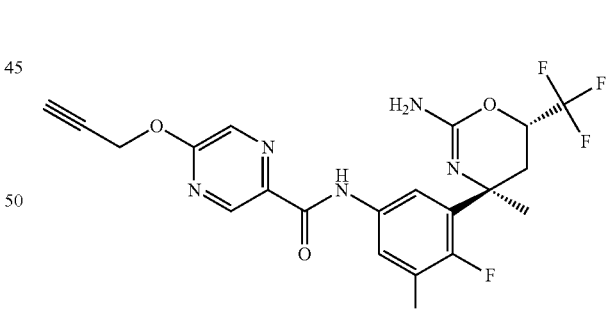

N-(3-((4S,6S)-2-amino-4-methyl-6-(trifluoromethyl)-5,6-dihydro-4H-1,3-oxazin-4-yl)-4,5-difluorophenyl)-5-(prop-2-yn-1-yloxy)pyrazine-2-carboxamide The title compound was synthesized by procedures and steps analogous to those described in Method Z, Example 186 above, but using 5-(prop-2-yn-1-yloxy)pyrazine-2-carboxylic acid (J. Med. Chem. 2013, 56, 3980).

MS m/z=470.1 [M+H]⁺. Calculated for C20H16F5N5O3: 469.36

Example 191

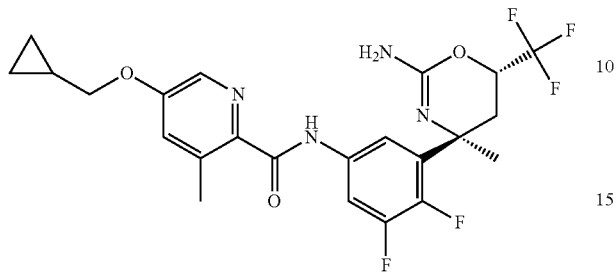

N-(3-((4S,6S)-2-amino-4-methyl-6-(trifluoromethyl)-5,6-dihydro-4H-1,3-oxazin-4-yl)-4,5-difluorophenyl)-5-(cyclopropylmethoxy)-3-methylpicolinamide The title compound was synthesized by procedures and steps analogous to those described in Method Z, Example 186 above, but using 5-(cyclopropylmethoxy)-3-methylpicolinic acid (WO2013061962). MS m/z=499.1 [M+H]⁺. Calculated for C23H23F5N4O3: 498.45

¹H NMR (300 MHz, CHLOROFORM-d) δ=10.07 (br. s., 1H), 8.18-7.99 (m, 2H), 7.03 (d, J=7.2 Hz, 2H), 4.79-4.36 (m, 2H), 4.11-3.97 (m, 1H), 3.90 (d, J=6.7 Hz, 2H), 2.86-2.65 (m, 4H), 1.90 (t, J=13.1 Hz, 1H), 1.65 (br. s., 3H), 1.38-1.24 (m, 1H), 0.70 (d, J=6.6 Hz, 2H), 0.40 (d, J=3.8 Hz, 2H)

Example 192

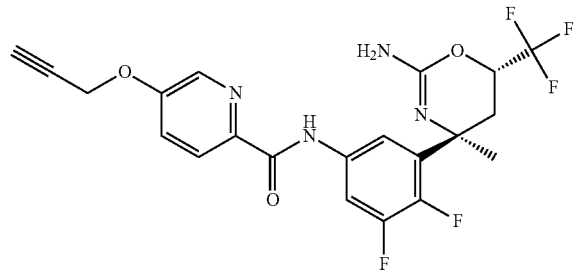 [SMILES: C#CCOc1ccc(C(=O)Nc2cc(F)c(F)c([C@]3(C)C[C@@H](C(F)(F)F)OC(N)=N3)c2)nc1]

N-(3-((4S,6S)-2-amino-4-methyl-6-(trifluoromethyl)-5,6-dihydro-4H-1,3-oxazin-4-yl)-4,5-difluorophenyl)-5-(prop-2-yn-1-yloxy)picolinamide The title compound was synthesized by procedures and steps analogous to those described in Method Z, Example 186 above, but using 5-(prop-2-yn-1-yloxy)picolinic acid (intermediate 26). MS m/z=469.1 [M+H]⁺. Calculated for C21H17F5N4O3: 468.38

¹H NMR (300 MHz, CHLOROFORM-d) δ=9.84 (br. s., 1H), 8.30 (d, J=2.6 Hz, 1H), 8.22 (d, J=8.6 Hz, 1H), 8.09 (ddd, J=2.6, 6.8, 11.7 Hz, 1H), 7.45 (dd, J=2.9, 8.7 Hz, 1H), 7.15-7.07 (m, 1H), 4.82 (d, J=2.3 Hz, 2H), 4.13-3.99 (m, J=5.8, 10.0 Hz, 1H), 2.78 (dd, J=2.4, 13.7 Hz, 1H), 2.61 (t, J=2.2 Hz, 1H), 1.91 (t, J=13.2 Hz, 1H), 1.65 (s, 3H)

Example 193

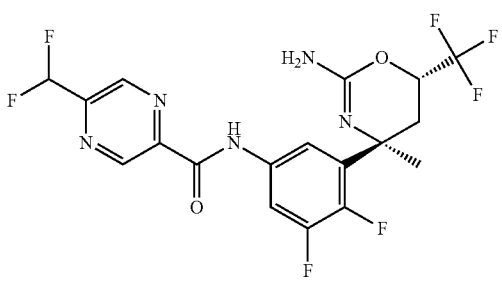 [SMILES: C[C@@]1(c2cc(NC(=O)c3cnc(C(F)F)cn3)cc(F)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-4,5-difluorophenyl)-5-(difluoromethyl)pyrazine-2-carboxamide The title compound was synthesized by procedures and steps analogous to those described in Method Z, Example 186 above, but using 5-(difluoromethyl)pyrazine-2-carboxylic acid (Aurigene Discovery Technologies). MS m/z=466.1 [M+H]⁺. Calculated for C18H14F7N5O2: 465.32

¹H NMR (300 MHz, CHLOROFORM-d) δ=9.65 (br. s., 1 H), 9.52 (s, 1 H), 8.93 (s, 1 H), 8.14-8.02 (m, 1 H), 7.15 (br. s., 1 H), 6.99-6.60 (m, 1 H), 4.13-3.98 (m, 1 H), 2.81 (d, J=13.6 Hz, 1 H), 1.94 (t, J=13.1 Hz, 1 H), 1.67 (s, 3 H)

Example 194

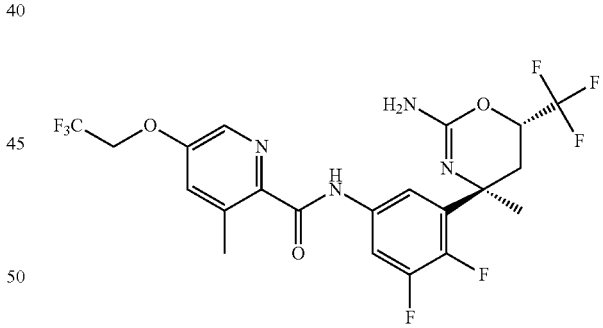

N-(3-((4S,6S)-2-amino-4-methyl-6-(trifluoromethyl)-5,6-dihydro-4H-1,3-oxazin-4-yl)-4,5-difluorophenyl)-3-methyl-5-(2,2,2-trifluoroethoxy)picolinamide The title compound was synthesized by procedures and steps analogous to those described in Method Z, Example 186 above, but using 3-methyl-5-(2,2,2-trifluoroethoxy)picolinic acid (Aurigene Discovery Technologies). MS m/z=527.2 [M+H]⁺. Calculated for C21H18F8N4O3: 526.38

¹H NMR (400 MHz, CHLOROFORM-d) δ=10.05 (br. s., 1 H), 8.17 (d, J=2.2 Hz, 1 H), 8.16-8.09 (m, 1 H), 7.15 (d, J=2.2

Hz, 1 H), 7.03-6.96 (m, 1 H), 4.47 (q, J=7.8 Hz, 2 H), 4.14-4.02 (m, 1 H), 2.85-2.81 (m, 1 H), 2.80 (s, 3 H), 1.93 (t, J=13.2 Hz, 1 H), 1.68 (s, 3 H)

Example 195

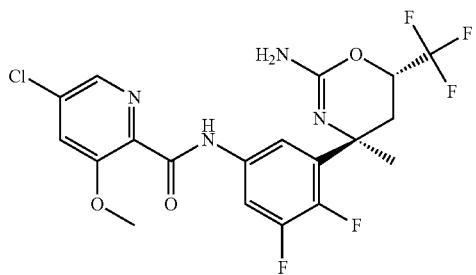 [SMILES: COc1cc(Cl)cnc1C(=O)Nc1cc(F)c(F)c([C@]2(C)C[C@@H](C(F)(F)F)OC(N)=N2)c1]

N-(3-((4S,6S)-2-amino-4-methyl-6-(trifluoromethyl)-5,6-dihydro-4H-1,3-oxazin-4-yl)-4,5-difluorophenyl)-5-chloro-3-methoxypicolinamide The title compound was synthesized by procedures and steps analogous to those described in Method Z, Example 186 above, but using 5-chloro-3-methoxypicolinic acid (Syngene). MS m/z=479.1 [M+H]⁺. Calculated for C19H16ClF5N4O3: 478.80

¹H NMR (300 MHz, CHLOROFORM-d) δ=9.75 (br. s., 1 H), 8.20-8.08 (m, 2 H), 7.44 (s, 1 H), 7.02 (br. s., 1 H), 4.12-4.02 (m, 1 H), 4.00 (s, 3 H), 2.80 (d, J=12.9 Hz, 1 H), 1.92 (t, J=13.2 Hz, 1 H), 1.66 (s, 3 H)

Example 196

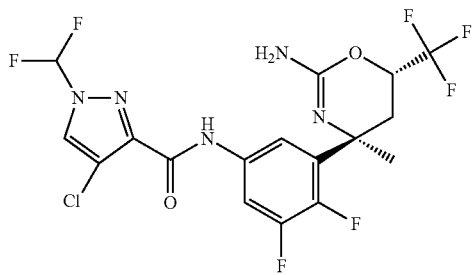 [SMILES: C[C@@]1(c2cc(NC(=O)c3nn(C(F)F)cc3Cl)cc(F)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-4,5-difluorophenyl)-4-chloro-1-(difluoromethyl)-1H-pyrazole-3-carboxamide The title compound was synthesized by procedures and steps analogous to those described in Method Z, Example 186 above, but using 4-chloro-1-(difluoromethyl)-1H-pyrazole-3-carboxylic acid (WO201169934). MS m/z=488.1 [M+H]⁺. Calculated for C17H13ClF7N5O2: 487.76

¹H NMR (400 MHz, CHLOROFORM-d) δ=8.57 (br. s., 1 H), 8.12-8.04 (m, 1 H), 7.93 (s, 1 H), 7.31-6.99 (t, 1 H), 6.99-6.95 (m, 1 H), 4.06 (m, 1 H), 2.80 (dd, J=2.2, 13.7 Hz, 1 H), 1.92 (t, J=13.1 Hz, 1 H), 1.65 (s, 3 H)

Example 197

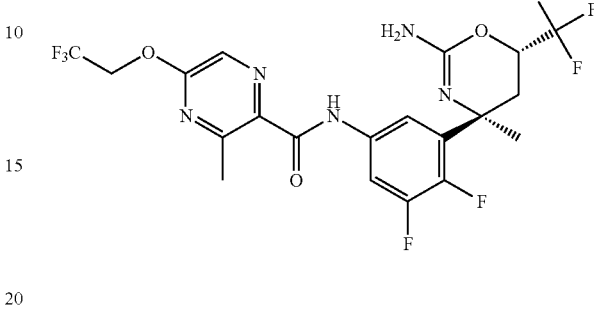

N-(3-((4S,6S)-2-amino-4-methyl-6-(trifluoromethyl)-5,6-dihydro-4H-1,3-oxazin-4-yl)-4,5-difluorophenyl)-3-methyl-5-(2,2,2-trifluoroethoxy)pyrazine-2-carboxamide The title compound was synthesized by procedures and steps analogous to those described in Method Z, Example 186 above, but using 3-methyl-5-(2,2,2-trifluoroethoxy)pyrazine-2-carboxylic acid (intermediate 24). MS m/z=528.0 [M+H]⁺. Calculated for C20H17F8N5O3: 527.37

¹H NMR (300 MHz, CHLOROFORM-d) δ=9.79 (br. s., 1 H), 8.15 (s, 1 H), 8.14-8.07 (m, 1 H), 7.01 (br. s., 1 H), 4.86 (q, J=8.4 Hz, 2 H), 4.19-4.03 (m, 1 H), 2.95 (s, 3 H), 2.85 (d, J=14.0 Hz, 1 H), 1.97 (t, J=13.5 Hz, 1 H), 1.70 (s, 3 H)

Example 198

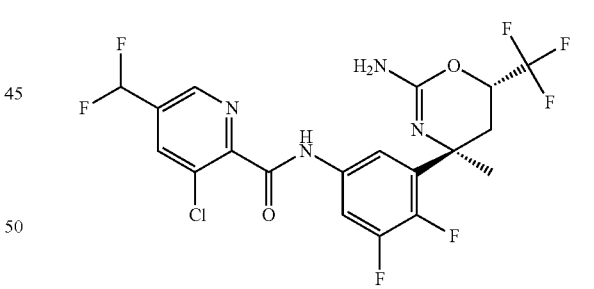

N-(3-((4S,6S)-2-amino-4-methyl-6-(trifluoromethyl)-5,6-dihydro-4H-1,3-oxazin-4-yl)-4,5-difluorophenyl)-3-chloro-5-(difluoromethyl)picolinamide The title compound was synthesized by procedures and steps analogous to those described in Method Z, Example 186 above, but using 3-chloro-5-(difluoromethyl)picolinic acid (WO2012095521). MS m/z=499.1 [M+H]⁺. Calculated for C19H14ClF7N4O2: 498.78

¹H NMR (400 MHz, CHLOROFORM-d) δ=9.87 (br. s., 1 H), 8.65 (br. s., 1 H), 8.17 (br. s., 1 H), 8.03 (br. s., 1 H), 7.04

(br. s., 1 H), 6.95-6.60 (m, 1 H), 4.12-4.00 (m, 1 H), 2.80 (d, J=13.7 Hz, 1 H), 1.92 (t, J=13.1 Hz, 1 H), 1.65 (br. s., 3 H)

Example 199

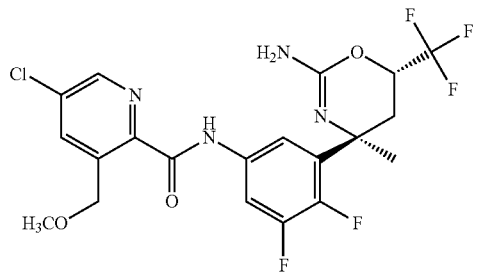 [SMILES: COCc1cc(Cl)cnc1C(=O)Nc1cc(F)c(F)c([C@]2(C)C[C@@H](C(F)(F)F)OC(N)=N2)c1]

N-(3-((4S,6S)-2-amino-4-methyl-6-(trifluoromethyl)-5,6-dihydro-4H-1,3-oxazin-4-yl)-4,5-difluorophenyl)-5-chloro-3-(methoxymethyl)picolinamide The title compound was synthesized by procedures and steps analogous to those described in Method Z, Example 186 above, but using 5-chloro-3-(methoxymethyl)picolinic acid (WO2012954463). MS m/z=493.1 [M+H]$^+$. Calculated for C20H18ClF5N4O3: 492.83

$^1$H NMR (400 MHz, CHLOROFORM-d) δ=10.03 (br. s., 1 H), 8.42 (s, 1 H), 8.21 (s, 1 H), 8.13-8.03 (m, 1 H), 7.07-6.98 (m, 1 H), 5.06 (s, 2 H), 4.06 (dd, J=5.4, 9.9 Hz, 1 H), 3.55 (s, 3 H), 2.85-2.76 (m, 1 H), 1.92 (t, J=13.2 Hz, 1 H), 1.66 (s, 3 H)

Example 200

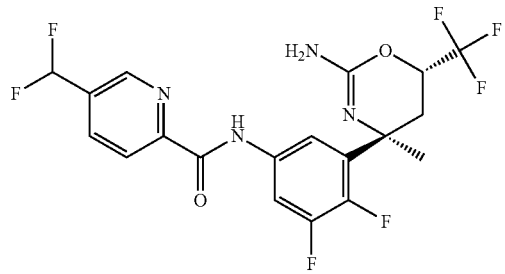

N-(3-((4S,6S)-2-amino-4-methyl-6-(trifluoromethyl)-5,6-dihydro-4H-1,3-oxazin-4-yl)-4,5-difluorophenyl)-5-(difluoromethyl)picolinamide The title compound was synthesized by procedures and steps analogous to those described in Method Z, Example 186 above, but using 5-(difluoromethyl)picolinic acid (intermediate 12). MS m/z=465.0 [M+H]$^+$. Calculated for C19H15F7N4O2: 464.34

$^1$H NMR (400 MHz, CHLOROFORM-d) δ=9.97 (br. s., 1 H), 8.76 (br. s., 1 H), 8.38 (d, J=8.2 Hz, 1 H), 8.16-8.02 (m, 2 H), 7.15 (br. s., 1 H), 6.97-6.62 (m, 1 H), 4.13-4.00 (m, 1 H), 2.80 (d, J=13.7 Hz, 1 H), 1.93 (t, J=13.2 Hz, 1 H), 1.67 (br. s., 3 H)

Example 201

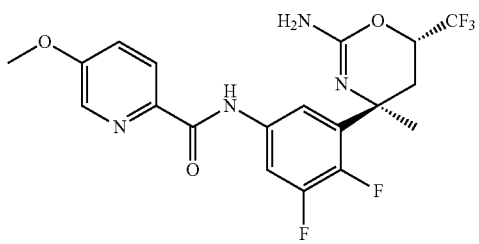 [SMILES: COc1ccc(C(=O)Nc2cc(F)c(F)c([C@]3(C)C[C@@H](C(F)(F)F)OC(N)=N3)c2)nc1]

N-(3-((4S,6S)-2-amino-4-methyl-6-(trifluoromethyl)-5,6-dihydro-4H-1,3-oxazin-4-yl)-4,5-difluorophenyl)-5-methoxypicolinamide The title compound was synthesized by procedure and steps analogous to those described in Method Z, Example 186 above, but using 5-methoxypicolinic acid (Ark Pharm). MS m/z=444.9 [M+H]$^+$. Calculated for C$_{19}$H$_{17}$F$_5$N$_4$O$_3$: 444.12.
$^1$H NMR (300 MHz, DMSO-d$_6$) δ ppm 1.53 (s, 3 H) 1.82 (t, J=12.72 Hz, 1 H) 3.94 (s, 3 H) 4.21-4.36 (m, 1 H) 5.93 (s, 2 H) 7.64 (br. s., 2 H) 7.88-8.02 (m, 1 H) 8.13 (d, J=8.48 Hz, 1 H) 8.40 (s, 1 H) 10.65 (s, 1 H).

Example 202

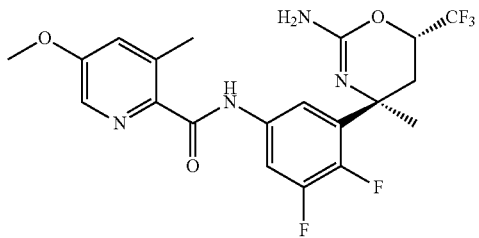 [SMILES: COc1cnc(C(=O)Nc2cc(F)c(F)c([C@]3(C)C[C@@H](C(F)(F)F)OC(N)=N3)c2)c(C)c1]

N-(3-((4S,6S)-2-amino-4-methyl-6-(trifluoromethyl)-5,6-dihydro-4H-1,3-oxazin-4-yl)-4,5-difluorophenyl)-5-methoxy-3-methylpicolinamide The title compound was synthesized by procedure and steps analogous to those described in Method Z, Example 186 above, but using 5-methoxy-3-methylpicolinic acid (WO2012095463). MS m/z=458.9 [M+H]$^+$. Calculated for C$_{20}$H$_{19}$F$_5$N$_4$O$_3$: 458.14.

¹H NMR (300 MHz, DMSO-d₆) δ ppm 1.52 (s, 3 H) 1.81 (t, J=12.93 Hz, 1 H) 2.61 (s, 3 H) 3.91 (s, 3 H) 4.22-4.37 (m, 1 H) 5.93 (s, 2 H) 7.42 (s, 1 H) 7.48 (br. s., 1 H) 7.95 (s, 1 H) 8.24 (s, 1 H) 10.59 (s, 1 H).

Example 203

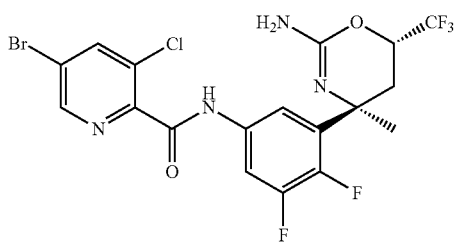

N-(3-((4S,6S)-2-amino-4-methyl-6-(trifluoromethyl)-5,6-dihydro-4H-1,3-oxazin-4-yl)-4,5-difluorophenyl)-5-bromo-3-chloropicolinamide The title compound was synthesized by procedure and steps analogous to those described in Method Z, Example 186 above, but using 5-bromo-3-chloropyridine-2-carboxylic acid (Matrix Scientific). MS m/z=527.0/529.0 [M+H]⁺. Calculated for C18H13BrClF5N4O2: 527.670.

¹H NMR (400 MHz, CHLOROFORM-d) δ=9.78 (br. s., 1H), 8.58 (s, 1H), 8.21-8.12 (m, 1H), 8.08 (s, 1H), 7.04-6.97 (m, 1H), 4.12-4.01 (m, 1H), 2.81 (d, J=11.7 Hz, 1H), 1.92 (t, J=13.2 Hz, 1H), 1.66 (s, 3H)

Example 204

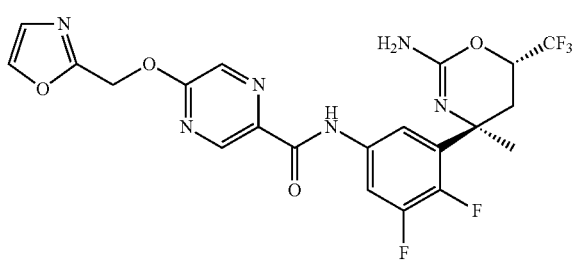 [SMILES: C[C@@]1(c2cc(NC(=O)c3cnc(OCc4ncco4)cn3)cc(F)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-4,5-difluorophenyl)-5-(oxazol-2-ylmethoxy)pyrazine-2-carboxamide The title compound was synthesized by procedures and steps analogous to those described in Method Y, Example 163 above, but using 5-(oxazol-2-ylmethoxy)pyrazine-2-carboxylic acid (Intermediate 23) in step 10. MS m/z=512.9 [M+H]⁺. Calculated for C21H17F5N6O4: 512.3

¹H NMR (400 MHz, DMSO-d₆) δ ppm 10.94 (s, 1 H), 10.85 (s, 1 H), 9.38 (br. s., 1 H), 8.92 (d, J=1.37 Hz, 1 H), 8.76 (br. s., 1 H), 8.56 (d, J=1.17 Hz, 1 H), 8.20 (d, J=0.78 Hz, 1 H), 8.15 (ddd, J=12.47, 6.90, 2.35 Hz, 1 H), 7.74 (m, J=6.30 Hz, 1 H), 7.29 (d, J=0.78 Hz, 1 H), 5.62 (s, 2 H), 5.10 (m, J=9.98, 5.48 Hz, 1 H), 2.70-2.81 (m, 1 H), 2.56 (d, J=12.91 Hz, 1 H), 1.80 (s, 3 H)

Example 205 (Method A1)

N-(3-((4S,6S)-2-amino-4-methyl-6-(trifluoromethyl)-5,6-dihydro-4H-1,3-oxazin-4-yl)-4,5-difluorophenyl)-5-cyano-3-fluoropicolinamide

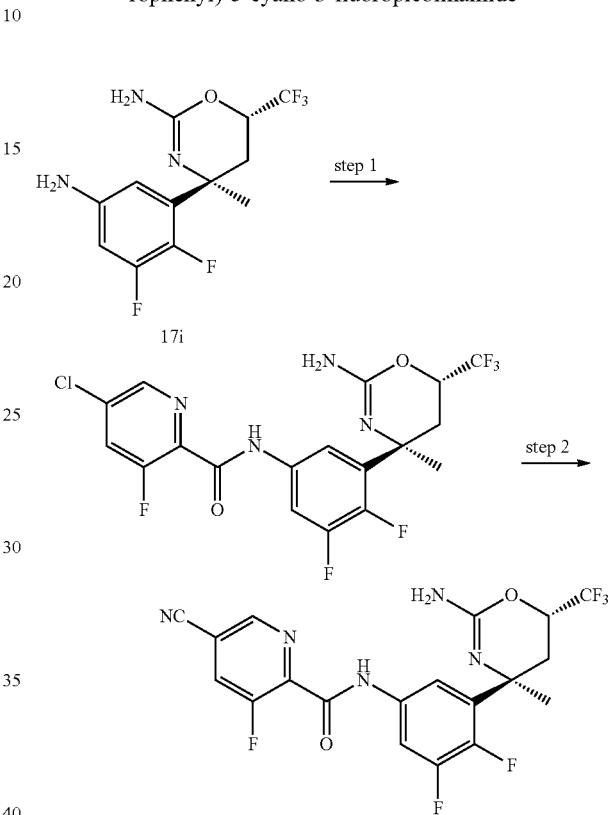

Step 1: N-(3-((4S,6S)-2-amino-4-methyl-6-(trifluoromethyl)-5,6-dihydro-4H-1,3-oxazin-4-yl)-4,5-difluorophenyl)-5-chloro-3-fluoropicolinamide The title compound was synthesized by procedures and steps analogous to those described in Method Y, Example 163 above but using 5-chloro-3-fluoropyridine-2-carboxylic acid (Frontier Scientific) in step 10. MS m/z=466.9 [M+H]⁺. Calculated for C18H13ClF6N4O2: 466.765.

Step 2: N-(3-((4S,6S)-2-amino-4-methyl-6-(trifluoromethyl)-5,6-dihydro-4H-1,3-oxazin-4-yl)-4,5-difluorophenyl)-5-cyano-3-fluoropicolinamide A microwave vial was charged with N-(3-((4S,6S)-2-amino-4-methyl-6-(trifluoromethyl)-5,6-dihydro-4H-1,3-oxazin-4-yl)-4,5-difluorophenyl)-5-chloro-3-fluoropicolinamide (0.182 g, 0.390 mmol), zinc cyanide (0.056 g, 0.468 mmol, Sigma Aldrich), 2-dicyclohexylphosphino-2',6'-dimethoxy-1'1'-biphenyl (0.032 g, 0.078 mmol, Strem), and tris(dibenzylideneacetone)dipalladium (0) (0.036 g, 0.039 mmol, Strem). The vial was sealed and evacuated/backfilled with nitrogen three times. 1 ml of a premixed 99:1 DMA:water solution was added and the reaction was heated to 120° C. in the microwave for 20 minutes. Upon cooling, the reaction was diluted with water and EtOAc. The organic layer was separated, washed with brine and dried over magnesium sulfate. The crude residue was purified via silica gel flash chromatography using a gradient of 20-100% EtOAc in hexanes) to afford the title compound (0.0904 g, 0.198 mmol, 50.7% yield) as a yellow solid. MS m/z=458.0 [M+H]$^+$. Calculated for $C_{19}H_{13}F_6N_5O_2$: 457.329.

$^1$H NMR (300 MHz, DMSO-$d_6$) δ ppm 1.35-1.63 (m, 3 H) 1.35-1.63 (m, 3 H) 1.51 (s, 3 H) 1.74-1.89 (m, 1 H) 2.52-2.64 (m, 1 H) 4.18-4.41 (m, 1 H) 5.94 (s, 2 H) 7.48 (br. s., 1 H) 7.94 (d, J=11.40 Hz, 1 H) 8.66 (d, J=10.38 Hz, 1 H) 9.04 (s, 1 H) 11.09 (br. s., 1 H)

Example 206 (Method A2)

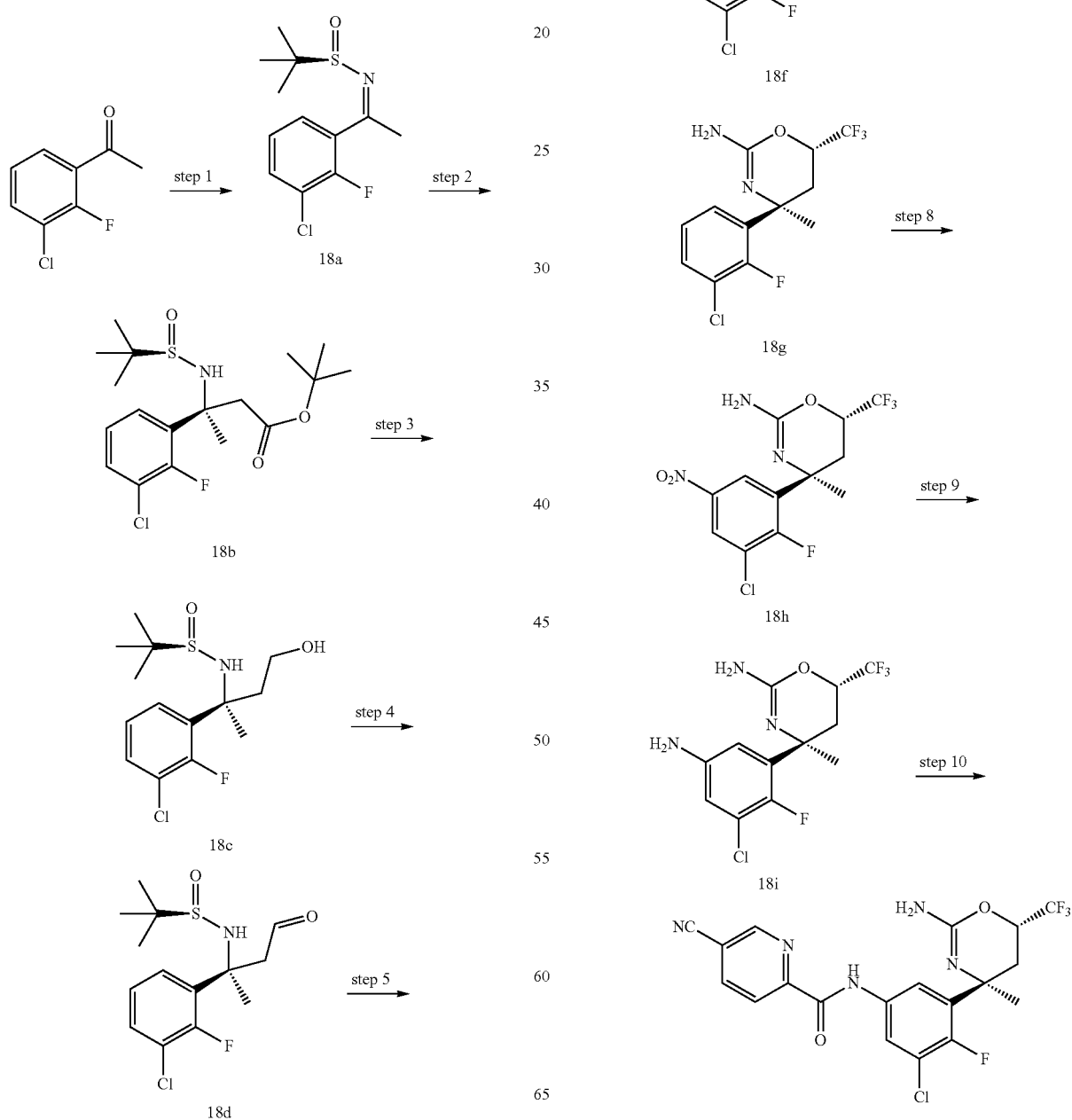

Synthesis of N-(3-((4S,6S)-2-amino-4-methyl-6-(trifluoromethyl)-5,6-dihydro-4H-1,3-oxazin-4-yl)-5-chloro-4-fluorophenyl)-5-cyanopicolinamide

Step 1: (R,E)-N-(1-(3-chloro-2-fluorophenyl)ethylidene)-2-methylpropane-2-sulfinamide (18a)

To a solution of 1-(3-chloro-2-fluorophenyl)ethanone (5.60 g, 31.5 mmol) and (R)-2-methylpropane-2-sulfinamide (5.72 g, 47.2 mmol) in THF (50.0 mL) was added tetraethoxytitanium (16.50 mL, 79 mmol) and the overall bright yellow solution was heated at 70° C. for overnight. The reaction was slightly cooled with ice-water bath, then was added EtOAc (50 mL), NaHCO$_3$ (10 mL), and brine (10 mL). The slurry was filtered through a short path of Celite and the wet cake was washed with EtOAc. The resulted bright yellow solution was phase separated, and the organic layer was concentrated to afford the title compound (8.3 g, 30.1 mmol, 96% yield) as a light yellow oil. This material was used in the next step without purification. MS m/z=276.0 [M+H]$^+$. Calculated for C12H15ClFNOS: 275.77.

Step 2: (5)-tert-butyl 3-(3-chloro-2-fluorophenyl)-3-((R)-1,1-dimethylethylsulfinamido) butanoate (18b)

The title compound was synthesized by procedures and steps analogous to those described in Method Y, Example 163, but using (R,E)-N-(1-(3-chloro-2-fluorophenyl)ethylidene)-2-methylpropane-2-sulfinamide (18a) in step 2. MS m/z=414.2 [M+Na]$^+$. Calculated for C18H27ClFNO3S: 391.93

Step 3: (R)-N-(2-(3-chloro-2-fluorophenyl)-4-hydroxybutan-2-yl)-2-methylpropane-2-sulfinamide (18c)

The title compound was synthesized by procedures and steps analogous to those described in Method Y, Example 163, but using (5)-tert-butyl 3-(3-chloro-2-fluorophenyl)-3-((R)-1,1-dimethylethylsulfinamido) butanoate (18b) in step 3. MS m/z=322.1 [M+H]$^+$. Calculated for C14H21ClFNO2S: 321.84

Step 4: (R)-N-((S)-2-(3-chloro-2-fluorophenyl)-4-oxobutan-2-yl)-2-methylpropane-2-sulfinamide (18d)

The title compound was synthesized by procedures and steps analogous to those described in Method Y, Example 163, but using (R)-N-(2-(3-chloro-2-fluorophenyl)-4-hydroxybutan-2-yl)-2-methylpropane-2-sulfinamide (18c) in step 4. MS m/z=320.1 [M+H]$^+$. Calculated for C14H19ClFNO2S: 319.82

Step 5: (R)-N-((4S)-2-(3-chloro-2-fluorophenyl)-5,5,5-trifluoro-4-hydroxypentan-2-yl)-2-methylpropane-2-sulfinamide (18e)

The title compound was synthesized by procedures and steps analogous to those described in Method Y, Example 163, but using (R)-N-((S)-2-(3-chloro-2-fluorophenyl)-4-oxobutan-2-yl)-2-methylpropane-2-sulfinamide (18d) in step 5. MS m/z=390.0 [M+H]$^+$. Calculated for C15H20ClF4NO2S: 389.83

Step 6: N-((4S,6S)-4-(3-chloro-2-fluorophenyl)-4-methyl-6-(trifluoromethyl)-5,6-dihydro-4H-1,3-oxazin-2-yl)-benzamide (18f)

The title compound was synthesized by procedures and steps analogous to those described in Method Y, Example 163, but using (R)-N-((4S)-2-(3-chloro-2-fluorophenyl)-5,5,5-trifluoro-4-hydroxypentan-2-yl)-2-methylpropane-2-sulfinamide (18e) in step 6. MS m/z=415.1 [M+H]$^+$. Calculated for C19H15ClF4N2O2: 414.78

Step 7: (4S,6S)-4-(3-chloro-2-fluorophenyl)-4-methyl-6-(trifluoromethyl)-5,6-dihydro-4H-1,3-oxazin-2-amine (18g)

The title compound was synthesized by procedures and steps analogous to those described in Method Y, Example 163, but using N-((4S,6S)-4-(3-chloro-2-fluorophenyl)-4-methyl-6-(trifluoromethyl)-5,6-dihydro-4H-1,3-oxazin-2-yl)benzamide (18f) in step 7. MS m/z=311.1 [M+H]$^+$. Calculated for C12H11ClF4N2O: 310.67

Step 8: (4S,6S)-4-(3-chloro-2-fluoro-5-nitrophenyl)-4-methyl-6-(trifluoromethyl)-5,6-dihydro-4H-1,3-oxazin-2-amine (18h)

The title compound was synthesized by procedures and steps analogous to those described in Method Y, Example 163, but using (4S,6S)-4-(3-chloro-2-fluorophenyl)-4-methyl-6-(trifluoromethyl)-5,6-dihydro-4H-1,3-oxazin-2-amine (18g) in step 8. MS m/z=356.0 [M+H]$^+$. Calculated for C12H10ClF4N3O3: 355.67

Step 9: (4S,6S)-4-(5-amino-3-chloro-2-fluorophenyl)-4-methyl-6-(trifluoromethyl)-5,6-dihydro-4H-1,3-oxazin-2-amine (18i)

The title compound was synthesized by procedures and steps analogous to those described in Method Y, Example 163, but using (4S,6S)-4-(3-chloro-2-fluoro-5-nitrophenyl)-4-methyl-6-(trifluoromethyl)-5,6-dihydro-4H-1,3-oxazin-2-amine (18h) in step 9. MS m/z=326.0 [M+H]$^+$. Calculated for C12H12ClF4N3O: 325.69

Step 10: N-(3-((4S,6S)-2-amino-4-methyl-6-(trifluoromethyl)-5,6-dihydro-4H-1,3-oxazin-4-yl)-5-chloro-4-fluorophenyl)-5-cyanopicolinamide To a cooled (ice bath) solution of (4S,6S)-4-(5-amino-3-chloro-2-fluorophenyl)-4-methyl-6-(trifluoromethyl)-5,6-dihydro-4H-1,3-oxazin-2-amine (0.090 g, 0.276 mmol) and 5-cyano-2-pyridinecarboxylic acid (0.060 g, 0.405 mmol) in n,n-Dimethylformamide (1.5 mL) was added dropwise 2,4,6-tripropyl-1,3,5,2,4,6-trioxatriphosphinane 2,4,6-trioxide (0.352 mL, 0.553 mmol). After stirred for 1.5 h, reaction went to completion. The reaction mixture was quenched with saturated NaHCO3 and diluted with water. The resulted suspension was stirred for 30 min, and filtered. The filter caked was washed with water and purified by Shimadzu HPLC to afford the title compound (0.086 g, 0.189 mmol, 68.3% yield) as off-white solid. MS m/z=456.0 [M+H]$^+$. Calculated for C19H14ClF4N5O2: 455.79

$^1$H NMR (400 MHz, CHLOROFORM-d) δ ppm 1.67 (s, 3 H) 1.94 (t, J=13.20 Hz, 1 H) 2.76-2.85 (m, 1 H) 4.05 (m, 1 H)

7.40 (br. s., 1 H) 8.21 (dd, J=8.22, 1.96 Hz, 2 H) 8.41 (dd, J=8.02 Hz, 1 H) 8.89 (s, 1 H) 9.88 (br. s., 1 H)

Example 207

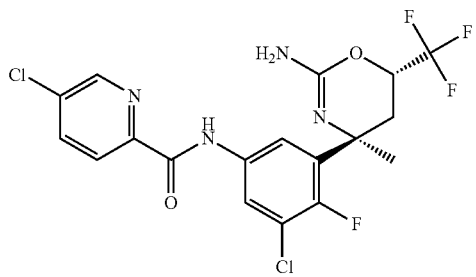 [SMILES: C[C@@]1(c2cc(NC(=O)c3ccc(Cl)cn3)cc(Cl)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-5-chloro-4-fluorophenyl)-5-chloropicolinamide The title compound was synthesized by procedures and steps analogous to those described in Method A2, Example 206 above, but using 5-chloro-2-pyridinecarboxylic acid (Oakwood Products, Inc.) in step 10. MS m/z=465.0 [M+H]$^+$. Calculated for C18H14Cl2F4N4O2: 465.23

$^1$H NMR (400 MHz, CHLOROFORM-d) δ ppm 1.69 (s, 3 H) 1.94 (t, J=13.40 Hz, 1 H) 2.82 (dd, J=13.89, 2.35 Hz, 1 H) 4.07 (m, 1 H) 7.35 (br. s, 1 H) 7.89 (dd, J=8.41, 2.35 Hz, 1 H) 8.22 (d, J=8.22 Hz, 2 H) 8.56 (d, J=1.96 Hz, 1 H) 9.85 (br. s., 1 H)

Example 208

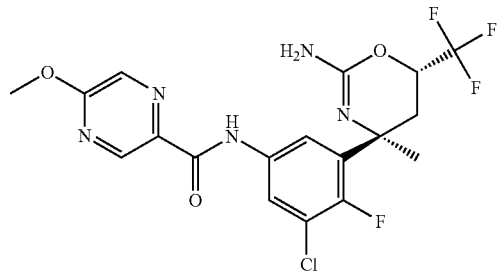 [SMILES: COc1ccc(C(=O)Nc2cc(Cl)c(F)c([C@]3(C)C[C@@H](C(F)(F)F)OC(N)=N3)c2)nc1]

N-(3-((4S,6S)-2-amino-4-methyl-6-(trifluoromethyl)-5,6-dihydro-4H-1,3-oxazin-4-yl)-5-chloro-4-fluorophenyl)-5-methoxypyrazine-2-carboxamide The title compound was synthesized by procedures and steps analogous to those described in Method A2, Example 206 above, but using 5-methoxy-pyrazinecarboxylic acid (Ark Pharm, Inc.) in step 10. MS m/z=462.0 [M+H]$^+$. Calculated for C18H16ClF4N5O3: 461.798

$^1$H NMR (400 MHz, CHLOROFORM-d) δ=9.47 (br. s., 1H), 8.98 (br. s., 1H), 8.29-7.97 (m, 2H), 7.35 (br. s., 1H), 4.18-3.89 (m, 4H), 2.79 (d, J=13.1 Hz, 1H), 1.91 (t, J=13.1 Hz, 1H), 1.66 (br. s., 3H)

Example 209

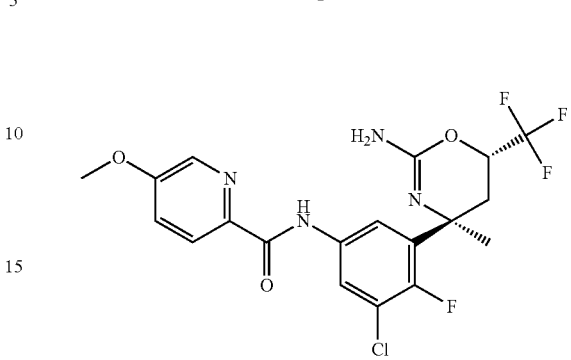

N-(3-((4S,6S)-2-amino-4-methyl-6-(trifluoromethyl)-5,6-dihydro-4H-1,3-oxazin-4-yl)-5-chloro-4-fluorophenyl)-5-methoxypicolinamide The title compound was synthesized by procedures and steps analogous to those described in Method A2, Example 206 above, but using 5-methoxy-2-pyridinecarboxylic acid (Ark Pharm, Inc.) in step 10. MS m/z=461.1 [M+H]$^+$. Calculated for C19H17ClF4N4O3: 460.810

$^1$H NMR (400 MHz, CHLOROFORM-d) δ=9.82 (s, 1H), 8.31-8.17 (m, 3H), 7.39-7.28 (m, 2H), 4.05 (ddd, J=2.6, 6.0, 12.3 Hz, 1H), 3.94 (s, 3H), 2.79 (dd, J=2.6, 13.8 Hz, 1H), 1.90 (t, J=13.2 Hz, 1H), 1.65 (s, 3H)

Example 210

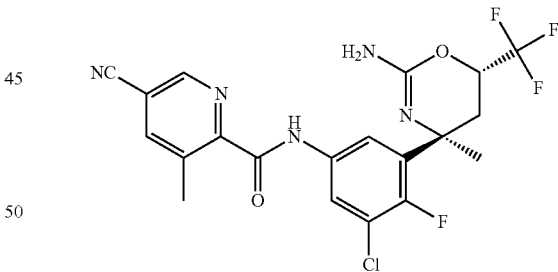

N-(3-((4S,6S)-2-amino-4-methyl-6-(trifluoromethyl)-5,6-dihydro-4H-1,3-oxazin-4-yl)-5-chloro-4-fluorophenyl)-5-cyano-3-methylpicolinamide The title compound was synthesized by procedures and steps analogous to those described in Method A2, Example 206 above, but using 5-cyano-3-methylpicolinic acid (intermediate 16) in step 10. MS m/z=470.1 [M+H]$^+$. Calculated for C20H16ClF4N5O2: 469.820.

$^1$H NMR (300 MHz, CHLOROFORM-d) δ=10.05 (s, 1H), 8.72 (d, J=1.5 Hz, 1H), 8.27 (dd, J=2.8, 6.1 Hz, 1H), 7.98 (d,

J=1.2 Hz, 1H), 7.25 (dd, J=2.8, 6.3 Hz, 1H), 4.11-3.99 (m, 1H), 2.88 (s, 3H), 2.82 (dd, J=2.7, 13.8 Hz, 1H), 1.99-1.87 (m, 1H), 1.67 (s, 3H)

Example 211

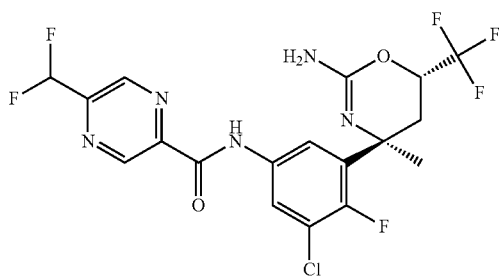 [SMILES: C[C@@]1(c2cc(NC(=O)c3cnc(C(F)F)cn3)cc(Cl)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-5-chloro-4-fluorophenyl)-5-(difluoromethyl)pyrazine-2-carboxamide The title compound was synthesized by procedures and steps analogous to those described in Method A2, Example 206 above, but using 5-(difluoromethyl)pyrazine-2-carboxylic acid (Aurigene Discovery Technologies Ltd.) in step 10. MS m/z=482.1 [M+H]$^+$. Calculated for C18H14ClF6N5O2: 481.779

$^1$H NMR (400 MHz, CHLOROFORM-d) δ=9.61 (br. s., 1H), 9.51 (s, 1H), 8.91 (s, 1H), 8.18 (dd, J=2.5, 6.1 Hz, 1H), 7.44-7.35 (m, 1H), 7.02-6.60 (m, 1H), 4.35 (br. s., 2H), 4.11-3.96 (m, 1H), 2.80 (dd, J=2.2, 13.9 Hz, 1H), 1.92 (t, J=13.2 Hz, 1H), 1.65 (s, 3H)

Example 212

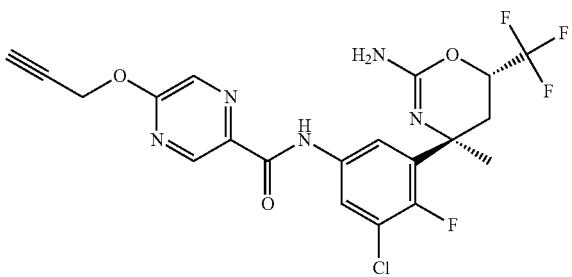 [SMILES: C#CCOc1cnc(C(=O)Nc2cc(Cl)c(F)c([C@]3(C)C[C@@H](C(F)(F)F)OC(N)=N3)c2)cn1]

N-(3-((4S,6S)-2-amino-4-methyl-6-(trifluoromethyl)-5,6-dihydro-4H-1,3-oxazin-4-yl)-5-chloro-4-fluorophenyl)-5-(prop-2-yn-1-yloxy)pyrazine-2-carboxamide The title compound was synthesized by procedures and steps analogous to those described in Method A2, Example 206 above, but using 5-(prop-2-yn-1-yloxy)pyrazine-2-carboxylic acid (J. Med. Chem. 2013, 56, 3980) in step 10. MS m/z=486.1 [M+H]$^+$. Calculated for C20H16ClF4N5O3: 485.819

$^1$H NMR (400 MHz, CHLOROFORM-d) δ=9.48 (br. s., 1H), 9.02 (s, 1H), 8.24-8.14 (m, 2H), 7.32 (d, J=3.5 Hz, 1H), 5.09 (d, J=2.2 Hz, 2H), 4.35 (br. s., 2H), 4.09-3.99 (m, 1H), 2.79 (dd, J=2.4, 13.8 Hz, 1H), 2.55 (m, 1H), 1.90 (t, J=13.3 Hz, 1H), 1.64 (s, 3H)

Example 213

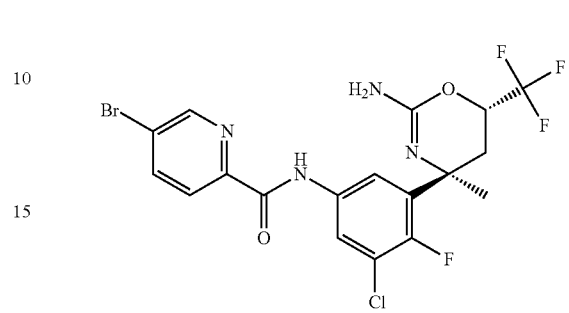 [SMILES: C[C@@]1(c2cc(NC(=O)c3cnc(OCC(F)(F)F)cn3)cc(Cl)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-5-chloro-4-fluorophenyl)-5-bromopicolinamide The title compound was synthesized by procedures and steps analogous to those described in Method A2, Example 206 above, but using 5-bromopyridine-2-carboxylic acid (Sigma-Aldrich Chemical Company, Inc.) in step 10. MS m/z=509.0/511.0 [M+H]$^+$. Calculated for C18H14BrClF4N4O2: 509.680.

$^1$H NMR (300 MHz, CHLOROFORM-d) δ=9.85 (s, 1H), 8.68 (d, J=2.2 Hz, 1H), 8.23 (dd, J=2.8, 6.1 Hz, 1H), 8.20-8.16 (m, 1H), 8.09-8.05 (m, 1H), 7.35 (dd, J=2.8, 6.1 Hz, 1H), 4.06 (ddd, J=2.8, 5.9, 12.5 Hz, 1H), 2.81 (dd, J=2.7, 13.8 Hz, 1H), 1.99-1.88 (m, 1H), 1.67 (d, J=1.2 Hz, 3H)

Example 214

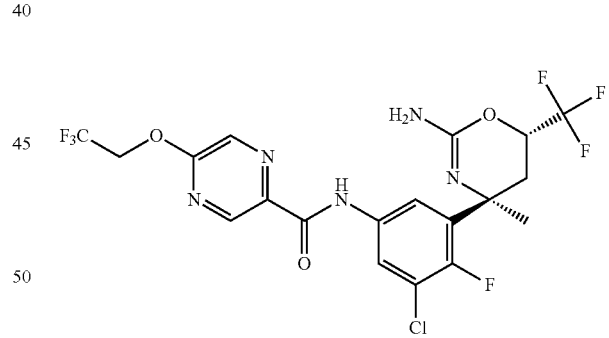

N-(3-((4S,6S)-2-amino-4-methyl-6-(trifluoromethyl)-5,6-dihydro-4H-1,3-oxazin-4-yl)-5-chloro-4-fluorophenyl)-5-(2,2,2-trifluoroethoxy)pyrazine-2-carboxamide The title compound was synthesized by procedures and steps analogous to those described in Method A2, Example 206 above, but using 5-(2,2,2-trifluoroethoxy)pyrazine-2-carboxylic acid (WO2011044181) in step 10. MS m/z=530.1 [M+H]$^+$. Calculated for C19H15ClF7N5O3: 529.796.

$^1$H NMR (400 MHz, CHLOROFORM-d) δ=9.50 (br. s., 1H), 9.01 (s., 1H), 8.30 (s., 1H), 8.19 (s., 1H), 7.34 (s., 1H), 4.87 (d, J=7.8 Hz, 2H), 4.10 (br. s., 1H), 2.84 (d, J=13.7 Hz, 1H), 1.97 (t, J=13.0 Hz, 1H), 1.70 (s., 3H)

Example 215

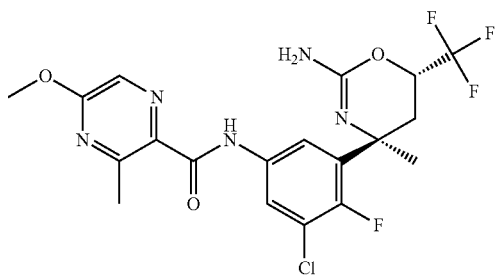 [SMILES: COc1cnc(C(=O)Nc2cc(Cl)c(F)c([C@]3(C)C[C@@H](C(F)(F)F)OC(N)=N3)c2)c(C)n1]

N-(3-((4S,6S)-2-amino-4-methyl-6-(trifluoromethyl)-5,6-dihydro-4H-1,3-oxazin-4-yl)-5-chloro-4-fluorophenyl)-5-methoxy-3-methylpyrazine-2-carboxamide The title compound was synthesized by procedures and steps analogous to those described in Method A2, Example 206 above, but using 5-methoxy-3-methylpyrazine-2-carboxylic acid (intermediate 13) in step 10. MS m/z=476.1 [M+H]$^+$. Calculated for C19H18ClF4N5O3: 475.825.
$^1$H NMR (400 MHz, CHLOROFORM-d) δ=9.79 (br. s., 1H), 8.26 (d, J=3.9 Hz, 1H), 7.98 (s, 1H), 7.19 (d, J=3.7 Hz, 1H), 4.14-3.99 (m, 4H), 2.93 (s, 3H), 2.81 (d, J=11.5 Hz, 1H), 1.92 (t, J=13.2 Hz, 1H), 1.66 (s, 3H)

Example 216 (Method A3)

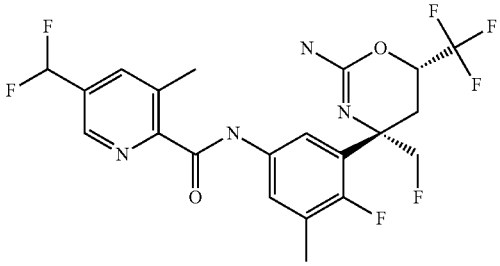 [SMILES: Cc1cc(C(F)F)cnc1C(=O)Nc1cc(C)c(F)c([C@]2(CF)C[C@@H](C(F)(F)F)OC(N)=N2)c1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethyl)-3-methylpicolinamide Step 1:
2-fluoro-1-(2-fluoro-3-methylphenyl)ethanone:

A solution of 1-bromo-2-fluoro-3-methylbenzene (7.0 g, 37.0 mmol) in THF (60 mL) was brought to −78° C. followed by the dropwise addition of butyllithium (15.55 ml, 38.9 mmol). The resulting mixture was stirred at −78° C. for 1 h then neat ethyl 2-fluoroacetate (3.76 ml, 38.9 mmol) was added dropwise. After 30 min the reaction went to completion. The reaction was quenched at −78° C. with saturated NH$_4$Cl, warmed to rt and transferred to a separatory funnel. The aqueous phase was extracted with EtOAc and the combined organic extracts were washed with brine, dried over Na$_2$SO$_4$, filtered, concentrated and chromatographed on silica gel using 0-10% EtOAc/hexanes to afford a colorless oil that turned into a white solid as 2-fluoro-1-(2-fluoro-3-methylphenyl)ethanone (5.03 g, 29.6 mmol, 80% yield). MS m/z=171 [M+H]$^+$. Calculated for C$_9$H$_8$F$_2$O: 170.05.

Step 2: R,E)-N-(2-fluoro-1-(2-fluoro-3-methylphenyl)ethylidene)-2-methylpropane-2-sulfinamide To a solution of 2-fluoro-1-(2-fluoro-3-methylphenyl)ethanone (5.03 g, 29.6 mmol) in THF (70 mL) were added (R)-2-methylpropane-2-sulfinamide (7.17 g, 59.1 mmol) and titanium (iv) ethoxide (15.30 ml, 73.9 mmol) and the resulting mixture was heated to reflux for 1.5 h. The reaction went to completion, brought to rt, and brine was added. The suspension was filtered, the filtrate was washed with brine, the organics extracts were combined, dried over Na$_2$SO$_4$, concentrated and chromatographed on silica gel using 0-30% EtOAc/hexanes to afford a light yellow oil as (R,E)-N-(2-fluoro-1-(2-fluoro-3-methylphenyl)ethylidene)-2-methylpropane-2-sulfinamide (4.71 g, 17.23 mmol, 58.3% yield). MS m/z=274 [M+H]$^+$. Calculated for C$_{13}$H$_{17}$F$_2$NOS: 273.10.

Step 3: (R)-N-((Z)-4-(2,2-dimethylhydrazono)-1,5,5,5-tetrafluoro-2-(2-fluoro-3-methylphenyl)pentan-2-yl)-2-methylpropane-2-sulfinamide To a solution of (E)-1,1-dimethyl-2-(1,1,1-trifluoropropan-2-ylidene)hydrazine (2.256 g, 14.63 mmol) in dry THF (20 mL) at −78° C. were added n,n,n',n'-tetramethylethylenediamine (2.190 ml, 14.63 mmol) and lithium diisopropylamide, 2.0m heptane/tetrahydrofuran/ethylbenzene (7.32 ml, 14.63 mmol) and stirred at this temperature for 30 min. A solution of (R,E)-N-(2-fluoro-1-(2-fluoro-3-methylphenyl)ethylidene)-2-methylpropane-2-sulfinamide (2.0 g, 7.32 mmol) in toluene (12 mL) at −78° C. was treated with trimethylaluminum, 2.0m solution in toluene (3.66 ml, 7.32 mmol) for 10 min and added dropwise to the solution containing the hydrazine at −78° C. The resulting mixture was stirred at this temperature for 1.5 h. The mixture was quenched with saturated NH$_4$Cl, and extracted with EtOAc. The combined organics were dried over Na$_2$SO$_4$, filtered, concentrated and chromatographed on silica gel using 0-50% EtOAc/hexanes to afford a bright yellow oil as (R)-N-((Z)-4-(2,2-dimethylhydrazono)-1,5,5,5-tetrafluoro-2-(2-fluoro-3-methylphenyl)pentan-2-yl)-2-methylpropane-2-sulfinamide (5.66 g, 77% yield, combined). MS m/z=427.9 [M+H]$^+$. Calculated for C$_{18}$H$_{26}$F$_5$N$_3$OS: 427.17.

Step 4: (R)-2-methyl-N-((S)-1,5,5,5-tetrafluoro-2-(2-fluoro-3-methylphenyl)-4-oxopentan-2-yl)propane-2-sulfinamide To a solution of (R)-N-((Z)-4-(2,2-dimethylhydrazono)-1,5,5,5-tetrafluoro-2-(2-fluoro-3-methylphenyl)pentan-2-yl)-2-methylpropane-2-sulfinamide (5.66 g, 13.24 mmol) in 10% water (5 mL) in dioxane (50 mL) was added hydrogen chloride, 1m in diethyl ether (26.5 ml, 26.5 mmol) and the resulting mixture was stirred at 40° C. for 1 h. The reaction was quenched with water, diluted with EtOAc and washed with water. The organic phase was dried over Na$_2$SO$_4$, filtered, concentrated and chromatographed on silica gel using 0-40% EtOAc/hexanes to afford a yellow oil as (R)-2-methyl-N-((S)-1,5,5,5-tetrafluoro-2-(2-fluoro-3-methylphenyl)-4-oxopentan-2-yl)propane-2-sulfinamide (3.80 g, 75% yield). MS m/z=385.9 [M+H]$^+$. Calculated for $C_{16}H_{20}F_5NO_2S$: 385.11.

Step 5: (R)-2-methyl-N-((2S,4S)-1,5,5,5-tetrafluoro-2-(2-fluoro-3-methylphenyl)-4-hydroxypentan-2-yl)propane-2-sulfinamide Ru[p-cymeme](1S,2S)-N-(p-toluenesulfonyl)-1,2-diphenylethylenediamine (2.365 g, 3.94 mmol) was added in one portion to a solution of (R)-2-methyl-N-((S)-1,5,5,5-tetrafluoro-2-(2-fluoro-3-methylphenyl)-4-oxopentan-2-yl)propane-2-sulfinamide (3.80 g, 9.86 mmol) in IPA (100 ml) (which had been degassed by bubbling nitrogen through the solution for 30 minutes prior to use) under $N_2$ atmosphere. The reaction was stirred at rt for 2 h. The reaction went to completion. The reaction was quenched with saturated $NaHCO_3$, extracted with EtOAc and the combined organic extracts were washed with water, brine, dried over $Na_2SO_4$, filtered, concentrated and chromatographed on silica gel using 0-40% EtOAc/hexanes to afford a light brown solid as (R)-2-methyl-N-((2S,4S)-1,5,5,5-tetrafluoro-2-(2-fluoro-3-methylphenyl)-4-hydroxypentan-2-yl)propane-2-sulfinamide (2.0 g, 5.16 mmol, 52.4% yield). MS m/z=387.9 [M+H]$^+$. Calculated for $C_{16}H_{22}F_5NO_2S$: 387.13.

Step 6: N-((4S,6S)-4-(2-fluoro-3-methylphenyl)-4-(fluoromethyl)-6-(trifluoromethyl)-5,6-dihydro-4H-1,3-oxazin-2-yl)benzamide To a solution of (R)-2-methyl-N-((2S,4S)-1,5,5,5-tetrafluoro-2-(2-fluoro-3-methylphenyl)-4-hydroxypentan-2-yl)propane-2-sulfinamide (2.0 g, 5.16 mmol) in DCM (20 mL) and MeOH (10 mL) was added hydrogen chloride, 4.0m solution in 1,4-dioxane (12.91 ml, 51.6 mmol) and stirred at rt for 15 min. The reaction went to completion, concentrated, diluted with DCM and washed with 1N NaOH. The organic phase was separated, dried over $Na_2SO_4$, filtered and concentrated to afford (2S,4S)-4-amino-1,1,1,5-tetrafluoro-4-(2-fluoro-3-methylphenyl)pentan-2-ol. This amino-alcohol was dissolved in THF (12 mL) followed by the addition of benzoyl isothiocyanate (0.764 ml, 5.68 mmol) and the resulting mixture was stirred at rt for 40 min. The reaction went to completion then triethylamine (0.862 ml, 6.20 mmol) and 1-(3-dimethylaminopropyl)-3-ethylcarbodiimide hcl (1.089 g, 5.68 mmol) were added and the resulting mixture was heated at 70° C. for 1 h. The reaction went to completion. The mixture was diluted with water and extracted with EtOAc. The combined organics were washed with brine, dried over $Na_2SO_4$, filtered, concentrated and chromatographed on silica gel using 0-20% EtOAc/hexanes to afford a white solid as N-((4S,6S)-4-(2-fluoro-3-methylphenyl)-4-(fluoromethyl)-6-(trifluoromethyl)-5,6-dihydro-4H-1,3-oxazin-2-yl)benzamide (1.69 g, 4.10 mmol, 79% yield). MS m/z=412.9 [M+H]$^+$. Calculated for $C_{20}H_{17}F_5N_2O_2S$: 412.12.

Step 7: (4S,6S)-4-(2-fluoro-3-methylphenyl)-4-(fluoromethyl)-6-(trifluoromethyl)-5,6-dihydro-4H-1,3-oxazin-2-amine To a solution of N-((4S,6S)-4-(2-fluoro-3-methylphenyl)-4-(fluoromethyl)-6-(trifluoromethyl)-5,6-dihydro-4H-1,3-oxazin-2-yl)benzamide (1.69 g, 4.10 mmol) in MeOH (20 mL) was added dbu (0.741 ml, 4.92 mmol) and the resulting mixture was heated at 50° C. for 17 h. The reaction went to completion. The mixture was concentrated and chromatographed on silica gel using 0-30% EtOAc/hexanes to afford a white foam as (4S,6S)-4-(2-fluoro-3-methylphenyl)-4-(fluoromethyl)-6-(trifluoromethyl)-5,6-dihydro-4H-1,3-oxazin-2-amine (1.13 g, 3.67 mmol, 89% yield). MS m/z=308.9 [M+H]$^+$. Calculated for $C_{13}H_{13}F_5N_2O$: 308.09.

Step 8: (4S,6S)-4-(2-fluoro-3-methyl-5-nitrophenyl)-4-(fluoromethyl)-6-(trifluoromethyl)-5,6-dihydro-4H-1,3-oxazin-2-amine (4S,6S)-4-(2-fluoro-3-methylphenyl)-4-(fluoromethyl)-6-(trifluoromethyl)-5,6-dihydro-4H-1,3-oxazin-2-amine (1.13 g, 3.67 mmol) was dissolved in conc. $H_2SO_4$ (20 mL) and cooled in an ice-bath. Then potassium nitrate (0.264 ml, 5.50 mmol) was added in one portion and the reaction was stirred for 5 min, removed from the ice-bath and after 5 min at room temperature LCMS showed the reaction went to completion and ice was added. The reaction mixture was poured into a mixture of DCM, water, ice and potassium phosphate tribasic (61.5 g, 290 mmol) and stirred for 5 min followed by the slowly addition of saturated $NaHCO_3$. The mixture was neutralized with 5 N NaOH and extracted with DCM. The combined organics were dried over $Na_2SO_4$, filtered and concentrated to afford a pale yellow foam as (4S,6S)-4-(2-fluoro-3-methyl-5-nitrophenyl)-4-(fluoromethyl)-6-(trifluoromethyl)-5,6-dihydro-4H-1,3-oxazin-2-amine (1.26 g, 3.57 mmol, 97% yield). MS m/z=353.9 [M+H]$^+$. Calculated for $C_{13}H_{12}F_5N_3O_3$: 353.08.

Step 9: (4S,6S)-4-(5-amino-2-fluoro-3-methylphenyl)-4-(fluoromethyl)-6-(trifluoromethyl)-5,6-dihydro-4H-1,3-oxazin-2-amine A solution of (4S,6S)-4-(2-fluoro-3-methyl-5-nitrophenyl)-4-(fluoromethyl)-6-(trifluoromethyl)-5,6-dihydro-4H-1,3-oxazin-2-amine (1.26 g, 3.57 mmol) in EtOH (15 mL) was purged with $N_2$ followed by the addition of acetic acid, glacial (0.412 ml, 7.13 mmol) and palladium, 10% wt. on activated carbon (0.047 ml, 5.35 mmol). The resulting mixture was purged with $N_2$ again and $H_2$ was bubbled through a balloon for 1 h. The mixture was filtered through celite, concentrated, diluted washed with 10% $Na_2CO_3$, 1 N NaOH, extracted with DCM and chromatographed on silica gel using 0-5% MeOH/DCM to afford a white solid as (4S,6S)-4-(5-amino-2-fluoro-3-methylphenyl)-4-(fluoromethyl)-6-(trifluoromethyl)-5,6-dihydro-4H-1,3-oxazin-2-amine (1.11 g, 3.43 mmol, 96% yield). MS m/z=323.9 [M+H]$^+$. Calculated for $C_{13}H_{14}F_5N_3O$: 323.11.

$^1$H NMR (300 MHz, DMSO-$d_6$) δ ppm 1.92 (t, J=12.93 Hz, 1 H) 2.09 (d, J=1.90 Hz, 3 H) 2.43 (dd, J=13.15, 2.48 Hz, 1 H) 4.17-4.67 (m, 3 H) 4.92 (s, 2 H) 6.01 (s, 2 H) 6.37 (dd, J=6.07, 2.70 Hz, 1 H) 6.45 (dd, J=6.43, 2.92 Hz, 1 H).

Step 10: N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethyl)-3-methylpicolinamide To a solution of (4S,6S)-4-(5-amino-2-fluoro-3-methylphenyl)-4-(fluoromethyl)-6-(trifluoromethyl)-5,6-dihydro-4H-1,3-oxazin-2-amine (0.075 g, 0.232 mmol) and 5-(difluoromethyl)-3-methylpicolinic acid (0.048 g, 0.255 mmol) in DMF (2 mL) at 0° C. was added 1-propanephosphonic acid cyclic anhydride (0.177 ml, 0.278 mmol) and the resulting mixture was stirred at 0° C. for 2 h, the ice bath was removed and stirred at rt for 1 h. The reaction was diluted with EtOAc, washed with water, sat. $NaHCO_3$, and chromatographed on silica gel using 0-4% MeOH/DCM to afford a white solid as N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethyl)-3-methylpicolinamide (0.0145 g, 0.029 mmol, 12.69% yield). MS m/z=492.9 [M+H]+. Calculated for $C_{21}H_{19}F_7N_4O_2$: 492.14.

$^1$H NMR (300 MHz, DMSO-$d_6$) δ ppm 1.97 (t, J=12.86 Hz, 1 H) 2.26 (d, J=1.75 Hz, 3 H) 2.43 (dd, J=13.15, 2.48 Hz, 1 H) 2.58 (s, 3 H) 4.28-4.71 (m, 3 H) 6.09 (s, 2 H) 7.25 (t, J=55.20 Hz, 1 H) 7.57 (dd, J=6.80, 2.85 Hz, 1 H) 7.83 (dd, J=6.36, 2.56 Hz, 1 H) 8.03 (s, 1 H) 8.71 (s, 1 H) 10.62 (s, 1 H).

Example 217

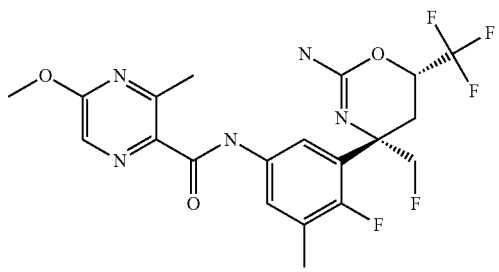 [SMILES: COc1cnc(C(=O)Nc2cc(C)c(F)c([C@]3(CF)C[C@@H](C(F)(F)F)OC(N)=N3)c2)c(C)n1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxy-3-methylpyrazine-2-carboxamide The title compound was synthesized by procedure and steps analogous to those described in Method A3, Example 216 above, but using 5-methoxy-3-methylpyrazine-2-carboxylic acid (intermediate 13) in step 10. MS m/z=473.9 [M+H]+. Calculated for $C_{20}H_{20}F_5N_5O_3$: 473.15.

$^1$H NMR (300 MHz, DMSO-$d_6$) δ ppm 1.97 (t, J=12.70 Hz, 1 H) 2.25 (d, J=1.90 Hz, 3 H) 2.47 (br. s., 1 H) 2.75 (s, 3 H) 3.99 (s, 3 H) 4.28-4.70 (m, 3 H) 6.09 (s, 2 H) 7.56 (dd, J=6.80, 2.70 Hz, 1 H) 7.80 (d, J=3.80 Hz, 1 H) 8.23 (s, 1 H) 10.41 (s, 1 H).

Example 218

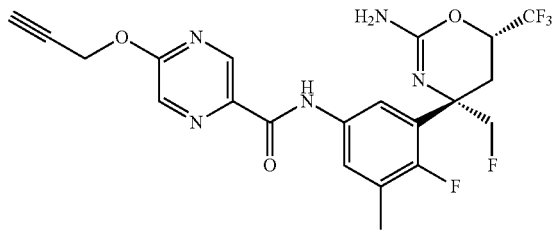 [SMILES: C#CCOc1cnc(C(=O)Nc2cc(C)c(F)c([C@]3(CF)C[C@@H](C(F)(F)F)OC(N)=N3)c2)cn1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(prop-2-yn-1-yloxy)pyrazine-2-carboxamide The title compound was synthesized by procedure and steps analogous to those described in Method A3, Example 216 above, but using 5-(prop-2-yn-1-yloxy)pyrazine-2-carboxylic acid (J. Med. Chem. 2013, 56, 3980) in step 10. MS m/z=483.9 [M+H]+. Calculated for $C_{21}H_{18}F_5N_5O_3$: 483.13.

$^1$H NMR (300 MHz, DMSO-$d_6$) δ ppm 1.97 (t, J=12.86 Hz, 1 H) 2.25 (s, 3 H) 2.44-2.47 (m, 1 H) 3.64 (t, J=2.48 Hz, 1 H) 4.30-4.71 (m, 3 H) 5.14 (d, J=2.48 Hz, 2 H) 6.08 (s, 2 H) 7.68-7.80 (m, 2 H) 8.48 (d, J=1.32 Hz, 1 H) 8.89 (d, J=1.32 Hz, 1 H) 10.49 (s, 1 H).

Example 219

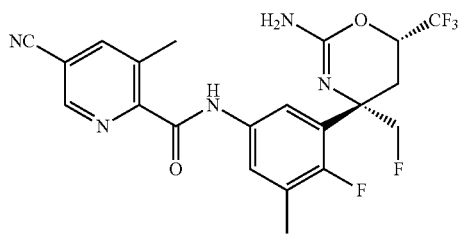 [SMILES: Cc1cc(C#N)cnc1C(=O)Nc1cc(C)c(F)c([C@]2(CF)C[C@@H](C(F)(F)F)OC(N)=N2)c1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-cyano-3-methylpicolinamide The title compound was synthesized by procedure and steps analogous to those described in Method A3, Example 216 above, but using 5-cyano-3-methylpicolinic acid (intermediate 16) in step 10. MS m/z=467.9 [M+H]+. Calculated for $C_{21}H_{18}F_5N_5O_2$: 467.14.

$^1$H NMR (300 MHz, DMSO-$d_6$) δ ppm 1.97 (t, J=13.01 Hz, 1 H) 2.26 (d, J=1.90 Hz, 3 H) 2.47 (br. s., 1 H) 2.53 (s, 3 H) 4.28-4.69 (m, 3 H) 6.09 (s, 2 H) 7.54 (dd, J=6.43, 2.63 Hz, 1 H) 7.82 (dd, J=6.21, 2.41 Hz, 1 H) 8.38 (d, J=1.17 Hz, 1 H) 8.97 (d, J=1.46 Hz, 1 H) 10.63 (s, 1 H).

Example 220

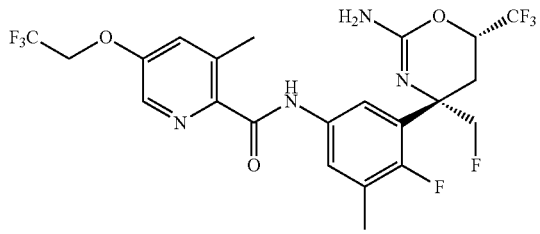 [SMILES: Cc1cc(OCC(F)(F)F)cnc1C(=O)Nc1cc(C)c(F)c([C@]2(CF)C[C@@H](C(F)(F)F)OC(N)=N2)c1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-3-methyl-5-(2,2,2-trifluoroethoxy)picolinamide The title compound was synthesized by procedure and steps analogous to those described in Method A3, Example 216 above, but using 3-methyl-5-(2,2,2-trifluoroethoxy)picolinic acid (Aurigene Discovery) in step 10. MS m/z=540.9 [M+H]+. Calculated for $C_{22}H_{20}F_8N_4O_3$: 540.14.

$^1$H NMR (300 MHz, DMSO-$d_6$) δ ppm 1.97 (t, J=13.08 Hz, 1 H) 2.25 (d, J=1.61 Hz, 3 H) 2.47 (br. s., 1 H) 2.61 (s, 3 H) 4.28-4.69 (m, 3 H) 4.98 (q, J=8.92 Hz, 2 H) 6.09 (s, 2 H)

7.51-7.61 (m, 2 H) 7.81 (d, J=3.51 Hz, 1 H) 8.34 (d, J=2.92 Hz, 1 H) 10.23-10.52 (m, 1 H) 10.41 (s, 1 H).

Example 221

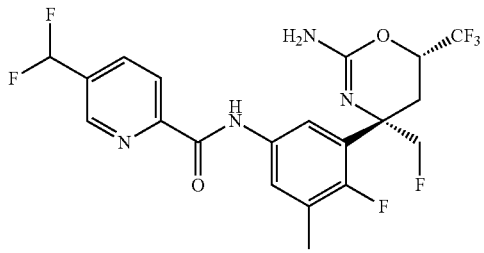 [SMILES: Cc1cc(NC(=O)c2ccc(C(F)F)cn2)cc([C@]2(CF)C[C@@H](C(F)(F)F)OC(N)=N2)c1F]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethyl)picolinamide The title compound was synthesized by procedure and steps analogous to those described in Method A3, Example 216 above, but using 5-(difluoromethyl)picolinic acid (intermediate 12) in step 10. MS m/z=478.9 [M+H]$^+$. Calculated for $C_{20}H_{17}F_7N_4O_2$: 478.12.

$^1$H NMR (300 MHz, DMSO-d$_6$) δ ppm 1.98 (t, J=12.86 Hz, 1 H) 2.26 (d, J=1.90 Hz, 3 H) 2.47 (br. s., 1 H) 4.28-4.71 (m, 3 H) 6.09 (s, 2 H) 7.29 (t, J=54.10 Hz, 1 H) 7.73 (dd, J=6.65, 2.56 Hz, 1 H) 7.82 (dd, J=3.70, 2.80 Hz, 1 H) 8.27 (d, J=1.32 Hz, 2 H) 8.94 (s, 1 H) 10.71 (s, 1 H).

Example 222

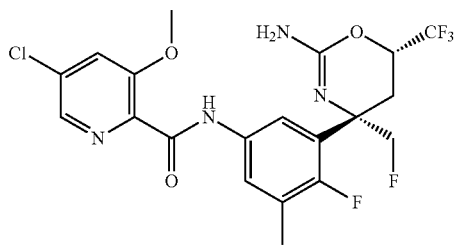 [SMILES: COc1cc(Cl)cnc1C(=O)Nc1cc(C)c(F)c([C@]2(CF)C[C@@H](C(F)(F)F)OC(N)=N2)c1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-chloro-3-methoxypicolinamide The title compound was synthesized by procedure and steps analogous to those described in Method A3, Example 216 above, but using 5-chloro-3-methoxypicolinic acid (intermediate 14) in step 10. MS m/z=492.9 [M+H]$^+$. Calculated for $C_{20}H_{18}ClF_5N_4O_3$: 492.10.

$^1$H NMR (300 MHz, DMSO-d$_6$) δ ppm 1.96 (t, J=12.93 Hz, 1 H) 2.25 (d, J=1.75 Hz, 3 H) 2.47 (br. s., 1 H) 3.89 (s, 3 H) 4.28-4.68 (m, 3 H) 6.08 (s, 2 H) 7.48 (dd, J=6.80, 2.56 Hz, 1 H) 7.78 (dd, J=6.36, 2.56 Hz, 1 H) 7.83 (d, J=1.90 Hz, 1 H) 8.25 (d, J=1.90 Hz, 1 H) 10.38 (s, 1 H).

Example 223

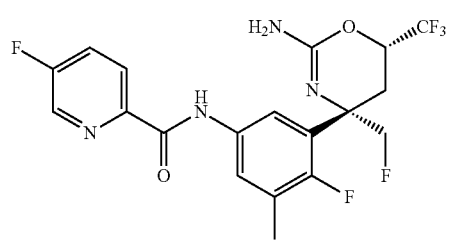 [SMILES: Cc1cc(NC(=O)c2ccc(F)cn2)cc([C@]2(CF)C[C@@H](C(F)(F)F)OC(N)=N2)c1F]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-fluoropicolinamide The title compound was synthesized by procedure and steps analogous to those described in Method A3, Example 216 above, but using 5-fluoro-2-pyridinecarboxylic acid (Frontier Scientific, Inc.) in step 10. MS m/z=446.9 [M+H]$^+$. Calculated for $C_{19}H_{16}F_6N_4O_2$: 446.12.

$^1$H NMR (300 MHz, DMSO-d$_6$) δ ppm 1.97 (t, J=12.93 Hz, 1 H) 2.25 (d, J=1.90 Hz, 3 H) 2.46 (br. s., 1 H) 4.29-4.70 (m, 3 H) 6.09 (s, 2 H) 7.70 (dd, J=6.58, 2.78 Hz, 1 H) 7.79 (dd, J=6.43, 2.48 Hz, 1 H) 7.98 (td, J=8.70, 2.78 Hz, 1 H) 8.22 (dd, J=8.92, 4.53 Hz, 1 H) 8.73 (d, J=2.92 Hz, 1 H) 10.60 (s, 1 H).

Example 224

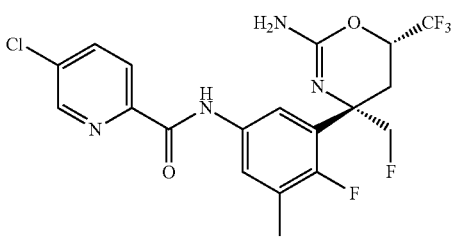 [SMILES: Cc1cc(NC(=O)c2ccc(Cl)cn2)cc([C@]2(CF)C[C@@H](C(F)(F)F)OC(N)=N2)c1F]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-chloropicolinamide The title compound was synthesized by procedure and steps analogous to those described in Method A3, Example 216 above, but using 5-chloro-2-pyridinecarboxylic acid (Oakwood Products, Inc.) in step 10. MS m/z=462.9 [M+H]$^+$. Calculated for $C_{19}H_{16}ClF_5N_4O_2$: 462.09.

$^1$H NMR (300 MHz, DMSO-d$_6$) δ ppm 1.97 (t, J=12.79 Hz, 1 H) 2.25 (d, J=1.90 Hz, 3 H) 2.46 (br. s., 1 H) 4.29-4.70 (m, 3 H) 6.09 (s, 2 H) 7.70 (dd, J=6.65, 2.85 Hz, 1 H) 7.76-7.84 (m, 1 H) 8.11-8.23 (m, 2 H) 8.79 (d, J=1.61 Hz, 1 H) 10.56 (s, 1 H).

Example 225

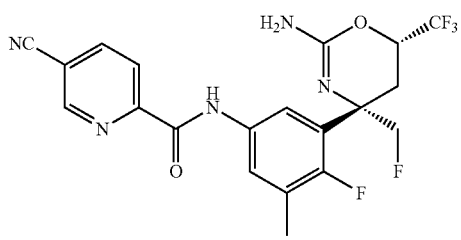 [SMILES: Cc1cc(NC(=O)c2ccc(C#N)cn2)cc([C@]2(CF)C[C@@H](C(F)(F)F)OC(N)=N2)c1F]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-cyanopicolinamide The title compound was synthesized by procedure and steps analogous to those described in Method A3, Example 216 above, but using 5-cyano-2-pyridinecarboxylic acid (Aldrich) in step 10. MS m/z=453.9 [M+H]$^+$. Calculated for $C_{20}H_{16}F_5N_5O_2$: 453.12. $^1$H NMR (300 MHz, DMSO-d$_6$) δ ppm 1.98 (t, J=13.15 Hz, 1 H) 2.26 (s, 3 H) 2.46 (br. s., 1 H) 4.28-4.71 (m, 3 H) 6.09 (s, 2 H) 7.74 (d, J=6.14 Hz, 1 H) 7.81 (d, J=5.41 Hz, 1 H) 8.27 (d, J=8.33 Hz, 1 H) 8.58 (d, J=8.18 Hz, 1 H) 9.20 (s, 1 H) 10.79 (s, 1 H).

Example 226

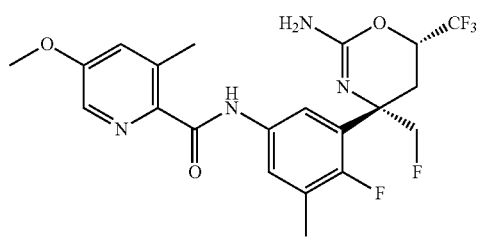 [SMILES: COc1cnc(C(=O)Nc2cc(C)c(F)c([C@]3(CF)C[C@@H](C(F)(F)F)OC(N)=N3)c2)c(C)c1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxy-3-methylpicolinamide The title compound was synthesized by procedure and steps analogous to those described in Method A3, Example 216 above, but using 5-methoxy-3-methylpicolinic acid (WO2012095463) in step 10. MS m/z=472.9 [M+H]$^+$. Calculated for $C_{21}H_{21}F_5N_4O_3$: 472.15.

$^1$H NMR (300 MHz, DMSO-d$_6$) δ ppm 1.97 (t, J=12.93 Hz, 1 H) 2.25 (d, J=1.75 Hz, 3 H) 2.44-2.48 (m, 1 H) 2.62 (s, 3 H) 3.91 (s, 3 H) 4.28-4.70 (m, 3 H) 6.09 (s, 2 H) 7.40 (d, J=2.48

Hz, 1 H) 7.54 (d, J=3.80 Hz, 1 H) 7.81 (d, J=6.28 Hz, 1 H) 8.23 (d, J=2.63 Hz, 1 H) 10.36 (s, 1 H).

Example 227

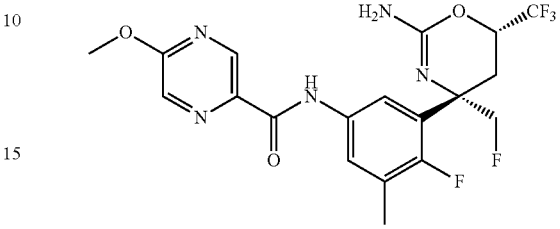

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxypyrazine-2-carboxamide The title compound was synthesized by procedure and steps analogous to those described in Method A3, Example 216 above, but using 5-methoxy-pyrazinecarboxylic acid (Ark Pharm.) in step 10. MS m/z=459.9 [M+H]$^+$. Calculated for $C_{19}H_{15}F_5N_5O_3$: 459.13.

$^1$H NMR (300 MHz, DMSO-d$_6$) δ ppm 1.97 (t, J=12.64 Hz, 1 H) 2.25 (s, 3 H) 2.46 (br. s., 1 H) 4.02 (s, 3 H) 4.26-4.71 (m, 3 H) 6.08 (s, 2 H) 7.74 (dd, J=14.91, 5.41 Hz, 2 H) 8.41 (s, 1 H) 8.88 (s, 1 H) 10.45 (s, 1 H).

Example 228

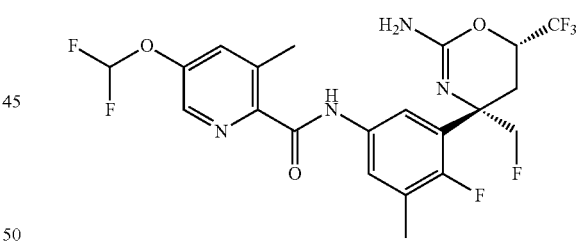

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethoxy)-3-methylpicolinamide The title compound was synthesized by procedure and steps analogous to those described in Method A3, Example 216 above, but using 5-(difluoromethoxy)-3-methylpicolinic acid (WO2012095463) in step 10. MS m/z=508.9 [M+H]$^+$. Calculated for $C_{21}H_{19}F_7N_4O_3$: 508.13.

$^1$H NMR (300 MHz, DMSO-d$_6$) δ ppm 1.97 (t, J=12.93 Hz, 1 H) 2.25 (d, J=1.90 Hz, 3 H) 2.46-2.48 (m, 1 H) 2.58 (s, 3 H)

4.28-4.69 (m, 3 H) 6.09 (s, 2 H) 7.16-7.68 (m, 2 H) 7.71 (d, J=2.34 Hz, 1 H) 7.76-7.86 (m, 1 H) 8.42 (d, J=2.34 Hz, 1 H) 10.50 (s, 1 H).

Example 229

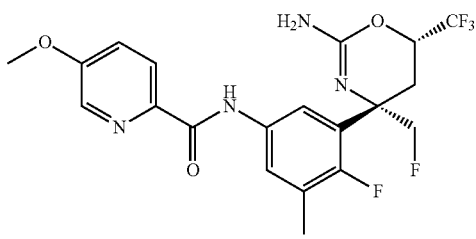 [SMILES: COc1ccc(C(=O)Nc2cc(C)c(F)c([C@]3(CF)C[C@@H](C(F)(F)F)OC(N)=N3)c2)nc1]

N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxypicolinamide The title compound was synthesized by procedure and steps analogous to those described in Method A3, Example 216 above, but using 5-methoxypicolinic acid (Ark Pharm.) in step 10. MS m/z=458.9 [M+H]⁺. Calculated for $C_{20}H_{19}F_5N_4O_3$: 458.14.

¹H NMR (300 MHz, DMSO-d₆) δ ppm 1.97 (t, J=12.72 Hz, 1 H) 2.25 (s, 3 H) 2.46 (br. s., 1 H) 3.94 (s, 3 H) 4.27-4.72 (m, 3 H) 6.08 (s, 2 H) 7.57-7.71 (m, 2 H) 7.80 (br. s., 1 H) 8.12 (d, J=8.92 Hz, 1 H) 8.39 (s, 1 H) 10.39 (s, 1 H).

Example 230 (Method A4)

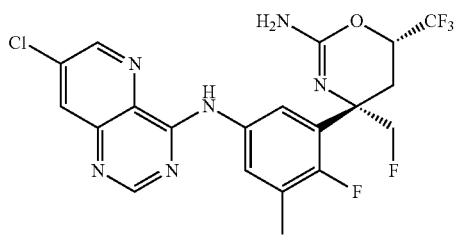 [SMILES: Cc1cc(Nc2ncnc3cc(Cl)cnc23)cc([C@]2(CF)C[C@@H](C(F)(F)F)OC(N)=N2)c1F]

(4S,6S)-4-(5-((7-chloropyrido[3,2-d]pyrimidin-4-yl)amino)-2-fluoro-3-methylphenyl)-4-(fluoromethyl)-6-(trifluoromethyl)-5,6-dihydro-4H-1,3-oxazin-2-amine To a mixture of (4S,6S)-4-(5-amino-2-fluoro-3-methylphenyl)-4-(fluoromethyl)-6-(trifluoromethyl)-5,6-dihydro-4H-1,3-oxazin-2-amine (0.044 g, 0.136 mmol) and 4,7-dichloropyrido[3,2-d]pyrimidine (0.030 g, 0.150 mmol) in iPrOH (2 mL) was added a catalytic amount of concentrated $H_2SO_4$ and the resulting mixture was heated in microwave at 100° C. for 45 min. The mixture was diluted with DCM, washed with 1 N NaOH and extracted with DCM. The combined organics were dried over $Na_2SO_4$, filtered, concentrated and chromatographed on silica gel using 0-4% MeOH/DCM to afford a light brown solid as (4S,6S)-4-(5-((7-chloropyrido[3,2-d]pyrimidin-4-yl)amino)-2-fluoro-3-methylphenyl)-4-(fluoromethyl)-6-(trifluoromethyl)-5,6-dihydro-4H-1,3-oxazin-2-amine (0.033 g, 0.068 mmol, 49.8% yield). MS m/z=486.9 [M+H]⁺. Calculated for $C_{20}H_{16}ClF_5N_6O$: 486.10.

¹H NMR (300 MHz, DMSO-d₆) δ ppm 1.99 (t, J=12.86 Hz, 1 H) 2.28 (d, J=1.90 Hz, 3 H) 4.29-4.74 (m, 3 H) 6.09 (s, 2 H) 7.89 (d, J=6.28 Hz, 2 H) 8.39 (d, J=2.05 Hz, 1 H) 8.65 (s, 1 H) 8.93 (d, J=2.19 Hz, 1 H) 10.38 (s, 1 H).

Example 231

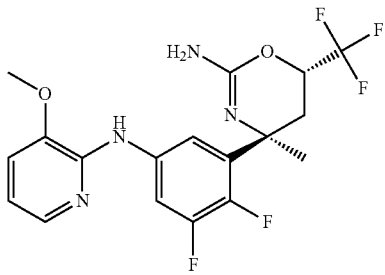 [SMILES: COc1cccnc1Nc1cc(F)c(F)c([C@]2(C)C[C@@H](C(F)(F)F)OC(N)=N2)c1]

(4S,6S)-4-(2,3-difluoro-5-((3-methoxypyridin-2-yl)amino)phenyl)-4-methyl-6-(trifluoromethyl)-5,6-dihydro-4H-1,3-oxazin-2-amine The title compound was synthesized by procedures and steps analogous to those described in Method B, Example 8 above, but using 2-bromo-3-methoxypyridine and (4S,6S)-4-(5-amino-2,3-difluorophenyl)-4-methyl-6-(trifluoromethyl)-5,6-dihydro-4H-1,3-oxazin-2-amine in step 2. MS m/z=417 [M+H]⁺. Calculated for $C_{18}H_{17}F_5N_4O_2$: 416.3.

¹H NMR (400 MHz, CHLOROFORM-d) δ=8.22 (ddd, J=2.7, 6.9, 12.8 Hz, 1H), 7.80 (d, J=4.9 Hz, 1H), 7.10-6.87 (m, 3H), 6.72 (dd, J=5.1, 7.8 Hz, 1H), 4.43 (br. s., 2H), 4.16-3.99 (m, 1H), 3.86 (s, 3H), 2.76 (dd, J=2.5, 13.7 Hz, 1H), 1.97-1.81 (m, 1H), 1.64 (s, 3H).

Example 232

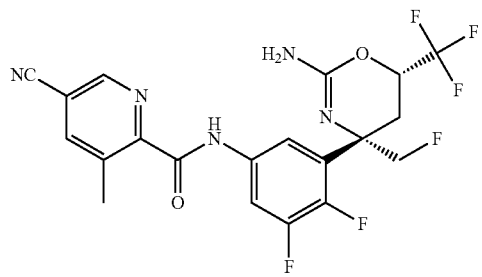 [SMILES: Cc1cc(C#N)cnc1C(=O)Nc1cc(F)c(F)c([C@]2(CF)C[C@@H](C(F)(F)F)OC(N)=N2)c1]

N-(3-((4S,6S)-2-amino-4-(fluoromethyl)-6-(trifluoromethyl)-5,6-dihydro-4H-1,3-oxazin-4-yl)-4,5-difluorophenyl)-5-cyano-3-methylpicolinamide The title compound was synthesized using steps and procedures analogous to those described in Method X, Example 151 above, but using 5-cyano-3-methylpicolinic acid (intermediate 16) in step 10. MS m/z=472.0 [M]⁺. Calculated for $C_{20}H_{15}F_6N_5O_2$: 471.36.

¹H NMR (300 MHz, CHLOROFORM-d) δ ppm 2.18 (t, J=13.23 Hz, 1 H) 2.69 (dd, J=13.67, 2.56 Hz, 1 H) 2.86 (s, 3 H) 4.09-4.22 (m, 1 H) 4.27-4.80 (m, 4 H) 7.13-7.22 (m, 1 H)

7.96 (d, J=1.17 Hz, 1 H) 8.18 (ddd, J=11.77, 6.94, 2.78 Hz, 1 H) 8.72 (d, J=1.46 Hz, 1 H) 10.09 (s, 1 H).

Example 233

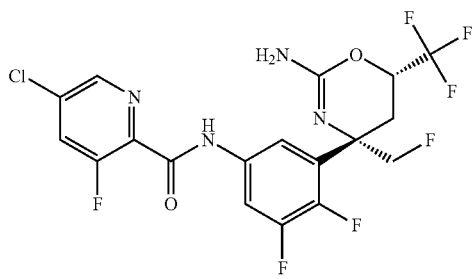 [SMILES: NC1=N[C@](CF)(c2cc(NC(=O)c3ncc(Cl)cc3F)cc(F)c2F)C[C@@H](C(F)(F)F)O1]

N-(3-((4S,6S)-2-amino-4-(fluoromethyl)-6-(trifluoromethyl)-5,6-dihydro-4H-1,3-oxazin-4-yl)-4,5-difluorophenyl)-5-chloro-3-fluoropicolinamide The title compound was synthesized using steps and procedures analogous to those described in Method X, Example 151 above, but using 5-chloro-3-fluoropicolinic acid (Frontier Scientific) in step 10. MS m/z=484.9 [M]$^+$. Calculated for $C_{18}H_{12}ClF_7N_4O_2$: 484.76.

$^1$H NMR (300 MHz, CHLOROFORM-d) δ ppm 2.17-2.32 (m, 1 H) 2.73 (dd, J=13.74, 2.63 Hz, 1 H) 4.15-4.29 (m, 1 H) 4.40-4.82 (m, 2 H) 7.14-7.23 (m, 1 H) 7.67 (dd, J=9.94, 1.90 Hz, 1 H) 8.20 (ddd, J=11.69, 7.02, 2.78 Hz, 1 H) 8.43 (d, J=1.32 Hz, 1 H) 9.73 (s, 1 H).

Example 234

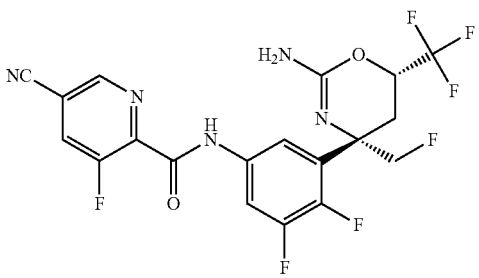 [SMILES: N#Cc1cnc(C(=O)Nc2cc(F)c(F)c([C@]3(CF)C[C@@H](C(F)(F)F)OC(N)=N3)c2)c(F)c1]

N-(3-((4S,6S)-2-amino-4-(fluoromethyl)-6-(trifluoromethyl)-5,6-dihydro-4H-1,3-oxazin-4-yl)-4,5-difluorophenyl)-5-cyano-3-fluoropicolinamide A microwave vial was charged with N-(3-((4S,6S)-2-amino-4-(fluoromethyl)-6-(trifluoromethyl)-5,6-dihydro-4H-1,3-oxazin-4-yl)-4,5-difluorophenyl)-5-chloro-3-fluoropicolinamide (Example 224 above, 0.125 g, 0.258 mmol), zinc cyanide (0.037 g, 0.309 mmol), 2-dicyclohexylphosphino-2',6'-dimethoxy-1'1'-biphenyl-SPhos (0.021 g, 0.052 mmol), and tris(dibenzylideneacetone)dipalladium (0) (0.024 g, 0.026 mmol). The vial was sealed and evacuated/backfilled with nitrogen 3 times. 1.1 mL of a premixed 99:1 n,n-dimethyl acetamide:water solution was added and the reaction was heated to 120° C. in the microwave for 20 minutes. Upon cooling, the reaction mixture was diluted with water and EtOAc. The organic layer was separated, washed with brine and dried over sodium sulfate. The crude residue was purified via Biotage (10 g Ultra column, 0-35-50% EtOAc:Hexanes) to afford N-(3-((4S,6S)-2-amino-4-(fluoromethyl)-6-(trifluoromethyl)-5,6-dihydro-4H-1,3-oxazin-4-yl)-4,5-difluorophenyl)-5-cyano-3-fluoropicolinamide (0.088 g, 0.185 mmol, 71.8% yield) as a light-yellow solid. MS m/z=475.32 [M]$^+$. Calculated for $C_{19}H_{12}F_7N_5O_2$: 475.9.

$^1$H NMR (300 MHz, CHLOROFORM-d) δ ppm 2.18 (t, J=13.15 Hz, 1 H) 2.70 (dd, J=13.74, 2.63 Hz, 1 H) 4.06-4.25 (m, 1 H) 4.38-4.76 (m, 2 H) 7.22 (dd, J=5.41, 2.34 Hz, 1 H) 7.93 (dd, J=9.50, 1.61 Hz, 1 H) 8.16 (ddd, J=11.47, 6.94, 2.78 Hz, 1 H) 8.72 (d, J=1.17 Hz, 1 H) 9.71 (s, 1 H).

Example 235 (Method A5)

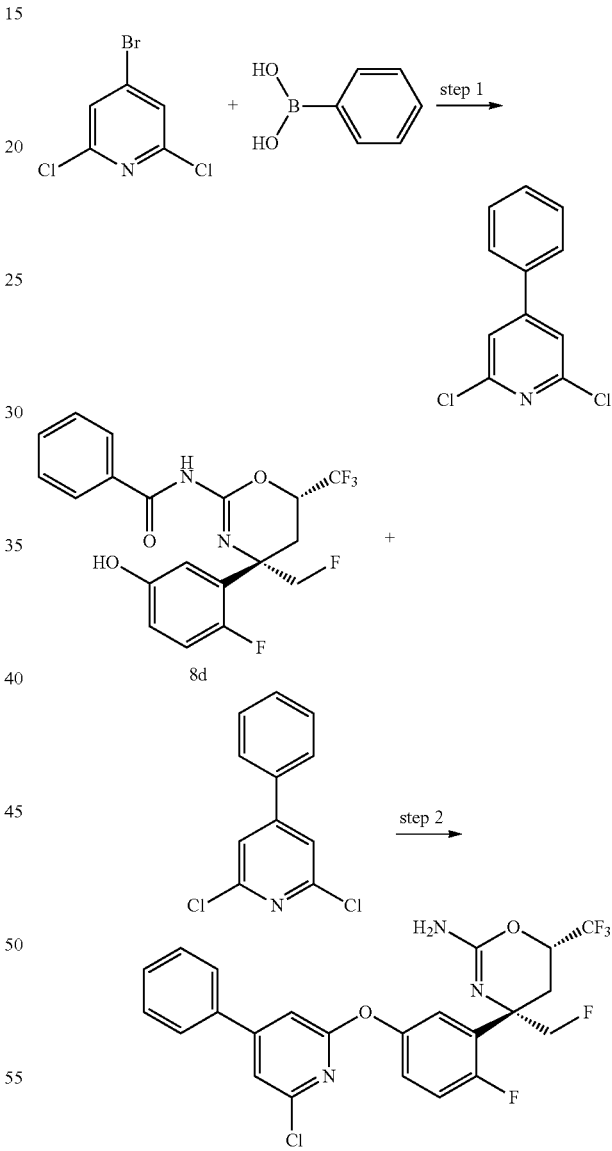

Step 1: 4-bromo-2-chloro-6-phenylpyridine

A round-bottomed flask was charged with 4-bromo-2,6-dichloropyridine (Combi-Blocks Inc., 553 mg, 2.437 mmol), phenylboronic acid (446 mg, 3.66 mmol) and trans-dichlorobis(triphenylphosphine)palladium (ii) (27.8 mg, 0.04 mmol). The vial was placed under nitrogen atmosphere using two evacuation/backfill cycles. 1,4-dioxane (12 ml) and sodium carbonate (775 mg, 7.31 mmol) in water (4.1 ml) were added. The reaction mixture was sealed under nitrogen and heated at 80° C. for 1.5 h. The reaction mixture combined with that on pp14 was partitioned between EtOAc and brine. The aqueous layer was back extracted with EtOAc (2×) and the combined EtOAc layers were dried (Na₂SO₄) and concentrated. The crude material was dissolved in DCM, and purified by chromatography through a Redi-Sep pre-packed silica gel column (40 g), eluting with a gradient of 0% to 20% EtOAc in hexane, to provide 2,6-dichloro-4-phenylpyridine (146 mg, 0.652 mmol, 26.7% yield) as light-yellow oil. MS m/z=224.0 [M]

Step 2: (4S,6S)-4-(5-((6-chloro-4-phenylpyridin-2-yl)oxy)-2-fluorophenyl)-4-(fluoromethyl)-6-(trifluoromethyl)-5,6-dihydro-4H-1,3-oxazin-2-amine In round-bottomed flask were added N-((4S,6S)-4-(2-fluoro-5-hydroxyphenyl)-4-(fluoromethyl)-6-(trifluoromethyl)-5,6-dihydro-4H-1,3-oxazin-2-yl)benzamide (225 mg, 0.543 mmol), 2,6-dichloro-4-phenylpyridine (146 mg, 0.652 mmol), cesium carbonate (230 mg, 0.706 mmol) in DMSO (1358 µl). The flask was heated in 100° C. oil bath for 7 h. After cooling to RT, the reaction mixture was partitioned between EtOAc and water. The aqueous layer was back extracted with EtOAc (2×) and the combined organics was dried (Na₂SO₄) and concentrated. The crude material was purified by chromatography through a Redi-Sep pre-packed silica gel column (12 g), eluting with a gradient of 0% to 50% EtOAc in hexane, followed by reverse-phase preparative HPLC using a Phenomenex Gemini column, 10 micron, C18, 110 Å, 150×30 mm, 0.1% TFA in CH₃CN/H₂O, gradient 10% to 70% over 15 min, then neutralized with saturated NaHCO₃ and extracted with DCM, to provide (4S,6S)-4-(5-((6-chloro-4-phenylpyridin-2-yl)oxy)-2-fluorophenyl)-4-(fluoromethyl)-6-(trifluoromethyl)-5,6-dihydro-4H-1,3-oxazin-2-amine (8 mg, 0.016 mmol, 2.96% yield) as a off-white solid.

MS m/z=499.0 [M]⁺. Calculated for $C_{23}H_{17}ClF_5N_3O_2$: 497.845.

¹H NMR (300 MHz, CHLOROFORM-d) δ ppm 2.18-2.35 (m, 1 H) 2.69 (d, J=13.30 Hz, 1 H) 4.44 (d, J=6.58 Hz, 1 H) 4.60-4.99 (m, 2 H) 5.82 (br. s., 1 H) 7.09 (s, 1 H) 7.15-7.22 (m, 1 H) 7.22-7.39 (m, 3 H) 7.52 (d, J=5.55 Hz, 3 H) 7.58-7.70 (m, 2 H)

Example 236 (Method A6)

Synthesis of N-(3-((4S,6S)-2-amino-4-methyl-6-(trifluoromethyl)-5,6-dihydro-4H-1,3-oxazin-4-yl)-4-chloro-5-fluorophenyl)-5-chloropicolinamide

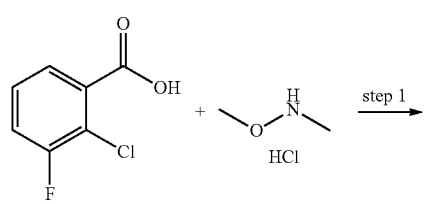

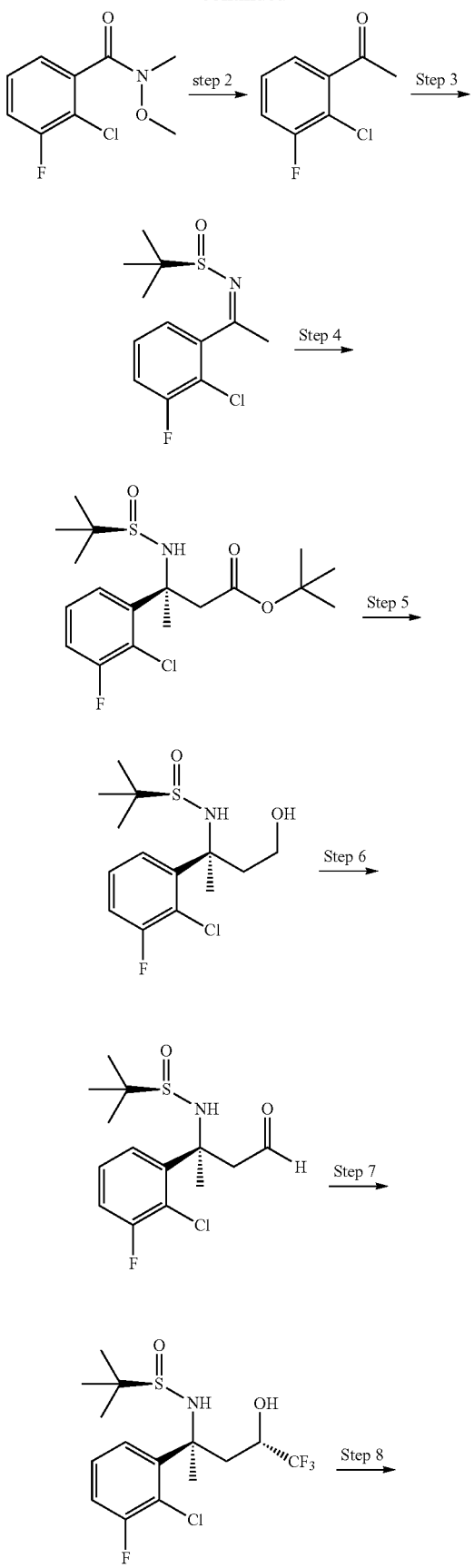

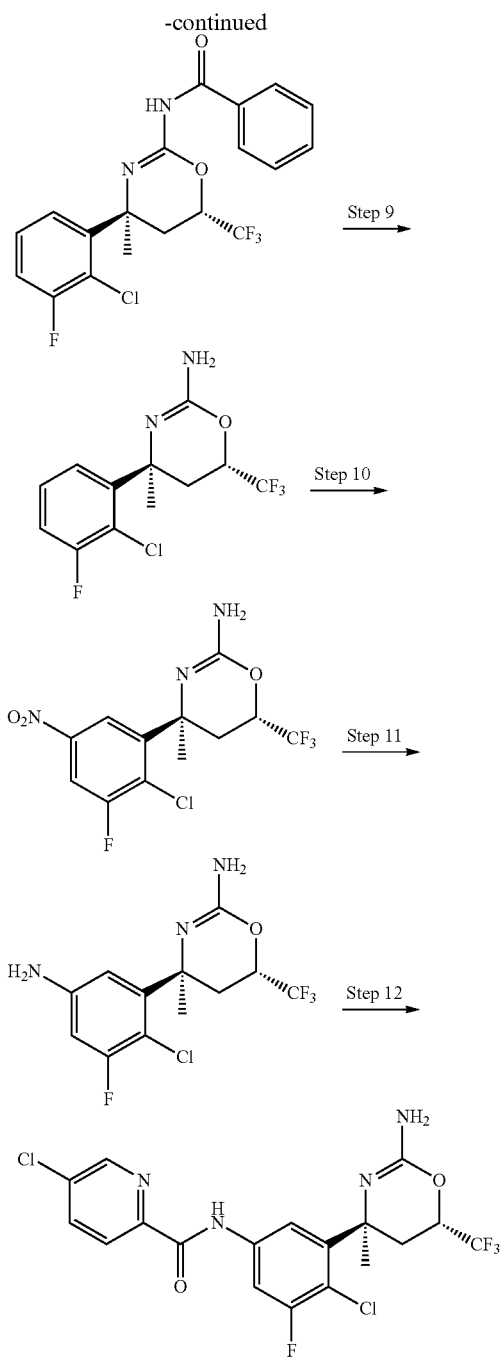

Step 1:
2-chloro-3-fluoro-N-methoxy-N-methylbenzamide

To a solution of 2-chloro-3-fluorobenzoic acid (3.32 g, 19.02 mmol) in DMF (60 mL) was added N,O-dimethylhydroxylamine hydrochloride, 98% (2.30 g, 23.58 mmol), O-(-7-azabenzotriazol-1-yl)-N,′N,′N,′N′-tetramethyluronium-hexafluorophosphate (HATU) (8.82 g, 23.20 mmol) and triethylamine (6.63 mL, 47.5 mmol). The mixture was stirred at rt for 3 h. The reaction was quenched with saturated $Na_2CO_3$ and extracted with EtOAc. The organic solution was washed with water and brine, dried over $Na_2SO_4$, filtered, and concentrated in vacuo. The crude was purified by flash chromatography on silica gel (80 g, 10-100% EtOAc/hexane in 25 min) to give 2-chloro-3-fluoro-N-methoxy-N-methylbenzamide as colorless oil, which turned to solid on vacuum (3.95 g, 95% yield). MS m/z=218 [M+H]$^+$. Calculated for $C_9H_9ClFNO_2$: 217.6.

Step 2: 1-(2-chloro-3-fluorophenyl)ethanone

To a 2L flask was added 2-chloro-3-fluoro-N-methoxy-N-methylbenzamide (41.49 g, 191 mmol) and tetrahydrofuran (800 mL). The solution was cooled to 0° C., then methylmagnesium chloride, 3.0M solution in THF (254 mL, 763 mmol) was added dropwise through addition funnel. The mixture was gradually warmed to 5° C. The reaction was quenched with 5N HCl (190 mL) until it is acidic and extracted with EtOAc twice. The organic solution was washed with brine, dried over sodium sulfate, filtered, and concentrated in vacuo. The crude was purified by flash chromatography on silica gel (330 g, 0-50% EtOAc/hexane in 20 min) to give 1-(2-chloro-3-fluorophenyl)ethanone as a colorless oil (31.3 g, 95% yield). MS m/z=173 [M+H]$^+$. Calculated for $C_8H_6ClFO$: 172.6.

Step 3: (R,Z)-N-(1-(2-chloro-3-fluorophenyl)ethylidene)-2-methylpropane-2-sulfinamide To a solution of 1-(2-chloro-3-fluorophenyl)ethanone (31.21 g, 181 mmol) in tetrahydrofuran (500 mL) was added (R)-2-methylpropane-2-sulfinamide (32.9 g, 271 mmol) and titanium(IV) isopropoxide (111 mL, 371 mmol). The mixture was heated to 65° C. overnight. LCMS showed 25% starting material remaining. Additional 16 g sulfinamide and 30 mL Ti(OPr)$_4$ was added and the reaction was continued at 70° C. overnight. The mixture was diluted with brine (600 mL), and EtOAc. The solid was filtered through a pad of celite and washed with EtOAc. The organic layer was washed with brine, dried over sodium sulfate, filtered and concentrated in vacuo. The crude material was purified by silica gel chromatography (330 g, 0-60% EtOAc-hexane in 20 min) to give (R,Z)-N-(1-(2-chloro-3-fluorophenyl)ethylidene)-2-methyl-propane-2-sulfinamide (40.8 g, 82% yield) as yellow oil. MS m/z=276 [M+H]$^+$. Calculated for $C_{12}H_{15}ClFOS$: 275.8.

Step 4: (5)-tert-butyl 3-(2-chloro-3-fluorophenyl)-3-((R)-1,1-dimethylethylsulfinamido)butanoate A solution of (R,Z)-N-(1-(2-chloro-3-fluorophenyl)ethylidene)-2-methylpropane-2-sulfinamide (24.50 g, 89 mmol) in tetrahydrofuran (300 mL) was cooled to 0° C. under argon, then 0.5M solution of (2-(tert-butoxy)-2-oxoethyl)zinc(II) chloride in diethyl ether (444 mL, 222 mmol) was added dropwise. The resulting solution was allowed to slowly warm up to ambient temperature and then stirred overnight. Additional 70 mL of zinc reagent was added and the reaction was continued for 3.5 h. The reaction was quenched with saturated aqueous $NH_4Cl$ (70 mL). The mixture was extracted with EtOAc. The organic extracts were dried ($Na_2SO_4$), filtered and concentrated. The crude was purified by silica gel chromatography: 330 g, 0-100% EtOAc-hexane to give (S)-tert-butyl 3-(2-chloro-3-fluorophenyl)-3-((R)-1,1-dimethylethylsulfinamido) butanoate as an orange oil (32 g, 92% yield). MS m/z=392 [M+H]$^+$. Calculated for $C_{18}H_{27}ClFNO_3S$: 391.9.

Step 5: (R)-N-((S)-2-(2-chloro-3-fluorophenyl)-4-hydroxybutan-2-yl)-2-methylpropane-2-sulfinamide To a solution of (5)-tert-butyl 3-(2-chloro-3-fluorophenyl)-3-((R)-1,1-dimethylethylsulfinamido)butanoate (8.75 g, 22.33 mmol) in tetrahydrofuran (100 mL) was added lithium borohydride, 2.0M in THF (29.9 mL, 59.8 mmol) dropwise, followed by MeOH (7.05 mL, 174 mmol). The reaction was stirred for 40 min and was carefully quenched by the addition of saturated ammonium chloride (75 mL), followed by water (100 mL) and EtOAc. The separated organic phase was washed with brine, dried over sodium sulfate and filtered to give (R)-N-((S)-2-(2-chloro-3-fluorophenyl)-4-hydroxybutan-2-yl)-2-methylpropane-2-sulfinamide as a white solid (7.2 g, 100% yield). MS m/z=322 [M+H]$^+$. Calculated for $C_{14}H_{21}ClFNO_2S$: 321.8.

Step 6: (R)-N-((S)-2-(2-chloro-3-fluorophenyl)-4-oxobutan-2-yl)-2-methylpropane-2-sulfinamide A mixture of (R)-N-((S)-2-(2-chloro-3-fluorophenyl)-4-hydroxybutan-2-yl)-2-methylpropane-2-sulfinamide (9.30 g, 28.9 mmol), dichloromethane (150 mL) and dess-martin periodinane (14.22 g, 33.5 mmol) was stirred at rt for 1 h. The mixture was diluted with water (150 mL), DCM and sodium bicarbonate (12.14 g, 144 mmol). The mixture was filtered through celite. The aqueous layer was extracted with DCM. The organic layer was washed with brine, dried over sodium sulfate, filtered and concentrated in vacuo. The crude was purified by silica gel chromatography: 240 g, 5-25% EtOAc-hexane in 5 min, 25-80% in 20 min to give (R)-N-((S)-2-(2-chloro-3-fluorophenyl)-4-oxobutan-2-yl)-2-methylpropane-2-sulfinamide as yellow oil (8.98 g, 97%). MS m/z=320 [M+H]$^+$. Calculated for $C_{14}H_{19}ClFNO_2S$: 319.8.

Step 7: (R)-N-((2S,4S)-2-(2-chloro-3-fluorophenyl)-5,5,5-trifluoro-4-hydroxypentan-2-yl)-2-methylpropane-2-sulfinamide To a cooled solution of (R)-N-((S)-2-(2-chloro-3-fluorophenyl)-4-oxobutan-2-yl)-2-methylpropane-2-sulfinamide (5.8 g, 18.14 mmol) in tetrahydrofuran (80 mL) at −78° C. was added trimethyl(trifluoromethyl)silane (26.8 mL, 181 mmol). After stirred for 20 min, tetrabutylammonium fluoride, 1.0M solution in THF (27.2 mL, 27.2 mmol) was added dropwise. After 3 h, the reaction was quenched with 1N HCl (30 ml), and then the cooling bath was removed. The reaction mixture was diluted with water (60 mL) and EtOAc (60 mL), and warmed to ambient temperature. The solution was extracted with EtOAc twice. The organic extracts were washed with brine, dried over sodium sulfate, filtered and concentrated in vacuo. The residue was triturated with MTBE (15 mL). The resulted solid was filtered and washed with DCM. The filtrate was concentrated in vacuo and purified by silica gel column (240 g, 0-100% EtOA/hexane in 25 min) to afford additional product. The solids were combined to give (R)-N-((2S,4S)-2-(2-chloro-3-fluorophenyl)-5,5,5-trifluoro-4-hydroxypentan-2-yl)-2-methylpropane-2-sulfinamide (1.75 g, 25% yield). MS m/z=390 [M+H]$^+$. Calculated for $C_{15}H_{20}ClF_4NO_2S$: 389.8.

Step 8: N-((4S,6S)-4-(2-chloro-3-fluorophenyl)-4-methyl-6-(trifluoromethyl)-5,6-dihydro-4H-1,3-oxazin-2-yl)benzamide To a solution of (R)-N-((2S,4S)-2-(2-chloro-3-fluorophenyl)-5,5,5-trifluoro-4-hydroxypentan-2-yl)-2-methylpropane-2-sulfinamide (1.75 g, 4.49 mmol) in DCM (10 mL) and methanol (5.00 mL) was added hydrogen chloride, 4M in 1,4-dioxane (11.22 mL, 44.9 mmol). After 30 min, the mixture was concentrated, diluted with DCM and saturated $NaHCO_3$. The organic layer was washed with brine, dried over sodium sulfate and concentrated in vacuo. This material was dissolved in THF (25 mL) and then treated with benzoyl isothiocyanate (0.695 mL, 5.16 mmol). After 30 min, triethylamine (0.751 mL, 5.39 mmol) and N-(3-dimethylaminopropyl)-N'-ethylcarbodiimide hydrochloride (0.947 g, 4.94 mmol) were added, and the resulted reaction mixture was brought up to 70° C. for 40 min. The reaction mixture was partitioned between EtOAc and water. The separated organic layer was washed with brine, dried over sodium sulfate and filtered. The filtrate was concentrated in vacuo and the crude was purified by silica gel column (40 g, 0-40% EtOAc/hexane in 25 min) to afford N-((4S,6S)-4-(2-chloro-3-fluorophenyl)-4-methyl-6-(trifluoromethyl)-5,6-dihydro-4H-1,3-oxazin-2-yl)benzamide as an off-white solid (1.73 g, 93% yield). MS m/z=415 [M+H]$^+$. Calculated for $C_{19}H_{15}ClF_4N_2O_2$: 414.8.

Step 9: (4S,6S)-4-(2-chloro-3-fluorophenyl)-4-methyl-6-(trifluoromethyl-5,6-dihydro-4H-1,3-oxazin-2-amine A solution of N-((4S,6S)-4-(2-chloro-3-fluorophenyl)-4-methyl-6-(trifluoromethyl)-5,6-dihydro-4H-1,3-oxazin-2-yl)benzamide (1.73 g, 4.17 mmol), methanol (25 mL) and DBU (0.798 mL, 5.30 mmol) was stirred at 55° C. overnight. The mixture was concentrated in vacuo, diluted with water and EtOAc. The organic layer was washed with brine, dried over sodium sulfate and concentrated in vacuo. The crude was purified by silica gel chromatography: 0-100% EtOAc-hexane to give (4S,6S)-4-(2-chloro-3-fluorophenyl)-4-methyl-6-(trifluoromethyl)-5,6-dihydro-4H-1,3-oxazin-2-amine as a white solid (1.07 g, 82% yield). MS m/z=415 [M+H]$^+$. Calculated for $C_{19}H_{15}ClF_4N_2O_2$: 414.8.

Step 10: (4S,6S)-4-(2-chloro-3-fluoro-5-nitrophenyl)-4-methyl-6-(trifluoromethyl)-5,6-dihydro-4H-1,3-oxazin-2-amine To a solution of (4S,6S)-4-(2-chloro-3-fluorophenyl)-4-methyl-6-(trifluoromethyl)-5,6-dihydro-4H-1,3-oxazin-2-amine (1.06 g, 3.41 mmol) in sulfuric acid (13.64 ml, 256 mmol) cooled in an ice bath was added potassium nitrate (0.448 g, 4.44 mmol) in one portion. After stirred for 15 min, ice bath was removed, and the mixture was stirred at room temperature for 40 min. The reaction mixture was poured into ice water containing sodium carbonate (40 g). The resulted suspension was extracted with EtOAc. The organic layer was washed with brine, dried over sodium sulfate and filtered. The filtrate was concentrated and dried in vacuum to afford the crude (4S,6S)-4-(2-chloro-3-fluoro-5-nitrophenyl)-4-methyl-6-(trifluoromethyl)-5,6-dihydro-4H-1,3-oxazin-2-amine as a light yellow solid, which was used in next step without purification. MS m/z=356 [M+H]$^+$. Calculated for $C_{12}H_{10}ClF_4N_3O_3$: 355.6.

Step 11: (4S,6S)-4-(5-amino-2-chloro-3-fluorophenyl)-4-methyl-6-(trifluoromethyl)-5,6-dihydro-4H-1,3-oxazin-2-amine To a cooled (cold water) solution of (4S,6S)-4-(2-chloro-3-fluoro-5-nitrophenyl)-4-methyl-6-(trifluoromethyl)-5,6-dihydro-4H-1,3-oxazin-2-amine (1.2 g, 3.37 mmol) in acetic acid (14 mL) was added 2,2,2-trifluoroacetic acid (2.00 mL, 27.0 mmol) followed by zinc, dust (1.19 g, 18.22 mmol) in one portion (exothermic). After stirred for 10 min, water bath was removed. The mixture was stirred at ambient temperature for 1.5 hrs and then concentrated. The residue was basified with 1N NaOH. The aqueous layer was extracted three times with DCM. The organic extracts were combined, dried over sodium sulfate, filtered and concentrated in vacuo. The crude was purified by silica gel chromatography (2-10% MeOH-DCM) to give (4S,6S)-4-(5-amino-2-chloro-3-fluorophenyl)-4-methyl-6-(trifluoromethyl)-5,6-dihydro-4H-1,3-oxazin-2-amine as an off-white solid (0.636 g, 57.9% yield). MS m/z=326 [M+H]$^+$. Calculated for $C_{12}H_{12}ClF_4N_3O$: 325.7.

Step 12: N-(3-((4S,6S)-2-amino-4-methyl-6-(trifluoromethyl)-5,6-dihydro-4H-1,3-oxazin-4-yl)-4-chloro-5-fluorophenyl)-5-chloropicolinamide To a mixture of (4S,6S)-4-(5-amino-2-chloro-3-fluorophenyl)-4-methyl-6-(trifluoromethyl)-5,6-dihydro-4H-1,3-oxazin-2-amine (0.060 g, 0.184 mmol) and 5-chloropicolinic acid (0.035 g, 0.221 mmol) in DMF (1.5 mL) at 0° C. was added 1-propanephosphonic acid cyclic anhydride, 50% solution in ethyl acetate (0.130 mL, 0.221 mmol). The reaction was gradually warmed to rt and stirred for 2 h. The reaction mixture was partitioned between EtOAc and saturated solution of NaHCO$_3$. The organic layer was separated, washed twice with water, then washed with brine, dried over MgSO$_4$, filtered, and concentrated in vacuo. The crude was purified by flash chromatography on silica gel (12 g, 0-100% EtOAc/DCM in 15 min). The fractions were combined and concentrated in vacuo. The resulting white solid was dissolved in MeOH and purified by reverse phase prep HPLC: 10-80% MeCH in Water (with 0.1% TFA). The fractions were collected and neutralized with solid Na$_2$CO$_3$, extracted with DCM three times. The organic solution was dried over sodium sulfate and concentrated in vacuo to give N-(3-((4S,6S)-2-amino-4-methyl-6-(trifluoromethyl)-5,6-dihydro-4H-1,3-oxazin-4-yl)-4-chloro-5-fluorophenyl)-5-chloropicolinamide (20 mg, 23.3% yield). MS m/z=465 [M+H]$^+$. Calculated for $C_{18}H_{14}Cl_2F_4N_4O_2$: 465.2.

$^1$H NMR (400 MHz, CHLOROFORM-d) δ=9.81 (s, 1H), 8.49 (d, J=2.2 Hz, 1H), 8.18 (d, J=8.4 Hz, 1H), 8.01 (dd, J=2.4, 10.5 Hz, 1H), 7.87 (dd, J=2.2, 8.3 Hz, 1H), 7.38 (s, 1H), 5.04-4.32 (br s, 2H), 4.05-3.88 (m, 1H), 3.37 (dd, J=2.5, 13.9 Hz, 1H), 1.86 (t, J=13.3 Hz, 1H), 1.78 (s, 3H).

Example 237

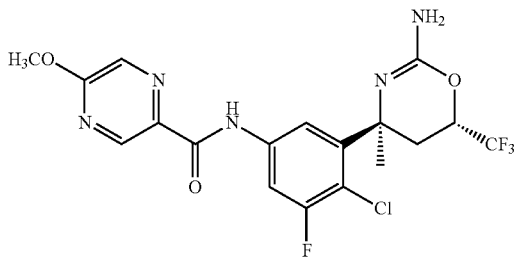 [SMILES: COc1cnc(C(=O)Nc2cc(F)c(Cl)c([C@]3(C)C[C@@H](C(F)(F)F)OC(N)=N3)c2)cn1]

N-(3-((4S,6S)-2-amino-4-methyl-6-(trifluoromethyl)-5,6-dihydro-4H-1,3-oxazin-4-yl)-4-chloro-5-fluorophenyl)-5-methoxypyrazine-2-carboxamide The title compound was synthesized using procedures analogous to those described in Method A6 Step 12 (Example 236) above, but using 5-methoxypyrazine-2-carboxylic acid (Ark Pharm.). MS m/z=462 [M+H]$^+$. Calculated for $C_{18}H_{16}ClF_4N_5O_3$: 461.8

$^1$H NMR (400 MHz, CHLOROFORM-d) δ=9.56 (s, 1H), 9.05-8.94 (m, 1H), 8.14 (d, J=1.4 Hz, 1H), 8.08 (dd, J=2.5, 10.6 Hz, 1H), 7.35-7.31 (m, 1H), 4.41 (br. s., 2H), 4.07 (s, 3H), 4.03-3.92 (m, 1H), 3.38 (dd, J=2.5, 13.9 Hz, 1H), 1.84 (dd, J=12.8, 13.8 Hz, 1H), 1.76 (s, 3H).

Example 238

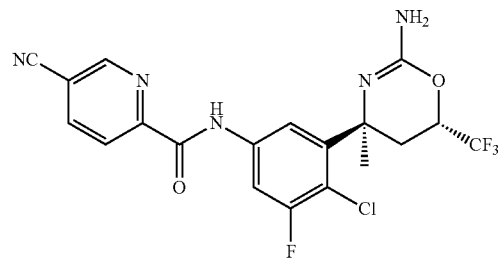 [SMILES: C[C@@]1(c2cc(NC(=O)c3ccc(C#N)cn3)cc(F)c2Cl)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-4-chloro-5-fluorophenyl)-5-cyanopicolinamide The title compound was synthesized using procedures analogous to those described in Method A6 Step 12 (Example 236) above, but using 5-cyanopicolinic acid (Aldrich). MS m/z=456 [M+H]$^+$. Calculated for $C_{19}H_{14}ClF_4N_5O_2$: 455.8

$^1$H NMR (400 MHz, CHLOROFORM-d) δ=9.88 (s, 1H), 8.87 (d, J=1.2 Hz, 1H), 8.40 (d, J=8.2 Hz, 1H), 8.22 (dd, J=2.0, 8.2 Hz, 1H), 8.06 (dd, J=2.7, 10.4 Hz, 1H), 7.43-7.34 (m, 1H), 4.47 (br. s., 2H), 4.04-3.87 (m, 1H), 3.38 (dd, J=2.5, 13.9 Hz, 1H), 1.86 (dd, J=12.9, 13.7 Hz, 1H), 1.77 (s, 3H).

Example 239

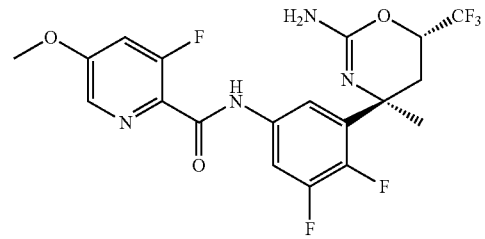 [SMILES: COc1cnc(C(=O)Nc2cc(F)c(F)c([C@]3(C)C[C@@H](C(F)(F)F)OC(N)=N3)c2)c(F)c1]

N-(3-((4S,6S)-2-amino-4-methyl-6-(trifluoromethyl)-5,6-dihydro-4H-1,3-oxazin-4-yl)-4,5-difluorophenyl)-3-fluoro-5-methoxypicolinamide The title compound was synthesized by procedure and steps analogous to those described in Method Z, Example 186 above, but using 3-fluoro-5-methoxypicolinic acid (intermediate 33). MS m/z=463.1 [M+H]$^+$. Calculated for C19H16F6N4O3: 462.346.

¹H NMR (300 MHz, CHLOROFORM-d) δ ppm 1.68 (s, 3 H) 1.94 (t, J=13.17 Hz, 1H) 2.81 (d, J=13.41 Hz, 1H) 3.96 (s, 3 H) 3.99 (s, 2H) 4.07 (m, 1H) 7.07 (m, 2H) 8.14 (m, 2H) 9.71 (br. s., 1H)

Example 240

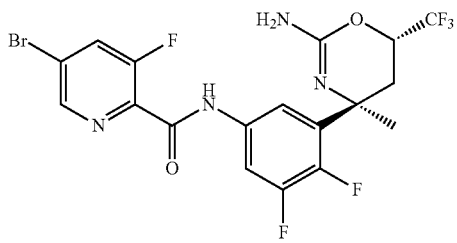 [SMILES: C[C@@]1(c2cc(NC(=O)c3ncc(Br)cc3F)cc(F)c2F)C[C@@H](C(F)(F)F)OC(N)=N1]

N-(3-((4S,6S)-2-amino-4-methyl-6-(trifluoromethyl)-5,6-dihydro-4H-1,3-oxazin-4-yl)-4,5-difluorophenyl)-5-bromo-3-chloropicolinamide The title compound was synthesized by procedure and steps analogous to those described in Method Z, Example 186 above, but using 5-bromo-3-chloropyridine-2-carboxylic acid (Matrix Scientific). MS m/z=527.0/529.0 [M+H]⁺. Calculated for C18H13BrClF5N4O2: 527.670.

¹H NMR (400 MHz, CHLOROFORM-d) δ=9.78 (br. s., 1H), 8.58 (s, 1H), 8.21-8.12 (m, 1H), 8.08 (s, 1H), 7.04-6.97 (m, 1H), 4.12-4.01 (m, 1H), 2.81 (d, J=11.7 Hz, 1H), 1.92 (t, J=13.2 Hz, 1H), 1.66 (s, 3H)

Intermediate 1

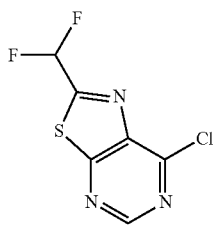

Synthesis of 7-chloro-2-(difluoromethyl)thiazolo[5,4-d]pyrimidine

Step 1: 5-aminopyrimidine-4,6-dithiol

A mixture of 5-amino-4,6-dichloropyrimidine (1.63 g, 9.94 mmol, Oakwood) and sodium hydrosulfide hydrate (5.30 g, 71.5 mmol, Aldrich) in water (40 ml) was heated at 100° C. for 3 h. The reaction was cooled to 0° C. and quenched with conc HCl dropwise until pH 3. The yellow solid was filtered, washed with cold water and dried in vacuo at 60° C. to give an orange-yellow solid (1.46 g, 9.2 mmol, 92%). MS m/z=159.9 [M+H]⁺. Calculated for C4H5N3S: 159.

Step 2: 2-(difluoromethyl)thiazolo[5,4-d]pyrimidin-7-ol

A glass microwave reaction vessel was charged with 5-aminopyrimidine-4,6-dithiol (1.00 g, 6.28 mmol) and a pipette tip of 4-pyrrolidinopyridine (pipette tip) in pyridine (6 mL). Difluoroacetic anhydride (3.00 mL, 24.13 mmol, Matrix) was added via syringe resulting in an exotherm. After 30 min at rt the reaction mixture was capped and heated at 130° C. in an Initiator microwave reactor (Biotage AB, Inc., Upssala, Sweden) for 15 min. The mixture was diluted with DCM and the volatiles were removed in vacuo. The residue was dissolved in MeOH, evaporated onto silica gel and purified by flash chromatography (Isco (80 gram)) eluting with 25% EtOH/EtOAc:hexanes (0:1→1:1) to give a brown semi-solid (1.31 g). MS m/z=203.9 [M+H]⁺. Calculated for C6H3F2N3OS: 203.

Step 3: 7-chloro-2-(difluoromethyl)thiazolo[5,4-d]pyrimidine

A mixture of 2-(difluoromethyl)thiazolo[5,4-d]pyrimidin-7-ol, N,N-dimethylaniline (0.800 mL, 6.31 mmol) and phosphorus oxychloride (6.00 mL, 65.5 mmol) in toluene (20 mL) was heated at 80° C. for 6 h. The reaction mixture was cooled of rt and the solvent removed invacuo. The residue was dissolved in DCM, evaporated onto silica gel and purified by flash chromatography (Isco (80 gram)) eluting with (EtOAc):hexanes (0:1→1:3) to give an off-white crystalline solid (252 mg, 18% over 2 steps). MS m/z=221.9, 223.9 [M+H]⁺. Calculated for C6H2F2N3S: 221.

Intermediate 2

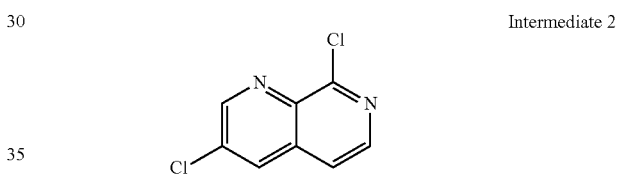

Synthesis of 3,8-Dichloro-1,7-naphthyridine

Step 1: 3-Bromo-5-chloropicolinonitrile

A microwave vial was charged with copper (I) cyanide (1.089 g, 12.16 mmol), 2,3-dibromo-5-chloropyridine (3 g, 11.06 mmol), and propionitrile (15 mL). The vial was capped and irradiated in a microwave reactor at 150° C. for 2.5 hours. The solution was concentrated, diluted with DCM (25 mL), and filtered. The filtrate was concentrated, and the residue was purified by silica gel chromatography, eluting with 0-30% EtOAc in heptanes, to afford the title compound (2 g, 9.20 mmol). MS m/z=219 (M+H).

Step 2: 5-Chloro-3-((trimethylsilyl)ethynyl)picolinonitrile

A pressure vessel was charged with TEA (7.65 mL, 55.2 mmol), ethynyltrimethylsilane (2.32 mL, 16.6 mmol), copper (I) iodide (0.263 g, 1.380 mmol), palladium (0) tetrakis(triphenylphosphine) (0.558 g, 0.483 mmol), 3-bromo-5-chloropicolinonitrile (3.0 g, 13.8 mmol), and DMF (50 ml). The vessel was flushed with argon, sealed, stirred at ambient temperature for 15 minutes, and then heated at 50° C. for 4 hours. The solution was diluted with water and extracted with EtOAc. The combined organic layers were concentrated, and the residue was purified by silica-gel chromatography, eluting 0-50% ethyl acetate in hexane, to afford the title compound (1.3 g, 5.5 mmol). MS m/z=235 (M+H).

Step 3: 5-Chloro-3-(2,2-dimethoxyethyl)picolinonitrile

A pressure vessel was charged with 5-chloro-3-((trimethylsilyl)ethynyl)picolinonitrile (2 g, 8.52 mmol) and sodium methoxide (0.5 M in methanol, 42.6 mL, 21.30 mmol), sealed, and stirred at 55° C. for one hour. The solution was concentrated, and the residue was purified via silica gel chromatography, eluting with 10% methanol in DCM to afford the title compound (1.7 g, 7.50 mmol). MS m/z=227 (M+H).

Step 4: 3-Chloro-1,7-naphthyridin-8(7H)-one

To a solution of 5-chloro-3-(2,2-dimethoxyethyl)picolinonitrile (1.7 g, 7.50 mmol) in acetone (50 mL) and water (150 mL) was added aqueous saturated sodium carbonate (37.5 mL, 113 mmol) and 30% aqueous hydrogen peroxide (38.3 mL, 375 mmol). The reaction was stirred at RT for one hour, concentrated to remove most of the acetone, and extracted with DCM. The combined organic layers were concentrated.

To a solution of this intermediate (1.8 g, 7.36 mmol) in benzene (20 mL) was added p-toluenesulfonic acid (0.350 g, 1.839 mmol) and the reaction was sonicated for 10 minutes. The solution was stirred overnight at 80° C. and concentrated. The crude product was purified via silica gel, eluting with 0-100% (80/20/1 ethyl acetate/methanol/ammonium hydroxide) in EtOAc, to the title intermediate (1.1 g, 6.1 mmol). MS m/z=181 (M+H).

Step 5: 3,8-Dichloro-1,7-naphthyridine

A suspension of -chloro-1,7-naphthyridin-8(7H)-one (250 mg, 1.384 mmol) in phosphorus oxychloride (1.94 mL, 20.8 mmol) was stirred at 95° C. for one hour. The solution was concentrated to afford the title compound (276 mg, 1.39 mmol). MS m/z=199 (M+H).

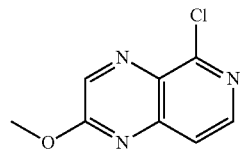

Intermediate 3

Synthesis of 5-Chloro-2-methoxypyrido[3,4-b]pyrazine

Step 1: 5-Chloropyrido[3,4-b]pyrazin-2(1H)-one

A suspension 2-chloropyridine-3,4-diamine (2.5 g, 17.41 mmol) and a 50% solution of ethyl glyoxalate in toluene (3.45 mL, 17.41 mmol) in ethanol (34.8 mL) was stirred at reflux for 24 hours. The solution was cooled to −20° C. for 16 hours, and the resulting precipitate was collected by vacuum filtration and rinsed with ethanol. The crude product was purified via reverse-phase HPLC, eluting with 5-50% acetonitrile/0.1% trifluoroacetic acid in water/0.1% TFA, to afford the title compound (570 mg, 3.14 mmol). MS m/z=182 (M+H).

Step 2: 2,5-Dichloropyrido[3,4-b]pyrazine

A suspension of 5-chloropyrido[3,4-b]pyrazin-2(1H)-one (0.57 g, 3.14 mmol) in phosphorus oxychloride (10.24 mL, 110 mmol) was stirred at 110° C. for two hours, and then concentrated. The residue was dissolved in DCM, washed with saturated sodium bicarbonate, dried over anhydrous sodium sulfate, filtered, and concentrated to afford the title compound (580 mg, 2.90 mmol). MS m/z=200 (M+H).

Step 3: 5-Chloro-2-methoxypyrido[3,4-b]pyrazine

To a solution of 2,5-dichloropyrido[3,4-b]pyrazine (580 mg, 2.90 mmol) in N,N-dimethylformamide (10 mL) was added a 0.5-M solution of sodium methoxide in methanol (6.09 mL, 3.04 mmol), and the reaction was stirred at RT for 5 minutes. The solution was diluted with water and extracted with ethyl acetate. The organic layer was dried with sodium sulfate, filtered and concentrated to afford the title compound (550 mg, 2.81 mmol). MS m/z=196 (M+H).

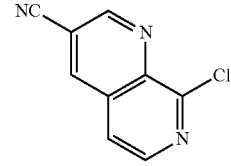

Intermediate 4

Synthesis of 8-Chloro-1,7-naphthyridine-3-carbonitrile

A screw-cap vial was charged with 3-chloro-1,7-naphthyridin-8(7H)-one (100 mg, 0.554 mmol), zinc cyanide (52.7 μL, 0.831 mmol), 2-dicyclohexylphosphino-2',6'-dimethoxybiphenyl (45.5 mg, 0.111 mmol), tris(dibenzylideneacetone)dipalladium(0) (40.6 mg, 0.044 mmol), DMF (2.74 mL) and water (28 μL). The vial was purged with argon, sealed, and stirred at 110° C. for 1 hour. The mixture was filtered through a pad of Celite, which was rinsed with methanol and dimethylsulfoxide. The combined filtrates were concentrated, and a few drops of water were added. The resulting solids were collected by vacuum filtration, rinsed with water and dried.

The solids were suspended in toluene (3.5 mL), and phosphorus oxychloride (98 μL, 1.052 mmol) and DIPEA (122 μL, 0.701 mmol) were added. The reaction was stirred at 120° C. for 1.5 hours, cooled to RT, diluted with EtOAc, and washed with 2 M aqueous sodium carbonate. The organic portion was dried over anhydrous sodium sulfate, filtered and concentrated. The crude material was purified by silica gel chromatography, eluting with 5-50% EtOAc in heptanes, to provide the title compound (50 mg, 0.264 mmol) as a white solid. LC/MS (ESI⁺) m/z=190 (M+H).

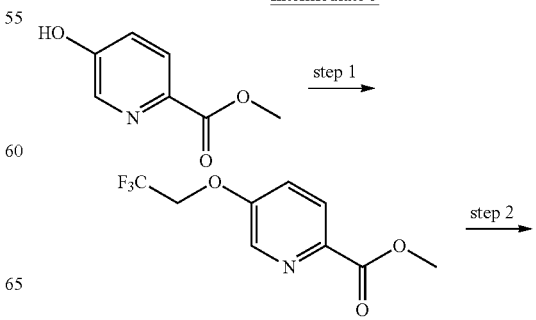

Intermediate 5

-continued

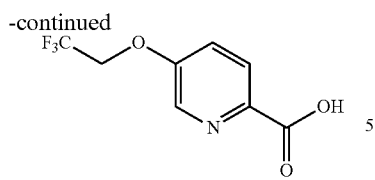

Synthesis of 5-(2,2,2-trifluoroethoxy)picolinic acid

Step 1: methyl 5-(2,2,2-trifluoroethoxy)picolinate

To a solution of methyl 5-hydroxypicolinate (0.50 g, 3.27 mmol, Frontier Scientific) in DMF (5 mL) were added cesium carbonate (1.383 g, 4.24 mmol, Aldrich) and 2,2,2-trifluoroethyl ester (0.909 ml, 3.92 mmol) and the resulting suspension was stirred at RT for 1 hour. The reaction was diluted with water and EtOAc. The organic layer was washed with 1M LiCl (aq) solution and brine before drying over magnesium sulfate and concentrating under reduced pressure to afford the crude title compound as a yellow oil, which was used directly in the next step without further purification. MS m/z=236.0 [M+H]$^+$. Calculated for $C_9H_8F_3NO_3$: 235.160

Step 2: 5-(2,2,2-trifluoroethoxy)picolinic acid

The crude material from the previous reaction was taken up in THF (5 mL) and lithium hydroxide, 2.0M, (aq) (4.90 ml, 9.80 mmol) was added. The reaction was stirred at RT for 16 hours. The reaction was diluted with water and acidified with 1.0N HCl (aq) solution was added until pH=1 (by pH paper). The solution was extracted with DCM and the organic layer was washed with brine, dried over magnesium sulfate and concentrated under reduced pressure to afford the title compound as a white solid. (0.194 g, 0.877 mmol, 26.9% yield). MS m/z=221.9 [M+H]$^+$. Calculated for $C_8H_6F_3NO_3$: 221.133

$^1$H NMR (300 MHz, DMSO-d$_6$) δ ppm 5.00 (q, J=8.77 Hz, 2 H) 7.66 (dd, J=8.77, 2.92 Hz, 1 H) 8.07 (d, J=8.77 Hz, 1 H) 8.50 (d, J=2.92 Hz, 1 H) 13.00 (br. S., 1 H)

Intermediate 6

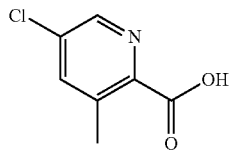

Synthesis of 5-chloro-3-methylpicolinic acid

Step 1: Synthesis of 5-chloro-3-methylpicolinonitrile

A mixture of 2-bromo-5-chloro-3-methylpyridine (45 g, 218 mmol), zinc cyanide (8.30 mL, 131 mmol), tris(dibenzylideneacetone)dipalladium (0) (4.99 g, 5.45 mmol), and 1,1'-bis(diphenylphosphino)ferrocene (6.04 g, 10.90 mmol) in dimethylacetamide (40 mL) was heated to 110° C. for 4 hours. The reaction mixture was cooled to RT, diluted with water and extracted with ethyl acetate. The organic phase obtained was concentrated under reduced pressure and residue purified by chromatography on silica gel using ISCO eluting with 0-60% EtOAc/hex to afford the title compound 5-chloro-3-methylpicolinonitrile (25.4 g, 166 mmol, 76% yield). LC/MS (ESI$^+$) m/z=153.1 (M+H).

Step 2: Synthesis of 5-chloro-3-methylpicolinic acid

To a solution of 5-chloro-3-methylpicolinonitrile (24.0 g, 157 mmol) in EtOH (100 mL) was added NaOH 5.0N (110 ml, 550 mmol). The resulting mixture was refluxed at 90° C. for 18 h. After cooling to RT, the reaction mixture was concentrated, diluted with water and the pH of the solution was adjusted to 4 by addition of 5N HCl. The solid that precipitated was filtered and set aside. The filtrate was extracted with EtOAc (2×). The aqueous layer was again acidified with 5N HCl to pH 4 and extracted with EtOAc (2×). The EtOAc extracts were combined, dried, and concentrated. The solid obtained from all the workup steps were combined and dried in a high vac oven at 40° C. for 12 h to give the title compound 5-chloro-3-methylpicolinic acid (24.1 g, 140 mmol, 89% yield). LC/MS (ESI$^+$) m/z=172.0 (M+H); $^1$H NMR (400 MHz, CHLOROFORM-d) δ ppm 11.29 (br. s., 1 H), 8.41 (d, J=1.76 Hz, 1 H), 7.73 (d, J=1.76 Hz, 1 H), 2.75 (s, 3 H).

Intermediate 7

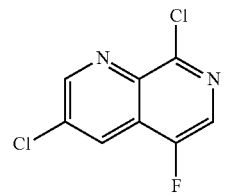

Synthesis of 3,8-Dichloro-5-fluoro-1,7-naphthyridine

Step 1: 3-chloro-5-fluoro-6-methoxy-6,7-dihydro-1,7-naphthyridin-8(5H)-one

A pressure bottle was charged with 3-chloro-1,7-naphthyridin-8(7H)-one (15 g, 83 mmol), methanol (34.6 mL), ACN (173 mL) and 1-chloromethyl-4-fluoro-1,4-diazoniabicyclo [2.2.2]octane bis(tetrafluoroborate) (30.9 g, 87 mmol), and the mixture was heated at 45° C. for 15 hours. Water and ethyl acetate were added, and the layers were separated. The aqueous portion was extracted twice with ethyl acetate and once with DCM, and the combined organic layers were dried with anhydrous sodium sulfate, filtered and concentrated. The crude solid was triturated with a minimum amount of ethyl acetate and filtered. The title intermediate was isolated as an off-white solid (15.34 g, 80%) as a 3:1 mixture of diastereomers.

Step 2: 3,8-dichloro-5-fluoro-1,7-naphthyridine

A vial was charged with 3-chloro-5-fluoro-6-methoxy-6, 7-dihydro-1,7-naphthyridin-8(5H)-one (7.5 g, 32.5 mmol), acetonitrile (130 mL) and phosphorus oxychloride (9.09 mL, 98 mmol), and the mixture was stirred at 75° C. for 15 hours. The mixture was concentrated, and the crude material was purified by silica gel chromatography, eluting with 0-50% ethyl acetate in heptanes, to provide the title compound (5.57 g, 25.7 mmol, 79% yield) as a white solid. LC/MS (ESI$^+$) m/z=217 (M+H).

Intermediate 8

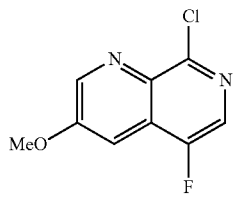

Synthesis of 8-Chloro-5-fluoro-3-methoxy-1,7-naphthyridine

Using an analogous sequence of reactions to those described for Intermediate 3, 3-chloro-1,7-naphthyridin-8(7H)-one was converted to the title compound. LC/MS (ESI$^+$) m/z=213 (M+H).

Intermediate 9

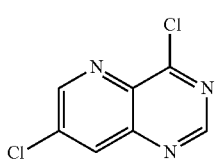

Synthesis of 4,7-Dichloropyrido[3,2-d]pyrimidine

Step 1: 3-Amino-5-chloropicolinamide

To a suspension of 5-chloro-2-cyano-3-nitropyridine (1.274 mL, 10.9 mmol) in water (22 mL) was added 28% aqueous ammonium hydroxide (3.94 mL, 28.3 mmol), and the reaction was stirred at RT for 20 minutes. Sodium hydrosulfite (2.68 mL, 32.7 mmol) was added, and the reaction mixture was stirred at RT for 70 minutes. The yellow precipitate was collected by vacuum filtration to provide the title compound (1.097 g, 6.39 mmol) as yellow solid. $^1$H-NMR (400 MHz, DMSO-d$_6$): δ 7.88 (br. s, 1 H), δ 7.73 (s, 1 H), δ 7.39 (br. s, 1 H), δ 7.23 (s, 1 H), δ 7.06 (br. s, 2 H). LC/MS (ESI$^+$) m/z=172 (M+H).

Step 2: 7-Chloropyrido[3,2-d]pyrimidin-4(1H)-one

A suspension of 3-amino-5-chloropicolinamide (1.1 g, 6.41 mmol) in triethyl orthoformate (15.99 mL, 96 mmol) was stirred at 155° C. for 22 hours. After cooling to RT, the yellow precipitate was collected by vacuum filtration and washed with hexanes to yield the title intermediate (1.03 g, 5.67 mmol) as a yellow solid. $^1$H NMR (400 MHz, DMSO-d$_6$) δ ppm 8.20 (s, 1 H) 8.27 (d, J=2.35 Hz, 1 H) 8.80 (d, J=2.25 Hz, 1 H) 12.68 (br. s., 1 H). LC/MS (ESI$^+$) m/z=182 (M+H).

Step 3: 4,7-Dichloropyrido[3,2-d]pyrimidine

To a mixture of 7-chloropyrido[3,2-d]pyrimidin-4(1H)-one (250 mg, 1.377 mmol) in toluene (12 mL) were added DIPEA (0.73 mL, 4.20 mmol) and phosphorus oxychloride (0.391 mL, 4.27 mmol), and the reaction was stirred at reflux for 1 hour. After cooling to RT, the reaction mixture was concentrated to provide the title compound. LC/MS (ESI$^+$) m/z=200 (M+H).

Intermediate 10

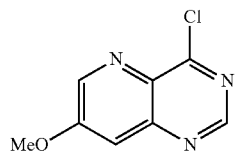

Synthesis of 4-Chloro-7-methoxypyrido[3,2-d]pyrimidine

Step 1: 7-Methoxypyrido[3,2-d]pyrimidin-4(1H)-one

A microwave vial was charged with 7-chloropyrido[3,2-d]pyrimidin-4(1H)-one (110 mg, 0.606 mmol), a 0.5 M solution of sodium methoxide in methanol (3.65 mL, 1.817 mmol) and sodium methoxide (327 mg, 6.06 mmol). The vial was capped and irradiated in a microwave reactor at 145° C. for 30 minutes. The reaction was neutralized with saturated aqueous ammonium chloride (3 mL), concentrated, and diluted with cold water. The resulting precipitate was collected by vacuum filtration and dried in vacuo to provide the title compound (107 mg, 0.604 mmol) as pink solid. $^1$H NMR (400 MHz, DMSO-d$_6$) δ ppm 3.95 (s, 3 H) 7.49 (d, J=2.74 Hz, 1 H) 8.11 (s, 1 H) 8.47 (d, J=2.74 Hz, 1 H). LC/MS (ESI$^+$) m/z=178 (M+H).

Step 2: 4-Chloro-7-methoxypyrido[3,2-d]pyrimidine

Using an analogous reaction to that described for Intermediate 14, step 3, 7-methoxypyrido[3,2-d]pyrimidin-4(1H)-one was converted to the title compound. LC/MS (ESI$^+$) m/z=196 (M+H).

Intermediate 11

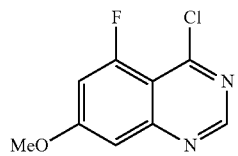

Synthesis of 4-Chloro-5-fluoro-7-methoxyquinazoline

Step 1: 2-Amino-6-fluoro-4-methoxybenzonitrile

Ammonia gas was bubbled through a solution of 2,6-difluoro-4-methoxybenzonitrile (1.0 g, 5.91 mmol) in dimethylsulfoxide (11.83 mL) for 10 minutes. The reaction was then sealed and stirred at 90° C. for 24 hours. The reaction mixture was cooled to ambient temperature and concentrated in vacuo to afford a tan residue. The residue was triturated with water, collected be vacuum filtration, and dried in vacuo to afford the title intermediate (0.9 g, 5.42 mmol) as a white solid. LC/MS (ESI$^+$) m/z=167 (M+H).

Step 2: 5-Fluoro-7-methoxyquinazolin-4-ol

To a mixture of formic acid (11.43 mL, 298 mmol) and sulfuric acid (0.866 mL, 16.25 mmol) was added 2-amino-6-fluoro-4-methoxybenzonitrile (0.9 g, 5.42 mmol) in portions. The reaction mixture was stirred at 100° C. for 1 hour, cooled to ambient temperature, and poured into 80 mL of an ice-water mixture. The resulting precipitate was collected by vacuum filtration and dried in vacuo to provide the title intermediate (0.8 g, 4.12 mmol) as an off-white solid. LC/MS (ESI⁺) m/z=195 (M+H).

Step 3: 4-Chloro-5-fluoro-7-methoxyquinazoline

To a suspension of 5-fluoro-7-methoxyquinazolin-4-ol (0.125 g, 0.644 mmol) in thionyl chloride (1.410 mL, 19.31 mmol) was added N,N-dimethylformamide (0.028 mL, 0.361 mmol). The reaction was stirred at 80° C. for 6 hours and concentrated in vacuo. The residue was suspended in saturated aqueous sodium bicarbonate and extracted with dichloromethane. The organic layer was concentrated in vacuo to generate the title compound (0.13 g, 0.611 mmol) as a yellow solid. LC/MS (ESI⁺) m/z=213 (M+H).

Intermediate 12

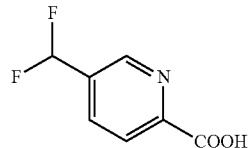

Synthesis of 5-(Difluoromethyl)picolinic acid

Step 1: 5-Formylpicolinonitrile

A suspension of 2-bromo-5-formylpyridine (940 mg, 5.05 mmol) and copper (I) cyanide (233 μL, 7.58 mmol) in DMF (8.4 mL) was stirred at 120° C. for 1.5 hours, cooled to RT, and partitioned between water and EtOAc. The solids were removed from the aqueous layer by filtration, and the filtrate was extracted with ethyl acetate. The combined organic layers were washed with brine, dried over anhydrous magnesium sulfate, filtered and concentrated. The crude product was purified by silica-gel chromatography, eluting with a gradient of 40%-60% (40% ethyl acetate in heptane) in heptane, to provide the title compound (236 mg, 1.786 mmol) as white solid. LC/MS (ESI⁺) m/z=133 (M+H).

Step 2: 5-(Difluoromethyl)picolinonitrile

To a solution of 5-formylpicolinonitrile (74 mg, 0.560 mmol) in toluene (0.25 mL) was added bis(2-methoxyethyl) aminosulfur trifluoride (0.258 mL, 1.400 mmol), and the reaction was stirred at RT overnight. The reaction mixture was carefully quenched with saturated aqueous sodium bicarbonate, diluted with water, and extracted with DCM.
The organic layer was washed with brine, dried over anhydrous magnesium sulfate, filtered, and concentrated. The crude material was purified by silica-gel chromatography, eluting with a gradient of 40% to 60% (40% ethyl acetate/heptane) in heptane, to provide the title compound (48 mg, 0.311 mmol) as white solid. LC/MS (ESI⁺) m/z=155 (M+H).

Step 3: 5-(difluoromethyl)picolinic acid

A suspension of 5-(difluoromethyl)picolinonitrile (48 mg, 0.311 mmol) in 12 N aqueous hydrochloric acid (4.3 mL, 140 mmol) was stirred at 110° C. for 1.5 hours. After cooling to ambient temperature, the reaction mixture was concentrated and treated with DIPEA (2 mL). The mixture was concentrated and dried in vacuo to provide the title compound in quantitative yield. LC/MS (ESI⁺) m/z=174 (M+H).

Intermediate 13

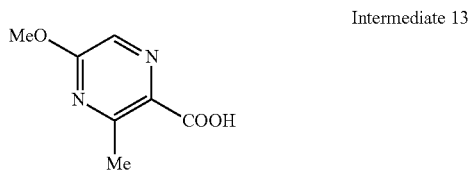 [SMILES: COc1cnc(C(=O)O)c(C)n1]

Synthesis of 5-methoxy-3-methylpyrazine-2-carboxylic acid

Step 1: Methyl 3-methylpyrazine-2-carboxylate

In a 2-L flask, 3-methylpyrazine-2-carboxylic acid (Matrix, 19.95 g, 144 mmol) was suspended in MeOH (500 mL). The suspension was cooled in an ice-water bath, and concentrated sulfuric acid (Fluka, 27.3 mL, 506 mmol) was added over a time period of 5 min. The reaction mixture was heated to 80° C. for 5 h. The reaction mixture was concentrated under reduced pressure and the residue was taken up in DCM (750 mL). The excess acid was neutralized carefully with aqueous NaOH (5m, 200 mL). The aqueous layer was separated and extracted with DCM (250 mL). The combined organic layers were combined, dried over MgSO₄ and concentrated to afford 16.15 g of the title compound (106 mmol, 73%). MS m/z=153 [M+H]⁺. Calculated for $C_7H_8N_2O_2$: 152.

Step 2: 3-(Methoxycarbonyl)-2-methylpyrazine 1-oxide

In a 1-L flask, the methyl 3-methylpyrazine-2-carboxylate (step 1, 16.08 g, 106 mmol) was suspended in CHCl₃ (300 mL). 3-chlorobenzoperoxoic acid (Aldrich, 24.62 g, 143 mmol) was added. The reaction mixture was heated to 70° C. for 16 h. The reaction mixture was quenched with saturated NaHCO₃ (200 mL). The layers were separated, and the aqueous layer was further extracted with DCM (2×100 mL). The combined organic layers were dried over MgSO₄, and the filtrate was concentrated to afford the title compound. MS m/z=169 [M+H]⁺. Calculated for $C_7H_8N_2O_3$: 168.

Step 3: Methyl 5-chloro-3-methylpyrazine-2-carboxylate

In a 1-L flask, the crude 3-(methoxycarbonyl)-2-methylpyrazine 1-oxide (step 2, 17.77 g, 106 mmol) was dissolved in DMF (300 mL). Neat phosphoryl trichloride (29.6 mL, 317 mmol) was added. The reaction mixture was heated to 100° C. After 1 h, the reaction mixture was concentrated to remove most of the DMF. The flask was cooled in an ice water bath, and 1 M aqueous Na₂CO₃ (300 mL) was added slowly, followed by 80% EtOAc-hexane (400 mL). The mixture was filtered through Celite. The resulting filtrate was partitioned and the aqueous phase was extracted further with 80% EtOAc-hexane (2×250 mL). The combined organic layers were dried over MgSO₄ and concentrated. The material was purified through silica gel using 11% EtOAc-hexane to afford the title compound (4.29 g, 23 mmol, 22%). MS m/z=187 [M+H]⁺. Calculated for $C_7H_7ClN_2O_2$: 186. ¹H NMR in CDCl₃ δ: 8.51 (s, 1H), 4.01 (s, 3H), 2.86 (s, 3H).

Step 4: 5-Methoxy-3-methylpyrazine-2-carboxylic acid

A flask was charged with sodium (0.813 g, 35.4 mmol), purged with Argon. and placed in a room temperature water bath. Methanol (47.7 mL, 1179 mmol) was added slowly. After 40 min, methyl 5-chloro-3-methylpyrazine-2-carboxylate (step 3, 2.2 g, 11.79 mmol) was added. The vessel was sealed and heated to 45° C. for 1.5 hs. Sodium hydroxide (1M, 12.97 mL, 12.97 mmol) was added and heating was continued for 1.5 hs. The reaction mixture was concentrated uncle reduced pressure and the residue was dissolved in a minimum amount of water (50 mL). The aqueous phase was extracted with diethyl ether (15 mL), which was discarded. The aqueous phase was acidified with HCl (5M, 11 mL, 55 mmol). The mixture was extracted with DCM (3×60 mL). The combined organic extracts were dried over MgSO$_4$ and the filtrate was concentrated to afford the title compound (2.0 g, 100%). MS m/z=169 [M+H]$^+$. Calculated for C$_7$H$_8$N$_2$O$_3$: 168. $^1$H NMR in CDCl$_3$ δ: 10.70 (br, 1H), 7.98 (s, 1H), 4.00 (s, 3H), 2.91 (s, 3H).

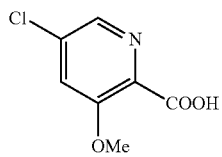

Intermediate 14

Synthesis of 5-chloro-3-methoxypicolinic acid

In a 1-L flask, 5-chloro-3-nitropicolinonitrile (Oakwood, 6.67 g, 36.3 mmol) was dissolved in MeOH (185 mL). The solution was cooled to 0° C., and sodium hydroxide (3M, 36.3 mL, 109 mmol) was added. The reaction mixture was warmed to room temperature and stirred overnight. The reaction was concentrated under reduced pressure and the residue was taken up in absolute ethanol (100 mL). NaOH (5M, 3 equiv, 109 mmol, 22 mL) was added, and the reaction mixture was heated to 100° C. for 1 h. The reaction mixture was concentrated under reduced pressure and the residue was taken up in water (100 mL). The aqueous layer was extracted with diethyl ether (30 mL), which was discarded. The aqueous phase was acidified with HCl (5M, 55 mL), saturated with NaCl, and extracted with EtOAc (5×75 mL). The combined organic extracts were dried over MgSO$_4$ and the filtrate was concentrated under reduced pressure. The resulting solid was triturated with diethyl ether to afford the title compound (5.63 g, 30 mmol, 83%). MS m/z=188 [M+H]$^+$. Calculated for C$_7$H$_6$ClNO$_3$: 187. $^1$H NMR in CDCl$_3$ δ: 8.18 (d, 1H, J=1.8), 7.49 (d, 1H, J=1.8), 4.03 (s, 3H).

Synthesis of 5-cyano-3-methoxypicolinic acid

Step 1: Methyl 5-chloro-3-methoxypicolinate

In a 350-mL resealable vessel, 5-chloro-3-methoxypicolinic acid (intermediate 14, 7.51 g, 40.0 mmol) was dissolved in MeOH (120 mL). The solution was cooled to 0° C., and concentrated sulfuric acid (7.57 mL, 140 mmol) was added. The vessel was sealed and heated to 95° C. for 1.5 h. The reaction mixture was cooled to 0° C., and quenched with Na$_2$CO$_3$ (1M, 140 mL). The reaction mixture was concentrated under reduced pressure and the residue was extracted with EtOAc (3×100 mL). The combined organics extracts were dried over MgSO$_4$ and the filtrate was concentrated under reduced pressure. The residue was by silica gel chromatography (gradient 20%-33% EtOAc/hexane) to afford the title compound as a yellow solid (5.59 g, 27.7 mmol, 67%). MS m/z=202 [M+H]$^+$. Calculated for C$_8$H$_8$ClNO$_3$: 201. $^1$H NMR in CDCl$_3$ δ: 8.24 (d, 1H, J=1.9), 7.37 (d, 1H, J=1.9), 3.97 (s, 3H), 3.94 (s, 3H).

Step 2: Methyl 5-cyano-3-methoxypicolinate

In a 350-mL resealable vessel, Pd$_2$dba$_3$ (1.487 g, 1.623 mmol), dicyclohexyl(2',6'-dimethoxy-[1,1'-biphenyl]-2-yl)phosphine (1.444 g, 3.52 mmol), dicyanozinc (3.18 g, 27.1 mmol), and methyl 5-chloro-3-methoxypicolinate (step 1, 5.455 g, 27.1 mmol) were taken up in DMF (80 mL). The reaction mixture was purged with Argon and subsequently heated to 120° C. for 2 h. Upon cooling, the reaction mixture was concentrated under reduced pressure. The residue was filtered through Celite, and the filter cake was rinsed with 1% MeOH/DCM. The filtrate was concentrated under reduced pressure and the residue was purified by silica gel chromatography (33%-40% EtOAc/hexane) to afford the title compound as a white solid (4.51 g, 23.5 mmol, 87%)., MS m/z=193 [M+H]$^+$. Calculated for C$_9$H$_8$N$_2$O$_3$: 192. $^1$H NMR in CDCl$_3$ δ: 8.51 (d, 1H, J=1.6), 7.55 (d, 1H, J=1.6), 4.00 (s, 3H), 3.97 (s, 3H).

Step 3: 5-Cyano-3-methoxypicolinic acid

In a 1-L flask, the methyl 5-cyano-3-methoxypicolinate (step 2, 4.51 g, 23.5 mmol) was taken up in THF (74 mL). The suspension was cooled to 0° C., and sodium hydroxide (1M, 24.64 mL, 24.64 mmol) was added. After 1 h, the reaction was concentrated under reduced pressure. The residue was taken up in 100 mL of water, and the aqueous phase was extracted with diethyl ether (50 mL), which was discarded. The aqueous phase was acidified with HCl (5M, 5.16 mL, 25.8 mmol). The aqueous phase was extracted with DCM (11×150 mL). The combined organic extracts were dried over MgSO$_4$ and the filtrate was concentrated under reduced pressure to afford the title compound as a white solid. MS m/z=179 [M+H]$^+$. Calculated for C$_8$H$_6$N$_2$O$_3$: 178. $^1$H NMR in CDCl$_3$ δ: 8.48 (d, 1H, J=1.6), 7.71 (d, 1H, J=1.6), 4.08 (s, 3H).

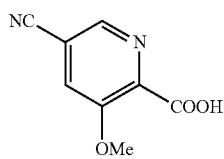

Intermediate 15

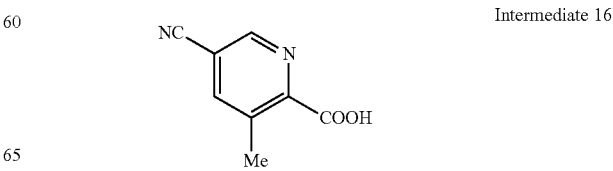

Intermediate 16

Synthesis of 5-cyano-3-methylpicolinic acid

To a solution of tert-butyl 5-cyano-3-methylpicolinate (synthesized according to procedure described in WO2012095521; 4.18 g, 19.15 mmol) in dichloromethane (96 ml) was added TFA (Aldrich, 148 ml, 1915 mmol). The reaction mixture was stirred at room temperature for 2 hrs. The reaction mixture was concentrated under reduced pressure and the residue was triturated with EtOAc. The yellow slurry was concentrated under reduced pressure. The residue was triturated with 30 mL of methyl tert-butyl ether (30 mL) and of hexanes (50 mL) to yield 5-cyano-3-methylpicolinic acid (2.91 g, 17.95 mmol, 94% yield) as yellow solid.

MS m/z=163.2 [M+H]$^+$. Calculated for C8H6N2O2: 162.0

Intermediate 17

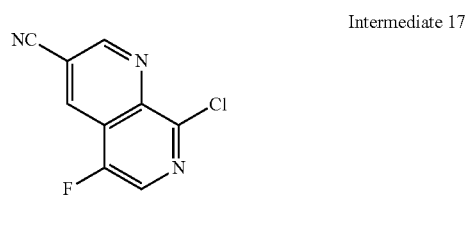 [SMILES: N#Cc1cnc2c(Cl)ncc(F)c2c1]

Synthesis of 8-chloro-5-fluoro-1,7-naphthyridine-3-carbonitrile

Step 1: 3-Chloro-5-fluoro-6-methoxy-6,7-dihydro-1,7-naphthyridin-8(5H)-one

A pressure bottle was charged with 3-chloro-1,7-naphthyridin-8(7H)-one (Anichem, 15 g, 83 mmol), MeOH (34 ml), acetonitrile (173 ml) and 1-(chloromethyl)-4-fluoro-1,4-diazabicyclo[2.2.2]octane-1,4-diium tetrafluoroborate (Aldrich, 30.9 g, 87 mmol). The mixture was heated to 45-50° C. After 6 hs additional 1-(chloromethyl)-4-fluoro-1,4-diazabicyclo[2.2.2]octane-1,4-diium tetrafluoroborate (2.5 g) was added and heating was continued overnight. Water and EtOAc were added to the cooled reaction mixture and the layers were separated. The aqueous layer was extracted with EtOAc, and the combined organic layers were dried over MgSO$_4$. The filtrate was concentrated under reduced pressure a the residue was triturated with EtOAc. The solid was filtered off and the title compound (15.34 g, 66.5 mmol, 80% yield) was isolated as a white solid. MS m/z=231 [M+H]$^+$. Calculated for C$_9$H$_8$ClFN$_2$O$_2$: 230.0

Step 2: 5-Fluoro-6-methoxy-8-oxo-5,6,7,8-tetrahydro-1,7-naphthyridine-3-carbonitrile A pressure bottle was charged with Pd(dba)$_3$ (Strem, 1.032 g, 1.127 mmol), 2-dicyclohexylphosphino-2',6'-dimethoxybiphenyl (Strem 1.157 g, 2.82 mmol), zinc cyanide (Alfa Aesar, 2.482 g, 21.14 mmol), 3-chloro-5-fluoro-6-methoxy-6,7-dihydro-1,7-naphthyridin-8(5H)-one (step 1, 3.25 g, 14.09 mmol) and DMF (70 ml). The bottle was purged with Argon and the reaction mixture was heated to 110° C. for 1 h. The crude reaction mixture was filtered through a pad of Celite and the filtercake was washed with MeOH. The combined filtrates were concentrated under reduced pressure. The residue was triturated with DCM. The solid was filtered off and washed with DCM. The title compound (2.27 g, 10.26 mmol, 72.8% yield) was obtained as an off white solid. MS m/z=222 [M+H]$^+$. Calculated for C$_{10}$H$_8$FN$_3$O$_2$: 221.1

Step 3: 8-Chloro-5-fluoro-1,7-naphthyridine-3-carbonitrile

A pressure bottle was charged with 5-fluoro-6-methoxy-8-oxo-5,6,7,8-tetrahydro-1,7-naphthyridine-3-carbonitrile (step 3, 2.27 g, 10.26 mmol), acetonitrile (41 ml) and phosphorus oxychloride (Aldrich, 3.35 ml, 35.9 mmol). The bottle was sealed and the reaction mixture was heated to 75° C. overnight. The reaction mixture was concentrated and the crude material was purified by silica gel chromatography (gradient 0-20% (10 MeOH in DCM)/DCM to afford the title compound (1.2 g, 5.78 mmol, 56.3% yield) as a white solid. MS m/z=208 [M+H]$^+$. Calculated for C$_9$H$_3$ClFN$_3$: 207.0

Intermediate 18 (Method AA)

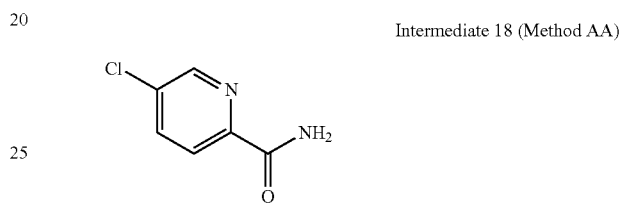

Synthesis of 5-chloropicolinamide

A 500-mL round-bottomed flask was charged with 5-chloro-2-pyridinecarboxylic acid (Ark Pharm, 10.00 g, 63.5 mmol) and thionyl chloride (Aldrich, 100 ml, 1371 mmol). A catalytic amount of DMF (0.2 ml) was added and the reaction mixture was heated to 80° C. under Argon atmosphere for 4 hours. The reaction mixture was cooled to room temperature and concentrated under reduced pressure. The residue was diluted with DCM (100 ml) and added slowly to a stirred solution of ammonium hydroxide (131 ml, 3364 mmol) at 0° C. After completed addition, the reaction mixture was allowed to stir an additional 10 min. The reaction mixture was concentrated under reduced pressure and the precipitate was filtered off. The solid was washed with water and dried to give the title compound (8.686 g, 55.5 mmol, 87% yield) as an off-white solid. MS m/z=157 [M+H]$^+$. Calculated for C$_6$H$_5$ClN$_2$O: 156

Intermediate 19

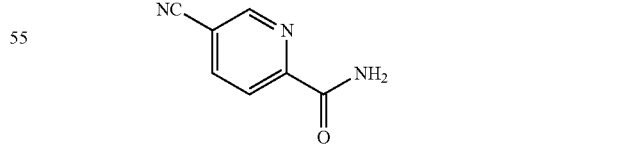

Synthesis of 5-cyanopicolinamide

The title compound was synthesized according to Method AA starting from 5-cyanopicolinic acid (Aldrich). MS m/z=147.9 [M+H]$^+$. Calculated for C$_7$H$_5$N$_3$O:147

Intermediate 20

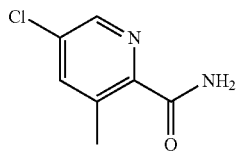

Synthesis of 5-chloro-3-methylpicolinamide

The title compound was synthesized according to Method AA starting from 5-chloro-3-methylpicolinic acid (intermediate 6). MS m/z=171.1 [M+H]$^+$. Calculated for C$_7$H$_7$ClN$_2$O: 170

Intermediate 21

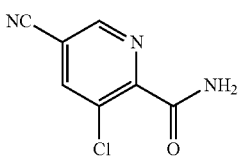

Synthesis of 3-chloro-5-cyanopicolinamide

The title compound was synthesized according to Method AA starting from 3-chloro-5-cyanopicolinic acid (Bionet Research). MS m/z=181.9 [M+H]$^+$. Calculated for C$_7$H$_4$ClN$_3$O: 181

Intermediate 22

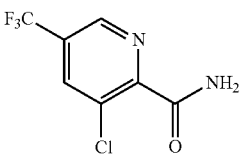

Synthesis of 3-chloro-5-(trifluoromethyl)picolinamide

The title compound was synthesized according to Method AA starting from 3-chloro-5-(trifluoromethyl)picolinic acid (Ark Pharm). MS m/z=224.9 [M+H]$^+$. Calculated for C$_7$H$_4$ClF$_3$N$_2$O: 224

Intermediate 23

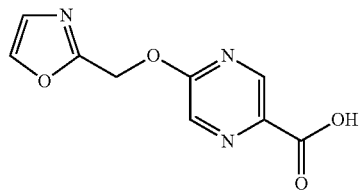

Synthesis of 5-(Oxazol-2-ylmethoxy)pyrazine-2-carboxylic acid

Step 1: Methyl 5-(oxazol-2-ylmethoxy)pyrazine-2-carboxylate

To a flask was added methyl 5-chloropyrazine-2-carboxylate (1.5179 g, 8.80 mmol), oxazol-2-ylmethanol (0.697 ml, 8.80 mmol), and cesium carbonate (0.845 ml, 10.56 mmol) in DMF (25.1 mL) to stir at 40° C. for 24 h. The reaction mixture was diluted with water and extracted with EtOAc. The organic extract was washed with water, brine, and dried over MgSO$_4$, filtered and concentrated in vacuo. The crude product was adsorbed onto a plug of silica gel and chromatographed through a Biotage SNAP HP-silica gel column (100 g), eluting with a gradient of 10-100% EtOAc/hexane, to provide methyl 5-(oxazol-2-ylmethoxy)pyrazine-2-carboxylate (0.547 g, 2.327 mmol, 26.5% yield). MS m/z=236.0 [M+H]$^+$. Calculated for C$_{10}$H$_9$N$_3$O$_4$: 235.059

$^1$H NMR (400 MHz, DMSO-d$_6$) ppm 3.89 (s, 3 H) 5.59 (s, 2 H) 7.28 (d, J=0.78 Hz, 1 H) 8.18 (d, J=0.78 Hz, 1 H) 8.52 (d, J=1.17 Hz, 1 H) 8.84 (d, J=1.37 Hz, 1 H)

Step 2: 5-(Oxazol-2-ylmethoxy)pyrazine-2-carboxylic acid

To a solution of methyl 5-(oxazol-2-ylmethoxy)pyrazine-2-carboxylate (0.761 g, 3.23 mmol) in 1,4-dioxane (16.17 mL) was added sodium hydroxide 1.0N solution (3.23 ml, 3.23 mmol) to stir at room temperature for 16 h. Then HCl, 4.0M solution in 1,4-dioxane (1.617 ml, 6.47 mmol,) was added to stir for 10 min. The reaction mixture was concentrated in vacuo. MS m/z=221.9 [M+H]$^+$. Calculated for C$_9$H$_7$N$_3$O$_4$: 221.044

$^1$H NMR (400 MHz, DMSO-d$_6$) ppm 5.58 (s, 2 H) 7.28 (d, J=0.59 Hz, 1 H) 8.18 (d, J=0.78 Hz, 1 H) 8.50 (d, J=1.17 Hz, 1 H) 8.81 (d, J=1.17 Hz, 1 H)

Intermediate 24

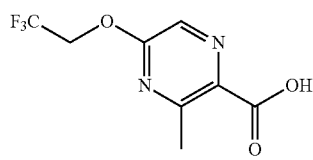

Synthesis of 3-methyl-5-(2,2,2-trifluoroethoxy)pyrazine-2-carboxylic acid

The title compound was synthesized according to Intermediate 13, using 2,2,2,-trifluoroethanol (Aldrich) in Step 4. MS m/z=237 (M+H).

Intermediate 25 (Method AB)

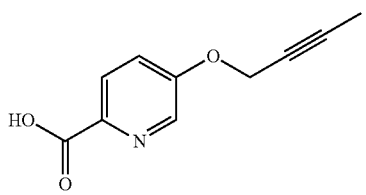

Synthesis of 5-(but-2-yn-1-yloxy)picolinic acid

Step 1: Methyl 5-(but-2-yn-1-yloxy)picolinate

A solution of methyl 5-hydroxypyridine-2-carboxylate (1.5 g, 9.8 mmol, Molbridge) in THF (39 ml) under argon was cooled to 0° C. and 2-butyn-1-ol (1.5 ml, 20 mmol, Aldrich), triphenyl phosphine (2.95 g, 11.2 mmol, Aldrich) and diisopropyl azodicarboxylate (2.2 ml, 11.2 mmol, Aldrich) were added consecutively. The reaction mixture was stirred at room temperature for 2 h. Additional diisopropyl azodicarboxylate (1 ml) was added and the reaction mixture was stirred at room temperature for another 1 h. The reaction mixture was diluted with $CH_2Cl_2$ and washed with saturated $NaHCO_3$ solution; the aqueous layer was back-extracted with $CH_2Cl_2$. The combined organic extracts were dried over $MgSO_4$ and concentrated in vacuo. Purification by silica gel chromatography (0% to 50% EtOAc/Hexanes) afforded the title compound as a light tan solid. MS m/z=206.0 [M+H]$^+$.

Step 2: 5-(But-2-yn-1-yloxy)picolinic acid

Using an analogous reaction to that described for Intermediate 5, step 2 methyl 5-(but-2-yn-1-yloxy)picolinate was converted to 5-(But-2-yn-1-yloxy)picolinic acid MS m/z=192.1 [M+H]$^+$.

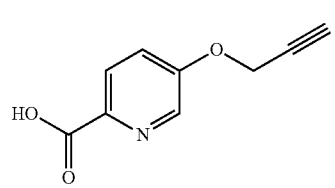

Intermediate 26

Synthesis of 5-(prop-2-yn-1-yloxy)picolinic acid

The title compound was synthesized analogously according to Method AB starting from propargyl alcohol (Aldrich). MS m/z=178.1 [M+H]$^+$.

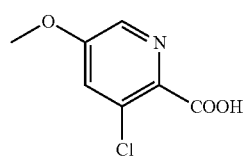

Intermediate 27

Synthesis of 3-chloro-5-methoxypicolinic acid

Step 1: methyl 3-chloro-5-methoxypicolinate

In a 1-L flask, methyl 3-chloro-5-hydroxypicolinate (Afferchem, 25.00 g, 133 mmol) and cesium carbonate (87 g, 267 mmol) were suspended in DMF (200 mL) and iodomethane (41.7 mL, 666 mmol) was added dropwise. A water-cooled condenser was attached, and the reaction vessel was heated in a 55° C. oil bath. After 3 h the reaction was concentrated under reduced pressure. The residue was taken up in 1.2 L of 80% EtOAc-hexane and 500 mL brine. The mixture was filtered through Celite. The filtrate was transferred into a separation funnel. The organic layer was separated, washed with brine (100 mL), dried over $MgSO_4$ and concentrated under reduced pressure. The residue was purified by silica gel chromatography eluting with 30% to 40% EtOAc-hexane, affording the title compound (19.1 g) as a tan solid. MS m/z=202 (M+H).

Step 2: 3-chloro-5-methoxypicolinic acid

Using an analogous reaction to that described for Intermediate 5, step 2 methyl 3-chloro-5-methoxypicolinate was converted to the title compound. MS m/z=188 (M+H).

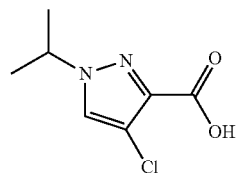

Intermediate 28

Synthesis of 4-Chloro-1-isopropyl-1H-pyrazole-3-carboxylic acid

Step 1: Methyl 1-isopropyl-1H-pyrazole-3-carboxylate

To a solution of 1-isopropyl-1h-pyrazole-3-carboxylic acid (0.9757 g, 6.33 mmol, Matrix Scientific) in MeOH (31.6 ml) in a glass pressure vessel was added sulfuric acid (0.355 ml, 6.33 mmol Sigma Aldrich). The vessel was sealed and the rxn was brought to reflux to stir. (NOTE: A portable blast shield was used.) Rxn was allowed to stir for 5 hours. The rxn was concentrated in vacuo. The residue was diluted with water and extracted with EtOAc. The organic extract was washed with water, dried over $MgSO_4$, filtered and concentrated in vacuo to give methyl 1-isopropyl-1H-pyrazole-3-carboxylate (0.8073 g, 4.80 mmol, 76% yield) as a clear oil. MS m/z=168.9 [M+H]$^+$. Calculated for $C_8H_{12}N_2O_2$: 168.09. $^1$H NMR (400 MHz, CHLOROFORM-d) δ ppm 1.55 (d, J=6.85 Hz, 6 H) 3.93 (s, 3 H) 4.63 (dt, J=13.50, 6.75 Hz, 1 H) 6.83 (d, J=2.35 Hz, 1 H) 7.46 (d, J=2.35 Hz, 1 H)

Step 2: Methyl 4-chloro-1-isopropyl-1H-pyrazole-3-carboxylate

To a solution of methyl 1-isopropyl-1H-pyrazole-3-carboxylate (0.8073 g, 4.80 mmol) in DMF (9.60 ml) was added n-chlorosuccinimide (3.20 g, 24.00 mmol, Sigma Aldrich). The reaction mixture was heated to 70° C. for 4.5 h. The reaction mixture was diluted with water and extracted with EtOAc. The organic extract was washed with water, brine, dried over $MgSO_4$, filtered and concentrated in vacuo. The crude product was purified by silica gel chromatography, eluting with a gradient of 10% to 30% EtOAc in hexane, to provide methyl 4-chloro-1-isopropyl-1H-pyrazole-3-carboxylate (0.2705 g, 1.335 mmol, 27.8% yield) as an off-white solid. MS m/z=203.0[M+H]$^+$. Calculated for $C_8H_{11}ClN_2O_2$: 202.051. $^1$H NMR (400 MHz, DMSO-d$_6$) δ ppm 1.42 (d, J=6.85 Hz, 6 H) 3.80 (s, 3 H) 4.55 (dt, J=13.30, 6.65 Hz, 1 H) 8.23 (s, 1 H)

Step 3: 4-chloro-1-isopropyl-1H-pyrazole-3-carboxylic acid

Using an analogous reaction to that described for Intermediate 5, step 2 methyl 4-chloro-1-isopropyl-1H-pyrazole-3- carboxylate was converted into the title compound. MS m/z=188.9 [M+H]⁺. Calculated for $C_7H_9ClN_2O_2$: 188.035. ¹H NMR (400 MHz, DMSO-$d_6$) δ ppm 1.41 (d, J=6.65 Hz, 6 H) 4.52 (quin, J=6.70 Hz, 1 H) 8.17 (s, 1 H) 12.89 (br. s., 1 H)

Intermediate 29

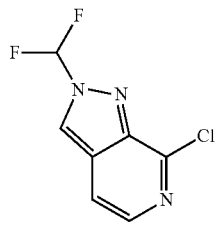

Synthesis of 7-chloro-2-(difluoromethyl)-2H-pyrazolo[3,4-c]pyridine

Step 1: 7-chloro-1H-pyrazolo[3,4-c]pyridine

To a cooled (internal temperature of <13° C.) mixture of 3-amino-2-chloro-4-methylpyridine (10.14 g, 71.1 mmol, Matrix) and potassium acetate (9.02 g, 92 mmol) in AcOH (200 mL) was added a solution of sodium nitrite (7.36 g, 107 mmol) in water (30 mL) dropwise while maintaining an internal temperature <13° C. The reaction was allowed to warm slowly to rt and stirred for 66 h. The mixture was concentrated under reduced pressure and the residue was basified with saturated NaHCO₃. The solid was filtered and washed with water. The solid was stirred over EtOAc overnight and filtered. The filtrate was combined with the organic extracts, evaporated onto silica gel and purified by flash chromatography (Isco (120 gram)) eluting with EtOAc:hexanes (0:1→1:1) to give a white crystalline solid (4.99 g, 46%). MS m/z=153.9, 155.9 [M+H]⁺. Calculated for $C_6H_4ClN_3$: 153.

Step 2: 7-chloro-2-(difluoromethyl)-2H-pyrazolo[3,4-c]pyridine

A mixture of 7-chloro-1H-pyrazolo[3,4-c]pyridine (4.99 g, 32.5 mmol), sodium chlorodifluoroacetate (14.86 g, 97 mmol), and cesium carbonate (40.2 g, 123 mmol) in DMF (81 ml) was heated at 95° C. for 4 h. The reaction was allowed to cool to rt and the solids were filtered. The filtrate was diluted with water and extracted with EtOAc. The organic extract was washed with water, satd NaCl, dried over MgSO₄, filtered and concentrated in vacuo. The crude product was adsorbed onto a plug of silica gel and chromatographed through a Biotage SNAP HP-silica gel column (100 g), eluting with a gradient of 5% to 60% EtOAc in hexane, to provide a white solid (1.4117 g, 6.93 mmol, 21.34% yield). MS m/z=203.9 [M+H]⁺. Calculated for $C_7H_4ClF_2N_3$: 203.

Intermediate 30

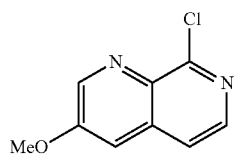

Synthesis of 8-Chloro-3-methoxy-1,7-naphthyridine

Step 1: 3-chloro-5-methoxypicolinonitrile

To a solution of 3,5-dichloropicolinonitrile (22.5 g, 130 mmol) in DMF (500 mL) at 0° C. was added sodium methoxide (6.67 g, 124 mmol) slowly. The reaction was stirred for 5 minutes at 0° C., then allowed to warm to RT and stir for 30 minutes. The solution was partitioned between water and EtOAc. The organic layer was washed with water and concentrated. The crude product was purified via silica gel chromatography, eluting with 0-75% ethyl acetate in heptanes, to afford a 1:1 ratio of the desired isomer 3-chloro-5-methoxypicolinonitrile and 5-chloro-3-methoxypicolinonitrile (7.0 g, 41.5 mmol). The material was used without further purification. MS m/z=169 (M+H).

Step 2: 5-Methoxy-3-((triethylsilyl)ethynyl)picolinonitrile

A sealable vessel was charged with bis(acetonitrile)palladium (II) chloride (0.154 g, 0.593 mmol), dicyclohexyl(2',4',6'-triisopropyl-[1',1'-biphenyl]-2-yl)phosphine (0.848 g, 1.780 mmol), cesium carbonate (25.1 g, 77 mmol), the product of Intermediate 9, step 1 (5 g, 29.7 mmol), and ACN (60 mL). The vessel was flushed with argon, sealed, and stirred at RT for 25 minutes. To the reaction was added triethyl(ethynyl)silane (5.41 g, 38.6 mmol), and the vessel was resealed and stirred at 90° C. for 3 hours. The solution was concentrated, and the residue was purified via silica gel chromatography, eluting with 0-50% ethyl acetate in heptanes, to afford the title compound (3.8 g, 13.9 mmol). MS m/z=273 (M+H).

Step 3: 3-(2,2-Dimethoxyethyl)-5-methoxypicolinonitrile

A pressure vessel was charged with 5-methoxy-3-((triethylsilyl)ethynyl)picolinonitrile (3.8 g, 13.95 mmol) and sodium methoxide (0.5 M in methanol, 69.7 mL, 34.9 mmol). The vessel was sealed and stirred at 55° C. for 2 hours. The reaction was concentrated to afford the title intermediate (3.1 g, 13.95 mmol).

Step 4: 3-(2,2-dimethoxyethyl)-5-methoxypicolinamide

To a 1 L round-bottomed flask was added 3-(2,2-dimethoxyethyl)-5-methoxypicolinonitrile (8.550 g, 38.5 mmol), water (480 ml), and acetone (120 ml). An aqueous solution of sodium carbonate (3M; 154 ml, 462 mmol) was added followed by hydrogen peroxide (35 wt. % solution in water; 138 ml, 1347 mmol). The tan mixture was stirred vigorously at rt for 2 h. The organic solvent was removed uncle reduced pressure and the aqueous residue was extracted with DCM (3x). The combined organic fractions were dried over sodium sulfate. The filtrate was concentrated under reduced pressure to afford 3-(2,2-dimethoxyethyl)-5-methoxypicolinamide (8.200 g, 34.1 mmol, 89% yield) as an off-white solid that was advanced without further purification. MS m/z=263.2 (M+Na)

Step 4: 3-methoxy-1,7-naphthyridin-8(7H)-one

To a mixture of 3-(2,2-dimethoxyethyl)-5-methoxypicolinamide (6.74 g, 28.1 mmol) in toluene (112 ml) was added 4-methylbenzene sulfonic acid (monohydrate; 0.534 g, 2.81 mmol). The reaction mixture was heated to reflux for 20 h.

The reaction mixture was cooled to rt and concentrated in vacuo to a volume of ca. 15 mL. The residue was triturated with heptanes and filtered to afford 3-methoxy-1,7-naphthyridin-8(7H)-one (4.53 g, 25.7 mmol, 92% yield) as a crude, tan solid that was advanced without further purification. Crude LCMS showed complete conversion to product MS m/z=177.1 [M+H]

Step 5: 8-chloro-3-methoxy-1,7-naphthyridine

To a mixture of 3-methoxy-1,7-naphthyridin-8(7H)-one (4.50 g, 25.5 mmol) in acetonitrile (102 ml) was added phosphorus oxychloride (11.69 ml, 128 mmol). The reaction mixture was heated to 85° C. for 5 h. The solution was cooled to rt and concentrated in vacuo. The resulting brown residue was partitioned between $CH_2Cl_2$ and aqueous saturated NaHCO3 solution; the aqueous layer was back-extracted with DCM (3×). The combined organic extracts were dried over sodium sulfate, the filtrate was concentrated in vacuo, and the residue was purified by silica gel chromatography (5%-30% of 9:1 DCM:MeOH in DCM) to afford 8-chloro-3-methoxy-1,7-naphthyridine (3.00 g, 15.41 mmol, 60.3% yield) as an off-white solid. MS m/z=195 (M+H).

Intermediate 31

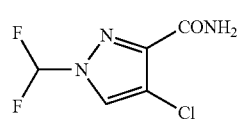

Synthesis of 4-chloro-1-(difluoromethyl)-1H-pyrazole-3-carboxamide

The title compound was prepared according to Method AA starting from 4-chloro-1-(difluoromethyl)-1H-pyrazole-3-carboxylic acid (WO201169934). MS m/z=196 (M+H).

Intermediate 32

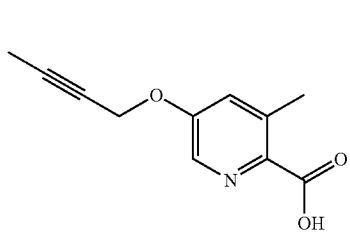

Step 1: Synthesis of 6-chloro-5-methylpyridine-3-amine

Fe powder (9.75 g, 0.174 mol, Sigma-Aldrich) was added in portions over a period of 2 h to a stirred solution of 2-chloro-3-methyl-5-nitropyridine (10 g, 0.058 mol, Combiblocks) in acetic acid/water (29 mL: 88 mL). After 3 h, the reaction mixture was filtered through celite and the filter cake was washed with ethyl acetate. The organic layer was separated and the aqueous layer was extracted with EtOAc. The combined organic layers were washed with aqueous sodium bicarbonate, brine and dried over Na2SO4. The solvent was removed under reduced pressure to yield 6-chloro-5-methylpyridine-3-amine as a brown solid (8.0 g; 97%). MS m/z=142.03 [M+H]$^+$.

$^1$H-NMR (300 MHz, DMSO-d6): δ 7.54 (d, J=30 Hz, 1H), 6.91-6.90 (dd, J=0.6 Hz & 2.7 Hz, 1H), 5.39 (s, 2H), 2.17 (s, 3H)

Step 2: Synthesis of 6-chloro-5-methylpyridine-3-ylacetate

In a 100 mL R.B. flask, Boron trifluoride diethyl etherate (1.8 mL, 0.0143 mol, Sigma Aldrich) was added drop wise to a cooled mixture (−15° C.) of 6-chloro-5-methylpyridine-3-amine (1.0 g, 0.0070 mol) in DME (7.5 mL) and dichloromethane (2.5 mL). Then tert-butyl nitrite (0.85 g, 0.0082 mol, Sigma-Aldrich) was added drop wise and the reaction mixture was stirred at −10° C. for 25 min. The reaction mixture was allowed to warm to 0° C. and stirred for additional 20 min. The reaction mixture was diluted with pentane (50 mL) and the tetrafluoroborate diazonium salt was collected by filtration. The salt was dissolved in acetic anhydride (10 mL) and heated at 95° C. for 2 h. The reaction mixture was cooled to ambient temperature and then partitioned between ethyl acetate (50 mL) and sat.aq.sodium bicarbonate solution (100 mL). The aqueous solution was separated and extracted with ethyl acetate (2×100 mL). The combined organic layers were washed with brine, dried over anhydrous sodium sulfate, filtered and concentrated to afford a brown oil. This oil was purified by column chromatography on silica gel, eluting with 5% ethyl acetate in petroleum ether to give 6-chloro-5-methylpyridine-3-yl acetate as pale yellow oil (780 mg, 62%)
MS m/z=185.02 [M+H]$^+$.
1H-NMR (300 MHz, DMSO-d$_6$): δ 8.13 (d, J=2.4 Hz, 1H), 7.72 (d, J=2.7 Hz 1 H), 2.34 (s, 3H), 2.30 (s, 3H)

Step-3: Synthesis of 6-chloro-5-methylpyridine-3-ol

Potassium carbonate (1.10 g, 0.0081 mol) was added to a stirred solution of 6-chloro-5-methylpyridine-3-yl acetate (750 mg, 0.004 mol) in MeOH (15 mL) at ambient temperature. The reaction mixture was stirred for 1 h at ambient temperature. The reaction mixture was concentrated under reduced pressure and the residue was diluted with minimum amounts of water and neutralized with 1N HCl (15 mL). After neutralization, the solution was extracted with ethyl acetate (2×100 mL). The combined organic layers were washed with brine, dried over anhydrous sodium sulfate and concentrated to give 6-chloro-5-methylpyridine-3-ol as an off white solid (500 mg, 89%). MS m/z=143.01 [M+H]$^+$.
$^1$H-NMR (300 MHz, DMSO-d$_6$): δ 10.09 (s, 1H), 7.76 (d, J=3 Hz, 1H), 7.18 (d, J=3.6 Hz, 1H), 2.24 (s, 3H).

Step 4: Synthesis of 2-chloro-5-((4-methoxybenzyl)oxy)-3-methylpyridine

A mixture of 6-chloro-5-methylpyridin-3-ol (250 mg, 0.0017 mol), 1-(chloromethyl)-4-methoxybenzene (0.328 g, 0.0020 mol, Sigma Aldrich), and potassium carbonate (0.482 g, 0.0034 mol) in DMF (5 mL) was allowed to stir for 3 h at 60° C. After completion of the reaction, reaction mixture was cooled to ambient temperature and poured into ice cold water (25 mL). The obtained solid was filtered, washed with water (2×10 mL) and dried to obtain 2-chloro-5-((4-methoxybenzyl)oxy)-3-methylpyridine as an off white solid (400 mg, 87%).
MS m/z=263.9 [M+H]$^+$.
$^1$H-NMR (300 MHz, CDCl$_3$): δ 7.96 (d, J=2.7 Hz, 1H), 7.34 (d, J=8.7 Hz, 2H), 7.15 (d, J=3 Hz, 1H), 6.94-6.89 (m, 2H), 4.99 (s, 2H), 3.81 (s, 3H), 2.33 (s, 3H).

Step 5: Synthesis of 5-((4-methoxybenzyl)oxy)-3-methyl-2-vinylpyridine

A 25 mL sealable tube was charged with a mixture of 2-chloro-5-(difluoromethoxy)-3-methylpyridine (330 mg, 0.0012 mmol), toluene (10 mL), and tributyl(vinyl)stannane (447 mg, 0.0015 mmol). The reaction mixture was purged with Argon gas for 10 min. Then Pd(PPh$_3$)$_4$ (144 mg, 0.00018 mol, Alfa-Aesar) was added and the reaction mixture was allowed to stir for 16 h at 100° C. The reaction mixture was cooled to ambient temperature and filtered through celite. The filter cake was washed with ethyl acetate and concentrated to get a crude residue. The residue was purified by column chromatography using silica and eluting with 5-10% ethyl acetate in petroleum ether to give 5-((4-methoxybenzyl)oxy)-3-methyl-2-vinylpyridine as an off white solid (250 mg, 65%). MS m/z=256.1 [M+H]$^+$.

$^1$H-NMR (300 MHz, CDCl$_3$): δ 8.20 (d, J=2.7 Hz, 1H), 7.37-7.33 (m, 2H), 7.02 (d, J=2.7 Hz, 1H), 6.94-6.87 (m, 3H), 6.21 (dd, J=1.8 Hz & 16.8 Hz, 1H), 5.39 (dd, J=2.1 Hz & 10.5 Hz, 1H), 5.01 (s, 2H), 3.81 (s, 3H), 2.33 (s, 3H).

Step 6: Synthesis of 5-methyl-6-vinylpyridin-3-ol

Trifluoroacetic acid (1.25 mL, 5 times) was added to a stirred solution of 5-((4-methoxybenzyl)oxy)-3-methyl-2-vinylpyridine (250 mg, 0.00098 mmol) in anisole (0.5 mL). The reaction mixture was stirred for 2 h at ambient temperature. After completion of the reaction, the reaction mixture was concentrated and quenched with saturated NaHCO3 solution (2 ml). The reaction mixture was extracted with ethyl acetate (2×10 mL) and the combined organic layers were washed with brine, dried over anhydrous sodium sulfate and concentrated under reduced pressure. The crude residue was triturated with pentane to afford 5-methyl-6-vinylpyridin-3-ol as an off white solid (100 mg, 76%). MS m/z=136.15 [M+H]$^+$.

$^1$H-NMR (400 MHz, CDCl$_3$): δ 9.86 (s, 1H), 7.96 (d, J=2.8 Hz, 1H), 6.94-6.86 (m, 2H), 6.07 (dd, J=2.4 Hz & 16.8 Hz, 1H), 5.26 (dd, J=2.8 Hz & 10.4 Hz, 1H), 2.25 (s, 3H).

Step 7: Synthesis of 5-(but-2-yn-1-yloxy)-3-methyl-2-vinylpyridine

A reaction mixture of 5-methyl-6-vinylpyridin-3-ol (100 mg, 0.00074 mmol), sodium 1-bromobut-2-yne (118 mg, 0.00088 mol, Alfa-Aesar) and cesium carbonate (361 mg, 0.0011 mol) in DMF (2 mL) was stirred for 2 h at 80° C. After completion of the reaction, reaction mixture was cooled to ambient temperature, poured into ice-cold water (10 mL) and extracted with ethyl acetate (3×10 mL). The combined organic layers were washed with brine, dried over sodium sulfate and concentrated under reduced pressure. The crude residue was purified by column chromatography using silica gel and eluting with 0-10% ethyl acetate in petroleum ether to give 5-(but-2-yn-1-yloxy)-3-methyl-2-vinylpyridine as an off white solid (85 mg, 61.5%). MS m/z=188.3 [M+H]$^+$.

$^1$H-NMR (400 MHz, CDCl$_3$): δ 8.21 (d, J=2.8 Hz, 1H), 7.03 (d, J=2.4 Hz, 1H), 6.96-6.89 (m, 1H), 6.22 (dd, J=2.4 Hz & 17.2 Hz, 1H), 5.40 (dd, J=2 Hz & 10.8 Hz, 1H), 4.68-4.67 (m, 2H), 2.35 (s, 3H), 1.85 (t, J=2.4 Hz, 3H).

Step 8: Synthesis of 5-(but-2-yn-1-yloxy)-3-methylpicolinaldehyde

OsO$_4$ (2.5 wt. % sol. in tert-Butanol) (0.86 mL, 0.0027 mol) was added to a stirred solution of 5-(but-2-yn-1-yloxy)-3-methyl-2-vinylpyridine (5.1 g, 0.027 mol) in acetone/water (100:100 mL) at 0° C. The reaction mixture was allowed to stir for 30 min at ambient temperature. Then NaIO$_4$ (23.2 g, 0.108 mol) was added and the reaction mixture was allowed to stir for additional 4 h at ambient temperature. The reaction mixture was diluted with ice cold water (200 mL) and extracted with EtOAc (3×200 mL). The combined organic layers were washed with brine, dried over Na$_2$SO$_4$ and concentrated under reduced pressure. The crude residue was purified by flash column chromatography on silica gel, eluting with 5-10% EtOAc in petroleum ether to give 5-(but-2-yn-1-yloxy)-3-methylpicolinaldehyde as an off white solid (3.6 g, 69.9%). MS m/z=189.9 [M+H]$^+$.

$^1$H-NMR (400 MHz, CDCl$_3$): δ 10.10 (s, 1H), 8.37 (d, J=2.8 Hz, 1H), 7.13 (d, J=2.8 Hz, 1H), 4.77 (d, J=2.4 Hz, 2H), 2.67 (s, 3H), 1.86 (t, J=2 Hz, 3H).

Step 9: Synthesis of 5-(but-2-yn-1-yloxy)-3-methylpicolinic acid

A stirred solution of 5-(but-2-yn-1-yloxy)-3-methylpicolinaldehyde (3.6 g, 0.019 mol) in water (216 mL)/acetone (36 mL) was treated with sulphamic acid (2.5 g, 0.025 mol) and 85% sodium chlorite (2.65 g, 0.029 mol). The reaction mixture was allowed to stir for 2 h at ambient temperature. The reaction mixture was extracted with ethyl acetate (2×100 ml). The combined organic layer were washed with brine, dried over Na$_2$SO$_4$ and concentrated under reduced pressure. The crude residue was triturated with n-pentane to get 5-(but-2-yn-1-yloxy)-3-methylpicolinaldehyde as an off white solid (3.2 g, 82%). MS m/z=206.3 [M+H]$^+$.

$^1$H-NMR (400 MHz, CD3OD): δ 8.16 (d, J=2.8 Hz, 1H), 7.38 (d, J=2.4 Hz, 1H), 4.84-4.82 (m, 2H), 2.63 (s, 3H), 1.83 (t, J=2 Hz, 3H).

Intermediate 33

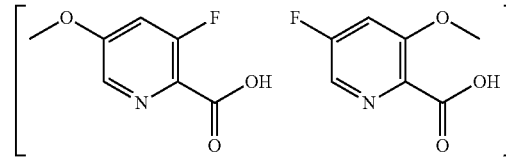

Synthesis of a mixture of 3-fluoro-5-methoxypicolinic acid and 5-fluoro-3-methoxypicolinic acid

Step 1: Mixture of 3-fluoro-5-hydroxypicolinic acid and 5-fluoro-3-hydroxypicolinic acid To a sealable tube was added 3,5-difluoropyridine-2-carboxylic acid (2.0 g, 12.57 mmol, Lancaster Synthesis Ltd.), lithium hydroxide hydrate (5.28 g, 126 mmol, Aldrich), and water (50 mL). The resulting mixture was stirred at 100° C. for 20 h. Trifluoroacetic acid (5.0 mL, 67.3 mmol, Aldrich) was added to the mixture. The mixture was concentrated and dried in vacuo overnight to provide 12.6 g of a crude product mixture of 3-fluoro-5-hydroxypicolinic acid and 5-fluoro-3-hydroxypicolinic acid, as a white solid, used directly in the next step. MS (ESI, positive ion) m/z: 158.1 (M+H) observed for both isomers.

Step 2: Mixture of methyl 3-fluoro-5-methoxypicolinate and methyl 5-fluoro-3-methoxypicolinate To a solution of 3-fluoro-5-hydroxypicolinic acid (1.98 g, 12.57 mmol) and 5-fluoro-3-hydroxypicolinic acid in DMF (100 mL, Aldrich) was added cesium carbonate (2.5 mL, 31.4 mmol, Aldrich) and iodomethane, stabilized (1.7 mL, 27.7 mmol, Alfa Aesar, A Johnson Matthey Company). The reaction was stirred at room temperature for 48 hours. Cesium carbonate (20.48 g, 62.8 mmol, Aldrich) and iodomethane, stabilized (3.4 mL, 55.4 mmol, Alfa Aesar) were added. The resulting mixture was stirred at room temperature for 16 hours. The mixture was diluted with $H_2O$ (500 mL) and extracted with EtOAc (2×500 mL). The combined extracts were washed with $H_2O$ (1×500 mL), dried over $MgSO_4$, concentrated, and dried in vacuo to give 1.18 g of products as a mixture of methyl 3-fluoro-5-methoxypicolinate and methyl 5-fluoro-3-methoxypicolinate as a light yellow solid. MS (ESI, positive ion) m/z: 186.1 (M+H) observed for both isomers.

Step 3: Mixture of 3-fluoro-5-methoxypicolinic acid and 5-fluoro-3-methoxypicolinic acid To a solution of methyl 3-fluoro-5-methoxypicolinate (1.18 g, 6.37 mmol) and methyl 5-fluoro-3-methoxypicolinate in MeOH (30 mL, Aldrich) and water (10 mL) at 0° C. was added lithium hydroxide hydrate (0.53 g, 12.74 mmol, Aldrich). After addition, the mixture was then stirred at room temperature for 1 h. The mixture was concentrated and $H_2O$ (25 mL) was added. The resulting mixture was adjusted to pH=5-6 by HCl (2N). The mixture was concentrated and dried. The residue was dissolved in MeOH (100 mL), adsorbed onto silica, and purified by silica gel flash chromatography using a gradient of 0%-40% MeOH in DCM to give 1.67 g (white solid) of products as a mixture of 3-fluoro-5-methoxypicolinic acid and 5-fluoro-3-methoxypicolinic acid. MS (ESI, positive ion) m/z: 172.1 (M+H) observed for both isomers.

General amidation procedures: The following method may be used to couple the amine core intermediates (see examples and intermediates).
Method: HATU Procedure To a solution of the aniline (1 equivalent) and the carboxylic acid (1.1 equivalent) in DCM is added triethylamine (1.5 eq) and 1-[bis(dimethylamino)methylene]-1H-1,2,3-triazolo[4,5-b]pyridinium 3-oxide hexafluorophosphate (HATU, 1.1 equivalent). The reaction mixture is stirred at RT for 3 hours, diluted with DCM, and washed with water and brine. The organic layer is concentrated.

The amine protecting group, where applicable, may be removed using DBU and MeOH. The residue is taken up in MeOH, to which DBU is added and the reaction is heated in the microwave for about 1.5 hours at 75° C. Standard work-up protocols can be employed to isolate a crude product. The crude product may be purified by silica-gel chromatography to provide the title compound.

Alternatively, the protecting group may be removed by taking the intermediate up in MeOH and treating it with 2M ammonia, then heating it at 75° C. overnight in a microwave, and working it up the next morning using convention methods.

The following compounds in Table 1 are examples of compounds of Formulas I, II and III, and sub-formulas thereof, provided by the present invention. The methods used to prepare the exemplary compounds are included in Table 1. Table I further provides the mass found, method used to make the compound, as well as the biological data (average uM $IC_{50}$'s for the BACE enzyme and cell assays, and enzyme assay for cathepsin D) for each compound, where available. A blank indicates that no data was available at the time this application was filed.

TABLE 1

| Example No | Compound Name | BACE 1 FRET assay $IC_{50}$ (uM) | HEK cell assay $IC_{50}$ (uM) | CatD IC50 (μM) | MS m/z [M + H]+ | Method used to make example |
|---|---|---|---|---|---|---|
| 2 | N-(3-((4S,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide | 0.021 | 0.032 | >400 | 446 | A |
| 25 | rac. mixture of N-(3-((4R,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide & N-(3-((4S,6R)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide | 0.813 | 2.37 | >400 | 446 | C |
| 3 | N-(3-((4S,6S)-2-amino-4-(fluoromethyl)-6-(trifluoromethyl)-5,6-dihydro-4H-1,3-oxazin-4-yl)-4-fluorophenyl)-5-chloro-2-pyridinecarboxamide | 0.018 | 0.032 | >400 | 448.9 | A |
| 8 | N-(3-((4S,6S)-2-amino-4-(fluoromethyl)-6-(trifluoromethyl)-5,6-dihydro-4H-1,3-oxazin-4-yl)-4-fluorophenyl)-3-chloro-1,7-naphthyridin-8-amine | 0.018 | 0.203 | >400 | 472 | B |
| 9 | rac. mixture of N-(3-((4R,6R)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine &N-(3-((4S,6S)-2-amino-4-(fluoromethyl)-6-(trifluoromethyl)-5,6- | 0.050 | 0.372 | >400 | 469 | B |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| | dihydro-4H-1,3-oxazin-4-yl)-4-fluorophenyl)-2-methoxypyrido[3,4-b]pyrazin-5-amine | | | | | |
| 4 | N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methyl-2-pyridinecarboxamide | 0.008 | 0.031 | >400 | 463 | A |
| 6 | N-(3-((4S,6S)-2-amino-4-(fluoromethyl)-6-(trifluoromethyl)-5,6-dihydro-4H-1,3-oxazin-4-yl)-4-fluorophenyl)-6-chloro-3-methylimidazo[1,2-a]pyridine-2-carboxamide | 0.036 | 0.0522 | >400 | 501.9 | A |
| 27 | N-(3-((4S,6S)-2-amino-4-methyl-6-(trifluoromethyl)-5,6-dihydro-4H-1,3-oxazin-4-yl)-4-fluorophenyl)-5-methoxy-2-pyrazinecarboxamide | 0.030 | | >400 | 428 | C |
| 5 | N-(3-((4S,6S)-2-amino-4-(fluoromethyl)-6-(trifluoromethyl)-5,6-dihydro-4H-1,3-oxazin-4-yl)-4-fluorophenyl)-5-(2,2,2-trifluoroethoxy)-2-pyridinecarboxamide | 0.043 | 0.263 | >400 | 512.9 | A |
| 22 | 8-((3-((4S,6S)-2-amino-4-(fluoromethyl)-6-(trifluoromethyl)-5,6-dihydro-4H-1,3-oxazin-4-yl)-4-fluorophenyl)amino)-1,7-naphthyridine-3-carbonitrile | 0.021 | 0.057 | >133 | 463 | C |
| 61 | N-(5-((4S,6S)-2-amino-4-methyl-6-(trifluoromethyl)-5,6-dihydro-4H-1,3-oxazin-4-yl)-6-fluoropyridin-3-yl)-5-chloro-3-methylpicolinamide | .0552 | .0391 | >400 | 466 | G |
| 59 | N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide | .0179 | .027 | >400 | 439.3 | F |
| 31 | N-(3-((4S,6S)-2-amino-4-methyl-6-(trifluoromethyl)-5,6-dihydro-4H-1,3-oxazin-4-yl)-4-fluorophenyl)-5-chloro-3-methyl-2-pyridinecarboxamide and N-(3-((4R,6R)-2-amino-4-methyl-6-(trifluoromethyl)-5,6-dihydro-4H-1,3-oxazin-4-yl)-4-fluorophenyl)-5-chloro-3-methyl-2-pyridinecarboxamide | .0165 | .0144 | 202 | 444 | See eg 31 |
| 32 | N-(3-((4S,6S)-2-amino-4-(fluoromethyl)-6-(trifluoromethyl)-5,6-dihydro-4H-1,3-oxazin-4-yl)-4-fluorophenyl)-3-chloro-5-cyano-2-pyridinecarboxamide | .0285 | .0544 | >400 | 473.1 | F |
| 33 | N-(3-((4S,6S)-2-amino-4-(fluoromethyl)-6-(trifluoromethyl)-5,6-dihydro-4H-1,3-oxazin-4-yl)-4-fluorophenyl)-5-methoxy-3-methylpyrazine-2-carboxamide | .0736 | .1 | >400 | 459.1 | F |
| 47 | N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methoxypicolinamide | .0564 | .0679 | >400 | 478.1 | F |
| 60 | N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide | .0528 | .0135 | >400 | 431.8 | G |
| 26 | N-(3-((4S,6S)-2-amino-4-methyl-6-(trifluoromethyl)-5,6-dihydro-4H-1,3-oxazin-4-yl)-4-fluorophenyl)-5-chloropicolinamide | .0123 | .0049 | >400 | 431.0 | E |
| 62 | N-(5-((4S,6S)-2-amino-4-methyl-6-(trifluoromethyl)-5,6-dihydro-4H-1,3-oxazin-4-yl)-6-fluoropyridin-3-yl)-5-cyanopicolinamide | .0523 | .0286 | >400 | 422.3 | G |
| 185 | N-(3-((4S,6S)-2-amino-4-methyl-6-(trifluoromethyl)-5,6-dihydro-4H-1,3- | .0132 | .0025 | >400 | 422.1 | E |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 50 | oxazin-4-yl)-4-fluorophenyl)-5 cyanopicolinamide N-(3-((4S,6S)-2-amino-4-(fluoromethyl)-6-(trifluoromethyl)-5,6-dihydro-4H-1,3-oxazin-4-yl)-4-fluorophenyl)-3-chloro-5-methoxypicolinamide | .0238 | .0265 | >400 | 478.1 | F |
| 10 | 8-((3-((4S,6S)-2-amino-4-(fluoromethyl)-6-(trifluoromethyl)-5,6-dihydro-4H-1,3-oxazin-4-yl)-4-fluorophenyl)amino)-5-fluoro-1,7-naphthyridine-3-carbonitrile | .0101 | .108 | >44 | 480.1 | B |
| 37 | N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methoxypicolinamide | .0129 | .0157 | >400 | 453.1 | F |
| 48 | N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide | .0418 | .0322 | >400 | 469.1 | C |
| 52 | N-(3-((4S,6S)-2-amino-4-methyl-6-(trifluoromethyl)-5,6-dihydro-4H-1,3-oxazin-4-yl)-4-fluorophenyl)-5-chloropicolinamide | .01 | .0176 | >400 | 492 | F |
| 66 | N-(5-((4S,6S)-2-amino-4-methyl-6-(trifluoromethyl)-5,6-dihydro-4H-1,3-oxazin-4-yl)-6-fluoropyridin-3-yl)-5-cyanopicolinamide | .0605 | .0351 | >400 | 456.8 | H |
| 78 | N-(3-((4S,6S)-2-amino-4-methyl-6-(trifluoromethyl)-5,6-dihydro-4H-1,3-oxazin-4-yl)-4-fluorophenyl)-5-cyanopicolinamide | .0613 | .0641 | >400 | 463.4 | I |
| 11 | N-(3-((4S,6S)-2-amino-4-(fluoromethyl)-6-(trifluoromethyl)-5,6-dihydro-4H-1,3-oxazin-4-yl)-4-fluorophenyl)-3-chloro-5-methoxypicolinamide | .0272 | .0635 | 54.4 | 472.1 | B |
| 23 | 8-((3-((4S,6S)-2-amino-4-(fluoromethyl)-6-(trifluoromethyl)-5,6-dihydro-4H-1,3-oxazin-4-yl)-4-fluorophenyl)amino)-5-fluoro-1,7-naphthyridine-3-carbonitrile | .0256 | .192 | >400 | 463.1 | C |
| 49 | N-(3-((4S,6S)-2-amino-4-(fluoromethyl)-6-(trifluoromethyl)-5,6-dihydro-4H-1,3-oxazin-4-yl)-4-fluorophenyl)-5-methoxypicolinamide | .029 | .0197 | >400 | 444.1 | F |
| 79 | N-(6-((4S,6S)-2-amino-4-methyl-6-(trifluoromethyl)-5,6-dihydro-4H-1,3-oxazin-4-yl)-5-fluoropyridin-2-yl)-5-cyanopicolinamide | .0304 | .0115 | >400 | 422 | K |
| 76 | (4S,6S)-4-(5-((3-chloro-1,7-naphthyridin-8-yl)amino)-2-fluoropyridin-3-yl)-4-methyl-6-(trifluoromethyl)-5,6-dihydro-4H-1,3-oxazin-2-amine | .0329 | .042 | >400 | 454.8 | I |
| 74 | (4S,6S)-4-(5-((7-chloropyrido[3,2-d]pyrimidin-4-yl)amino)-2-fluoropyridin-3-yl)-4-methyl-6-(trifluoromethyl)-5,6-dihydro-4H-1,3-oxazin-2-amine | .088 | .0376 | >400 | 455.8 | I |
| 67 | N-(5-((4S,6S)-2-amino-4-methyl-6-(trifluoromethyl)-5,6-dihydro-4H-1,3-oxazin-4-yl)-6-fluoropyridin-3-yl)-5-cyano-3-methylpicolinamide | .0348 | .023 | >400 | 436.4 | H |
| 69 | N-(5-((4S,6S)-2-amino-4-methyl-6-(trifluoromethyl)-5,6-dihydro-4H-1,3-oxazin-4-yl)-6-fluoropyridin-3-yl)-3-chloro-5-methoxypicolinamide | .0485 | .0253 | >400 | 461.8 | H |
| 77 | 8-((5-((4S,6S)-2-amino-4-methyl-6-(trifluoromethyl)-5,6-dihydro-4H-1,3-oxazin-4-yl)-6-fluoropyridin-3-yl)amino)-1,7-naphthyridine-3-carbonitrile | .0956 | .0248 | >400 | 445.4 | C |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 75 | 4-((5-((4S,6S)-2-amino-4-methyl-6-(trifluoromethyl)-5,6-dihydro-4H-1,3-oxazin-4-yl)-6-fluoropyridin-3-yl)amino)pyrido[3,2-d]pyrimidine-7-carbonitrile | .368 | .0912 | >400 | 446.4 | C |
| 68 | N-(5-((4S,6S)-2-amino-4-methyl-6-(trifluoromethyl)-5,6-dihydro-4H-1,3-oxazin-4-yl)-6-fluoropyridin-3-yl)-3,5-dichloropicolinamide | .0751 | .111 | >400 | 466.2 | H |
| 90 | N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methylpyridine-2-carbothioamide | 1.76 | .909 | >400 | 478 (M) | See eg 50 |
| 7 | N-(3-((4S,6S)-2-amino-4-(fluoromethyl)-6-(trifluoromethyl)-5,6-dihydro-4H-1,3-oxazin-4-yl)-4-fluorophenyl)-3-methylimidazo[1,2-a]pyridine-2-carboxamide | 1.52 | .888 | >400 | 467.4 | See eg 7 |
| 193 | N-(6-((4S,6S)-2-amino-4-methyl-6-(trifluoromethyl)-5,6-dihydro-4H-1,3-oxazin-4-yl)-5-fluoropyridin-2-yl)-3,5-dichloropicolinamide | .0461 | .0213 | >400 | 466.2 | K |
| 89 | 8-((6-((4S,6S)-2-amino-4-methyl-6-(trifluoromethyl)-5,6-dihydro-4H-1,3-oxazin-4-yl)-5-fluoropyridin-2-yl)amino)-5-fluoro-1,7-naphthyridine-3-carbonitrile | .188 | .383 | 229 | 463 | See eg 49 |
| 81 | N-(6-((4S,6S)-2-amino-4-methyl-6-(trifluoromethyl)-5,6-dihydro-4H-1,3-oxazin-4-yl)-5-fluoropyridin-2-yl)-3-chloro-5-(trifluoromethyl)picolinamide | .124 | .0186 | >400 | 499.8 | L |
| 82 | N-(6-((4S,6S)-2-amino-4-methyl-6-(trifluoromethyl)-5,6-dihydro-4H-1,3-oxazin-4-yl)-5-fluoropyridin-2-yl)-3-chloro-5-cyanopicolinamide | .0188 | .0045 | >400 | 457 | L |
| 57 | N-(3-((4S,6S)-2-amino-4-(fluoromethyl)-6-(trifluoromethyl)-5,6-dihydro-4H-1,3-oxazin-4-yl)-4-fluorophenyl)-5-fluoropicolinamide | .0725 | .106 | 4060 | 432 (M) | F |
| 58 | N-(3-((4S,6S)-2-amino-4-(fluoromethyl)-6-(trifluoromethyl)-5,6-dihydro-4H-1,3-oxazin-4-yl)-4-fluorophenyl)-3,5-dichloropicolinamide | .023 | .0652 | 2390 | 482 (M) | F |
| 83 | N-(6-((4S,6S)-2-amino-4-methyl-6-(trifluoromethyl)-5,6-dihydro-4H-1,3-oxazin-4-yl)-5-fluoropyridin-2-yl)-5-chloropicolinamide | .103 | .0389 | >400 | 431.8 | See eg 47 |
| 84 | N-(6-((4S,6S)-2-amino-4-methyl-6-(trifluoromethyl)-5,6-dihydro-4H-1,3-oxazin-4-yl)-5-fluoropyridin-2-yl)-5-cyano-3-methylpicolinamide | .0274 | .0048 | 900 | 436 | See eg 48 |
| 56 | N-(3-((4S,6S)-2-amino-4-(fluoromethyl)-6-(trifluoromethyl)-5,6-dihydro-4H-1,3-oxazin-4-yl)-4-fluorophenyl)-5-bromo-3-chloro-2-pyridinecarboxamide | .0278 | .0377 | >400 | 527.7 | F |
| 136 | N-(6-((4R,6S)-2-amino-4-(difluoromethyl)-6-(trifluoromethyl)-5,6-dihydro-4H-1,3-oxazin-4-yl)-5-fluoropyridin-2-yl)-5-chloropicolinamide | 32 | >15.6 | >400 | 467.9 | See eg 137 |
| 103 | 5-(3-((4S,6S)-2-amino-4-(fluoromethyl)-6-(trifluoromethyl)-5,6-dihydro-4H-1,3-oxazin-4-yl)-4-fluorophenyl)nicotinonitrile | 3.42 | 3.85 | 129 | 397 | See eg103 |
| 106 | methyl 2-(3-((4S,6S)-2-amino-4-(fluoromethyl)-6-(trifluoromethyl)-5,6-dihydro-4H-1,3-oxazin-4-yl)-4-fluorophenoxy)isonicotinate | 4.07 | 3.56 | 1170 | 446 | N |
| 92 | (4S,6S)-4-(2-fluoro-5-(pyrazin-2-yloxy)phenyl)-4-(fluoromethyl)-6- | 1.64 | 1.65 | >400 | 389 | M |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| | (trifluoromethyl)-5,6-dihydro-4H-1,3-oxazin-2-amine | | | | | |
| 93 | (4S,6S)-4-(5-((4-bromopyridin-2-yl)oxy)-2-fluorophenyl)-4-(fluoromethyl)-6-(trifluoromethyl)-5,6-dihydro-4H-1,3-oxazin-2-amine | .896 | 1.84 | 2140 | 466, 468 | M |
| 93 | ((4S,6S)-2-amino-4-(5-((4-bromopyridin-2-yl)oxy)-2-fluorophenyl)-6-(trifluoromethyl)-5,6-dihydro-4H-1,3-oxazin-4-yl)methanol | >40.0 | 4.85 | 557 | 464, 466 | M side prod |
| 94 | (4S,6S)-4-(2-fluoro-5-((3-fluoropyridin-2-yl)oxy)phenyl)-4-(fluoromethyl)-6-(trifluoromethyl)-5,6-dihydro-4H-1,3-oxazin-2-amine | .398 | .294 | 2220 | 406 | M |
| 106 | 2-(3-((4S,6S)-2-amino-4-(fluoromethyl)-6-(trifluoromethyl)-5,6-dihydro-4H-1,3-oxazin-4-yl)-4-fluorophenoxy)isonicotinonitrile | 1.36 | 2.14 | >400 | 413 | N |
| 95 | (4S,6S)-4-(5-((5-chloro-3-fluoropyridin-2-yl)oxy)-2-fluorophenyl)-4-(fluoromethyl)-6-(trifluoromethyl)-5,6-dihydro-4H-1,3-oxazin-2-amine | 2.89 | 2.59 | >400 | 440 | M |
| 107 | 2-(3-((4S,6S)-2-amino-4-(fluoromethyl)-6-(trifluoromethyl)-5,6-dihydro-4H-1,3-oxazin-4-yl)-4-fluorophenoxy)nicotinonitrile | 5.87 | 3.61 | 1400 | 413 | N |
| 108 | (4S,6S)-4-(2-fluoro-5-(pyrimidin-2-yloxy)phenyl)-4-(fluoromethyl)-6-(trifluoromethyl)-5,6-dihydro-4H-1,3-oxazin-2-amine | 9.97 | >15.6 | >400 | 389 | N |
| 96 | 2-(3-((4S,6S)-2-amino-4-(fluoromethyl)-6-(trifluoromethyl)-5,6-dihydro-4H-1,3-oxazin-4-yl)-4-fluorophenoxy)-N-methylisonicotinamide | 8.13 | 3.27 | >400 | 445 | M |
| 109 | (4S,6S)-4-(2-fluoro-5-((3-fluoro-4-(trifluoromethyl)pyridin-2-yl)oxy)phenyl)-4-(fluoromethyl)-6-(trifluoromethyl)-5,6-dihydro-4H-1,3-oxazin-2-amine | 9.52 | 8.18 | >400 | 474 | N |
| 97 | (4S,6S)-4-(5-((3-chloropyridin-2-yl)oxy)-2-fluorophenyl)-4-(fluoromethyl)-6-(trifluoromethyl)-5,6-dihydro-4H-1,3-oxazin-2-amine | .993 | 1.5 | 1010 | 422 | M |
| 110 | (4S,6S)-4-(2-fluoro-5-((6-(trifluoromethyl)pyridin-2-yl)oxy)phenyl)-4-(fluoromethyl)-6-(trifluoromethyl)-5,6-dihydro-4H-1,3-oxazin-2-amine | 3.41 | 4.56 | 1820 | 456 | N |
| 98 | (4S,6S)-4-(5-((4-bromo-6-chloropyridin-2-yl)oxy)-2-fluorophenyl)-4-(fluoromethyl)-6-(trifluoromethyl)-5,6-dihydro-4H-1,3-oxazin-2-amine | 1.95 | 2.9 | >400 | 500, 502 | M |
| 99 | (4S,6S)-4-(2-fluoro-5-((4-(trifluoromethyl)pyridin-2-yl)oxy)phenyl)-4-(fluoromethyl)-6-(trifluoromethyl)-5,6-dihydro-4H-1,3-oxazin-2-amine | 3.17 | 3.76 | >400 | 455.9 | M |
| 102 | (4S,6S)-4-(2-fluoro-5-((4-phenylpyridin-2-yl)oxy)phenyl)-4-(fluoromethyl)-6-(trifluoromethyl)-5,6-dihydro-4H-1,3-oxazin-2-amine | 0.83 | 2.82 | 114 | 464 | See eg 102 |
| 138 | (4S,6S)-4-(5-amino-2-fluoropyridin-3-yl)-4-(fluoromethyl)-6-(trifluoromethyl)-5,6-dihydro-4H-1,3-oxazin-2-amine | >40.0 | >15.6 | >400 | 311 | S |
| 139 | N-(5-((4S,6S)-2-amino-4-(fluoromethyl)-6-(trifluoromethyl)-5,6-dihydro-4H-1,3-oxazin-4-yl)-6-fluoropyridin-3-yl)-5-chloropicolinamide | .0965 | .418 | >400 | 450 | S |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 140 | N-(5-((4S,6S)-2-amino-4-(fluoromethyl)-6-(trifluoromethyl)-5,6-dihydro-4H-1,3-oxazin-4-yl)-6-fluoropyridin-3-yl)-5-cyano-3-methylpicolinamide | .113 | .338 | >400 | 455.1 | S |
| 141 | N-(5-((4S,6S)-2-amino-4-(fluoromethyl)-6-(trifluoromethyl)-5,6-dihydro-4H-1,3-oxazin-4-yl)-6-fluoropyridin-3-yl)-5-cyanopicolinamide | .171 | .639 | 1790 | 441 | S |
| 142 | N-(5-((4S,6S)-2-amino-4-(fluoromethyl)-6-(trifluoromethyl)-5,6-dihydro-4H-1,3-oxazin-4-yl)-6-fluoropyridin-3-yl)-5-methoxypicolinamide | .114 | .587 | 5520 | 446 | S |
| 143 | N-(3-((4S,6S)-2-amino-4-(fluoromethyl)-6-(trifluoromethyl)-5,6-dihydro-4H-1,3-oxazin-4-yl)phenyl)-5-chloropicolinamide | .117 | .154 | 2370 | 430.9 | T |
| 144 | N-(3-((4S,6S)-2-amino-4-(fluoromethyl)-6-(trifluoromethyl)-5,6-dihydro-4H-1,3-oxazin-4-yl)phenyl)-5-cyanopicolinamide | .0892 | .067 | 665 | 422 | T |
| 145 | N-(3-((4S,6S)-2-amino-4-(fluoromethyl)-6-(trifluoromethyl)-5,6-dihydro-4H-1,3-oxazin-4-yl)phenyl)-5-methoxypicolinamide | .334 | 0.055 | 3520 | 427 | T |
| 146 | (4S,6S)-4-(3-((3-chloro-1,7-naphthyridin-8-yl)amino)phenyl)-4-(fluoromethyl)-6-(trifluoromethyl)-5,6-dihydro-4H-1,3-oxazin-2-amine | .067 | .119 | 733 | 454.1 | B |
| 147 | N-(5-((4S,6S)-2-amino-4-(fluoromethyl)-6-(trifluoromethyl)-5,6-dihydro-4H-1,3-oxazin-4-yl)-6-methoxypyridin-3-yl)-5-chloropicolinamide | .249 | .119 | 1420 | 443.9 | U |
| 149 | N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-cyanopicolinamide | .239 | .021 | >400 | 434.9 | V |
| 148 | N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-chloropicolinamide | .366 | .0127 | >400 | 444 | V |
| 150 | N-(5-((4S,6S)-2-amino-4-methyl-6-(trifluoromethyl)-5,6-dihydro-4H-1,3-oxazin-4-yl)-1-methyl-6-oxo-1,6-dihydropyridin-3-yl)-5-cyano-3-methylpicolinamide | .121 | .0101 | >400 | 449 | V |
| 12 | (4S,6S)-4-(5-amino-2-fluorophenyl)-4-(fluoromethyl)-6-(trifluoromethyl)-5,6-dihydro-4H-1,3-oxazin-2-amine | 0.375 | 0.163 | >400 | 468 | B |
| 13 | (4S,6S)-4-(5-amino-2-fluorophenyl)-4-(fluoromethyl)-6-(trifluoromethyl)-5,6-dihydro-4H-1,3-oxazin-2-amine | .0722 | .0959 | >400 | 469.1 | B |
| 85 | N-(6-((4S,6S)-2-amino-4-methyl-6-(trifluoromethyl)-5,6-dihydro-4H-1,3-oxazin-4-yl)-5-fluoropyridin-2-yl)-5-(difluoromethoxy)-3-methylpicolinamide | .103 | .0295 | 492 | 478 | See eg 84 |
| 86 | N-(6-((4S,6S)-2-amino-4-methyl-6-(trifluoromethyl)-5,6-dihydro-4H-1,3-oxazin-4-yl)-5-fluoropyridin-2-yl)-5-bromo-3-chloropicolinamide | .0336 | .0219 | 636 | 510, 512 | See eg 84 |
| 87 | N-(6-((4S,6S)-2-amino-4-methyl-6-(trifluoromethyl)-5,6-dihydro-4H-1,3-oxazin-4-yl)-5-fluoropyridin-2-yl)-5-(prop-2-yn-1-yloxy)pyrazine-2-carboxamide | .0254 | .0084 | 609 | 453 | See eg 84 |
| 28 | N-(3-((4S,6S)-2-amino-4-methyl-6-(trifluoromethyl)-5,6-dihydro-4H-1,3- | .0176 | .0093 | 666 | 451 | See eg |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| | oxazin-4-yl)-4-fluorophenyl)-5-(prop-2-yn-1-yloxy)picolinamide | | | | | 27 |
| 105 | (4S,6S)-4-(5-(6-chlorobenzo[d]oxazol-2-yl)-2-fluorophenyl)-4-(fluoromethyl)-6-(trifluoromethyl)-5,6-dihydro-4H-1,3-oxazin-2-amine | .542 | 2.81 | >44.4 | 446 | See eg 105 |
| 104 | (4S,6S)-4-(2-fluoro-5-(5-(prop-1-yn-1-yl)pyridin-3-yl)phenyl)-4-(fluoromethyl)-6-(trifluoromethyl)-5,6-dihydro-4H-1,3-oxazin-2-amine | .318 | 1.25 | 220 | 410 | See eg 104 |
| 111 | (4S,6S)-4-(2-fluoro-5-(6-((trimethylsilyl)ethynyl)pyridin-3-yl)phenyl)-4-(fluoromethyl)-6-(trifluoromethyl)-5,6-dihydro-4H-1,3-oxazin-2-amine | 37.2 | >15.6 | >400 | 468 | O |
| 112 | (4S,6S)-4-(5-(6-ethynylpyridin-3-yl)-2-fluorophenyl)-4-(fluoromethyl)-6-(trifluoromethyl)-5,6-dihydro-4H-1,3-oxazin-2-amine | >40.0 | >15.6 | >400 | 396 | See eg 112 |
| 113 | (4S,6S)-4-(2-fluoro-5-(6-(prop-1-yn-1-yl)pyridin-3-yl)phenyl)-4-(fluoromethyl)-6-(trifluoromethyl)-5,6-dihydro-4H-1,3-oxazin-2-amine | 27.4 | >15.6 | 170 | 410 | O |
| 114 | (4S,6S)-4-(2-fluoro-5-(6-fluoroquinazolin-2-yl)phenyl)-4-(fluoromethyl)-6-(trifluoromethyl)-5,6-dihydro-4H-1,3-oxazin-2-amine | >40.0 | >15.6 | 758 | 441 | O |
| 116 | (4S,6S)-4-(2-fluoro-5-(6-fluoroquinolin-2-yl)phenyl)-4-(fluoromethyl)-6-(trifluoromethyl)-5,6-dihydro-4H-1,3-oxazin-2-amine | >40.0 | >15.6 | >133 | 440 | O |
| 117 | (4S,6S)-4-(2-fluoro-5-(7-fluoroquinolin-2-yl)phenyl)-4-(fluoromethyl)-6-(trifluoromethyl)-5,6-dihydro-4H-1,3-oxazin-2-amine | >40.0 | >15.6 | >133 | 440 | O |
| 29 | N-(3-((4S,6S)-2-amino-4-methyl-6-(trifluoromethyl)-5,6-dihydro-4H-1,3-oxazin-4-yl)-4-fluorophenyl)-6-chlorobenzo[d]oxazol-2-amine | >40.0 | 3.01 | 210 | 443 | See eg 29 |
| 118 | (4S,6S)-4-(5-(5-(1,3,4-oxadiazol-2-yl)pyridin-3-yl)-2-fluorophenyl)-4-(fluoromethyl)-6-(trifluoromethyl)-5,6-dihydro-4H-1,3-oxazin-2-amine | 8.36 | >15.6 | 454 | 440 | O |
| 30 | N-(3-((4S,6S)-2-amino-4-methyl-6-(trifluoromethyl)-5,6-dihydro-4H-1,3-oxazin-4-yl)-4-fluorophenyl)-5-chlorobenzo[d]oxazol-2-amine | 26.8 | 2.88 | 162 | 443 | See eg 29 |
| 14 | (4S,6S)-4-(2-fluoro-5-((3-fluoropyridin-2-yl)amino)phenyl)-4-(fluoromethyl)-6-(trifluoromethyl)-5,6-dihydro-4H-1,3-oxazin-2-amine | 0.574 | 0.758 | 879 | 405 | B |
| 15 | (4S,6S)-4-(2-fluoro-5-((3-methoxypyridin-2-yl)amino)phenyl)-4-(fluoromethyl)-6-(trifluoromethyl)-5,6-dihydro-4H-1,3-oxazin-2-amine | 0.165 | 0.122 | 1080 | 417 | B |
| 16 | (4S,6S)-4-(5-((4-chloropyridin-2-yl)amino)-2-fluorophenyl)-4-(fluoromethyl)-6-(trifluoromethyl)-5,6-dihydro-4H-1,3-oxazin-2-amine | 23.7 | 5.82 | 1630 | 421 | B |
| 17 | (4S,6S)-4-(5-((2-bromopyridin-4-yl)amino)-2-fluorophenyl)-4-(fluoromethyl)-6-(trifluoromethyl)-5,6-dihydro-4H-1,3-oxazin-2-amine | 6.49 | 4.34 | 469 | 465, 467 | B |
| 115 | (4S,6S)-4-(2-fluoro-5-((4-phenylpyridin-2-yl)amino)phenyl)-4-(fluoromethyl)-6-(trifluoromethyl)-5,6-dihydro-4H-1,3-oxazin-2-amine | 7.88 | 3.16 | 316 | 463 | O |
| 100 | (4S,6S)-4-(5-((6-chloropyridin-2-yl)oxy)-2-fluorophenyl)-4-(fluoromethyl)-6-(trifluoromethyl)-5,6-dihydro-4H-1,3-oxazin-2-amine | 1.57 | 3.26 | 1930 | 422 | M |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 101 | (4S,6S)-4-(2-fluoro-5-(pyridin-2-yloxy)phenyl)-4-(fluoromethyl)-6-(trifluoromethyl)-5,6-dihydro-4H-1,3-oxazin-2-amine | 0.56 | 2.11 | >400 | 388 | M |
| 24 | 4-((3-((4S,6S)-2-amino-4-(fluoromethyl)-6-(trifluoromethyl)-5,6-dihydro-4H-1,3-oxazin-4-yl)-4-fluorophenyl)amino)picolinonitrile | 19 | 7 | 1760 | 412 | C |
| 88 | N-(6-((4S,6S)-2-amino-4-methyl-6-(trifluoromethyl)-5,6-dihydro-4H-1,3-oxazin-4-yl)-5-fluoropyridin-2-yl)-4-chloro-1-(difluoromethyl)-1H-pyrazole-3-carboxamide | .032 | .010 | 712 | 471 | See eg 84 |
| 34 | N-(3-((4S,6S)-2-amino-4-(fluoromethyl)-6-(trifluoromethyl)-5,6-dihydro-4H-1,3-oxazin-4-yl)-4-fluorophenyl)-5-chloro-3-fluoropicolinamide | .051 | .042 | >400 | 466.8 | F |
| 35 | N-(3-((4S,6S)-2-amino-4-(fluoromethyl)-6-(trifluoromethyl)-5,6-dihydro-4H-1,3-oxazin-4-yl)-4-fluorophenyl)-5-(prop-2-yn-1-yloxy)pyrazine-2-carboxamide | .0023 | .0051 | >400 | 469.9 | F |
| 36 | N-(3-((4S,6S)-2-amino-4-(fluoromethyl)-6-(trifluoromethyl)-5,6-dihydro-4H-1,3-oxazin-4-yl)-4 fluorophenyl)-4-chloro-1-(difluoromethyl)-1H-pyrazole-3-carboxamide | 0.020 | 0.024 | 2380 | 487.8 | F |
| 53 | N-(3-((4S,6S)-2-amino-4-(fluoromethyl)-6-(trifluoromethyl)-5,6-dihydro-4H-1,3-oxazin-4-yl)-4-fluorophenyl)-5-(cyclopropylethynyl)picolinamide | 0.023 | 0.196 | 2990 | 479 | See eg 53 |
| 37 | N-(3-((4S,6S)-2-amino-4-(fluoromethyl)-6-(trifluoromethyl)-5,6-dihydro-4H-1,3-oxazin-4-yl)-4-fluorophenyl)-5-(cyclopropylmethoxy)-3-methylpicolinamide | 0.12 | 0.487 | >400 | 498.9 | F |
| 38 | N-(3-((4S,6S)-2-amino-4-(fluoromethyl)-6-(trifluoromethyl)-5,6-dihydro-4H-1,3-oxazin-4-yl)-4-fluorophenyl)-3-methyl-5-(2,2,2-trifluoroethoxy)pyrazine-2-carboxamide | 0.049 | 0.325 | >400 | 527.8 | F |
| 39 | N-(3-((4S,6S)-2-amino-4-(fluoromethyl)-6-(trifluoromethyl)-5,6-dihydro-4H-1,3-oxazin-4-yl)-4-fluorophenyl)-5-(but-2-yn-1-yloxy)pyrazine-2-carboxamide | .0007 | .0032 | >400 | 483.9 | F |
| 40 | N-(3-((4S,6S)-2-amino-4-(fluoromethyl)-6-(trifluoromethyl)-5,6-dihydro-4H-1,3-oxazin-4-yl)-4-fluorophenyl)-3-chloro-5-(difluoromethyl)picolinamide | 0.13 | 0.105 | >400 | 498.8 | F |
| 41 | N-(3-((4S,6S)-2-amino-4-(fluoromethyl)-6-(trifluoromethyl)-5,6-dihydro-4H-1,3-oxazin-4-yl)-4-fluorophenyl)-5-(difluoromethyl)picolinamide | .072 | .088 | >400 | 464.9 | F |
| 42 | N-(3-((4S,6S)-2-amino-4-(fluoromethyl)-6-(trifluoromethyl)-5,6-dihydro-4H-1,3-oxazin-4-yl)-4-fluorophenyl)-5-(difluoromethoxy)-3-methylpicolinamide | .026 | .051 | >400 | 494.9 | F |
| 44 | N-(3-((4S,6S)-2-amino-4-(fluoromethyl)-6-(trifluoromethyl)-5,6-dihydro-4H-1,3-oxazin-4-yl)-4-fluorophenyl)-3-chloro-5-(trifluoromethyl)picolinamide | .074 | .088 | >400 | 516.8 | F |
| 18 | (4S,6S)-4-(2-fluoro-5-((2-(trifluoromethyl)pyrido[3,4-b]pyrazin-5-yl)amino)phenyl)-4-(fluoromethyl)- | .118 | .336 | >14.8 | 506.9 | B |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| | 6-(trifluoromethyl)-5,6-dihydro-4H-1,3-oxazin-2-amine | | | | | |
| 19 | (4S,6S)-4-(5-((3-chloro-5-fluoro-1,7-naphthyridin-8-yl)amino)-2-fluorophenyl)-4-(fluoromethyl)-6-(trifluoromethyl)-5,6-dihydro-4H-1,3-oxazin-2-amine | .029 | .552 | >133 | 489.8 | B |
| 54 | (4S,6S)-4-(5-((3-(cyclopropylethynyl)-5-fluoro-1,7-naphthyridin-8-yl)amino)-2-fluorophenyl)-4-(fluoromethyl)-6-(trifluoromethyl)-5,6-dihydro-4H-1,3-oxazin-2-amine | 0.033 | 2.33 | >133 | 519.9 | See eg 53 |
| 55 | (4S,6S)-4-(5-((3-(cyclopropylethynyl)-1,7-naphthyridin-8-yl)amino)-2-fluorophenyl)-4-(fluoromethyl)-6-(trifluoromethyl)-5,6-dihydro-4H-1,3-oxazin-2-amine | 0.098 | 1.02 | >400 | 501.9 | See eg 53 |
| 20 | (4S,6S)-4-(5-((2-(difluoromethyl)-2H-pyrazolo[3,4-c]pyridin-7-yl)amino)-2-fluorophenyl)-4-(fluoromethyl)-6-(trifluoromethyl)-5,6-dihydro-4H-1,3-oxazin-2-amine 2,2,2-trifluoroacetate | 33 | 10.6 | >400 | 476.9 | B |
| 46 | N-(3-((4S,6S)-2-amino-4-(fluoromethyl)-6-(trifluoromethyl)-5,6-dihydro-4H-1,3-oxazin-4-yl)-4-fluorophenyl)-5-(oxazol-2-ylmethoxy)pyrazine-2-carboxamide | 0.011 | 0.019 | >400 | 512.9 | F |
| 190 | 3-((4S,6S)-2-amino-4-(fluoromethyl)-6-(trifluoromethyl)-5,6-dihydro-4H-1,3-oxazin-4-yl)-4-fluoro-N-((S)-1-methoxypropan-2-yl)benzamide | >40 | >15.6 | >400 | 410.0 | W |
| 182 | 3-((4S,6S)-2-amino-4-(fluoromethyl)-6-(trifluoromethyl)-5,6-dihydro-4H-1,3-oxazin-4-yl)-N-cyclopropyl-4-fluorobenzamide | 11.4 | >15.6 | 3490 | 377.9 | W |
| 21 | (4S,6S)-4-(5-((2-(difluoromethyl)thiazolo[5,4-d]pyrimidin-7-yl)amino)-2-fluorophenyl)-4-(fluoromethyl)-6-(trifluoromethyl)-5,6-dihydro-4H-1,3-oxazin-2-amine | 0.269 | 0.506 | >400 | 494.9 | B |
| 119 | N-(3-((4S,6S)-2-amino-4-methyl-6-(trifluoromethyl)-5,6-dihydro-4H-1,3-oxazin-4-yl)-4-fluorophenyl)-4-methoxypiperidine-1-carboxamide | 55.8 | 2.08 | >400 | 433 | P |
| 120 | N-(3-((4S,6S)-2-amino-4-methyl-6-(trifluoromethyl)-5,6-dihydro-4H-1,3-oxazin-4-yl)-4-fluorophenyl)-4-(prop-2-yn-1-yloxy)piperidine-1-carboxamide | 13.7 | 1.14 | >400 | 457 | P |
| 121 | N-(3-((4S,6S)-2-amino-4-methyl-6-(trifluoromethyl)-5,6-dihydro-4H-1,3-oxazin-4-yl)-4-fluorophenyl)-3,4-dihydroisoquinoline-2(1H)-carboxamide | 7.53 | 0.687 | 3610 | 451 | P |
| 122 | N-(3-((4S,6S)-2-amino-4-methyl-6-(trifluoromethyl)-5,6-dihydro-4H-1,3-oxazin-4-yl)-4-fluorophenyl)-4-(difluoromethyl)piperidine-1-carboxamide | 2.45 | 0.826 | >14.8 | 453 | P |
| 123 | N-(3-((4S,6S)-2-amino-4-methyl-6-(trifluoromethyl)-5,6-dihydro-4H-1,3-oxazin-4-yl)-4-fluorophenyl)-5,6-dihydropyridine-1(2H)-carboxamide | 11.5 | 0.908 | >400 | 401 | P |
| 124 | N-(3-((4S,6S)-2-amino-4-methyl-6-(trifluoromethyl)-5,6-dihydro-4H-1,3-oxazin-4-yl)-4-fluorophenyl)-4-(cyclopropylethynyl)-5,6-dihydropyridine-1(2H)-carboxamide | 1.68 | 0.525 | 810 | 465 | See eg 124 |
| 80 | N-(6-((4S,6S)-2-amino-4-methyl-6-(trifluoromethyl)-5,6-dihydro-4H-1,3-oxazin-4-yl)-5-fluoropyridin-2-yl)-3-chloro-5-methoxypicolinamide | 0.254 | 0.051 | 658 | 461.9 | K |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 134 | N-(6-((4S,6S)-2-amino-4-(fluoromethyl)-6-(trifluoromethyl)-5,6-dihydro-4H-1,3-oxazin-4-yl)-5-fluoropyridin-2-yl)-5-cyanopicolinamide | 0.079 | 0.055 | >400 | 440.9 | R |
| 135 | N-(6-((4S,6S)-2-amino-4-(fluoromethyl)-6-(trifluoromethyl)-5,6-dihydro-4H-1,3-oxazin-4-yl)-5 fluoropyridin-2-yl)-4-chloro-1-(difluoromethyl)-1H-pyrazole-3-carboxamide | 0.052 | 0.031 | 1170 | 488.9 | R |
| 136 | N-(6-((4S,6S)-2-amino-4-(fluoromethyl)-6-(trifluoromethyl)-5,6-dihydro-4H-1,3-oxazin-4-yl)-5-fluoropyridin-2-yl)-5-chloropicolinamide | 0.169 | 0.132 | 717 | 449.9 | R |
| 70 | N-(5-((4S,6S)-2-amino-4-methyl-6-(trifluoromethyl)-5,6-dihydro-4H-1,3-oxazin-4-yl)-6-fluoropyridin-3-yl)-5-methoxypyrazine-2-carboxamide | 0.102 | 0.031 | 397 | 429 | H |
| 63 | N-(5-((4S,6S)-2-amino-4-methyl-6-(trifluoromethyl)-5,6-dihydro-4H-1,3-oxazin-4-yl)-6-fluoropyridin-3-yl)-5-methoxypicolinamide | 0.119 | 0.024 | >400 | 428.1 | G |
| 64 | N-(5-((4S,6S)-2-amino-4-methyl-6-(trifluoromethyl)-5,6-dihydro-4H-1,3-oxazin-4-yl)-6-fluoropyridin-3-yl)-5-fluoropicolinamide | 0.206 | 0.038 | >400 | 416.1 | G |
| 65 | N-(5-((4S,6S)-2-amino-4-methyl-6-(trifluoromethyl)-5,6-dihydro-4H-1,3-oxazin-4-yl)-6-fluoropyridin-3-yl)-5-(2,2,2-trifluoroethoxy)picolinamide | 0.079 | 0.124 | 150 | 496.1 | G |
| 192 | N-(5-((4S,6S)-2-amino-4-methyl-6 (trifluoromethyl)-5,6-dihydro-4H-1,3-oxazin-4-yl)-6-fluoropyridin-3-yl)-5-bromopicolinamide | 0.060 | 0.075 | 1330 | 476/478 | H |
| 71 | N-(5-((4S,6S)-2-amino-4-methyl-6-(trifluoromethyl)-5,6-dihydro-4H-1,3-oxazin-4-yl)-6-fluoropyridin-3-yl)-4-chloro-1-isopropyl-1H-pyrazole-3-carboxamide | 38.9 | 5.14 | >400 | 463.1 | H |
| 72 | N-(5-((4S,6S)-2-amino-4-methyl-6-(trifluoromethyl)-5,6-dihydro-4H-1,3-oxazin-4-yl)-6-fluoropyridin-3-yl)-4-chloro-1-(difluoromethyl)-1H-pyrazole-3-carboxamide | 0.024 | 0.031 | 844 | 471 | H |
| 151 | N-(3-((4S,6S)-2-amino-4-(fluoromethyl)-6-(trifluoromethyl)-5,6-dihydro-4H-1,3-oxazin-4-yl)-4,5-difluorophenyl)-5-cyanopicolinamide | 0.033 | 0.078 | 2200 | 458.1 | X |
| 152 | N-(3-((4S,6S)-2-amino-4-(fluoromethyl)-6-(trifluoromethyl)-5,6-dihydro-4H-1,3-oxazin-4-yl)-4,5-difluorophenyl)-5-chloropicolinamide | .026 | .087 | 2750 | 467 | X |
| 153 | N-(3-((4S,6S)-2-amino-4-(fluoromethyl)-6-(trifluoromethyl)-5,6-dihydro-4H-1,3-oxazin-4-yl)-4,5-difluorophenyl)-5-methoxypyrazine-2-carboxamide | 0.050 | 0.126 | 3360 | 464.1 | X |
| 151 | (4S,6S)-4-(5-amino-2,3-difluorophenyl)-4-(fluoromethyl)-6-(trifluoromethyl)-5,6-dihydro-4H-1,3-oxazin-2-amine | >40 | >15.6 | 3120 | 328.1 | X, 16i |
| 154 | N-(3-((4S,6S)-2-amino-4-(fluoromethyl)-6-(trifluoromethyl)-5,6-dihydro-4H-1,3-oxazin-4-yl)-4,5-difluorophenyl)-5-(prop-2-yn-1-yloxy)pyrazine-2-carboxamide | .0014 | .0096 | >400 | 488.1 | X |
| 155 | N-(3-((4S,6S)-2-amino-4-(fluoromethyl)-6-(trifluoromethyl)-5,6-dihydro-4H-1,3-oxazin-4-yl)-4,5-difluorophenyl)-5-(but-2-yn-1-yloxy)pyrazine-2-carboxamide | 0.00087 | 0.00367 | >400 | 502.1 | X |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 156 | N-(3-((4S,6S)-2-amino-4-(fluoromethyl)-6-(trifluoromethyl)-5,6-dihydro-4H-1,3-oxazin-4-yl)-4,5-difluorophenyl)-5-methoxypicolinamide | 0.062 | 0.123 | >400 | 463 | X |
| 157 | N-(3-((4S,6S)-2-amino-4-(fluoromethyl)-6-(trifluoromethyl)-5,6-dihydro-4H-1,3-oxazin-4-yl)-4,5-difluorophenyl)-5-bromopicolinamide | 0.019 | 0.081 | >400 | 510.8/ 512.8 | X |
| 159 | N-(3-((4S,6S)-2-amino-4-(fluoromethyl)-6-(trifluoromethyl)-5,6-dihydro-4H-1,3-oxazin-4-yl)-4,5-difluorophenyl)-5-(prop-2-yn-1-yloxy)picolinamide | 0.013 | 0.093 | >400 | 487.1 | X |
| 160 | N-(3-((4S,6S)-2-amino-4-(fluoromethyl)-6-(trifluoromethyl)-5,6-dihydro-4H-1,3-oxazin-4-yl)-4,5-difluorophenyl)-5-(but-2-yn-1-yloxy)picolinamide | .0035 | 0.021 | >400 | 501.1 | X |
| 161 | (4S,6S)-4-(5-((3-chloro-1,7-naphthyridin-8-yl)amino)-2,3-difluorophenyl)-4-(fluoromethyl)-6-(trifluoromethyl)-5,6-dihydro-4H-1,3-oxazin-2-amine | 0.023 | 0.535 | >400 | 490.1 | B |
| 162 | 8-((3-((4S,6S)-2-amino-4-(fluoromethyl)-6-(trifluoromethyl)-5,6-dihydro-4H-1,3-oxazin-4-yl)-4,5-difluorophenyl)amino)-1,7-naphthyridine-3-carbonitrile | 0.037 | 0.271 | >400 | 481.1 | C |
| 158 | N-(3-((4S,6S)-2-amino-4-(fluoromethyl)-6-(trifluoromethyl)-5,6-dihydro-4H-1,3-oxazin-4-yl)-4,5-difluorophenyl)-5-(cyclopropylethynyl)picolinamide | 0.021 | 0.379 | >400 | 497.1 | See eg 158 |
| 163 | N-(3-((4S,6S)-2-amino-4-methyl-6-(trifluoromethyl)-5,6-dihydro-4H-1,3-oxazin-4-yl)-4,5-difluorophenyl)-5-cyanopicolinamide | .020 | .0028 | 901 | 440.1 | Y |
| 164 | N-(3-((4S,6S)-2-amino-4-methyl-6-(trifluoromethyl)-5,6-dihydro-4H-1,3-oxazin-4-yl)-4,5-difluorophenyl)-5-chloropicolinamide | .024 | .0052 | 1350 | 449 | Y |
| 165 | N-(3-((4S,6S)-2-amino-4-methyl-6-(trifluoromethyl)-5,6-dihydro-4H-1,3-oxazin-4-yl)-4,5-difluorophenyl)-5-methoxypyrazine-2-carboxamide | .078 | .0098 | 5350 | 446.1 | Y |
| 166 | N-(3-((4S,6S)-2-amino-4-methyl-6-(trifluoromethyl)-5,6-dihydro-4H-1,3-oxazin-4-yl)-4,5-difluorophenyl)-5-cyano-3-methylpicolinamide | .014 | .0068 | 1070 | 454.1 | Y |
| 167 | N-(3-((4S,6S)-2-amino-4-methyl-6-(trifluoromethyl)-5,6-dihydro-4H-1,3-oxazin-4-yl)-4,5-difluorophenyl)-3-chloro-5-cyanopicolinamide | .030 | .0057 | 113 | 473.9 | Y |
| 168 | N-(3-((4S,6S)-2-amino-4-methyl-6-(trifluoromethyl)-5,6-dihydro-4H-1,3-oxazin-4-yl)-4,5-difluorophenyl)-5-cyano-3-methoxypicolinamide | .051 | .0061 | >400 | 470 | Y |
| 169 | N-(3-((4S,6S)-2-amino-4-methyl-6-(trifluoromethyl)-5,6-dihydro-4H-1,3-oxazin-4-yl)-4,5-difluorophenyl)-3-chloro-5-methoxypicolinamide | .037 | .0089 | >400 | 478.9 | Y |
| 170 | N-(3-((4S,6S)-2-amino-4-methyl-6-(trifluoromethyl)-5,6-dihydro-4H-1,3-oxazin-4-yl)-4,5-difluorophenyl)-5-chloro-3-methylpicolinamide | .0095 | .014 | 733 | 463 | Y |
| 171 | N-(3-((4S,6S)-2-amino-4-methyl-6-(trifluoromethyl)-5,6-dihydro-4H-1,3-oxazin-4-yl)-4,5-difluorophenyl)-5-(difluoromethyl)-3-methylpicolinamide | 0.043 | 0.017 | 2060 | 479 | Y |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 172 | N-(3-((4S,6S)-2-amino-4-methyl-6-(trifluoromethyl)-5,6-dihydro-4H-1,3-oxazin-4-yl)-4,5-difluorophenyl)-3,5-dichloropicolinamide | 0.019 | 0.019 | 394 | 482.9 | Y |
| 163 | (4S,6S)-4-(5-amino-2,3-difluorophenyl)-4-methyl-6-(trifluoromethyl)-5,6-dihydro-4H-1,3-oxazin-2-amine | 49.7 | 2.86 | 1790 | 310.1 | Y, 17i |
| 176 | (4S,6S)-4-(5-((3-chloro-1,7-naphthyridin-8-yl)amino)-2,3-difluorophenyl)-4-methyl-6-(trifluoromethyl)-5,6-dihydro-4H-1,3-oxazin-2-amine | 0.021 | 0.102 | 104 | 472.1 | B step 2 |
| 180 | 8-((3-((4S,6S)-2-amino-4-methyl-6-(trifluoromethyl)-5,6-dihydro-4H-1,3-oxazin-4-yl)-4,5-difluorophenyl)amino)-1,7-naphthyridine-3-carbonitrile | 0.014 | 0.036 | >400 | 463.1 | C |
| 177 | 8-((3-((4S,6S)-2-amino-4-methyl-6-(trifluoromethyl)-5,6-dihydro-4H-1,3-oxazin-4-yl)-4,5-difluorophenyl)amino)-5-fluoro-1,7-naphthyridine-3-carbonitrile | 0.030 | 0.275 | >4.94 | 481.1 | B step 2 |
| 178 | (4S,6S)-4-(2,3-difluoro-5-((2-methoxypyrido[3,4-b]pyrazin-5-yl)amino)phenyl)-4-methyl-6-(trifluoromethyl)-5,6-dihydro-4H-1,3-oxazin-2-amine | 0.062 | 0.24 | 519 | 469.1 | B step 2 |
| 179 | (4S,6S)-4-(2,3-difluoro-5-((3-methoxy-1,7-naphthyridin-8-yl)amino)phenyl)-4-methyl-6-(trifluoromethyl)-5,6-dihydro-4H-1,3-oxazin-2-amine | 0.178 | 0.224 | >400 | 468.2 | B step 2 |
| 173 | N-(3-((4S,6S)-2-amino-4-methyl-6-(trifluoromethyl)-5,6-dihydro-4H-1,3-oxazin-4-yl)-4,5-difluorophenyl)-5-methoxy-3-methylpyrazine-2-carboxamide | 0.118 | 0.085 | >400 | 460.1 | Y |
| 174 | N-(3-((4S,6S)-2-amino-4-methyl-6-(trifluoromethyl)-5,6-dihydro-4H-1,3-oxazin-4-yl)-4,5-difluorophenyl)-5-(difluoromethoxy)-3-methylpicolinamide | 0.029 | 0.026 | >400 | 495 | Y |
| 175 | N-(3-((4S,6S)-2-amino-4-methyl-6-(trifluoromethyl)-5,6-dihydro-4H-1,3-oxazin-4-yl)-4,5-difluorophenyl)-5-bromopicolinamide | .022 | .0066 | 424 | 492.9/ 494.9 | Y |
| 91 | N-(3-((4S,6S)-2-amino-4-(fluoromethyl)-6-(trifluoromethyl)-5,6-dihydro-4H-1,3-oxazin-4-yl)-4-fluorophenyl)-5-chloropyridine-2-carbothioamide | 0.086 | 0.548 | 805 | 465 | See eg 90 |
| 73 | N-(5-((4S,6S)-2-amino-4-methyl-6-(trifluoromethyl)-5,6-dihydro-4H-1,3-oxazin-4-yl)-6-fluoropyridin-3-yl)-5-(prop-2-yn-1-yloxy)pyrazine-2-carboxamide | .0047 | .0025 | 1690 | 453 | H |
| 45 | N-(3-((4S,6S)-2-amino-4-methyl-6-(trifluoromethyl)-5,6-dihydro-4H-1,3-oxazin-4-yl)-4-fluorophenyl)-5-(prop-2-yn-1-yloxy)pyrazine-2-carboxamide | .0023 | .0005 | 2570 | 452.1 | F |
| 125 | 6-((3-((4S,6S)-2-amino-4-(fluoromethyl)-6-(trifluoromethyl)-5,6-dihydro-4H-1,3-oxazin-4-yl)-4-fluorophenyl)ethynyl)nicotinonitrile | 0.509 | 0.509 | >400 | 421 | Q |
| 126 | 6-((3-((4S,6S)-2-amino-4-(fluoromethyl)-6-(trifluoromethyl)-5,6-dihydro-4H-1,3-oxazin-4-yl)-4-fluorophenyl)ethynyl)-N-methylnicotinamide | 26.6 | 7.46 | >400 | 452.9 | Q |
| 127 | (4S,6S)-4-(5-((5-(difluoromethoxy)pyridin-2-yl)ethynyl)-2-fluorophenyl)-4- | 2.96 | 2.46 | 605 | 461.9 | Q |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 128 | (4S,6S)-4-(5-((5-cyclobutoxypyridin-2-yl)ethynyl)-2-fluorophenyl)-4-(fluoromethyl)-6-(trifluoromethyl)-5,6-dihydro-4H-1,3-oxazin-2-amine | 20.5 | 5.98 | 1060 | 466 | Q |
| 129 | 2-((3-((4S,6S)-2-amino-4-(fluoromethyl)-6-(trifluoromethyl)-5,6-dihydro-4H-1,3-oxazin-4-yl)-4-fluorophenyl)ethynyl)-N-methylisonicotinamide | >40.0 | >15.6 | >400 | 452.9 | Q |
| 130 | (4S,6S)-4-(5-((1H-indol-4-yl)ethynyl)-2-fluorophenyl)-4-(fluoromethyl)-6-(trifluoromethyl)-5,6-dihydro-4H-1,3-oxazin-2-amine | 5.62 | 2.08 | 578 | 434 | Q |
| 131 | (4S,6S)-4-(5-((1H-indol-5-yl)ethynyl)-2-fluorophenyl)-4-(fluoromethyl)-6-(trifluoromethyl)-5,6-dihydro-4H-1,3-oxazin-2-amine | 0.577 | 1.81 | 381 | 434 | Q |
| 132 | (4S,6S)-4-(5-((1H-indol-6-yl)ethynyl)-2-fluorophenyl)-4-(fluoromethyl)-6-(trifluoromethyl)-5,6-dihydro-4H-1,3-oxazin-2-amine | 2.2 | 3.1 | 721 | 434 | Q |
| 133 | (4S,6S)-4-(5-((1H-indol-7-yl)ethynyl)-2-fluorophenyl)-4-(fluoromethyl)-6-(trifluoromethyl)-5,6-dihydro-4H-1,3-oxazin-2-amine | 5.6 | 4.6 | 1130 | 434 | Q |
| 235 | (4S,6S)-4-(5-((6-chloro-4-phenylpyridin-2-yl)oxy)-2-fluorophenyl)-4-(fluoromethyl)-6-(trifluoromethyl)-5,6-dihydro-4H-1,3-oxazin-2-amine | >40.0 | 8.17 | >133 | 499 | A5 |
| 234 | N-(3-((4S,6S)-2-amino-4-(fluoromethyl)-6-(trifluoromethyl)-5,6-dihydro-4H-1,3-oxazin-4-yl)-4,5-difluorophenyl)-5-cyano-3-fluoropicolinamide | 0.038 | 0.057 | >400 | 475.9 | A1 |
| 233 | N-(3-((4S,6S)-2-amino-4-(fluoromethyl)-6-(trifluoromethyl)-5,6-dihydro-4H-1,3-oxazin-4-yl)-4,5-difluorophenyl)-5-chloro-3-fluoropicolinamide | 0.029 | 0.078 | >400 | 484.9 | X |
| 232 | N-(3-((4S,6S)-2-amino-4-(fluoromethyl)-6-(trifluoromethyl)-5,6-dihydro-4H-1,3-oxazin-4-yl)-4,5-difluorophenyl)-5-cyano-3-methylpicolinamide | 0.016 | 0.055 | 568.1 | 472 | X |
| 231 | (4S,6S)-4-(2,3-difluoro-5-((3-methoxypyridin-2-yl)amino)phenyl)-4-methyl-6-(trifluoromethyl)-5,6-dihydro-4H-1,3-oxazin-2-amine | 0.177 | 0.162 | 282.0 | 417 | B |
| 216 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethyl)-3-methylpicolinamide | 0.094 | 0.035 | >400 | 492.9 | A3 |
| 217 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxy-3-methylpyrazine-2-carboxamide | 0.081 | 0.038 | 634 | 473.9 | A3 |
| 218 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(prop-2-yn-1-yloxy)pyrazine-2-carboxamide | 0.001 | 0.002 | 188.5 | 483.9 | A3 |
| 219 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-cyano-3-methylpicolinamide | 0.020 | 0.011 | >400 | 467.9 | A3 |
| 220 | N-(3-((4S,6S)-2-amino-4-(fluoromethyl)-6-(trifluoromethyl)-5,6-dihydro-4H-1,3-oxazin-4-yl)-4-fluoro-5- | 0.066 | 0.429 | 263 | 540.9 | A3 |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| | methylphenyl)-3-methyl-5-(2,2,2-trifluoroethoxy)picolinamide | | | | | |
| 221 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethyl)picolinamide | 0.073 | 0.033 | 991.7 | 478.9 | A3 |
| 222 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-chloro-3-methoxypicolinamide | 0.091 | 0.029 | >400 | 492.9 | A3 |
| 223 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-fluoropicolinamide | 0.057 | 0.029 | 832.9 | 446.9 | A3 |
| 201 | N-(3-((4S,6S)-2-amino-4-methyl-6-(trifluoromethyl)-5,6-dihydro-4H-1,3-oxazin-4-yl)-4,5-difluorophenyl)-5-methoxypicolinamide | 0.045 | 0.015 | 761.6 | 444.9 | Z |
| 224 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-chloropicolinamide | 0.013 | 0.007 | 515.2 | 462.9 | A3 |
| 225 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-cyanopicolinamide | 0.057 | 0.024 | >400 | 453.9 | A3 |
| 226 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxy-3-methylpicolinamide | 0.048 | 0.049 | 780.5 | 472.9 | A3 |
| 202 | N-(3-((4S,6S)-2-amino-4-methyl-6-(trifluoromethyl)-5,6-dihydro-4H-1,3-oxazin-4-yl)-4,5-difluorophenyl)-5-methoxy-3-methylpicolinamide | 0.061 | 0.035 | 1138 | 458.9 | Z |
| 227 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxypyrazine-2-carboxamide | 0.03 | 0.023 | >400 | 459.9 | A3 |
| 228 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-(difluoromethoxy)-3-methylpicolinamide | 0.032 | 0.028 | 775 | 508.9 | A3 |
| 229 | N-(3-((4S,6S)-2-amino-4-(fluoromethyl)-6-(trifluoromethyl)-5,6-dihydro-4H-1,3-oxazin-4-yl)-4-fluoro-5-methylphenyl)-5-methoxypicolinamide | 0.044 | 0.034 | 1119 | 458.9 | A3 |
| 230 | (4S,6S)-4-(5-((7-chloropyrido[3,2-d]pyrimidin-4-yl)amino)-2-fluoro-3-methylphenyl)-4-(fluoromethyl)-6-(trifluoromethyl)-5,6-dihydro-4H-1,3-oxazin-2-amine | 0.049 | 0.057 | >400 | 486.9 | A4 |
| 205 | N-(3-((4S,6S)-2-amino-4-methyl-6-(trifluoromethyl)-5,6-dihydro-4H-1,3-oxazin-4-yl)-4,5-difluorophenyl)-5-cyano-3-fluoropicolinamide | 0.039 | 0.01 | >400 | 458 | A1 |
| 204 | N-(3-((4S,6S)-2-amino-4-methyl-6-(trifluoromethyl)-5,6-dihydro-4H-1,3-oxazin-4-yl)-4,5-difluorophenyl)-5-(oxazol-2-ylmethoxy)pyrazine-2-carboxamide 2,2,2-trifluoroacetate | 0.006 | 0.003 | 1045 | 512.9 | Y |
| 206 | N-(3-((4S,6S)-2-amino-4-methyl-6-(trifluoromethyl)-5,6-dihydro-4H-1,3-oxazin-4-yl)-5-chloro-4-fluorophenyl)-5-cyanopicolinamide | 0.023 | 0.012 | 487.9 | 456 | A2 |
| 187 | N-(3-((4S,6S)-2-amino-4-methyl-6-(trifluoromethyl)-5,6-dihydro-4H-1,3-oxazin-4-yl)-4,5-difluorophenyl)-3-chloro-5-(trifluoromethyl)picolinamide | 0.075 | 0.015 | >400 | 517.1 | Z |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 188 | N-(3-((4S,6S)-2-amino-4-methyl-6-(trifluoromethyl)-5,6-dihydro-4H-1,3-oxazin-4-yl)-4,5-difluorophenyl)-5-(but-2-yn-1-yloxy)-3-methylpicolinamide | 0.006 | 0.012 | 286 | 497.1 | Z |
| 189 | N-(3-((4S,6S)-2-amino-4-methyl-6-(trifluoromethyl)-5,6-dihydro-4H-1,3-oxazin-4-yl)-4,5-difluorophenyl)-5-(but-2-yn-1-yloxy)picolinamide | 0.003 | 0.003 | 783.8 | 483.1 | Z |
| 190 | N-(3-((4S,6S)-2-amino-4-methyl-6-(trifluoromethyl)-5,6-dihydro-4H-1,3-oxazin-4-yl)-4,5-difluorophenyl)-5-(prop-2-yn-1-yloxy)pyrazine-2-carboxamide | 0.002 | 0.002 | 504.9 | 470.1 | Z |
| 191 | N-(3-((4S,6S)-2-amino-4-methyl-6-(trifluoromethyl)-5,6-dihydro-4H-1,3-oxazin-4-yl)-4,5-difluorophenyl)-5-(cyclopropylmethoxy)-3-methylpicolinamide | 0.097 | 0.549 | 510.8 | 499.1 | Z |
| 192 | N-(3-((4S,6S)-2-amino-4-methyl-6-(trifluoromethyl)-5,6-dihydro-4H-1,3-oxazin-4-yl)-4,5-difluorophenyl)-5-(prop-2-yn-1-yloxy)picolinamide | 0.010 | 0.012 | 1189 | 469.1 | Z |
| 193 | N-(3-((4S,6S)-2-amino-4-methyl-6-(trifluoromethyl)-5,6-dihydro-4H-1,3-oxazin-4-yl)-4,5-difluorophenyl)-5-(difluoromethyl)pyrazine-2-carboxamide | 0.075 | 0.018 | 1271 | 466.1 | Z |
| 194 | N-(3-((4S,6S)-2-amino-4-methyl-6-(trifluoromethyl)-5,6-dihydro-4H-1,3-oxazin-4-yl)-4,5-difluorophenyl)-3-methyl-5-(2,2,2-trifluoroethoxy)picolinamide | 0.156 | 0.213 | >400 | 527.2 | V |
| 195 | N-(3-((4S,6S)-2-amino-4-methyl-6-(trifluoromethyl)-5,6-dihydro-4H-1,3-oxazin-4-yl)-4,5-difluorophenyl)-5-chloro-3-methoxypicolinamide | 0.071 | 0.011 | >400 | 479.1 | Z |
| 186 | N-(3-((4S,6S)-2-amino-4-methyl-6-(trifluoromethyl)-5,6-dihydro-4H-1,3-oxazin-4-yl)-4,5-difluorophenyl)-5-(2,2,2-trifluoroethoxy)pyrazine-2-carboxamide | 0.021 | 0.015 | >400 | 514.2 | Z |
| 196 | N-(3-((4S,6S)-2-amino-4-methyl-6-(trifluoromethyl)-5,6-dihydro-4H-1,3-oxazin-4-yl)-4,5-difluorophenyl)-4-chloro-1-(difluoromethyl)-1H-pyrazole-3-carboxamide | 0.011 | 0.007 | 627.6 | 488.1 | Z |
| 197 | N-(3-((4S,6S)-2-amino-4-methyl-6-(trifluoromethyl)-5,6-dihydro-4H-1,3-oxazin-4-yl)-4,5-difluorophenyl)-3-methyl-5-(2,2,2-trifluoroethoxy)pyrazine-2-carboxamide | 0.027 | 0.049 | >400 | 528 | Z |
| 198 | N-(3-((4S,6S)-2-amino-4-methyl-6-(trifluoromethyl)-5,6-dihydro-4H-1,3-oxazin-4-yl)-4,5-difluorophenyl)-3-chloro-5-(difluoromethyl)picolinamide | 0.058 | 0.015 | >400 | 499.1 | Z |
| 199 | N-(3-((4S,6S)-2-amino-4-methyl-6-(trifluoromethyl)-5,6-dihydro-4H-1,3-oxazin-4-yl)-4,5-difluorophenyl)-5-chloro-3-(methoxymethyl)picolinamide | 0.016 | 0.013 | 1712 | 493.1 | Z |
| 200 | N-(3-((4S,6S)-2-amino-4-methyl-6-(trifluoromethyl)-5,6-dihydro-4H-1,3-oxazin-4-yl)-4,5-difluorophenyl)-5-(difluoromethyl)picolinamide | 0.04 | 0.014 | 997.3 | 465 | Z |
| 207 | N-(3-((4S,6S)-2-amino-4-methyl-6-(trifluoromethyl)-5,6-dihydro-4H-1,3-oxazin-4-yl)-5-chloro-4-fluorophenyl)-5-chloropicolinamide | 0.011 | 0.02 | 385.6 | 465 | A2 |
| 208 | N-(3-((4S,6S)-2-amino-4-methyl-6-(trifluoromethyl)-5,6-dihydro-4H-1,3-oxazin-4-yl)-5-chloro-4-fluorophenyl)-5-methoxypyrazine-2-carboxamide | 0.012 | 0.003 | 393.6 | 462 | A2 |

TABLE 1-continued

| Example No | Compound Name | BACE 1 FRET assay IC$_{50}$ (uM) | HEK cell assay IC$_{50}$ (uM) | CatD IC50 (μM) | MS m/z [M + H]+ | Method used to make example |
|---|---|---|---|---|---|---|
| 209 | N-(3-((4S,6S)-2-amino-4-methyl-6-(trifluoromethyl)-5,6-dihydro-4H-1,3-oxazin-4-yl)-5-chloro-4-fluorophenyl)-5-methoxypicolinamide | 0.015 | 0.035 | 622 | 461.1 | A2 |
| 210 | N-(3-((4S,6S)-2-amino-4-methyl-6-(trifluoromethyl)-5,6-dihydro-4H-1,3-oxazin-4-yl)-5-chloro-4-fluorophenyl)-5-cyano-3-methylpicolinamide | 0.011 | 0.034 | 416 | 470.1 | A2 |
| 211 | N-(3-((4S,6S)-2-amino-4-methyl-6-(trifluoromethyl)-5,6-dihydro-4H-1,3-oxazin-4-yl)-5-chloro-4-fluorophenyl)-5-(difluoromethyl)pyrazine-2-carboxamide | 0.062 | 0.047 | 604 | 482.1 | A2 |
| 212 | N-(3-((4S,6S)-2-amino-4-methyl-6-(trifluoromethyl)-5,6-dihydro-4H-1,3-oxazin-4-yl)-5-chloro-4-fluorophenyl)-5-(prop-2-yn-1-yloxy)pyrazine-2-carboxamide | <0.002 | 0.001 | 554 | 486.1 | A2 |
| 213 | N-(3-((4S,6S)-2-amino-4-methyl-6-(trifluoromethyl)-5,6-dihydro-4H-1,3-oxazin-4-yl)-5-chloro-4-fluorophenyl)-5-bromopicolinamide | 0.010 | 0.0319 | 739 | 509/511 | A2 |
| 215 | N-(3-((4S,6S)-2-amino-4-methyl-6-(trifluoromethyl)-5,6-dihydro-4H-1,3-oxazin-4-yl)-5-chloro-4-fluorophenyl)-5-methoxy-3-methylpyrazine-2-carboxamide | 0.048 | 0.063 | >400 | 476.1 | A2 |
| 214 | N-(3-((4S,6S)-2-amino-4-methyl-6-(trifluoromethyl)-5,6-dihydro-4H-1,3-oxazin-4-yl)-5-chloro-4-fluorophenyl)-5-(2,2,2-trifluoroethoxy)pyrazine-2-carboxamide | 0.008 | 0.029 | >400 | 530.1 | A2 |
| 236 | N-(3-((4S,6S)-2-amino-4-methyl-6-(trifluoromethyl)-5,6-dihydro-4H-1,3-oxazin-4-yl)-4-chloro-5-fluorophenyl)-5-chloropicolinamide | 0.011 | 0.039 | 407.9 | 465 | A6 |
| 237 | N-(3-((4S,6S)-2-amino-4-methyl-6-(trifluoromethyl)-5,6-dihydro-4H-1,3-oxazin-4-yl)-4-chloro-5-fluorophenyl)-5-methoxypyrazine-2-carboxamide | 0.029 | 0.013 | 194 | 462 | A6 |
| 238 | N-(3-((4S,6S)-2-amino-4-methyl-6-(trifluoromethyl)-5,6-dihydro-4H-1,3-oxazin-4-yl)-4-chloro-5-fluorophenyl)-5-cyanopicolinamide | 0.008 | 0.006 | 131 | 456 | A6 |
| 239 | N-(3-((4S,6S)-2-amino-4-methyl-6-(trifluoromethyl)-5,6-dihydro-4H-1,3-oxazin-4-yl)-4,5-difluorophenyl)-3-fluoro-5-methoxypicolinamide | 0.033 | 0.012 | 1185 | 463.1 | Z |
| 240 | N-(3-((4S,6S)-2-amino-4-methyl-6-(trifluoromethyl)-5,6-dihydro-4H-1,3-oxazin-4-yl)-4,5-difluorophenyl)-5-bromo-3-chloropicolinamide | 0.02 | 0.022 | 928 | 527/529 | Z |

The present invention also provides methods for making compounds of Formulas I-III, and sub-formulas therein. For example, the compounds of the present invention and additional examples may be made by the following methods, as similarly described in the literature references mentioned below.

In one embodiment of the invention, there is provided a method of making a compound of Formula I-A having a general structure of

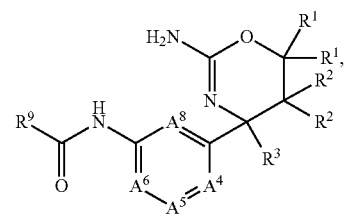

the method comprising the step of reacting a compound 20

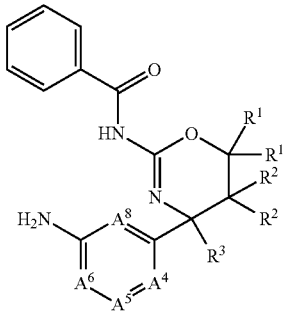

wherein $A^4, A^5, A^6, A^8$, each $R^1$, each $R^2$ and $R^3$ of Formula I-A are as defined herein, with a compound having the structure $R^9$—COOH, wherein $R^9$ is as defined herein, to make a compound of Formula I-A.

In another embodiment of the invention, there is provided a method of making a compound of Formula I-A-1 having a general structure of

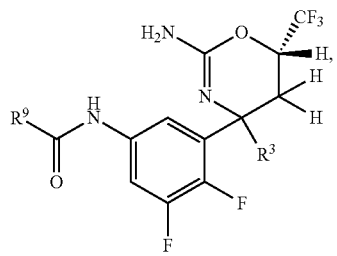

the method comprising the step of reacting a compound 20

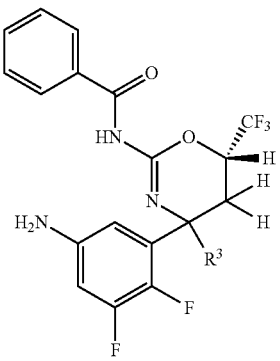

wherein $R^3$ of Formula I-A are as defined herein, with a compound having the structure $R^9$—COOH, wherein $R^9$ is as defined herein, to make a compound of Formula I-A.

In one embodiment of the invention, there is provided a method of making a compound of Formula I-B having a general structure of

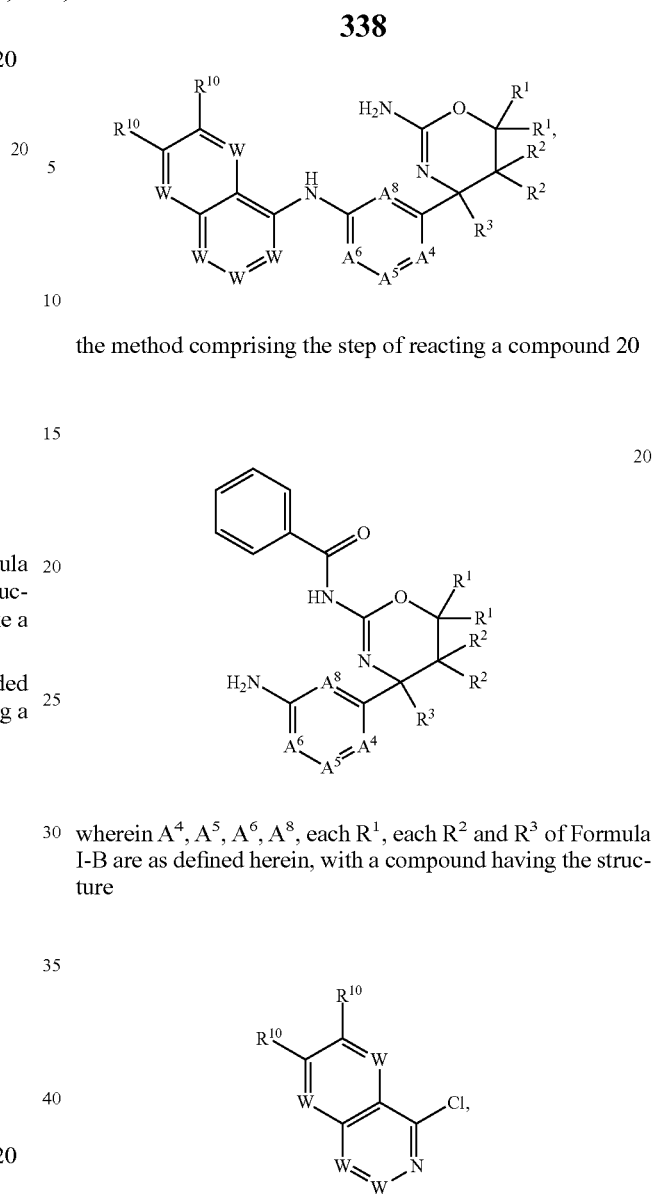

the method comprising the step of reacting a compound 20 wherein $A^4, A^5, A^6, A^8$, each $R^1$, each $R^2$ and $R^3$ of Formula I-B are as defined herein, with a compound having the structure wherein each W and each $R^{10}$ are, independently, as defined herein, in the presence of acid to make a compound of Formula I-B.

In one embodiment of the invention, there is provided a method of making a compound of Formula I-C

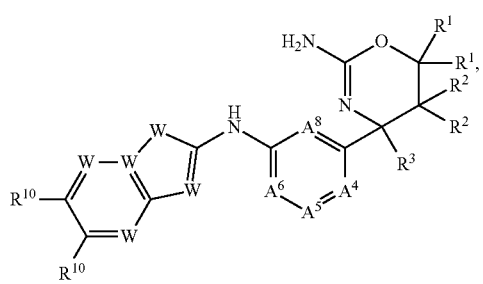

the method comprising the step of reacting a compound 20

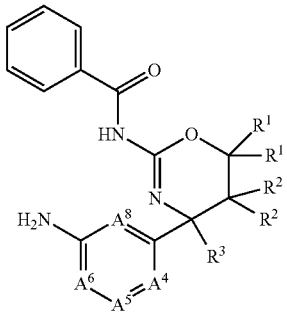

wherein $A^4$, $A^5$, $A^6$, $A^8$, each $R^1$, each $R^2$ and $R^3$ of Formula I-C are as defined herein, with a compound having the structure

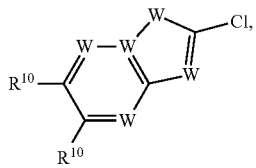

wherein each W and each $R^{10}$ are, independently, as defined herein, to make a compound of Formula I-C.

In another embodiment of the invention, there is provided a method of making a compound of Formula III having a general formula of

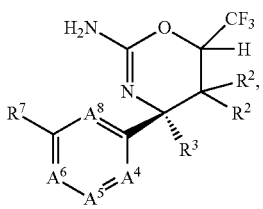

the method comprising the step of reacting a compound 30

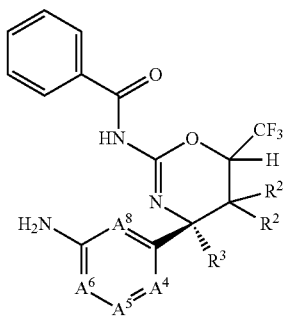

wherein $A^4$, $A^5$, $A^6$, $A^8$, each $R^2$, $R^3$ and $R^7$ of Formula III are as defined herein, with a compound having either structure of $R^9$—COOH in the presence of a base or $R^9$ in the presence of an acid, wherein $R^9$ is as defined herein, to make a compound of Formula III.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H (deuterium), $^3$H (tritium), $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Deuterated ($^2$H), Tritiated ($^3$H) and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Table I)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table 1.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table 1.

In Vitro Enzymatic Cathepsin D (Cat D) FRET (Fluorescence Resonance Energy Transfer) Assay Recombinant Cat D was expressed in CHO cells. The assay buffer for CathepsinD is 0.05 M citrate pH 3.5, 10% DMSO final, 5 mM CHAPS. The Cat D enzyme (9 nM) is pre-incubated for one hour with inhibitors, typically in about 1 uL of DMSO according to a serial dilution, is added thereto. The assays are effectively started by the addition of different FRET substrates (20 nM for Cat D) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The Cat D substrate peptide sequence is based on sequence #1 of Table 1 from Gulnik et al. FEBS Letters v413 p 379-384 1997. Proteolytic cleavage of the FRET substrate releases quenching of fluorescence (Cat D excitation 500 nm and emission 580 nm).

Alternatively, a Cat D assay may also be run according to the procedure described in the article, Characterization of new fluorgenic substrates for the rapid and sensitive assay of cathepsin E and cathepsin D, *J. Biochem.*, 125:1137, 1999. In addition, the cathepsin D and cathepsin E assays are described in PCT publication WO2011069934. This WIPO publication describes BACE inhibitor compounds having an amide linker connecting two aromatic groups with extremely poor cathepsin D and/or cathepsin E inhibitory activity (see Table 1).

Where available, the in-vitro Cat D FRET assay data for each of the Examples, conducted by the first procedure, is provided. For example, the compound of example 43 has a Cat D $IC_{50}$ value of >400 uM. As shown by the high micromolar Cat D data (very poorly active or inactive against cat D), the compounds of the present invention possess the unexpected property of little to no ability to inhibit the activity of Cat D. It was surprisingly found that incorporation of an amino- or amido-linker between the core of the compounds and the $R^7$ and $R^9$ groups, respectively, has conferred a significantly reduced, poor or no potency on the protein Cat D. Thus, with this surprising selectivity profile, the compounds of the present invention are believed to minimize, reduce or completely eliminate any risk of retinal atrophy and abnormal development of the eye and of the retinal pigmented epithelium as it relates to the normal function and activity of Cat D.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, Science 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, Journal of Neurochemistry, 76,173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, Journal of Pharmacology and Experimental Therapeutics, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
IV: 5% EtOH, 45% Propylene glycol in 5% Dextrose The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
|---|---|---|
| 2 | 70 | 61 |
| 3 | 72 | 58 |
| 59 | 78 | 81 |
| 32 | 21 | -3 |
| 60 | 79 | 72 |
| 16 | 83 | 87 |
| 50 | 50 | 22 |
| 51 | 68 | 59 |

-continued

| Ex. No. | % reduction of rat CSF levels at 10 pmk | % reduction of rat brain levels at 10 mpk |
|---|---|---|
| 52 | 61 | 54 |
| 79 | 83 | 79 |
| 135 | 64 | 55 |
| 154 | 67 | 71 |
| 155 | 26 | 11 |
| 163 | 81 | 86 |
| 164 | 77 | 75 |
| 165 | 75 | 76 |
| 166 | 77 | 75 |
| 167 | 42 | 15 |
| 169 | 48 | 46 |
| 171 | 25 | 10 |
| 201 | 75 | 76 |
| 224 | 62 | 51 |
| 227 | 69 | 65 |

Indications

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. Arch Neurol. 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, Cell, (120): 545-555, 2005; Walsh and Selkoe, Neuron, (44): 181-193, 2004). Although the precise mechanisms of Ab toxicity are unclear, oligomeric forms of Ab may contribute to cognitive decline by altering synaptic structure and function (Palop and Mucke, Nat. Neuroscience, (13): 812-818, 2010; Selkoe, Behavioral Brain Res., (192): 106-113, 2008; Shankar et al., Nat. Medicine (14): 837-842, 2008). Transgenic mouse models that overexpress mutant APP and produce high levels of Ab show amyloid plaque deposition, synaptic deficits, learning and memory impairments, and other behavioral abnormalities (Games et al., Nature, (373): 523-527, 1995; Götz et al., Molecular Psychiatry (9): 664-683, 2004; Hsia et al., Proc. Natl. Academy of Science USA (96): 3228-3233, 1999; Hsiao et al., Science (274): 99-102, 1996, citing Harris et al, Neuron (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

MK-8931, a small molecule inhibitor of BACE (structure unknown) was tested in a two-part randomised, double-blind, placebo-controlled phase 1 clinical trial in 88 healthy individuals (18-45 years old). MK-8931 seemed to be generally well tolerated (66 patients), and no serious adverse events were reported. A major goal of the trial was to determine whether MK-8931 was able to enter the brain and block β secretase. To monitor this, biomarkers of BACE1 activity in the CSF were measured, including Aβ40 and Aβ42, as was soluble peptide APP (sAPPβ), a direct product of BACE1 cleavage of APP. MK-8931 significantly reduced CSF Aβ concentrations in a sustained and dose-dependent manner. At 36 h post-dose, a single dose of 100 mg reduced CSF Aβ40 concentrations by 75% and a single dose of 550 mg by 92%. Similar reductions of CSF concentrations of Aβ42 and sAPPβ, the BACE1-cleaved ectodomain of APP, were also observed. Vassar & Yan, *Lancet Neurology,* 13:319-329 (2014). Currently, MK-8931 is enrolling mild-to-moderate Alzheimer's Disease patients in a Ph 2/3 trial; and enrolling participants with prodomal Alzheimer's disease in a Ph III safety and efficacy trial. (US clinical trials; Merck Newsroom, 2014).

Bapineuzamab, a monoclonal amino-terminus specific anti-amyloid antibody is presently in Phase III clinical trials for the treatment of AD. *Alzheimer's Research & Therapy,* 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier and more common. It is firmly believed that by reducing the formation of A-beta, one can begin to pre-treat AD. Vassar et al, *Journal of Neuroscience,* 29 (41):12787-12794, 2009. One published pathway for treatment of AD is inhibition of beta-secretase. Tirrell, *Bloomberg News, The Boston Globe,* Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [(S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from preclinical animal models to man. Because of toxicology findings identified in longer-term preclinical studies, this compound is no longer progressing in clinical development. However, BACE1 remains a viable target because the adverse effects reported here were recapitulated in LY2811376-treated BACE1 KO mice and thus are unrelated to BACE 1 inhibition. The magnitude and duration of central Aβ reduction obtainable with BACE1 inhibition positions this protease as a tractable small-molecule target through which to test the amyloid hypothesis in man. *Neuroscience,* 31(46):16507-16515, 2011

The compounds of the invention have been shown to modulate, and specifically inhibit the activity of the beta-secretase enzyme, thereby reducing the A-beta peptide fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I

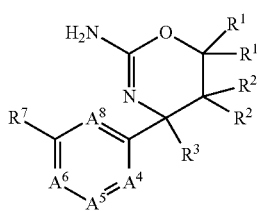

I or a stereoisomer, tautomer, hydrate, solvate or pharmaceutically acceptable salt thereof, wherein
  $A^4$ is $CR^4$ or N;
  $A^5$ is $CR^5$ or N;
  $A^6$ is $CR^6$ or N;
  $A^8$ is $CR^8$ or N, provided that no more than two of $A^4$, $A^5$, $A^6$ and $A^8$ is N;
  one $R^1$ is $C_{1-3}$haloalkyl and the other $R^1$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

each of $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, —$S(O)C_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —NH—C(=S)—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

2. The compound according to claim 1, or a stereoisomer or pharmaceutically acceptable salt thereof, wherein one $R^1$ is H and the other $R^1$ is $CF_3$.

3. The compound according to claim 1, or a stereoisomer or pharmaceutically acceptable salt thereof, wherein each $R^2$, independently, is H.

4. The compound according to claim 1, or a stereoisomer or pharmaceutically acceptable salt thereof, wherein $R^3$ is $CH_3$, $CF_3$, $CH_2F$ or $CHF_2$.

5. The compound according to claim 1, or a stereoisomer or pharmaceutically acceptable salt thereof, wherein $R^7$ is —NH—$R^9$, —NH—C(=O)—$R^9$, —NH—C(=S)—$R^9$, —O—$R^9$ or —S—$R^9$;
or $R^7$ is

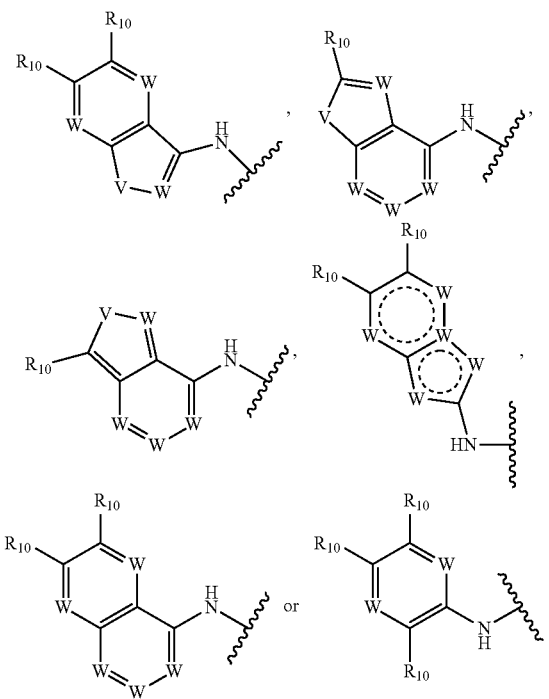

wherein V is $NR^{10}$, O or S; and
each W, independently, is CH, CF, CCl or N.

6. The compound according to claim 1, or a stereoisomer or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
one $R^1$ is $CF_3$ and the other $R^1$ is H, F, Cl, $CF_3$, $OCF_3$, methyl, ethyl, CN, $OCH_3$, $SCH_3$, $NHCH_3$, $C(O)CH_3$ or $CH_2OCHF_2$;
each $R^2$, independently, is H, Cl, $CF_3$, $OCF_3$, methyl, ethyl, CN, $OCH_3$, $NHCH_3$, $C(O)CH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_3$, $OCF_3$, methyl, ethyl, CN, OH, $OCH_3$, $NHCH_3$ or $C(O)CH_3$.

7. The compound according to claim 1, or a stereoisomer or pharmaceutically acceptable salt thereof, wherein
one $R^1$ is H and the other $R^1$ is $CF_3$;
$R^3$ is $CH_3$, $CF_3$, $CH_2F$ or $CHF_2$; and
$R^7$ is —NH—$R^9$, —NH—C(=O)-$R^9$, —NH—C(=S)—$R^9$ or

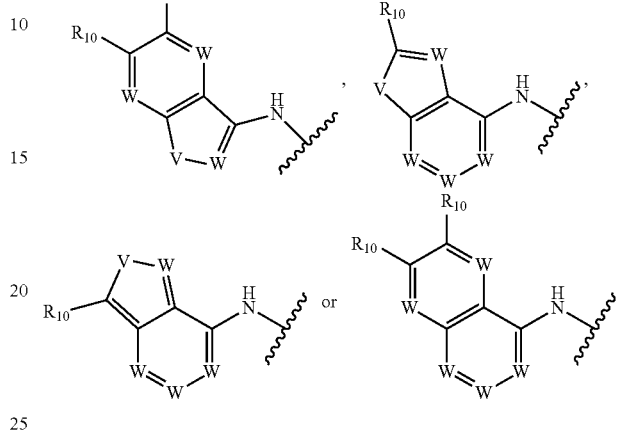

wherein V is $NR^{10}$, O or S; and
each W, independently, is CH, CF, CCl or N.

8. The compound according to claim 7, or a stereoisomer or pharmaceutically acceptable salt thereof, wherein $R^7$ is —NH—C(=O)—$R^9$.

9. The compound according to claim 1, or a stereoisomer or pharmaceutically acceptable salt thereof, wherein $R^7$ is —NH—$R^9$, —O—$R^9$ or —S—$R^9$.

10. The compound according to claim 8, or a stereoisomer or pharmaceutically acceptable salt thereof, wherein
$A^4$ is $CR^4$;
$A^5$ is $CR^5$ or N;
$A^6$ is $CR^6$; and
$A^8$ is $CR^8$ or N; wherein each of $R^4$, $R^5$, $R^6$ and $R^8$, independently, is H, F, $CF_3$, $CF_2H$, $CH_2F$ or $CH_3$;
provided that (1) no more than one of $A^5$ and $A^8$ is N; and (2) when $A^4$ is $CR^4$, $A^5$ is $CR^5$, $A^6$ is $CR^6$ and $A^8$ is $CR^8$, and each of $R^6$ and $R^8$, independently, is H, then $R^5$ is F, $CF_3$, $CF_2H$, $CH_2F$ or $CH_3$.

11. A compound according to claim 1, or a stereoisomer, tautomer, hydrate, solvate or pharmaceutically acceptable salt thereof, having a Formula II:

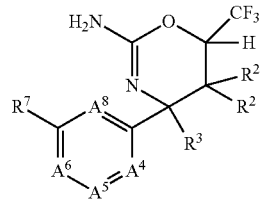

wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
each $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —S(O)C$_{1-6}$-alkyl, —NHC$_{1-6}$-alkyl or —C(O)C$_{1-6}$-alkyl, wherein each of the C$_{1-6}$-alkyl, C$_{2-4}$alkenyl, C$_{2-4}$alkynyl, and C$_{1-6}$-alkyl portion of —CH$_2$OC$_{1-6}$-alkyl, —OC$_{1-6}$-alkyl, —S(O)C$_{1-6}$-alkyl, —NHC$_{1-6}$-alkyl and —C(O)C$_{1-6}$-alkyl are optionally substituted with 1-4 substituents of F, oxo or OH;

alternatively, each R$^2$ taken together with the carbon atom to which they are attached form a C$_{3-6}$ spirocarbocyclic ring optionally including one heteroatom selected from O and N and optionally substituted with 1-4 F atoms on the carbon atoms and optionally substituted with a substituent of C$_{1-3}$alkyl, CH$_2$OC$_{1-2}$alkyl or C$_{1-3}$haloalkyl on the nitrogen atom;

R$^3$ is C$_{1-4}$alkyl, CH$_2$OH, CH$_2$OC$_{1-4}$alkyl, C$_{1-4}$haloalkyl or cyclopropyl, wherein each of the C$_{1-4}$alkyl, CH$_2$OC$_{1-4}$alkyl, C$_{1-4}$haloalkyl and cyclopropyl is optionally substituted with 1-4 F atoms;

each of R$^4$, R$^5$, R$^6$ and R$^8$, independently, is H, halo, haloalkyl, haloalkoxyl, C$_{1-4}$-alkyl, CN, OH, OC$_{1-4}$-alkyl, S(O)C$_{1-4}$-alkyl, NHC$_{1-4}$-alkyl or C(O)C$_{1-4}$-alkyl;

R$^7$ is —NH—R$^9$, —NH—C(=O)—R$^9$, —C(=O)NH—R$^9$, —O—R$^9$, —S—R$^9$;

or R$^7$ is

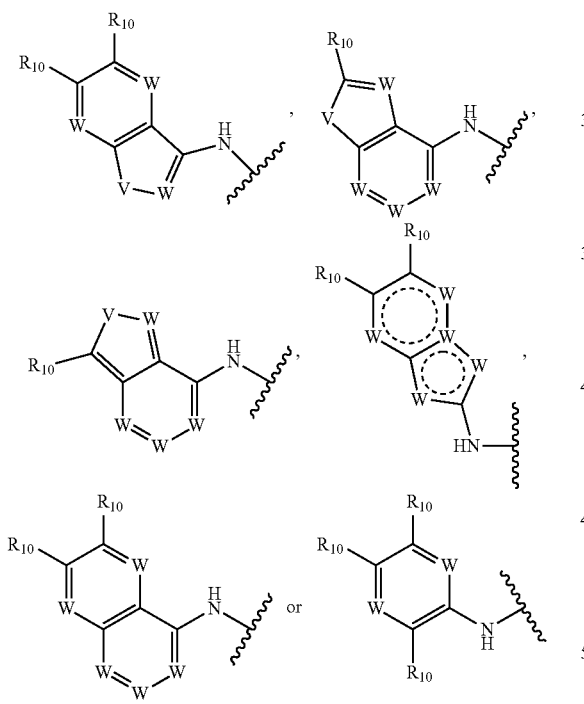

wherein V is NR$^{10}$, O or S; and
each W, independently, is CH, CF, CCl or N;

R$^9$ is acetyl, C$_{1-6}$-alkyl, C$_{2-4}$alkenyl, C$_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, C$_{1-3}$alkylamino-, C$_{1-3}$dialkylamino, C$_{1-3}$thioalkoxyl oxazolyl, or oxetan-3yl, provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is not H.

12. The compound according to claim 11, or a stereoisomer, tautomer or pharmaceutically acceptable salt thereof, wherein A$^4$ is CR$^4$ or N;

A$^5$ is CR$^5$ or N;

A$^6$ is CR$^6$ or N;

A$^8$ is CR$^8$ or N, provided no more than one of A$^4$, A$^5$, A$^6$ and A$^8$ is N;

each R$^2$, independently, is H, F, Cl, CF$_3$, OCF$_3$, methyl, ethyl, CN, OCH$_3$, NHCH$_3$, C(O)CH$_3$ or CH$_2$OCHF$_2$;

R$^3$ is C$_{1-4}$alkyl, C$_{1-4}$haloalkyl, CH$_2$OH, CH$_2$OCHF$_2$ or cyclopropyl; and each of R$^4$, R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$, provided that when A$^4$ is CR$^4$, A$^5$ is CR$^5$, A$^6$ is CR$^6$ and A$^8$ is CR$^8$, and each of R$^6$ and R$^8$, independently, is H, then R$^5$ is not H.

13. The compound according to claim 11, or a stereoisomer or pharmaceutically acceptable salt thereof, wherein A$^4$ is CR$^4$;

A$^5$ is CR$^5$;

A$^6$ is CR$^6$; and

A$^8$ is CR$^8$; wherein each of R$^4$, R$^5$, R$^6$ and R$^8$, independently, is H, F, CF$_3$, CF$_2$H, CH$_2$F or CH$_3$;

R$^3$ is CH$_3$, CF$_3$, CH$_2$F or CHF$_2$; and

R$^7$ is —NH—C(=O)—R$^9$ or

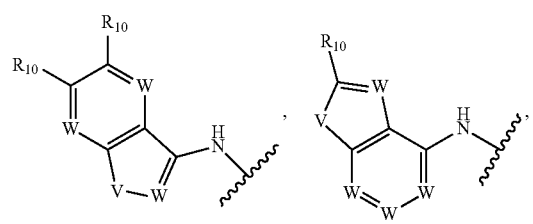

-continued

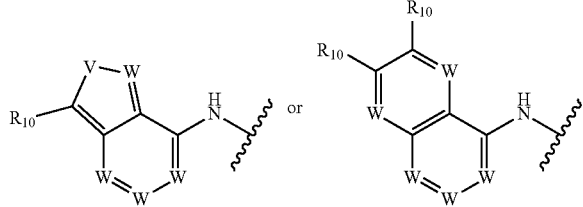

wherein V is NR¹⁰, O or S; and
each W, independently, is CH, CF, CCl or N.

14. The compound according to claim 13, or a stereoisomer or pharmaceutically acceptable salt thereof, wherein $R^7$ is —NH—C(=O)—$R^9$.

15. The compound according to claim 11, or a stereoisomer or pharmaceutically acceptable salt thereof, wherein $R^7$ is

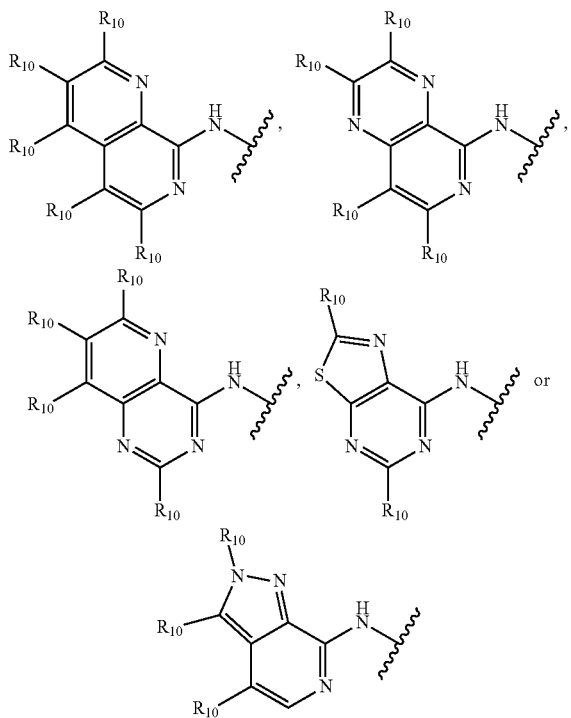

wherein each $R^{10}$, independently, is H, halo, haloalkyl, CN, SF₅, acetyl, —C(O)NHCH₃, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, CF₃, CHF₂, CH₂F, methyl, methoxy, ethyl, ethoxy, CH₂CF₃, CH₂CHF₂, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxazolyl, or oxetan-3yl.

16. The compound according to claim 1, or a stereoisomer or pharmaceutically acceptable salt thereof, having a Formula I-A

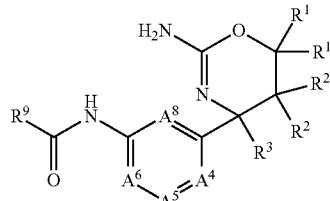

wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
one $R^1$ is $C_{1-3}$haloalkyl and the other $R^1$ is H, F, Cl, $C_{1-6}$-alkyl, $C_{2-4}$alkenyl, $C_{2-4}$alkynyl, CN, —CH₂O$C_{1-6}$-alkyl, —O$C_{1-6}$-alkyl, —S(O)$C_{1-6}$-alkyl, —NH$C_{1-6}$-alkyl or —C(O)$C_{1-6}$-alkyl, wherein each of the $C_{1-6}$-alkyl, $C_{2-4}$alkenyl, $C_{2-4}$alkynyl, and $C_{1-6}$-alkyl portion of —CH₂O$C_{1-6}$-alkyl, —O$C_{1-6}$-alkyl, —S(O)$C_{1-6}$-alkyl, —NH$C_{1-6}$-alkyl and —C(O)$C_{1-6}$-alkyl are optionally substituted with 1-4 substituents of F, oxo or OH;
each of $R^2$, independently, is H, F, Cl, $C_{1-4}$-alkyl, $C_{2-4}$alkenyl, $C_{2-4}$alkynyl, CN, —CH₂O$C_{1-3}$-alkyl, —O$C_{1-3}$-alkyl, wherein each of the $C_{1-4}$-alkyl, $C_{2-4}$alkenyl, $C_{2-4}$alkynyl and $C_{1-3}$-alkyl portion of —CH₂O$C_{1-3}$-alkyl and —O$C_{1-3}$-alkyl are optionally substituted with 1-4 substituents of F;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, CH₂O$C_{1-2}$alkyl or $C_{1-3}$haloalkyl on the nitrogen atom;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, CH₂O$C_{1-2}$alkyl or $C_{1-3}$haloalkyl on the nitrogen atom;
$R^3$ is $C_{1-4}$alkyl, CH₂O$C_{1-4}$alkyl, CH₂OH, $C_{1-4}$haloalkyl or cyclopropyl, wherein each of the $C_{1-4}$alkyl, CH₂O$C_{1-4}$ alkyl, $C_{1-4}$haloalkyl and cyclopropyl is optionally substituted with 1-4 F atoms;
each of $R^4$, $R^6$ and $R^8$, independently, is H or F;
$R^5$ is H, F or CH₃;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl, provided that when $A^4$ is $CR^4$, $A^5$ is $CR^5$, $A^6$ is $CR^6$ and $A^8$ is $CR^8$, and each of $R^6$ and $R^8$, independently, is H, then $R^5$ is not H.

17. The compound according to claim 16, or a stereoisomer, tautomer or pharmaceutically acceptable salt thereof, wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H or F;
one $R^1$ is H and the other $R^1$ is $CF_3$;
alternatively, each $R^1$ taken together with the carbon atom to which they are attached form a $C_{3-6}$ spirocarbocyclic ring optionally including one heteroatom selected from O and N and optionally substituted with 1-3 F atoms;
each of $R^2$, independently, is H, F, $CH_3$, $C_2H_5$, $CF_2H$, $CH_2F$, $CH_2OCH_2F$, $CH_2OCF_2H$ or $CH_2OCF_3$;
alternatively, each $R^2$ taken together with the carbon atom to which they are attached form a $C_{3-6}$ spirocarbocyclic ring optionally including one heteroatom selected from O and N and optionally substituted with 1-3 F atoms;
$R^3$ is $CH_3$, $C_2H_5$, $CF_2H$ or $CH_2F$;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl.

18. The compound according to claim 16, or a stereoisomer or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
one $R^1$ is H and the other $R^1$ is F, Cl, $CF_3$, $CF_2H$ or $CH_2F$; and
each $R^2$, independently, is H, F, Cl, $CF_3$, $CH_3$, $CF_2H$ or $CH_2F$; and
$R^3$ is $CF_3$, $CH_3$, $CF_2H$ or $CH_2F$.

19. The compound according to claim 1, or a stereoisomer, tautomer, hydrate, solvate or pharmaceutically acceptable salt thereof, having a Formula I-B:

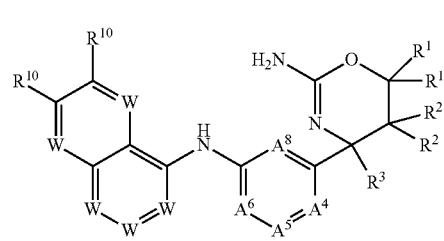

I-B wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-3}$-alkyl portion of —$CH_2OC_{1-3}$-alkyl and —$OC_{1-3}$-alkyl are optionally substituted with 1-4 substituents of F;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;
$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl; and each W, independently, is CH, CF, CCl or N.

20. The compound according to claim 19, or a stereoisomer or pharmaceutically acceptable salt thereof, wherein $A^4$ is $CR^4$;

$A^5$ is $CR^5$;

$A^6$ is $CR^6$;

$A^8$ is $CR^8$; wherein each of $R^4$, $R^5$, $R^6$ and $R^8$, independently, is H or F;

one $R^1$ is H and the other $R^1$ is $CF_3$;

alternatively, each $R^1$ taken together with the carbon atom to which they are attached form a $C_{3-6}$ spirocarbocyclic ring optionally including one heteroatom selected from O and N and optionally substituted with 1-3 F atoms;

each of $R^2$, independently, is H, F, $CH_3$, $C_2H_5$, $CF_2H$, $CH_2F$, $CH_2OCH_2F$, $CH_2OCF_2H$ or $CH_2OCF_3$; and alternatively, each $R^2$ taken together with the carbon atom to which they are attached form a $C_{3-6}$ spirocarbocyclic ring optionally including one heteroatom selected from O and N and optionally substituted with 1-3 F atoms;

$R^3$ is $CH_3$, $C_2H_5$, $CF_2H$ or $CH_2F$.

21. The compound according to claim 19, or a stereoisomer or pharmaceutically acceptable salt thereof, wherein $A^4$ is $CR^4$ or N;

$A^5$ is $CR^5$ or N;

$A^6$ is $CR^6$ or N;

$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;

each of $R^1$ and $R^2$, independently, is H, F, Cl, $CF_3$, $CH_3$, $CF_2H$ or $CH_2F$; and $R^3$ is $CF_3$, $CH_3$, $CF_2H$ or $CH_2F$.

22. The compound according to claim 1, or a stereoisomer, tautomer, hydrate, solvate or pharmaceutically acceptable salt thereof, having a Formula I-D:

I-D wherein $A^4$ is $CR^4$ or N;

$A^5$ is $CR^5$ or N;

$A^6$ is $CR^6$ or N;

$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and optionally substituted with a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl oxazolyl, or oxetan-3yl;

V is $NR^{10}$, O or S; and each W, independently, is CH, CF, CCl or N.

23. The compound according to claim 22, or a stereoisomer or pharmaceutically acceptable salt thereof, wherein A⁴ is CR⁴;
A⁵ is CR⁵;
A⁶ is CR⁶;
A⁸ is CR⁸; wherein each of R⁴, R⁵, R⁶ and R⁸, independently, is H or F;
one R¹ is H and the other R¹ is CF₃;
alternatively, each R¹ taken together with the carbon atom to which they are attached form a C₃₋₆ spirocarbocyclic ring optionally including one heteroatom selected from O and N and optionally substituted with 1-3 F atoms;
each of R², independently, is H, F, CH₃, C₂H₅, CF₂H, CH₂F, CH₂OCH₂F, CH₂OCF₂H or CH₂OCF₃; and
alternatively, each R² taken together with the carbon atom to which they are attached form a C₃₋₆ spirocarbocyclic ring optionally including one heteroatom selected from O and N and optionally substituted with 1-3 F atoms;
R³ is CH₃, C₂H₅, CF₂H or CH₂F.

24. The compound according to claim 22, or a stereoisomer or pharmaceutically acceptable salt thereof, wherein
A⁴ is CR⁴ or N;
A⁵ is CR⁵ or N;
A⁶ is CR⁶ or N;
A⁸ is CR⁸ or N, wherein each of R⁴, R⁵, R⁶ and R⁸, independently, is H or F and provided no more than one of A⁴, A⁵, A⁶ and A⁸ is N;
each of R¹ and R², independently, is H, F, Cl, CF₃, CH₃, CF₂H or CH₂F; and
R³ is CF₃, CH₃, CF₂H or CH₂F.

25. A compound, or a pharmaceutically acceptable salt thereof, selected from
N-(3-((4S,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide;
Racemic mixture of N-(3-((4R,6S)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide and N-(3-((4S,6R)-2-amino-4-(fluoromethyl)-6-(trifluoromethyl)-5,6-dihydro-4H-1,3-oxazin-4-yl)-4-fluorophenyl)-5-methoxy-2-pyrazinecarboxamide;
N-(3-((4S,6S)-2-amino-4-(fluoromethyl)-6-(trifluoromethyl)-5,6-dihydro-4H-1,3-oxazin-4-yl)-4-fluorophenyl)-5-chloro-2-pyridinecarboxamide;
N-(3-((4S,6S)-2-amino-4-(fluoromethyl)-6-(trifluoromethyl)-5,6-dihydro-4H-1,3-oxazin-4-yl)-4-fluorophenyl)-3-chloro-1,7-naphthyridin-8-amine;
Racemic mixture of N-(3-((4R,6R)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine and N-(3-((4S,6S)-2-amino-4-(fluoromethyl)-6-(trifluoromethyl)-5,6-dihydro-4H-1,3-oxazin-4-yl)-4-fluorophenyl)-2-methoxypyrido[3,4-b]pyrazin-5-amine;
N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methyl-2-pyridinecarboxamide;
N-(3-((4S,6S)-2-amino-4-(fluoromethyl)-6-(trifluoromethyl)-5,6-dihydro-4H-1,3-oxazin-4-yl)-4-fluorophenyl)-6-chloro-3-methylimidazo[1,2-a]pyridine-2-carboxamide;
N-(3-((4S,6S)-2-amino-4-methyl-6-(trifluoromethyl)-5,6-dihydro-4H-1,3-oxazin-4-yl)-4-fluorophenyl)-5-methoxy-2-pyrazinecarboxamide;
N-(3-((4S,6S)-2-amino-4-(fluoromethyl)-6-(trifluoromethyl)-5,6-dihydro-4H-1,3-oxazin-4-yl)-4-fluorophenyl)-5-(2,2,2-trifluoroethoxy)-2-pyridinecarboxamide;
8-((3-((4S,6S)-2-amino-4-(fluoromethyl)-6-(trifluoromethyl)-5,6-dihydro-4H-1,3-oxazin-4-yl)-4-fluorophenyl)amino)-1,7-naphthyridine-3-carbonitrile;
N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide;
Racemic mixture of N-(3-((4R,6S)-2-amino-4-(fluoromethyl)-6-(trifluoromethyl)-5,6-dihydro-4H-1,3-oxazin-4-yl)-4-fluorophenyl)-5chloro-3-pyrazinecarboxamide and N-(3-((4S,6R)-2-amino-4-methyl-6-(trifluoromethyl)-5,6-dihydro-4H-1,3-oxazin-4-yl)-4-fluorophenyl)-5-chloro-3-methyl-2-pyrazinecarboxamide;
N-(3-((4S,6S)-2-amino-4-(fluoromethyl)-6-(trifluoromethyl)-5,6-dihydro-4H-1,3-oxazin-4-yl)-4-fluorophenyl)-5-chloro-2-pyridinecarboxamide;
N-(3-((4S,6S)-2-amino-4-(fluoromethyl)-6-(trifluoromethyl)-5,6-dihydro-4H-1,3-oxazin-4-yl)-4-fluorophenyl)-5-methoxy-3-methylpyrazine-2-carboxamide;
N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methoxypicolinamide;
N-(3-((4S,6S)-2-amino-4-methyl-6-(trifluoromethyl)-5,6-dihydro-4H-1,3-oxazin-4-yl)-4-fluorophenyl)-5-chloropicolinamide;
N-(3-((4S,6S)-2-amino-4-methyl-6-(trifluoromethyl)-5,6-dihydro-4H-1,3-oxazin-4-yl)-4-fluorophenyl)-5-cyanopicolinamide;
N-(3-((4S,6S)-2-amino-4-(fluoromethyl)-6-(trifluoromethyl)-5,6-dihydro-4H-1,3-oxazin-4-yl)-4-fluorophenyl)-3-chloro-5-methoxypicolinamide;
N-(3-((4S,6S)-2-amino-4-(fluoromethyl)-6-(trifluoromethyl)-5,6-dihydro-4H-1,3-oxazin-4-yl)-4-fluorophenyl)-5-methoxypicolinamide;
N-(3-((4S,6S)-2-amino-4-(fluoromethyl)-6-(trifluoromethyl)-5,6-dihydro-4H-1,3-oxazin-4-yl)-4-fluorophenyl)-5-chloro-3-methylpyridine-2-carbothioamide;
N-(3-((4S, 6S)-2-amino-4-(fluoromethyl)-6-(trifluoromethyl)-5,6-dihydro-4H-1,3-oxazin-4-yl)-4-fluorophenyl)-5-fluoropicolinamide;
N-(3-((4S,6S)-2-amino-4-(fluoromethyl)-6-(trifluoromethyl)-5,6-dihydro-4H-1,3-oxazin-4-yl)-4-fluorophenyl)-3,5-dichloropicolinamide;
N-(3-((4S,6S)-2-amino-4-(fluoromethyl)-6-(trifluoromethyl)-5,6-dihydro-4H-1,3-oxazin-4-yl)-4-fluorophenyl)-5-bromo-3-chloro-2-pyridinecarboxamide;
8-((3-((4S,6S)-2-amino-4-(fluoromethyl)-6-(trifluoromethyl)-5,6-dihydro-4H-1,3-oxazin-4-yl)-4-fluorophenyl)amino)-5-fluoro-1,7-naphthyridine-3-carbonitrile;
N-(3-((4S,6S)-2-amino-4-(fluoromethyl)-6-(trifluoromethyl)-5,6-dihydro-4H-1,3-oxazin-4-yl)-4-fluorophenyl)-5-cyano-3-methylpicolinamide;
N-(3-((4S,6S)-2-amino-4-(fluoromethyl)-6-(trifluoromethyl)-5,6-dihydro-4H-1,3-oxazin-4-yl)-4-fluorophenyl)-5-bromopicolinamide; or
N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide.

26. The compound of claim 1, or a pharmaceutically acceptable salt thereof, selected from
N-(5-((4S,6S)-2-amino-4-methyl-6-(trifluoromethyl)-5,6-dihydro-4H-1,3-oxazin-4-yl)-6-fluoropyridin-3-yl)-5-chloro-3-methylpicolinamide;
N-(5-((4S,6S)-2-amino-4-methyl-6-(trifluoromethyl)-5,6-dihydro-4H-1,3-oxazin-4-yl)-6-fluoropyridin-3-yl)-5-chloropicolinamide;

N-(5-((4S,6S)-2-amino-4-methyl-6-(trifluoromethyl)-5,
6-dihydro-4H-1,3-oxazin-4-yl)-6-fluoropyridin-3-yl)-
5-cyanopicolinamide;
N-(5-((4S,6S)-2-amino-4-methyl-6-(trifluoromethyl)-5,
6-dihydro-4H-1,3-oxazin-4-yl)-6-fluoropyridin-3-yl)-
5-chloropicolinamide;
N-(5-((4S,6S)-2-amino-4-methyl-6-(trifluoromethyl)-5,
6-dihydro-4H-1,3-oxazin-4-yl)-6-fluoropyridin-3-yl)-
5-cyanopicolinamide;
N-(6-((4S,6S)-2-amino-4-methyl-6-(trifluoromethyl)-5,
6-dihydro-4H-1,3-oxazin-4-yl)-5-fluoropyridin-2-yl)-
5-cyanopicolinamide;
N-(5-((4S,6S)-2-amino-4-methyl-6-(trifluoromethyl)-5,
6-dihydro-4H-1,3-oxazin-4-yl)-6-fluoropyridin-3-yl)-
5-cyano-3-methylpicolinamide;
N-(5-((4S,6S)-2-amino-4-methyl-6-(trifluoromethyl)-5,
6-dihydro-4H-1,3-oxazin-4-yl)-6-fluoropyridin-3-yl)-
3-chloro-5-methoxypicolinamide;
N-(5-((4S,6S)-2-amino-4-methyl-6-(trifluoromethyl)-5,
6-dihydro-4H-1,3-oxazin-4-yl)-6-fluoropyridin-3-yl)-
3,5-dichloropicolinamide;
N-(6-((4S,6S)-2-amino-4-methyl-6-(trifluoromethyl)-5,
6-dihydro-4H-1,3-oxazin-4-yl)-5-fluoropyridin-2-yl)-
3,5-dichloropicolinamide;
N-(6-((4S,6S)-2-amino-4-methyl-6-(trifluoromethyl)-5,
6-dihydro-4H-1,3-oxazin-4-yl)-5-fluoropyridin-2-yl)-
3-chloro-5-(trifluoromethyl)picolinamide;
N-(6-((4S,6S)-2-amino-4-methyl-6-(trifluoromethyl)-5,
6-dihydro-4H-1,3-oxazin-4-yl)-5-fluoropyridin-2-yl)-
3-chloro-5-cyanopicolinamide;
N-(6-((4S,6S)-2-amino-4-methyl-6-(trifluoromethyl)-5,
6-dihydro-4H-1,3-oxazin-4-yl)-5-fluoropyridin-2-yl)-
5-chloropicolinamide;
N-(6-((4S,6S)-2-amino-4-methyl-6-(trifluoromethyl)-5,
6-dihydro-4H-1,3-oxazin-4-yl)-5-fluoropyridin-2-yl)-
5-cyano-3-methylpicolinamide.

27. The compound of claim 1, or a pharmaceutically acceptable salt thereof, selected from (4S,6S)-4-(5-((3-chloro-1,7-naphthyridin-8-yl)amino)-2-fluoropyridin-3-yl)-4-methyl-6-(trifluoromethyl)-5,6-dihydro-4H-1,3-oxazin-2-amine;
(4S,6S)-4-(5-((7-chloropyrido[3,2-d]pyrimidin-4-yl)amino)-2-fluoropyridin-3-yl)-4-methyl-6-(trifluoromethyl)-5,6-dihydro-4H-1,3-oxazin-2-amine;
4-((5-((4S,6S)-2-amino-4-methyl-6-(trifluoromethyl)-5,6-dihydro-4H-1,3-oxazin-4-yl)-6-fluoropyridin-3-yl)amino)pyrido[3,2-d]pyrimidine-7-carbonitrile;
8-((5-((4S,6S)-2-amino-4-methyl-6-(trifluoromethyl)-5,6-dihydro-4H-1,3-oxazin-4-yl)-6-fluoropyridin-3-yl)amino)-1,7-naphthyridine-3-carbonitrile; or
8-((6-((4S,6S)-2-amino-4-methyl-6-(trifluoromethyl)-5,6-dihydro-4H-1,3-oxazin-4-yl)-5-fluoropyridin-2-yl)amino)-5-fluoro-1,7-naphthyridine-3-carbonitrile.

28. The compound of claim 1, or a pharmaceutically acceptable salt thereof, selected from

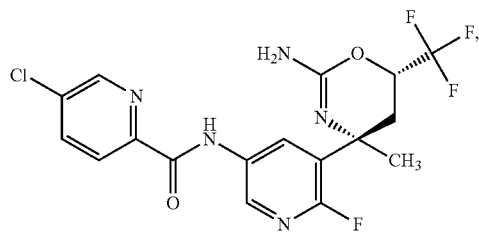

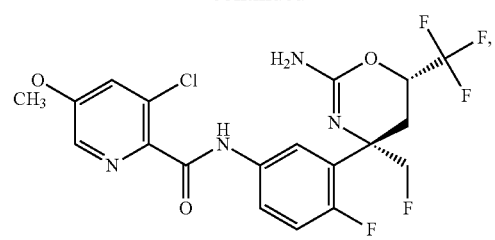

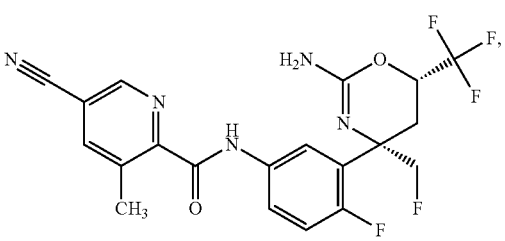

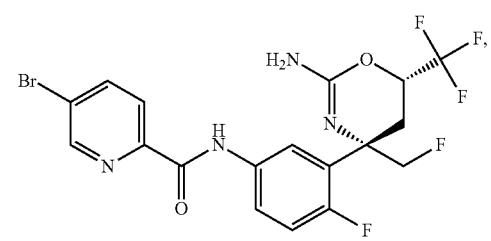

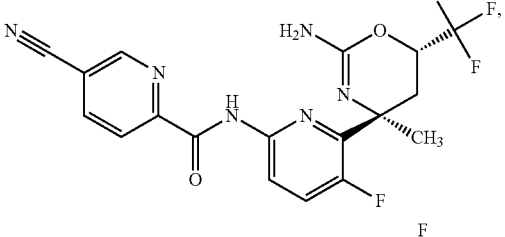

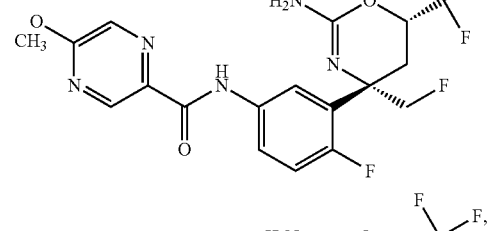

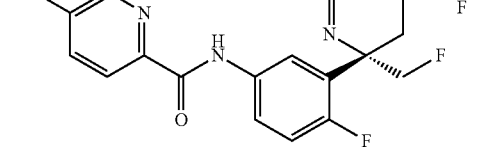

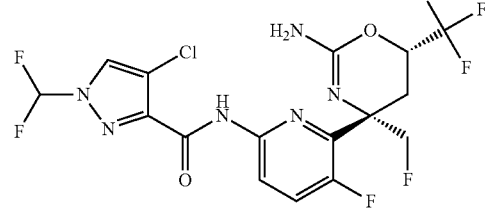

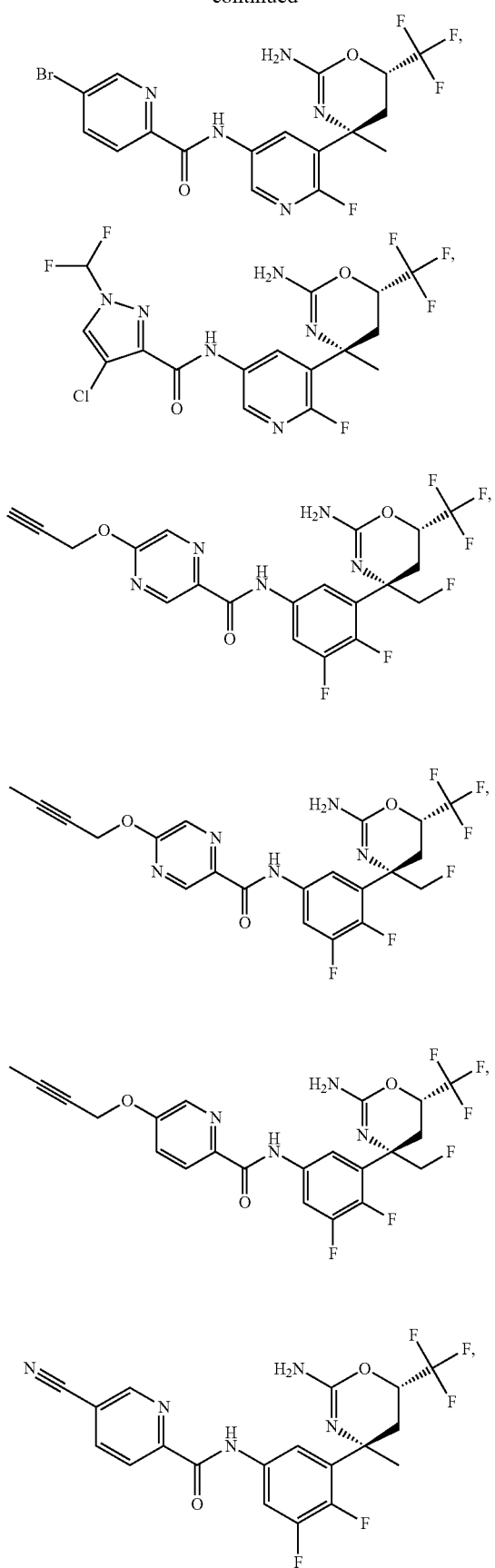
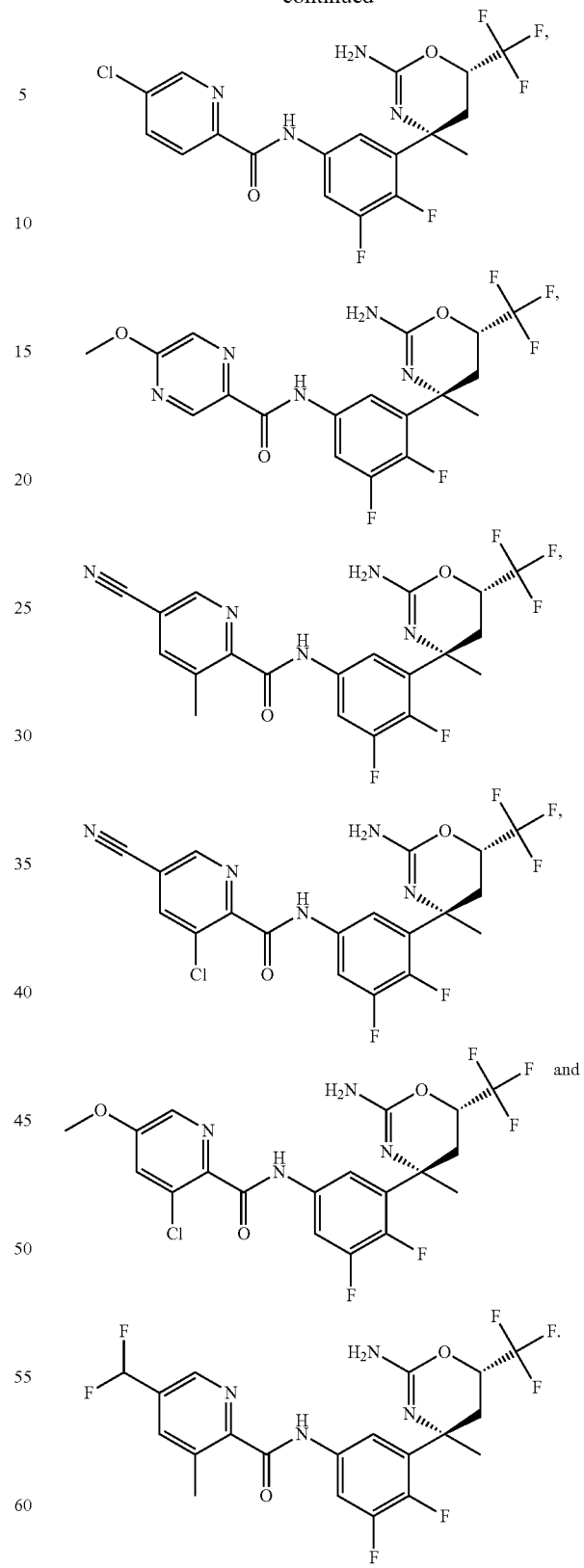
29. A pharmaceutical composition comprising a compound according to claim 1 and a pharmaceutically acceptable excipient.

30. A pharmaceutical composition comprising a compound according to claim 25 and a pharmaceutically acceptable excipient.

31. A pharmaceutical composition comprising a compound according to claim 26 and a pharmaceutically acceptable excipient.

32. A pharmaceutical composition comprising a compound according to claim 27 and a pharmaceutically acceptable excipient.

33. A pharmaceutical composition comprising a compound according to claim 28 and a pharmaceutically acceptable excipient.

34. A method of reducing beta amyloid peptide levels in the cerebral spinal fluid of a subject, the method comprising administering to the subject an effective dosage amount of a compound according to claim 1.

35. A method of treating Alzheimer's disease, cognitive impairment or a combination thereof in a subject, the method comprising administering to the subject an effective dosage amount of a compound according to claim 1.

36. A method of treating a neurological disorder selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of a compound according to claim 1.

37. A method of reducing the formation of plaque on the brain of a subject, the method comprising administering to the subject an effective dosage amount of a compound according to claim 1.

38. A process for preparing a compound according to claim 1, the process comprising the step of reacting a protected compound 20

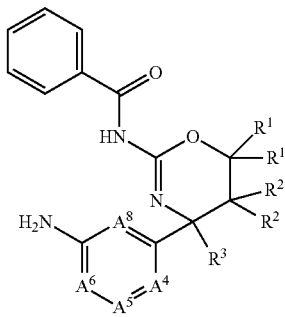

wherein each $R^1$ and each $R^2$, $R^3$, $A^4$, $A^5$, $A^6$ and $A^8$ of compound 20 are as defined in claim 1, with a compound having the structure or $R^9$—C(═O)OH or $R^9$—Cl, wherein $R^9$ is as defined in claim 1 to prepare the compound according to claim 1.

39. A process for preparing a compound according to claim 1, the process comprising the step of reacting a compound 21

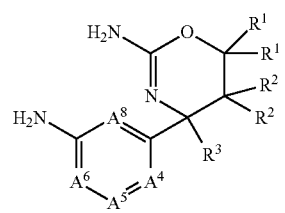

wherein each $R^1$ and each $R^2$, $R^3$, $A^4$, $A^5$, $A^6$ and $A^8$ of compound 21 are as defined in claim 1, with a compound having the structure $R^9$—Cl, wherein $R^9$ is as defined in claim 1 to prepare the compound according to claim 1.

* * * * *